US009605285B2

(12) United States Patent
Finley et al.

(10) Patent No.: US 9,605,285 B2
(45) Date of Patent: Mar. 28, 2017

(54) COMPOSITIONS AND METHODS FOR SUCCINATE PRODUCTION

(75) Inventors: Kenneth R. Finley, St. Bonifacius, MN (US); Jeanette M. Huryta, Excelsior, MN (US); Beth M. Mastel, Excelsior, MN (US); Thomas W. McMullin, Minnetonka, MN (US); Gregory M. Poynter, St. Paul, MN (US); Brian J. Rush, Minneapolis, MN (US); Kevin T. Watts, Minneapolis, MN (US); Arlene M. Fosmer, Eden Prairie, MN (US); Vernon L. McIntosh, Jr., Minneapolis, MN (US); Keith M. Brady, Eden Prairie, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 373 days.

(21) Appl. No.: 13/981,517

(22) PCT Filed: Jan. 25, 2012

(86) PCT No.: PCT/US2012/022612
§ 371 (c)(1),
(2), (4) Date: Jul. 24, 2013

(87) PCT Pub. No.: WO2012/103261
PCT Pub. Date: Aug. 2, 2012

(65) Prior Publication Data
US 2013/0302866 A1    Nov. 14, 2013

Related U.S. Application Data

(60) Provisional application No. 61/436,185, filed on Jan. 25, 2011.

(51) Int. Cl.
*C12P 7/46* (2006.01)
*C12N 9/04* (2006.01)
*C12N 9/02* (2006.01)
*C12N 9/88* (2006.01)
*C12N 9/00* (2006.01)
*C12N 15/81* (2006.01)

(52) U.S. Cl.
CPC .............. *C12P 7/46* (2013.01); *C12N 9/001* (2013.01); *C12N 9/0006* (2013.01); *C12N 9/88* (2013.01); *C12N 9/93* (2013.01); *C12N 15/815* (2013.01); *C12Y 101/01037* (2013.01); *C12Y 103/01006* (2013.01); *C12Y 402/01002* (2013.01); *C12Y 604/01001* (2013.01); *Y02P 20/52* (2015.11)

(58) Field of Classification Search
None
See application file for complete search history.

(56) References Cited

U.S. PATENT DOCUMENTS

| 4,275,234 A | 6/1981 | Baniel et al. |
|---|---|---|
| 4,771,001 A | 9/1988 | Bailey et al. |
| 5,132,456 A | 7/1992 | King et al. |
| 5,420,304 A | 5/1995 | Verser et al. |
| 5,510,526 A | 4/1996 | Baniel et al. |
| 5,641,406 A | 6/1997 | Sarhaddar et al. |
| 5,831,122 A | 11/1998 | Eyal |
| 5,876,983 A | 3/1999 | Sugimoto et al. |
| 6,485,947 B1 | 11/2002 | Rajgarhia et al. |
| 2003/0087381 A1 | 5/2003 | Gokarn et al. |
| 2004/0199940 A1 | 10/2004 | Karunanandaa et al. |
| 2007/0027309 A1 | 2/2007 | Weinstock et al. |
| 2007/0118916 A1 | 5/2007 | Puzio et al. |
| 2008/0009041 A1 | 1/2008 | Mizoguchi et al. |
| 2008/0090273 A1 | 4/2008 | Winkler et al. |
| 2008/0148432 A1 | 6/2008 | Abad |
| 2008/0293113 A1 | 11/2008 | Koseki et al. |
| 2009/0191599 A1 | 7/2009 | Devroe et al. |
| 2009/0226989 A1 | 9/2009 | Suominen et al. |
| 2010/0009419 A1 | 1/2010 | Burk et al. |
| 2010/0120105 A1 | 5/2010 | Anthony et al. |
| 2010/0184171 A1 | 7/2010 | Jantama et al. |
| 2010/0280803 A1 | 11/2010 | Famili et al. |
| 2011/0008861 A1 | 1/2011 | Berry et al. |
| 2011/0129885 A1 | 6/2011 | Lang et al. |
| 2011/0229945 A1 | 9/2011 | Jansen et al. |
| 2011/0300595 A1 | 12/2011 | Lang et al. |
| 2012/0135482 A1 | 5/2012 | Jansen et al. |
| 2013/0309736 A1 | 11/2013 | Finley et al. |
| 2014/0031587 A1 | 1/2014 | Verwaal et al. |

FOREIGN PATENT DOCUMENTS

| EP | 2 495 304 A1 | 9/2012 |
|---|---|---|
| KR | 2011 0004574 A | 1/2011 |
| WO | 9300440 A1 | 1/1993 |
| WO | 9914335 A1 | 3/1999 |
| WO | 0071738 A1 | 11/2000 |

(Continued)

OTHER PUBLICATIONS

Zelle et al., "Malic Acid Production by *Saccharomyces cerevisiae*: Engineering of Pyruvate Carboxylation, Oxaloacetate Reduction, and Malate Export", Applied and Environmental Microbiology, 74(9): 2766-2777 (May 2008).*

(Continued)

*Primary Examiner* — Anand Desai

(57) ABSTRACT

The present application provides genetically modified yeast cell comprising an active succinate fermentation pathway, as well as methods of using these cells to produce succinate.

20 Claims, 67 Drawing Sheets

(56) References Cited

FOREIGN PATENT DOCUMENTS

| WO | 0210425 A2 | 2/2002 |
| WO | 0242471 A2 | 5/2002 |
| WO | 03049525 A2 | 6/2003 |
| WO | 03102152 A2 | 12/2003 |
| WO | 03102200 A2 | 12/2003 |
| WO | 03102201 A2 | 12/2003 |
| WO | 2007061590 A1 | 5/2007 |
| WO | 2007106524 A2 | 9/2007 |
| WO | 2008144626 A1 | 11/2008 |
| WO | 2009011974 A1 | 1/2009 |
| WO | 2008128522 A3 | 4/2009 |
| WO | 2009/065778 A1 | 5/2009 |
| WO | 2009065780 A1 | 5/2009 |
| WO | 2009/101180 A2 | 8/2009 |
| WO | 2010003728 A1 | 1/2010 |
| WO | 2010043197 A1 | 4/2010 |
| WO | 2010147920 A1 | 12/2010 |
| WO | 2011023700 A2 | 3/2011 |
| WO | 2012/103261 A2 | 8/2012 |

OTHER PUBLICATIONS

Nissen et al., "Expression of a cytoplasmic transhydrogenase in *Saccharomyces cerevisiae* results in formation of 2-oxoglutarate due to depletion of the NADPH pool," Yeast, 2001, vol. 18, pp. 19-32.
Guccione at al., "Reduction of fumarate, mesaconate and crotonate by Mfr, a novel oxygen-regulated periplasm c reductase in Campylobacter jejuni," Environ Microbiol, 2010, vol. 12, No. 3, pp. 576-591.
Novick at al., "Experiments with the Chemostat on Spontaneous Mutations of Bacteria," Proc Nati Sci USA, 1950, vol. 36, pp. 708-719.
Harder et al., "Microbial Selection in Continuous Culture," J Appl Bacteriol. 1977, vol. 43, pp. 1-24.
Gross et al., "Acidophilic and acid-tolerant fungi and yeasts," Hydrobiologia, 2000, vol. 433, pp. 91-109.
Kurtzman et al., "identification and phylogeny of ascomycetous yeasts from analysis of nuclear large subunit (26S) ribosomal DNA partial sequences," Antonie van Leeuwenhoek, 1998, vol. 73, pp. 331-371.
Kurtzman et al., The Yeasts, A Taxonomic Study, Fourth Edition, 1998, Section 35, Issatchenkia Kudryavtsev, pp. 222-223.
Hjersted et al, "Genome-Scale Analysis of *Saccharomyces cerevisiae* Metabolism and Ethanol Production in Fed-Batch Culture," Biotechnol Bioeng, 2007, vol. 97, No. 5, pp. 1190-1204.
Famili et al., "*Saccharomyces cerevisiae* phenotypes can be predicted by using constraint-based analysis of a genome-scale reconstructed metabolic network," Proc Nail Aced Sci USA, 2003, vol. 100, No. 23, pp. 13134-13139.
Bioreact on Engineering Principles, Second Edition. 2003, Kluwer Academic/Plenum Publishers, p. 449, equation1, 1 page.
T.B. Vickroy, Comprehensive Biotechnology, 1985, Chapter 38, pp. 761-776.
Verduyn et al., "Effect of Benzoic Acid on Metabolic Fluxes in Yeasts: A Continuous-Culture Study on the Regulation of Respiration and Alcoholic Fermentation," Yeast 1992, vol. 8, pp. 501-517.
Datta et al., "Technological and economic potential of poly(lactic acid) and lactic acid derivatives," FEMS Microbiol Rev, 1995, vol. 16, pp. 221-231.
Patil et al., "Evolutionary programming as a platform for in silica metabolic engineering," BMC Bioinformatics, 2005, vol. 6, 12 pages.

The Genolevures Consortium, Comparative genomics of protoploid Saccharomycetaceae, Uniprot C5DSS7_ZYGRC, Jul. 28, 2009, Retrieved on Jul. 18, 2012, available at <://www.uniprot.org/uniprot/C5DSS7.txt?version=3>.
Souciet et al., Zygosaccharomyces rouxii strain CBS732 chromosome C complete sequence, GenBank Accession No. CU928175.1 Jan. 14, 2010, Retrieved on Jul. 18, 2012, available at <//www.ncbi.nlm.nih.gov/nuccore/CU928175>.
Pentose Phosphate Pathway, Sigma-Aldrich 2007 [online], Retrieved on Jul. 5, 2012 from the internet <URL: www.sigmaaldrich.com/technical-documents/articles/biofiles/pentose-phosphate.html>.
Thomas et al., "Identification of the structural gene for glucose-6-phosphate dehydrogenase in yeast. Inactivation leads to a nutritional requirement for organic sulfur," EMBO Journal, 1991, vol. 10, pp. 547-553.
Zhang et al., "Cloning and characterization of the partial gene CgZWF encoding glucose 6-phosphate dehydrogenase from Candida glycerinogenes," Uniprot A3FFK8_CANGY Mar. 20, 2007, Retrieved on Jul. 18, 2012, available at <www.uniprot.org/uniprot/A3FFKatxt?version=13>.
Zhang at al.: Candida glycerinogenes glucose 6-phosphate dehydrogenase gene, partial cds, GenBank Accession No. EF373653, Feb. 11, 2007, Retrieved on Jul. 18, 2012, available at <www.ncbi.nlm.nih.gov/nuccore/EF373653>.
Gietz et al., "Transformation of Yeast by Lithium Acetate/Single-Stranded Carrier DNA/Polyethylene Glycol Method," Met Enzymol, 2002, vol. 350, pp. 87-96.
Magnuson et al., "Organic Production by Filamentous Fungi," Advances in Fungal Biotechnology for Industry, Agriculture, and Medicine, 2004, pp. 307-340.
Cheng et al.; "Biotechnological production of succinic acid: current state and perspectives", Biofuels, Biproduction & Biorefining, vol. 6, Feb. 29, 2012, pp. 302-318, XP055091914.
Otero et al.; "Industrial systems biology of *Saccharomyces cerevisiae* enables novel succinic acid cell factory", Plos One, vol. 8(e54144), Jan. 21, 2013, pp. 1-10, XP002750949.
Papgianni: "Recent advances in engineering the central carbon metabolism of industrially important bacteria", Microbial Cell Factories, vol. 11, Apr. 30, 2012, pp. 1-13, XP021126659.
Raab et al.; "Metabolic engineering of *Saccharomyces cerevisiae* for the biotechnological production of succinic acid", Metabolic Engineering, vol. 12, 2010, pp. 518-525, XP055052799.
Thalagala et al.; "Study on ethanol fermentation using D-glucose rich fractions obtained from lignocelluloses by a two-step extraction with sulfuric acid and Issatchenkia orientalis MF 121", Journal of Applied Glycoscience, vol. 56, 2009, pp. 7-11, XP002750966.
Anonymous: "Candida krusei (Castellani) Berkhout, anamorph ATCC 60585(TM)", Jan. 1, 1982, XP055203286 Retrieved from the Internet URL: www.lgcstandards-atcc.org/products/all/60585.aspx?geo_country=nl#history [retrieved on Jul. 17, 2015] *Abstract*.
Anonymous: "Pichia fermentans Lodder ATCC 38617(TM)", , Jan. 1, 1978, XP055203287, Retrieved from the Internet: URL: lgcstandards-atcc.org/Products/All/38617.aspx#history [retrieved on Jul. 17, 205] *Abstract*.
Andreas M. Raab et al. "Oxidative versus reductive succinic acid production in the yeast *Saccharomyces cerevisiae*", Bioengineered Bugs, vol. 2, No. 2, Mar. 1, 2011, pp. 120-123, XP055087538, ISSN: 1949-1018, DOI: 10.4161/bbug.2.2.14549 *Abstract*.
Ok Taing et al."Production of malic and succinic acids by sugar-tolerant yeast Zygosaccharomyces rouxil", European Food Research and Technology; Forschung A, Springer, Berlin, DE, vol. 224, No. 3, Mar. 31, 2006, pp. 343-347, XP019458173, ISSN: 1438-2385, DOI: 10.1007/S00217-006-0323-Z.
NCBI Accession No. 476733.1, http://www.ncbi.nlm.nih.gov/nuccore/76152006?sat=11&satkey=491535), Sep. 23, 2005.
NCBI Accession No. 476733.1, http://www.ncbi.nlm.nih.gov/nuccore/CH476733#, Apr. 18, 2012.

* cited by examiner

COMPOSITIONS AND METHODS FOR SUCCINATE PRODUCTION

CROSS-REFERENCE TO RELATED APPLICATIONS

This application is a section 371 national-stage phase of international Application No. PCT/US2012/022612, filed 25 Jan. 2012, titled "COMPOSITIONS AND METHODS FOR SUCCINATE PRODUCTION" which claims priority to U.S. Application Ser. No. 61/436,185, filed 25 Jan. 2011, titled "COMPOSITIONS AND METHODS FOR SUCCINATE PRODUCTION" which is hereby incorporated by reference in its entirety."

BACKGROUND

Succinate (butanedioic acid) is a four carbon dicarboxylic acid that plays a key role in the citric acid cycle. Succinate was recently listed by the US Department of Energy at the top of its list of value added chemicals from biomass. Succinate is a precursor for a number of compounds, including tetrahydrofuran, 1,4-butanediol, and γ-butyrolactone. Succinate has a wide variety of potential applications including use in liquid antigels, heat transfer fluids, the solvents gamma butyrolactone (GBL) and dimethyl isosorbide, pigments, the polyesters poly-butylene succinate (PBS) and PEIT, synthesis intermediates and plasticizers.

Succinate has traditionally been derived from maleic anhydride, which is produced by oxidation of butane. In recent years, there have been several attempts to move away from these traditional production methods to biological production methods. Biological production provides several advantages over derivation from petrochemical sources, including increased efficiency and cost effectiveness and decreased environmental impact.

Previously developed biological succinate production methods have primarily utilized bacterial fermentation hosts. Although several bacterial species have been used successfully to produce succinate, bacteria present certain drawbacks for large-scale organic acid production. As organic acids are produced, the fermentation medium becomes increasingly acidic. These lower pH conditions result in lower costs for organic acid production, because the resultant product is partially or wholly in the acid form. However, most bacteria do not perform well in strongly acidic environments, and therefore either die or begin producing so slowly that they become economically unviable. To prevent this, it becomes necessary to buffer the medium to maintain a higher pH. However, this makes recovery of the organic acid product more difficult and expensive.

There has been increasing interest in recent years around the use of yeast to ferment sugars to organic acids. Yeast are used as biocatalysts in a number of industrial fermentations, and present several advantages over bacteria. While many bacteria are unable to synthesize certain amino acids or proteins that they need to grow and metabolize sugars efficiently, most yeast species can synthesize their necessary amino acids or proteins from inorganic nitrogen compounds. Yeast are also not susceptible to bacteriophage infection, which can lead to loss of productivity or of whole fermentation runs in bacteria.

Although yeast are attractive candidates for organic acid production, they present several difficulties. First, pathway engineering in yeast is typically more difficult than in bacteria. Enzymes in yeast are compartmentalized in the cytoplasm, mitochondria, or peroxisomes, whereas in bacteria they are pooled in the cytoplasm. This means that targeting signals may need to be removed in yeast to ensure that all the enzymes of the biosynthetic pathway co-exist in the same compartment within a single cell. Control of transport of pathway intermediates between the compartments may also be necessary to maximize carbon flow to the desired product. Second, not all yeast species meet the necessary criteria for economic fermentation on a large scale. In fact, only a small percentage of yeast possess the combination of sufficiently high volumetric and specific sugar utilization rates with the ability to grow robustly under low pH conditions. The Department of Energy has estimated that production rates of approximately 2.5 g/L/hour are necessary, using a minimal media, for economic fermentations of organic acid.

The yeast strains that have been developed thus far for succinate production have not exhibited high enough yields for economic production on an industrial scale. Therefore, there is a need for improved yeast strains that generate succinate on a large scale in a more cost-effective manner.

SUMMARY

Provided herein in certain embodiments are genetically modified yeast cells comprising an active succinate fermentation pathway from phosphoenolpyruvate or pyruvate to succinate. In certain embodiments, the yeast cells provided herein are succinate resistant. In certain embodiments, the active succinate fermentation pathway includes at least the following reactions 1) conversion of pyruvate and/or phosphoenolpyruvate to oxaloacetate, 2) conversion of oxaloacetate to malate, 3) conversion of malate to fumarate, and 4) conversion of fumarate. In certain embodiments, the pathway also includes export of succinate from inside the cell to the extracellular environment. Each of the reactions in the active succinate fermentation pathway is catalyzed by one or more enzymes, which in turn are encoded by one or more exogenous or endogenous succinate fermentation pathway genes. In certain embodiments, all of the enzymes catalyzing reactions in the active succinate fermentation pathway are encoded by endogenous genes. In other embodiments, all of the enzymes catalyzing reactions in the active succinate fermentation pathway are encoded by exogenous genes. In still other embodiments, the enzymes catalyzing reactions in the active succinate fermentation pathway are encoded by a mix of endogenous and exogenous genes.

In certain embodiments, the genetically modified yeast cells provided herein comprise one or more endogenous genes encoding enzymes that catalyze various reactions in the active succinate fermentation pathway, and in certain of these embodiments the cells comprise one or more copies of endogenous pyruvate carboxylase, phosphoenolpyruvate carboxylase, malate dehydrogenase, fumarase, fumarate reductase, and/or succinate exporter genes. In certain of these embodiments, the endogenous genes are operatively linked to endogenous regulatory elements only. In other embodiments, one or more of the endogenous genes are operatively linked to one or more exogenous regulatory elements.

In certain embodiments, the genetically modified yeast cells provided herein comprise one or more exogenous genes encoding enzymes that catalyze various reactions in the active succinate fermentation pathway, and in certain of these embodiments the cells comprise one or more copies of exogenous pyruvate carboxylase, phosphoenolpyruvate carboxylase, malate dehydrogenase, fumarase, fumarate reductase, and/or succinate exporter genes. In certain of these embodiments, the exogenous genes are operatively linked to exogenous regulatory elements only. In other embodiments, one or more of the exogenous genes are operatively linked to one or more endogenous regulatory elements.

In certain embodiments, the genetically modified yeast cells provided herein comprise an endogenous and/or exogenous pyruvate carboxylase gene. In certain of those embodiments where the cells comprise an exogenous pyruvate carboxylase gene, the exogenous pyruvate carboxylase gene is derived from a yeast source gene such as an *Issatchenkia orientalis, Saccharomyces cerevisiae*, or *Kluyveromyces marxianus* source gene, and in certain of these embodiments the exogenous pyruvate carboxylase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous pyruvate carboxylase gene encodes a polypeptide that comprises the amino acid sequence of SEQ ID NOs:8, 10, or 12, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:8, 10, or 12. In certain embodiments, the exogenous pyruvate carboxylase gene comprises the nucleotide sequence of SEQ ID NOs:7, 9, or 11, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:7, 9, or 11. In certain other embodiments where the cells comprise an exogenous pyruvate carboxylase gene, the exogenous pyruvate carboxylase gene is derived from a fungal source gene other than a *Rhizopus oryzae* source gene.

In certain embodiments, the genetically modified yeast cells provided herein comprise an endogenous and/or exogenous phosphoenolpyruvate carboxylase gene. In certain of these embodiments where the cells comprise an exogenous phosphoenolpyruvate carboxylase gene, the exogenous phosphoenolpyruvate carboxylase gene is derived from a bacterial source gene such as an *Escherichia coli* or *Mannheimia succiniciproducens* source gene, and in certain of these embodiments the exogenous phosphoenolpyruvate carboxylase gene encodes a polypeptide with at least 50%, at least 60%, at least 70%, at least 80%, at least 85%, at least 90%, at least 95%, at least 97%, or at least 99% sequence identity to a polypeptide encoded by the bacterial source gene. In certain embodiments, the exogenous phosphoenolpyruvate carboxylase gene encodes a polypeptide that comprises the amino acid sequence of SEQ ID NOs:4 or 6, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:4 or 6. In certain embodiments, the exogenous phosphoenolpyruvate carboxylase gene comprises the nucleotide sequence of SEQ ID NOs:3 or 5, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:3 or 5.

In certain embodiments, the genetically modified yeast cells provided herein comprise an endogenous and/or exogenous malate dehydrogenase gene. In certain of these embodiments where the cells comprise an exogenous malate dehydrogenase gene, the exogenous malate dehydrogenase gene is derived from a yeast source gene such as an *I. orientalis, Zygosaccharomyces rouxii*, or *K. marxianus* source gene, and in certain of these embodiments the exogenous malate dehydrogenase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous malate dehydrogenase gene encodes a polypeptide that comprises the amino acid sequence of SEQ ID NOs:14, 16, 18, 168, 20, 22, or 24, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:14, 16, 18, 168, 20, 22, or 24. In certain embodiments, the exogenous malate dehydrogenase gene comprises the nucleotide sequence of SEQ ID NOs:13, 15, 17, 167, 19, 21, or 23, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:13, 15, 17, 167, 19, 21, or 23. In certain other embodiments where the cells comprise an exogenous malate dehydrogenase gene, the exogenous malate dehydrogenase gene is derived from a bacterial source gene such as an *E. coli* source gene, and in certain of these embodiments the exogenous malate dehydrogenase gene encodes a polypeptide with at least 50%, at least 60%, at least 70%, at least 80%, at least 85%, at least 90%, at least 95%, at least 97%, or at least 99% sequence identity to a polypeptide encoded by the bacterial source gene. In certain embodiments, the exogenous malate dehydrogenase gene encodes a polypeptide that comprises the amino acid sequence of SEQ ID NO:170, or an amino acid sequence with at least 50%, at least 60%, at least 70%, at least 80%, at least 85%, at least 90%, at least 95%, at least 97%, or at least 99% sequence identity to the amino acid sequence of SEQ ID NO:170. In certain embodiments, the exogenous malate dehydrogenase gene comprises the nucleotide sequence of SEQ ID NO:169, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:169. In certain other embodiments where the cells comprise an exogenous malate dehydrogenase gene, the exogenous malate dehydrogenase gene is derived from a fungal source gene such as a *R. oryzae* source gene, and in certain of these embodiments the exogenous malate dehydrogenase gene encodes a polypeptide with at least 50%, at least 60%, at least 70%, at least 80%, at least 85%, at least 90%, at least 95%, at least 97%, or at least 99% sequence identity to a polypeptide encoded by the fungal source gene. In certain embodiments, the exogenous malate dehydrogenase gene encodes a polypeptide that comprises the amino acid sequence of SEQ ID NO:172, or an amino acid sequence with at least 50%, at least 60%, at least 70%, at least 80%, at least 85%, at least 90%, at least 95%, at least 97%, or at least 99% sequence identity to the amino acid sequence of SEQ ID NO:172. In certain embodiments, the exogenous malate dehydrogenase gene comprises the nucleotide sequence of SEQ ID NO:171, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:171.

In certain embodiments, the genetically modified yeast cells provided herein comprise an endogenous and/or exogenous fumarase gene. In certain of these embodiments where the cells comprise an exogenous fumarase gene, the exogenous fumarase gene is derived from a yeast source gene such as an *I. orientalis* source gene, and in certain of these embodiments the exogenous fumarase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous fumarase gene encodes a polypeptide that comprises the amino acid sequence of SEQ ID NO:2, or an amino acid sequence with at least 50%, at least 60%, at least 70%, at least 80%, at least 85%, at least 90%, at least 95%, at least 97%, or at least 99% sequence identity to the amino acid sequence of SEQ ID NO:2. In certain embodiments, the exogenous fumarase gene comprises the nucleotide sequence of SEQ ID NO:1, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:1.

In certain embodiments, the genetically modified yeast cells provided herein comprise an endogenous and/or exogenous fumarate reductase gene. In certain of these embodiments where the cells comprise an exogenous fumarate reductase gene, the exogenous fumarase gene is derived from a yeast source gene such as an *S. cerevisiae*, *Saccharomyces mikatae*, *Kluyveromyces polyspora*, or *K. marxianus* source gene, and in certain of these embodiments the exogenous fumarate reductase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous fumarate reductase gene encodes a polypeptide that comprises the amino acid sequence of SEQ ID NOs:26, 28, 30, or 32, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:26, 28, 30, or 32. In certain embodiments, the exogenous fumarate reductase gene comprises the nucleotide sequence of SEQ ID NOs:25, 27, 29, or 31, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:25, 27, 29, or 31. In certain other embodiments where the cells comprise an exogenous fumarate reductase gene, the exogenous fumarate reductase gene is derived from a protozoan source gene such as a *Trypanosoma brucei*, *Trypanosoma cruzi*, *Leishmania braziliensis*, or *Leishmania mexicana* source gene, and in certain of these embodiments the exogenous fumarate reductase gene encodes a polypeptide with at least 50%, at least 60%, at least 70%, at least 80%, at least 85%, at least 90%, at least 95%, at least 97%, or at least 99% sequence identity to a polypeptide encoded by the protozoan source gene. In certain embodiments, the exogenous fumarate reductase gene encodes a polypeptide that comprises the amino acid sequence of SEQ ID NOs:174, 176, 178, or 180, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:174, 176, 178, or 180. In certain embodiments, the exogenous fumarate reductase gene comprises the nucleotide sequence of SEQ ID NOs: 173, 175, 177, or 179, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:173, 175, 177, or 179.

In certain embodiments, the genetically modified yeast cells provided herein comprise an endogenous and/or exogenous succinate exporter gene. In certain of these embodiments where the cells comprise an exogenous succinate exporter gene, the exogenous succinate exporter gene is derived from a fungal source gene such as an *Schizosaccharomyces pombe* or *Aspergillus oryzae* source gene, and in certain of these embodiments the exogenous succinate exporter gene encodes a polypeptide with at least 50%, at least 60%, at least 70%, at least 80%, at least 85%, at least 90%, at least 95%, at least 97%, or at least 99% sequence identity to a polypeptide encoded by the fungal source gene. In certain embodiments, the exogenous succinate exporter gene encodes a polypeptide that comprises the amino acid sequence of SEQ ID NOs:182 or 184, or an amino acid sequence with at least 50%, at least 60%, at least 70%, at least 80%, at least 85%, at least 90%, at least 95%, at least 97%, or at least 99% sequence identity to the amino acid sequence of SEQ ID NOs:182 or 184. In certain embodiments, the exogenous succinate exporter gene comprises the nucleotide sequence of SEQ ID NOs:181 or 183, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:181 or 183.

In certain embodiments, the genetically modified yeast cells provided herein comprise, in addition to an active succinate fermentation pathway, an active reduction pathway from glucose-6-phosphate to ribulose-5-phosphate. In certain embodiments, this pathway includes at least the following reactions 1) conversion of glucose 6-phosphate to 6-phosphogluconaolactone, 2) conversion of 6-phosphogluconaolactone to 6-phosphogluconate, and 3) conversion of 6-phosphogluconate to ribulose 5-phosphate. Each of the reactions in the active reduction pathway is catalyzed by one or more enzymes, which in turn are encoded by one or more exogenous or endogenous reduction pathway genes. In certain embodiments, all of the enzymes catalyzing reactions in the active reduction pathway are encoded by endogenous genes. In other embodiments, all of the enzymes catalyzing reactions in the active reduction pathway are encoded by exogenous genes. In still other embodiments, the enzymes catalyzing reactions in the active reduction pathway are encoded by a mix of endogenous and exogenous genes.

In certain embodiments, the genetically modified yeast cells provided herein comprise one or more endogenous genes encoding enzymes that catalyze various reactions in the active reduction pathway, and in certain of these embodiments the cells comprise one or more copies of endogenous glucose 6-phosphate dehydrogenase, gluconolactonase, and/or 6-phosphogluconate dehydrogenase genes. In certain of these embodiments, the endogenous genes are operatively linked to endogenous regulatory elements only. In other embodiments, one or more of the endogenous genes are operatively linked to one or more exogenous regulatory elements.

In certain embodiments, the genetically modified yeast cells provided herein comprise one or more exogenous genes encoding enzymes that catalyze various reactions in the active reduction pathway, and in certain of these embodiments the cells comprise one or more copies of exogenous glucose 6-phosphate dehydrogenase, gluconolactonase, and/or 6-phosphogluconate dehydrogenase genes. In certain of these embodiments, the exogenous genes are operatively linked to exogenous regulatory elements only. In other embodiments, one or more of the exogenous genes are operatively linked to one or more endogenous regulatory elements.

In certain embodiments, the genetically modified yeast cells provided herein comprise an endogenous and/or exogenous glucose 6-phosphate dehydrogenase gene. In certain of these embodiments where the cells comprise an exogenous glucose 6-phosphate dehydrogenase gene, the exogenous glucose 6-phosphate dehydrogenase gene is derived from a yeast source gene such as an *I. orientalis* source gene, and in certain of these embodiments the exogenous glucose 6-phosphate dehydrogenase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous glucose 6-phosphate dehydrogenase gene encodes a polypeptide that comprises the amino acid sequence of SEQ ID NO:34, or an amino acid sequence with at least 50%, at least 60%, at least 70%, at least 80%, at least 85%, at least 90%, at least 95%, at least 97%, or at least 99% sequence identity to the amino acid sequence of SEQ ID NO:34. In certain embodiments, the exogenous glucose 6-phosphate dehydrogenase gene comprises the nucleotide sequence of SEQ ID NO:33, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:33.

In certain embodiments, the genetically modified yeast cells provided herein comprise an endogenous and/or exogenous gluconolactonase gene. In certain of these embodiments where the cells comprise an exogenous gluconolactonase gene, the exogenous gluconolactonase gene is derived from a yeast source gene such as an *I. orientalis* source gene, and in certain of these embodiments the exogenous gluconolactonase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous gluconolactonase gene encodes a polypeptide that comprises the amino acid sequence of SEQ ID NO:36, or an amino acid sequence with at least 50%, at least 60%, at least 70%, at least 80%, at least 85%, at least 90%, at least 95%, at least 97%, or at least 99% sequence identity to the amino acid sequence of SEQ ID NO:36. In certain embodiments, the exogenous gluconolactonase gene comprises the nucleotide sequence of SEQ ID NO:35, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:35.

In certain embodiments, the genetically modified yeast cells provided herein comprise an endogenous and/or exogenous 6-phosphogluconate dehydrogenase gene. In certain of these embodiments where the cells comprise an exogenous 6-phosphogluconate dehydrogenase gene, the exogenous 6-phosphogluconate dehydrogenase gene is derived from a yeast source gene such as an *I. orientalis* source gene, and in certain of these embodiments the exogenous 6-phosphogluconate dehydrogenase gene encodes a polypeptide with at least 50%, at least 60%, at least 70%, at least 80%, at least 85%, at least 90%, at least 95%, at least 97%, or at least 99% sequence identity to a polypeptide encoded by the yeast source gene. In certain embodiments, the exogenous 6-phosphogluconate dehydrogenase gene encodes a polypeptide that comprises the amino acid sequence of SEQ ID NO:38, or an amino acid sequence with at least 50%, at least 60%, at least 70%, at least 80%, at least 85%, at least 90%, at least 95%, at least 97%, or at least 99% sequence identity to the amino acid sequence of SEQ ID NO:38. In certain embodiments, the exogenous 6-phosphogluconate dehydrogenase gene comprises the nucleotide sequence of SEQ ID NO:37, or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:37.

In certain embodiments, the genetically modified yeast cells provided herein comprise a deletion or disruption of one or more endogenous genes. In certain of these embodiments, the cells comprise a deletion or disruption of an endogenous pyruvate carboxykinase, malic enzyme, pyruvate decarboxylase, and/or succinate importer gene.

In certain embodiments, the genetically modified yeast cells are derived from host yeast cells that exhibit a relatively high degree of succinate resistance. In certain embodiments, the cells provided herein belong to the genus *Issatchenkia*, *Candida*, *Pichia*, *Zygosaccharomyces*, *Kluyveromyces*, *Saccharomyces*, *Debaryomyces*, or *Saccharomycopsis*, and in certain of these embodiments the cells belong to the *Pichia fermentans/I. orientalis* clade. In certain embodiments, the cells belong to the species *I. orientalis*, *Candida lambica*, *Candida sorboxylosa*, *Candida zemplinina*, *Candida geochares*, *Pichia membranifaciens*, *Zygosaccharomyces kombuchaensis*, *Candida sorbosivorans*, *K. marxianus*, *Candida vanderwaltii*, *Candida sorbophila*, *Zygosaccharomyces bisporus*, *Zygosaccharomyces lentus*, *Saccharomyces bayanus*, *Saccharomyces bulderi*, *Debaryomyces castellii*, *Candida boidinii*, *Candida etchellsii*, *Kluyveromyces lactis*, *Pichia jadinii*, *Pichia anomala*, or *Saccharomycopsis crataegensis*.

Provided herein in certain embodiments are methods of producing succinate by culturing the genetically modified yeast cells provided herein in the presence of at least one carbon source, then isolating the succinate from the culture. In certain embodiments, the carbon source is one or more of glucose, xylose, arabinose, sucrose, fructose, cellulose, glucose oligomers, and glycerol. Also provided herein are processes for converting succinate produced by the methods provided herein to a product such as poly-butylene succinate (PBS), other polymers, cosmetics, foodstuff, feed, or pharmaceuticals.

DETAILED DESCRIPTION

Figure 1:
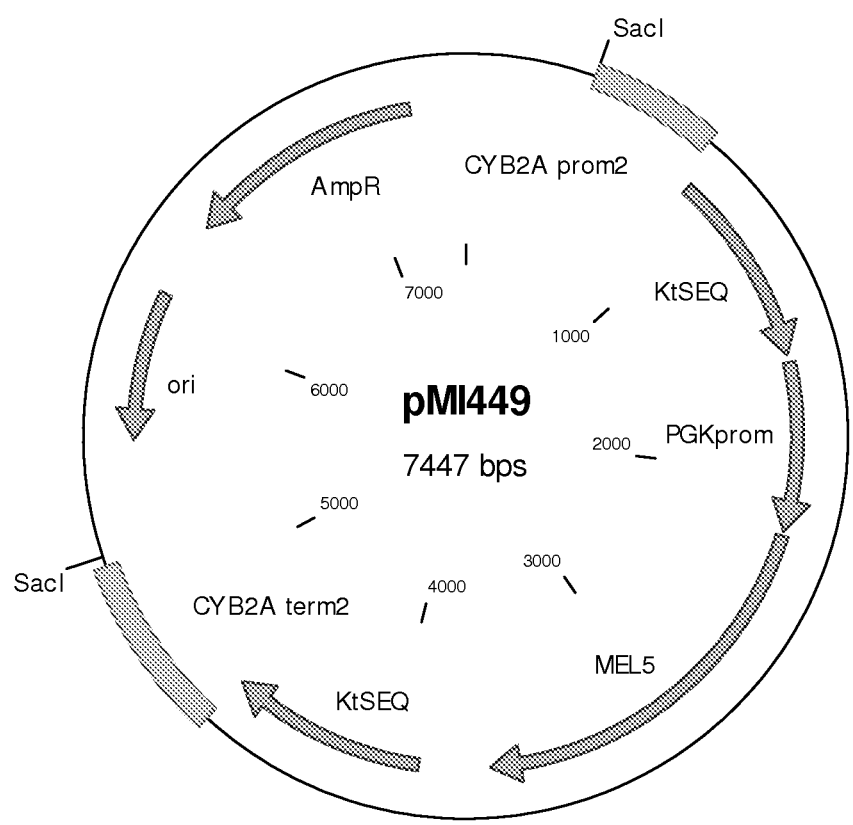
FIG. 1: pMI449, CYB2A deletion construct.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference in their entirety.

ABBREVIATIONS

α-KGDH, α-ketoglutarate dehydrogenase; CYB2, L-(+)-lactate:ferricytochrome c oxidoreductase; CYC, iso-2-cytochrome c; ENO1, enolase; FRD, fumarate reductase; FUM, fumarase; GAPDH, glyceraldehyde-3-phosphate dehydrogenase; GPD, glycerol 3-phosphate dehydrogenase; G6PD, glucose 6-phosphate dehydrogenase; IDH, isocitrate dehydrogenase; MAE, malic enzyme; MAE, malic anion exporter; MDH, malate dehydrogenase; OAA, oxaloacetate; OUR, oxygen uptake rate; PCK, phosphoenolpyruvate carboxykinase; PDC, pyruvate decarboxylase; PEP, phosphoenolpyruvate; 6PGDH, 6-phosphogluconate dehydrogenase; PGK, phosphoglycerate kinase; PFL, pyruvate formate lyase; PPC, phosphoenolpyruvate carboxylase; PYC, pyruvate carboxylase; RKI, ribose 5-phosphate ketol-isomerase; TAL, transaldolase; TCA, tricarboxylic acid; TEF, translation elongate factor; TKL, transketolase; URA3, orotidine 5'-phosphate decarboxylase; XDH, xylitol dehydrogenase; XR, xylose reductase; 6PGDH, 6-phosphogluconate dehydrogenase.

DESCRIPTION

Provided herein are genetically modified yeast cells for the production of succinate, methods of making these yeast cells, and methods of using these cells to produce succinate. "Succinate" as used herein includes salt and acid forms of succinate.

There are three primary fermentation pathways for producing succinate from a microorganism: reductive TCA, oxidative TCA, and glyoxylate shunt.

The reductive TCA pathway begins with carboxylation of the three carbon glycolytic intermediate phosphoenolpyruvate (PEP) or pyruvate to oxaloacetate (OAA) (by PEP carboxylase (PPC) and pyruvate carboxylase (PYC), respectively). OAA is converted to malate by malate dehydrogenase (MDH), malate is converted to fumarate by fumarase (FUM, also known as fumarate hydratase), and fumarate is converted to succinate by fumarate reductase (FRD). When written from the perspective of redox state, the net stoichiometry for this succinate production pathway is: 1 glucose $(C_6H_{12}O_6)+2\ CO_2+2\ (NADH+H^+)\rightarrow 2$ succinic acid $(C_4H_6O_4)+2H_2O+2\ NAD^+$. The reductive TCA pathway provides the highest succinate yield of the three succinate fermentation pathways, but it results in a net deficit in reducing power (NADH). This means that in isolation the pathway results in a redox imbalance. In order to provide redox balance, the reductive TCA pathway can be combined with one or both of the oxidative TCA or glyoxylate shunt pathways, or with one or more unrelated pathways that produce NADH or NADPH.

The oxidative TCA pathway begins with the conversion of OAA and acetyl-CoA to citrate by citrate synthase. OAA can be generated from carboxylation of PEP or pyruvate, while acetyl-CoA is generated from the decarboxylation of pyruvate by PDH or pyruvate formate lyase (PFL). Citrate is converted to isocitrate by aconitase, isocitrate is converted to α-ketoglutarate by isocitrate dehydrogenase (IDH), α-ketoglutarate is converted to succinyl-CoA by α-ketoglutarate dehydrogenase (α-KGDH), and succinyl-CoA is converted to succinate by succinyl coenzyme A synthetase (succinate thiokinase). The net stoichiometry for this succinate production pathway is: 1 glucose $(C_6H_{12}O_6)+2H_2O+5$ $NAD^+ \rightarrow 1$ succinic acid $(C_4H_6O_4)+2$ $CO_2+5$ $(NADH+H^+)$. This pathway has a lowest carbon yield of the three succinate fermentation pathways, but the highest yield of reducing power.

Like the oxidative TCA pathway, the glyoxylate shunt pathway begins with the generation of citrate from OAA and acetyl-CoA and the conversion of citrate to isocitrate. Isocitrate is converted to glyoxylate and succinate by isocitrate lyase. Glyoxylate is condensed with acetyl-CoA to form malate by malate synthase, and the resultant malate is converted to succinate via a fumarate intermediate. The net stoichiometry for this succinate production pathway is: 1 glucose $(C_6H_{12}O_6)+\frac{2}{3}H_2O+\frac{2}{3}NAD^+ \rightarrow 1\frac{2}{3}$ succinic acid $(C_4H_6O_4)+\frac{2}{3}CO_2+\frac{2}{3}(NADH+H^+)$.

Previous attempts to produce succinate from microorganisms at commercially viable levels have utilized bacterial fermentation hosts. These bacterial hosts are either native succinate producers or non-native succinate producers that have been genetically engineered to produce succinate. Examples of native succinate producers are *Actinobacillus succinogenes* (see, e.g., U.S. Pat. No. 5,504,004) and *M. succiniciproducens*, each of which primarily utilizes a reductive TCA pathway. *A. succinogenes* and *M. succiniciproducens* both produce relatively high titers of succinate, but they also produce various organic acid by-products. The presence of these by-products decreases yield and complicates succinate recovery. An example of a non-native succinate producer is *E. coli*. Although *E. coli* is capable of producing trace levels of succinate naturally, genetic modification is required to obtain useful titers. Significant efforts have been made previously to increase succinate yield in genetically modified *E. coli* by decreasing the formation of other organic acids and combining different succinate fermentation pathways. Although *E. coli* strains have been developed that produce fewer organic acid by-products, they still produce lower succinate titers than the native producers. In addition, *E. coli* requires aerobic conditions to grow, but produces succinic acid at high yields only under anaerobic conditions. This means that succinate production in *E. coli* requires a two-phase fermentation.

One drawback common to all of the bacterial hosts developed to date for succinate production is relatively poor performance in strongly acidic environments. However, allowing the low pH conditions to develop as organic acids are produced is preferred for commercial succinate production. The ideal host for commercial succinate production should produce high levels of succinate and relatively low levels of other organic acids, and should possess a high degree of pH resistance and the ability to both grow and ferment under anaerobic or substantially anaerobic conditions.

As disclosed herein, a set of yeast cells from various species were tested for succinate resistance. Cells exhibiting succinate resistance were further evaluated based on their growth rates and glucose consumption rates in media containing varying concentrations of succinate. Based on these experiments, a set of ideal host cells for succinate production were identified. These host cells were then genetically modified to contain an active succinate fermentation pathway, resulting in a set of genetically modified yeast cells that produce succinate under low pH conditions.

Provided herein in certain embodiments are genetically modified succinate-resistant yeast cells having at least one active succinate fermentation pathway from PEP or pyruvate to succinate. A yeast cell having an "active succinate fermentation pathway" as used herein produces active enzymes necessary to catalyze each reaction in a succinate fermentation pathway, and therefore is capable of producing succinate in measurable yields when cultured under fermentation conditions in the presence of at least one fermentable sugar. A yeast cell having an active succinate fermentation pathway comprises one or more succinate fermentation pathway genes. A "succinate fermentation pathway gene" as used herein refers to the coding region of a nucleotide sequence that encodes an enzyme involved in an active succinate fermentation pathway.

In certain embodiments, the yeast cells provided herein have a reductive TCA active succinate fermentation pathway that proceeds through PEP or pyruvate, OAA, malate, and fumarate intermediates. In these embodiments, the yeast cells comprise a set of succinate fermentation pathway genes comprising MDH, FUM, FRD, one or both of PPC and PYC genes, and, optionally, a succinate exporter gene.

In those embodiments where the yeast cells provided herein have a reductive TCA active succinate fermentation pathway, the cells may further have an active reduction pathway. An "active reduction pathway" as used herein produces NADH or NADPH from NAD or NADP, respectively, thereby helping to balance out redox imbalances generated by a reductive TCA pathway. A yeast cell having an active reduction pathway comprises one or more reduction pathway genes. A "reduction pathway gene" as used herein refers to the coding region of a nucleotide sequence that encodes an enzyme involved in an active reduction pathway.

In certain embodiments, the yeast cells provided herein have a pentose phosphate active reduction pathway that proceeds through glucose 6-phosphate, 6-phosphogluconaolactone, 6-phosphogluconate, and ribulose 5-phosphate intermediates. In these embodiments, the yeast cells comprise a set of reduction pathway genes comprising glucose 6-phosphate dehydrogenase (G6PD), gluconolactonase, and 6-phosphogluconate dehydrogenase (6PGDH) genes.

In certain embodiments, the yeast cells provided herein may have one or more active succinate fermentation pathways, or portions of such pathways, that are not reductive TCA active succinate fermentation pathways. In these embodiments, the other pathways or portions thereof may be present in addition to or in lieu of the reductive TCA pathway. For example, the cells may comprise a reductive TCA active succinate fermentation pathway and all or a part of an oxidative TCA or glyoxylate shunt active succinate fermentation pathway.

The succinate fermentation pathway and reduction pathway genes in the yeast cells provided herein may be endogenous or exogenous. "Endogenous" as used herein with regard to genetic components such as genes, promoters, and terminator sequences means that the genetic component is present at a particular location in the genome of a native form of a particular yeast cell. "Exogenous" as used herein with regard to genetic components means that the genetic component is not present at a particular location in the genome of a native form of a particular yeast cell. "Native" as used herein with regard to a yeast cell refers to a wild-type yeast cell of a particular yeast species. "Native" as used herein with regard to a metabolic pathway refers to a metabolic pathway that exists and is active in a native yeast cell.

An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous MDH gene that is identical to an endogenous MDH gene may be inserted into a yeast cell, resulting in a modified cell with a non-native (increased) number of MDH gene copies. Similarly, an exogenous PDC promoter that is identical to an endogenous PDC promoter can be inserted into a yeast cell such that it is operatively linked to an endogenous gene such as an MDH gene, resulting in altered expression of the endogenous gene. An exogenous genetic component with a non-native sequence comprises a sequence that is not found in the genome of a native cell. For example, an exogenous MDH gene from a particular species may be inserted into a yeast cell of another species. Similarly, an exogenous PDC promoter from a particular species may be inserted into a yeast cell of another species.

An exogenous gene is preferably integrated into the host cell genome in a functional manner, meaning that it is capable of producing an active protein in the host cell. However, in certain embodiments the exogenous gene may be introduced into the cell as part of a vector that is stably maintained in the host cytoplasm.

In certain embodiments, the genetically modified yeast cells provided herein comprise one or more exogenous succinate fermentation and/or reduction pathway genes. In certain embodiments, the yeast cells comprise a single exogenous gene. In other embodiments, the cells comprise multiple exogenous genes. In these embodiments, the yeast cells may comprise multiple copies of a single exogenous gene and/or copies of two or more different exogenous genes. Yeast cells comprising multiple exogenous genes may comprise any number of exogenous genes. For example, these yeast cells may comprise 1 to 20 exogenous genes, and in certain embodiments they may comprise 1 to 7 exogenous genes. Multiple copies of an exogenous gene may be integrated at a single locus such that they are adjacent to one another. Alternatively, they may be integrated at several loci within the host cell's genome.

In certain embodiments, the yeast cells provided herein comprise one or more endogenous succinate fermentation and/or reduction pathway genes. In certain of these embodiments, the cells may be engineered to overexpress one or more of these endogenous genes, meaning that the modified cells express the endogenous gene at a higher level than a native cell under at least some conditions. In certain of these embodiments, the endogenous gene being overexpressed may be operatively linked to one or more exogenous regulatory elements. For example, one or more native or non-native exogenous strong promoters may be introduced into a cell such that they are operatively linked to one or more endogenous succinate fermentation pathway genes.

In certain embodiments, the yeast cells provided herein comprise one or more endogenous succinate fermentation and/or reduction pathway genes and one or more exogenous succinate fermentation and/or reduction pathway genes. In these embodiments, the yeast cells may have an active succinate fermentation pathway that comprises one or more endogenous succinate fermentation pathway genes and one or more exogenous succinate fermentation pathway genes. For example, a yeast cell may comprise endogenous copies of PYC, MDH, and/or FUM genes and exogenous copies of FRD and/or PPC genes. In certain embodiments, the yeast cells may comprise both endogenous and exogenous copies of a single succinate fermentation pathway gene. For example, a yeast cell may comprise both endogenous and exogenous copies of an MDH gene.

Succinate fermentation and/or reduction pathway genes in the modified yeast cells provided herein may be operatively linked to one or more regulatory elements such as a promoter or terminator. As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 1000 bp, preferably within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety).

Regulatory elements linked to succinate fermentation and/or reduction pathway genes in the yeast cells provided herein may be endogenous or exogenous. For example, an endogenous succinate fermentation pathway gene may be operatively linked to only endogenous regulatory elements, or it may be linked to one or more exogenous regulatory elements. Endogenous genes operatively linked to one or more exogenous regulatory elements may exhibit higher expression levels than the same genes linked to only endogenous regulatory elements. Similarly, an exogenous succinate fermentation pathway gene may be inserted into a yeast cell such that it is operatively linked to endogenous regulatory elements only, or it may be linked to one or more exogenous regulatory elements. For example, an exogenous gene may be introduced into the cell as part of an exogenous gene expression construct that comprises one or more exogenous regulatory elements. In certain embodiments, exogenous regulatory elements, or at least the functional portions of exogenous regulatory elements, may comprise native sequences. In other embodiments, exogenous regulatory elements may comprise non-native sequences. In these embodiments, the exogenous regulatory elements may comprise a sequence with a relatively high degree of sequence identity to a native regulatory element. For example, an exogenous gene may be linked to an exogenous promoter or terminator having at least 50%, at least 60%, at least 70%, at least 80%, or at least 90% sequence identity to a native promoter or terminator. Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. For example, a sequence having an identity score of at least 90% using the BLAST version 2.2.1 algorithm with default parameters is considered to have at least 90% sequence identity. The BLAST software is available from the NCBI, Bethesda, Md. In those embodiments wherein multiple exogenous genes are inserted into a host cell, each exogenous gene may be under the control of a different regulatory element, or two or more exogenous genes may be under the control of the same regulatory elements. For example, where a first exogenous gene is linked to a first regulatory element, a second exogenous gene may also be linked to the first regulatory element, or it may be linked to a second regulatory element. The first and second regulatory elements may be identical or share a high degree of sequence identity, or they be wholly unrelated.

Examples of promoters that may be linked to one or more succinate fermentation and/or reduction pathway genes in the yeast cells provided herein include, but are not limited to, promoters for pyruvate decarboxylase (PDC1), phosphoglycerate kinase (PGK), xylose reductase (XR), xylitol dehydrogenase (XDH), L-(+)-lactate-cytochrome c oxidoreductase (CYB2), translation elongation factor-1 or -2 (TEF1, TEF2), enolase (ENO1), glyceraldehyde-3-phosphate dehydrogenase (GAPDH), and orotidine 5'-phosphate decarboxylase (URA3) genes. In these examples, the succinate fermentation and/or reduction pathway genes may be linked to endogenous or exogenous promoters for PDC1, PGK, XR, XDH, CYB2, TEF1, TEF2, ENO1, GAPDH, or URA3 genes. Where the promoters are exogenous, they may be identical to or share a high degree of sequence identity (i.e., at least about 80%, at least about 85%, at least about 90%, at least about 95%, or at least about 99%) with native promoters for PDC1, PGK, XR, XDH, CYB2, TEF1, TEF2, ENO1, GAPDH, or URA3 genes.

Examples of terminators that may be linked to one or more succinate fermentation and/or reduction pathway genes in the yeast cells provided herein include, but are not limited to, terminators for PDC1, XR, XDH, transaldolase (TAL), transketolase (TKL), ribose 5-phosphate ketolisomerase (RKI), CYB2, or iso-2-cytochrome c (CYC) genes or the galactose family of genes (especially the GAL10 terminator). In these examples, the succinate fermentation and/or reduction pathway genes may be linked to endogenous or exogenous terminators for PDC1, XR, XDH, TAL, TKL, RKI, CYB2, or CYC genes or galactose family genes. Where the terminators are exogenous, they may be identical to or share a high degree of sequence identity (i.e., at least about 80%, at least about 85%, at least about 90%, at least about 95%, or at least about 99%) with native terminators for PDC1, XR, XDH, TAL, TKL, RKI, CYB2, or CYC genes or galactose family genes. In certain embodiments, succinate fermentation and/or reduction pathway fermentation pathway genes are linked to a terminator that comprises a functional portion of a native GAL10 gene native to the host cell or a sequence that shares at least 80%, at least 85%, at least 90%, or at least 95% sequence identity with a native GAL10 terminator.

Exogenous genes may be inserted into a yeast host cell via any method known in the art. In preferred embodiments, the genes are integrated into the host cell genome. Exogenous genes may be integrated into the genome in a targeted or a random manner. In those embodiments where the gene is integrated in a targeted manner, it may be integrated into the loci for a particular gene, such that integration of the exogenous gene is coupled to deletion or disruption of a native gene. For example, introduction of an exogenous succinate fermentation pathway gene may be coupled to deletion or disruption of one or more genes encoding enzymes involved in other fermentation product pathways. Alternatively, the exogenous gene may be integrated into a portion of the genome that does not correspond to a gene.

Targeted integration and/or deletion may utilize an integration construct. The term "construct" as used herein refers to a DNA sequence that is used to transform a cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. Methods for transforming a yeast cell with an exogenous construct are described in, for example, WO99/14335, WO00/71738, WO02/42471, WO03/102201, WO03/102152, and WO03/049525. An integration construct can be assembled using two cloned target DNA sequences from an insertion site target. The two target DNA sequences may be contiguous or non-contiguous in the native host genome. In this context, "non-contiguous" means that the DNA sequences are not immediately adjacent to one another in the native genome, but are instead are separated by a region that is to be deleted. "Contiguous" sequences as used herein are directly adjacent to one another in the native genome. Where targeted integration is to be coupled to deletion or disruption of a target gene, the integration construct may also be referred to as a deletion construct. In a deletion construct, one of the target sequences may include a region 5' to the promoter of the target gene, all or a portion of the promoter region, all or a portion of the target gene coding sequence, or some combination thereof. The other target sequence may include a region 3' to the terminator of the target gene, all or a portion of the terminator region, and/or all or a portion of the target gene coding sequence. Where targeted integration is not to be coupled to deletion or disruption of a native gene, the target sequences are selected such that insertion of an intervening sequence will not disrupt native gene expression. An integration or deletion construct is prepared such that the two target sequences are oriented in the same direction in relation to one another as they natively appear in the genome of the host cell. Where an integration or deletion construct is used to introduce an exogenous gene into a host cell, a gene expression cassette is cloned into the construct between the two target gene sequences to allow for expression of the exogenous gene. The gene expression cassette contains the exogenous gene, and may further include one or more regulatory sequences such as promoters or terminators operatively linked to the exogenous gene. Deletion constructs can also be constructed that do not contain a gene expression cassette. Such constructs are designed to delete or disrupt a gene sequence without the insertion of an exogenous gene.

An integration or deletion construct may comprise one or more selection marker cassettes cloned into the construct between the two target DNA sequences. The selection marker cassette contains at least one selection marker gene that allows for selection of transformants. A "selection marker gene" is a gene that encodes a protein needed for the survival and/or growth of the transformed cell in a selective culture medium, and therefore can be used to apply selection pressure to the cell. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *K. marxianus* LEU2 gene), uracil (e.g., *K. marxianus, S. cerevisiae*, or *I. orientalis* URA3 gene), or tryptophan (e.g., *K. marxianus, S. cerevisiae*, or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiose) enzyme and confers the ability to grow on melibiose as the sole carbon source). Preferred selection markers include the URA3 gene, zeocin resistance gene, G418 resistance gene, MEL5 gene, and hygromycin resistance gene. Another preferred selection marker is a CYB2 gene cassette, provided that the host cell either natively lacks such a gene or that its native CYB2 gene(s) are first deleted or disrupted. A selection marker gene is operatively linked to one or more promoter and/or terminator sequences that are operable in the host cell. In certain embodiments, these promoter and/or terminator sequences are exogenous promoter and/or terminator sequences that are included in the selection marker cassette. Suitable promoters and terminators are as described above.

An integration or deletion construct is used to transform the host cell. Transformation may be accomplished using, for example, electroporation and/or chemical transformation (e.g., calcium chloride, lithium acetate-based, etc.) methods. Selection or screening based on the presence or absence of the selection marker may be performed to identify successful transformants. In successful transformants, a homologous recombination event at the locus of the target site results in the disruption or the deletion of the target site sequence. Where the construct targets a native gene for deletion or disruption, all or a portion of the native target gene, its promoter, and/or its terminator may be deleted during this recombination event. The expression cassette, selection marker cassette, and any other genetic material between the target sequences in the integration construct is inserted into the host genome at the locus corresponding to the target sequences. Analysis by PCR or Southern analysis can be performed to confirm that the desired insertion/deletion has taken place.

In some embodiments, cell transformation may be performed using DNA from two or more constructs, PCR products, or a combination thereof, rather than a single construct or PCR product. In these embodiments, the 3' end of one integration fragment overlaps with the 5' end of another integration fragment. In one example, one construct will contain the first sequence from the locus of the target sequence and a non-functional part of the marker gene cassette, while the other will contain the second sequence from the locus of the target sequence and a second non-functional part of the marker gene cassette. The parts of the marker gene cassette are selected such that they can be combined to form a complete cassette. The cell is transformed with these pieces simultaneously, resulting in the formation of a complete, functional marker or structural gene cassette. Successful transformants can be selected for on the basis of the characteristic imparted by the selection marker. In another example, the selection marker resides on one fragment but the target sequences are on separate fragments, so that the integration fragments have a high probability of integrating at the site of interest. In other embodiments, transformation from three linear DNAs can be used to integrate exogenous genetic material. In these embodiments, one fragment overlaps on the 5' end with a second fragment and on the 3' end with a third fragment.

An integration or deletion construct may be designed such that the selection marker gene and some or all of its regulatory elements can become spontaneously deleted as a result of a subsequent homologous recombination event. A convenient way of accomplishing this is to design the construct such that the selection marker gene and/or regulatory elements are flanked by repeat sequences. Repeat sequences are identical DNA sequences, native or non-native to the host cell, and oriented on the construct in the same direction with respect to one another. The repeat sequences are advantageously about 25 to 1500 bp in length, and do not have to encode for anything. Inclusion of the repeat sequences permits a homologous recombination event to occur, which results in deletion of the selection marker gene and one of the repeat sequences. Since homologous recombination occurs with relatively low frequency, it may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene. In certain cases, expression of a recombinase enzyme may enhance recombination between the repeated sites.

An exogenous succinate fermentation or reduction pathway gene in the modified yeast cells provided herein may be derived from a source gene from any suitable source organism. For example, an exogenous gene may be derived from a yeast, fungal, bacterial, plant, insect, or mammalian source. As used herein, an exogenous gene that is "derived from" a source gene encodes a polypeptide that 1) is identical to a polypeptide encoded by the source gene, 2) shares at least 50%, at least 60%, at least 70%, at least 80%, at least 85%, at least 90%, at least 95%, at least 97%, or at least 99% sequence identity with a polypeptide encoded by the source gene, and/or 3) has the same function in a succinate fermentation or reduction pathway as the polypeptide encoded by the source gene. For example, a FUM gene that is derived from an *I. orientalis* FUM gene may encode a polypeptide comprising the amino acid sequence of SEQ ID NO:2, a polypeptide with at least 50%, at least 60%, at least 70%, at least 80%, at least 85%, at least 90%, at least 95%, at least 97%, or at least 99% sequence identity to the amino acid sequence of SEQ ID NO:2, and/or a polypeptide that has the ability to catalyze the conversion of malate to fumarate. A gene derived from a source gene may comprise a nucleotide sequence with at least 50%, at least 60%, at least 70%, at least 80%, at least 85%, at least 90%, at least 95%, at least 97%, or at least 99% sequence identity to the coding region of the source gene. In certain embodiments, a gene derived from a source gene may comprise a nucleotide sequence that is identical to the coding region of the source gene. For example, a FUM gene that is derived from an *I. orientalis* FUM gene may comprise the nucleotide sequence of SEQ ID NO:1 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:1.

In certain embodiments of the modified yeast cells provided herein, an exogenous succinate fermentation or reduction pathway gene may be derived from the host yeast species. For example, where the host cell is *I. orientalis*, an exogenous gene may be derived from a native *I. orientalis* gene. In these embodiments, the exogenous gene may comprise a nucleotide sequence identical to the coding region of the native gene, such that incorporation of the exogenous gene into the host cell increases the copy number of a native gene sequence and/or changes the regulation or expression level of the gene if under the control of a promoter that is different from the promoter that drives expression of the gene in a wild-type cell. In other embodiments, the exogenous gene may comprise a nucleotide sequence that differs from the coding region of a native gene, but nonetheless encodes a polypeptide that is identical to the polypeptide encoded by the native gene. In still other embodiments, the exogenous gene may comprise a nucleotide sequence that encodes a polypeptide with at least 50%, at least 60%, at least 70%, at least 80%, at least 85%, at least 90%, at least 95%, at least 97%, or at least 99% sequence identity to a polypeptide encoded by one or more native genes. In certain of these embodiments, the exogenous gene comprises a nucleotide sequence with at least 50%, at least 60%, at least 70%, at least 80%, at least 85%, at least 90%, at least 95%, at least 97%, or at least 99% sequence identity to the coding region of one or more native genes. In still other embodiments, the exogenous gene may encode a polypeptide that has less than 50% sequence identity to a polypeptide encoded by a native gene, but which nonetheless has the same function as the native polypeptide in a succinate fermentation or reduction pathway (i.e., the ability to catalyze the same reaction between reaction intermediates).

In other embodiments, an exogenous succinate fermentation or reduction pathway gene may be derived from a species that is different than that of the host yeast cell. In certain of these embodiments, the exogenous gene may be derived from a different yeast species than the host cell. For example, where the host cell is *I. orientalis*, the exogenous gene may be derived from *S. cerevisiae*. In other embodiments, the exogenous gene may be derived from a fungal, bacterial, plant, insect, or mammalian source. For example, where the host cell is *I. orientalis*, the exogenous gene may be derived from a bacterial source such as *E. coli*. In those embodiments where the exogenous gene is derived from a non-yeast source, the exogenous gene sequence may be codon optimized for expression in a yeast host cell.

In those embodiments where the exogenous succinate fermentation or reduction pathway gene is derived from a species other than the host cell species, the exogenous gene may encode a polypeptide identical to a polypeptide encoded by a native gene from the source organism. In certain of these embodiments, the exogenous gene may be identical to a native gene from the source organism. In other embodiments, the exogenous gene may share at least 50%, at least 60%, at least 70%, at least 80%, at least 85%, at least 90%, at least 95%, at least 97%, or at least 99% sequence identity to the coding region of a native gene from the source organism. In other embodiments, the exogenous gene may encode a polypeptide that shares at least 50%, at least 60%, at least 70%, at least 80%, at least 85%, at least 90%, at least 95%, at least 97%, or at least 99% sequence identity with a polypeptide encoded by a native gene from the source organism. In certain of these embodiments, the exogenous gene may comprise a nucleotide sequence with at least 50%, at least 60%, at least 70%, at least 80%, at least 85%, at least 90%, at least 95%, at least 97%, or at least 99% sequence identity to the coding region of one or more native genes from the source organism. In still other embodiments, the exogenous gene may encode a polypeptide that has less than 50% sequence identity to a polypeptide encoded by a native gene from the source organism, but which nonetheless has the same function as the native polypeptide from the source organism in an active succinate fermentation or active reduction pathway. An exogenous source gene may be subjected to mutagenesis if necessary to provide a coding sequence starting with the usual eukaryotic starting codon (ATG), or for other purposes.

In certain embodiments, the genetically modified yeast cells provided herein have a reductive TCA active succinate fermentation pathway that proceeds via PEP or pyruvate, OAA, malate, and fumarate intermediates. In these embodiments, the cells comprise one or more succinate fermentation pathway genes encoding enzymes selected from the group consisting PPC, PYC, MDH, FUM, FRD, and/or succinate exporter genes. In certain embodiments, the cells also have one or more active reduction pathways. In these embodiments, the cells comprise one or more reduction pathway genes encoding enzymes selected from the group consisting of G6PD, gluconolactonase, and 6PGDH. In certain embodiments, the cells may comprise all or part of an active oxidative TCA or glyoxylate shunt succinate fermentation pathway. In these embodiments, the cells comprise one or more genes encoding enzymes selected from the group consisting of citrate synthase, PDH, PFL, aconitase, IDH, α-KGDH, succinate thiokinase, isocitrate lyase, and malate synthase. In certain embodiments, the cells have reduced activity of endogenous succinate dehydrogenase (SDH), which catalyzes the back-reaction of succinate to fumarate.

A "PEP carboxylase gene" or "PPC gene" as used herein refers to any gene that encodes a polypeptide with PEP carboxylase activity, meaning the ability to catalyze the conversion of PEP to OAA. In certain embodiments, a PPC gene may be derived from a bacterial source. For example, a PPC gene may be derived from an *E. coli* PPC gene encoding the amino acid sequence set forth in SEQ ID NO:4 or a *M. succiniciproducens* PPC gene encoding the amino acid sequence set forth in SEQ ID NO:6. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:4 or 6. In certain embodiments, a bacterial-derived PPC gene may comprise the nucleotide sequence set forth in SEQ ID NOs:3 or 5, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:3 or 5. In other embodiments, a PPC gene may be derived from a plant source.

A "pyruvate carboxylase gene" or "PYC gene" as used herein refers to any gene that encodes a polypeptide with pyruvate carboxylase activity, meaning the ability to catalyze the conversion of pyruvate to OAA. In certain embodiments, a PYC gene may be derived from a yeast source. For example, the PYC gene may be derived from an *I. orientalis* PYC gene encoding the amino acid sequence set forth in SEQ ID NO:8, an *S. cerevisiae* PYC1 gene encoding the amino acid sequence set forth in SEQ ID NO:10, or a *K. marxianus* PYC1 gene encoding the amino acid sequence set forth in SEQ ID NO:12. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:8, 10, or 12. In certain embodiments, a yeast-derived PYC gene may comprise the nucleotide sequence set forth in SEQ ID NOs:7, 9, or 11, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:7, 9, or 11. In other embodiments, a PYC gene may be derived from a fungal source other than *R. oryzae*.

A "malate dehydrogenase gene" or "MDH gene" as used herein refers to any gene that encodes a polypeptide with malate dehydrogenase activity, meaning the ability to catalyze the conversion of OAA to malate. In certain embodiments, an MDH gene may be derived from a yeast source. For example, the MDH gene may be derived from an *I. orientalis* MDH1, MDH2, or MDH3 gene encoding the amino acid sequence set forth in SEQ ID NOs:14, 16, or 18, respectively, a *Z. rouxii* MDH gene encoding the amino acid sequence set forth in SEQ ID NO:168, or a *K. marxianus* MDH1, MDH2, or MDH3 gene encoding the amino acid sequence set forth in SEQ ID NOs:20, 22, or 24, respectively. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:14, 16, 18, 168, 20, 22, or 24. In certain embodiments, a yeast-derived MDH gene may comprise the nucleotide sequence set forth in SEQ ID NOs:13, 15, 17, 167, 19, 21, or 23 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:13, 15, 17, 167, 19, 21, or 23. In certain embodiments, an MDH gene may be derived from a bacterial source. For example, the MDH gene may be derived from an *E. coli* MDH gene encoding the amino acid sequence set forth in SEQ ID NO:170. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:170. In certain embodiments, a bacterial-derived MDH gene may comprise the nucleotide sequence set forth in SEQ ID NO:169 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:169. In certain embodiments, an MDH gene may be derived from a fungal source. For example, the MDH gene may be derived from an *R. oryzae* MDH gene encoding the amino acid sequence set forth in SEQ ID NO:172. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:172. In certain embodiments, a fungal-derived MDH gene may comprise the nucleotide sequence set forth in SEQ ID NO:171 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:171.

A "fumarase gene" or "FUM gene" as used herein refers to any gene that encodes a polypeptide with fumarase activity, meaning the ability to catalyze the conversion of malate to fumarate. In certain embodiments, a FUM gene may be derived from a yeast source. For example, the FUM gene may be derived from an *I. orientalis* FUM gene encoding the amino acid sequence set forth in SEQ ID NO:2. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:2. In certain embodiments, a yeast-derived FUM gene may comprise the nucleotide sequence set forth in SEQ ID NO:1 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:1. In other embodiments, a FUM gene may be derived from a bacterial source outside of the *Mannheimia* genus.

A "fumarate reductase gene" or "FRD gene" as used herein refers to any gene that encodes a polypeptide with fumarate reductase activity, meaning the ability to catalyze the conversion of fumarate to succinate. In certain embodiments, an FRD gene may be derived from a yeast source. For example, the FRD gene may be derived from an *S. cerevisiae* FRD1 gene encoding the amino acid sequence set forth in SEQ ID NO:26, a *S. mikatae* FRD1 gene encoding the amino acid sequence set forth in SEQ ID NO:28, a *K. polyspora* FRD1 gene encoding the amino acid sequence set forth in SEQ ID NO:30, or a *K. marxianus* FRD1 gene encoding the amino acid sequence set forth in SEQ ID NO:32. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:26, 28, 30, or 32. In certain embodiments, a yeast-derived FRD gene may comprise the nucleotide sequence set forth in SEQ ID NOs:25, 27, 29, or 31, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:25, 27, 29, or 31. In certain embodiments, an FRD gene may be derived from protozoan source. For example, the FRD gene may be derived from a *T. brucei* FRD gene encoding the amino acid sequence set forth in SEQ ID NO:174, a *T. cruzi* FRD gene encoding the amino acid sequence set forth in SEQ ID NO:176, a *L. braziliensis* FRD gene encoding the amino acid sequence set forth in SEQ ID NO:178, or a *L. mexicana* FRD gene encoding the amino acid sequence set forth in SEQ ID NO:180. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:174, 176, 178, or 180. In certain embodiments, a protozoan-derived FRD gene may comprise the nucleotide sequence set forth in SEQ ID NOs:173, 175, 177, or 179, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:173, 175, 177, or 179.

A "succinate exporter gene" as used herein refers to any gene that encodes a polypeptide with succinate export activity, meaning the ability to transport succinate out of a cell and into the extracellular environment. In certain embodiments, a succinate exporter gene may be derived from a fungal source. For example, the succinate exporter gene may be derived from a *S. pombe* malic anion exporter (MAE) gene encoding the amino acid sequence set forth in SEQ ID NO:182 or an *A. oryzae* malic anion transporter encoding the amino acid sequence set forth in SEQ ID NO:184. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:182 or 184. In certain embodiments, a fungal-derived succinate exporter gene may comprise the nucleotide sequence set forth in SEQ ID NOs:181 or 183, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:181 or 183.

A "glucose 6-phosphate dehydrogenase" or "G6PD gene" as used herein refers to any gene that encodes a polypeptide with glucose 6-phosphate dehydrogenase activity, meaning the ability to catalyze the conversion of glucose 6-phosphate to 6-phosphogluconolactone. In certain embodiments, a G6PD gene may be derived from a yeast source. For example, the G6PD gene may be derived from an *I. orientalis* G6PD gene (ZWF1) encoding the amino acid sequence set forth in SEQ ID NO:34. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:34. In certain embodiments, a yeast-derived G6PD gene may comprise the nucleotide sequence set forth in SEQ ID NO:33 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:33.

A "gluconolactonase gene" as used herein refers to any gene that encodes a polypeptide with gluconolactonase activity, meaning the ability to catalyze the conversion of 6-phosphogluconolactone to 6-phosphogluconate. In certain embodiments, a gluconolactonase gene may be derived from a yeast source. For example, the gluconolactonase gene may be derived from an *I. orientalis* gluconolactonase gene encoding the amino acid sequence set forth in SEQ ID NO:36. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:36. In certain embodiments, a yeast-derived gluconolactonase gene may comprise the nucleotide sequence set forth in SEQ ID NO:35 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:35.

A "6-phosphogluconate dehydrogenase gene" or "6PGDH gene" as used herein refers to any gene that encodes a polypeptide with 6-phosphogluconate dehydrogenase activity, meaning the ability to catalyze the conversion of 6-phosphogluconate to ribulose-5-phosphate. In certain embodiments, a 6PGDH gene may be derived from a yeast source. For example, the 6PGDH gene may be derived from an *I. orientalis* 6PGDH gene encoding the amino acid sequence set forth in SEQ ID NO:38. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:38. In certain embodiments, a yeast-derived 6PGDH gene may comprise the nucleotide sequence set forth in SEQ ID NO:37 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:37.

In certain embodiments, the genetically modified yeast cells provided herein further comprise a deletion or disruption of one or more native genes. "Deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. "Deletion or disruption" with regard to a metabolic pathway means that the pathway is either inoperative or else exhibits activity that is reduced by at least 75%, at least 85%, or at least 95% relative to the native pathway. In certain embodiments, deletion or disruption of a native metabolic pathway is accomplished by incorporating one or more genetic modifications that result in decreased expression of one or more native genes that reduce succinate production.

In certain embodiments, deletion or disruption of native gene can be accomplished by forced evolution, mutagenesis, or genetic engineering methods, followed by appropriate selection or screening to identify the desired mutants. In certain embodiments, deletion or disruption of a native host cell gene may be coupled to the incorporation of one or more exogenous genes into the host cell, i.e., the exogenous genes may be incorporated using a gene expression integration construct that is also a deletion construct. In other embodiments, deletion or disruption may be accomplished using a deletion construct that does not contain an exogenous gene or by other methods known in the art.

In certain embodiments, the modified yeast cells provided herein comprise a deletion or disruption of one or more native genes encoding an enzyme involved in ethanol fermentation or consumption, including for example pyruvate decarboxylase (PDC, catalyzes the conversion of pyruvate to acetaldehyde) and/or alcohol dehydrogenase 1 (ADH1, catalyzes the conversion of acetaldehyde to ethanol) or 2 (ADH2, catalyzes the conversion of ethanol to acetaldehyde). Such modifications decrease the ability of the yeast cell to produce ethanol, thereby maximizing succinate production. In certain embodiments wherein the modified yeast cell is *I. orientalis*, the cells comprise a deletion or disruption of a PDC gene encoding the amino acid sequence of SEQ ID NO:40, an ADHa gene encoding the amino acid sequence of SEQ ID NO:42, and/or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs:40 or 42. In certain of these embodiments, the deleted or disrupted gene may comprise the nucleotide sequence of SEQ ID NOs:39 or 41, or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:39 or 41.

In certain embodiments, the modified yeast cells provided herein comprise a deletion or disruption of one or more native genes encoding an enzyme involved in producing alternate fermentative products such as glycerol or other by-products such as acetate or diols, including for example glycerol 3-phosphate dehydrogenase (GPD, catalyzes the conversion of dihydroxyacetone phosphate to glycerol 3-phosphate). In certain embodiments wherein the modified yeast cell is *I. orientalis*, the cells comprise a deletion or disruption of a GPD gene encoding the amino acid sequence of SEQ ID NO:44 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:44. In certain of these embodiments, the deleted or disrupted GPD gene may comprise the nucleotide sequence of SEQ ID NO:43 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:43.

In certain embodiments, the modified yeast cells provided herein comprise a deletion or disruption of one or more native genes encoding an enzyme that catalyzes a reverse reaction in a succinate fermentation pathway. For example, in certain embodiments the modified yeast cells provided herein comprise a deletion or disruption of a native PEP carboxykinase (PCK) gene, which encodes an enzyme that converts OAA to PEP. In certain embodiments wherein the modified yeast cell is *I. orientalis*, the cells comprise a deletion or disruption of a PCK gene encoding the amino acid sequence of SEQ ID NO:46 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:46. In certain of these embodiments, the deleted or disrupted PCK gene may comprise the nucleotide sequence of SEQ ID NO:45 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:45. In another example, the modified yeast cells provided herein comprise a deletion or disruption of a native malic enzyme (MAE) gene, which encodes an enzyme that converts malate to pyruvate. In certain embodiments wherein the modified yeast cell is *I. orientalis*, the cells comprise a deletion or disruption of an MAE gene encoding the amino acid sequence of SEQ ID NO:48 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:48. In certain of these embodiments, the deleted or disrupted MAE gene may comprise the nucleotide sequence of SEQ ID NO:47 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:47. In another example, the modified yeast cells provided herein comprise a deletion or disruption of a native succinate importer gene, which as used herein refers to any gene that encodes a polypeptide that allows for growth on and consumption of succinate. In certain embodiments wherein the modified yeast cell is *I. orientalis*, the cells comprise a deletion or disruption of a succinate importer gene RIOR43690 encoding the amino acid sequence of SEQ ID NO:186 or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO:186. In certain of these embodiments, the deleted or disrupted RIOR43690 gene may comprise the nucleotide sequence of SEQ ID NO:185 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:185.

In certain embodiments, the genetically modified yeast cells provided herein comprise a deletion or disruption of one or more native genes encoding an enzyme involved in an undesirable reaction with a succinate fermentation pathway product or intermediate.

In certain embodiments, the genetically modified yeast cells provided herein comprise a deletion or disruption of one or more native genes encoding an enzyme that has a neutral effect on a succinate fermentation pathway, including for example native genes encoding an enzyme selected from the group consisting of ammonia transport outward (ATO), L-lactate cytochrome-c oxidoreductase (CYB2A or CYB2B, catalyzes the conversion of lactate to pyruvate), and alcohol dehydrogenase (ADHa or ADHb, catalyzes the conversion between acetaldehyde and ethanol). Deletion or disruption of neutral genes allows for insertion of one or more exogenous genes without affecting succinate fermentation pathways. In certain embodiments wherein the modified yeast cell is *I. orientalis*, the cells comprise a deletion or disruption of a CYB2A gene encoding the amino acid sequence of SEQ ID NO:50, a CYB2B gene encoding the amino acid sequence of SEQ ID NO:52, an ATO2 gene encoding the amino acid sequence of SEQ ID NO:54 an ADHb gene encoding the amino acid sequence of SEQ ID NO:217, and/or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NOs:50, 52, 54, or 217. In certain of these embodiments, the deleted or disrupted gene may comprise the nucleotide sequence of SEQ ID NOs:49, 51, 53, or 216 or a nucleotide sequence with at least 50%, at least 60%, at least 70%, at least 80%, at least 85%, at least 90%, at least 95%, at least 97%, or at least 99% sequence identity to the nucleotide sequence of SEQ ID NOs:49, 51, 53, or 216.

In certain embodiments, the genetically modified yeast cells provided herein are succinate resistant yeast cells. A "succinate-resistant yeast cell" as used herein refers to a yeast cell that exhibits a growth rate in media containing 75 g/L or greater succinate at pH 2.8 that is at least 50% as high as its growth rate in the same media containing 0 g/L succinate (see, e.g., the cells disclosed in Example 1 below). In certain of these embodiments, the yeast cells may exhibit succinate resistance in their native form. In other embodiments, the cells may have undergone mutation and/or selection before, during, or after introduction of genetic modifications related to an active succinate fermentation pathway, such that the mutated and/or selected cells possess a higher degree of resistance to succinate than wild-type cells of the same species. In certain embodiments, mutation and/or selection may be carried out on cells that exhibit succinate resistance in their native form. Cells that have undergone mutation and/or selection may be tested for sugar consumption and other characteristics in the presence of varying levels of succinate in order to determine their potential as industrial hosts for succinate production. In addition to succinate resistance, the yeast cells provided herein may have undergone mutation and/or selection for resistance to one or more additional organic acids or to other fermentation products, by-products, or media components.

Selection for resistance to succinate or other compounds may be accomplished using methods well known in the art. For example, selection may be carried out using a chemostat. A chemostat is a device that allows for a continuous culture of microorganisms (e.g., yeast) wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., decreasing the concentration of a secondary carbon source necessary to the growth of the inoculum strain, among others), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture. The operation of chemostats and their use in the directed evolution of microorganisms is well known in the art (see, e.g., Novick Proc Natl Acad Sci USA 36:708-719 (1950), Harder J Appl Bacteriol 43:1-24 (1977).

As disclosed herein, yeast strains exhibiting succinate resistance were identified based on their growth rate and glucose consumption rates in succinate containing media. One such succinate resistant strain was *I. orientalis* strain CD1822. Strain CD1822 was generated by evolving *I. orientalis* ATCC PTA-6658 for 91 days in a glucose limited chemostat. The system was fed with 15 g/L glucose in a DM medium, and operated at a dilution rate of 0.06 $h^{-1}$ at pH=3 with added lactic acid in the feed medium. The conditions were maintained with a low oxygen transfer rate of approximately 2 mmol $L^{-1}h^{-1}$, and dissolved oxygen concentration remained constant at 0% of air saturation. Single colony isolates from the final time point were characterized in two shake flask assays. In the first assay, the strains were characterized for their ability to ferment glucose to ethanol in the presence of 25 g/L total lactic acid with no pH adjustment in the DM defined medium. In the second assay, the growth rate of the isolates were measured in the presence of 25, 32 and 45 g/L of total lactic, with no pH adjustment in DM defined medium. Strain CD1822 was a single isolate selected based on the measured fermentation rates and growth rates.

Yeast strains exhibiting the best combinations of growth and glucose consumption in succinate media as disclosed in the examples below are preferred host cells for various genetic modifications relating to succinate fermentation pathways. Yeast genera that possess the potential for a high degree of succinate resistance, as indicated by growth in the presence of 150 g/L succinate at a pH of 2.8, include for example *Issatchenkia* and *Candida*. Other yeast genera with the potential for a relatively high degree of succinate resistance, as indicated by growth in the presence of 100 g/L succinate, include for example *Pichia, Zygosaccharomyces, Kluyveromyces, Saccharomyces, Debaryomyces*, and *Saccharomycopsis*. Species exhibiting a high degree of succinate resistance included *I. orientalis* (also known as *Candida krusei*), *C. lambica* (also known as *Pichia fermentans*), *C. sorboxylosa, C. zemplinina, C. geochares, P. membranifaciens, Z. kombuchaensis, C. sorbosivorans, K. marxianus, C. vanderwaltii, C. sorbophila, Z. bisporus, Z. lentus, S. bayanus, S. bulderi, D. castellii, C. boidinii, C. etchellsii, K. lactis, P. jadinii, P. anomala*, and *S. crataegensis*. *I. orientalis* and *C. lambica* belong to the *I. orientalis/P. fermentans* clade. Specific strains exhibiting succinate resistance included *I. orientalis* strains PTA-6658, 60585, and 24210, *C. lambica* strain 38617, and *C. sorboxylosa* strain 24120.

Other wild-type yeast or fungi may be tested in a similar manner and identified to have acceptable levels of growth and glucose utilization in the presence of high levels of succinate as described herein. For example, Gross and Robbins (Hydrobiologia 433(103):91-109) have compiled a list of 81 fungal species identified in low pH (<4) environments that could be relevant to test as potential production hosts.

In certain embodiments, the modified yeast cells provided herein are generated by incorporating one or more genetic modifications into a Crabtree-negative host yeast cell. In certain of these embodiments the host yeast cell belongs to the genus *Issatchenkia* or *Candida*, and in certain of these embodiments the host cell belongs to the *I. orientalis/P. fermentans* clade. In certain of embodiments, the host cell is *I. orientalis* or *C. lambica*.

The *I. orientalis/P. fermentans* clade is the most terminal clade that contains at least the species *I. orientalis, Pichia galeiformis, Pichia* sp. YB-4149 (NRRL designation), *Candida ethanolica, Pichia deserticola, P. membranifaciens*, and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," Antonie van Leeuwenhoek 73:331-371, 1998, incorporated herein by reference (see especially p. 349). Analysis of the variable D1/D2 domain of the 26S ribosomal DNA from hundreds of ascomycetes has revealed that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA and comparing to that of other members of the clade and closely related species outside of the clade, using Kurtzman and Robnett's methods.

In certain embodiments, the genetically modified yeast cells provided herein belong to the genus *Issatchenkia*, and in certain of these embodiments the yeast cells are *I. orientalis*. When first characterized, the species *I orientalis* was assigned the name *Pichia kudriavzevii*. The anamorph (asexual form) of *I. orientalis* is known as *C. krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)).

The ideal yeast cell for succinate production is ideally capable of conducting fermentation at low pH levels. The ability to conduct fermentation at a low pH decreases downstream recovery costs, resulting in more economical production. Therefore, in certain embodiments the yeast host cell is capable of conducting fermentation at low pH levels.

A suitable host cell may possess one or more favorable characteristics in addition to succinate resistance and/or low pH growth capability. For example, potential host cells exhibiting succinate resistance may be further selected based on glycolytic rates, specific growth rates, thermotolerance, tolerance to biomass hydrolysate inhibitors, overall process robustness, and so on. These criteria may be evaluated prior to any genetic modification relating to a succinate fermentation or reduction pathway, or they may be evaluated after one or more such modifications have taken place.

The level of gene expression and/or the number of exogenous genes to be utilized in a given cell will vary depending upon the identity of the host cell. For fully genome-sequenced yeasts, whole-genome stoichiometric models may be used to determine which enzymes should be expressed to develop a desired pathway succinate fermentation pathway. Whole-genome stoichiometric models are described in, for example, Hjersted Biotechnol Bioeng 97:1190 (2007) and Famili Proc Natl Acad Sci USA 100:13134 (2003).

For yeasts without a known genome sequence, sequences for genes of interest (either as overexpression candidates or as insertion sites) can typically be obtained using techniques known in the art. Routine experimental design can be employed to test expression of various genes and activity of various enzymes, including genes and enzymes that function in a succinate fermentation or reduction pathway. Experiments may be conducted in which each enzyme is expressed in the yeast individually and in blocks of enzymes up to and including preferably all pathway enzymes, to establish which are needed (or desired) for improved succinate production. One illustrative experimental design tests expression of each individual enzyme as well as of each unique pair of enzymes, and further can test expression of all required enzymes, or each unique combination of enzymes. A number of approaches can be taken, as will be appreciated.

In certain embodiments, methods are provided for producing succinate from a genetically modified yeast cell as provided herein. In certain embodiments, these methods comprise providing a modified yeast cell as provided herein with at least one carbon source and culturing the yeast cell such that succinate is produced. The carbon source may be any carbon source that can be fermented by the yeast cell. Examples include, but are not limited to, twelve carbon sugars such as sucrose, hexose sugars such as glucose or fructose, glycan, starch, or other polymer of glucose, glucose oligomers such as maltose, maltotriose and isomaltotriose, panose, and fructose oligomers, and pentose sugars such as xylose, xylan, other oligomers of xylose, or arabinose. In certain embodiments, more than one type of genetically modified yeast cell may be present in the culture. Likewise, in certain embodiments one or more native yeast cells of the same or a different species than the genetically modified yeast cell may be present in the culture.

In certain embodiments, culturing of the cells provided herein to produce succinate may be divided up into phases. For example, the cell culture process may be divided into a cultivation phase, a production phase, and a recovery phase. The following represent examples of specific conditions that may be used for each of these phases. One of ordinary skill in the art will recognize that these conditions may be varied based on factors such as the species of yeast being used, the desired yield, or other factors.

The medium will typically contain nutrients as required by the particular cell, including a source of nitrogen (such as amino acids, proteins, inorganic nitrogen sources such as ammonia or ammonium salts, and the like), and various vitamins, minerals and the like. In some embodiments, the cells of the invention can be cultured in a chemically defined medium. In one example, the medium is a DM medium containing around 5 g/L ammonium sulfate, around 3 g/L potassium dihydrogen phosphate, around 0.5 g/L magnesium sulfate, trace elements, vitamins and around 150 g/L glucose. The pH is adjusted may be allowed to range freely during cultivation, or may be buffered if necessary to prevent the pH from falling below or rising above predetermined levels. For example, the medium may be buffered to prevent the pH of the solution from falling below around 2.0 or rising above around 8.0 during cultivation. In certain of these embodiments, the medium may be buffered to prevent the pH of the solution from falling below around 3.0 or rising above around 7.0, and in certain of these embodiments the medium may be buffered to prevent the pH of the solution from falling below around 4.0 or rising above around 6.0. In certain embodiments, the fermentation medium is inoculated with sufficient yeast cells that are the subject of the evaluation to produce an $OD_{600}$ of 1.0. Unless explicitly noted otherwise, $OD_{600}$ as used herein refers to an optical density measured at a wavelength of 600 nm with a 1 cm pathlength using a model DU600 spectrophotometer (Beckman Coulter). The cultivation temperature may range from around 25-50° C., and the cultivation time may be up to around 120 hours. During cultivation, aeration and agitation conditions are selected to produce a desired oxygen uptake rate. In one example, conditions are selected to produce an oxygen uptake rate of around 2-25 mmol/L/hr, preferably from around 5-20 mmol/L/hr, and more preferably from around 8-15 mmol/L/hr. "Oxygen uptake rate" or OUR as used herein refers to the volumetric rate at which oxygen is consumed during the fermentation. Inlet and outlet oxygen concentrations can be measured with exhaust gas analysis, for example by mass spectrometers. OUR can be calculated by one of ordinary skill in the art using the Direct Method described in *Bioreaction Engineering Principles* $2^{nd}$ Edition, 2003, Kluwer Academic/Plenum Publishers, p. 449, equation 1.

In one example, the concentration of cells in the fermentation medium is typically in the range of about 0.1 to 20, preferably from about 0.1 to 5, even more preferably from about 1 to 3 g dry cells/liter of fermentation medium during the production phase. The fermentation may be conducted aerobically, microaerobically, or anaerobically, depending on pathway requirements. If desired, oxygen uptake rate can be varied throughout fermentation as a process control (see, e.g., WO03/102200). In certain embodiments, the modified yeast cells provided herein may perform especially well when cultivated under microaerobic conditions characterized by an oxygen uptake rate of from about 2 to 25 mmol/L/hr, preferably from about 5 to 20 mmol/L/hr, and more preferably from about 8 to 15 mmol/L/hr. The medium may be buffered during the production phase such that the pH is maintained in a range of about 2.0 to about 8.0, about 3.0 to about 7.0, or about 3.5 to about 6.0. Suitable buffering agents are basic materials that neutralize the acid as it is formed, and include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional fermentation processes are also suitable here.

In those embodiments where a buffered fermentation is utilized, acidic fermentation products may be neutralized to the corresponding salt as they are formed. In these embodiments, recovery of the acid involves regeneration of the free acid. This may be done by removing the cells and acidulating the fermentation broth with a strong acid such as sulfuric acid. This results in the formation of a salt by-product. For example, where a calcium salt is utilized as the neutralizing agent and sulfuric acid is utilized as the acidulating agent, gypsum is produced as a salt by-product. This by-product is separated from the broth, and the acid is recovered using techniques such as liquid-liquid extraction, distillation, absorption, and others (see, e.g., T. B. Vickroy, Vol. 3, Chapter 38 of *Comprehensive Biotechnology*, (ed. M. Moo-Young), Pergamon, Oxford, 1985; R. Datta, et al., FEMS Microbiol Rev, 1995, 16:221-231; U.S. Pat. Nos. 4,275,234, 4,771,001, 5,132,456, 5,420,304, 5,510,526, 5,641,406, and 5,831,122, and WO93/00440.

In other embodiments, the pH of the fermentation medium may be permitted to drop during cultivation from a starting pH that is at or above the lower pKa (4.207) of succinate, typically 8 or higher, to at or below the lower pKa of the acid fermentation product, such as in the range of about 2.0 to about 4.2, in the range of from about 3.0 to about 4.2, or in the range from about 3.8 to about 4.2.

In still other embodiments, fermentation may be carried out to produce a product acid by adjusting the pH of the fermentation broth to at or below the lower pKa of the product acid prior to or at the start of the fermentation process. The pH may thereafter be maintained at or below the lower pKa of the product acid throughout the cultivation. In certain embodiments, the pH may be maintained at a range of about 2.0 to about 4.2, in the range of from about 3.0 to about 4.2, or in the range from about 3.8 to about 4.2.

In certain embodiments of the methods provided herein, the genetically modified yeast cells produce relatively low levels of ethanol. In certain embodiments, ethanol may be produced in a yield of 10% or less, preferably in a yield of 2% or less. In certain of these embodiments, ethanol is not detectably produced. In other embodiments, however, succinate and ethanol may be co-produced. In these embodiments, ethanol may be produced at a yield of greater than 10%, greater than 25%, or greater than 50%.

In certain embodiments of the methods provided herein, the final yield of succinate on the carbon source is at least 10%, at least 20%, at least 30%, at least 40%, at least 50%, or greater than 50% of the theoretical yield. In certain embodiments, the cells provided herein are capable of converting at least 80% or at least 90% by weight of a carbon source to succinate. The concentration, or titer, of succinate will be a function of the yield as well as the starting concentration of the carbon source. In certain embodiments, the titer may reach at least 1-3, at least 5, at least 10, at least 20, at least 30, at least 40, at least 50, or greater than 50 g/L at some point during the fermentation, and preferably at the end of the fermentation. In certain embodiments, the final yield of succinate may be increased by increasing or decreasing the temperature of the fermentation medium, particularly during the production phase.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1A

Selection of Host Yeast Cells Based on Succinate Tolerance

A set of wild-type yeast strains were tested for their ability to grow in the presence of succinate.

The range of succinate concentrations to utilize in primary screening procedures was determined by evaluating the ability of seven wild-type yeast strains (*Candida sonorensis, Candida zemplinina, I. orientalis* strain PTA-6658, *K. lactis, K. marxianus, S. cerevisiae* strain CENPK 113-7D, and *I. orientalis* strain CD1822) to grow on media containing varying levels of succinate. Cells were streaked onto YPD plates and grown overnight. A cell slurry with an $OD_{600}$ of around 4 was made in YPD media, pH 3.0, and this slurry was used to inoculate microtiter wells containing various concentrations of succinate to an $OD_{600}$ of 0.05. Plates were covered with a gas permeable membrane and incubated in a 30° C./300 rpm shaker overnight. The optical densities of each well were measured at a wavelength of 600 nm in a GENios model plate reader (Tecan), and plates were observed visually for growth. The highest succinate concentration that one or more of the strains grew in (150 g/L) was chosen as the upper range for primary screening procedure.

For the primary screening procedure, 91 yeast strains were screened for growth on microtiter plates at 0 g/L, 100 g/L, or 150 g/L succinate and pH 2.8 using the same protocol used for range finding. Solubility issues presented challenges when trying to test succinate concentrations greater than 150 g/L, so low pH rather than higher succinate concentration was used to test more stringent conditions. For these samples, strains were screened for growth at 150 g/L succinate and pH 2.5.

A fresh YPD plate was used for each strain, and a slurry with an $OD_{600}$ of around 4 was made in YPD media, pH 3.0. The slurry was used to inoculate each well to an $OD_{600}$ of 0.05. Plates were covered with a gas permeable membrane, and incubated in a 30° C./300 rpm shaker overnight. Optical densities of each well were measured at 600 nm in a GENios model plate reader, and plates were observed visually for growth.

A similar protocol was run to evaluate growth at lactic acid concentration of 0 g/L, 30 g/L, 45 g/L, and 60 g/L. Table 1 summarizes the highest concentrations of succinate or lactic acid at which growth was observed.

TABLE 1

Primary screen for growth on succinate or lactic acid:

| ATCC# | Genus/species | Lactic acid (g/L) | Succinate (g/L) |
|---|---|---|---|
| PTA-6658 | *Issatchenkia orientalis* | 60 | 150 (pH 2.5) |
| CD1822 (Cargill collection) | *Issatchenkia orientalis* | 60 | 150 (pH 2.5) |
| PYCC 04-501 | *Candida zemplinina* | 60 | 100 |
| Cargill | *Candida geochares* | 60 | 100 |
| NCYC 2696 | *Pichia membranifaciens* | 60 | 100 |
| NCYC2897 | *Zygosaccharomyces kombuchaensis* | 60 | 100 |
| mya-402 | *Saccharomyces bulderi* | 60 | 0 |
| 38619 | *Candida sorbosivorans* | 60 | 100 |
| NCYC 535 | *Schizosaccharomyces pombe* | 60 | 0 |
| 52486 | *Kluyveromyces marxianus* | 45 | 100 |
| 113-7D | *Saccharomyces cerevisiae-* CENPK | 45 | 0 |
| MUCL 300000 | *Candida vanderwaltii* | 45 | 100 |
| Cargill | *Candida sorbophila* | 45 | 100 |
| NCYC 3134 | *Zygosaccharomyces bisporus* | 45 | 100 |
| NCYC 2928 | *Zygosaccharomyces lentus* | 45 | 100 |
| NCYC 734 | *Saccharomyces ludwigii* | 45 | 0 |
| 60585 | *Issatchenkia orientalis* | 45 | 150 (pH 2.8) |
| 46330 | *Yarrowia lipolytica* | 45 | 0 |
| 36946 | *Zygosaccharomyces bailii* | 45 | 0 |

TABLE 1-continued

Primary screen for growth on succinate or lactic acid:

| ATCC# | Genus/species | Lactic acid (g/L) | Succinate (g/L) |
|---|---|---|---|
| 60592 | Candida milleri | 45 | 0 |
| 38617 | Candida lambica | 45 | 150 (pH 2.8) |
| 20306 | Candida rugosa | 45 | 0 |
| 28525 | Candida valida | 45 | 0 |
| 20347 | Candida zeylanoides | 45 | 0 |
| 24210 | Issatchenkia orientalis | 45 | 150 (pH 2.5) |
| 20282 | Kodamaea ohmeri | 45 | 0 |
| 90739 | Saccharomyces bayanus | 45 | 100 |
| MYA-404 | Saccharomyces bulderi | 45 | 0/100 |
| MUCL 31237 | Saccharomycopsis javensis | 45 | 0 |
| 32109 | Candida sonorensis | 30 | 0 |
| PYCC 70-1022 | Debaryomyces castellii | 30 | 100 |
| PYCC 70-104 | Candida boidinii | 30 | 100 |
| PYCC 60-8 | Candida etchellsii | 30 | 100 |
| 44691 | Candida kefyr | 30 | 0 |
| 34890 | Zygosaccharomyces rouxii | 30 | 0 |
| 60591 | Candida milleri | 30 | 0 |
| 24120 | Candida sorboxylosa | 30 | 150 (pH 2.5) |
| 28526 | Pichia fermentans | 30 | 0 |
| 96784 | Saccharomyces cerevisiae | 0/30 | 0 |
| 52709 | Kluyveromyces thermotolerans | 0/30 | 0 |
| NCYC 614 | Pachysolen tannophilus | 0/30 | 0 |
| CBS 8452 | Wickerhamiella occidentalis | 0/30 | 0 |
| 18735 | Candida blankii | 0/30 | 0 |
| 8585 | Kluyveromyces lactis | 0 | 100 |
| 9950 | Pichia jadinii | 0 | 100 |
| 38623 | Candida fluviatilis | 0 | 0 |
| 20033 | Saccharomyces capsularis | 0 | NG |
| 20284 | Candida famata | 0 | NG |
| 20118 | Candida guilliermondii | 0 | 0 |
| 20178 | Candida intermedia | 0 | 0 |
| 20179 | Candida parapsilosis | 0 | 0 |
| 96309 | Candida pseudolambica | 0 | 0 |
| 20280 | Debaryomyces polymorphus | 0 | 0 |
| 20277 | Dekkera anomala | 0 | 0 |
| 10563 | Dekkera lambica | 0 | 0 |
| 20030 | Hyphopichia burtonii | 0 | 0 |
| 9889 | Metschnikowia pulcherrima | 0 | 0 |
| 2102 | Pichia anomala | 0 | 0/100 |
| 24116 | Pichia nakasei | 0 | 0 |
| 16768 | Pichia silvicola | 0 | 0 |
| 34024 | Pichia strasburgensis | 0 | 0 |
| 2261 | Pichia tannicola | 0 | 0 |
| 76514 | Saccharomyces uvarum | 0 | 0 |
| 52714 | Torulaspora delbrueckii | 0 | 0 |
| 90197 | Yamadazyma guilliermondii | 0 | 0 |
| 20321 | Yamadazyma halophila | 0 | 0 |
| MUCL 44417 | Saccharomycopsis crataegensis | 0 | 100 |
| NRRL Y-7290 | Saccharomycopsis vini | 0 | 0 |
| 9950 | Pichia jadinii | 0 | 100 |
| CBS 6054 | Pichia stipitis | 0 | 0 |
| NCYC 2389 | Candida shehatae | 0 | 0 |
| 201225 | Yamadazyma stipitis | 0 | 0 |
| 10660 | Schizosaccharomyces japonicus | 0 | NG |
| 12659 | Lipomyces starkeyi | 0 | 0 |
| 42479 | Torulaspora pretoriensis | 0 | 0 |
| 90624 | Debaryomyces hansenii | NG | NG |
| 20117 | Candida catenulata | NG | NG |
| 96927 | Candida lactiscondensi | NG | NG |
| 36592 | Candida pignaliae | NG | NG |
| 34087 | Citeromyces matritensis | NG | NG |
| 36591 | Kluyveromyces yarrowii | NG | NG |
| 20292 | Nematospora coryli | NG | NG |
| 28778 | Pichia fluxuum | NG | NG |
| 58362 | Pichia toletana | NG | NG |
| 96272 | Bulleromyces albus | NG | NG |
| MUCL 47216 or MUCL 31253B | Candida tenuis | NG | NG |
| 20361 | Candida methanosorbosa | NG | NG |
| NCYC 813 | Brettanomyces naardenensis | NG | NG/0 |
| 76214 | Myxozyma kluyveri | NG | NG |
| 56306 | Lipomyces tetrasporus | NG | NG |
| 56465 | Candida naeodendra | NG | NG |

All six strains that exhibited growth at 150 g/L succinate were selected for secondary screening. For the first secondary screen, growth rates were measured in YPD media containing 0 g/L succinate at pH 3.0 or 75 g/L succinate at pH 2.85. Shake flasks were inoculated with biomass harvested from seed flasks grown overnight to an $OD_{600}$ of 6 to 10. 250 mL baffled growth rate flasks (50 mL working volume) were inoculated to an $OD_{600}$ of 0.1 and grown at 250 rpm and 30° C. Samples were taken throughout the time course of the assay and analyzed for biomass growth via $OD_{600}$. The resulting $OD_{600}$ data was plotted and growth rates were established. Results are summarized in Table 2.

TABLE 2

Growth rate in succinate:

| Strain | 0 g/L succinate (pH 3.0) ($h^{-1}$) | 75 g/L succinate (pH 2.85) ($h^{-1}$) |
|---|---|---|
| Issatchenkia orientalis ATCC PTA-6658 | 0.71 | 0.50 |
| Issatchenkia orientalis CD1822 | 0.69 | 0.47 |
| Issatchenkia orientalis ATCC 60585 | 0.73 | 0.46 |
| Candida lambica ATCC 38617 | 0.81 | 0.48 |
| Candida sorboxylosa ATCC 24120 | 0.66 | 0.36 |
| Issatchenkia orientalis ATCC 24210 | 0.74 | 0.45 |

For the second secondary screen, glucose consumption was measured in YPD media containing 0 g/L succinate at pH 3.0 or 75 g/L succinate at pH 2.85. Shake flasks were inoculated with biomass harvested from seed flasks grown overnight to an $OD_{600}$ of 6 to 10. 250 mL baffled glycolytic assay flasks (50 mL working volume) were inoculated to an $OD_{600}$ of 0.1 and grown at 250 RPM and 30° C. Samples were taken throughout the time course of the assay and analyzed for glucose consumption using a 2700 Biochemistry Analyzer (Yellow Springs Instruments, YSI). The resulting data was plotted and glucose consumption rates were established. Results are summarized in Table 3.

TABLE 3

Glucose consumption rate in succinate:

| Strain | 0 g/L succinate (pH 3.0) (g $L^{-1}$ $h^{-1}$) | 75 g/L succinate (pH 2.85) (g $L^{-1}$ $h^{-1}$) |
|---|---|---|
| Issatchenkia orientalis ATCC PTA-6658 | >4.2 g/L/h | >2.3 g/L/h |
| Issatchenkia orientalis CD1822 | >4.2 g/L/h | >2.3 g/L/h |
| Issatchenkia orientalis ATCC 60585 | >4.2 g/L/h | 2.3-2.8 g/L/h |

TABLE 3-continued

Glucose consumption rate in succinate:

| Strain | 0 g/L succinate (pH 3.0) (g $L^{-1}$ $h^{-1}$) | 75 g/L succinate (pH 2.85) (g $L^{-1}$ $h^{-1}$) |
|---|---|---|
| *Candida lambica* ATCC 38617 | >4.2 g/L/h | >2.3 g/L/h |
| *Candida sorboxylosa* ATCC 24120 | 3.1 g/L/h | 0.7 g/L/h |
| *Issatchenkia orientalis* ATCC 24210 | >4.2 g/L/h | >2.3 g/L/h |

To identify the most attractive candidates for succinate production, strain performance was graded in three categories. Two of these categories were based on different aspects of growth rate: 1) growth rate at highest acid concentration and 2) slope of the growth rates plotted against acid concentration. The third category was the glycolytic rate at the highest acid concentration. Grading was done on a normalized scale using the highest and lowest value for each rating as the normalized boundaries. Each strain thus received a grade of 0 to 1 for each category, with 1 being the highest possible score. The overall rating of a strain was the sum of the normalized value for the three categories. A weighted score was made in which the growth rate and glycolytic rate were equally weighted. In this case the glycolytic rate at the highest acid concentration was weighted at 50%, while the two growth rate ratings were weighted at 25% each. In accordance with the description above, the final score for each strain was calculated as follows:

Final score for strain $X =$ (actual growth rate in highest acid concentration $-$ slowest growth rate) $*$ 0.25 (fastest growth rate $-$ slowest growth rate) $+$ (slope of growth rates of strain $X -$ lowest growth rate slope) $*$ 0.25 (largest growth rate slope $-$ lowest growth rate slope) $+$ (actual glycolytic rate in highest acid concentration $-$ slowest glycolytic rate) $* 0.50$ (fastest glycolytic rate $-$ slowest glycolytic rate)

Normalized values for each category and the final weighted score for each strain are summarized in Table 4.

TABLE 4

Normalized strain grades in succinate:

| Strain | Growth rate @ 75 g/L succinate | Growth rate slope | Glycolic rate | Weighted score |
|---|---|---|---|---|
| *Issatchenkia orientalis* ATCC PTA-6658 | 1.00 | 1.00 | 0.76 | 0.88 |
| *Issatchenkia orientalis* CD1822 | 0.79 | 0.94 | 0.76 | 0.81 |
| *Issatchenkia orientalis* ATCC 60585 | 0.71 | 0.50 | 1.00 | 0.80 |
| *Candida lambica* ATCC 38617 | 0.86 | 0.00 | 0.76 | 0.60 |
| *Candida sorboxylosa* ATCC 24120 | 0.00 | 0.25 | 0.00 | 0.06 |
| *Issatchenkia orientalis* ATCC 24210 | 0.64 | 0.31 | 0.79 | 0.63 |

The same procedures were utilized to screen, rate, and score the original 91 yeast strains from the primary screen with media containing 0, 30, 45, and 60 g/L lactic acid at pH 3.0 (~80% free acid). Due to difficulties in properly scoring some very weak growth that occasionally occurred at 60 g/L, 21 strains were re-tested in the primary screen. Of these 21 strains, eight were eliminated due to very slow growth relative to the rest of the test group. The remaining 13 strains were advanced into secondary screening, and normalized values and weighted and summed scores were derived for each strain. These results are summarized in Table 5.

TABLE 5

Normalized strain grades in lactic acid:

| Strain | Growth rate 50 g/L lactic acid | Growth rate slope | Glycolic rate | Weighted score |
|---|---|---|---|---|
| *Candida lambica* ATCC 38617 | 0.92 | 1 | 1 | 0.98 |
| *Issatchenkia orientalis* ATCC PTA-6658 | 0.94 | 0.95 | 1 | 0.97 |
| *Issatchenkia orientalis* CD1822 | 1.00 | 0.86 | 1 | 0.97 |
| *Issatchenkia orientalis* ATCC 24210 | 0.89 | 0.73 | 1 | 0.91 |
| *Candida zemplinina* | 0.22 | 0.95 | 1 | 0.79 |
| *Saccharomyces bulderi* ATCC MYA-404 | 0.47 | 0.45 | 1 | 0.73 |
| *Saccharomyces bayanus* | 0.08 | 0.91 | 0.96 | 0.73 |
| *Saccharomyces bulderi* ATCC MYA-402 | 0.5 | 0.23 | 1 | 0.68 |
| *Candida milleri* ATCC 60592 | 0 | 0.64 | 0.92 | 0.62 |
| *Candida sorbosivorans* | 0.28 | 0.95 | 0.59 | 0.60 |
| *Kodamaea ohmeri* | 0.42 | 0 | 0.76 | 0.49 |
| *Candida geochares* | 0.17 | 0.27 | 0.69 | 0.46 |
| *Saccharomyces javensis* | 0.11 | 0.68 | 0 | 0.20 |

Of the strains tested in lactic acid, only *S. javensis* did not achieve a 2.5 g/L/hr glucose utilization rate at pH 2.85 in media with 50 g/L lactic acid. While *I. orientalis* and *C. lambica* showed tolerance for both succinic and lactic acids, there were a number of species and strains that were tolerant for only one of the acids. Additionally, the rank order of the strains is different for each acid. This is even more clearly illustrated in the primary screen results (Table 1), where more strains were included. The most succinate tolerant strains are scattered among the top three tiers for lactic acid tolerance. Further, one of the strains that grew at the highest lactic acid concentration in the primary screen and scored highly in the secondary screen (*S. bulderi*) did not grow even at the lowest non-zero concentration of succinic acid tested. Thus, tolerance to lactic acid was shown to be a very poor predictor of tolerance to succinic acid, meaning that ideal strains for succinate production cannot be identified based on tolerance to lactic acid. This is further highlighted by comparing the strains that showed succinate resistance above with the list of eight strains identified as preferred hosts for organic acid production in WO03/049525. While two of those strains (*C. diddensiae* and *C. entomophila*) could not be obtained for testing, the other six (*C. sonorensis, C. methanosorbosa, C. parapsilosis, C. naeodendra, C krusei,* and *C. blankii*) were included in the primary screen described above. Of these six, only *C. krusei* (tested as *I.*

*orientalis*) was able to grow in the presence of 150 g/L succinate at either pH 2.5 or pH 2.8.

Example 1B

Mutagenesis and Selection of Mutant Strains Having Succinate Resistance

Yeast cells selected in Example 1A are subjected to mutagenesis and exposed to selection pressure in order to identify mutants with high succinate tolerance.

For example, yeast cells from a fresh YP (yeast extract/peptone)+20 g/L glucose plate or liquid culture ($OD_{600}$ 1-4) are resuspended in sterile water to an $OD_{600}$ of around 10. 200 µL aliquots of this cell suspension are pipetted into individual tubes and exposed to 3 µL ethane methyl sulfonate (EMS) for approximately one hour, which kills around 65% of the cells. Higher EMS concentrations can also be used to increase the kill rate. After exposure, cells are neutralized with 5% sodium thiosulfate, washed in PBS buffer, recovered in rich media for approximately four hours, and cultured on selective media. Mock samples (no EMS) are also run to ensure that the conditions are selective. Alternatively, cell can be mutagenized using UV irradiation.

To select for succinate resistant mutant strains, aliquots of the EMS-treated cell suspension (approximately $2 \times 10^8$ of mutagenized cells) are plated onto a potato glucose agar (PDA) or another media containing succinate at a level at which the parental strain does not grow or grows very slowly. These plates are incubated for several days until colonies appear. Single colonies are purified, streaked on non-selective media to eliminate any adaptive effects of the selection, and re-tested on selective media to confirm increased resistance. Resistant strains are then tested in a shake flask format with periodic sampling for HPLC analysis of products and substrates. Alternatively, selection for succinate tolerance may be done by chemostat or serial shake flask evolution. Additional rounds of mutagenesis and selection can be performed. Mutagenesis can be used to increase the resistance of a host that does not natively meet succinate production requirements so that it has the necessary attributes for commercial succinate production.

Example 2

Deletion of Both Alleles of CYB2A, GPD1, and CYB2B from *I. orientalis* Strain CD1822

Both alleles of CYB2A, GPD1, and CYB2B are deleted from *I. orientalis* strain CD1822. As discussed above, CD1822 is an evolved lactic acid resistant strain isolated from a chemostat that also exhibited a high degree of succinate tolerance.

Example 2A

Deletion of Both CYB2A Alleles from *I. orientalis* Strain CD1822

Figure 2:
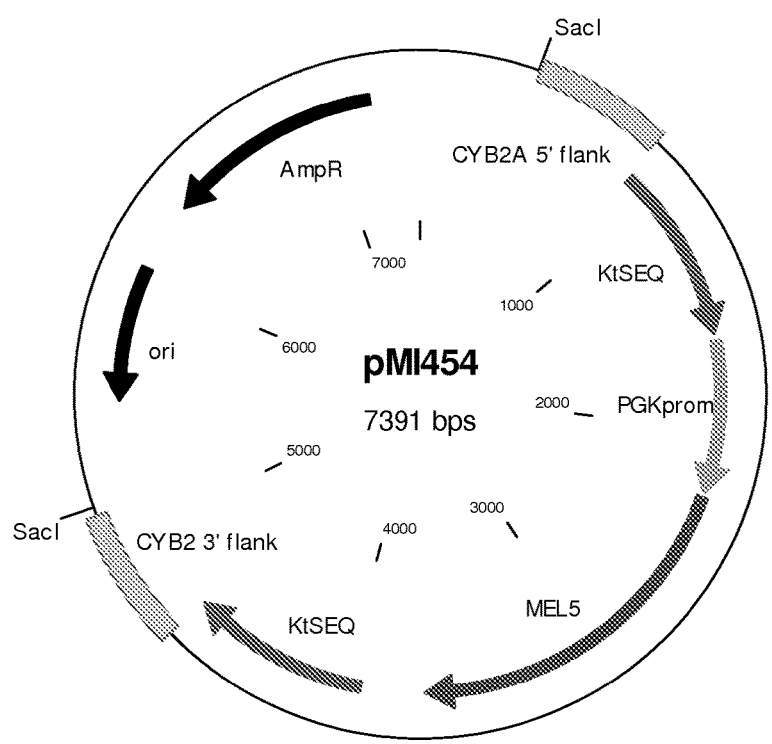
FIG. 2: pMI454, CYB2A deletion construct.

Plasmids pMI449 (FIG. 1) and pMI454 (FIG. 2) are used to delete both copies of the L-lactate:ferricytochrome c oxidoreductase (CYB2A) gene (SEQ ID NO:49) in *I. orientalis* strain CD1822, a lactic acid resistant strain of *I. orientalis* isolated from the environment. pMI449 and pMI454 were both described in WO07/106,524. Each plasmid contains 5' and 3' flanking regions from *I. orientalis* CYB2A separated by a selection marker cassette comprising the *S. cerevisiae* MEL5 gene operatively linked to a PGK promoter. This selection marker cassette is flanked on either end by a sequence ("KtSEQ") from *K. thermotolerans*. The 5' and 3' CYB2A flanking regions in pMI449 correspond to nucleotides from 913 to 487 bp upstream of the start of the predicted ORF and nucleotides from 90 to 676 bp downstream of the stop codon of the predicted ORF, respectively. The 5' and 3' CYB2A flanking regions in pMI454 correspond to nucleotides from 466 to 7 bp upstream of the predicted ORF and nucleotides from 402 bp upstream to 77 bp downstream of the predicted stop codon, respectively.

The first CYB2A allele is deleted by transforming strain CD1822 with pMI449 digested with SacI using lithium acetate transformation (Gietz Met Enzymol 350:87 (2002)). Transformants are selected on yeast nitrogen base (YNB)+2% melibiose plate containing x-α-gal (5-bromo-4-chloro-3-indolyl-α-D-galactoside). Blue-colored transformants are visible after around 4 days of growth at 30° C. Transformants are picked and plated for single colonies on Yeast Extract/Peptone/20 g/L glucose plates (YPD) containing x-α-gal. A single blue colony for each transformant is picked and re-streaked to YPD plates. Genomic DNA is isolated from the purified transformants, and replacement of the CYB2A gene is confirmed by PCR. To obtain strains where the MEL5 marker has undergone spontaneous recombination to excise it from the chromosome, the transformant is grown for several rounds in liquid YPD (100 g/L glucose) at 250 rpm and 30° C. A dilution series is plated onto YPD plates overlaid with x-α-gal, and grown overnight at 30° C. A white colony (indicative of the loop-out of the MEL5 marker cassette) is selected and re-streaked to YPD+x-α-gal plates. A white colony is selected and genomic DNA is prepared. Disruption of one allele of the native CYB2A gene is verified by PCR using primers oMM173 (SEQ ID NO:58) and oTM123 (SEQ ID NO:62).

The second CYB2A allele is deleted from this transformant by transforming with pMI454 digested with SacI. Transformants are obtained and purified as described above and analyzed by PCR for the absence of a 1000 bp CYB2A-specific PCR product using primers oMM175 (SEQ ID NO:60) and oMM176 (SEQ ID NO:61). The MEL5 marker derived from plasmid pMI454 is looped out of a transformant having a deletion of both CYB2A alleles via recombination as before, and confirmed by PCR using primers oMM172 (SEQ ID NO:57) and oMM173. This transformant is designated strain 2610.

Example 2B

Deletion of Both GPD1 Alleles from *I. orientalis* Strain 2610

Figure 3:
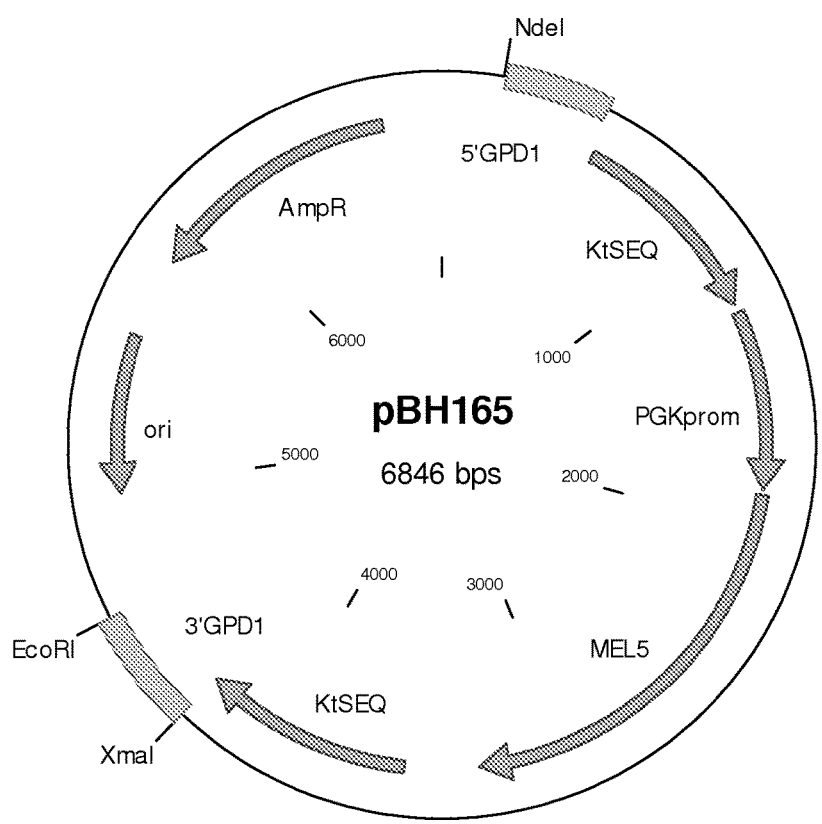
FIG. 3: pBH165, GPD1 deletion construct.

Plasmid pBH165 (FIG. 3) is used to delete one allele of the GPD1 gene (SEQ ID NO:43) from *I. orientalis* strain 2610. pBH165, which was described in WO07/106,524, contains upstream and downstream fragments of the *I. orientalis* GPD1 gene separated by a selection marker cassette comprising *S. cerevisiae* MEL5 operatively linked to a PGK promoter and surrounded by KtSEQ flanking sequences. The upstream and downstream fragments of the GPD1 gene correspond to nucleotides from 1 to 302 bp and from 322 to 608 bp downstream of the start codon, respectively.

Strain 2610 is transformed with pBH165 digested with NdeI and EcoRI using lithium acetate transformation, and transformants are selected on YNB+2% melibiose plate overlaid with x-α-gal. Blue-colored transformants are visible after around 4 to 7 days of growth at 30° C. Transformants are picked and plated for single colonies on YPD plates containing x-α-gal, and a single transformant is picked and re-streaked to YPD plates. Genomic DNA is isolated from the transformants, and disruption of one allele of the GPD1 gene is confirmed by one or more PCR reactions. The resulting transformant is designated strain 2639.

To obtain strains where the MEL5 marker has undergone spontaneous recombination to excise it from the chromosome, strain 2639 is grown for several rounds in liquid YPD (100 g/L glucose) at 250 rpm and 30° C. A dilution series is plated onto YPD plates overlaid with x-α-gal, and grown overnight at 30° C. A white colony (indicative of the loop-out of the MEL5 marker cassette) is selected and re-streaked to YPD+x-α-gal plates. A white colony is selected and streaked onto a YPD plate. Disruption of one allele of the native GPD1 gene and loss of the MEL5 marker is verified by PCR. The resultant transformant is designated strain 2643.

Figure 4:
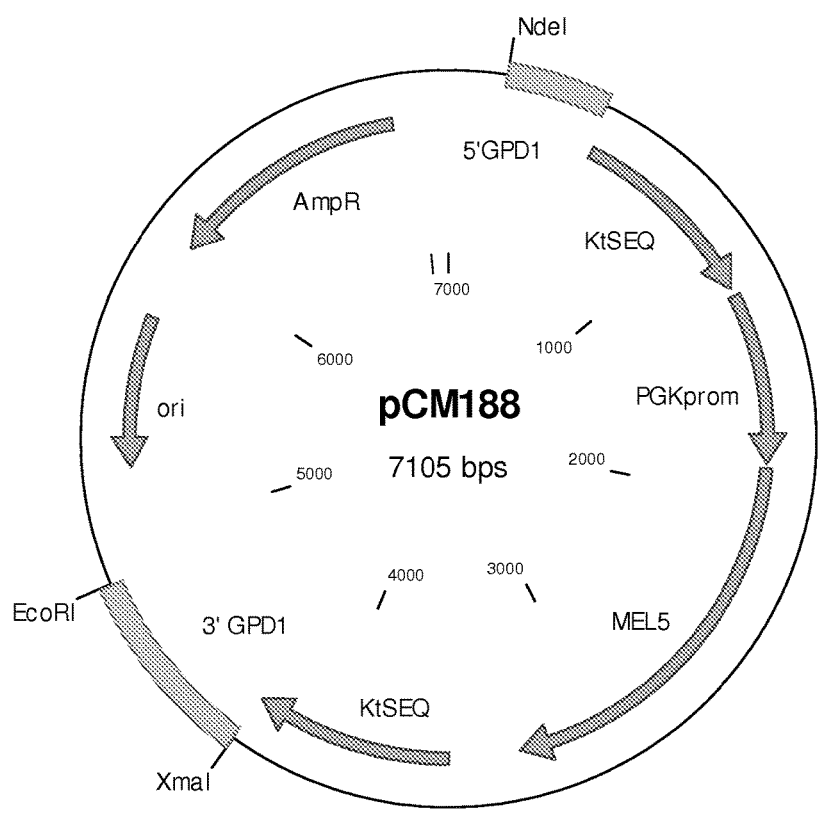
FIG. 4: pCM188, GPD1 deletion construct.

Plasmid pCM188 (FIG. 4) is used to delete the second GPD1 allele from *I. orientalis* strain 2643. pCM188 was generated by amplifying a 3' flanking region (corresponding to nucleotides from 1169 to 1770 bp downstream of the GPD1 gene start codon) of the GPD1 gene using primers CM0588 (SEQ ID NO:65) and CM0589 (SEQ ID NO:66). The primers included nucleotides for incorporating an XmaI site at the 5' end and an EcoRI site at the 3' end of the amplified DNA. The resultant product is digested with XmaI and EcoRI and ligated to similarly digested pBH165 to generate pCM188, which contains upstream and downstream fragments of the *I. orientalis* GPD1 gene separated by a selection marker cassette comprising *S. cerevisiae* MEL5 operatively linked to a PGK promoter and surrounded by KtSEQ flanking sequences.

Strain 2643 is transformed with pCM188 digested with NdeI and EcoRI using lithium acetate transformation, and transformants are selected on YNB+2% melibiose plate overlaid with x-α-gal. Blue-colored transformants are visible after around 4 to 7 days of growth at 30° C. Transformants are picked and plated for single colonies on YPD plates containing x-α-gal, and a single transformant is picked and re-streaked to YPD plates. Genomic DNA is isolated from the transformants, and disruption of the second GPD1 allele is confirmed by one or more PCR reactions. The resulting transformant is designated strain 2644.

To obtain strains where the MEL5 marker has undergone spontaneous recombination to excise it from the chromosome, strain 2644 is grown for several rounds in liquid YPD (100 g/L glucose) at 250 rpm and 30° C. A dilution series is plated onto YPD plates overlaid with x-α-gal, and grown overnight at 30° C. A white colony (indicative of the loop-out of the MEL5 marker cassette) is selected and re-streaked to YPD+x-α-gal plates. A white colony is selected and streaked onto a YPD plate. Disruption of the second allele of the native GPD1 gene and loss of the MEL5 marker is verified by PCR. The resultant transformant is designated strain 2652.

Example 2C

Deletion of Both CYB2B Alleles from *I. orientalis* Strain 2652

Figure 5:
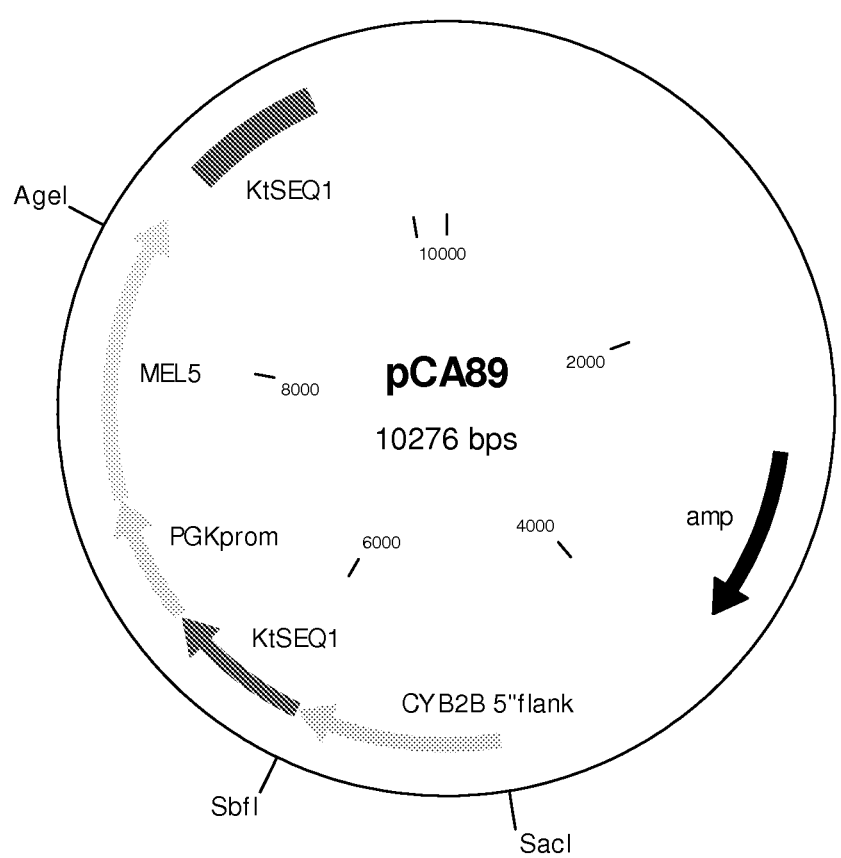
FIG. 5: pCA89, CYB2B deletion construct.
Figure 6:
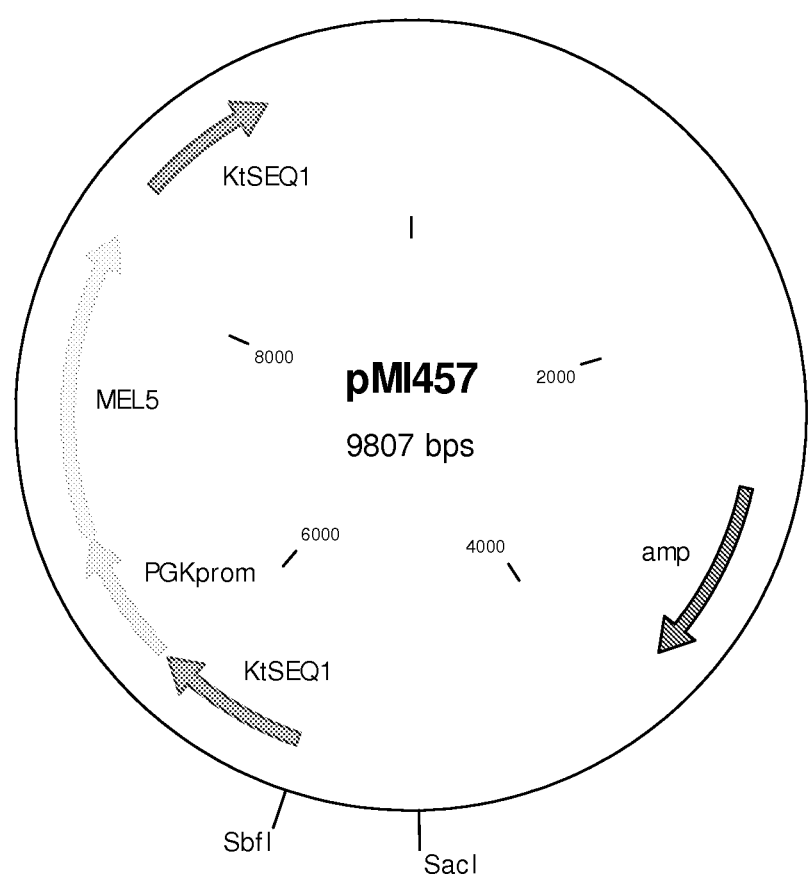
FIG. 6: pMI457, PGK:MEL5 construct.
Figure 7:
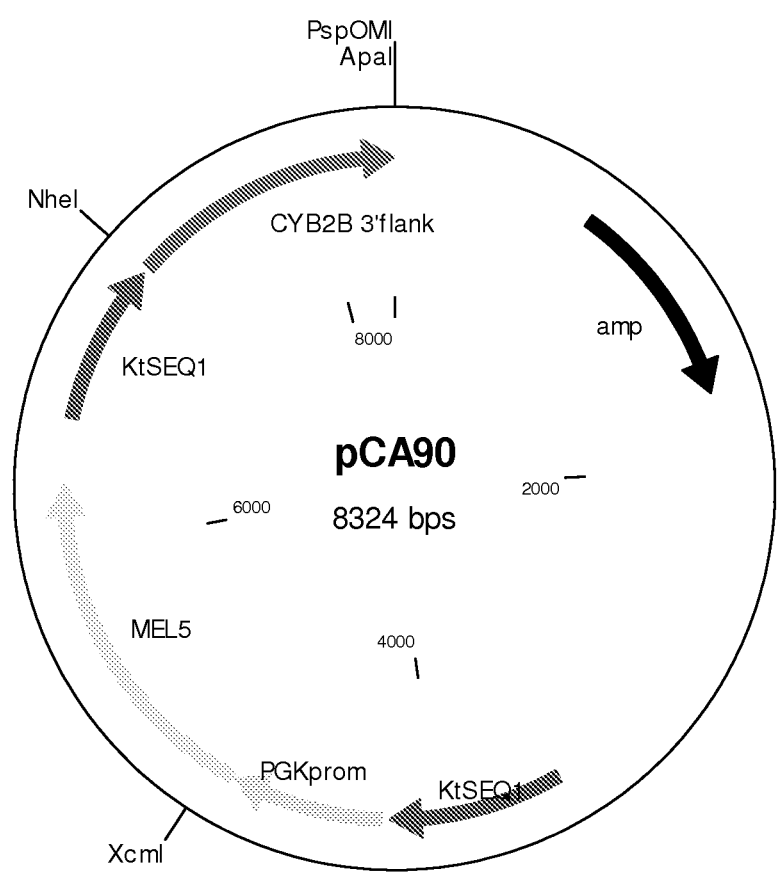
FIG. 7: pCA90, CYB2B deletion construct.

Plasmids pCA89 and pCA90 are used to delete one allele of the CYB2B gene (SEQ ID NO:51) from *I. orientalis* strain 2652. pCA89 (FIG. 5) is generated by amplifying a 5' flanking region of CYB2B using PCR primers oCA385 (SEQ ID NO:67) and oCA386 (SEQ ID NO:68), which incorporates SacI and SbfI restriction sites into the PCR product, then digesting the product and ligating to pMI457 cut with the same enzymes. pMI457 (FIG. 6) contains a MEL5 gene operatively linked to a PGK promoter and surrounded by KtSEQ flanking sequences. pCA90 (FIG. 7) is generated by amplifying a 3' flanking region of CYB2B using PCR primers oCA387 (SEQ ID NO:69) and oCA388 (SEQ ID NO:70), which incorporates NheI and PspOMI restriction sites into the PCR product, then digesting the product and ligating to pMI457 cut with the same enzymes.

Strain 2652 is transformed with pCA89 digested with SacI and AgeI and pCA90 digested with XcmI and ApaI using lithium acetate transformation. The two plasmid fragments are able to recombine during transformation to form a functional MEL5 gene. Transformants are selected on YNB+2% melibiose plate overlaid with x-α-gal. Blue-colored transformants are visible after around 4 to 7 days of growth at 30° C. Transformants are picked and plated for single colonies on YPD plates containing x-α-gal, and a single transformant is picked and re-streaked to YPD plates. Genomic DNA is isolated from the transformants, and replacement of a first CYB2B allele is confirmed by one or more PCR reactions. The resulting transformant is designated strain 2719.

To obtain strains where the MEL5 marker has undergone spontaneous recombination to excise it from the chromosome, strain 2719 is grown for several rounds in liquid YPD (100 g/L glucose) at 250 rpm and 30° C. A dilution series is plated onto YPD plates overlaid with x-α-gal, and grown overnight at 30° C. A white colony (indicative of the loop-out of the MEL5 marker cassette) is selected and re-streaked to YPD+x-α-gal plates. A white colony is selected and streaked onto a YPD plate. Disruption of a first allele of the native CYB2B gene and loss of the MEL5 marker is verified by PCR. The resultant transformant is designated strain 2721.

The second CYB2B allele is deleted from strain 2721 by transforming with the same pCA89 and pCA90 fragments used to transform strain 2652. Transformants are obtained and purified as described above, and strains from which the MEL5 marker has been excised by recombination are generated using the methods described above. Disruption of both CYB2B alleles and loss of the MEL5 gene is verified by PCR. The resultant transformant is designated strain 2732.

The various CYB2A, GPD1, and CYB2B deletion strains generated in Example 2 are summarized in Table 6.

TABLE 6

*I. orientalis* CYB2A, GPD1, and CYB2B deletion strains:

| Strain name | Description | Parent strain |
| --- | --- | --- |
| CD1822 | Lactic acid-resistant parent strain | — |
| 2610 | CYB2A deletion (2) | |
| 2639/2643 | CYB2A deletion (2) GPD1 deletion (1) | 2610 |
| 2644/2652 | CYB2A deletion (2) GPD1 deletion (2) | 2643 |
| 2719/2721 | CYB2A deletion (2) GPD1 deletion (2) CYB2B deletion (1) | 2652 |
| 2732 | CYB2A deletion (2) GPD1 deletion (2) CYB2B deletion (2) | 2721 |

Example 3

Construction of cre Expression Plasmids pVB10 and pVB32

Figure 8:
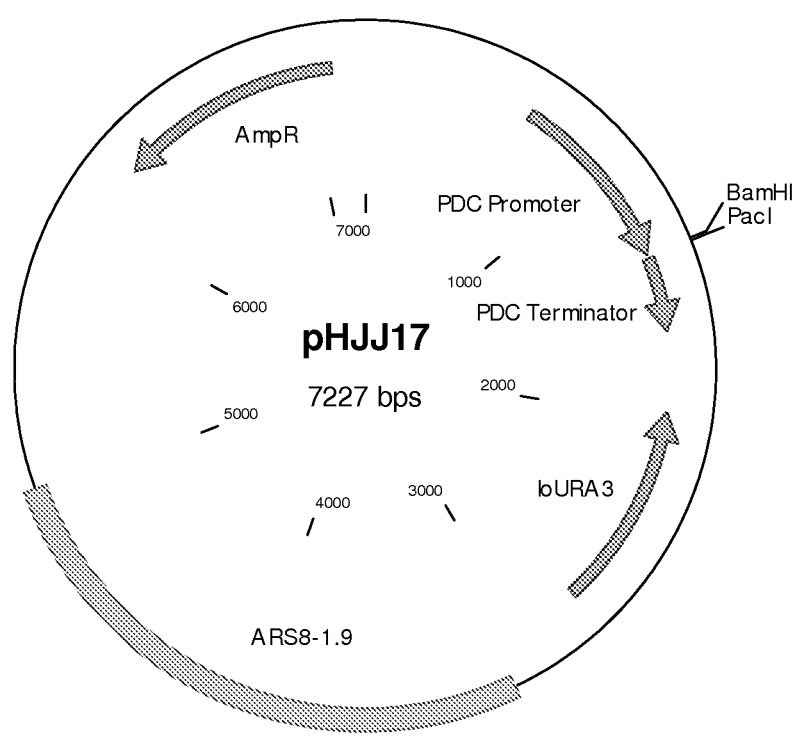
FIG. 8: pHJJ17.
Figure 9:
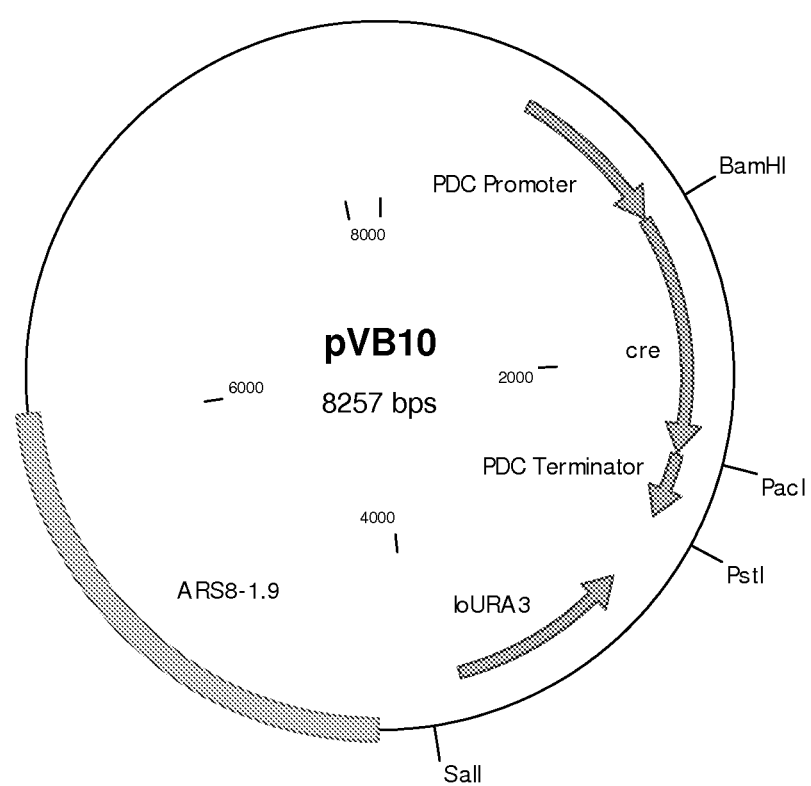
FIG. 9: pVB10, PDC:cre construct

The cre recombinase gene is synthesized using the native cre protein sequence as a reference. This gene is PCR amplified from template DNA (Blue Heron Biotechnologies) representing a codon-optimized version of the bacteriophage P1 CRE gene (SEQ ID NO:55, encoding polypeptide of SEQ ID NO:56) using PCR primers oVB5 (SEQ ID NO:72) and oVB6 (SEQ ID NO:73) and cloned into pCR2.1-TOPO (Invitrogen) to produce pVB15a. pVB15a is digested with BamHI and PacI to generate a 1 kb cre fragment, and this fragment is ligated into similarly digested pHJJ17 (FIG. 8). The resultant vector, pVB10 (FIG. 9), contains the cre gene operatively linked to a PDC promoter and terminator. The vector also contains a URA3 selection marker gene from I. orientalis.

Figure 10:
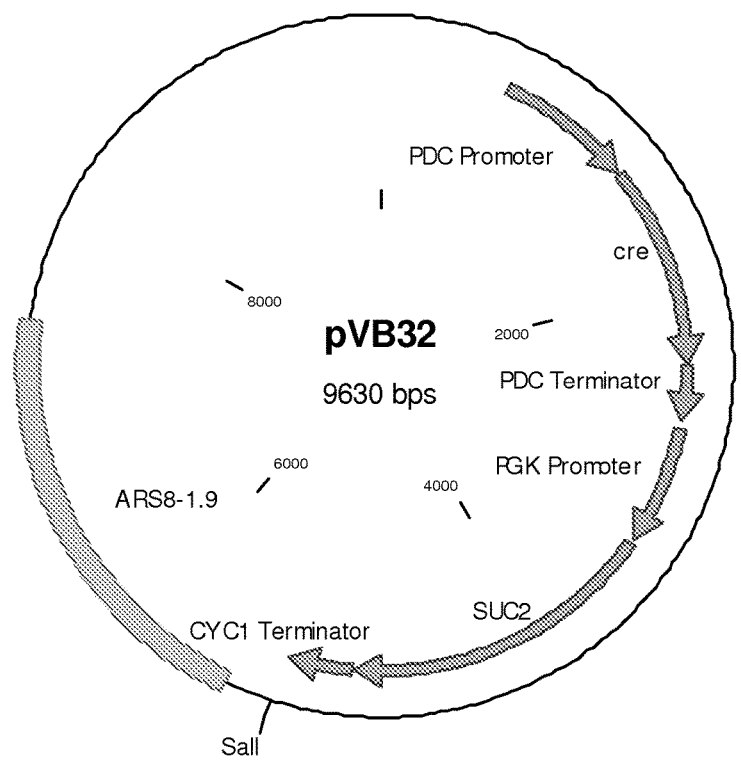
FIG. 10: pVB32.

To replace the URA3 selection marker in pVB10 with the SUC2 selection marker, a SUC2 expression cassette was amplified from pTMC82. This SUC2 expression cassette contains the S. cerevisiae SUC2 gene operatively linked to the I. orientalis PGK1 promoter and the S. cerevisiae CYC1 terminator. Amplification was performed using primers oTM298 (SEQ ID NO:63) and oTM299 (SEQ ID NO:64), which add NsiI and SalI restriction sites to the product. The PCR product was digested with NsiI and SalI and ligated to pVB10 digested with SalI and PstI (NsiI and PstI have compatible cohesive ends) to produce pVB32 (FIG. 10).

Example 4

Insertion of PYC1 at the PDC1 Locus in I. orientalis Strain 2732

A PYC1 expression cassette is inserted at one or both PDC1 alleles in I. orientalis strain 2732 (Example 2).

Example 4A

Construction of PDC1 Deletion Construct pKWB21

Figure 14:
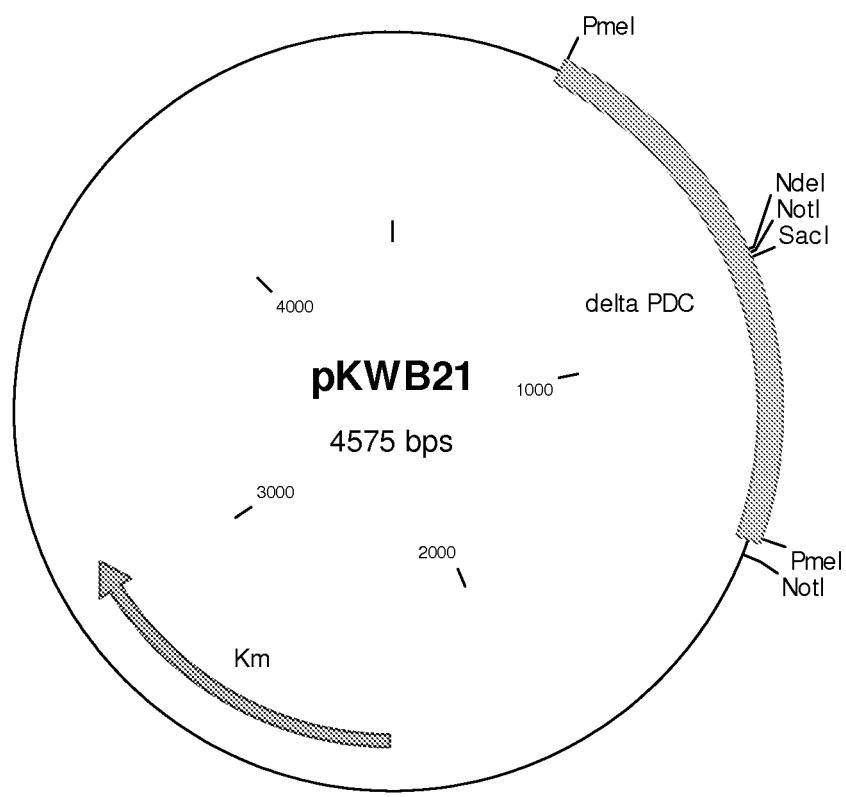
FIG. 14: pKWB21, PDC1 deletion construct.

Upstream and downstream regions of the PDC1 gene (SEQ ID NO:39) were amplified in order to generate a PDC1 deletion construct. The upstream and downstream regions correspond to nucleotides from 496 bp upstream to the start codon of PDC1 and from the stop codon to 539 bp downstream, respectively. Amplification of the upstream region is performed using primers oKW70 (forward, SEQ ID NO:92) and oKW71 (reverse, SEQ ID NO:93), which adds a PmeI restriction site and NdeI, NotI, and SacI restriction sites, respectively, to the product. Amplification of the downstream region is performed using primers oKW72 (forward, SEQ ID NO:94) and oKW73 (reverse, SEQ ID NO:95), which adds NdeI, NotI, and SacI restriction sites and a PmeI restriction site, respectively, to the product. The two fragments are amplified independently, then assembled into a full-length product with a 2-stage PCR protocol. The first stage uses 10 cycles (98° C. 10 s, 55° C. 20 s, 72° C. 60 s) with no primers, and the second stage uses 20 cycles (98° C. 10 s, 55° C. 20 s, 72° C. 60 s) with upstream forward and downstream reverse primers. The full-length product is gel purified, cloned into pCR-BluntII (Invitrogen), and sequenced. The plasmid confirmed to have correct sequence is subjected to quickchange PCR using Phusion polymerase to eliminate the plasmid borne SacI site. Correct plasmids are confirmed by digestion with SacI and sequencing. The final PDC1 deletion construct is designated pKWB21 (FIG. 14).

Example 4B

Construction of I. orientalis PYC1 Expression Constructs pKF043 and pKF045

Figure 11:
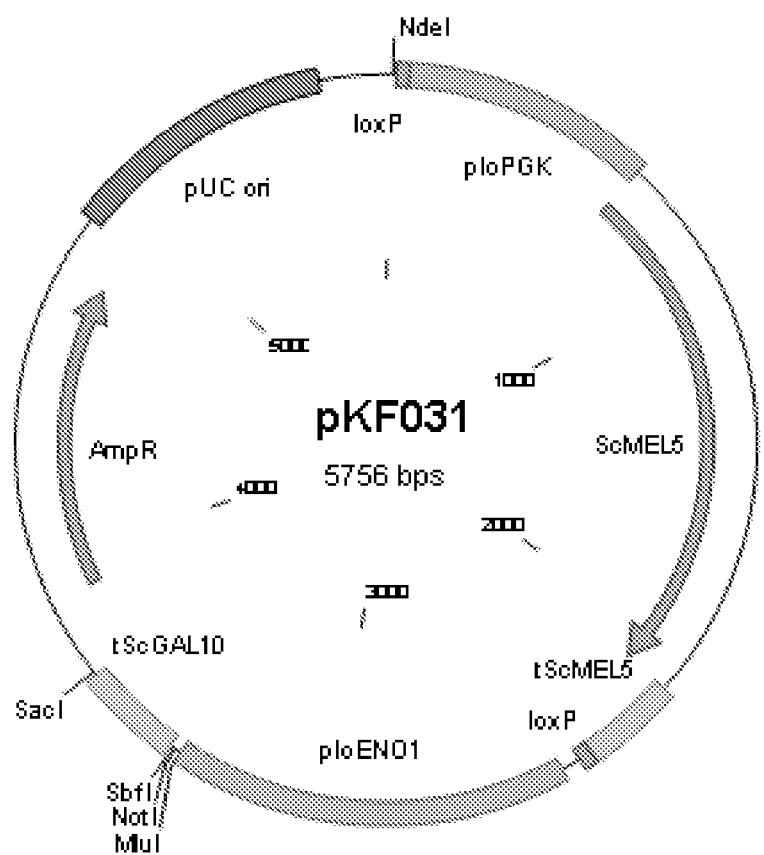
FIG. 11: pKF031, PGK:MEL5 construct.

The PYC1 gene from I. orientalis (SEQ ID NO:7) is amplified from genomic DNA using Phusion polymerase and primers oKF245 (SEQ ID NO:134) and oKF246 (SEQ ID NO:135), which contain an MluI site and an SbfI site, respectively. After amplification, the product is gel purified, digested with MluI and SbfI, and ligated to similarly digested pKF031 and pKF044. pKF031 (FIG. 11) and pKF044 (FIG. 12) are constructed from pUC19 backbones, and both contain a multiple cloning site containing MluI, NotI, and SbfI sites operatively linked to the I. orientalis ENO promoter and the S. cerevisiae GAL10 terminator. pKF031 also contains a selection marker cassette comprising the S. cerevisiae MEL5 gene operatively linked to the I. orientalis PGK promoter. This selection marker cassette is flanked by loxP sites. pKF044 contains an expression cassette comprising the I. orientalis CYB2A promoter, gene, and terminator. This expression cassette is flanked by loxP sites.

Figure 15:
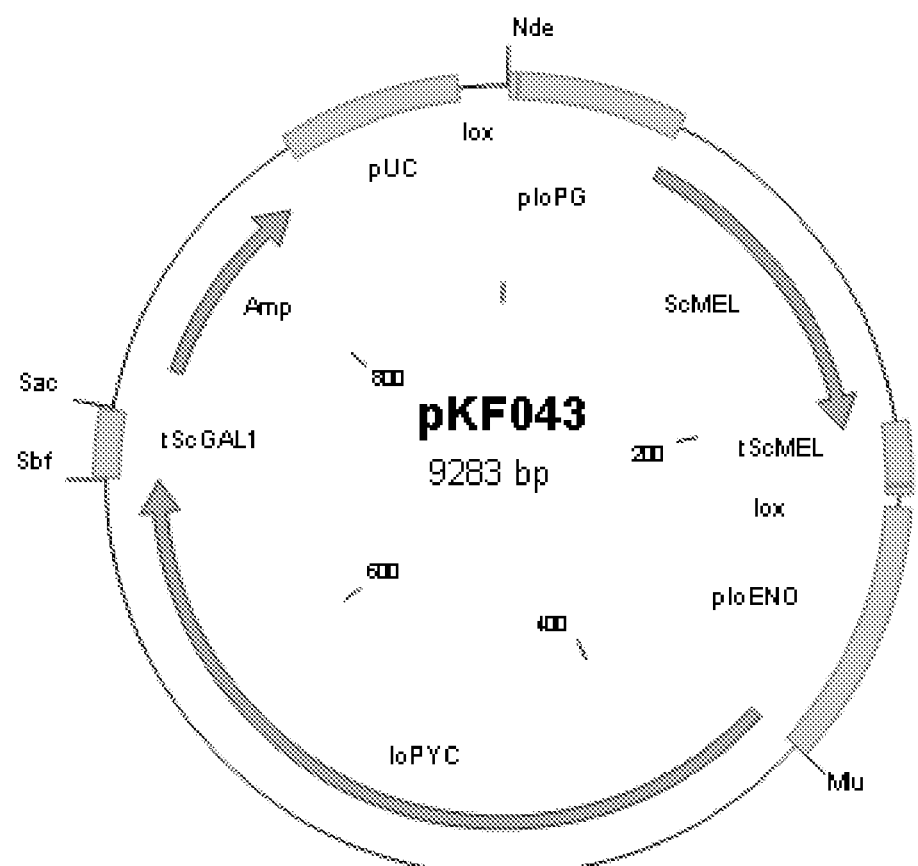
FIG. 15: pKF043, *I. orientalis* PYC1 expression construct.
Figure 16:
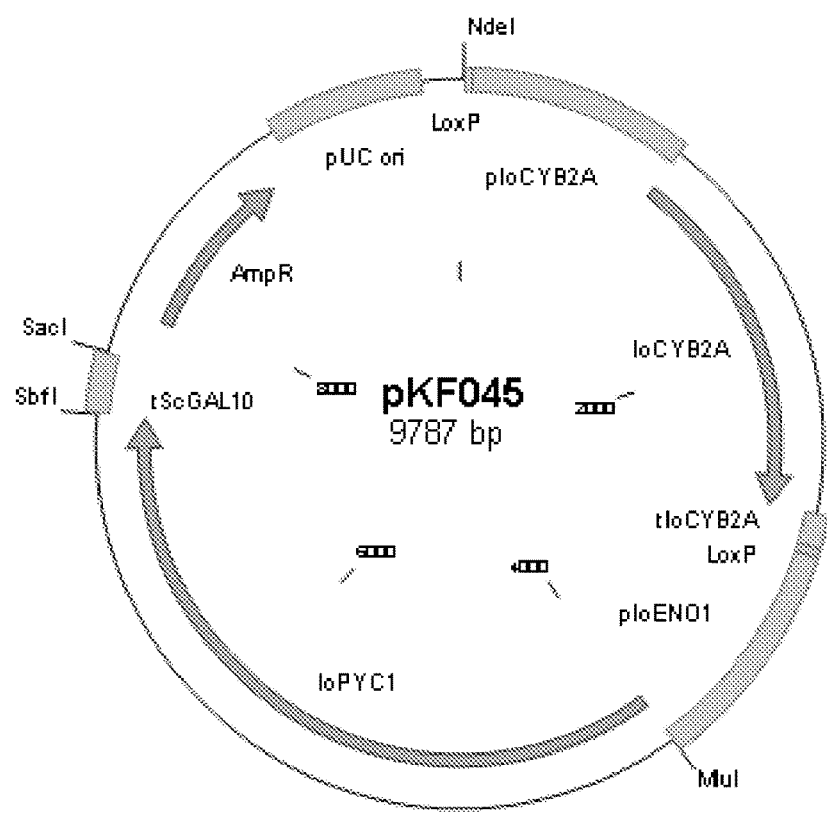
FIG. 16: pKF045, *I. orientalis* PYC1 expression construct.

The plasmids are transformed into E. coli, and transformants are selected on LB plates containing 100 µg/ml carbenicillin and screened using primers flanking the NotI site of pKF031 and pKF044 (oKW93 (SEQ ID NO:108) and oKW95 (SEQ ID NO:109)). Quickchange PCR is performed using primers oKW96 (SEQ ID NO:110) and oKW97 (SEQ ID NO:111) to eliminate an internal NdeI site (T2847C). Correct plasmids are confirmed by sequencing, and the final constructs are designated pKF043 (MEL5 marker) (FIG. 15) and pKF045 (CYB2A marker) (FIG. 16).

Example 4C

Construction of S. cerevisiae PYC1 Expression Constructs pKWB14 and pKWB15

Figure 17:
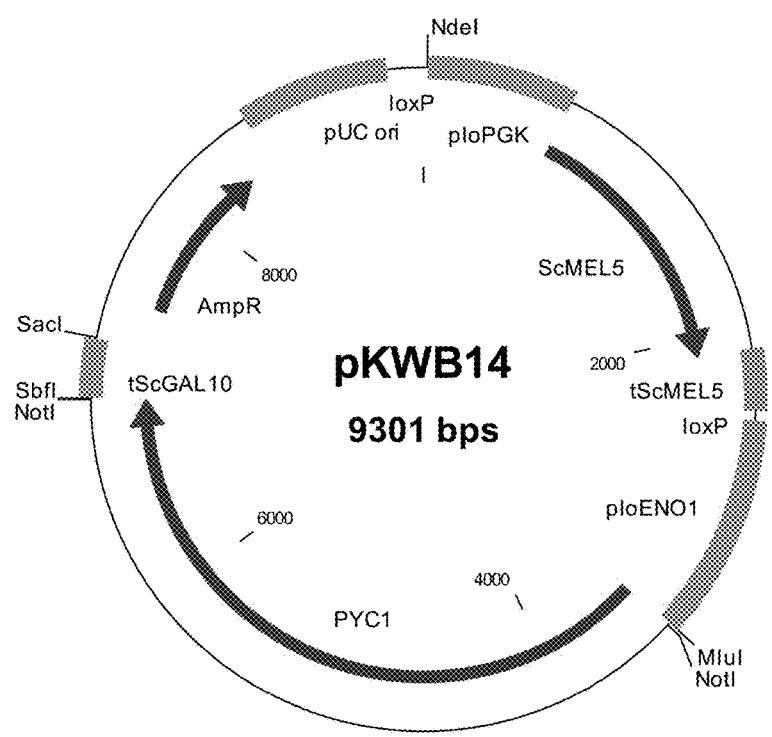
FIG. 17: pKWB14, *S. cerevisiae* PYC1 expression construct.
Figure 18:
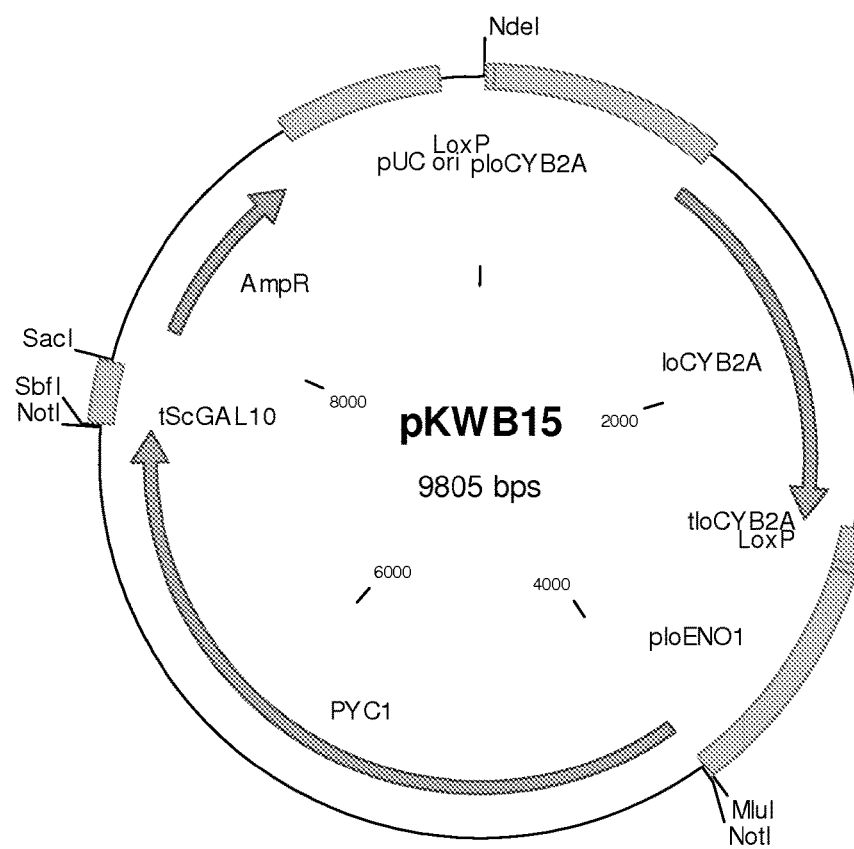
FIG. 18: pKWB15, *S. cerevisiae* PYC1 expression construct.

The PYC1 gene from S. cerevisiae (SEQ ID NO:9) is amplified from genomic DNA using Phusion polymerase and primers oKW29 (SEQ ID NO:80) and oKW30 (SEQ ID NO:81), both of which contain at their 5' end 23 bp flanking the NotI site in pKF031 and pKF044 to enable directional ligation-less cloning. After amplification, the product is gel purified and co-transformed into E. coli with NotI-digested pKF031 and pKF044. Transformants are selected on LB plates containing 100 µg/ml carbenicillin, and screened using primers oKW93 (SEQ ID NO:108) and oKW95 (SEQ ID NO:109). Quickchange PCR is performed using primers oKW81 (SEQ ID NO:102) and oKW82 (SEQ ID NO:103) to eliminate an internal NdeI site (T2838C). Correct plasmids are confirmed by sequencing, and the final constructs are designated pKWB14 (MEL5 marker) (FIG. 17) and pKWB15 (CYB2A marker) (FIG. 18).

Example 4D

Construction of K. marxianus PYC1 Expression Constructs pKWB16 and pKWB17

Figure 19:
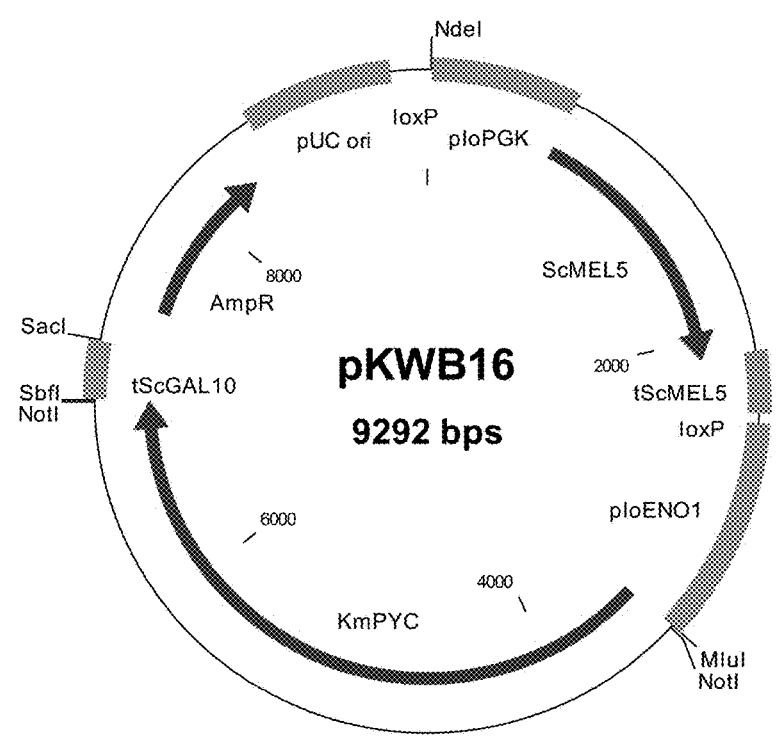
FIG. 19: pKWB16, *K. marxianus* PYC1 expression construct.
Figure 20:
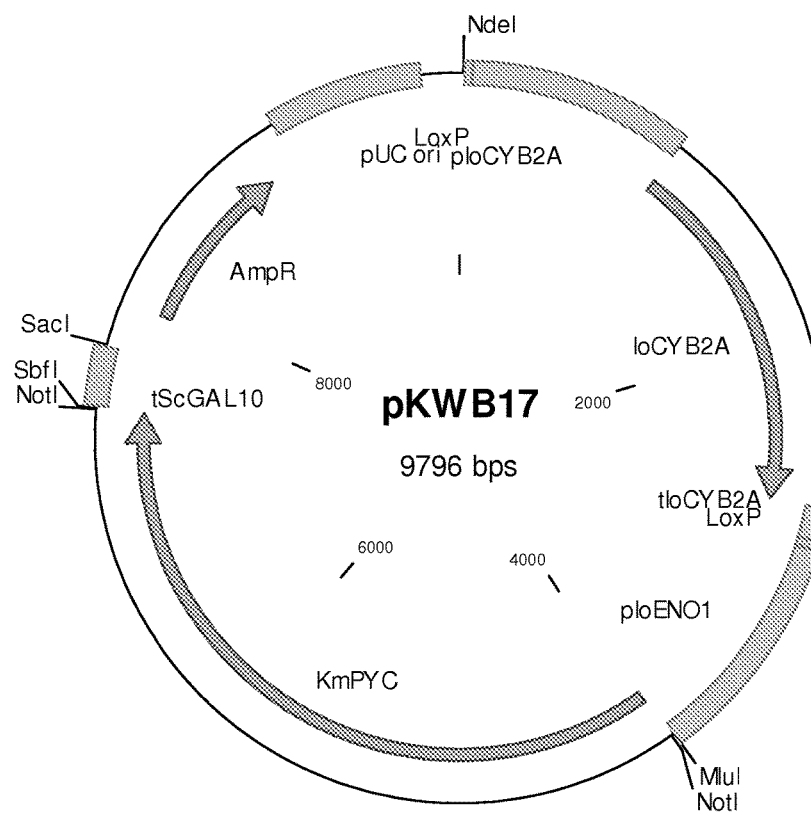
FIG. 20: pKWB17, *K. marxianus* PYC1 expression construct

K. marxianus is streaked on YPD plates, and after around 3 days the PYC1 gene (SEQ ID NO:11) is amplified from genomic DNA by colony PCR using primers oKW85 (SEQ ID NO:106) and oKW86 (SEQ ID NO:107). After amplification, the product is gel purified and co-transformed into E. coli with NotI-digested pKF031 and pKF044. Transformants are selected on LB plates containing 100 µg/ml carbenicillin, and screened using primers oKW93 (SEQ ID NO:108) and oKW95 (SEQ ID NO:109). Quickchange PCR is performed using primers oKW83 (SEQ ID NO:104) and oKW84 (SEQ ID NO:105) to eliminate an internal SacI site (T1446A). Correct plasmids are confirmed by sequencing, and the final constructs are designated pKWB16 (contains MEL5 marker) (FIG. 19) and pKWB17 (contains CYB2A marker) (FIG. 20).

Example 4E

Insertion of *I. orientalis* PYC1 at the First and Second PDC1 Loci in *I. orientalis* Strain 2732 pKF043 and pKF045 are both amplified from the loxP site on the 5' end to the GAL10 terminator on the 3' end. pKF043 is amplified using primers oKF243 (SEQ ID NO:132) and oKF244 (SEQ ID NO:133), and pKF045 is amplified using primers oKF255 (SEQ ID NO:137) and oKF244 (SEQ ID NO:133). Each of these primers contains on their 5' end 65 bp of sequence specific to the 65 bp immediately upstream and downstream of the PDC1 locus in *I. orientalis*. This recombination sequence enables double recombination and integration at the PDC1 locus.

The PCR product amplified from pKF043 is used to transform *I. orientalis* strain 2732. Transformants are selected on YNB+melibiose+x-α-gal and, and integration of PYC1 at a first PDC1 allele is confirmed by PCR using primers oCM566 (SEQ ID NO:138), oKF151 (SEQ ID NO:129), oKF252 (SEQ ID NO:136), and oCM587 (SEQ ID NO:139). The correct heterozygous strain is designated SSK10.

Strain SSK10 is transformed with the PCR product from pKF045 amplification to generate a homozygous strain with PYC1 inserted at both PDC1 alleles. Integration is confirmed by PCR using the primers oCM566 (SEQ ID NO:138), oMM174 (SEQ ID NO:59), oCM587 (SEQ ID NO:139), and oCA397 (SEQ ID NO:71). The correct homozygous strain is designated 12339.

For marker recycling, *I. orientalis* 12339 was grown to around $OD_{600}$ of 1.0 in YP+100 g/L glucose (50 ml media in a 250 ml flask; 30° C./250 rpm). Cells were transformed with pVB32 using lithium acetate transformation, and transformants were selected on YNB+2% sucrose plates overlaid with x-α-gal. After 4 to 5 days, white colonies were streaked to YP+20 g/L glucose plates overlaid with x-α-gal and grown at 37° C. for 2 days. Genomic DNA from white colonies was screened for retention of the expression cassette at the *I. orientalis* PDC1 locus and for loss of the selectable markers using PCR primers oGPB9 (SEQ ID NO:140), oGPB10 (SEQ ID NO:141), oGPB11 (SEQ ID NO:142), and oGPB12 (SEQ ID NO:143). Positive transformants were confirmed to have lost the marker by a phenotypic screen showing no growth on YNB+2% lactic, 2% melabiose, or 2% sucrose. The homozygous strain with both markers removed was designated 12429.

Example 4F

Insertion of *S. cerevisiae* PYC1 at First and Second PDC1 Loci in *I. orientalis* Strain 12429 pKWB14 and pKWB15 are both digested with NdeI/SacI to liberate the fragment containing the marker cassette, ENO promoter, PYC1 gene, and terminator. These fragments are cloned into pKWB21 digested with NdeI and SacI, and the resultant plasmid is transformed into *E. coli*. Transformants are selected on LB+kanamycin, and colonies are screened with M13F and M13R primers. Clones having the desired insert are designated pKWB45 (MEL5 marker) and pKWB46 (CYB2B marker).

pKWB45 is digested with PmeI, gel purified, and transformed into *I. orientalis* strain 12429. Transformants are selected on YNB+lactate or YNB+melibiose+x-α-gal and screened by PCR using flanking primers oKW70 (SEQ ID NO:92) and oKW73 (SEQ ID NO:95) and nested primers oGPB53 (SEQ ID NO:149), oGPB55 (SEQ ID NO:151), oKW121 (SEQ ID NO:121), oKW122 (SEQ ID NO:122) to verify correct insertion at the PDC1 locus. A heterozygous strain with the *S. cerevisiae* PYC1 gene inserted at a first PDC1 locus is designated ySBCK9.

Strain ySBCK9 is transformed with pKWB46 digested with PmeI, and transformants are screened for integration as above. Strains homozygous for *S. cerevisiae* PYC1 at the PDC1 loci are designated ySBCK10.

Marker recycling is carried out, and the homozygous strain with both markers removed is designated ySBCK11.

Example 4G

Insertion of *K. marxianus* PYC1 at First and Second PDC1 Loci in *I. orientalis* Strain 12429 pKWB16 and pKWB17 are both digested with NdeI/SacI to liberate the fragment containing the marker cassette, ENO promoter, PYC gene, and terminator. These fragments are cloned into pKWB21 digested with NdeI and SacI, and the resultant plasmid is transformed into *E. coli*. Transformants are selected on LB+kanamycin, and colonies are screened with M13F and M13R primers. Clones having the desired insert are designated pKWB47 (MEL5 marker) and pKWB48 (CYB2A marker).

pKWB47 is digested with PmeI, gel purified, and transformed into *I. orientalis* 12429. Transformants are selected on YNB+lactate or YNB+melibiose and screened by PCR using flanking primers oKW70 (SEQ ID NO:92) and oKW73 (SEQ ID NO:95) and nested primers oGPB53 (SEQ ID NO:149), oGPB55 (SEQ ID NO:151), oKW83 (SEQ ID NO:104), oKW84 (SEQ ID NO:105) to verify correct insertion at the PDC1 locus. A heterozygous strain *K. marxianus* PYC1 gene inserted at a first PDC1 locus is designated ySBCK12.

Strain ySBCK12 is transformed with pKWB48 digested with PmeI, and transformants are screened for integration as above. Strains homozygous for *K. marxianus* PYC1 are designated ySBCK13. Marker recycling is carried out, and the homozygous strain with both markers removed is designated ySBCK14.

The various PYC1 insertion/PDC1 deletion strains generated in Example 4 are summarized in Table 7.

TABLE 7

| *I. orientalis* PYC1 insertion strains: | | |
|---|---|---|
| Strain name | Description | Parent strain |
| SSK10 | CYB2A deletion (2) GPD1 deletion (2) CYB2B deletion (2) *I. orientalis* PYC1 insertion at PDC1 (1) | 2732 |

TABLE 7-continued

*I. orientalis* PYC1 insertion strains:

| Strain name | Description | Parent strain |
|---|---|---|
| 12339/12429 | CYB2A deletion (2)<br>GPD1 deletion (2)<br>CYB2B deletion (2) | SSK10 |
| ySBCK9 | *I. orientalis* PYC1 insertion at PDC1 (2)<br>CYB2A deletion (2)<br>GPD1 deletion (2)<br>CYB2B deletion (2) | 12429 |
| ySBCK10/<br>ySBCK11 | *S. cerevisiae* PYC1 insertion at PDC1 (1)<br>CYB2A deletion (2)<br>GPD1 deletion (2)<br>CYB2B deletion (2) | ySBCK9 |
| ySBCK12 | *S. cerevisiae* PYC1 insertion at PDC1 (2)<br>CYB2A deletion (2)<br>GPD1 deletion (2)<br>CYB2B deletion (2) | 12429 |
| ySBCK13/<br>ySBCK14 | *K. marxianus* PYC1 insertion at PDC1 (1)<br>CYB2A deletion (2)<br>GPD1 deletion (2)<br>CYB2B deletion (2)<br>*K. marxianus* PYC1 insertion at PDC1 (2) | ySBCK12 |

Example 5

Insertion of MDH at the ATO2 Locus in *I. orientalis* Strain 12429

An MDH expression cassette is inserted at one or both ATO2 alleles of *I. orientalis* strain 12429 (Example 4).

Example 5A

Construction of ATO2 Deletion Construct pKWB18

Figure 13:
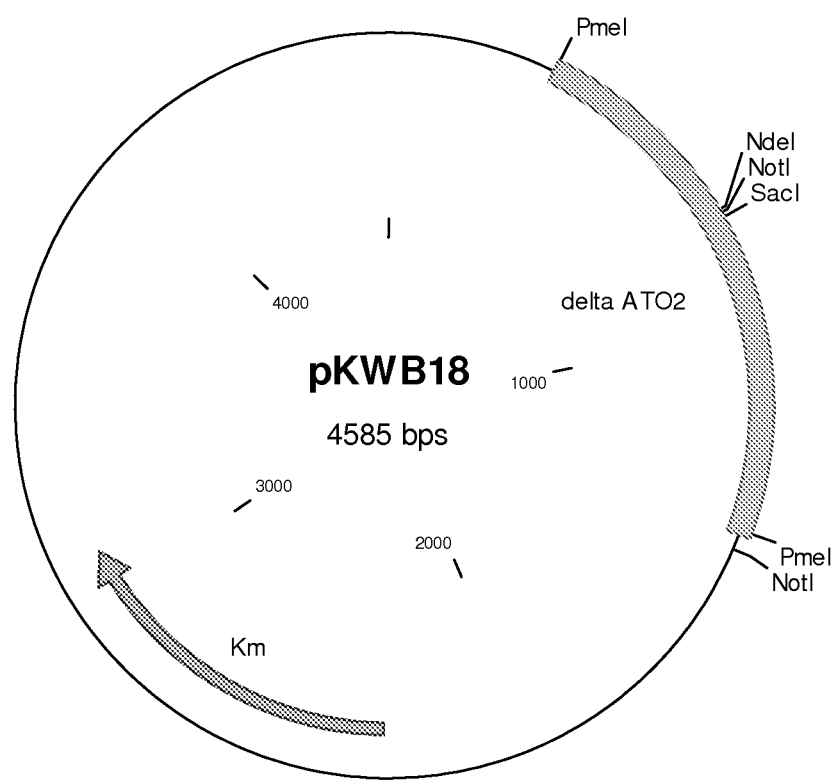
FIG. 13: pKWB18, ATO2 deletion construct

Upstream and downstream regions of *I. orientalis* ATO2 (SEQ ID NO:53) were amplified in order to generate an ATO2 deletion construct. The upstream and downstream regions correspond to nucleotides from 419 bp upstream to the start codon of ATO2 and from the stop codon to 625 bp downstream, respectively. Amplification of the upstream region is performed using primers oKW66 (forward, SEQ ID NO:88) and oKW67 (reverse, SEQ ID NO:89), which adds a PmeI restriction site and NdeI, NotI, and SacI restriction sites, respectively, to the product. Amplification of the downstream region is performed using primers oKW68 (forward, SEQ ID NO:90) and oKW69 (reverse, SEQ ID NO:91), which adds NdeI, NotI, and SacI restriction sites and a PmeI restriction site, respectively, to the product. The two fragments are amplified independently, then assembled into a full-length product with a two stage PCR protocol. The first stage uses 10 cycles (98° C. 10 s, 55° C. 20 s, 72° C. 60 s) with no primers, and the second stage uses 20 cycles (98° C. 10 s, 55° C. 20 s, 72° C. 60 s) with upstream forward and downstream reverse primers. The full-length product is gel purified, cloned into pCR-BluntII (Invitrogen), and sequenced. The plasmid confirmed to have correct sequence is subjected to quickchange PCR using Phusion polymerase to eliminate the plasmid-borne SacI site. Correct plasmids are confirmed by digestion with SacI and sequencing. The final ATO2 deletion construct is designated pKWB18 (FIG. 13).

Example 5B

Construction of *I. orientalis* MDH Expression Constructs pKWB2-pKWB7

The MDH1, MDH2, and MDH3 genes from *I. orientalis* (SEQ ID NOs:13, 15, and 17, respectively) are amplified from genomic DNA using primers designed for ligation-less cloning into the NotI site of pKF031 and pKF044. MDH1 is amplified using primers oKW13 (SEQ ID NO:74) and oKW14 (SEQ ID NO:75), MDH2 is amplified using primers oKW15 (SEQ ID NO:76) and oKW16 (SEQ ID NO:77), and MDH3 is amplified using primers oKW114 (SEQ ID NO:118) and oKW18 (SEQ ID NO:79). After amplification, the product is gel purified and co-transformed into *E. coli* with NotI-digested pKF031 and pKF044. Transformants are selected on LB plates containing 100 µg/ml carbenicillin, and screened using primers oKW93 and oKW95. Correct plasmids are confirmed by sequencing, and the final constructs are designated pKWB2 (MDH1, MEL5 marker), pKWB3 (MDH2, MEL5 marker), pKWB4 (MDH3, MEL5 marker), pKWB5 (MDH1, CYB2A marker), pKWB6 (MDH2, CYB2A marker), and pKWB7 (MDH3, CYB2A marker).

Example 5C

Construction of *K. marxianus* MDH Expression Constructs pKWB8-pKWB13

The MDH1, MDH2, and MDH3 genes from *K. marxianus* (SEQ ID NOs:19, 21, and 23, respectively) are amplified from genomic DNA using primers designed for ligation-less cloning into the NotI site of pKF031 and pKF044. MDH1 is amplified using primers oKW100 (SEQ ID NO:112) and oKW101 (SEQ ID NO:113), MDH2 is amplified using primers oKW102 (SEQ ID NO:114) and oKW103 (SEQ ID NO:115), and MDH3 is amplified using primers oKW104 (SEQ ID NO:116) and oKW105 (SEQ ID NO:117). After amplification, the product is gel purified and co-transformed into *E. coli* with NotI-digested pKF031 and pKF044. Transformants are selected on LB plates containing 100 µg/ml carbenicillin, and screened using primers oKW93 (SEQ ID NO:108) and oKW95 (SEQ ID NO:109). Quickchange PCR is performed on MDH2 using primers oKW132 (SEQ ID NO:123), oKW133 (SEQ ID NO:124), oKW134 (SEQ ID NO:125), and oKW135 (SEQ ID NO:126) to eliminate internal SacI sites (G609A and G819A). Quickchange PCR is performed on MDH3 using primers oKW136 and oKW137 to eliminate an internal NdeI site (T18C). Correct plasmids are confirmed by sequencing, and the final constructs are designated pKWB8 (MDH1, MEL5 marker), pKWB9 (MDH2, MEL5 marker), pKWB10 (MDH3, MEL5 marker), pKWB11 (MDH1, CYB2a marker), pKWB12 (MDH2, CYB2a marker), and pKWB13 (MDH3, CYB2a marker).

Example 5D

Insertion of *I. orientalis* MDH1, MDH2, and MDH3 at First and Second ATO2 Loci in *I. orientalis* Strain 12429 pKWB2, pKWB3, pKWB4, pKWB5, pKWB6, and pKWB7 are digested with NdeI and SacI to liberate the fragment containing selectable marker, ENO promoter, *I. orientalis* MDH1, 2, or 3, and terminator. These fragments are cloned into NdeI/SacI digested pKWB18 (ATO2 deletion construct), followed by selection on LB+kanamycin. Colonies are screened with M13F (SEQ ID NO:152) and M13R (SEQ ID NO:153) primers to confirm correct clones, which are designated pKWB33 (MDH1, MEL5), pKWB34

(MDH2, MEL5), pKWB35 (MDH3, MEL5), pKWB36 (MDH1, CYB2A), pKWB37 (MDH2, CYB2A), and pKWB38 (MDH3, CYB2A).

pKWB33, pKWB34, and pKWB35 are digested with PmeI and the appropriate fragments transformed into *I. orientalis* strain 12429 by lithium acetate transformation. Transformants are selected by growth on YNB+lactate or YNB+melibiose and screened by PCR with primers flanking the ATO2 locus (oKW66 (SEQ ID NO:88) and oKW69 (SEQ ID NO:91)) along with nested primers specific to each MDH (oKW13 (SEQ ID NO:74), oKW14 (SEQ ID NO:75), oKW15 (SEQ ID NO:76), oKW16 (SEQ ID NO:77), oKW114 (SEQ ID NO:118), oKW18 (SEQ ID NO:79)). Colonies with the correct insertion of MDH at a first ATO2 locus are designated ySBCK15 (MDH1), ySBCK18 (MDH2), and ySBCK21 (MDH3).

ySBCK15, ySBCK18, and ySBCK21 are transformed with pKWB36, pKWB37, and pKWB38, respectively, and transformants are screened for MDH integration as above. Strains homozygous for *I. orientalis* MDH at the ATO2 loci are designated ySBCK16 (MDH1), ySBCK19 (MDH2), and ySBCK22 (MDH3).

Marker recycling is carried out using pVB32, and homozygous strains with both markers removed are designated ySBCK17 (MDH1), ySBCK20 (MDH2), and ySBCK23 (MDH3).

Example 5E

Insertion of *K. marxianus* MDH1, MDH2, and MDH3 at First and Second ATO2 Loci in *I. orientalis* Strain 12429 pKWB8, pKWB9, pKWB10, pKWB11, pKWB12, and pKWB13 are digested with NdeI and SacI to liberate the fragment containing selectable marker, ENO promoter, *K. marxianus* MDH1, 2, or 3, and terminator. These fragments are cloned into NdeI/SacI digested pKWB18 (ATO2 deletion construct), transformed into *E. coli*, and selected on LB+kanamycin. Colonies are screened with M13F (SEQ ID NO:152) and M13R (SEQ ID NO:153) primers to confirm correct clones, which are designated pKWB39 (MDH1, MEL5), pKWB40 (MDH2, MEL5), pKWB41 (MDH3, MEL5), pKWB42 (MDH1, CYB2A), pKWB43 (MDH2, CYB2A), pKWB44 (MDH3, CYB2A).

pKWB39, pKWB40, and pKWB41 are digested with PmeI and the appropriate fragments are used to transform *I. orientalis* strain 12429 by lithium acetate transformation. Transformants are selected by growth on YNB+lactate or YNB+melibiose and screened by PCR with primers flanking the ATO2 locus (oKW66 (SEQ ID NO:88) and oKW69 (SEQ ID NO:91)) along with nested primers specific to each MDH (oKW100 (SEQ ID NO:112), oKW101 (SEQ ID NO:113), oKW102 (SEQ ID NO:114), oKW103 (SEQ ID NO:115), oKW104 (SEQ ID NO:116), oKW105 (SEQ ID NO:117)). Colonies with the correct insertion of MDH at a first ATO2 locus are designated ySBCK24 (MDH1), ySBCK27 (MDH2), and ySBCK30 (MDH3).

pKWB42, pKWB43, and pKWB44 are digested with PmeI and transformed into ySBCK24, ySBCK27, and ySBCK30, respectively, and transformants are screened for MDH integration as above. Strains homozygous for *K. marxianus* MDH at the ATO2 loci are designated ySBCK25 (MDH1), ySBCK28 (MDH2), and ySBCK31 (MDH3).

Marker recycling is carried out using pVB32, and homozygous strains with both markers removed are designated ySBCK26 (MDH1), ySBCK29 (MDH2), and ySBCK32 (MDH3).

The various MDH insertion/ATO2 deletion strains generated in Example 5 are summarized in Table 8.

TABLE 8

*I. orientalis* MDH insertion strains:

| Strain name | Description | Parent strain |
|---|---|---|
| ySBCK15 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (1) | 12429 |
| ySBCK16/<br>ySBCK17 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2) | ySBCK15 |
| ySBCK18 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (1) | 12429 |
| ySBCK19/<br>ySBCK20 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (2) | ySBCK18 |
| ySBCK21 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (1) | 12429 |
| ySBCK22/<br>ySBCK23 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2) | ySBCK21 |
| ySBCK24 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (1) | 12429 |
| ySBCK25/<br>ySBCK26 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2) | ySBCK24 |
| ySBCK27 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (1) | 12429 |
| ySBCK28/<br>ySBCK29 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2) | ySBCK27 |
| ySBCK30 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (1) | 12429 |
| ySBCK31/<br>ySBCK32 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2) | ySBCK30 |

Example 6

Insertion of FRD1 at the ADHa Locus in *I. orientalis* Strains 12429, ySBCK17, ySBCK20, ySBCK23, ySBCK26, ySBCK29, and ySBCK32

An FRD1 expression cassette is inserted at one or both ADHa alleles of *I. orientalis* strains 12429 (Example 4) and strains ySBCK17, ySBCK20, ySBCK23, ySBCK26, ySBCK29, and ySBCK32 (Example 5).

Example 6A

Figure 21:
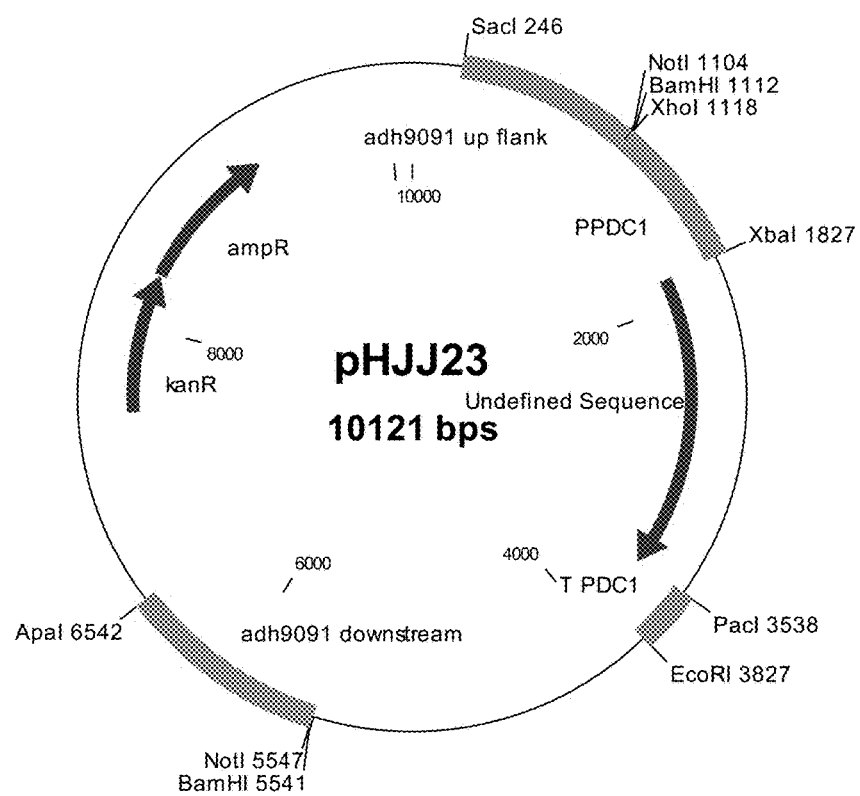
FIG. 21: pHJJ23
Figure 22:
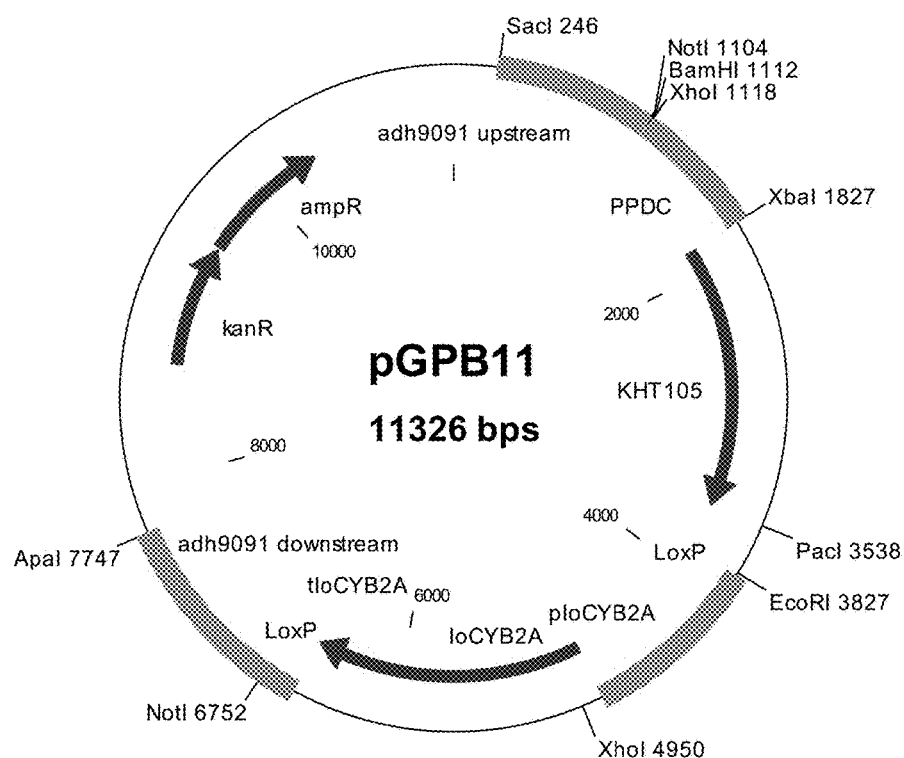
FIG. 22: pGPB11, ADHa deletion construct.
Figure 23:
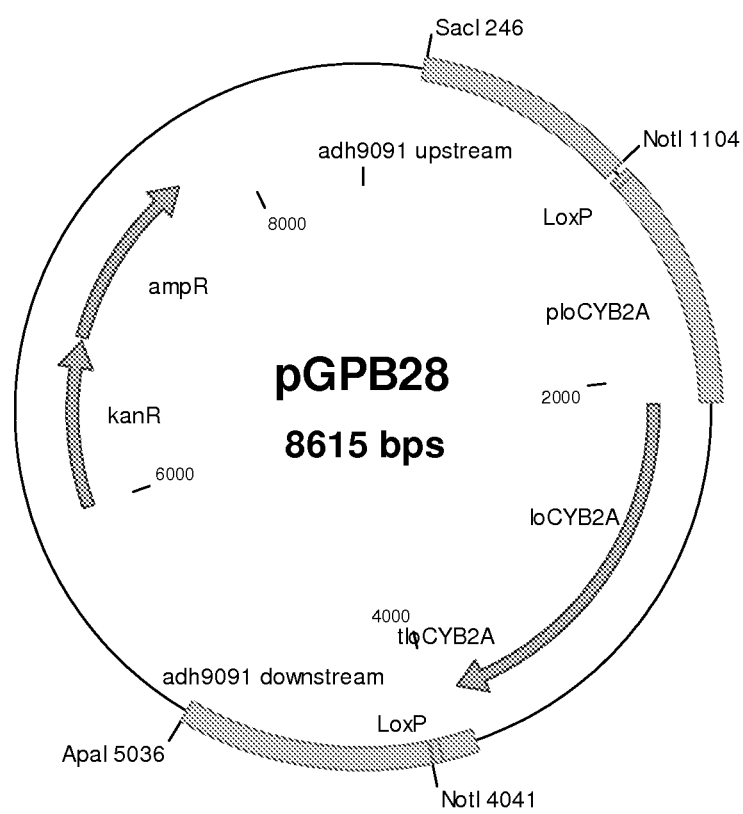
FIG. 23: pGPB28, ADHa deletion construct.
Figure 24:
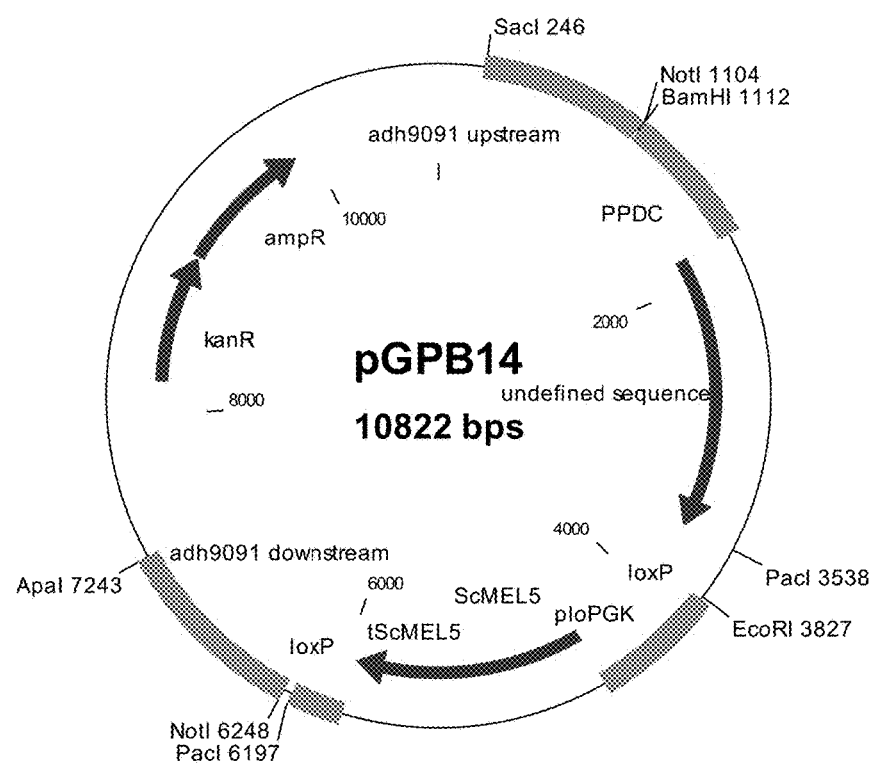
FIG. 24: pGPB14, ADHa deletion construct.
Figure 25:
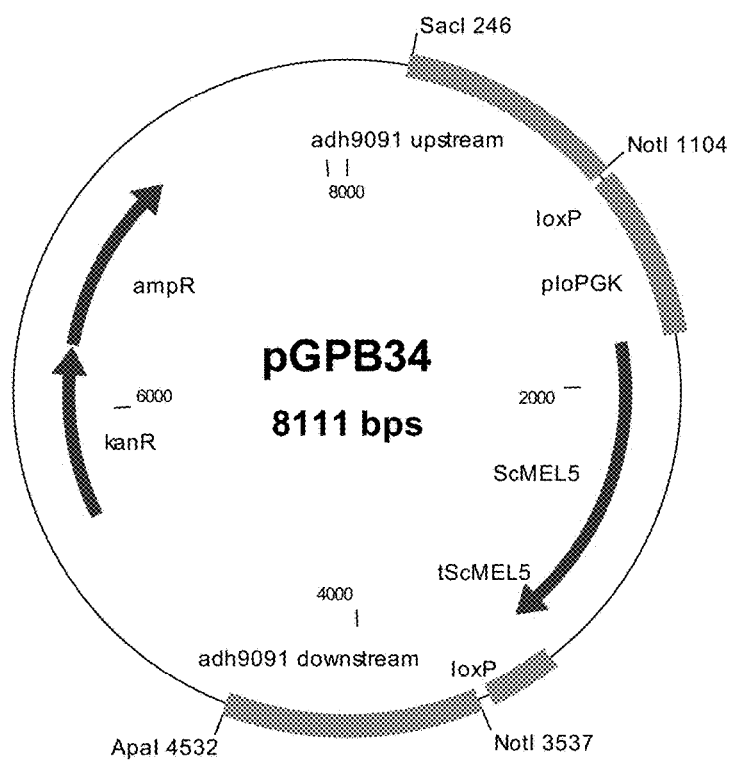
FIG. 25: pGPB34, ADHa deletion construct.

Construction of ADHa Deletion Constructs pGPB11, pGPB14, pGPB28, and pGPB34 pKF044 was used as a template for quickchange mutagenesis using oligonucleotides oKW64 (SEQ ID NO:86) and oKW65 (SEQ ID NO:87) to delete an EcoRI site at nucleotide 932 of the *I. orientalis* CYB2A gene. The resulting plasmid was designated pKW49. pKW49 was digested with EcoRI and BglII and the resultant fragment ligated to EcoRI and BamHI digested pHJJ23 (FIG. 21). The resulting ADHa deletion construct, designated pGPB11 (FIG. 22), contains the *I. orientalis* PDC1 promoter (amplified using primers oJLJ3 (SEQ ID NO:156) and oJLJ19 (SEQ ID NO:157)) and terminator (amplified using primers oJLJ1 (SEQ ID NO:154) and oJLJ2 (SEQ ID NO:155)) and a CYB2A marker element between an 858 bp fragment corresponding to the region immediately 5' of the *I. orientalis* AHD2a open reading frame (amplified using primers oHJJ71 (SEQ ID NO:159) and oHJJ72 (SEQ ID NO:160)) and a 996 bp fragment corresponding to the region immediately 3' of the *I. orientalis* ADHa open reading frame (amplified using primer oHJJ73 (SEQ ID NO:161) and oHJJ74 (SEQ ID NO:162)).

pKF046, which contains an *S. cerevisiae* MEL5 marker gene operatively linked to a *I. orientalis* PGK promoter and an *S. cerevisiae* MEL5 terminator and flanked by LoxP sites, was used as a template for quickchange mutagenesis using oligonucleotides oKW74 (SEQ ID NO:96) and oKW75 (SEQ ID NO:97) to delete an EcoRI site at nucleotide 2392 of the plasmid. The resulting plasmid was designated pKW50. pKW50 was digested with EcoRI and BglII and the resultant fragment ligated to EcoRI and BamHI digested pHJJ23. The resulting plasmid, designated pGPB14 (FIG. 24), contains the same elements as pGPB11, but with the CYB2A selectable marker element replaced by the *S. cerevisiae* MEL5 selectable marker element.

pGPB11 and pGPB14 were each digested with EcoRI and BamHI to remove those portions of the plasmids corresponding to the PDC promoter and terminator, and each plasmid backbone was blunted with Klenow fragment and ligated to recirculariize the plasmid. The plasmids were then transformed into *E. coli*. Plasmid isolated from positive colonies was designated pGPB28 (FIG. 23, derived from pGPB11) and pGPB34 (FIG. 25, derived from pGPB14).

Example 6B

Construction of FRD1 Expression Constructs pGPB20, pGPB22, pGPB25, pGPB26, pGPB36, pGPB37, pGPB39, and pGPB40

Figure 26:
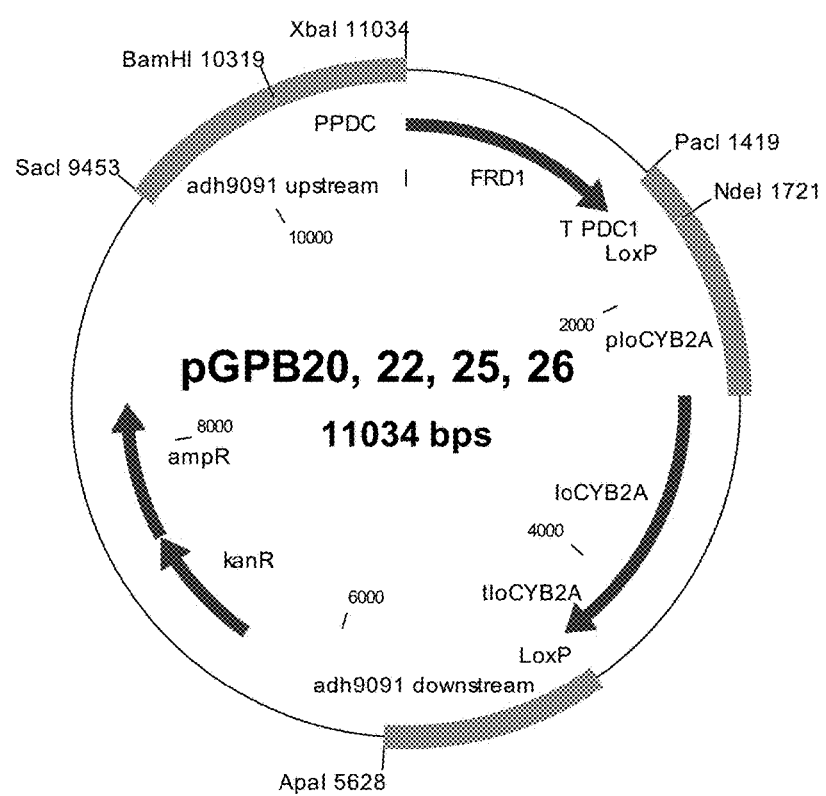
FIG. 26: pGPB20, 22, 25, and 26, FRD1 expression constructs.
Figure 27:
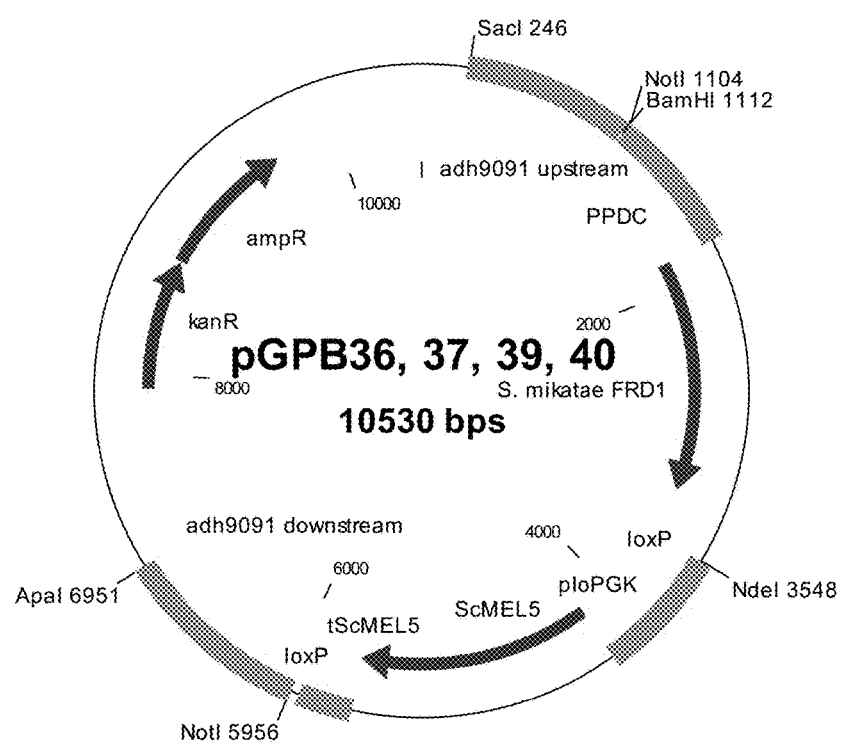
FIG. 27: pGPB36, 37, 39, and 40, FRD1 expression constructs.

Expression cassettes for the FRD1 gene from various sources were inserted into the ADHa deletion construct pGPB11. Sources for the FRD1 gene were *S. cerevisiae* (SEQ ID NO:25), *S. mikatae* (SEQ ID NO:27), *K. polyspora* (SEQ ID NO:29), and *K. marxianus* (SEQ ID NO:31). The latter three genes were all codon optimized to *I. orientalis*. Plasmids containing *S. cerevisiae*, *S. mikatae*, *K. polyspora*, or *K. marxianus* FRD1 genes were digested with XbaI and PacI, and the FRD1 fragments were ligated to similarly digested pGPB11. The resulting plasmids, which contained the FRD1 coding sequence flanked by the *I. orientalis* PDC1 promoter and terminator and also contained the *I. orientalis* CYB2A selectable marker, were designated pGPB20 (*S. mikatae* FRD1), pGPB22 (*K. marxianus* FRD1), pGPB25 (*K. polyspora* FRD1), and pGPB26 (*S. cerevisiae* FRD1) (FIG. 26).

pGPB20, pGP22, pGPB25, and pGPB26 were digested with BamHI and NdeI and ligated to similarly digested pGPB14. The resulting plasmids, which contained the FRD1 coding sequence flanked by the *I. orientalis* PDC1 promoter and terminator and also contained the *S. cerevisiae* MEL5 selectable marker were designated pGPB36 (*S. mikatae* FRD1), pGP37 (*K. marxianus* FRD1), pGPB39 (*K. polyspora* FRD1), and pGPB40 (*S. cerevisiae* FRD1) (FIG. 27).

Example 6C

Insertion of *K. marxianus* FRD1 at First ADHa Loci of *I. orientalis* Strain 12429 pGPB22 is digested with SacI and ApaI and transformed into *I. orientalis* strain 12429 by lithium acetate transformation. Transformants are selected on YNB+2% lactic plates overlaid with x-α-gal. After around six days, white transformants are picked and plated for single colonies on YP+20 g/L glucose plates containing x-α-gal. White colonies are picked, and genomic DNA is isolated and screened by PCR to confirm integration of the FRD1 expression cassette at the ADHa locus using primers oGPB47 (SEQ ID NO:147), oJLJ43 (SEQ ID NO:158), oKW64 (SEQ ID NO:86), and oGPB46 (SEQ ID NO:146). Strains with the correct integration of the FRD1 gene are designated ySBCG4, ySBCG5, and ySBCG6.

Example 6D

Insertion of FRD1 at First and Second ADHa Loci of *I. orientalis* Strains ySBCK17, ySBCK20, ySBCK23, ySBCK26, ySBCK29, and ySBCK32 pGPB20 (*S. mikatae* FRD1), pGPB22 (*K. marxianus* FRD1), pGPB25 (*K. polyspora* FRD1), and pGPB26 (*S. cerevisiae* FRD1) are digested with SacI and ApaI and transformed into strains ySBCK17, ySBCK20, ySBCK23, ySBCK26, ySBCK29, and ySBCK32 by lithium acetate transformation. Transformants are screened by PCR to confirm correct integration of the FRD1 expression cassette at a first ADHa locus using primers oGPB47 (SEQ ID NO:147), oJLJ43 (SEQ ID NO:158), oKW64 (SEQ ID NO:86), and oGPB46 (SEQ ID NO:146). The resulting strains are designated ySBCGH1-24.

pGPB36 (*S. mikatae* FRD1), pGPB37 (*K. marxianus* FRD1), pGPB39 (*K. polyspora* FRD1), and pGPB40 (*S. cerevisiae* FRD1) are digested with SacI and ApaI and transformed into strains ySBCGH1-24 by lithium acetate transformation. Transformants are screened by PCR to confirm correct integration of the FRD1 expression cassette at the second ADHa locus using primers oGPB47 (SEQ ID NO:147), oJLJ43 (SEQ ID NO:158), oGPB54 (SEQ ID NO:150), and oGPB46 (SEQ ID NO:146). The resulting strains are designated ySBCGH25-48.

Marker recycling is carried out with plasmid pVB32. The correct homozygous strains with both markers removed are designated ySBCGH49-72.

The various FRD1 insertion/ADHa deletion strains generated in Example 6 are summarized in Table 9.

TABLE 9

| Strain name | Description | Parent strain |
|---|---|---|
| ySBCG4/ySBCG5/ySBCG6 | CYB2A deletion (2)<br>GPD1 deletion (2)<br>CYB2B deletion (2)<br>*I. orientalis* PYC1 insertion at PDC1 (2)<br>*K. marxianus* FRD1 insertion at ADHa (1) | 12429 |
| ySBCGH1 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. mikatae* FRD1 insertion at ADHa (1) | ySBCK17 |
| ySBCGH25/ySBCGH49 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. mikatae* FRD1 insertion at ADHa (2) | ySBCGH1 |
| ySBCGH2 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. marxianus* FRD1 insertion at ADHa (1) | ySBCK17 |
| ySBCGH26/ySBCGH50 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. marxianus* FRD1 insertion at ADHa (2) | ySBCGH2 |
| ySBCGH3 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. polyspora* FRD1 insertion at ADHa (1) | ySBCK17 |
| ySBCGH27/ySBCGH51 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. polyspora* FRD1 insertion at ADHa (2) | ySBCGH3 |
| ySBCGH4 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. cerevisiae* FRD1 insertion at ADHa (1) | ySBCK17 |
| ySBCGH28/ySBCGH52 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. cerevisiae* FRD1 insertion at ADHa (2) | ySBCGH4 |
| ySBCGH5 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (2)<br>*S. mikatae* FRD1 insertion at ADHa (1) | ySBCK20 |
| ySBCGH29/ySBCGH53 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (2)<br>*S. mikatae* FRD1 insertion at ADHa (2) | ySBCGH5 |
| ySBCGH6 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (2)<br>*K. marxianus* FRD1 insertion at ADHa (1) | ySBCK20 |
| ySBCGH30/ySBCGH54 | CYB2A deletion (2)<br>GPD1 deletion (2)<br>CYB2B deletion (2)<br>*I. orientalis* PYC1 insertion at PDC1 (2) | ySBCGH6 |

TABLE 9-continued

| *I. orientalis* FRD1 insertion strains: | | |
|---|---|---|
| Strain name | Description | Parent strain |
| ySBCGH7 | *I. orientalis* MDH2 insertion at ATO2 (2)<br>*K. marxianus* FRD1 insertion at ADHa (2)<br>CYB2A deletion (2)<br>GPD1 deletion (2)<br>CYB2B deletion (2) | ySBCK20 |
| ySBCGH31/ySBCGH55 | *I. orientalis* PYC1 insertion at PDC1 (2)<br>*I. orientalis* MDH2 insertion at ATO2 (2)<br>*K. polyspora* FRD1 insertion at ADHa (1)<br>CYB2A deletion (2)<br>GPD1 deletion (2)<br>CYB2B deletion (2) | ySBCGH7 |
| ySBCGH8 | *I. orientalis* PYC1 insertion at PDC1 (2)<br>*I. orientalis* MDH2 insertion at ATO2 (2)<br>*K. polyspora* FRD1 insertion at ADHa (2)<br>CYB2A deletion (2)<br>GPD1 deletion (2)<br>CYB2B deletion (2) | ySBCK20 |
| ySBCGH32/ySBCGH56 | *I. orientalis* PYC1 insertion at PDC1 (2)<br>*I. orientalis* MDH2 insertion at ATO2 (2)<br>*S. cerevisiae* FRD1 insertion at ADHa (1)<br>CYB2A deletion (2)<br>GPD1 deletion (2)<br>CYB2B deletion (2) | ySBCGH8 |
| ySBCGH9 | *I. orientalis* PYC1 insertion at PDC1 (2)<br>*I. orientalis* MDH2 insertion at ATO2 (2)<br>*S. cerevisiae* FRD1 insertion at ADHa (2)<br>CYB2A deletion (2)<br>GPD1 deletion (2)<br>CYB2B deletion (2) | ySBCK23 |
| ySBCGH33/ySBCGH57 | *I. orientalis* PYC1 insertion at PDC1 (2)<br>*I. orientalis* MDH3 insertion at ATO2 (2)<br>*S. mikatae* FRD1 insertion at ADHa (1)<br>CYB2A deletion (2)<br>GPD1 deletion (2)<br>CYB2B deletion (2) | ySBCGH9 |
| ySBCGH10 | *I. orientalis* PYC1 insertion at PDC1 (2)<br>*I. orientalis* MDH3 insertion at ATO2 (2)<br>*S. mikatae* FRD1 insertion at ADHa (2)<br>CYB2A deletion (2)<br>GPD1 deletion (2)<br>CYB2B deletion (2) | ySBCK23 |
| ySBCGH34/ySBCGH58 | *I. orientalis* PYC1 insertion at PDC1 (2)<br>*I. orientalis* MDH3 insertion at ATO2 (2)<br>*K. marxianus* FRD1 insertion at ADHa (1)<br>CYB2A deletion (2)<br>GPD1 deletion (2)<br>CYB2B deletion (2) | ySBCGH10 |
| ySBCGH11 | *I. orientalis* PYC1 insertion at PDC1 (2)<br>*I. orientalis* MDH3 insertion at ATO2 (2)<br>*K. marxianus* FRD1 insertion at ADHa (2)<br>CYB2A deletion (2)<br>GPD1 deletion (2)<br>CYB2B deletion (2) | ySBCK23 |
| ySBCGH35/ySBCGH59 | *I. orientalis* PYC1 insertion at PDC1 (2)<br>*I. orientalis* MDH3 insertion at ATO2 (2)<br>*K. polyspora* FRD1 insertion at ADHa (1)<br>CYB2A deletion (2)<br>GPD1 deletion (2)<br>CYB2B deletion (2) | ySBCGH11 |
| ySBCGH12 | *I. orientalis* PYC1 insertion at PDC1 (2)<br>*I. orientalis* MDH3 insertion at ATO2 (2)<br>*K. polyspora* FRD1 insertion at ADHa (2)<br>CYB2A deletion (2)<br>GPD1 deletion (2)<br>CYB2B deletion (2) | ySBCK23 |
| ySBCGH36/ySBCGH60 | *I. orientalis* PYC1 insertion at PDC1 (2)<br>*I. orientalis* MDH3 insertion at ATO2 (2)<br>*S. cerevisiae* FRD1 insertion at ADHa (1)<br>CYB2A deletion (2)<br>GPD1 deletion (2)<br>CYB2B deletion (2) | ySBCGH12 |
| ySBCGH13 | *I. orientalis* PYC1 insertion at PDC1 (2)<br>*I. orientalis* MDH3 insertion at ATO2 (2)<br>*S. cerevisiae* FRD1 insertion at ADHa (2)<br>CYB2A deletion (2)<br>GPD1 deletion (2) | ySBCK26 |

TABLE 9-continued

*I. orientalis* FRD1 insertion strains:

| Strain name | Description | Parent strain |
|---|---|---|
| ySBCGH37/ySBCGH61 | CYB2B deletion (2)<br>*I. orientalis* PYC1 insertion at PDC1 (2)<br>*K. marxianus* MDH1 insertion at ATO2 (2)<br>*S. mikatae* FRD1 insertion at ADHa (1)<br>CYB2A deletion (2)<br>GPD1 deletion (2) | ySBCGH13 |
| ySBCGH14 | CYB2B deletion (2)<br>*I. orientalis* PYC1 insertion at PDC1 (2)<br>*K. marxianus* MDH1 insertion at ATO2 (2)<br>*S. mikatae* FRD1 insertion at ADHa (2)<br>CYB2A deletion (2)<br>GPD1 deletion (2) | ySBCK26 |
| ySBCGH38/ySBCGH62 | CYB2B deletion (2)<br>*I. orientalis* PYC1 insertion at PDC1 (2)<br>*K. marxianus* MDH1 insertion at ATO2 (2)<br>*K. marxianus* FRD1 insertion at ADHa (1)<br>CYB2A deletion (2)<br>GPD1 deletion (2) | ySBCGH14 |
| ySBCGH15 | CYB2B deletion (2)<br>*I. orientalis* PYC1 insertion at PDC1 (2)<br>*K. marxianus* MDH1 insertion at ATO2 (2)<br>*K. marxianus* FRD1 insertion at ADHa (2)<br>CYB2A deletion (2)<br>GPD1 deletion (2) | ySBCK26 |
| ySBCGH39/ySBCGH63 | CYB2B deletion (2)<br>*I. orientalis* PYC1 insertion at PDC1 (2)<br>*K. marxianus* MDH1 insertion at ATO2 (2)<br>*K. polyspora* FRD1 insertion at ADHa (1)<br>CYB2A deletion (2)<br>GPD1 deletion (2) | ySBCGH15 |
| ySBCGH16 | CYB2B deletion (2)<br>*I. orientalis* PYC1 insertion at PDC1 (2)<br>*K. marxianus* MDH1 insertion at ATO2 (2)<br>*K. polyspora* FRD1 insertion at ADHa (2)<br>CYB2A deletion (2)<br>GPD1 deletion (2) | ySBCK26 |
| ySBCGH40/ySBCGH64 | CYB2B deletion (2)<br>*I. orientalis* PYC1 insertion at PDC1 (2)<br>*K. marxianus* MDH1 insertion at ATO2 (2)<br>*S. cerevisiae* FRD1 insertion at ADHa (1)<br>CYB2A deletion (2)<br>GPD1 deletion (2) | ySBCGH16 |
| ySBCGH17 | CYB2B deletion (2)<br>*I. orientalis* PYC1 insertion at PDC1 (2)<br>*K. marxianus* MDH1 insertion at ATO2 (2)<br>*S. cerevisiae* FRD1 insertion at ADHa (2)<br>CYB2A deletion (2)<br>GPD1 deletion (2) | ySBCK29 |
| ySBCGH41/ySBCGH65 | CYB2B deletion (2)<br>*I. orientalis* PYC1 insertion at PDC1 (2)<br>*K. marxianus* MDH2 insertion at ATO2 (2)<br>*S. mikatae* FRD1 insertion at ADHa (1)<br>CYB2A deletion (2)<br>GPD1 deletion (2) | ySBCGH17 |
| ySBCGH18 | CYB2B deletion (2)<br>*I. orientalis* PYC1 insertion at PDC1 (2)<br>*K. marxianus* MDH2 insertion at ATO2 (2)<br>*S. mikatae* FRD1 insertion at ADHa (2)<br>CYB2A deletion (2)<br>GPD1 deletion (2) | ySBCK29 |
| ySBCGH42/ySBCGH66 | CYB2B deletion (2)<br>*I. orientalis* PYC1 insertion at PDC1 (2)<br>*K. marxianus* MDH2 insertion at ATO2 (2)<br>*K. marxianus* FRD1 insertion at ADHa (1)<br>CYB2A deletion (2)<br>GPD1 deletion (2) | ySBCGH18 |
| ySBCGH19 | CYB2B deletion (2)<br>*I. orientalis* PYC1 insertion at PDC1 (2)<br>*K. marxianus* MDH2 insertion at ATO2 (2)<br>*K. marxianus* FRD1 insertion at ADHa (2)<br>CYB2A deletion (2)<br>GPD1 deletion (2) | ySBCK29 |
|  | CYB2B deletion (2)<br>*I. orientalis* PYC1 insertion at PDC1 (2)<br>*K. marxianus* MDH2 insertion at ATO2 (2)<br>*K. polyspora* FRD1 insertion at ADHa (1) |  |

TABLE 9-continued

| *I. orientalis* FRD1 insertion strains: | | |
|---|---|---|
| Strain name | Description | Parent strain |
| ySBCGH43/ySBCGH67 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. polyspora* FRD1 insertion at ADHa (2) | ySBCGH19 |
| ySBCGH20 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 insertion at ADHa (1) | ySBCK29 |
| ySBCGH44/ySBCGH68 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 at ADHa (2) | ySBCGH20 |
| ySBCGH21 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. mikatae* FRD1 insertion at ADHa (1) | ySBCK32 |
| ySBCGH45/ySBCGH69 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. mikatae* FRD1 insertion at ADHa (2) | ySBCGH21 |
| ySBCGH22 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. marxianus* FRD1 insertion at ADHa (1) | ySBCK32 |
| ySBCGH46/ySBCGH70 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. marxianus* FRD1 insertion at ADHa (2) | ySBCGH22 |
| ySBCGH23 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. polyspora* FRD1 insertion at ADHa (1) | ySBCK32 |
| ySBCGH47/ySBCGH71 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. polyspora* FRD1 insertion at ADHa (2) | ySBCGH23 |
| ySBCGH24 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. cerevisiae* FRD1 insertion at ADHa (1) | ySBCK32 |
| ySBCGH48/ySBCGH72 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. cerevisiae* FRD1 insertion at ADHa (2) | ySBCGH24 |

Example 7

Insertion of Single Copies of *I. orientalis* MDH Genes at the ATO2 Locus in *I. orientalis* Strain ySBCG5

*I. orientalis* MDH1, -MDH2, or MDH3 expression cassettes are inserted at one or both ATO2 alleles of *I. orientalis* strain ySBCG5 (Example 6).

Example 7A

Insertion of *I. orientalis* MDH1 at a First ATO2 Locus of *I. orientalis* Strain ySBCG5

A PCR product amplified with the primers oKF254 and oKF202 using pKWB2 as the template is transformed into strain ySBCG5 by lithium acetate transformation, and transformants are selected on YNB+2% melibiose plates overlaid with x-α-gal. Blue-colored transformants are visible after around 6 days of growth at 30° C. Transformants are picked and plated for single colonies on YP+20 g/L glucose plates containing x-α-gal. Blue colonies are picked, and genomic DNA is isolated and screened for correct integration of the MDH1 expression cassette at the ATO2 locus by PCR using primers oGPB55 (SEQ ID NO:151), oKW66 (SEQ ID NO:88), oKW69 (SEQ ID NO:91), and oGPB54 (SEQ ID NO:150). Sister strains with the correct integration of the MDH1 gene are designated ySBCG22 and ySBCG23.

Example 7B

Insertion of *I. orientalis* MDH2 at a First ATO2 Loci of *I. orientalis* Strain ySBCG5

A PCR product amplified with the primers oKF254 and oKF202 using pKWB3 as the template is transformed into strain ySBCG5 by lithium acetate transformation, and transformants are selected on YNB+2% melibiose plates overlaid with x-α-gal. Blue-colored transformants are visible after around 6 days of growth at 30° C. Transformants are picked and plated for single colonies on YP+20 g/L glucose plates containing x-α-gal. Blue colonies are picked, and genomic DNA is isolated and screened for correct integration of the MDH2 expression cassette at the ATO2 locus by PCR using primers oGPB55 (SEQ ID NO:151), oKW66 (SEQ ID NO:88), oKW69 (SEQ ID NO:91), and oGPB54 (SEQ ID NO:150). Strains with the correct integration of the MDH2 gene are designated ySBCG25 and ySBCG26.

The various MDH insertion/ATO2 deletion strains generated in Example 7 are summarized in Table 10.

TABLE 10

*I. orientalis* MDH insertion strains:

| Strain name | Description | Parent strain |
|---|---|---|
| ySBCG22/ ySBCG23 | CYB2A deletion (2) GPD1 deletion (2) CYB2B deletion (2) *I. orientalis* PYC1 insertion at PDC1 (2) *K. marxianus* FRD1 insertion at ADHa (1) *I. orientalis* MDH1 insertion at ATO2 (1) | ySBCG5 |
| ySBCG25/ ySBCG26 | CYB2A deletion (2) GPD1 deletion (2) CYB2B deletion (2) *I. orientalis* PYC1 insertion at PDC1 (2) *K. marxianus* FRD1 insertion at ADHa (1) *I. orientalis* MDH2 insertion at ATO2 (1) | ySBCG5 |

TABLE 10-continued

*I. orientalis* MDH insertion strains:

| Strain name | Description | Parent strain |
|---|---|---|
| | *K. marxianus* FRD1 insertion at ADHa (1) *I. orientalis* MDH2 insertion at ATO2 (1) | |

Example 8

Insertion of *I. orientalis* FUM1 Genes at the CYB2A Locus in *I. orientalis* Strains ySBCGH49-72

*I. orientalis* FUM1 expression cassettes are inserted at both alleles of CYB2A of *I. orientalis* strains ySBCGH49-72 (Example 6).

Example 8A

Construction of *I. orientalis* FUM1 Expression Constructs pGPB30, pGPB42, pGPB44, and pGPB47

Figure 28:
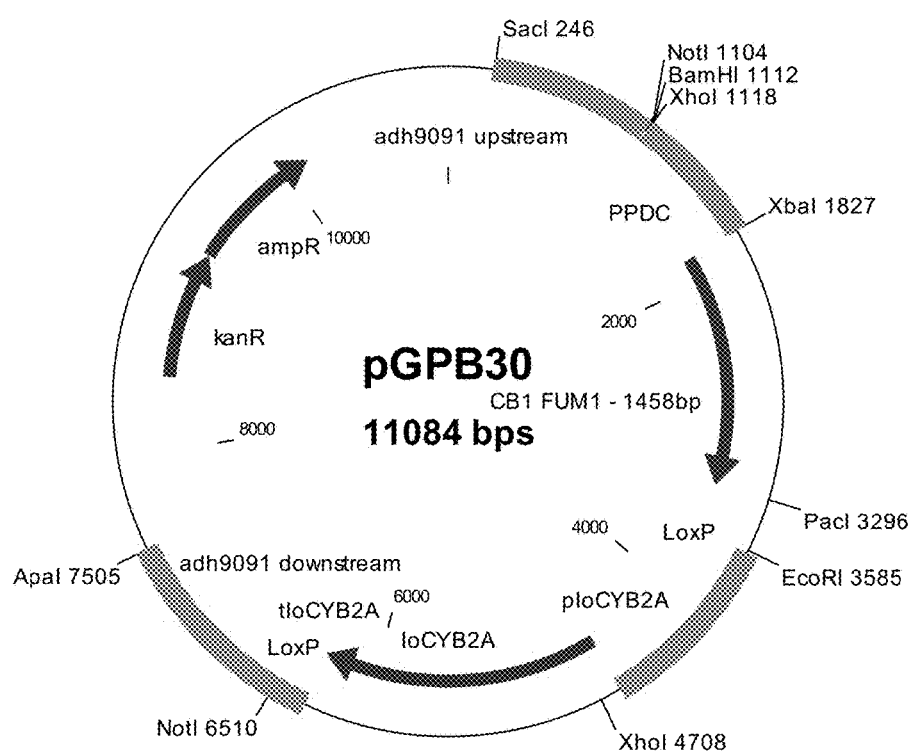
FIG. 28: pGPB30, FUM1 expression constructs.
Figure 30:
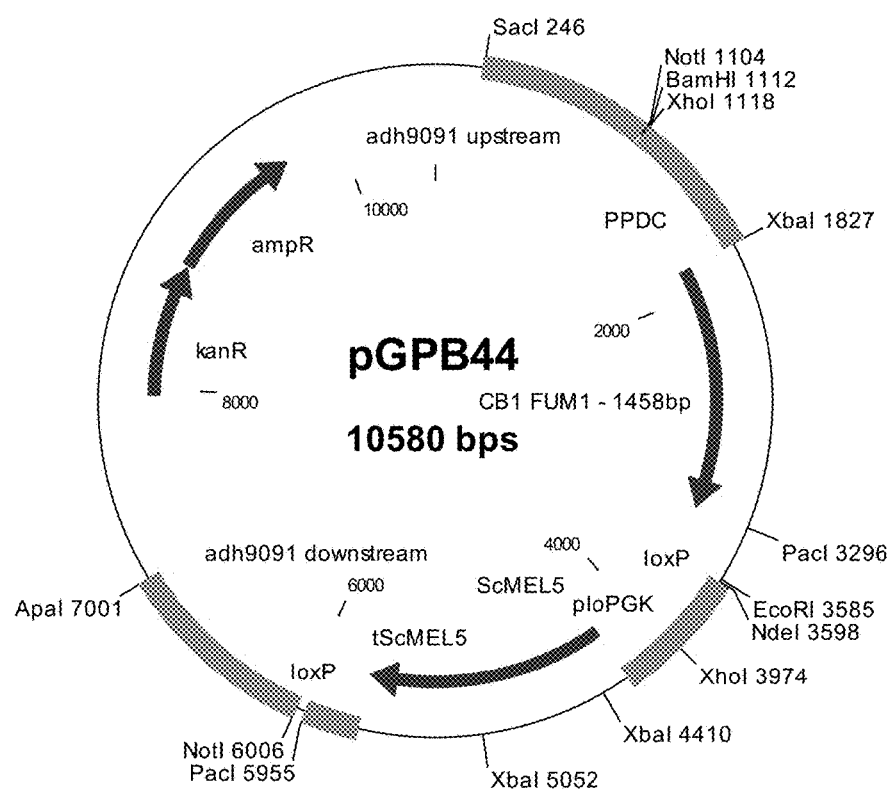
FIG. 30: pGPB44, FUM1 expression constructs.

An expression cassette for the *I. orientalis* FUM1 gene (SEQ ID NO:1) is inserted into the ADHa deletion construct pGPB11. PCR primers oGPB38 (SEQ ID NO:144) and oGPB40 (SEQ ID NO:145) are used to amplify FUM1 using *I. orientalis* genomic DNA as the template. The 5' primer adds an XbaI site at the start site of the coding sequence and the 3' primer adds a PacI site 3' of the stop codon. The resulting PCR product is digested with XbaI and PacI and ligated to similarly digested pGPB11. The resulting plasmid, which contains the FUM1 coding sequence flanked by the *I. orientalis* PDC1 promoter and terminator and the CYB2A selectable marker, is designated pGPB30 (FIG. 28).

pGPB30 is digested with BamHI and NdeI and ligated into similarly digested pGPB14. The resulting plasmid is designated pGPB44 (FIG. 30).

Figure 29:
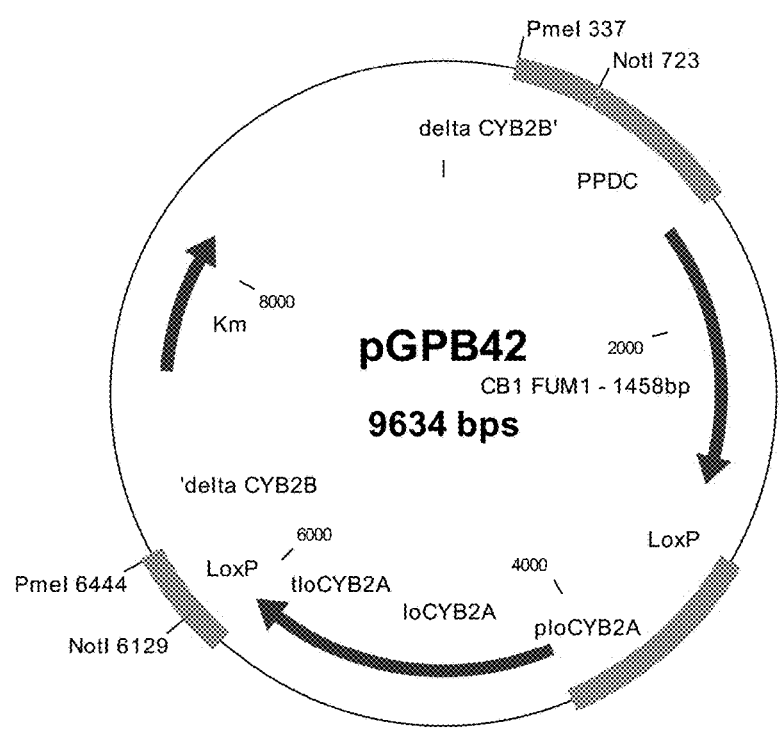
FIG. 29: pGPB42, FUM1 expression constructs.

The expression cassette from pGPB30 is excised using NotI and ligated to the NotI cut pKW22. The resulting plasmid is designated pGPB42 (FIG. 29).

Figure 31:
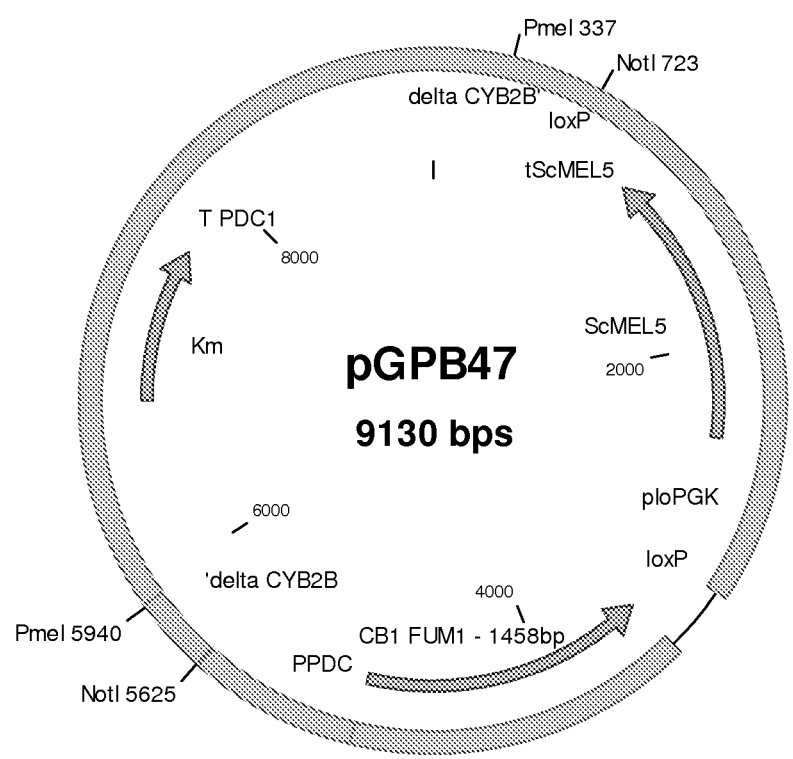
FIG. 31: pGPB47, FUM1 expression constructs.

The expression cassette from pGPB44 is excised using NotI and ligated to the NotI cut pKW22. The resulting plasmid is designated pGPB47 (FIG. 31).

Example 8B

Insertion of *I. orientalis* FUM1 at One or Both *I. orientalis* CYB2B Loci Integration of the first copy of the FUM1 expression cassette at the CYB2B locus is performed using plasmids containing the CYB2A selectable marker. pGPB42 is digested with SacI and ApaI and transformed into *I. orientalis* strains ySBCGH49-72 using lithium acetate transformation. Transformants are screened by PCR to confirm correct integration of the FUM1 expression cassette at the first CYB2B locus using primers oKW117 (SEQ ID NO:119), oJLJ43 (SEQ ID NO:158), oKW120 (SEQ ID NO:120), and oGPB46 (SEQ ID NO:146). The resulting strains are designated ySBCGH73-96.

Integration of the second copy of the FUM1 expression cassette at the CYB2B locus is performed using plasmids containing the MEL5 selectable marker. pGPB47 is digested with SacI and ApaI and transformed into ySBCGH73-96 using lithium acetate transformation. Transformants are screened by PCR to confirm correct integration of the FUM1 expression cassette at the second CYB2B locus using primers oKW117 (SEQ ID NO:119), oJLJ43 (SEQ ID NO:158), oKW120 (SEQ ID NO:120), and oGPB46 (SEQ ID NO:146). The resulting strains are designated ySBCGH97-120.

Marker recycling is carried out with plasmid pVB32. The correct homozygous strains with both markers removed are designated ySBCGH121-144.

The various FUM1 insertion/CYB2B deletion strains generated in Example 8 are summarized in Table 11.

TABLE 11

*I. orientalis* FUM1 insertion strains:

| Strain name | Description | Parent strain |
| --- | --- | --- |
| ySBCGH73 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. mikatae* FRD1 insertion at ADHa (2) | ySBCGH49 |
| ySBCGH97/ySBCGH121 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. mikatae* FRD1 insertion at ADHa (2)<br>*I. orientalis* FUM1 insertion at CYB2B (1)<br>*I. orientalis* FUM1 insertion at CYB2B (2) | ySBCGH73 |
| ySBCGH74 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. marxianus* FRD1 insertion at ADHa (2) | ySBCGH50 |
| ySBCGH98/ySBCGH122 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. marxianus* FRD1 insertion at ADHa (2)<br>*I. orientalis* FUM1 insertion at CYB2B (1)<br>*I. orientalis* FUM1 insertion at CYB2B (2) | ySBCGH74 |
| ySBCGH75 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. polyspora* FRD1 insertion at ADHa (2) | ySBCGH51 |
| ySBCGH99/ySBCGH123 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*K. polyspora* FRD1 insertion at ADHa (2)<br>*I. orientalis* FUM1 insertion at CYB2B (1)<br>*I. orientalis* FUM1 insertion at CYB2B (2) | ySBCGH75 |
| ySBCGH76 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. cerevisiae* FRD1 insertion at ADHa (2) | ySBCGH52 |
| ySBCGH100/ySBCGH124 | CYB2A deletion (2)<br>GPD1 deletion (2)<br>CYB2B deletion (2)<br>*I. orientalis* PYC1 insertion at PDC1 (2)<br>*I. orientalis* MDH1 insertion at ATO2 (2)<br>*S. cerevisiae* FRD1 insertion at ADHa (2)<br>*I. orientalis* FUM1 insertion at CYB2B (1)<br>*I. orientalis* FUM1 insertion at CYB2B (2) | ySBCGH76 |
| ySBCGH77 | CYB2A deletion (2)<br>GPD1 deletion (2)<br>CYB2B deletion (2)<br>*I. orientalis* PYC1 insertion at PDC1 (2)<br>*I. orientalis* MDH2 insertion at ATO2 (2)<br>*S. mikatae* FRD1 insertion at ADHa (2) | ySBCGH53 |
| ySBCGH101/ySBCGH125 | CYB2A deletion (2)<br>GPD1 deletion (2)<br>CYB2B deletion (2)<br>*I. orientalis* FUM1 insertion at CYB2B (1) | ySBCGH77 |

TABLE 11-continued

*I. orientalis* FUM1 insertion strains:

| Strain name | Description | Parent strain |
|---|---|---|
| ySBCGH78 | *I. orientalis* PYC1 insertion at PDC1 (2)<br>*I. orientalis* MDH2 insertion at ATO2 (2)<br>*S. mikatae* FRD1 insertion at ADHa (2)<br>*I. orientalis* FUM1 insertion at CYB2B (2)<br>CYB2A deletion (2)<br>GPD1 deletion (2)<br>CYB2B deletion (2) | ySBCGH54 |
| ySBCGH102/ySBCGH126 | *I. orientalis* PYC1 insertion at PDC1 (2)<br>*I. orientalis* MDH2 insertion at ATO2 (2)<br>*K. marxianus* FRD1 insertion at ADHa (2)<br>*I. orientalis* FUM1 insertion at CYB2B (1)<br>CYB2A deletion (2)<br>GPD1 deletion (2)<br>CYB2B deletion (2) | ySBCGH78 |
| ySBCGH79 | *I. orientalis* PYC1 insertion at PDC1 (2)<br>*I. orientalis* MDH2 insertion at ATO2 (2)<br>*K. marxianus* FRD1 insertion at ADHa (2)<br>*I. orientalis* FUM1 insertion at CYB2B (2)<br>CYB2A deletion (2)<br>GPD1 deletion (2)<br>CYB2B deletion (2) | ySBCGH55 |
| ySBCGH103/ySBCGH127 | *I. orientalis* PYC1 insertion at PDC1 (2)<br>*I. orientalis* MDH2 insertion at ATO2 (2)<br>*K. polyspora* FRD1 insertion at ADHa (2)<br>*I. orientalis* FUM1 insertion at CYB2B (1)<br>CYB2A deletion (2)<br>GPD1 deletion (2)<br>CYB2B deletion (2) | ySBCGH79 |
| ySBCGH80 | *I. orientalis* PYC1 insertion at PDC1 (2)<br>*I. orientalis* MDH2 insertion at ATO2 (2)<br>*K. polyspora* FRD1 insertion at ADHa (2)<br>*I. orientalis* FUM1 insertion at CYB2B (2)<br>CYB2A deletion (2)<br>GPD1 deletion (2)<br>CYB2B deletion (2) | ySBCGH56 |
| ySBCGH104/ySBCGH128 | *I. orientalis* PYC1 insertion at PDC1 (2)<br>*I. orientalis* MDH2 insertion at ATO2 (2)<br>*S. cerevisiae* FRD1 insertion at ADHa (2)<br>*I. orientalis* FUM1 insertion at CYB2B (1)<br>CYB2A deletion (2)<br>GPD1 deletion (2)<br>CYB2B deletion (2) | ySBCGH80 |
| ySBCGH81 | *I. orientalis* PYC1 insertion at PDC1 (2)<br>*I. orientalis* MDH2 insertion at ATO2 (2)<br>*S. cerevisiae* FRD1 insertion at ADHa (2)<br>*I. orientalis* FUM1 insertion at CYB2B (2)<br>CYB2A deletion (2)<br>GPD1 deletion (2)<br>CYB2B deletion (2) | ySBCGH57 |
| ySBCGH105/ySBCGH129 | *I. orientalis* PYC1 insertion at PDC1 (2)<br>*I. orientalis* MDH3 insertion at ATO2 (2)<br>*S. mikatae* FRD1 insertion at ADHa (2)<br>*I. orientalis* FUM1 insertion at CYB2B (1)<br>CYB2A deletion (2)<br>GPD1 deletion (2)<br>CYB2B deletion (2) | ySBCGH81 |
| ySBCGH82 | *I. orientalis* PYC1 insertion at PDC1 (2)<br>*I. orientalis* MDH3 insertion at ATO2 (2)<br>*S. mikatae* FRD1 insertion at ADHa (2)<br>*I. orientalis* FUM1 insertion at CYB2B (2)<br>CYB2A deletion (2)<br>GPD1 deletion (2)<br>CYB2B deletion (2) | ySBCGH58 |
| ySBCGH106/ySBCGH130 | *I. orientalis* PYC1 insertion at PDC1 (2)<br>*I. orientalis* MDH3 insertion at ATO2 (2)<br>*K. marxianus* FRD1 insertion at ADHa (2)<br>*I. orientalis* FUM1 insertion at CYB2B (1)<br>CYB2A deletion (2)<br>GPD1 deletion (2)<br>CYB2B deletion (2) | ySBCGH82 |
| ySBCGH83 | *I. orientalis* PYC1 insertion at PDC1 (2)<br>*I. orientalis* MDH3 insertion at ATO2 (2)<br>*K. marxianus* FRD1 insertion at ADHa (2)<br>*I. orientalis* FUM1 insertion at CYB2B (2)<br>CYB2A deletion (2)<br>GPD1 deletion (2) | ySBCGH59 |

TABLE 11-continued

*I. orientalis* FUM1 insertion strains:

| Strain name | Description | Parent strain |
|---|---|---|
| ySBCGH107/ySBCGH131 | CYB2B deletion (2)<br>*I. orientalis* PYC1 insertion at PDC1 (2)<br>*I. orientalis* MDH3 insertion at ATO2 (2)<br>*K. polyspora* FRD1 insertion at ADHa (2)<br>*I. orientalis* FUM1 insertion at CYB2B (1)<br>CYB2A deletion (2)<br>GPD1 deletion (2) | ySBCGH83 |
| ySBCGH84 | CYB2B deletion (2)<br>*I. orientalis* PYC1 insertion at PDC1 (2)<br>*I. orientalis* MDH3 insertion at ATO2 (2)<br>*K. polyspora* FRD1 insertion at ADHa (2)<br>*I. orientalis* FUM1 insertion at CYB2B (2)<br>CYB2A deletion (2)<br>GPD1 deletion (2) | ySBCGH60 |
| ySBCGH108/ySBCGH132 | CYB2B deletion (2)<br>*I. orientalis* PYC1 insertion at PDC1 (2)<br>*I. orientalis* MDH3 insertion at ATO2 (2)<br>*S. cerevisiae* FRD1 insertion at ADHa (2)<br>*I. orientalis* FUM1 insertion at CYB2B (1)<br>CYB2A deletion (2)<br>GPD1 deletion (2) | ySBCGH84 |
| ySBCGH85 | CYB2B deletion (2)<br>*I. orientalis* PYC1 insertion at PDC1 (2)<br>*I. orientalis* MDH3 insertion at ATO2 (2)<br>*S. cerevisiae* FRD1 insertion at ADHa (2)<br>*I. orientalis* FUM1 insertion at CYB2B (2)<br>CYB2A deletion (2)<br>GPD1 deletion (2) | ySBCGH61 |
| ySBCGH109/ySBCGH133 | CYB2B deletion (2)<br>*I. orientalis* PYC1 insertion at PDC1 (2)<br>*K. marxianus* MDH1 insertion at ATO2 (2)<br>*S. mikatae* FRD1 insertion at ADHa (2)<br>*I. orientalis* FUM1 insertion at CYB2B (1)<br>CYB2A deletion (2)<br>GPD1 deletion (2) | ySBCGH85 |
| ySBCGH86 | CYB2B deletion (2)<br>*I. orientalis* PYC1 insertion at PDC1 (2)<br>*K. marxianus* MDH1 insertion at ATO2 (2)<br>*S. mikatae* FRD1 insertion at ADHa (2)<br>*I. orientalis* FUM1 insertion at CYB2B (2)<br>CYB2A deletion (2)<br>GPD1 deletion (2) | ySBCGH62 |
| ySBCGH110/ySBCGH134 | CYB2B deletion (2)<br>*I. orientalis* PYC1 insertion at PDC1 (2)<br>*K. marxianus* MDH1 insertion at ATO2 (2)<br>*K. marxianus* FRD1 insertion at ADHa (2)<br>*I. orientalis* FUM1 insertion at CYB2B (1)<br>CYB2A deletion (2)<br>GPD1 deletion (2) | ySBCGH86 |
| ySBCGH87 | CYB2B deletion (2)<br>*I. orientalis* PYC1 insertion at PDC1 (2)<br>*K. marxianus* MDH1 insertion at ATO2 (2)<br>*K. marxianus* FRD1 insertion at ADHa (2)<br>*I. orientalis* FUM1 insertion at CYB2B (2)<br>CYB2A deletion (2)<br>GPD1 deletion (2) | ySBCGH63 |
| ySBCGH111/ySBCGH135 | CYB2B deletion (2)<br>*I. orientalis* PYC1 insertion at PDC1 (2)<br>*K. marxianus* MDH1 insertion at ATO2 (2)<br>*K. polyspora* FRD1 insertion at ADHa (2)<br>*I. orientalis* FUM1 insertion at CYB2B (1)<br>CYB2A deletion (2)<br>GPD1 deletion (2) | ySBCGH87 |
| ySBCGH88 | CYB2B deletion (2)<br>*I. orientalis* PYC1 insertion at PDC1 (2)<br>*K. marxianus* MDH1 insertion at ATO2 (2)<br>*K. polyspora* FRD1 insertion at ADHa (2)<br>*I. orientalis* FUM1 insertion at CYB2B (2)<br>CYB2A deletion (2)<br>GPD1 deletion (2) | ySBCGH64 |
| | CYB2B deletion (2)<br>*I. orientalis* PYC1 insertion at PDC1 (2)<br>*K. marxianus* MDH1 insertion at ATO2 (2)<br>*S. cerevisiae* FRD1 insertion at ADHa (2)<br>*I. orientalis* FUM1 insertion at CYB2B (1) | |

TABLE 11-continued

*I. orientalis* FUM1 insertion strains:

| Strain name | Description | Parent strain |
|---|---|---|
| ySBCGH112/ySBCGH136 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*S. cerevisiae* FRD1 insertion at ADHa (2)<br>*I. orientalis* FUM1 insertion at CYB2B (2) | ySBCGH88 |
| ySBCGH89 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. mikatae* FRD1 insertion at ADHa (2)<br>*I. orientalis* FUM1 insertion at CYB2B (1) | ySBCGH65 |
| ySBCGH113/ySBCGH137 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. mikatae* FRD1 insertion at ADHa (2)<br>*I. orientalis* FUM1 insertion at CYB2B (2) | ySBCGH89 |
| ySBCGH90 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. marxianus* FRD1 insertion at ADHa (2)<br>*I. orientalis* FUM1 insertion at CYB2B (1) | ySBCGH66 |
| ySBCGH114/ySBCGH138 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. marxianus* FRD1 insertion at ADHa (2)<br>*I. orientalis* FUM1 insertion at CYB2B (2) | ySBCGH90 |
| ySBCGH91 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. polyspora* FRD1 insertion at ADHa (2)<br>*I. orientalis* FUM1 insertion at CYB2B (1) | ySBCGH67 |
| ySBCGH115/ySBCGH139 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. polyspora* FRD1 insertion at ADHa (2)<br>*I. orientalis* FUM1 insertion at CYB2B (2) | ySBCGH91 |
| ySBCGH92 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 insertion at ADHa (2)<br>*I. orientalis* FUM1 insertion at CYB2B (1) | ySBCGH68 |
| ySBCGH116/ySBCGH140 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 insertion at ADHa (2)<br>*I. orientalis* FUM1 insertion at CYB2B (2) | ySBCGH92 |
| ySBCGH93 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. mikatae* FRD1 insertion at ADHa (2)<br>*I. orientalis* FUM1 insertion at CYB2B (1) | ySBCGH69 |
| ySBCGH117/ySBCGH141 | CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2) | ySBCGH93 |

TABLE 11-continued

I. orientalis FUM1 insertion strains:

| Strain name | Description | Parent strain |
|---|---|---|
| ySBCGH94 | S. mikatae FRD1 insertion at ADHa (2)<br>I. orientalis FUM1 insertion at CYB2B (2)<br>CYB2A deletion (2)<br>GPD1 deletion (2)<br>CYB2B deletion (2) | ySBCGH70 |
| ySBCGH118/ySBCGH142 | I. orientalis PYC1 insertion at PDC1 (2)<br>K. marxianus MDH3 insertion at ATO2 (2)<br>K. marxianus FRD1 insertion at ADHa (2)<br>I. orientalis FUM1 insertion at CYB2B (1)<br>I. orientalis FUM1 insertion at CYB2B (2)<br>CYB2A deletion (2)<br>GPD1 deletion (2)<br>CYB2B deletion (2) | ySBCGH94 |
| ySBCGH95 | I. orientalis PYC1 insertion at PDC1 (2)<br>K. marxianus MDH3 insertion at ATO2 (2)<br>K. marxianus FRD1 insertion at ADHa (2)<br>I. orientalis FUM1 insertion at CYB2B (2)<br>CYB2A deletion (2)<br>GPD1 deletion (2)<br>CYB2B deletion (2) | ySBCGH71 |
| ySBCGH119/ySBCGH143 | I. orientalis PYC1 insertion at PDC1 (2)<br>K. marxianus MDH3 insertion at ATO2 (2)<br>K. polyspora FRD1 insertion at ADHa (2)<br>I. orientalis FUM1 insertion at CYB2B (1)<br>I. orientalis FUM1 insertion at CYB2B (2)<br>CYB2A deletion (2)<br>GPD1 deletion (2)<br>CYB2B deletion (2) | ySBCGH95 |
| ySBCGH96 | I. orientalis PYC1 insertion at PDC1 (2)<br>K. marxianus MDH3 insertion at ATO2 (2)<br>K. polyspora FRD1 insertion at ADHa (2)<br>I. orientalis FUM1 insertion at CYB2B (2)<br>CYB2A deletion (2)<br>GPD1 deletion (2)<br>CYB2B deletion (2) | ySBCGH72 |
| ySBCGH120/ySBCGH144 | I. orientalis PYC1 insertion at PDC1 (2)<br>K. marxianus MDH3 insertion at ATO2 (2)<br>S. cerevisiae FRD1 insertion at ADHa (2)<br>I. orientalis FUM1 insertion at CYB2B (1)<br>CYB2A deletion (2)<br>GPD1 deletion (2)<br>CYB2B deletion (2)<br>I. orientalis PYC1 insertion at PDC1 (2)<br>K. marxianus MDH3 insertion at ATO2 (2)<br>S. cerevisiae FRD1 insertion at ADHa (2)<br>I. orientalis FUM1 insertion at CYB2B (2) | ySBCGH96 |

Example 9

Insertion of ZWF1 at the GPD1 Locus in I. orientalis Strains ySBCGH121-144

A ZWF1 expression cassette is inserted at one or both GPD1 alleles in I. orientalis strains ySBCGH121-144 (Example 8).

Example 9A

Construction of I. orientalis ZWF1 Expression Constructs pKF033 and pGPB56

Figure 32:
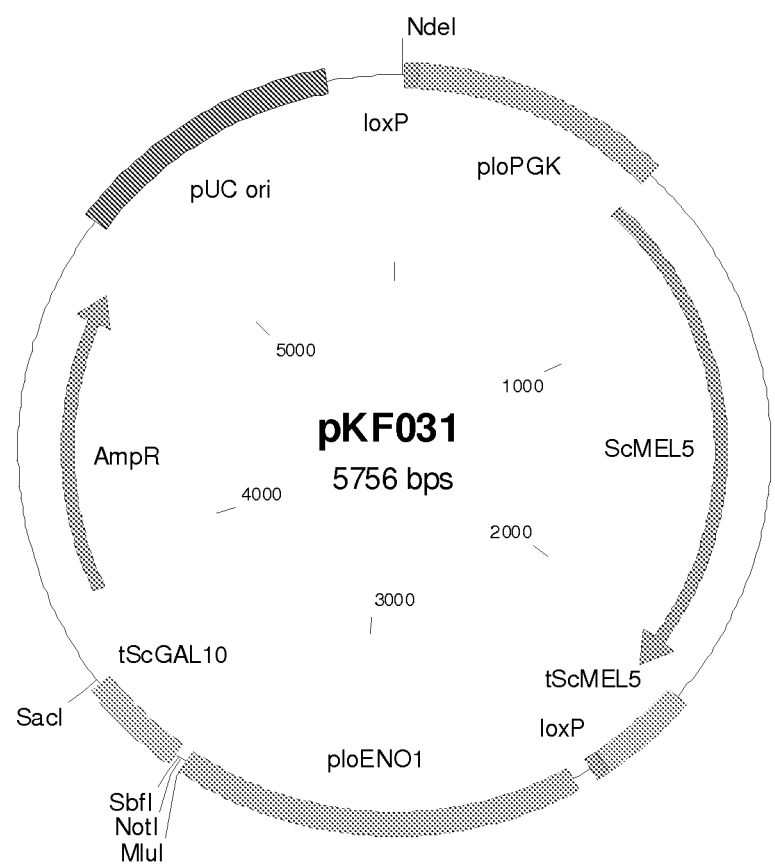
FIG. 32: pKF031, ZWF1 expression construct.
Figure 33:
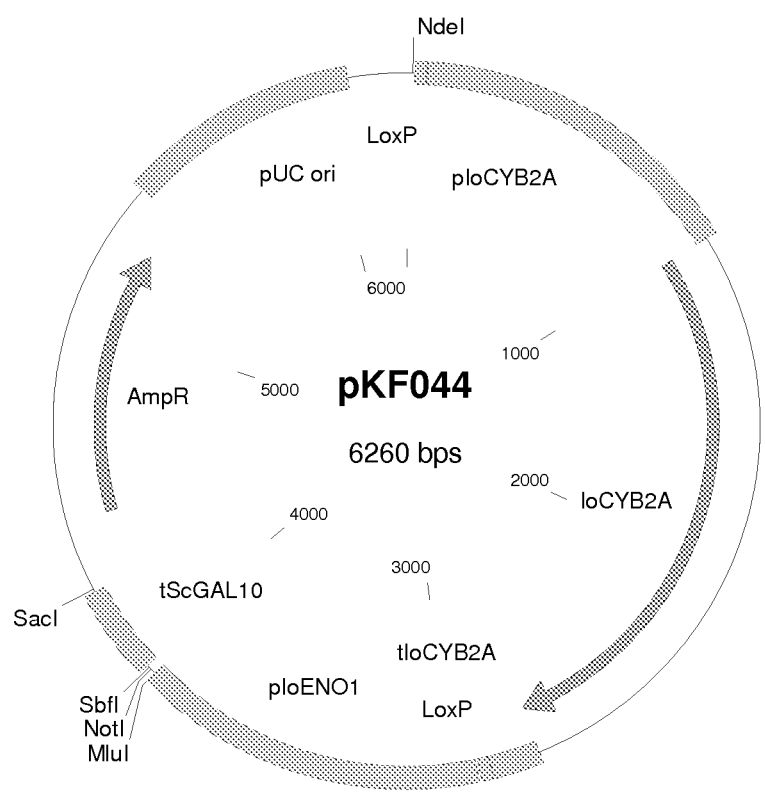
FIG. 33: pKF044, ZWF1 expression construct.

The ZWF1 gene from I. orientalis (SEQ ID NO:33) is amplified from genomic DNA using Phusion polymerase and primers oKF168 (SEQ ID NO:131) and oKF163 (SEQ ID NO:130), which contain an MluI site and an SbfI site, respectively. After amplification, the product is gel purified, digested with MluI and SbfI, and ligated to similarly digested pKF031 (SEQ ID NO:127) and pKF044 (SEQ ID NO:128). pKF031 (FIG. 32) and pKF044 (FIG. 33) are constructed from pUC19 backbones, and both contain a multiple cloning site containing MluI, NotI, and SbfI sites operatively linked to the I. orientalis ENO promoter and the S. cerevisiae GAL10 terminator. pKF031 also contains a selection marker cassette comprising the S. cerevisiae MEL5 gene operatively linked to the I. orientalis PGK promoter. This selection marker cassette is flanked by loxP sites. pKF044 contains an expression cassette comprising the I. orientalis CYB2A promoter, gene, and terminator. This expression cassette is flanked by loxP sites.

Figure 34:
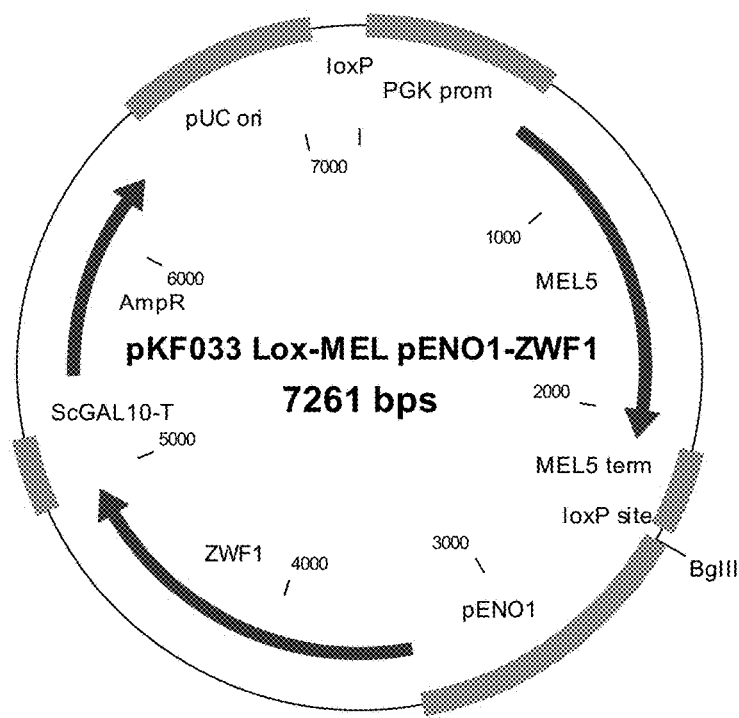
FIG. 34: pKF033, ZWF1 expression construct.
Figure 35:
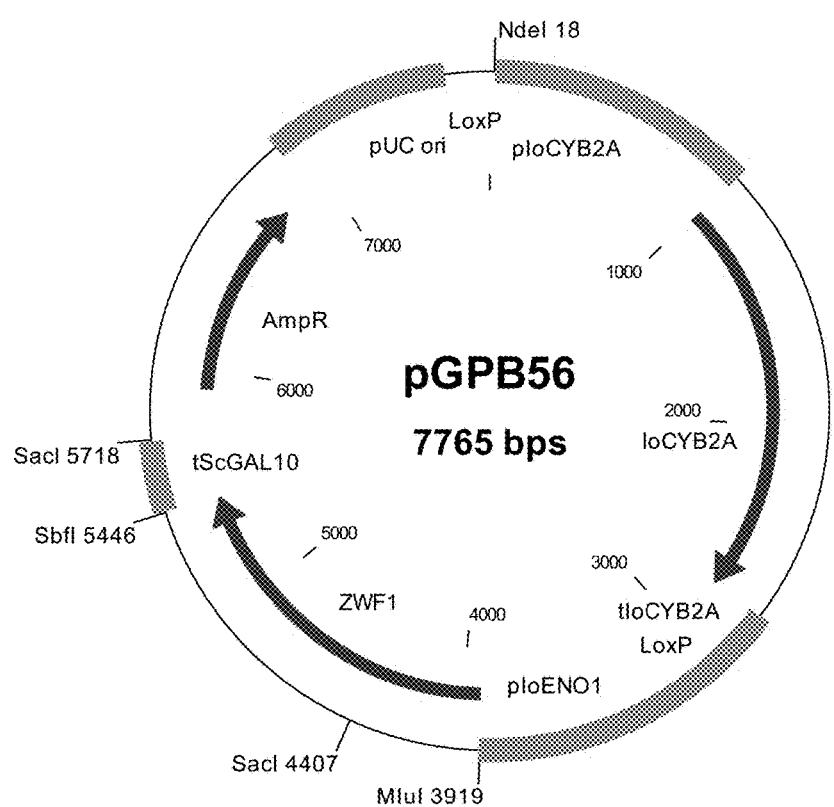
FIG. 35: pGPB056, ZWF1 expression construct.

The plasmids are transformed into E. coli, and transformants are selected on LB plates containing 100 µg/ml carbenicillin and screened using primers flanking the NotI site of pKF031 and pKF044 (oKW93 (SEQ ID NO:108) and oKW95 (SEQ ID NO:109)). Correct plasmids are confirmed by sequencing, and the final constructs are designated pKF033 (MEL5 marker) (FIG. 34) and pGPB056 (CYB2A marker) (FIG. 35).

Example 9B

Insertion of I. orientalis ZWF1 at the First and Second GPD1 Loci in I. orientalis Strains ySBCGH121-144 pKF033 and pGPB56 are both amplified from the loxP site on the 5' end to the GAL10 terminator on the 3' end using primers oGPBH1 (SEQ ID NO:163) and oGPBH2 (SEQ ID NO:164). Each of these primers contains on their 5' end 65 bp of sequence specific to the 65 bp immediately upstream and downstream of the GPD1 locus in *I. orientalis*. This recombination sequence enables double recombination and integration at the GPD1 locus.

The PCR product amplified from pKF033 is used to transform *I. orientalis* strains ySBCGH121-144. Transformants are selected on YNB+melibiose+x-α-gal, and integration of ZWF1 at a first GPD1 allele is confirmed by PCR using primers oGPBH3 (SEQ ID NO:165), oGPBH4 (SEQ ID NO:166), oGPB55 (SEQ ID NO:151), and oGPB11 (SEQ ID NO:142). The correct heterozygous strains are designated ySBCGH145-168.

To generate homozygous strains with ZWF1 inserted at both GPD1 alleles, strains ySBCGH145-168 are transformed with the PCR product amplified from pGPB56. Transformants are selected on YNB+2% lactic acid+x-α-gal, and integration of ZWF1 is confirmed by PCR using the primers oGPBH3 (SEQ ID NO:165), oGPBH4 (SEQ ID NO:166), oGPB53 (SEQ ID NO:149), and oGPB52 (SEQ ID NO:148). The correct homozygous strains are designated ySBCGH169-192.

Marker recycling is carried out with plasmid pVB32. The correct homozygous strains with both markers removed are designated ySBCGH193-216.

The various ZWF1 insertion/GPD1 deletion strains generated in Example 9 are summarized in Table 12.

TABLE 12

*I. orientalis* ZWF1 insertion strains:

| Strain name | Description | Parent strain |
| --- | --- | --- |
| ySBCGH145 | CYB2A deletion (2) | ySBCGH121 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *S. mikatae* FRD1 at ADHa (2) | |
| | *I. orientalis* FUM1 at CYB2B (2) | |
| | *I. orientalis* ZWF1 at GPD1 (1) | |
| ySBCGH169/ySBCGH193 | CYB2A deletion (2) | ySBCGH145 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *S. mikatae* FRD1 at ADHa (2) | |
| | *I. orientalis* FUM1 at CYB2B (2) | |
| | *I. orientalis* ZWF1 at GPD1 (2) | |
| ySBCGH146 | CYB2A deletion (2) | ySBCGH122 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *K. marxianus* FRD1 at ADHa (2) | |
| | *I. orientalis* FUM1 at CYB2B (2) | |
| | *I. orientalis* ZWF1 at GPD1 (1) | |
| ySBCGH170/ySBCGH194 | CYB2A deletion (2) | ySBCGH146 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *K. marxianus* FRD1 at ADHa (2) | |
| | *I. orientalis* FUM1 at CYB2B (2) | |
| | *I. orientalis* ZWF1 at GPD1 (2) | |
| ySBCGH147 | CYB2A deletion (2) | ySBCGH123 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *K. polyspora* FRD1 at ADHa (2) | |
| | *I. orientalis* FUM1 at CYB2B (2) | |
| | *I. orientalis* ZWF1 at GPD1 (1) | |
| ySBCGH171/ySBCGH195 | CYB2A deletion (2) | ySBCGH147 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *K. polyspora* FRD1 at ADHa (2) | |
| | *I. orientalis* FUM1 at CYB2B (2) | |
| | *I. orientalis* ZWF1 at GPD1 (2) | |
| ySBCGH148 | CYB2A deletion (2) | ySBCGH124 |
| | GPD1 deletion (2) | |
| | CYB2B deletion (2) | |
| | *I. orientalis* PYC1 insertion at PDC1 (2) | |
| | *I. orientalis* MDH1 insertion at ATO2 (2) | |
| | *S. cerevisiae* FRD1 at ADHa (2) | |
| | *I. orientalis* FUM1 at CYB2B (2) | |
| | *I. orientalis* ZWF1 at GPD1 (1) | |
| ySBCGH172/ySBCGH196 | CYB2A deletion (2) | ySBCGH148 |
| | GPD1 deletion (2) | |

TABLE 12-continued

I. orientalis ZWF1 insertion strains:

| Strain name | Description | Parent strain |
|---|---|---|
| | CYB2B deletion (2)<br>I. orientalis PYC1 insertion at PDC1 (2)<br>I. orientalis MDH1 insertion at ATO2 (2)<br>S. cerevisiae FRD1 at ADHa (2)<br>I. orientalis FUM1 at CYB2B (2)<br>I. orientalis ZWF1 at GPD1 (2) | |
| ySBCGH149 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>S. mikatae FRD1 at ADHa (2)<br>I. orientalis FUM1 at CYB2B (2)<br>I. orientalis ZWF1 at GPD1 (1) | ySBCGH125 |
| ySBCGH173/ySBCGH197 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>S. mikatae FRD1 at ADHa (2)<br>I. orientalis FUM1 at CYB2B (2)<br>I. orientalis ZWF1 at GPD1 (2) | ySBCGH149 |
| ySBCGH150 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>K. marxianus FRD1 at ADHa (2)<br>I. orientalis FUM1 at CYB2B (2)<br>I. orientalis ZWF1 at GPD1 (1) | ySBCGH126 |
| ySBCGH174/ySBCGH198 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>K. marxianus FRD1 at ADHa (2)<br>I. orientalis FUM1 at CYB2B (2)<br>I. orientalis ZWF1 at GPD1 (2) | ySBCGH150 |
| ySBCGH151 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>K. polyspora FRD1 at ADHa (2)<br>I. orientalis FUM1 at CYB2B (2)<br>I. orientalis ZWF1 at GPD1 (1) | ySBCGH127 |
| ySBCGH175/ySBCGH199 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>K. polyspora FRD1 at ADHa (2)<br>I. orientalis FUM1 at CYB2B (2)<br>I. orientalis ZWF1 at GPD1 (2) | ySBCGH151 |
| ySBCGH152 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>S. cerevisiae FRD1 at ADHa (2)<br>I. orientalis FUM1 at CYB2B (2)<br>I. orientalis ZWF1 at GPD1 (1) | ySBCGH128 |
| ySBCGH176/ySBCGH200 | CYB2A deletion (2)<br>GPD1 deletion (2)<br>CYB2B deletion (2)<br>I. orientalis PYC1 insertion at PDC1 (2)<br>I. orientalis MDH2 insertion at ATO2 (2)<br>S. cerevisiae FRD1 at ADHa (2)<br>I. orientalis FUM1 at CYB2B (2)<br>I. orientalis ZWF1 at GPD1 (2) | ySBCGH152 |
| ySBCGH153 | CYB2A deletion (2)<br>GPD1 deletion (2)<br>CYB2B deletion (2)<br>I. orientalis PYC1 insertion at PDC1 (2)<br>I. orientalis MDH3 insertion at ATO2 (2)<br>S. mikatae FRD1 at ADHa (2) | ySBCGH129 |

TABLE 12-continued

*I. orientalis* ZWF1 insertion strains:

| Strain name | Description | Parent strain |
|---|---|---|
| ySBCGH177/ySBCGH201 | *I. orientalis* FUM1 at CYB2B (2)<br>*I. orientalis* ZWF1 at GPD1 (1)<br>CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*S. mikatae* FRD1 at ADHa (2)<br>*I. orientalis* FUM1 at CYB2B (2) | ySBCGH153 |
| ySBCGH154 | *I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2)<br>*I. orientalis* ZWF1 at GPD1 (1) | ySBCGH130 |
| ySBCGH178/ySBCGH202 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2)<br>*I. orientalis* ZWF1 at GPD1 (2) | ySBCGH154 |
| ySBCGH155 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*K. polyspora* FRD1 at ADHa (2)<br>*I. orientalis* FUM1 at CYB2B (2)<br>*I. orientalis* ZWF1 at GPD1 (1) | ySBCGH131 |
| ySBCGH179/ySBCGH203 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*K. polyspora* FRD1 at ADHa (2)<br>*I. orientalis* FUM1 at CYB2B (2)<br>*I. orientalis* ZWF1 at GPD1 (2) | ySBCGH155 |
| ySBCGH156 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2)<br>*I. orientalis* ZWF1 at GPD1 (1) | ySBCGH132 |
| ySBCGH180/ySBCGH204 | CYB2A deletion (2)<br>GPD1 deletion (2)<br>CYB2B deletion (2)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2)<br>*I. orientalis* ZWF1 at GPD1 (2) | ySBCGH156 |
| ySBCGH157 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1)<br>*I. orientalis* ZWF1 at GPD1 (1) | ySBCGH133 |
| ySBCGH181/ySBCGH205 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1)<br>*I. orientalis* ZWF1 at GPD1 (2) | ySBCGH157 |
| ySBCGH158 | CYB2A deletion (2)<br>GPD1 deletion (2) | ySBCGH134 |

TABLE 12-continued

*I. orientalis* ZWF1 insertion strains:

| Strain name | Description | Parent strain |
|---|---|---|
| | CYB2B deletion (2)<br>*I. orientalis* PYC1 insertion at PDC1 (2)<br>*K. marxianus* MDH1 insertion at ATO2 (2)<br>*K. marxianus* FRD1 at ADHa (2)<br>*I. orientalis* FUM1 at CYB2B (2)<br>*I. orientalis* ZWF1 at GPD1 (1) | |
| ySBCGH182/ySBCGH206 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*K. marxianus* FRD1 at ADHa (2)<br>*I. orientalis* FUM1 at CYB2B (2)<br>*I. orientalis* ZWF1 at GPD1 (2) | ySBCGH158 |
| ySBCGH159 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2)<br>*I. orientalis* ZWF1 at GPD1 (1) | ySBCGH135 |
| ySBCGH183/ySBCGH207 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2)<br>*I. orientalis* ZWF1 at GPD1 (2) | ySBCGH159 |
| ySBCGH160 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*S. cerevisiae* FRD1 at ADHa (2)<br>*I. orientalis* FUM1 at CYB2B (2)<br>*I. orientalis* ZWF1 at GPD1 (1) | ySBCGH136 |
| ySBCGH184/ySBCGH208 | CYB2A deletion (2)<br>GPD1 deletion (2)<br>CYB2B deletion (2)<br>*I. orientalis* PYC1 insertion at PDC1 (2)<br>*K. marxianus* MDH1 insertion at ATO2 (2)<br>*S. cerevisiae* FRD1 at ADHa (2)<br>*I. orientalis* FUM1 at CYB2B (2)<br>*I. orientalis* ZWF1 at GPD1 (2) | ySBCGH160 |
| ySBCGH161 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. mikatae* FRD1 at ADHa (2)<br>*I. orientalis* FUM1 at CYB2B (2)<br>*I. orientalis* ZWF1 at GPD1 (1) | ySBCGH137 |
| ySBCGH185/ySBCGH209 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. mikatae* FRD1 at ADHa (2)<br>*I. orientalis* FUM1 at CYB2B (2)<br>*I. orientalis* ZWF1 at GPD1 (2) | ySBCGH161 |
| ySBCGH162 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. marxianus* FRD1 at ADHa (2)<br>*I. orientalis* FUM1 at CYB2B (2)<br>*I. orientalis* ZWF1 at GPD1 (1) | ySBCGH138 |
| ySBCGH186/ySBCGH210 | CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. marxianus* FRD1 at ADHa (2) | ySBCGH162 |

TABLE 12-continued

| | *I. orientalis* ZWF1 insertion strains: | |
|---|---|---|
| Strain name | Description | Parent strain |
| ySBCGH163 | *I. orientalis* FUM1 at CYB2B (2)<br>*I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. polyspora* FRD1 at ADHa (2) | ySBCGH139 |
| ySBCGH187/ySBCGH211 | *I. orientalis* FUM1 at CYB2B (2)<br>*I. orientalis* ZWF1 at GPD1 (1)<br>CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*K. polyspora* FRD1 at ADHa (2) | ySBCGH163 |
| ySBCGH164 | *I. orientalis* FUM1 at CYB2B (2)<br>*I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 at ADHa (2) | ySBCGH140 |
| ySBCGH188/ySBCGH212 | *I. orientalis* FUM1 at CYB2B (2)<br>*I. orientalis* ZWF1 at GPD1 (1)<br>CYB2A deletion (2)<br>GPD1 deletion (2)<br>CYB2B deletion (2)<br>*I. orientalis* PYC1 insertion at PDC1 (2)<br>*K. marxianus* MDH2 insertion at ATO2 (2)<br>*S. cerevisiae* FRD1 at ADHa (2) | ySBCGH164 |
| ySBCGH165 | *I. orientalis* FUM1 at CYB2B (2)<br>*I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. mikatae* FRD1 at ADHa (2) | ySBCGH141 |
| ySBCGH189/ySBCGH213 | *I. orientalis* FUM1 at CYB2B (2)<br>*I. orientalis* ZWF1 at GPD1 (1)<br>CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*S. mikatae* FRD1 at ADHa (2) | ySBCGH165 |
| ySBCGH166 | *I. orientalis* FUM1 at CYB2B (2)<br>*I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. marxianus* FRD1 at ADHa (2) | ySBCGH142 |
| ySBCGH190/ySBCGH214 | *I. orientalis* FUM1 at CYB2B (2)<br>*I. orientalis* ZWF1 at GPD1 (1)<br>CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. marxianus* FRD1 at ADHa (2) | ySBCGH166 |
| ySBCGH167 | *I. orientalis* FUM1 at CYB2B (2)<br>*I. orientalis* ZWF1 at GPD1 (2)<br>CYB2A deletion (2)<br>GPD1 deletion (2)<br>CYB2B deletion (2)<br>*I. orientalis* PYC1 insertion at PDC1 (2)<br>*K. marxianus* MDH3 insertion at ATO2 (2)<br>*K. polyspora* FRD1 at ADHa (2) | ySBCGH143 |
| ySBCGH191/ySBCGH215 | *I. orientalis* FUM1 at CYB2B (2)<br>*I. orientalis* ZWF1 at GPD1 (1)<br>CYB2A deletion (2)<br>GPD1 deletion (2) | ySBCGH167 |

TABLE 12-continued

I. orientalis ZWF1 insertion strains:

| Strain name | Description | Parent strain |
|---|---|---|
| ySBCGH168 | CYB2B deletion (2)<br>I. orientalis PYC1 insertion at PDC1 (2)<br>K. marxianus MDH3 insertion at ATO2 (2)<br>K. polyspora FRD1 at ADHa (2)<br>I. orientalis FUM1 at CYB2B (2)<br>I. orientalis ZWF1 at GPD1 (2)<br>CYB2A deletion (2)<br>GPD1 deletion (2)<br>CYB2B deletion (2)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2)<br>I. orientalis ZWF1 at GPD1 (1) | ySBCGH144 |
| ySBCGH192/ySBCGH216 | CYB2A deletion (2)<br>GPD1 deletion (2)<br>CYB2B deletion (2)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2)<br>I. orientalis ZWF1 at GPD1 (2) | ySBCGH168 |

Example 10

Shake Flask Characterization of Succinate Production in I. orientalis Strains ySBCGH169/ySBCGH193

Shake flasks are used to test the ZWF1 insertion strains ySBCGH169/ySBCGH193 (Example 9). Shake flasks are inoculated with biomass harvested from seed flasks grown overnight to an $OD_{600}$ of 2 to 6. 250 mL baffled flasks (50 mL working volume) are inoculated to an $OD_{600}$ of 0.2 and fermentation occurs at 100 rpm and 30° C. DM defined medium is used in flasks, with pH control and $CO_2$ provided by calcium carbonate addition at a concentration of 0.255M (1.28 g $CaCO_3$ per 50 ml flask). Samples are taken throughout the time course of the assay and analyzed for biomass growth via $OD_{600}$, and succinate and glucose are monitored via high performance liquid chromatography (HPLC). The resulting data shows production of greater than 40 g/L succinate by strain ySBCGH169/ySBCGH193.

Example 11

Deletion of the First and Second PCK1 Loci in I. orientalis Strains ySBCGH121-144

The first and second PCK1 loci in I. orientalis strains ySBCGH121-144 (Example 8) are deleted using a PCK deletion construct.

Example 11A

Construction of I. orientalis PCK Deletion Constructs

Figure 39:
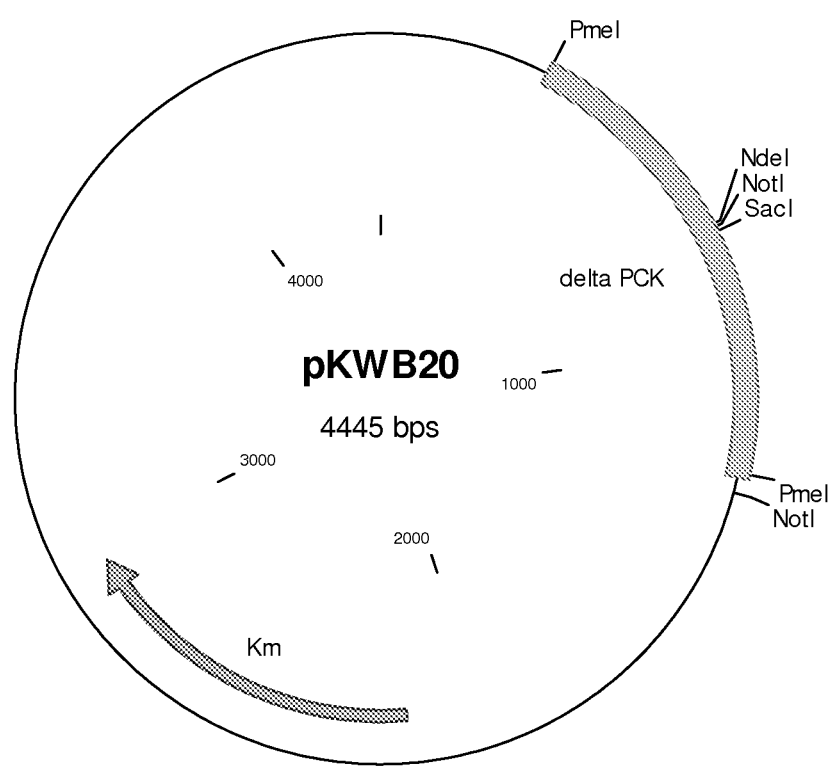
FIG. 39: pKWB20, PCK1 deletion construct.
Figure 40:
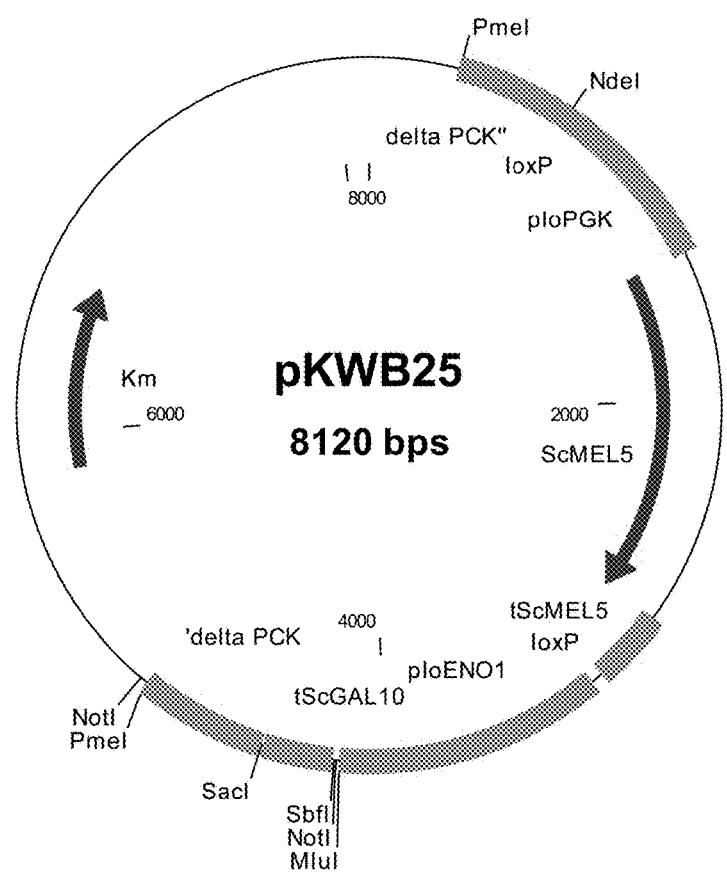
FIG. 40: pKWB25, PCK1 deletion construct.
Figure 41:
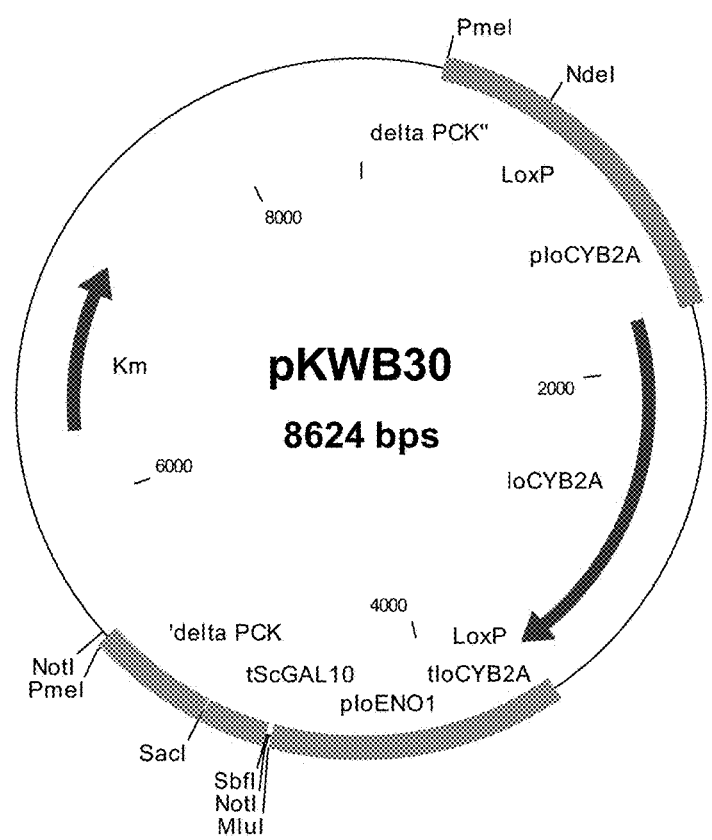
FIG. 41: pKWB30, PCK1 deletion construct.

The PCK upstream region from 432 bp upstream to the start codon is amplified by PCR. Sequence corresponding to the restriction sites NdeI/NotI/SacI is added to the 5' end of the reverse upstream primer (oKW78, SEQ ID NO:99). A PmeI restriction site is added to the 5' end of the forward upstream primer (oKW77, SEQ ID NO:98). The PCK downstream region is amplified from the stop codon to 472 bp downstream. The downstream forward primer (oKW79, SEQ ID NO:100) contained the same NdeI/NotI/SacI sequence as the reverse upstream primer. The 5' end of the reverse downstream primer also has a PmeI site (oKW80, SEQ ID NO:101). The two fragments are amplified independently using Phusion polymerase, then assembled into a full-length (926 bp) product via a two-stage PCR protocol (10 cycles (98° C. 10 s, 55° C. 20 s, 72° C. 60 s) with no primers, followed by 20 cycles (98° C. 10 s, 55° C. 20 s, 72° C. 60 s) with upstream forward and downstream reverse primers). Full-length product is gel purified and cloned into pCR-BluntII (Invitrogen) and sequenced. The plasmid confirmed to have correct sequence is subjected to quickchange PCR using Phusion polymerase to eliminate the plasmid borne SacI site. Correct plasmids are confirmed by digestion with SacI and sequencing. The final construct is named pKWB20 (FIG. 39).

pKWB20 is digested with NdeI and SacI and the resulting 4.4 kb DNA fragment is gel purified. Plasmid pKF031 is digested with NdeI and SacI to create a fragment of 3.7 kb that contains the MEL5 marker flanked by loxP sites. In the same way, pKF044 is digested to create a 4.2 kb fragment containing the CYB2A marker flanked by loxP sites. Marker fragments are ligated into the digested pKWB20 plasmid to create pKWB25 (FIG. 40), containing the MEL5 marker, and pKWB30 (FIG. 41), containing the CYB2A marker. Correct constructs are confirmed by PCR and restriction digestion.

Example 11B

Deletion of PCK1 in I. orientalis Strains ySBCGH121-ySBCGH144

Plasmid pKWB25 is digested with PmeI to create a 5 kb fragment containing the MEL5 marker surrounded by PCK1 flanking sequence. The fragment is gel purified prior to transformation. In the same way, pKWB30 is digested with PmeI to create a 5.4 kb fragment containing the CYB2A marker with PCK1 flanking sequence. The fragment is gel purified prior to transformation.

The DNA fragment from pKWB30, containing the CYB2A marker, is transformed into strains ySBCGH121-ySBCGH144. Transformants are selected on YNB+lactate, and deletion of PCK at the first allele is confirmed by PCR using primers oKW77 (SEQ ID NO:98), oKW80 (SEQ ID NO:101), oGPB52 (SEQ ID NO:148), and oGPB53 (SEQ ID NO:149). The correct heterozygous strains are designated ySBCGH289-312.

Strains ySBCGH289-312 are transformed with the PmeI digestion product from pKWB30 and selected on YNB+melibiose+x-α-gal to generate a homozygous strain with PCK deleted at both alleles. Integration is confirmed by PCR using the primers oKW77 (SEQ ID NO:98), oKW80 (SEQ ID NO:101), oGPB54 (SEQ ID NO:150), and oGPB55 (SEQ ID NO:151). The correct homozygous strains are designated ySBCGH313-336.

Marker recycling is carried out with plasmid pVB32. The correct homozygous strains with both markers removed are designated ySBCGH337-360.

The various PCK deletion strains generated in Example 11 are summarized in Table 13.

TABLE 13

*I. orientalis* PCK deletion strains:

| Strain name | Description | Parent strain |
|---|---|---|
| ySBCGH289 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH1 insertion at ATO2 (2)<br>*S. mikatae* FRD1 at ADHa (2)<br>*I. orientalis* FUM1 at CYB2B (2) | ySBCGH121 |
| ySBCGH313/ySBCGH337 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH1 insertion at ATO2 (2)<br>*S. mikatae* FRD1 at ADHa (2)<br>*I. orientalis* FUM1 at CYB2B (2) | ySBCGH289 |
| ySBCGH290 | CYB2A deletion (2)<br>GPD1 deletion (2)<br>CYB2B deletion (2)<br>PCK deletion (1)<br>*I. orientalis* PYC1 insertion at PDC1 (2)<br>*I. orientalis* MDH1 insertion at ATO2 (2)<br>*K. marxianus* FRD1 at ADHa (2)<br>*I. orientalis* FUM1 at CYB2B (2) | ySBCGH122 |
| ySBCGH314/ySBCGH338 | CYB2A deletion (2)<br>GPD1 deletion (2)<br>CYB2B deletion (2)<br>PCK deletion (2)<br>*I. orientalis* PYC1 insertion at PDC1 (2)<br>*I. orientalis* MDH1 insertion at ATO2 (2)<br>*K. marxianus* FRD1 at ADHa (2)<br>*I. orientalis* FUM1 at CYB2B (2) | ySBCGH290 |
| ySBCGH291 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH1 insertion at ATO2 (2)<br>*K. polyspora* FRD1 at ADHa (2)<br>*I. orientalis* FUM1 at CYB2B (2) | ySBCGH123 |
| ySBCGH315/ySBCGH339 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH1 insertion at ATO2 (2)<br>*K. polyspora* FRD1 at ADHa (2)<br>*I. orientalis* FUM1 at CYB2B (2) | ySBCGH291 |
| ySBCGH292 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH1 insertion at ATO2 (2)<br>*S. cerevisiae* FRD1 at ADHa (2)<br>*I. orientalis* FUM1 at CYB2B (2) | ySBCGH124 |
| ySBCGH316/ySBCGH340 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH1 insertion at ATO2 (2) | ySBCGH292 |

TABLE 13-continued

*I. orientalis* PCK deletion strains:

| Strain name | Description | Parent strain |
|---|---|---|
| ySBCGH293 | *S. cerevisiae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH2 insertion at ATO2 (2) | ySBCGH125 |
| ySBCGH317/ySBCGH341 | *S. mikatae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH2 insertion at ATO2 (2) | ySBCGH293 |
| ySBCGH294 | *S. mikatae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH2 insertion at ATO2 (2) | ySBCGH126 |
| ySBCGH318/ySBCGH342 | *K. marxianus* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH2 insertion at ATO2 (2) | ySBCGH294 |
| ySBCGH295 | *K. marxianus* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH2 insertion at ATO2 (2) | ySBCGH127 |
| ySBCGH319/ySBCGH343 | *K. polyspora* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH2 insertion at ATO2 (2) | ySBCGH295 |
| ySBCGH296 | *K. polyspora* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH2 insertion at ATO2 (2) | ySBCGH128 |
| ySBCGH320/ySBCGH344 | *S. cerevisiae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH2 insertion at ATO2 (2) | ySBCGH296 |
| ySBCGH297 | *S. cerevisiae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH3 insertion at ATO2 (2) | ySBCGH129 |
| ySBCGH321/ySBCGH345 | *S. mikatae* FRD1 at ADHa (2)<br>*I. orientalis* FUM1 at CYB2B (2)<br>CYB2A deletion (2)<br>GPD1 deletion (2) | ySBCGH297 |

TABLE 13-continued

*I. orientalis* PCK deletion strains:

| Strain name | Description | Parent strain |
|---|---|---|
| | CYB2B deletion (2)<br>PCK1 deletion (2)<br>*I. orientalis* PYC1 insertion at PDC1 (2)<br>*I. orientalis* MDH3 insertion at ATO2 (2)<br>*S. mikatae* FRD1 at ADHa (2)<br>*I. orientalis* FUM1 at CYB2B (2) | |
| ySBCGH298 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2) | ySBCGH130 |
| ySBCGH322/ySBCGH346 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2) | ySBCGH298 |
| ySBCGH299 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH3 insertion at ATO2 (2)<br>*K. polyspora* FRD1 at ADHa (2)<br>*I. orientalis* FUM1 at CYB2B (2) | ySBCGH131 |
| ySBCGH323/ySBCGH347 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH3 insertion at ATO2 (2)<br>*K. polyspora* FRD1 at ADHa (2)<br>*I. orientalis* FUM1 at CYB2B (2) | ySBCGH299 |
| ySBCGH300 | CYB2A deletion (2)<br>GPD1 deletion (2)<br>CYB2B deletion (2)<br>PCK1 deletion (1)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2) | ySBCGH132 |
| ySBCGH324/ySBCGH348 | CYB2A deletion (2)<br>GPD1 deletion (2)<br>CYB2B deletion (2)<br>PCK1 deletion (2)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2) | ySBCGH300 |
| ySBCGH301 | CYB2A deletion (2)<br>GPD1 deletion (2)<br>CYB2B deletion (2)<br>PCK1 deletion (1)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1) | ySBCGH133 |
| ySBCGH325/ySBCGH349 | CYB2A deletion (2)<br>GPD1 deletion (2)<br>CYB2B deletion (2)<br>PCK1 deletion (2)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1) | ySBCGH301 |
| ySBCGH302 | CYB2A deletion (2)<br>GPD1 deletion (2)<br>CYB2B deletion (2)<br>PCK1 deletion (1)<br>*I. orientalis* PYC1 insertion at PDC1 (2)<br>*K. marxianus* MDH1 insertion at ATO2 (2) | ySBCGH134 |

TABLE 13-continued

*I. orientalis* PCK deletion strains:

| Strain name | Description | Parent strain |
|---|---|---|
| ySBCGH326/ySBCGH350 | *K. marxianus* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2) | ySBCGH302 |
| ySBCGH303 | *I. orientalis* PYC1 insertion at PDC1 (2)<br>*K. marxianus* MDH1 insertion at ATO2 (2)<br>*K. marxianus* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1) | ySBCGH135 |
| ySBCGH327/ySBCGH351 | *I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2) | ySBCGH303 |
| ySBCGH304 | *I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1) | ySBCGH136 |
| ySBCGH328/ySBCGH352 | *I. orientalis* PYC1 insertion at PDC1 (2)<br>*K. marxianus* MDH1 insertion at ATO2 (2)<br>*S. cerevisiae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2) | ySBCGH304 |
| ySBCGH305 | *I. orientalis* PYC1 insertion at PDC1 (2)<br>*K. marxianus* MDH1 insertion at ATO2 (2)<br>*S. cerevisiae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1) | ySBCGH137 |
| ySBCGH329/ySBCGH353 | *I. orientalis* PYC1 insertion at PDC1 (2)<br>*K. marxianus* MDH2 insertion at ATO2 (2)<br>*S. mikatae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2) | ySBCGH305 |
| ySBCGH306 | *I. orientalis* PYC1 insertion at PDC1 (2)<br>*K. marxianus* MDH2 insertion at ATO2 (2)<br>*S. mikatae* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (1) | ySBCGH138 |
| ySBCGH330/ySBCGH354 | *I. orientalis* PYC1 insertion at PDC1 (2)<br>*K. marxianus* MDH2 insertion at ATO2 (2)<br>*K. marxianus* FRD1 at ADHa (2)<br>*I. orientalis* FUM1 at CYB2B (2)<br>CYB2A deletion (2)<br>GPD1 deletion (2)<br>CYB2B deletion (2)<br>PCK1 deletion (2) | ySBCGH306 |
| ySBCGH307 | *I. orientalis* PYC1 insertion at PDC1 (2)<br>*K. marxianus* MDH2 insertion at ATO2 (2)<br>*K. marxianus* FRD1 at ADHa (2)<br>*I. orientalis* FUM1 at CYB2B (2)<br>CYB2A deletion (2)<br>GPD1 deletion (2) | ySBCGH139 |

TABLE 13-continued

*I. orientalis* PCK deletion strains:

| Strain name | Description | Parent strain |
|---|---|---|
| | CYB2B deletion (2) | |
| | PCK1 deletion (1) | |
| | *I. orientalis* PYC1 insertion at PDC1 (2) | |
| | *K. marxianus* MDH2 insertion at ATO2 (2) | |
| | *K. polyspora* FRD1 at ADHa (2) | |
| | *I. orientalis* FUM1 at CYB2B (2) | |
| ySBCGH331/ySBCGH355 | CYB2A deletion (2) | ySBCGH307 |
| | GPD1 deletion (2) | |
| | CYB2B deletion (2) | |
| | PCK1 deletion (2) | |
| | *I. orientalis* PYC1 insertion at PDC1 (2) | |
| | *K. marxianus* MDH2 insertion at ATO2 (2) | |
| | *K. polyspora* FRD1 at ADHa (2) | |
| | *I. orientalis* FUM1 at CYB2B (2) | |
| ySBCGH308 | CYB2A deletion (2) | ySBCGH140 |
| | GPD1 deletion (2) | |
| | CYB2B deletion (2) | |
| | PCK1 deletion (1) | |
| | *I. orientalis* PYC1 insertion at PDC1 (2) | |
| | *K. marxianus* MDH2 insertion at ATO2 (2) | |
| | *S. cerevisiae* FRD1 at ADHa (2) | |
| | *I. orientalis* FUM1 at CYB2B (2) | |
| ySBCGH332/ySBCGH356 | CYB2A deletion (2) | ySBCGH308 |
| | GPD1 deletion (2) | |
| | CYB2B deletion (2) | |
| | PCK1 deletion (2) | |
| | *I. orientalis* PYC1 insertion at PDC1 (2) | |
| | *K. marxianus* MDH2 insertion at ATO2 (2) | |
| | *S. cerevisiae* FRD1 at ADHa (2) | |
| | *I. orientalis* FUM1 at CYB2B (2) | |
| ySBCGH309 | CYB2A deletion (2) | ySBCGH141 |
| | GPD1 deletion (2) | |
| | CYB2B deletion (2) | |
| | PCK1 deletion (1) | |
| | *I. orientalis* PYC1 insertion at PDC1 (2) | |
| | *K. marxianus* MDH3 insertion at ATO2 (2) | |
| | *S. mikatae* FRD1 at ADHa (2) | |
| | *I. orientalis* FUM1 at CYB2B (2) | |
| ySBCGH333/ySBCGH357 | CYB2A deletion (2) | ySBCGH309 |
| | GPD1 deletion (2) | |
| | CYB2B deletion (2) | |
| | PCK1 deletion (2) | |
| | *I. orientalis* PYC1 insertion at PDC1 (2) | |
| | *K. marxianus* MDH3 insertion at ATO2 (2) | |
| | *S. mikatae* FRD1 at ADHa (2) | |
| | *I. orientalis* FUM1 at CYB2B (2) | |
| ySBCGH310 | CYB2A deletion (2) | ySBCGH142 |
| | GPD1 deletion (2) | |
| | CYB2B deletion (2) | |
| | PCK1 deletion (1) | |
| | *I. orientalis* PYC1 insertion at PDC1 (2) | |
| | *K. marxianus* MDH3 insertion at ATO2 (2) | |
| | *K. marxianus* FRD1 at ADHa (2) | |
| | *I. orientalis* FUM1 at CYB2B (2) | |
| ySBCGH334/ySBCGH358 | CYB2A deletion (2) | ySBCGH310 |
| | GPD1 deletion (2) | |
| | CYB2B deletion (2) | |
| | PCK1 deletion (2) | |
| | *I. orientalis* PYC1 insertion at PDC1 (2) | |
| | *K. marxianus* MDH3 insertion at ATO2 (2) | |
| | *K. marxianus* FRD1 at ADHa (2) | |
| | *I. orientalis* FUM1 at CYB2B (2) | |
| ySBCGH311 | CYB2A deletion (2) | ySBCGH143 |
| | GPD1 deletion (2) | |
| | CYB2B deletion (2) | |
| | PCK1 deletion (1) | |
| | *I. orientalis* PYC1 insertion at PDC1 (2) | |
| | *K. marxianus* MDH3 insertion at ATO2 (2) | |
| | *K. polyspora* FRD1 at ADHa (2) | |
| | *I. orientalis* FUM1 at CYB2B (2) | |
| ySBCGH335/ySBCGH359 | CYB2A deletion (2) | ySBCGH311 |
| | GPD1 deletion (2) | |
| | CYB2B deletion (2) | |
| | PCK1 deletion (2) | |
| | *I. orientalis* PYC1 insertion at PDC1 (2) | |
| | *K. marxianus* MDH3 insertion at ATO2 (2) | |

TABLE 13-continued

I. orientalis PCK deletion strains:

| Strain name | Description | Parent strain |
|---|---|---|
| ySBCGH312 | K. polyspora FRD1 at ADHa (2)<br>I. orientalis FUM1 at CYB2B (2)<br>CYB2A deletion (2)<br>GPD1 deletion (2)<br>CYB2B deletion (2)<br>PCK1 deletion (1)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2) | ySBCGH144 |
| ySBCGH336/ySBCGH360 | CYB2A deletion (2)<br>GPD1 deletion (2)<br>CYB2B deletion (2)<br>PCK1 deletion (2)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2) | ySBCGH312 |

Example 12

Deletion of the First and Second MAE1 Loci in I. orientalis Strains ySBCGH121-144

The first and second MAE1 loci in I. orientalis strains ySBCGH121-144 (Example 8) are deleted using an MAE1 deletion construct.

Example 12A

Construction of I. orientalis MAE1 Deletion Constructs

Figure 36:
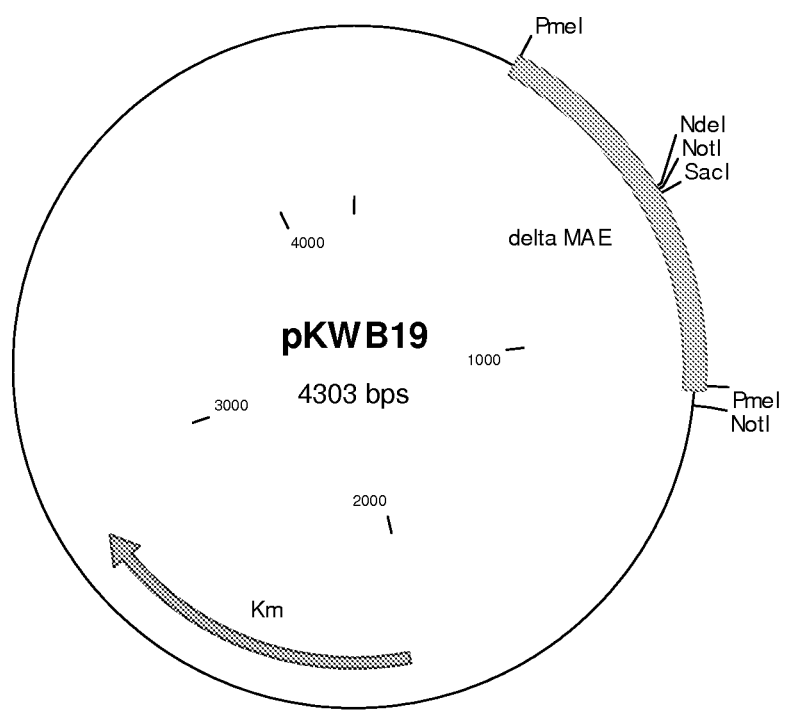
FIG. 36: pKWB19, MAE1 deletion construct.
Figure 37:
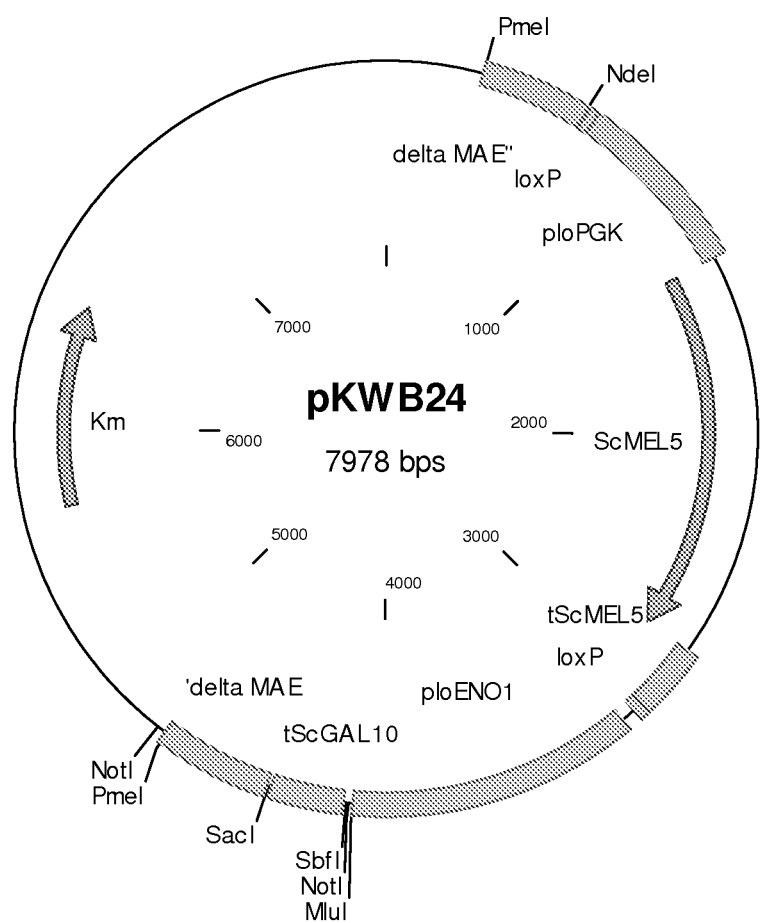
FIG. 37: pKWB24, MAE1 deletion construct.
Figure 38:
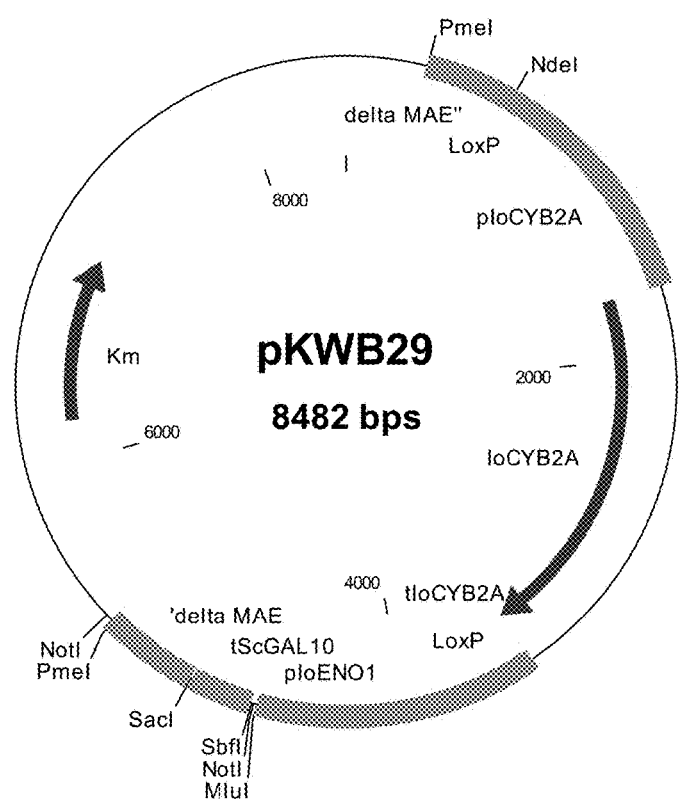
FIG. 38: pKWB29, MAE1 deletion construct.

The MAE1 upstream region from 370 bp upstream to the start codon is amplified by PCR. Sequence corresponding to the restriction sites NdeI/NotI/SacI is added to the 5' end of the reverse upstream primer (oKW61, SEQ ID NO:83). A PmeI restriction site is added to the 5' end of the forward upstream primer (oKW60, SEQ ID NO:82). The MAE1 downstream region is amplified from the stop codon to 392 bp downstream. The downstream forward primer (oKW62, SEQ ID NO:84) contains the same NdeI/NotI/SacI sequence as the reverse upstream primer. The 5' end of the reverse downstream primer also has a PmeI site (oKW63, SEQ ID NO:85). The two fragments are amplified independently using Phusion polymerase, then assembled into a full-length (784 bp) product via a two-stage PCR protocol (10 cycles (98° C. 10 s, 55° C. 20 s, 72° C. 60 s) with no primers, followed by 20 cycles (98° C. 10 s, 55° C. 20 s, 72° C. 60 s) with upstream forward and downstream reverse primers). Full-length product is gel purified and cloned into pCR-BluntII (Invitrogen) and sequenced. The plasmid confirmed to have correct sequence is subjected to quickchange PCR using Phusion polymerase to eliminate the plasmid borne SacI site. Correct plasmids are confirmed by digestion with SacI and sequencing. The final construct is named pKWB19 (FIG. 36).

pKWB19 is digested with NdeI and SacI and the resulting 4.3 kb DNA fragment is gel purified. Plasmid pKF031 is digested with NdeI and SacI to create a fragment of 3.7 kb that contains the MEL5 marker flanked by loxP sites. In the same way, pKF044 is digested to create a 4.2 kb fragment containing the CYB2A marker flanked by loxP sites. Marker fragments are ligated into the digested pKWB19 plasmid to create pKWB24 (FIG. 37), containing the MEL5 marker, and pKWB29 (FIG. 38), containing the CYB2A marker. Correct constructs are confirmed by PCR and restriction digestion.

Example 12B

Deletion of MAE1 in I. orientalis Strains ySBCGH121-ySBCGH144

Plasmid pKWB24 is digested with PmeI to create a 4.4 kb fragment containing the MEL5 marker surrounded by MAE flanking sequence. The fragment is gel purified prior to transformation. In the same way, pKWB29 is digested with PmeI to create a 5 kb fragment containing the CYB2A marker with MAE flanking sequence. The fragment is gel purified prior to transformation.

The DNA fragment containing the CYB2A marker is transformed into strains ySBCGH121-ySBCGH144. Transformants are selected on YNB+lactate, and deletion of MAE at the first allele is confirmed by PCR using primers oKW60 (SEQ ID NO:82), oKW63 (SEQ ID NO:85), oGPB52 (SEQ ID NO:148), and oGPB53 (SEQ ID NO:149). The correct heterozygous strains are designated ySBCGH217-240.

Strains ySBCGH217-240 are transformed with the PmeI digestion product from pKWB24 and selected on YNB+melibiose+x-α-gal to generate a homozygous strain with MAE deleted at both alleles. Integration is confirmed by PCR using the primers oKW60 (SEQ ID NO:82), oKW63 (SEQ ID NO:85), oGPB54 (SEQ ID NO:150), and oGPB55 (SEQ ID NO:151). The correct homozygous strains are designated ySBCGH241-264.

Marker recycling is carried out with plasmid pVB32. The correct homozygous strains with both markers removed are designated ySBCGH265-288.

The various MAE deletion strains generated in Example 12 are summarized in Table 14.

TABLE 14

I. orientalis MAE deletion strains:

| Strain name | Description | Parent strain |
|---|---|---|
| ySBCGH217 | CYB2A deletion (2)<br>GPD1 deletion (2) | ySBCGH121 |

TABLE 14-continued

*I. orientalis* MAE deletion strains:

| Strain name | Description | Parent strain |
|---|---|---|
| ySBCGH241/ ySBCGH265 | CYB2B deletion (2) MAE1 deletion (1) *I. orientalis* PYC1 insertion at PDC1 (2) *I. orientalis* MDH1 insertion at ATO2 (2) *S. mikatae* FRD1 at ADHa (2) *I. orientalis* FUM1 at CYB2B (2) CYB2A deletion (2) GPD1 deletion (2) CYB2B deletion (2) MAE1 deletion (2) *I. orientalis* PYC1 insertion at PDC1 (2) *I. orientalis* MDH1 insertion at ATO2 (2) *S. mikatae* FRD1 at ADHa (2) *I. orientalis* FUM1 at CYB2B (2) | ySBCGH217 |
| ySBCGH218 | CYB2A deletion (2) GPD1 deletion (2) CYB2B deletion (2) MAE1 deletion (1) *I. orientalis* PYC1 insertion at PDC1 (2) *I. orientalis* MDH1 insertion at ATO2 (2) *K. marxianus* FRD1 at ADHa (2) *I. orientalis* FUM1 at CYB2B (2) | ySBCGH122 |
| ySBCGH242/ ySBCGH266 | CYB2A deletion (2) GPD1 deletion (2) CYB2B deletion (2) MAE1 deletion (2) *I. orientalis* PYC1 insertion at PDC1 (2) *I. orientalis* MDH1 insertion at ATO2 (2) *K. marxianus* FRD1 at ADHa (2) *I. orientalis* FUM1 at CYB2B (2) | ySBCGH218 |
| ySBCGH219 | CYB2A deletion (2) GPD1 deletion (2) CYB2B deletion (2) MAE1 deletion (1) *I. orientalis* PYC1 insertion at PDC1 (2) *I. orientalis* MDH1 insertion at ATO2 (2) *K. polyspora* FRD1 at ADHa (2) *I. orientalis* FUM1 at CYB2B (2) | ySBCGH123 |
| ySBCGH243/ ySBCGH267 | CYB2A deletion (2) GPD1 deletion (2) CYB2B deletion (2) MAE1 deletion (2) *I. orientalis* PYC1 insertion at PDC1 (2) *I. orientalis* MDH1 insertion at ATO2 (2) *K. polyspora* FRD1 at ADHa (2) *I. orientalis* FUM1 at CYB2B (2) | ySBCGH219 |
| ySBCGH220 | CYB2A deletion (2) GPD1 deletion (2) CYB2B deletion (2) MAE1 deletion (1) *I. orientalis* PYC1 insertion at PDC1 (2) *I. orientalis* MDH1 insertion at ATO2 (2) *S. cerevisiae* FRD1 at ADHa (2) *I. orientalis* FUM1 at CYB2B (2) | ySBCGH124 |
| ySBCGH244/ ySBCGH268 | CYB2A deletion (2) GPD1 deletion (2) CYB2B deletion (2) MAE1 deletion (2) *I. orientalis* PYC1 insertion at PDC1 (2) *I. orientalis* MDH1 insertion at ATO2 (2) *S. cerevisiae* FRD1 at ADHa (2) *I. orientalis* FUM1 at CYB2B (2) | ySBCGH220 |
| ySBCGH221 | CYB2A deletion (2) GPD1 deletion (2) CYB2B deletion (2) MAE1 deletion (1) *I. orientalis* PYC1 insertion at PDC1 (2) *I. orientalis* MDH2 insertion at ATO2 (2) *S. mikatae* FRD1 at ADHa (2) *I. orientalis* FUM1 at CYB2B (2) | ySBCGH125 |
| ySBCGH245/ ySBCGH269 | CYB2A deletion (2) GPD1 deletion (2) CYB2B deletion (2) MAE1 deletion (2) *I. orientalis* PYC1 insertion at PDC1 (2) *I. orientalis* MDH2 insertion at ATO2 (2) *S. mikatae* FRD1 at ADHa (2) *I. orientalis* FUM1 at CYB2B (2) | ySBCGH221 |
| ySBCGH222 | CYB2A deletion (2) GPD1 deletion (2) CYB2B deletion (2) MAE1 deletion (1) *I. orientalis* PYC1 insertion at PDC1 (2) *I. orientalis* MDH2 insertion at ATO2 (2) *K. marxianus* FRD1 at ADHa (2) *I. orientalis* FUM1 at CYB2B (2) | ySBCGH126 |
| ySBCGH246/ ySBCGH270 | CYB2A deletion (2) GPD1 deletion (2) CYB2B deletion (2) MAE1 deletion (2) *I. orientalis* PYC1 insertion at PDC1 (2) *I. orientalis* MDH2 insertion at ATO2 (2) *K. marxianus* FRD1 at ADHa (2) *I. orientalis* FUM1 at CYB2B (2) | ySBCGH222 |
| ySBCGH223 | CYB2A deletion (2) GPD1 deletion (2) CYB2B deletion (2) MAE1 deletion (1) *I. orientalis* PYC1 insertion at PDC1 (2) *I. orientalis* MDH2 insertion at ATO2 (2) *K. polyspora* FRD1 at ADHa (2) *I. orientalis* FUM1 at CYB2B (2) | ySBCGH127 |
| ySBCGH247/ ySBCGH271 | CYB2A deletion (2) GPD1 deletion (2) CYB2B deletion (2) MAE1 deletion (2) *I. orientalis* PYC1 insertion at PDC1 (2) *I. orientalis* MDH2 insertion at ATO2 (2) *K. polyspora* FRD1 at ADHa (2) *I. orientalis* FUM1 at CYB2B (2) | ySBCGH223 |
| ySBCGH224 | CYB2A deletion (2) GPD1 deletion (2) CYB2B deletion (2) MAE1 deletion (1) *I. orientalis* PYC1 insertion at PDC1 (2) *I. orientalis* MDH2 insertion at ATO2 (2) *S. cerevisiae* FRD1 at ADHa (2) *I. orientalis* FUM1 at CYB2B (2) | ySBCGH128 |
| ySBCGH248/ ySBCGH272 | CYB2A deletion (2) GPD1 deletion (2) | ySBCGH224 |

TABLE 14-continued

*I. orientalis* MAE deletion strains:

| Strain name | Description | Parent strain |
|---|---|---|
| ySBCGH225 | CYB2B deletion (2)<br>MAE1 deletion (2)<br>*I. orientalis* PYC1 insertion at PDC1 (2)<br>*I. orientalis* MDH2 insertion at ATO2 (2)<br>*S. cerevisiae* FRD1 at ADHa (2)<br>*I. orientalis* FUM1 at CYB2B (2)<br>CYB2A deletion (2)<br>GPD1 deletion (2) | ySBCGH129 |
| ySBCGH249/<br>ySBCGH273 | CYB2B deletion (2)<br>MAE1 deletion (1)<br>*I. orientalis* PYC1 insertion at PDC1 (2)<br>*I. orientalis* MDH3 insertion at ATO2 (2)<br>*S. mikatae* FRD1 at ADHa (2)<br>*I. orientalis* FUM1 at CYB2B (2)<br>CYB2A deletion (2)<br>GPD1 deletion (2) | ySBCGH225 |
| ySBCGH226 | CYB2B deletion (2)<br>MAE1 deletion (2)<br>*I. orientalis* PYC1 insertion at PDC1 (2)<br>*I. orientalis* MDH3 insertion at ATO2 (2)<br>*S. mikatae* FRD1 at ADHa (2)<br>*I. orientalis* FUM1 at CYB2B (2)<br>CYB2A deletion (2)<br>GPD1 deletion (2) | ySBCGH130 |
| ySBCGH250/<br>ySBCGH274 | CYB2B deletion (2)<br>MAE1 deletion (1)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2)<br>CYB2A deletion (2)<br>GPD1 deletion (2) | ySBCGH226 |
| ySBCGH227 | CYB2B deletion (2)<br>MAE1 deletion (2)<br>*I. orientalis* PYC1 insertion at PDC1 (2)<br>*I. orientalis* MDH3 insertion at ATO2 (2)<br>*K. marxianus* FRD1 at ADHa (2)<br>*I. orientalis* FUM1 at CYB2B (2)<br>CYB2A deletion (2)<br>GPD1 deletion (2) | ySBCGH131 |
| ySBCGH251/<br>ySBCGH275 | CYB2B deletion (2)<br>MAE1 deletion (1)<br>*I. orientalis* PYC1 insertion at PDC1 (2)<br>*I. orientalis* MDH3 insertion at ATO2 (2)<br>*K. polyspora* FRD1 at ADHa (2)<br>*I. orientalis* FUM1 at CYB2B (2)<br>CYB2A deletion (2)<br>GPD1 deletion (2) | ySBCGH227 |
| ySBCGH228 | CYB2B deletion (2)<br>MAE1 deletion (2)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2)<br>CYB2A deletion (2)<br>GPD1 deletion (2) | ySBCGH132 |
| ySBCGH252/<br>ySBCGH276 | CYB2B deletion (2)<br>MAE1 deletion (2)<br>*I. orientalis* PYC1 insertion at PDC1 (2)<br>*I. orientalis* MDH3 insertion at ATO2 (2)<br>*S. cerevisiae* FRD1 at ADHa (2)<br>*I. orientalis* FUM1 at CYB2B (2)<br>CYB2A deletion (2)<br>GPD1 deletion (2) | ySBCGH228 |
| ySBCGH229 | CYB2B deletion (2)<br>MAE1 deletion (1)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1)<br>CYB2A deletion (2)<br>GPD1 deletion (2) | ySBCGH133 |
| ySBCGH253/<br>ySBCGH277 | CYB2B deletion (2)<br>MAE1 deletion (2)<br>*I. orientalis* PYC1 insertion at PDC1 (2)<br>*K. marxianus* MDH1 insertion at ATO2 (2)<br>*S. mikatae* FRD1 at ADHa (2)<br>*I. orientalis* FUM1 at CYB2B (1) | ySBCGH229 |
| ySBCGH230 | CYB2A deletion (2)<br>GPD1 deletion (2)<br>CYB2B deletion (2)<br>MAE1 deletion (1)<br>*I. orientalis* PYC1 insertion at PDC1 (2)<br>*K. marxianus* MDH1 insertion at ATO2 (2)<br>*K. marxianus* FRD1 at ADHa (2)<br>*I. orientalis* FUM1 at CYB2B (2) | ySBCGH134 |
| ySBCGH254/<br>ySBCGH278 | CYB2A deletion (2)<br>GPD1 deletion (2)<br>CYB2B deletion (2)<br>MAE1 deletion (2)<br>*I. orientalis* PYC1 insertion at PDC1 (2)<br>*K. marxianus* MDH1 insertion at ATO2 (2)<br>*K. marxianus* FRD1 at ADHa (2)<br>*I. orientalis* FUM1 at CYB2B (2) | ySBCGH230 |
| ySBCGH231 | CYB2A deletion (2)<br>GPD1 deletion (2)<br>CYB2B deletion (2)<br>MAE1 deletion (1)<br>*I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2) | ySBCGH135 |
| ySBCGH255/<br>ySBCGH279 | CYB2A deletion (2)<br>GPD1 deletion (2)<br>CYB2B deletion (2)<br>MAE1 deletion (2)<br>*I. orientalis* PYC1 insertion at PDC1 (2)<br>*K. marxianus* MDH1 insertion at ATO2 (2)<br>*K. polyspora* FRD1 at ADHa (2)<br>*I. orientalis* FUM1 at CYB2B (2) | ySBCGH231 |
| ySBCGH232 | CYB2A deletion (2)<br>GPD1 deletion (2) | ySBCGH136 |

TABLE 14-continued

I. orientalis MAE deletion strains:

| Strain name | Description | Parent strain |
|---|---|---|
| | CYB2B deletion (2)<br>MAE1 deletion (1)<br>I. orientalis PYC1 insertion at PDC1 (2)<br>K. marxianus MDH1 insertion at ATO2 (2)<br>S. cerevisiae FRD1 at ADHa (2)<br>I. orientalis FUM1 at CYB2B (2) | |
| ySBCGH256/<br>ySBCGH280 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH1 insertion at ATO2 (2)<br>S. cerevisiae FRD1 at ADHa (2)<br>I. orientalis FUM1 at CYB2B (2) | ySBCGH232 |
| ySBCGH233 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH2 insertion at ATO2 (2)<br>S. mikatae FRD1 at ADHa (2)<br>I. orientalis FUM1 at CYB2B (2) | ySBCGH137 |
| ySBCGH257/<br>ySBCGH281 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH2 insertion at ATO2 (2)<br>S. mikatae FRD1 at ADHa (2)<br>I. orientalis FUM1 at CYB2B (2) | ySBCGH233 |
| ySBCGH234 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH2 insertion at ATO2 (2)<br>K. marxianus FRD1 at ADHa (2)<br>I. orientalis FUM1 at CYB2B (2) | ySBCGH138 |
| ySBCGH258/<br>ySBCGH282 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH2 insertion at ATO2 (2)<br>K. marxianus FRD1 at ADHa (2)<br>I. orientalis FUM1 at CYB2B (2) | ySBCGH234 |
| ySBCGH235 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH2 insertion at ATO2 (2)<br>K. polyspora FRD1 at ADHa (2)<br>I. orientalis FUM1 at CYB2B (2) | ySBCGH139 |
| ySBCGH259/<br>ySBCGH283 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH2 insertion at | ySBCGH235 |
| | ATO2 (2)<br>K. polyspora FRD1 at ADHa (2)<br>I. orientalis FUM1 at CYB2B (2) | |
| ySBCGH236 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH2 insertion at ATO2 (2)<br>S. cerevisiae FRD1 at ADHa (2)<br>I. orientalis FUM1 at CYB2B (2) | ySBCGH140 |
| ySBCGH260/<br>ySBCGH284 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH2 insertion at ATO2 (2)<br>S. cerevisiae FRD1 at ADHa (2)<br>I. orientalis FUM1 at CYB2B (2) | ySBCGH236 |
| ySBCGH237 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH3 insertion at ATO2 (2)<br>S. mikatae FRD1 at ADHa (2)<br>I. orientalis FUM1 at CYB2B (2) | ySBCGH141 |
| ySBCGH261/<br>ySBCGH285 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH3 insertion at ATO2 (2)<br>S. mikatae FRD1 at ADHa (2)<br>I. orientalis FUM1 at CYB2B (2) | ySBCGH237 |
| ySBCGH238 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH3 insertion at ATO2 (2)<br>K. marxianus FRD1 at ADHa (2)<br>I. orientalis FUM1 at CYB2B (2) | ySBCGH142 |
| ySBCGH262/<br>ySBCGH286 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH3 insertion at ATO2 (2)<br>K. marxianus FRD1 at ADHa (2)<br>I. orientalis FUM1 at CYB2B (2) | ySBCGH238 |
| ySBCGH239 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH3 insertion at ATO2 (2)<br>K. polyspora FRD1 at ADHa (2)<br>I. orientalis FUM1 at CYB2B (2) | ySBCGH143 |
| ySBCGH263/<br>ySBCGH287 | CYB2A deletion (2)<br>GPD1 deletion (2) | ySBCGH239 |

TABLE 14-continued

I. orientalis MAE deletion strains:

| Strain name | Description | Parent strain |
|---|---|---|
| | CYB2B deletion (2)<br>MAE1 deletion (2)<br>I. orientalis PYC1 insertion at PDC1 (2)<br>K. marxianus MDH3 insertion at ATO2 (2)<br>K. polyspora FRD1 at ADHa (2)<br>I. orientalis FUM1 at CYB2B (2) | |
| ySBCGH240 | CYB2A deletion (2)<br>GPD1 deletion (2)<br>CYB2B deletion (2)<br>MAE1 deletion (1)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2) | ySBCGH144 |
| ySBCGH264/<br>ySBCGH288 | CYB2A deletion (2)<br>GPD1 deletion (2)<br>CYB2B deletion (2)<br>MAE1 deletion (2)<br>I. orientalis PYC1 insertion at PDC1 (2)<br>K. marxianus MDH3 insertion at ATO2 (2)<br>S. cerevisiae FRD1 at ADHa (2)<br>I. orientalis FUM1 at CYB2B (2) | ySBCGH240 |

Example 13

Insertion of PYC1 at the PDC1 Locus in I. orientalis Strains 2610 and 12506

A PYC1 expression cassette is inserted at one or both PDC1 alleles in I. orientalis strains 2610 (Example 2) and 12506.

Example 13A

Construction of I. orientalis PYC1 Expression Constructs pKF043 and pKF045

The PYC1 gene from I. orientalis (SEQ ID NO:7) is amplified from genomic DNA using Phusion polymerase and primers oKF245 (SEQ ID NO:134) and oKF246 (SEQ ID NO:135), which contain an MluI site and an SbfI site, respectively. After amplification, the product is gel purified, digested with MluI and SbfI, and ligated to similarly digested pKF031 and pKF044. pKF031 (FIG. 11) and pKF044 (FIG. 12) are constructed from pUC19 backbones, and both contain a multiple cloning site containing MluI, NotI, and SbfI sites operatively linked to the I. orientalis ENO promoter and the S. cerevisiae GAL10 terminator. pKF031 also contains a selection marker cassette comprising the S. cerevisiae MEL5 gene operatively linked to the I. orientalis PGK promoter. This selection marker cassette is flanked by loxP sites. pKF044 contains an expression cassette comprising the I. orientalis CYB2A promoter, gene, and terminator. This expression cassette is flanked by loxP sites.

The plasmids are transformed into E. coli, and transformants are selected on LB plates containing 100 μg/ml carbenicillin and screened using primers flanking the NotI site of pKF031 and pKF044 (oKW93 (SEQ ID NO:108) and oKW95 (SEQ ID NO:109)). Quickchange PCR is performed using primers oKW96 (SEQ ID NO:110) and oKW97 (SEQ ID NO:111) to eliminate an internal NdeI site (T2847C). Correct plasmids are confirmed by sequencing, and the final constructs are designated pKF043 (MEL5 marker) (FIG. 15) and pKF045 (CYB2A marker) (FIG. 16).

Example 13B

Construction of S. cerevisiae PYC1 Expression Constructs pKWB14 and pKWB15

The PYC1 gene from S. cerevisiae (SEQ ID NO:9) is amplified from genomic DNA using Phusion polymerase and primers oKW29 (SEQ ID NO:80) and oKW30 (SEQ ID NO:81), both of which contain at their 5' end 23 bp flanking the NotI site in pKF031 and pKF044 to enable directional ligation-less cloning. After amplification, the product is gel purified and co-transformed into E. coli with NotI-digested pKF031 and pKF044. Transformants are selected on LB plates containing 100 μg/ml carbenicillin, and screened using primers oKW93 (SEQ ID NO:108) and oKW95 (SEQ ID NO:109). Quickchange PCR is performed using primers oKW81 (SEQ ID NO:102) and oKW82 (SEQ ID NO:103) to eliminate an internal NdeI site (T2838C). Correct plasmids are confirmed by sequencing, and the final constructs are designated pKWB14 (MEL5 marker) (FIG. 17) and pKWB15 (CYB2A marker) (FIG. 18).

Example 13C

Construction of K. marxianus PYC1 Expression Constructs pKWB16 and pKWB17

K. marxianus is streaked on YPD plates, and after around 3 days the PYC1 gene (SEQ ID NO:11) is amplified from genomic DNA by colony PCR using primers oKW85 (SEQ ID NO:106) and oKW86 (SEQ ID NO:107). After amplification, the product is gel purified and co-transformed into E. coli with NotI-digested pKF031 and pKF044. Transformants are selected on LB plates containing 100 μg/ml carbenicillin, and screened using primers oKW93 (SEQ ID NO:108) and oKW95 (SEQ ID NO:109). Quickchange PCR is performed using primers oKW83 (SEQ ID NO:104) and oKW84 (SEQ ID NO:105) to eliminate an internal SacI site (T1446A). Correct plasmids are confirmed by sequencing, and the final constructs are designated pKWB16 (contains MEL5 marker) (FIG. 19) and pKWB17 (contains CYB2A marker) (FIG. 20).

Example 13D

Insertion of I. orientalis PYC1 at the First and Second PDC1 Loci in I. orientalis Strain 2610 pKF043 and pKF045 is amplified from the loxP site on the 5' end to the GAL10 terminator on the 3' end. pKF043 is amplified using primers oKF243 (SEQ ID NO:132) and oKF244 (SEQ ID NO:133), and pKF045 is amplified using primers oKF255 (SEQ ID NO:137) and oKF244 (SEQ ID NO:133). Each of these primers contains on their 5' end 65 bp of sequence specific to the 65 bp immediately upstream and downstream of the PDC1 locus in I. orientalis. This recombination sequence enables double recombination and integration at the PDC1 locus.

The PCR product amplified from pKF043 is used to transform I. orientalis strain 2610 (Example 2). Transformants are selected on YNB+melibiose+x-α-gal and, and integration of PYC1 at a first PDC1 allele is confirmed by PCR using primers oCM566 (SEQ ID NO:138), oKF151 (SEQ ID NO:129), oKF252 (SEQ ID NO:136), and oCM587 (SEQ ID NO:139). The correct heterozygous strain is designated 12626.

Strain 12626 is transformed with the PCR product from pKF045 amplification to generate a homozygous strain with PYC1 inserted at both PDC1 alleles. Integration is confirmed by PCR using the primers oCM566 (SEQ ID NO:138), oMM174 (SEQ ID NO:59), oCM587 (SEQ ID NO:139), and oCA397 (SEQ ID NO:71). The correct homozygous strain is designated 12629.

For marker recycling, *I. orientalis* 12629 is grown to around $OD_{600}$ of 1.0 in YP+100 g/L glucose (50 ml media in a 250 ml flask; 30° C./250 rpm). Cells are transformed with pVB32 using lithium acetate transformation, and transformants are selected on YNB+2% sucrose plates overlaid with x-α-gal. After 4 to 5 days, white colonies are streaked to YP+20 g/L glucose plates overlaid with x-α-gal and grown at 37° C. for 2 days. Genomic DNA from white colonies is screened for retention of the expression cassette at the *I. orientalis* PDC1 locus and for loss of the selectable markers using PCR primers oGPB9 (SEQ ID NO:140), oGPB10 (SEQ ID NO:141), oGPB11 (SEQ ID NO:142), and oGPB12 (SEQ ID NO:143). Positive transformants are confirmed to have lost the marker by a phenotypic screen showing no growth on YNB+2% lactic, 2% melabiose, or 2% sucrose. The homozygous strain with both markers removed is designated 12481.

Example 13E

Insertion of *S. cerevisiae* PYC1 at the First and Second PDC1 Loci in *I. orientalis* Strain 12506 pKWB14 and pKWB15 are both amplified from the loxP site on the 5' end to the GAL10 terminator on the 3' end. pKWB14 is amplified using primers oKF243 (SEQ ID NO:132) and oKF244 (SEQ ID NO:133), and pKWB15 is amplified using primers oKF255 (SEQ ID NO:137) and oKF244 (SEQ ID NO:133). The PCR product amplified from pKWB14 is used to transform *I. orientalis* strain 12506. Transformants are selected on YNB+melibiose+x-α-gal and integration of PYC1 at a first PDC1 allele is confirmed by PCR using primers oKW70 (SEQ ID NO:92), oGPB55 (SEQ ID NO:151), oGPB54 (SEQ ID NO:150), and oKW73 (SEQ ID NO:95). The correct heterozygous strain is designated 12688.

Strain 12688 is transformed with the PCR product from pKWB15 amplification to generate a homozygous strain with PYC1 inserted at both PDC1 alleles. Integration is confirmed by PCR using the primers oKW70 (SEQ ID NO:92), oGPB53 (SEQ ID NO:149), oGPB52 (SEQ ID NO:148), and oKW73 (SEQ ID NO:95). The correct homozygous strain is designated 12694.

Example 13F

Insertion of *K. marxianus* PYC1 at the First and Second PDC1 Loci in *I. orientalis* Strain 12506 pKWB16 and pKWB17 are both amplified from the loxP site on the 5' end to the GAL10 terminator on the 3' end. pKWB16 is amplified using primers oKF243 (SEQ ID NO:132) and oKF244 (SEQ ID NO:133), and pKWB17 is amplified using primers oKF255 (SEQ ID NO:137) and oKF244 (SEQ ID NO:133). The PCR product amplified from pKWB14 is used to transform *I. orientalis* strain 12506. Transformants are selected on YNB+melibiose+x-α-gal and integration of PYC1 at a first PDC1 allele is confirmed by PCR using primers oKW70 (SEQ ID NO:92), oGPB55 (SEQ ID NO:151), oGPB54 (SEQ ID NO:150), and oKW73 (SEQ ID NO:95). The correct heterozygous strain is designated 12634.

Strain 12634 is transformed with the PCR product from pKWB15 amplification to generate a homozygous strain with PYC1 inserted at both PDC1 alleles. Integration is confirmed by PCR using the primers oKW70 (SEQ ID NO:92), oGPB53 (SEQ ID NO:149), oGPB52 (SEQ ID NO:148), and oKW73 (SEQ ID NO:95). The correct homozygous strains are designated ySBCK140-ySBCK142.

The various PYC1 insertion/PDC1 deletion strains generated in Example 13 are summarized in Table 15.

TABLE 15

*I. orientalis* PYC1 insertion strains:

| Strain name | Description | Parent strain |
|---|---|---|
| 12506 | CYB2A deletion (2) *I. orientalis* PYC1 insertion at PDC1 (2) *I. orientalis* MDH2 insertion at ATO2 (2) | 12480 (Example 15H) |
| 12626 | CYB2A deletion (2) *I. orientalis* PYC1 insertion at PDC1 (1) | 2610 |
| 12629/12481 | CYB2A deletion (2) *I. orientalis* PYC1 insertion at PDC1 (2) | 12626 |
| 12688 | CYB2A deletion (2) *I. orientalis* PYC1 insertion at PDC1 (1) *I. orientalis* MDH2 insertion at ATO2 (2) *S. cerevisiae* PYC1 insertion at PDC1 (1) | 12506 |
| 12694 | CYB2A deletion (2) *I. orientalis* MDH2 insertion at ATO2 (2) *S. cerevisiae* PYC1 insertion at PDC1 (2) | 12688 |
| 12634 | CYB2A deletion (2) *I. orientalis* PYC1 insertion at PDC1 (1) *I. orientalis* MDH2 insertion at ATO2 (2) *K. marxianus* PYC1 insertion at PDC1 (1) | 12506 |
| ySBCK140/ ySBCK141/ ySBCK142 | CYB2A deletion (2) *I. orientalis* MDH2 insertion at ATO2 (2) *K. marxianus* PYC1 insertion at PDC1 (2) | 12634 |

Example 14

Insertion of FRD1 at the ADHa Locus in *I. orientalis* Strain 12481

An FRD1 expression cassette was inserted at one or both ADHa alleles of *I. orientalis* strains 12481 (Example 13D).

Example 14A

Construction of ADHa Deletion Constructs pGPB11, pGPB14, pGPB28, and pGPB34 pKF044 was used as a template for quickchange mutagenesis using oligonucleotides oKW64 (SEQ ID NO:86)

and oKW65 (SEQ ID NO:87) to delete an EcoRI site at nucleotide 932 of the *I. orientalis* CYB2A gene. The resulting plasmid was designated pKW49. pKW49 was digested with EcoRI and BglII and the resultant fragment ligated to EcoRI and BamHI digested pHJJ23 (FIG. 21). The resulting ADHa deletion construct, designated pGPB11 (FIG. 22), contains the *I. orientalis* PDC1 promoter (amplified using primers oJLJ3 (SEQ ID NO:156) and oJLJ19 (SEQ ID NO:157)) and terminator (amplified using primers oJLJ1 (SEQ ID NO:154) and oJLJ2 (SEQ ID NO:155)) and a CYB2A marker element between an 858 bp fragment corresponding to the region immediately 5' of the *I. orientalis* AHD2a open reading frame (amplified using primers oHJJ71 (SEQ ID NO:159) and oHJJ72 (SEQ ID NO:160)) and a 996 bp fragment corresponding to the region immediately 3' of the *I. orientalis* ADHa open reading frame (amplified using primer oHJJ73 (SEQ ID NO:161) and oHJJ74 (SEQ ID NO:162)).

pKF046, which contains an *S. cerevisiae* MEL5 marker gene operatively linked to a *I. orientalis* PGK promoter and an *S. cerevisiae* MEL5 terminator and flanked by LoxP sites, was used as a template for quickchange mutagenesis using oligonucleotides oKW74 (SEQ ID NO:96) and oKW75 (SEQ ID NO:97) to delete an EcoRI site at nucleotide 2392 of the plasmid. The resulting plasmid was designated pKW50. pKW50 was digested with EcoRI and BglII and the resultant fragment ligated to EcoRI and BamHI digested pHJJ23. The resulting plasmid, designated pGPB14 (FIG. 24), contains the same elements as pGPB11, but with the CYB2A selectable marker element replaced by the *S. cerevisiae* MEL5 selectable marker element.

pGPB11 and pGPB14 were each digested with EcoRI and BamHI to remove those portions of the plasmids corresponding to the PDC promoter and terminator, and each plasmid backbone was blunted with Klenow fragment and ligated to recircularize the plasmid. The plasmids were then transformed into *E. coli*. Plasmid isolated from positive colonies was designated pGPB28 (FIG. 23, derived from pGPB11) and pGPB34 (FIG. 25, derived from pGPB14).

Example 14B

Construction of FRD1 Expression Constructs pGPB20, pGPB22, pGPB25, pGPB26, pGPB36, pGPB37, pGPB39, and pGPB40

Expression cassettes for the FRD1 gene from various sources were inserted into the ADHa deletion construct pGPB11. Sources for the FRD1 gene were *S. cerevisiae* (SEQ ID NO:25), *S. mikatae* (SEQ ID NO:27), *K. polyspora* (SEQ ID NO:29), and *K. marxianus* (SEQ ID NO:31). The latter three genes were all codon optimized to *I. orientalis*.

Plasmids containing *S. cerevisiae*, *S. mikatae*, *K. polyspora*, or *K. marxianus* FRD1 genes were digested with XbaI and PacI, and the FRD1 fragments were ligated to similarly digested pGPB11. The resulting plasmids, which contained the FRD1 coding sequence flanked by the *I. orientalis* PDC1 promoter and terminator and also contained the *I. orientalis* CYB2A selectable marker, were designated pGPB20 (*S. mikatae* FRD1), pGP22 (*K. marxianus* FRD1), pGPB25 (*K. polyspora* FRD1), and pGPB26 (*S. cerevisiae* FRD1) (FIG. 26).

pGPB20, pGP22, pGPB25, and pGPB26 were digested with BamHI and NdeI and ligated to similarly digested pGPB14. The resulting plasmids, which contained the FRD1 coding sequence flanked by the *I. orientalis* PDC1 promoter and terminator and also contained the *S. cerevisiae* MEL5 selectable marker were designated pGPB36 (*S. mikatae* FRD1), pGPB37 (*K. marxianus* FRD1), pGPB39 (*K. polyspora* FRD1), and pGPB40 (*S. cerevisiae* FRD1) (FIG. 27).

Example 14C

Insertion of FRD1 at First and Second ADHa Loci of *I. orientalis* Strain 12481 pGPB36 (*S. mikatae* FRD1), pGPB37 (*K. marxianus* FRD1), pGPB39 (*K. polyspora* FRD1), and pGPB40 (*S. cerevisiae* FRD1) are digested with SacI and ApaI and transformed into *I. orientalis* strain 12481 by lithium acetate transformation. Transformants are selected on YNB+2% lactic plates overlaid with x-α-gal. After around six days, blue transformants are picked and plated for single colonies on YP+20 g/L glucose plates containing x-α-gal. Blue colonies are picked, and genomic DNA is isolated and screened by PCR to confirm integration of the FRD1 expression cassette at the ADHa locus using primers oGPB47 (SEQ ID NO:147), oGPB56 (SEQ ID NO:187), oGPB54 (SEQ ID NO:150), and oGPB46 (SEQ ID NO:146). Strains with the correct integration of the FRD1 gene are designated ySBCG95-106.

pGPB20 (*S. mikatae* FRD1), pGPB22 (*K. marxianus* FRD1), pGPB25 (*K. polyspora* FRD1), and pGPB26 (*S. cerevisiae* FRD1) are digested with SacI and ApaI and transformed into strains ySBCG95-106 by lithium acetate transformation. Transformants are screened by PCR to confirm correct integration of the FRD1 expression cassette at the ADHa locus using primers oGPB47 (SEQ ID NO:147), oGPB53 (SEQ ID NO:149), oGPB52 (SEQ ID NO:148), oGPB54 (SEQ ID NO:150), and oGPB46 (SEQ ID NO:146). The resulting strains are designated ySBCG123, ySBCG124, and ySBCG126-135.

Marker recycling is carried out with plasmid pVB32. The correct homozygous strains with both markers removed are designated 12750-12753, 12763-12766, ySBCG150-ySBCG152, and ySBCG141.

The various FRD1 insertion/ADHa deletion strains generated in Example 14 are summarized in Table 16.

TABLE 16

*I. orientalis* FRD1 insertion strains:

| Strain name | Description | Parent strain |
| --- | --- | --- |
| ySBCG95/ ySBCG96/ ySBCG97 | CYB2A deletion (2) *I. orientalis* PYC1 insertion at PDC1 (2) *S. mikatae* FRD1 insertion at ADHa (1) | 12481 |
| ySBCG98/ ySBCG99/ ySBCG100 | CYB2A deletion (2) *I. orientalis* PYC1 insertion at PDC1 (2) *K polyspora* FRD1 insertion at ADHa (1) | 12481 |
| ySBCG101/ ySBCG102/ ySBCG103 | CYB2A deletion (2) *I. orientalis* PYC1 insertion at PDC1 (2) *S. cerevisiae* FRD1 insertion at ADHa (1) | 12481 |
| ySBCG104/ ySBCG105/ ySBCG106 | CYB2A deletion (2) *I. orientalis* PYC1 insertion at PDC1 (2) *K. marxianus* FRD1 insertion at ADHa (1) | 12481 |
| ySBCG132/ ySBCG133/ ySBCG134 | CYB2A deletion (2) *I. orientalis* PYC1 insertion at PDC1 (2) | ySBCG95/ ySBCG97 |

TABLE 16-continued

*I. orientalis* FRD1 insertion strains:

| Strain name | Description | Parent strain |
|---|---|---|
| ySBCG135 | *S. mikatae* FRD1 insertion at ADHa (2) | |
| ySBCG123/ ySBCG124 | CYB2A deletion (2) *I. orientalis* PYC1 insertion at PDC1 (2) *K. polyspora* FRD1 insertion at ADHa (2) | ySBCG98/ ySBCG99 |
| ySBCG126/ ySBCG127/ ySBCG128 | CYB2A deletion (2) *I. orientalis* PYC1 insertion at PDC1 (2) *S. cerevisiae* FRD1 insertion at ADHa (2) | ySBCG101/ ySBCG102/ ySBCG103 |
| ySBCG129/ ySBCG130/ ySBCG131 | CYB2A deletion (2) *I. orientalis* PYC1 insertion at PDC1 (2) *K. marxianus* FRD1 insertion at ADHa (2) | ySBCG104/ ySBCG105/ ySBCG106 |
| 12765/12766 ySBCG150/ ySBCG151/ ySBCG152 12750/12751 | CYB2A deletion (2) *I. orientalis* PYC1 insertion at PDC1 (2) *S. mikatae* FRD1 insertion at ADHa (2) CYB2A deletion (2) *I. orientalis* PYC1 insertion at PDC1 (2) *K. polyspora* FRD1 insertion at ADHa (2) | ySBCG132/ ySBCG133/ ySBCG134/ ySBCG135 ySBCG123/ ySBCG124 |
| 12752/12753 ySBCG141 | CYB2A deletion (2) *I. orientalis* PYC1 insertion at PDC1 (2) *S. cerevisiae* FRD1 insertion at ADHa (2) | ySBCG126/ ySBCG127/ ySBCG128 |
| 12763/12764 | CYB2A deletion (2) *I. orientalis* PYC1 insertion at PDC1 (2) *K. marxianus* FRD1 insertion at ADHa (2) | ySBCG129/ ySBCG131 |

Example 15

Insertion of MDH at the ATO2 Locus in *I. orientalis* Strains 12481, 12750-12753, 12763, and 12765

An MDH expression cassette is inserted at one or both ATO2 alleles of *I. orientalis* strain 12481 (Example 13D) and strains 12750-12753 and 12763-12766 (Example 14C).

Example 15A

Construction of ATO2 Deletion Constructs pKWB18, pKWB23, pKWB28

Figure 12:
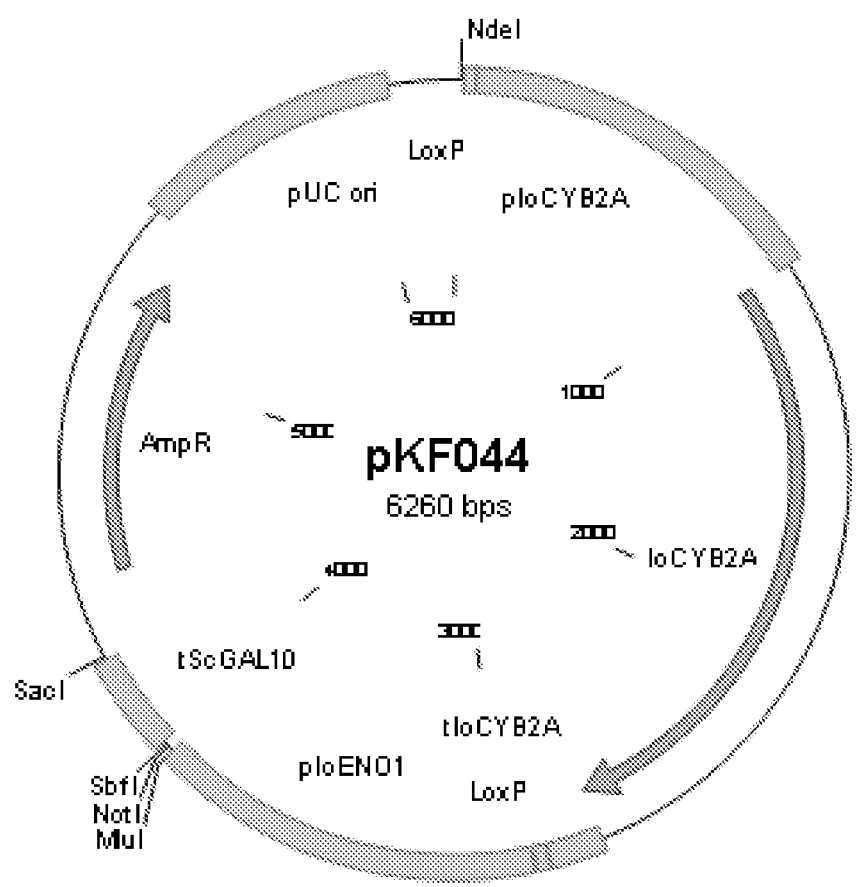
FIG. 12: pKF044, CYB2A construct.
Figure 42:
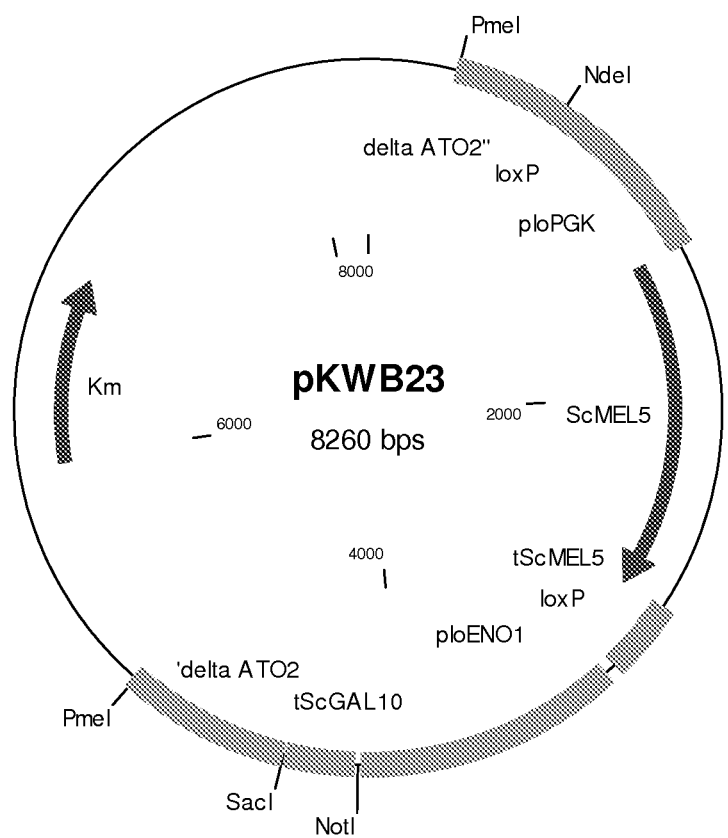
FIG. 42: pKWB23.
Figure 43:
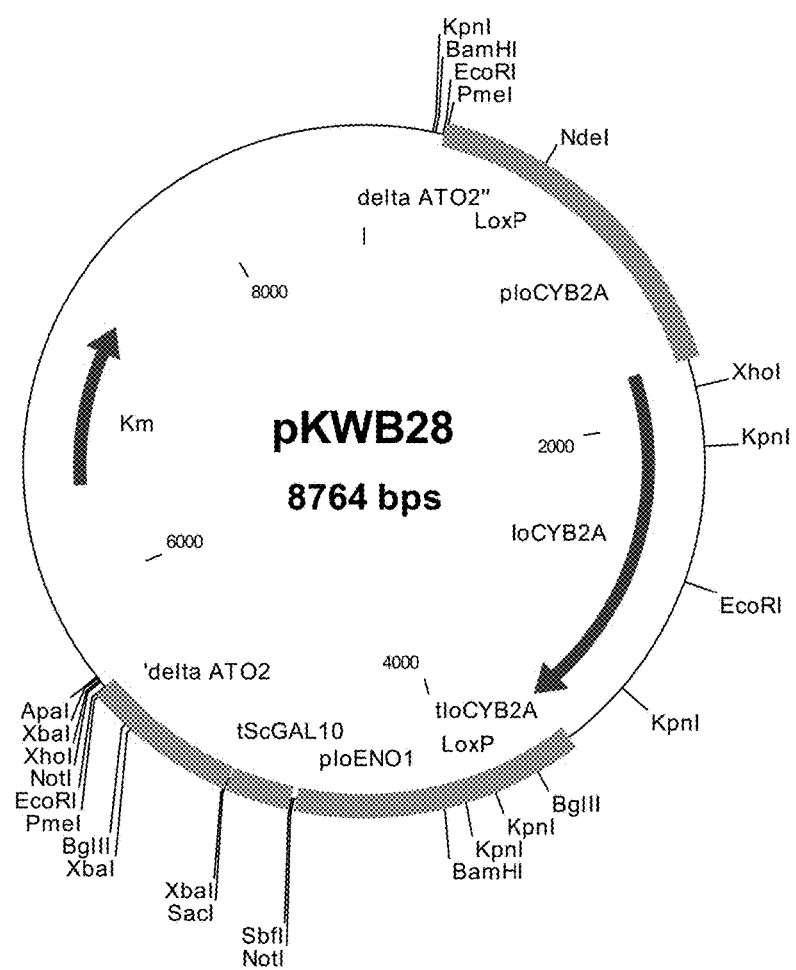
FIG. 43: pKWB28.

Upstream and downstream regions of *I. orientalis* ATO2 (SEQ ID NO:53) were amplified in order to generate ATO2 deletion constructs. The upstream and downstream regions correspond to nucleotides from 419 bp upstream to the start codon of ATO2 and from the stop codon to 625 bp downstream, respectively. Amplification of the upstream region is performed using primers oKW66 (forward, SEQ ID NO:88) and oKW67 (reverse, SEQ ID NO:89), which adds a PmeI restriction site and NdeI, NotI, and SacI restriction sites, respectively, to the product. Amplification of the downstream region is performed using primers oKW68 (forward, SEQ ID NO:90) and oKW69 (reverse, SEQ ID NO:91), which adds NdeI, NotI, and SacI restriction sites and a PmeI restriction site, respectively, to the product. The two fragments are amplified independently, then assembled into a full-length product with a two stage PCR protocol. The first stage uses 10 cycles (98° C. 10 s, 55° C. 20 s, 72° C. 60 s) with no primers, and the second stage uses 20 cycles (98° C. 10 s, 55° C. 20 s, 72° C. 60 s) with upstream forward and downstream reverse primers. The full-length product is gel purified, cloned into pCR-BluntII (Invitrogen), and sequenced. The plasmid confirmed to have correct sequence is subjected to quickchange PCR using Phusion polymerase to eliminate the plasmid-borne SacI site. Correct plasmids are confirmed by digestion with SacI and sequencing. The final ATO2 deletion construct is designated pKWB18 (FIG. 13).

pKWB18 was digested with NdeI and SacI and ligated to like-cut pKF031 (FIG. 11; *S. cerevisiae* MEL selectable marker) or pKF044 (FIG. 12; CYB2A selectable marker). The resulting ATO2 deletion constructs with MEL5 and CYB2A selectable markers are designed pKWB23 and pKWB28, respectively (FIGS. 42 and 43).

Example 15B

Construction of *E. coli*, *Z. rouxii*, and *R. oryzae* MDH Expression Constructs pGPB60, 62, 62, 64, 66, 78, and 79

The MDH genes from *E. coli*, *Z. rouxii*, and *R. oryzae* (SEQ ID NOs:169, 167, and 171, respectively) are amplified from genomic DNA using primers designed to add a MluI restriction site to the 5' end the start codon and an SbfI restriction site to the 3' end of the stop codon. *E. coli* MDH is amplified using primers oGPB61 (SEQ ID NO:188) and oGPB62 (SEQ ID NO:189), *Z. rouxii* MDH is amplified using primers oGPB67 (SEQ ID NO:190) and oGPB68 (SEQ ID NO:191), and *R. oryzae* MDH is amplified using primers oGPB65 (SEQ ID NO:192) and oGPB66 (SEQ ID NO:193). After amplification, the products are gel purified and cloned into pZeroBluntII and transformed into *E. coli*. Transformants are selected on LB plates containing 50 μg/ml kanamycin. Correct plasmids are confirmed by sequencing, and the final constructs are designated pGPB57 (*E. coli* MDH1), pGPB58 (*Z. rouxii* MDH), and pGPB68 (*R. oryzae* MDH). pGPB57, pGPB58, and pGPB59 are digested with MfuI and SbfI to liberate the fragment containing the respective MDH gene. The fragment is gel purified and cloned into like-cut pGPB54 and pGPB55. The resulting plasmids are designated pGPB60 (*E. coli* MDH, MEL5 marker), pGPB62 (*E. coli* MDH, CYB2A marker), pGPB64 (*Z. rouxii* MDH, MEL5 marker), pGPB66 (*Z. rouxii* MDH, CYB2A marker), pGPB78 (*R. oryzae* MDH, MEL5 marker), and pGPB79 (*R. oryzae* MDH, CYB2A marker).

Example 15C

Construction of *K. marxianus* MDH3 Expression Constructs pGPB54 and pGPB55

The MDH3 gene from *K. marxianus* (SEQ ID NO:23) is amplified from genomic DNA using primers designed for ligation-less cloning into the NotI site of pKF031 and pKF044. MDH3 is amplified using primers oKW104 (SEQ ID NO:116) and oKW105 (SEQ ID NO:117). After amplification, the product is gel purified and co-transformed into *E. coli* with NotI-digested pKF031 and pKF044. Transformants are selected on LB plates containing 100 μg/ml carbenicillin, and screened using primers oKW93 (SEQ ID NO:108) and oKW95 (SEQ ID NO:109). Quickchange PCR is performed on MDH3 using primers oKW136 and oKW137 to eliminate an internal NdeI site (T18C). Correct plasmids are confirmed by sequencing, and the final constructs are designated pKWB10 (MDH3, MEL5 marker), and pKWB13 (MDH3, CYB2A marker). pKWB10 and pKWB13 were digested with NdeI and SacI to liberate the fragment containing selectable marker, ENO promoter, *K. marxianus* MDH3, and terminator. The resulting fragments are ligated into like-cut pKWB54 containing the ATO2 deletion construct. The resulting plasmids are designated pGPB54 (*K. marxianus* MDH3, MEL5 marker) and pGPB55 (*K. marxianus* MDH3, CYB2A marker).

Example 15D

Insertion of MDH at First and Second ATO2 Loci in *I. orientalis* Strain 12750-12753, 12763, and 12765 pGPB64 (*Z. rouxii* MDH, MEL5 marker) is digested with PmeI and the appropriate fragments are used to transformed *I. orientalis* strains 12750-12753, 12763, and 12765 (Example 14) by lithium acetate transformation. Transformants are selected by growth on YNB+melibiose and screened by PCR with primers flanking the ATO2 locus (oKW214 (SEQ ID NO:194) and oKWB155 (SEQ ID NO:195)) along with nested primers specific to the MEL5 integration cassette (oGPB55 (SEQ ID NO:151) and oGPB11 (SEQ ID NO:142)). Colonies with the correct insertion of MDH at a first ATO2 locus are designated ySBCG153-161 and ySBCG166-171.

pGPB66 (*Z. rouxii* MDH, CYB2A marker) is digested with PmeI and the appropriate fragments are used to transformed *I. orientalis* strains ySBCG154-157, ySBCG160, and ySBCG166-171. Transformants are selected by growth on YNB+lactic+α-x-gal and screened by PCR with primers flanking the ATO2 locus (oKW214 (SEQ ID NO:194) and oKWB155 (SEQ ID NO:195)) along with nested primers specific to the MEL5 integration cassette (oGPB55 (SEQ ID NO:151) and the CYB2A integration cassette (oGPB52 (SEQ ID NO:148) and oGPB53 (SEQ ID NO:149)). Strains homozygous for MDH at the ATO2 loci are designated 12785-12787, 12783, 12784, and 12798-12803.

Plasmids containing an overexpression cassette with MDH from *E. coli*, *R. oryzae*, or *K. marxianus* (Examples 15B and 15C) can be integrated at the first and second ATO2 loci in *I. orientalis* strains 12750-12753, 12763, and 12765 using the same general techniques.

Marker recycling is carried out using pVB32, and homozygous *Z. rouxii* MDH strains with both markers removed are designated 12788-12792 and 12840-12846, and 12848.

Example 15E

Insertion of *K. marxianus* MDH3, *E. coli* MDH, *Z. rouxii* MDH, and Null Control at First and Second ATO2 Loci in *I. orientalis* Strain 12481 pKWB23, pGPB55, pGPB60, and pGPB64 are digested with PmeI and the appropriate fragments are used to transform *I. orientalis* strain 12481 by lithium acetate transformation. Transformants are selected by growth on YNB+ melibiose or YNB+2% lactic acid and screened by PCR with primers flanking the ATO2 locus (oKW214 (SEQ ID NO:194) and oKWB155 (SEQ ID NO:195)) along with nested primers specific to the MEL5 integration cassette (oGPB55 (SEQ ID NO:151) and oGPB11 (SEQ ID NO:142)) or the CYB2A integration cassette (oGPB53 (SEQ ID NO:149) and oGPB11 (SEQ ID NO:142)). Colonies with the correct insertion of MDH at a first ATO2 locus are designated ySBCG90-92 and ySBCG107-112. Likewise, a strain heterozygous for the ATO2 deletion is designated 12642.

pKWB28, pGPB54, pGPB62, and pGPB66 are digested with PmeI and the appropriate fragments are used to transform ySBCG90, ySBCG91, ySBCG107-109, ySBCG110, ySBCG111, and 12642. Transformants are selected by growth on YNB+melibiose+α-X-gal and screened by PCR with primers flanking the ATO2 locus (oKW214 (SEQ ID NO:194) and oKWB155 (SEQ ID NO:195)) along with nested primers specific to the MEL5 integration cassette (oGPB55 (SEQ ID NO:151) and oGPB54 (SEQ ID NO:150)) or the CYB2A integration cassette (oGPB52 (SEQ ID NO:148) and oGPB53 (SEQ ID NO:149)). Strains homozygous for MDH at the ATO2 loci are designated 12601, 12602, 12620-12622, and 12623-12625. Likewise, a strain homozygous for the ATO2 deletion is designated 12657.

Marker recycling is carried out using pVB32, and homozygous strains with both markers removed are designated 12712, 12715, and 12716.

Example 15F

Insertion of *I. orientalis* MDH1 at a First ATO2 Locus in *I. orientalis* Strain 12752

A PCR product amplified with the primers oKF254 (SEQ ID NO:197) and oKF202 (SEQ ID NO:198) using pKWB2 as the template is transformed into strain 12752 (Example 14C) by lithium acetate transformation, and transformants are selected on YNB+2% melibiose plates overlaid with x-α-gal. Blue-colored transformants are visible after around 6 days of growth at 30° C. Transformants are picked and plated for single colonies on YP+20 g/L glucose plates containing x-α-gal. Blue colonies are picked, and genomic DNA is isolated and screened for correct integration of the MDH1 expression cassette at the ATO2 locus by PCR using primers oGPB55 (SEQ ID NO:151), oKW66 (SEQ ID NO:88), oKW69 (SEQ ID NO:91), and oGPB54 (SEQ ID NO:150). Sister strains with the correct integration of the MDH1 gene are designated ySBCGH471 and ySBCGH472.

Example 15G

Insertion of *I. orientalis* MDH2 at a First ATO2 Locus in *I. orientalis* Strains 12752 and 12481

A PCR product amplified with the primers oKF254 (SEQ ID NO:197) and oKF202 (SEQ ID NO:198) using pKWB3 as the template is transformed into strains 12752 (Example 14C) and 12481 (Example 13D) by lithium acetate transformation, and transformants are selected on YNB+2% melibiose plates overlaid with x-α-gal. Blue-colored transformants are visible after around 6 days of growth at 30° C. Transformants are picked and plated for single colonies on YP+20 g/L glucose plates containing x-α-gal. Blue colonies are picked, and genomic DNA is isolated and screened for correct integration of the MDH2 expression cassette at the ATO2 locus by PCR using primers oGPB55 (SEQ ID NO:151), oKW66 (SEQ ID NO:88), oKW69 (SEQ ID NO:91), and oGPB54 (SEQ ID NO:150). Strains derived from strain 12752 with the correct integration of the MDH2 gene are designated ySBCGH473 and ySBCGH474. The strain derived from strain 12481 with the correct integration of the MDH2 gene is designated ySBCG48.

Example 15H

Insertion of *I. orientalis* MDH2 at a Second ATO2 Locus in *I. orientalis* Strain ySBCG48

To generate a strain homozygous for MDH2 at ATO2, a PCR product amplified with the primers oKF254 (SEQ ID NO:197) and oKF202 (SEQ ID NO:198) using pKWB6 (Example 5B) as the template is transformed into strain ySBCG48 by lithium acetate transformation, and transformants are selected on YNB+2% lactic acid plates. Colonies are picked, and genomic DNA is isolated and screened for correct integration of the MDH2 expression cassette at both ATO2 loci by PCR using primers oGPB53 (SEQ ID NO:149), oGPB54 (SEQ ID NO:150), oGPB55 (SEQ ID NO:151), oKW66 (SEQ ID NO:88), oKW69 (SEQ ID NO:91), and oGPB52 (SEQ ID NO:148). The strain derived from ySBCG48 with the correct integration of the MDH2 gene at both ATO2 loci is designated strain 12480.

Marker recycling is carried out on strain 12480 using pVB32, and the homozygous strain with both markers removed is designated 12506.

The various MDH insertion/ATO2 deletion strains generated in Example 15 are summarized in Table 17.

TABLE 17

*I. orientalis* MDH insertion strains:

| Strain name | Description | Parent strain |
|---|---|---|
| ySBCG153/ ySBCG154/ ySBCG155 | CYB2A deletion (2) *I. orientalis* PYC1 insertion at PDC1 (2) *K. polyspora* FRD1 insertion at ADHa (2) *Z. rouxii* MDH insertion at ATO2 (1) | 12750/12751 |
| ySBCG156/ ySBCG157/ ySBCG158/ ySBCG159/ ySBCG160/ ySBCG161 | CYB2A deletion (2) *I. orientalis* PYC1 insertion at PDC1 (2) *S. cerevisiae* FRD1 insertion at ADHa (2) *Z. rouxii* MDH insertion at ATO2 (1) | 12752/12753 |
| ySBCG166/ ySBCG167/ ySBCG168 | CYB2A deletion (2) *I. orientalis* PYC1 insertion at PDC1 (2) *K. marxianus* FRD1 insertion at ADHa (2) *Z. rouxii* MDH insertion at ATO2 (1) | 12763 |
| ySBCG169/ ySBCG170/ ySBCG171 | CYB2A deletion (2) *I. orientalis* PYC1 insertion at PDC1 (2) *S. mikatae* FRD1 insertion at ADHa (2) *Z. rouxii* MDH insertion at ATO2 (1) | 12765 |
| 12783/12784 | CYB2A deletion (2) *I. orientalis* PYC1 insertion at PDC1 (2) *K. polyspora* FRD1 insertion at ADHa (2) *Z. rouxii* MDH insertion at ATO2 (2) | ySBCG154/ ySBCG155 |
| 12785/12786/ 12787 | CYB2A deletion (2) *I. orientalis* PYC1 insertion at PDC1 (2) *S. cerevisiae* FRD1 insertion at ADHa (2) *Z. rouxii* MDH insertion at ATO2 (2) | ySBCG156/ ySBCG157/ ySBCG160 |
| 12798/12799/ 12800 | CYB2A deletion (2) *I. orientalis* PYC1 insertion at PDC1 (2) *K. marxianus* FRD1 insertion at ADHa (2) *Z. rouxii* MDH insertion at ATO2 (2) | ySBCG166/ ySBCG167/ ySBCG168 |
| 12801/12802/ 12803 | CYB2A deletion (2) *I. orientalis* PYC1 insertion at PDC1 (2) *S. mikatae* FRD1 insertion at ADHa (2) *Z. rouxii* MDH insertion at ATO2 (2) | ySBCG169/ ySBCG170/ ySBCG171 |
| 12788/12789 | CYB2A deletion (2) *I. orientalis* PYC1 insertion at PDC1 (2) *K. polyspora* FRD1 insertion at ADHa (2) *Z. rouxii* MDH insertion at ATO2 (2) | 12783/12784 |
| 12790/12791/ 12792 | CYB2A deletion (2) *I. orientalis* PYC1 insertion at PDC1 (2) *S. cerevisiae* FRD1 insertion at ADHa (2) *Z. rouxii* MDH insertion at ATO2 (2) | 12785/12786/ 12787 |
| 12840/12841/ 12842/12843 12844 | CYB2A deletion (2) *I. orientalis* PYC1 insertion at PDC1 (2) *K. marxianus* FRD1 insertion at ADHa (2) *Z. rouxii* MDH insertion at ATO2 (2) | 12798/12799/ 12800 |
| 12845/12846/ 12848 | CYB2A deletion (2) *I. orientalis* PYC1 insertion at PDC1 (2) *S. mikatae* FRD1 insertion at ADHa (2) *Z. rouxii* MDH insertion at ATO2 (2) | 12802/12803 |
| ySBCG90/ ySBCG91/ ySBCG92 | CYB2A deletion (2) *I. orientalis* PYC1 insertion at PDC1 (2) *K. marxianus* MDH insertion at ATO2 (1) | 12481 |
| ySBCG107/ ySBCG108/ ySBCG109 | CYB2A deletion (2) *I. orientalis* PYC1 insertion at PDC1 (2) *E. coli* MDH insertion at ATO2 (1) | 12481 |
| ySBCG110/ ySBCG111/ ySBCG112 | CYB2A deletion (2) *I. orientalis* PYC1 insertion at PDC1 (2) *Z. rouxii* MDH insertion at ATO2 (1) | 12481 |
| 12642 | CYB2A deletion (2) *I. orientalis* PYC1 insertion at PDC1 (2) Null insertion at ATO2 (1) | 12481 |
| 12601/12602 | CYB2A deletion (2) *I. orientalis* PYC1 insertion at PDC1 (2) *K. marxianus* MDH insertion at ATO2 (2) | ySBCG90/ ySBCG91 |
| 12620/12621/ 12622 | CYB2A deletion (2) *I. orientalis* PYC1 insertion at PDC1 (2) *E. coli* MDH insertion at ATO2 (2) | ySBCG107/ ySBCG108/ ySBCG109 |
| 12623/12624/ 12625 | CYB2A deletion (2) *I. orientalis* PYC1 insertion at PDC1 (2) *Z. rouxii* MDH insertion at ATO2 (2) | ySBCG111/ ySBCG112 |
| 12657 | CYB2A deletion (2) *I. orientalis* PYC1 insertion at PDC1 (2) Null insertion at ATO2 (2) | 12642 |
| 12712 | CYB2A deletion (2) *I. orientalis* PYC1 insertion at PDC1 (2) *E. coli* MDH insertion at ATO2 (2) | 12622 |
| 12715/12716 | CYB2A deletion (2) *I. orientalis* PYC1 insertion at PDC1 (2) *Z. rouxii* MDH insertion at ATO2 (2) | 12623/12625 |
| ySBCGH471/ ySBCGH472 | CYB2A deletion (2) *I. orientalis* PYC1 insertion at PDC1 (2) | 12752 |

TABLE 17-continued

*I. orientalis* MDH insertion strains:

| Strain name | Description | Parent strain |
|---|---|---|
| | *S. cerevisiae* FRD1 insertion at ADHa (2) | |
| | *I. orientalis* MDH1 insertion at ATO2 (1) | |
| ySBCGH473/ ySBCGH474 | CYB2A deletion (2) *I. orientalis* PYC1 insertion at PDC1 (2) *S. cerevisiae* FRD1 insertion at ADHa (2) *I. orientalis* MDH2 insertion at ATO2 (1) | 12752 |
| ySBCG48 | CYB2A deletion (2) *I. orientalis* PYC1 insertion at PDC1 (2) *I. orientalis* MDH2 insertion at ATO2 (1) | 12481 |
| 12480/12506 | CYB2A deletion (2) *I. orientalis* PYC1 insertion at PDC1 (2) *I. orientalis* MDH2 insertion at ATO2 (2) | ySBCG48 |

Example 16

Batch Fermentor Characterization of *I. orientalis* Strains 12657, 12601, 12620 and 12625

Figure 44:
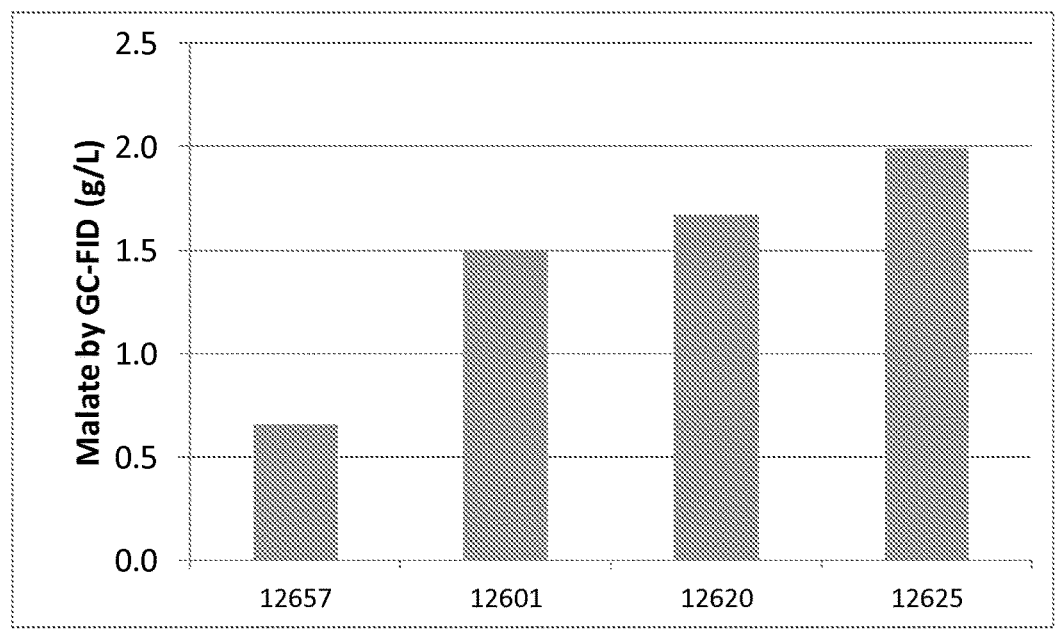
FIG. 44: Malate production by GC-FID (g/L) in strain 12657 (control) and strains 12601, 12620, and 12625 expressing exogenous malate dehydrogenase.

Replicate batch fermentations were run to compare strain performance. Fermentors were inoculated with biomass grown in the media outlined in Table 18. Seeds were run in 250 mL baffled flasks (50 mL working volume) at 250 rpm and 30° C. Flasks were harvested at 15 to 20 hours incubation time with a target seed $OD_{600}$ of 2 to 5. Fermentors were inoculated from these seeds to an initial $OD_{600}$ of 0.05 to 0.1. DM defined medium (adapted from Verduyn et al. Yeast 8:501-517 (1992); see Tables 18-20 was used in fermentors. pH was controlled at 4.45 with 30% $Ca(OH)_2$. The fermentor systems were sparged at 0.37 slpm with a blend of 69-72% pure $CO_2$ and 28-31% air. An agitation rate of 715 to 720 rpm was used. The sample taken at residual glucose concentration between 13 and 28 g/l was analyzed in each batch for biomass growth via $OD_{600}$, malate via gas chromatography with flame ionization detector and glucose by high performance liquid chromatography with refractive index detector. Malate is used as an indicator compound for flux through the MDH as strain 12657, 12601, 12620 and 12625 do not have the full reductive pathway to succinate. FIG. 44 shows increased malate production with all three MDH's tested. Malate production increased from 2.2 to 3-fold with the expression of MDH.

TABLE 18

Defined media for flask cultures:

| Compound | Concentration (g/kg) |
|---|---|
| $C_6H_{12}O_6$ | 120 |
| $(NH_2)_2CO$ | 2.38 |
| $KH_2PO_4$ | 3.0 |
| $MgSO_4$—$7H_2O$ | 0.5 |
| 1000x Vitamin Solution | 1 |
| 100x Trace Solution | 1 |
| $C_6H_{13}NO_4S$ | 3.9 |

TABLE 19

Trace element 1000x stock solution

| Chemical | Concentration (g/L) |
|---|---|
| $C_{10}H_{14}N_2Na_2O_8$ $2H_2O$ | 15.00 |
| $ZnSO_4$ $7H_2O$ | 4.50 |
| $MnCl_2$ $2H_2O$ | 1 |
| $CoCl_2$ $6H_2O$ | 0.30 |
| $CuSO_4$ $5H_2O$ | 0.30 |
| $Na_2MoO_4$ $2H_2O$ | 0.40 |
| $CaCl_2$ $2H_2O$ | 4.50 |
| $FeSO_4$ $7H_2O$ | 3.00 |
| $H_3BO_3$ | 1.00 |
| KI | 0.10 |

TABLE 20

Vitamin 1000x stock solution:

| Chemical | Concentration (g/L) |
|---|---|
| $C_{10}H_{16}N_2O_3S$ | 0.05 |
| $C_{18}H_{32}CaN_2O_{10}$ | 1.00 |
| $C_6H_5NO_2$ | 5 |
| $C_6H_{12}O_6$ | 25.00 |
| $C_{12}H_{18}C_{12}N_4OS \cdot xH_2O$ | 1.00 |
| $C_8H_{12}ClNO_3$ | 1.00 |
| $C_7H_7NO_2$ | 0.20 |

Example 17

Insertion of *I. orientalis* FUM1 Genes at the CYB2B Locus in *I. orientalis* Strains 12788, 12789, 12790, 12791 and 12792

*I. orientalis* FUM1 expression cassettes are inserted at both alleles of CYB2A of *I. orientalis* strains 12788, 12789, 12790, 12791 and 12792 (Example 15).

Example 17A

Construction of *I. orientalis* FUM1 Expression Constructs pGPB30, pGPB42, pGPB44, and pGPB47

An expression cassette for the *I. orientalis* FUM1 gene (SEQ ID NO:1) is inserted into the ADHa deletion construct pGPB11. PCR primers oGPB38 (SEQ ID NO:144) and oGPB40 (SEQ ID NO:145) are used to amplify FUM1 using *I. orientalis* genomic DNA as the template. The 5' primer adds an XbaI site at the start site of the coding sequence and the 3' primer adds a PacI site 3' of the stop codon. The resulting PCR product is digested with XbaI and PacI and ligated to similarly digested pGPB11. The resulting plasmid, which contains the FUM1 coding sequence flanked by the *I. orientalis* PDC1 promoter and terminator and the CYB2A selectable marker, is designated pGPB30 (FIG. 28).

pGPB30 is digested with BamHI and NdeI and ligated into similarly digested pGPB14. The resulting plasmid is designated pGPB44 (FIG. 30).

The expression cassette from pGPB30 is excised using NotI and ligated to the NotI cut pKW22. The resulting plasmid is designated pGPB42 (FIG. 29).

The expression cassette from pGPB44 is excised using NotI and ligated to the NotI cut pKW22. The resulting plasmid is designated pGPB47 (FIG. 31).

Example 17B

Insertion of *I. orientalis* FUM1 at One or Both *I. orientalis* CYB2B Loci

Integration of the first copy of the FUM1 expression cassette at the CYB2B locus is performed using plasmids containing the MEL5 selectable marker. pGPB47 is digested with SacI and ApaI and transformed into 12788, 12789, 12790, 12791 and 12792 using lithium acetate transformation. Transformants are screened by PCR to confirm correct integration of the FUM1 expression cassette at the second CYB2B locus using primers oKW202 (SEQ ID NO:200), oGPB54 (SEQ ID NO:150), oKW195 (SEQ ID NO:199), and oGPB56 (SEQ ID NO:187). The resulting strains are designated 12824-12828.

Figure 67:
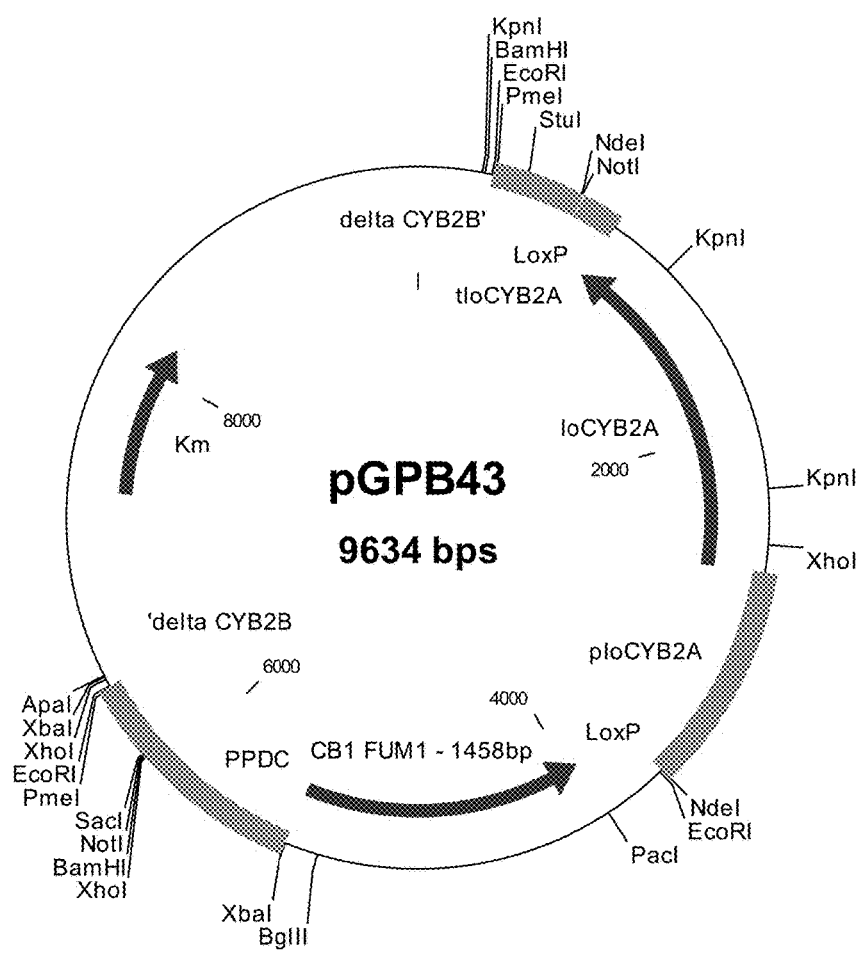
FIG. 67: pGPB43.

Integration of the second copy of the FUM1 expression cassette at the CYB2B locus is performed using plasmids containing the CYB2A selectable marker. pGPB43 (FIG. 67) is digested with SacI and ApaI and transformed into *I. orientalis* strains 12824-12828 using lithium acetate transformation. Transformants are screened by PCR to confirm correct integration of the FUM1 expression cassette at the first CYB2B locus using primers oKW202 (SEQ ID NO:200), oGPB54 (SEQ ID NO:150), oGPB52 (SEQ ID NO:148), oKW195 (SEQ ID NO:199), and oGPB53 (SEQ ID NO:149). The resulting strains are designated 12829-12839.

Marker recycling is carried out with plasmid pVB32. The correct homozygous strains with both markers removed are designated 12847, 12868, 12869, and 12870.

The various FUM1 insertion/CYB2B deletion strains generated in Example 17 are summarized in Table 21.

TABLE 21

*I. orientalis* FUM1 insertion strains:

| Strain name | Description | Parent strain |
|---|---|---|
| 12824/12825/ 12826 | CYB2A deletion (2) *I. orientalis* PYC1 insertion at PDC1 (2) *S. cerevisiae* FRD1 insertion at ADHa (2) *Z. rouxii* MDH insertion at ATO2 (2) *I. orientalis* FUM1 insertion at CYB2B (1) | 12790/12791/ 12792 |
| 12827/12828 | CYB2A deletion (2) *I. orientalis* PYC1 insertion at PDC1 (2) *K. polyspora* FRD1 insertion at ADHa (2) *Z. rouxii* MDH insertion at ATO2 (2) *I. orientalis* FUM1 insertion at CYB2B (1) | 12788/12789 |
| 12829/12830/ 12831/12832/ 12833/12834/ 12835 | CYB2A deletion (2) *I. orientalis* PYC1 insertion at PDC1 (2) *S. cerevisiae* FRD1 insertion at ADHa (2) *Z. rouxii* MDH insertion at ATO2 (2) *I. orientalis* FUM1 insertion at CYB2B (2) | 12824/12825/ 12826 |
| 12836/12837/ 12838/12839 | CYB2A deletion (2) *I. orientalis* PYC1 insertion at PDC1 (2) *K. polyspora* FRD1 insertion at ADHa (2) *Z. rouxii* MDH insertion at ATO2 (2) *I. orientalis* FUM1 insertion at CYB2B (2) | 12827/12828 |
| 12847/12868 | CYB2A deletion (2) *I. orientalis* PYC1 insertion at PDC1 (2) *S. cerevisiae* FRD1 insertion at ADHa (2) *Z. rouxii* MDH insertion at ATO2 (2) *I. orientalis* FUM1 insertion at CYB2B (2) | 12831/12833 |
| 12869/12870 | CYB2A deletion (2) *I. orientalis* PYC1 insertion at PDC1 (2) *K. polyspora* FRD1 insertion at ADHa (2) *Z. rouxii* MDH insertion at ATO2 (2) *I. orientalis* FUM1 insertion at CYB2B (2) | 12837/12838 |

Example 17C

Batch Fermentor Characterization of *I. orientalis* Strains 12791, 12824, 12826

Replicate batch fermentations were run to compare strain performance. Fermentors were inoculated with biomass grown in the media outlined in Table 18. Seeds were run in 250 mL baffled flasks (50 mL working volume) at 250 rpm and 30° C. Flasks were harvested at 15 to 20 hours incubation time with a target seed $OD_{600}$ of 2 to 5. Fermentors were inoculated from these seeds to an initial $OD_{600}$ of 0.05 to 0.1. DM defined medium (adapted from Verduyn et al. Yeast 8:501-517 (1992); see Tables 18-20) was used in fermentors. pH was controlled at 4.45 with 30% $Ca(OH)_2$. The fermentor systems were sparged at 0.37 slpm with a blend of 69-72% pure $CO_2$ and 28-31% air. An agitation rate of 715 to 720 rpm was used. The sample taken at residual glucose concentration between 13 and 28 g/l was analyzed in each batch for biomass growth via $OD_{600}$, succinate via gas chromatography with flame ionization detector and glucose by high performance liquid chromatography with refractive index detector.

Figure 45:
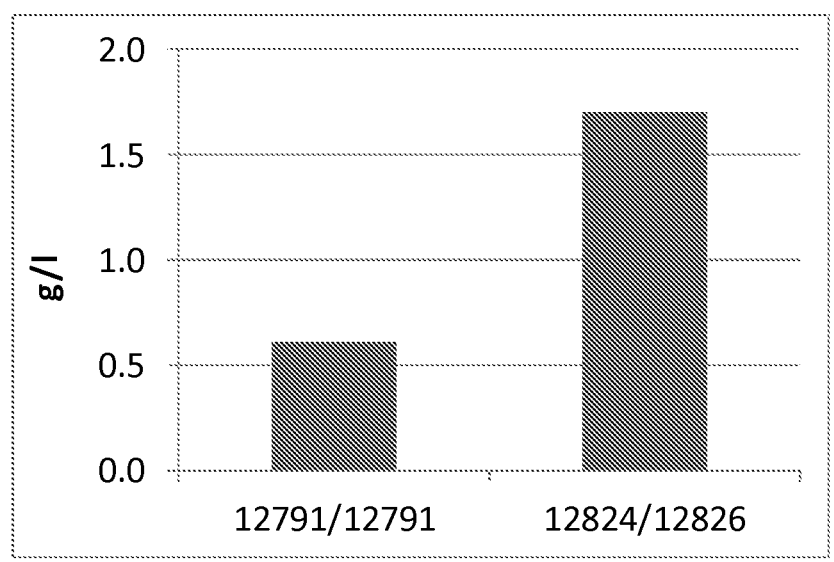
FIG. 45: Succinate production by GC-FID (g/L) in strains 12791/12791 (control) and strains 17824/12826 expressing exogenous fumarate.

FIG. 45 shows the impact of native fumarase overexpression on succinate production. Average succinate production increased 2.75-fold over strains with only native fumarase levels.

Example 18

Insertion of ZWF1 at the GPD1 Locus in *I. orientalis* Strain 12868 and 12869

A ZWF1 expression cassette is inserted at one or both GPD1 alleles in *I. orientalis* strains 12868 and 12869 (Example 17B).

Example 18A

Construction of *I. orientalis* ZWF1 Expression Constructs pKF033 and pGPB56

The ZWF1 gene from *I. orientalis* (SEQ ID NO:33) is amplified from genomic DNA using Phusion polymerase and primers oKF168 (SEQ ID NO:131) and oKF163 (SEQ ID NO:130), which contain an MluI site and an SbfI site, respectively. After amplification, the product is gel purified, digested with MluI and SbfI, and ligated to similarly digested pKF031 and pKF044. pKF031 (FIG. 32) and pKF044 (FIG. 33) are constructed from pUC19 backbones, and both contain a multiple cloning site containing MluI, NotI, and SbfI sites operatively linked to the *I. orientalis* ENO promoter and the *S. cerevisiae* GAL10 terminator. pKF031 also contains a selection marker cassette comprising the *S. cerevisiae* MEL5 gene operatively linked to the *I. orientalis* PGK promoter. This selection marker cassette is flanked by loxP sites. pKF044 contains an expression cassette comprising the *I. orientalis* CYB2A promoter, gene, and terminator. This expression cassette is flanked by loxP sites.

The plasmids are transformed into *E. coli*, and transformants are selected on LB plates containing 100 µg/ml carbenicillin and screened using primers flanking the NotI site of pKF031 and pKF044 (oKW93 (SEQ ID NO:108) and oKW95 (SEQ ID NO:109)). Correct plasmids are confirmed by sequencing, and the final constructs are designated pKF033 (MEL5 marker) (FIG. 34) and pGPB056 (CYB2A marker) (FIG. 35).

Example 18B

Insertion of *I. orientalis* ZWF1 at the First and Second GPD1 Loci in *I. orientalis* Strains 12868 and 12869 pKF033 and pGPB56 are both amplified from the loxP site on the 5' end to the GAL10 terminator on the 3' end using primers oGPBH1 (SEQ ID NO:163) and oGPBH2 (SEQ ID NO:164). Each of these primers contains on their 5' end 65 bp of sequence specific to the 65 bp immediately upstream and downstream of the GPD1 locus in *I. orientalis*. This recombination sequence enables double recombination and integration at the GPD1 locus.

The PCR product amplified from pKF033 is used to transform *I. orientalis* strains 12868 and 12869. Transformants are selected on YNB+melibiose+x-α-gal, and integration of ZWF1 at a first GPD1 allele is confirmed by PCR using primers oGPBH3 (SEQ ID NO:165), oGPBH4 (SEQ ID NO:166), oGPB55 (SEQ ID NO:151), and oGPB11 (SEQ ID NO:142). The correct heterozygous strains are designated ySBCGH464 and ySBCGH465.

To generate homozygous strains with ZWF1 inserted at both GPD1 alleles, strains ySBCGH464 and ySBCGH465 are transformed with the PCR product amplified from pGPB56. Transformants are selected on YNB+2% lactic acid+x-α-gal, and integration of ZWF1 is confirmed by PCR using the primers oGPBH3 (SEQ ID NO:165), oGPBH4 (SEQ ID NO:166), oGPB53 (SEQ ID NO:149), and oGPB52 (SEQ ID NO:148). The correct homozygous strains are designated ySBCGH466 and ySBCGH467.

Marker recycling is carried out with plasmid pVB32. The correct homozygous strains with both markers removed are designated ySBCGH468 and ySBCGH469.

The various ZWF1 insertion/GPD1 deletion strains generated in Example 18 are summarized in Table 22.

TABLE 22

| Strain name | Description | Parent strain |
|---|---|---|
| ySBCGH464 | CYB2A deletion (2) *I. orientalis* PYC1 insertion at PDC1 (2) *S. cerevisiae* FRD1 insertion at ADHa (2) *Z. rouxii* MDH insertion at ATO2 (2) *I. orientalis* FUM1 insertion at CYB2B (2) *I. orientalis* ZWF1 at GPD1 (1) | 12868 |
| ySBCGH465 | CYB2A deletion (2) *I. orientalis* PYC1 insertion at PDC1 (2) *K. polyspora* FRD1 insertion at ADHa (2) *Z. rouxii* MDH insertion at ATO2 (2) *I. orientalis* FUM1 insertion at CYB2B (2) *I. orientalis* ZWF1 at GPD1 (1) | 12869 |
| ySBCGH466/ ySBCGH468 | CYB2A deletion (2) *I. orientalis* PYC1 insertion at PDC1 (2) *S. cerevisiae* FRD1 insertion at ADHa (2) *Z. rouxii* MDH insertion at ATO2 (2) *I. orientalis* FUM1 insertion at CYB2B (2) *I. orientalis* ZWF1 at GPD1 (2) | ySBCGH464 |
| ySBCGH467/ ySBCGH469 | CYB2A deletion (2) *I. orientalis* PYC1 insertion at PDC1 (2) *K. polyspora* FRD1 insertion at ADHa (2) *Z. rouxii* MDH insertion at ATO2 (2) *I. orientalis* FUM1 insertion at CYB2B (2) *I. orientalis* ZWF1 at GPD1 (2) | ySBCGH465 |

Example 18C

Shake Flask Characterization of Succinate Production in *I. orientalis* Strains ySBCGH193 and ySBCG194

Shake flasks are used to test the ZWF1 insertion strains ySBCGH468 and ySBCG469. Shake flasks are inoculated with biomass harvested from seed flasks grown overnight to an $OD_{600}$ of 2 to 6. 250 mL baffled flasks (50 mL working volume) are inoculated to an $OD_{600}$ of 0.2 and fermentation occurs at 100 rpm and 30° C. DM defined medium is used in flasks, with pH control and $CO_2$ provided by calcium carbonate addition at a concentration of 0.255M (1.28 g $CaCO_3$ per 50 ml flask). Samples are taken throughout the time course of the assay and analyzed for biomass growth via $OD_{600}$, and succinate and glucose are monitored via high performance liquid chromatography (HPLC). The resulting data shows production of greater than 40 g/L succinate by strain ySBCGH468 and ySBCGH469.

Example 19

Deletion of the First and Second PCK1 Loci in *I. orientalis* Strains 12868 and 12869

The first and second PCK1 loci in *I. orientalis* strains 12868 and 12869 (Example 17B) are deleted using a PCK deletion construct.

Example 19A

Construction of *I. orientalis* PCK Deletion Constructs

The PCK upstream region from 432 bp upstream to the start codon is amplified by PCR. Sequence corresponding to the restriction sites NdeI/NotI/SacI is added to the 5' end of the reverse upstream primer (oKW78 (SEQ ID NO:99)). A PmeI restriction site is added to the 5' end of the forward upstream primer (oKW77 (SEQ ID NO:98)). The PCK downstream region is amplified from the stop codon to 472 bp downstream. The downstream forward primer (oKW79 (SEQ ID NO:100)) contained the same NdeI/NotI/SacI sequence as the reverse upstream primer. The 5' end of the reverse downstream primer also has a PmeI site (oKW80 (SEQ ID NO:101)). The two fragments are amplified independently using Phusion polymerase, then assembled into a full-length (926 bp) product via a two-stage PCR protocol (10 cycles (98° C. 10 s, 55° C. 20 s, 72° C. 60 s) with no primers, followed by 20 cycles (98° C. 10 s, 55° C. 20 s, 72° C. 60 s) with upstream forward and downstream reverse primers). Full-length product is gel purified and cloned into pCR-BluntII (Invitrogen) and sequenced. The plasmid confirmed to have correct sequence is subjected to quickchange PCR using Phusion polymerase to eliminate the plasmid borne SacI site. Correct plasmids are confirmed by digestion with SacI and sequencing. The final construct is named pKWB20 (FIG. 39).

pKWB20 is digested with NdeI and SacI and the resulting 4.4 kb DNA fragment is gel purified. Plasmid pKF031 is digested with NdeI and SacI to create a fragment of 3.7 kb that contains the MEL5 marker flanked by loxP sites. In the same way, pKF044 is digested to create a 4.2 kb fragment containing the CYB2A marker flanked by loxP sites. Marker fragments are ligated into the digested pKWB20 plasmid to create pKWB25 (FIG. 40), containing the MEL5 marker, and pKWB30 (FIG. 41), containing the CYB2A marker. Correct constructs are confirmed by PCR and restriction digestion.

Example 19B

Deletion of PCK1 in *I. orientalis* Strains 12868 and 12869

Plasmid pKWB25 is digested with PmeI to create a 5 kb fragment containing the MEL5 marker surrounded by PCK1 flanking sequence. The fragment is gel purified prior to transformation. In the same way, pKWB30 is digested with PmeI to create a 5.4 kb fragment containing the CYB2A marker with PCK1 flanking sequence. The fragment is gel purified prior to transformation.

The DNA fragment from pKWB30, containing the CYB2A marker, is transformed into strains 12868 and 12869. Transformants are selected on YNB+lactate, and deletion of PCK at the first allele is confirmed by PCR using primers oKW77 (SEQ ID NO:98), oKW80 (SEQ ID NO:101), oGPB52 (SEQ ID NO:148), and oGPB53 (SEQ ID NO:149). The correct heterozygous strains are designated ySBCGH475 and ySBCGH476.

Strains ySBCGH475 and ySBCGH476 are transformed with the PmeI digestion product from pKWB30 and selected on YNB+melibiose+x-α-gal to generate a homozygous strain with PCK deleted at both alleles. Integration is confirmed by PCR using the primers oKW77 (SEQ ID NO:98), oKW80 (SEQ ID NO:101), oGPB54 (SEQ ID NO:150), and oGPB55 (SEQ ID NO:151). The correct homozygous strains are designated ySBCGH477 and ySBCGH478.

The various PCK deletion strains generated in Example 19 are summarized in Table 23.

TABLE 23

*I. orientalis* PCK deletion strains:

| Strain name | Description | Parent strain |
|---|---|---|
| ySBCGH475 | PCK1 deletion (1)<br>I. CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2) | 12868 |
| ySBCGH476 | PCK1 deletion (1)<br>CYB2A deletion (2)<br>*I. orientalis* PYC1 insertion at PDC1 (2)<br>*K. polyspora* FRD1 insertion at ADHa (2)<br>*Z. rouxii* MDH insertion at ATO2 (2)<br>*I. orientalis* FUM1 insertion at CYB2B (2) | 12869 |
| ySBCGH477 | PCK1 deletion (2)<br>I. CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2) | ySBCGH475 |
| ySBCGH478 | PCK1 deletion (2)<br>I CYB2A deletion (2)<br>*I. orientalis* PYC1 insertion at PDC1 (2)<br>*K. polyspora* FRD1 insertion at ADHa (2)<br>*Z. rouxii* MDH insertion at ATO2 (2)<br>*I. orientalis* FUM1 insertion at CYB2B (2) | ySBCGH476 |

Example 20

Deletion of RIOR43690 in *I. orientalis* Strain 12868

An RIOR43690 deletion cassette is inserted at one or both RIOR43690 alleles in *I. orientalis* strain 12868 (Example 17B).

Example 20A

Synthesis of the RIOR43690 Deletion Construct pVMB54

Figure 46:
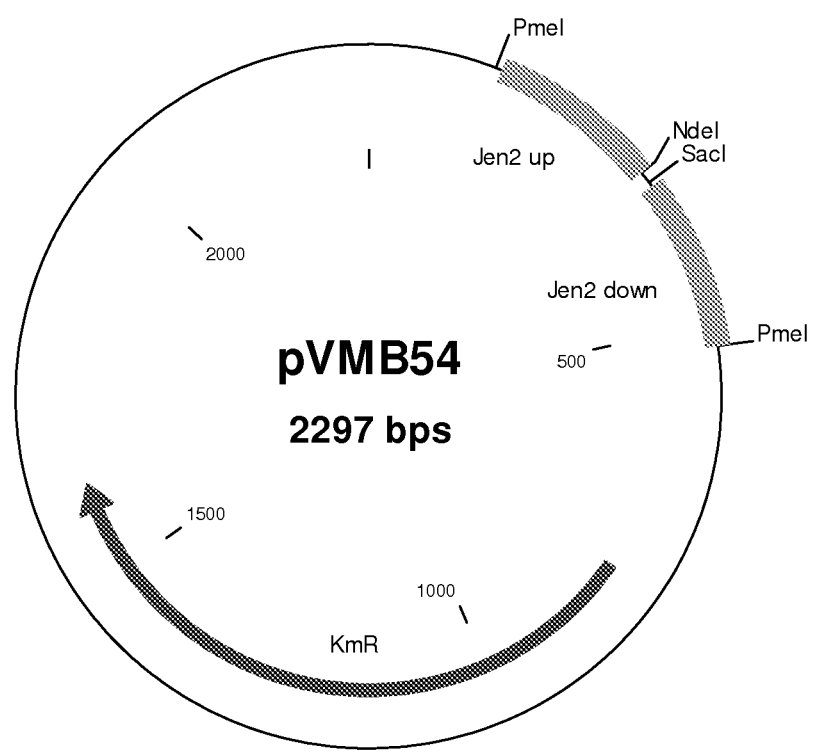
FIG. 46: pVMB54

The upstream 180 bp and downstream 180 bp regions of the RIOR43690 gene (SEQ ID NOs:205 and 206, respectively) are ordered from IDT (Coralville, Iowa) in the vector pIDTSmart. The upstream and downstream regions are flanked by PmeI sites, and contain internal NdeI and SacI restriction sites. The construct is named pVMB54 (FIG. 46).

Example 20B

Figure 47:
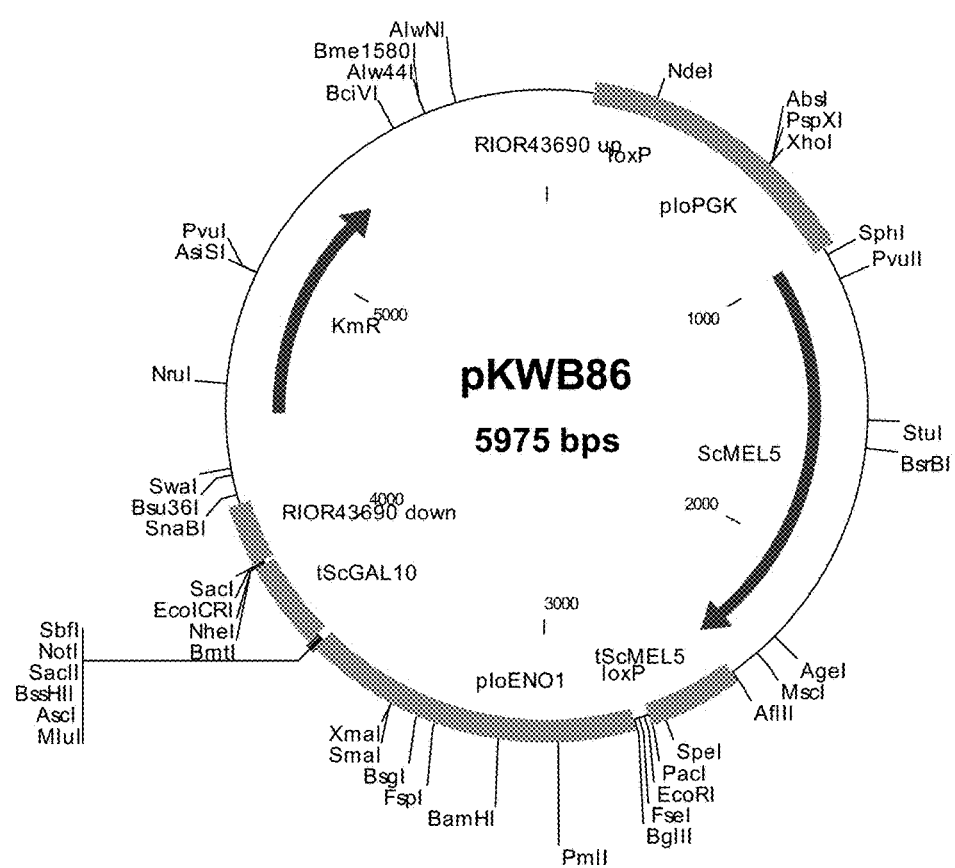
FIG. 47: pKWB86.

Construction of RIOR43690::MEL5 Deletion Construct pKWB86 pVMB54 is cut with NdeI/SacI and the 2281 bp fragment is gel purified. pKF031 (FIG. 11) is digested with NdeI/SacI to liberate the 3694 bp fragment containing the MEL5 marker cassette, ENO promoter, and GAL10 terminator. The fragment is gel purified, and ligated into purified cut pVMB54 using T4 DNA ligase, and transformed into E. coli. Transformants are selected on LB+kanamycin, and colonies are screened with M13F (SEQ ID NO:152) and oGPB55 (SEQ ID NO:151) primers to identify those containing the correct insert. A colony having the desired insert is miniprepped, sequenced and named pKWB86 (FIG. 47).

Example 20C

Figure 48:
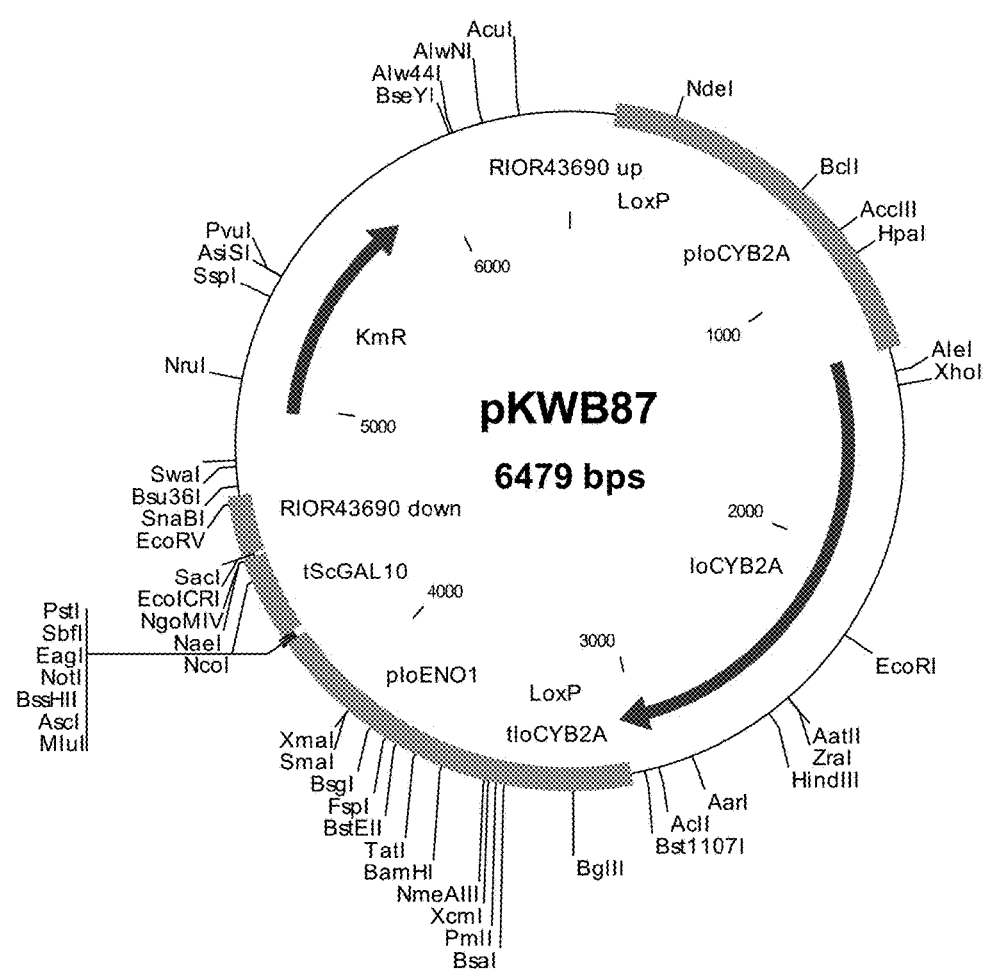
FIG. 48: pKWB87.

Construction of RIOR43690::CYB2A Deletion Construct pKWB87 pVMB54 is cut with NdeI/SacI and the 2281 bp fragment is gel purified. pKF044 (FIG. 12) is digested with NdeI/SacI to liberate the 4198 bp fragment containing the CYB2A marker cassette, ENO promoter, and GAL10 terminator. The fragment is gel purified, and ligated into purified cut pVMB54 using T4 DNA ligase, and transformed into E. coli. Transformants are selected on LB+kanamycin, and colonies are screened with M13F (SEQ ID NO:152) and oGPB53 (SEQ ID NO:149) primers to identify those containing the correct insert. A colony having the desired insert is miniprepped, sequenced and named pKWB87 (FIG. 48).

Example 20D

Construction of RIOR43690::MEL5 Deletion Strain 13054 pKWB86 is digested with PmeI, and the 4065 bp fragment corresponding to RIOR43690::MEL5 deletion cassette is gel purified. This fragment is then transformed into I. orientalis strain 12868. Transformants are selected on YNB+melibiose+x-gal and screened by PCR using flanking primers oKB86 (SEQ ID NO:203) and oKB87 (SEQ ID NO:204) and nested primers oGPB55 (SEQ ID NO:151) and oGPB54 (SEQ ID NO:150) to verify correct insertion at the RIOR43690 locus. A heterozygous strain with one copy of the RIOR43690 gene deleted is designated 13054.

Example 20E

Construction of Double RIOR43690 Deletion Strain 13055 pKWB87 is digested with PmeI, and the 4569 bp fragment corresponding to RIOR43690::CYB2A deletion cassette is gel purified. This fragment is then transformed into I. orientalis strain 13054. Transformants are selected on YNB+lactic and screened by PCR using flanking primers oKB86 (SEQ ID NO:203) and oKB87 (SEQ ID NO:204) and nested primers oGPB53 (SEQ ID NO:149) and oGPB52 (SEQ ID NO:148) to verify correct insertion at the RIOR43690 locus. A homozygous strain with both copies of the RIOR43690 gene deleted is designated 13055.

The various RIOR43690 deletion strains generated in Example 20 are summarized in Table 24.

TABLE 24

I. orientalis RIOR43690 deletion strains:

| Strain name | Description | Parent strain |
| --- | --- | --- |
| 13054 | CYB2A deletion (2)<br>GPD1 deletion (2)<br>CYB2B deletion (2)<br>RIOR43690 deletion (1)<br>I. orientalis PYC1 insertion at PDC1 (2)<br>I. orientalis FUM1 insertion at CYB2B (2)<br>S. cerevisiae FRD insertion at ADHa (2)<br>Z. rouxii MDH insertion at ATO2 (2) | 12868 |
| 13055 | CYB2A deletion (2)<br>GPD1 deletion (2)<br>CYB2B deletion (2)<br>RIOR43690 deletion (2)<br>I. orientalis PYC1 insertion at PDC1 (2)<br>I. orientalis FUM1 insertion at CYB2B (2)<br>S. cerevisiae FRD insertion at ADHa (2)<br>Z. rouxii MDH insertion at ATO2 (2) | 13054 |

Example 20F

Growth characterization of RIOR43690 Deletion Strain 13055

Plates are prepared having succinate as the sole carbon source at a final concentration of 2 g/L YNB agar is prepared, and a filter sterilized solution of succinate is added after autoclaving. The pH of the medium is adjusted to near 5 prior to pouring plates and allowed to drift up to near 6 as the plates cool.

Figure 49:
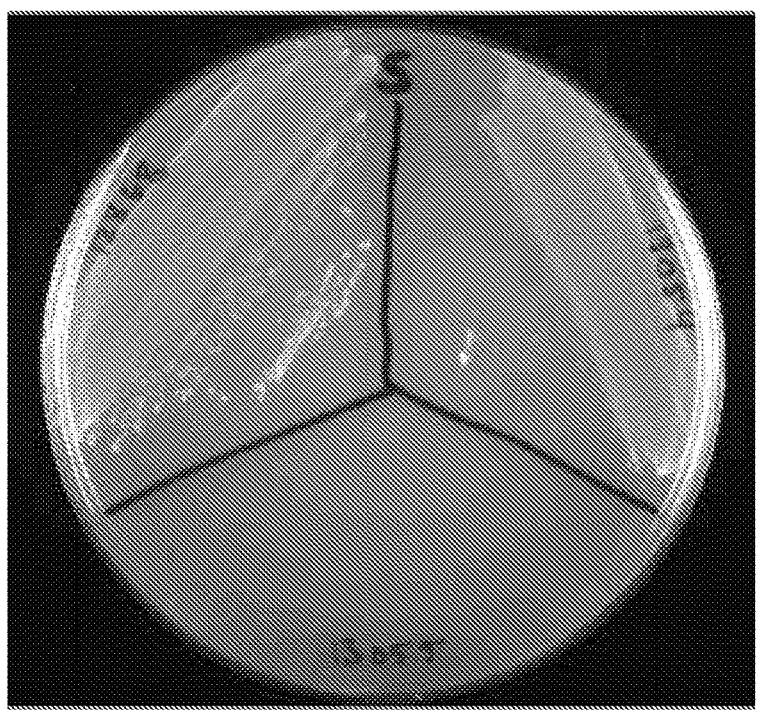
FIG. 49: Growth of RIOR43690 deletion strains on YNB-succinate plates.

Strain 12868 is streaked onto a YNB-succinate plate together with strains 13054 and 13055. After 3 days incubation at 30° C., growth is observed for strains 12868 and 13054. No growth is observed on the portion of the plate where strain 13055 is streaked indicating this gene is responsible for consumption of succinate (FIG. 49).

Example 21

Insertion of S. pombe MAE at the Putative RIOR43690 Locus in I. orientalis Strain 12868

An S. pombe MAE expression cassette was inserted at one or both RIOR43690 loci of I. orientalis strain 12868 (Example 17B).

Example 21A

Construction of S. pombe MAE Bipartite Integration Constructs pKWB95, pKWB96 and pKWB97

The malic anion exporter (MAE) gene from S. pombe (SEQ ID NO:181) was synthesized such that the coding sequence was segmented into five fragments with overlapping regions of homology. Fragments 2-5 (SEQ ID NO:207) were joined into one larger fragment via multi-fragment primerless PCR. The resulting fragment, which encoded the last 1154 bp of the S. pombe transporter, was topo cloned and sequenced for verification. Fragment 1 (SEQ ID NO:208)

was topo cloned separately and encoded the first 384 bp of the *S. pombe* transporter. Each of the fragments was flanked by MluI and SbfI restriction sites. After restriction digest, the fragments were gel purified, and ligated to similarly digested pKW086 and pKW087. pKW086 and pKW087 are constructed from pVMB54 backbones, and both contain a multiple cloning site containing MluI, NotI, and SbfI sites operatively linked to the *I. orientalis* ENO promoter and the *S. cerevisiae* GAL10 terminator. pKW086 also contains a selection marker cassette comprising the *S. cerevisiae* MEL5 gene operatively linked to the *I. orientalis* PGK promoter. This selection marker cassette is flanked by loxP sites. pKW087 contains an expression cassette comprising the *I. orientalis* CYB2A promoter, gene, and terminator. This expression cassette is flanked by loxP sites.

Figure 50:
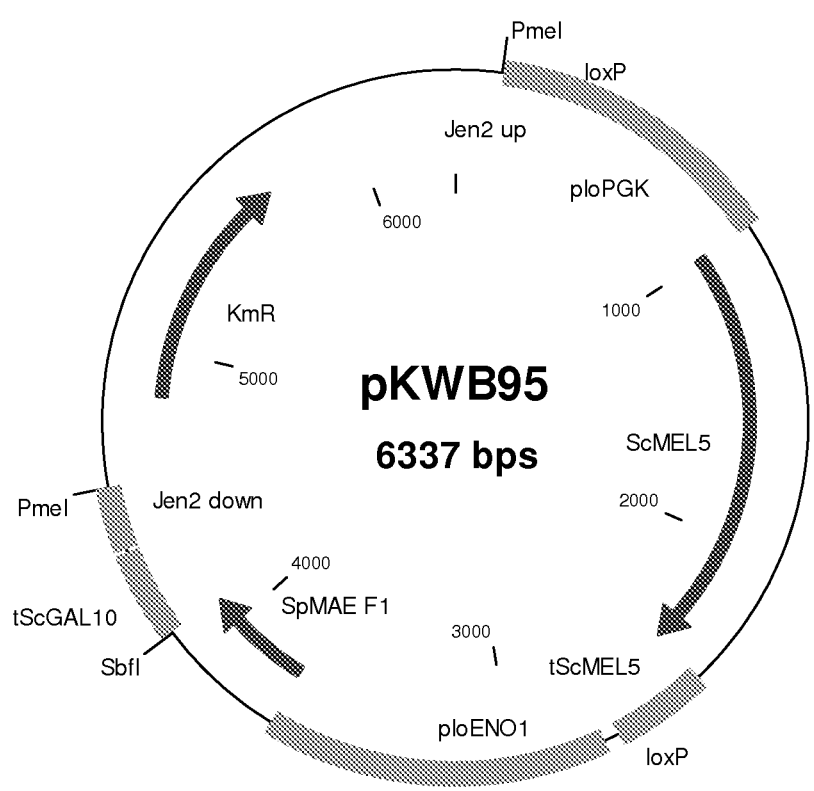
FIG. 50: pKWB95.
Figure 51:
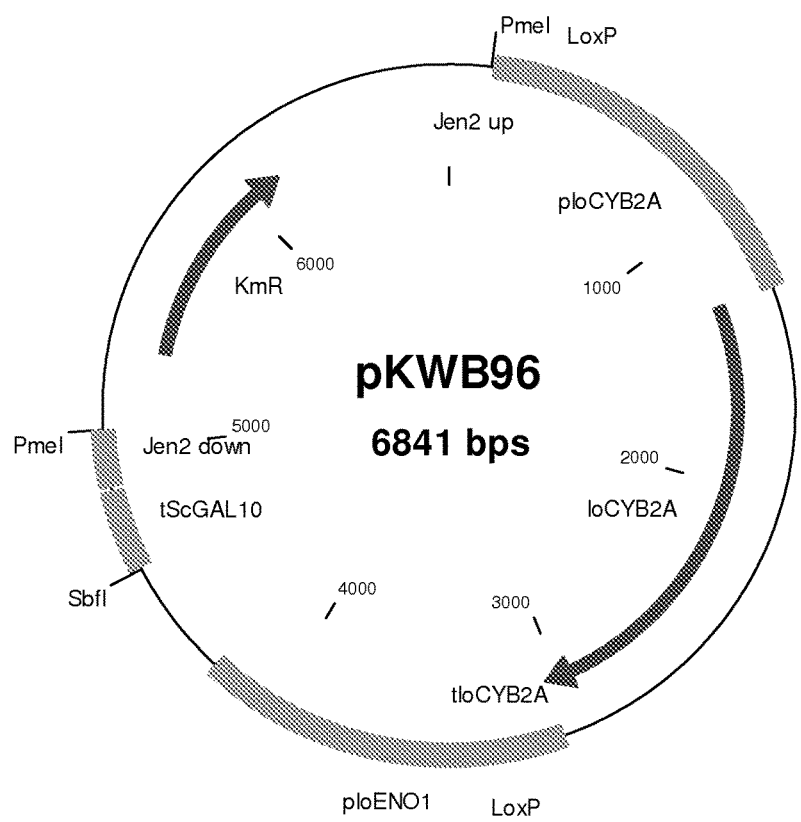
FIG. 51: pKWB96.
Figure 52:
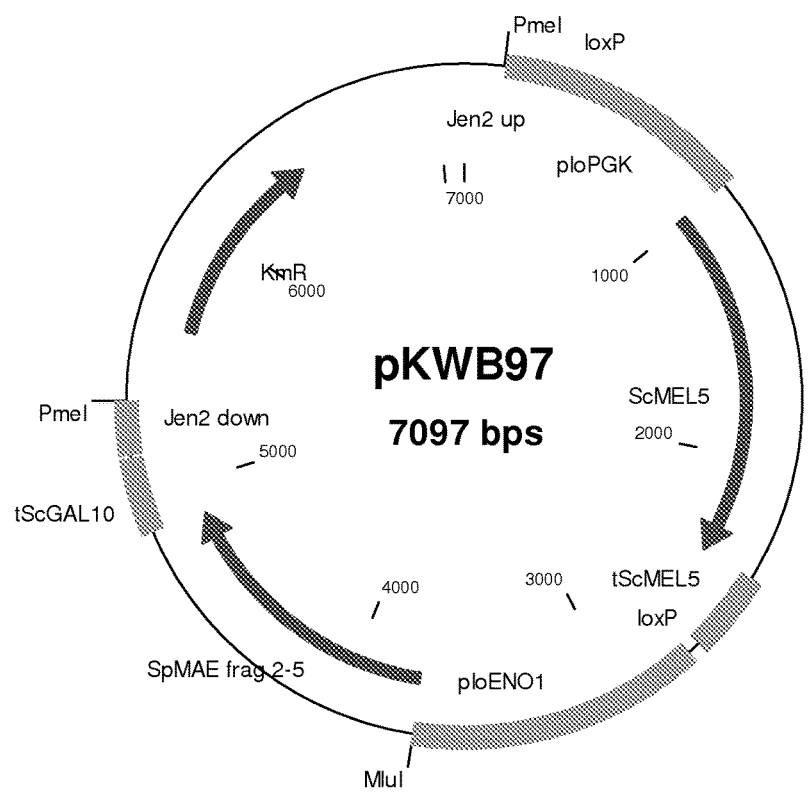
FIG. 52: pKWB97.

The plasmids were transformed into *E. coli*, and transformants were selected on LB plates containing 50 µg/ml Kanamycin and screened using primers flanking the NotI site of pKW087 and pKW086 (oKW93 (SEQ ID NO:108) and oKW95 (SEQ ID NO:109)). Correct plasmids were designated pKWB95 (fragment 1 with MEL5 marker) (FIG. 50), pKWB96 (fragment 1 with CYB2A marker) (FIG. 51) and pKWB97 (Fragment 2 with MEL5 marker) (FIG. 52).

Example 21B

Construction of *A. oryzae* MAE Expression Constructs pVMB108 and pVMB109

Figure 53:
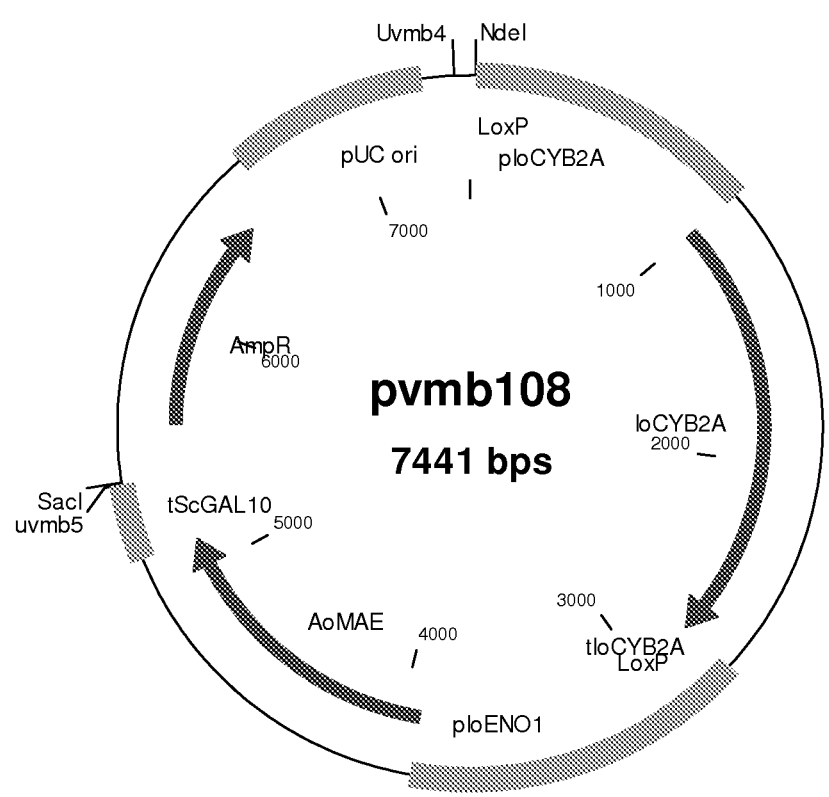
FIG. 53: pVMB108.
Figure 54:
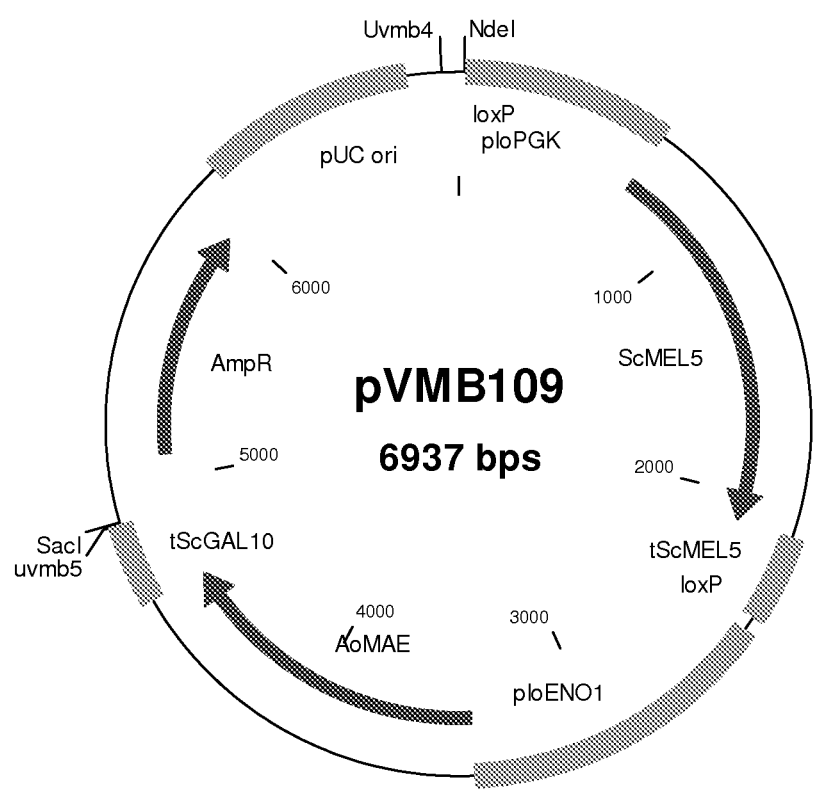
FIG. 54: pVMB109.

The putative dicarboxylic acid transporter gene from *A. oryzae* was codon optimized and synthesized by DNA 2.0 flanked by a 5' MluI restriction site and a 3' SbfI restriction site (SEQ ID NO:183). The resulting fragment was cloned into pJ201 containing the Kanamycin resistance marker. This plasmid was digested with MluI and SbfI and the fragment containing the *A. oryzae* MAE gene was gel purified and ligated into both pKF31 and pKF44 which had been similarly digested. pKF031 and pKF044 are constructed from pUC backbones, and both contain a multiple cloning site containing MluI, NotI, and SbfI sites operatively linked to the *I. orientalis* ENO promoter and the *S. cerevisiae* GAL10 terminator. pKWB31 also contains a selection marker cassette comprising the *S. cerevisiae* MEL5 gene operatively linked to the *I. orientalis* PGK promoter. This selection marker cassette is flanked by loxP sites. pKWB44 contains an expression cassette comprising the *I. orientalis* CYB2A promoter, gene, and terminator. This expression cassette is flanked by loxP sites. The plasmids were transformed into *E. coli*, and transformants were selected on LB plates containing 100 µg/ml ampicillin and screened using primers flanking the cloning site of pKF031 and pKF044 (oKW93 (SEQ ID NO:108) and oKW95 (SEQ ID NO:109)). Correct plasmids were designated pVMB108 (MEL5 marker) (FIG. 53) and pVMB109 (CYB2A marker) (FIG. 54).

Example 21C

Construction of *A. oryzae* MAE Integration Constructs pVMB116 and pVMB117

Figure 55:
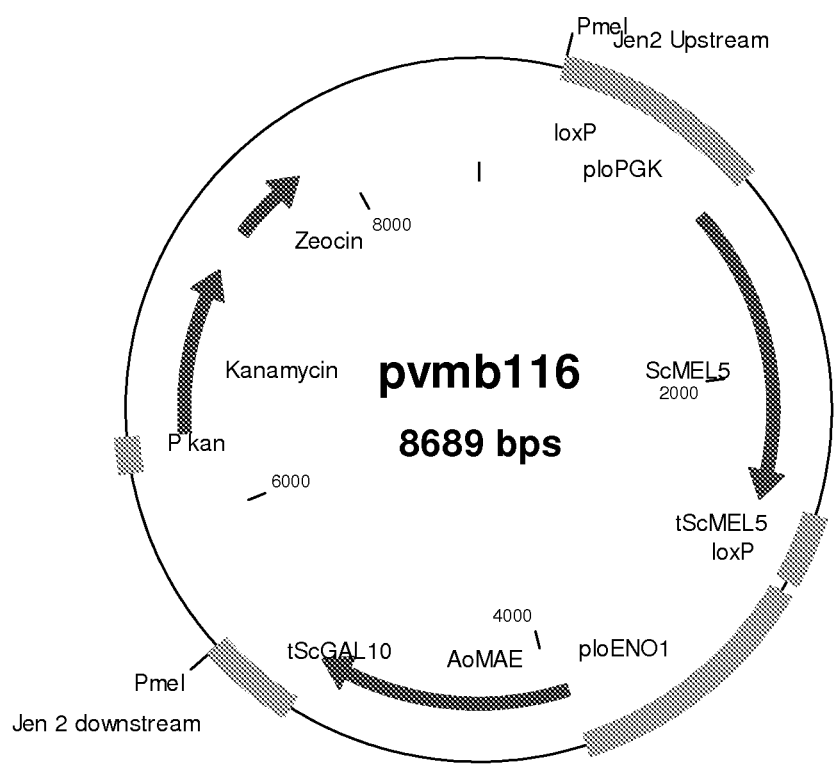
FIG. 55: pVMB116.
Figure 56:
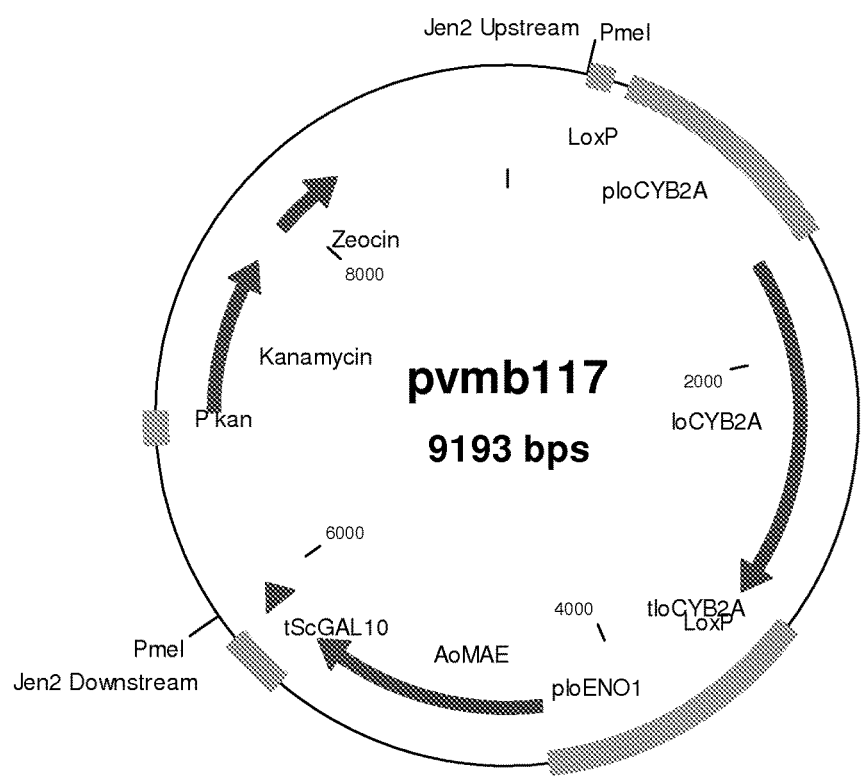
FIG. 56: pVMB117.

*A. oryzae* MAE expression constructs were amplified from plasmid DNA using Phusion polymerase and primers uVMB4 (SEQ ID NO:209) and uVMB5 (SEQ ID NO:210). uVMB4 contains 100 bp of sequence identity to the upstream flanking region of the RIOR43960 locus, uVMB5 contains 100 bp of sequence identity to the downstream flanking region of the RIOR43690 locus. After amplification, the product is gel purified and used as a template for amplification using primers oVMB145 (SEQ ID NO:218) and oVMB146 (SEQ ID NO:219) which serves to add PmeI sites to the 5' and 3' end of the preceding fragment. This fragment is topo cloned. The plasmids were transformed into *E. coli* and transformants are selected on LB plates containing 50 µg/ml kanamycin, and screened using diagnostic digests involving PmeI, NdeI, and SbfI. Correct plasmids are confirmed by sequencing, and the final constructs are designated pVMB116 (MEL5 marker) (FIG. 55) and pVMB117 (CYB2A marker) (FIG. 56).

Example 21D

Integration of *S. pombe* MAE at CB1 RIOR43690 in *I. orientalis* Strain 12868

Plasmids pKWB95 and pKWB96 were digested with PmeI and SbfI and gel purified. Each of these digests served to liberate a DNA fragment containing the upstream flanking region, the selective marker and fragment 1 from the vector backbone. pKWB097 was digested with PmeI and MluI. This digest liberated fragment 2 through the GAL10 terminator and the downstream flanking region from the vector backbone. Strain 12868 (Example 17B) was transformed with the fragments purified from both pKWB95 and pKWB97 simultaneously. This transformation was designed such that integration of both fragments reconstitutes the intact coding sequence intracellularly to produce a functional transport protein. Crossover events occur between the flanking regions of the fragments and genomic DNA as well as the overlapping regions of the *S. pombe* MAE gene. Transformants are selected on YNB+melibiose+x-α-gal and, and integration of *S. pombe* MAE at a first RIOR43690 locus is confirmed by PCR. The correct heterozygous strain is designated strain 13050.

A second integration targeting the second RIOR43690 locus is performed using the fragment purified from pKW096 and pKW097. Transformants are selected on YNB+lactic+x-α-gal and, and integration of *S. pombe* MAE at the second RIOR43690 locus is confirmed by PCR. The correct heterozygous strain is designated strain 13051.

Marker recycling is carried out with plasmid pVB32. The correct homozygous strains with both markers removed are designated 13053.

Example 21E

Integration of *A. oryzae* MAE at CB1 RIOR43690 in 12868

Integration of one copy of *A. oryzae* MAE at the RIOR43690 locus is performed using plasmids containing the CYB2A selectable marker. Strain 12868 was transformed with lithium acetate transformation using PmeI and MluI purified digest from pVMB117. Transformants were selected on YNB+lactic and integration of *A. oryzae* MAE at a first RIOR43690 locus is confirmed by PCR. The correct heterozygous strain was designated strain 13125.

The various MAE C4 transporter strains generated in Example 21 are summarized in Table 25.

TABLE 25

*I. orientalis* C4 transporter strains:

| Strain name | Description | Parent strain |
|---|---|---|
| 13050 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*S. pombe* MAE insertion at RIOR43690 (1) | 12868 |
| 13051/13053 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*S. pombe* MAE insertion at RIOR43690 (2) | 13050 |
| 13125 | CYB2A deletion (2)<br>*I. orientalis* PYC1 insertion at PDC1 (2)<br>*S. cerevisiae* FRD1 insertion at ADHa (2)<br>*Z. rouxii* MDH insertion at ATO2 (2)<br>*I. orientalis* FUM1 insertion at CYB2B (2)<br>*A. oryzae* MAE insertion at RIOR43690 (1) | 12868 |

Example 21F

Shake Flask Characterization of Succinate Production in *I. orientalis* Strains 13125, 13051, and 12868

Shake flasks were used to test the strains. Shake flasks were inoculated with biomass harvested from yeast peptone glucose plates (YPD). 250 mL baffled flasks (50 mL working volume) were inoculated to an $OD_{600}$ of 0.2. Incubation conditions were 100 rpm and 30° C. DM defined medium (adapted from Verduyn et al. Yeast 8:501-517 (1992); see Tables 18-20) was used in flasks, with pH control and $CO_2$ provided by calcium carbonate addition at a concentration of 0.255M (1.28 g $CaCO_3$ per 50 ml culture). Samples from triplicate flasks were taken at 96 hours and averaged for biomass growth via $OD_{600}$, succinate via gas chromatography with flame ionization detector and glucose by high performance liquid chromatography with refractive index detector.

Figure 57:
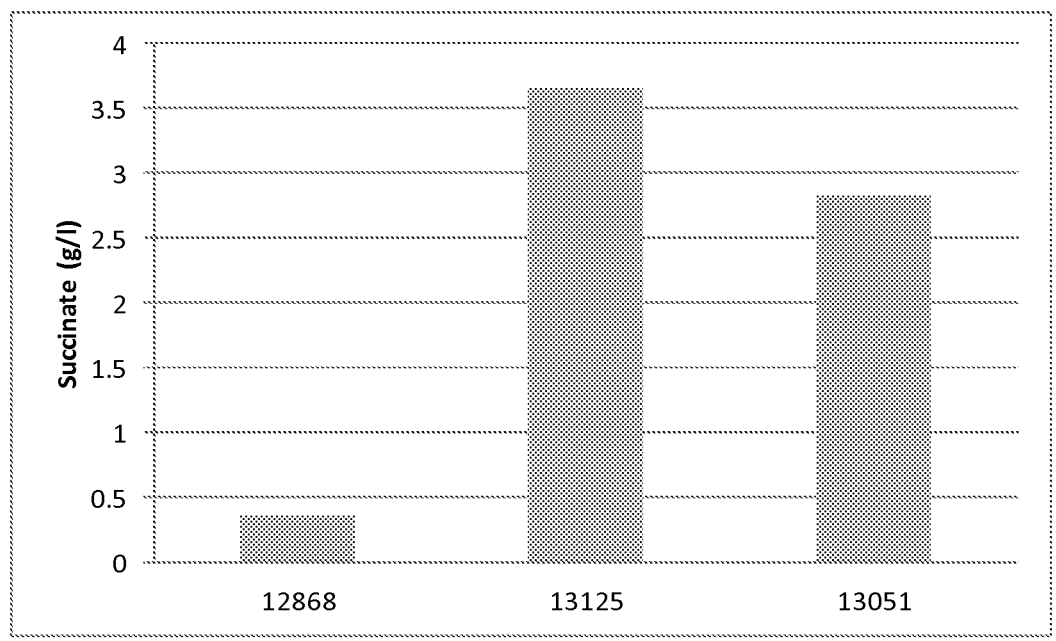
FIG. 57: Succinate production (g/L) in strain 12868 (control) and strains 13125 and 13051 expressing exogenous succinate transporter.

Results are shown in FIG. 57. Expression of one copy of *S. pombe* MAE or *A. oryzae* MAE resulted in a 7 to 10-fold increase in succinate production.

Example 22

Deletion of MAE1 in *I. orientalis* Strain 13053

An MAE1 deletion cassette is inserted at one or both MAE1 alleles in *I. orientalis* strain 13053 (Example 21D).

Example 22A

Construction of MAE::CYB2A Deletion Strain 13126 pKWB29 (FIG. 38) was digested with PmeI, and the 4955 bp fragment corresponding to the MAE::CYB2A deletion cassette was gel purified. This purified fragment was then transformed into *I. orientalis* strain 13053. Transformants were selected on YNB+lactate and screened by PCR using flanking primers oGPB1 (SEQ ID NO:201) and oGPB4 (SEQ ID NO:202) and nested primers oGPB52 (SEQ ID NO:148) and oGPB53 (SEQ ID NO:149) to verify correct insertion at the MAE1 locus. A heterozygous strain with one copy of the MAE1 gene deleted was designated strain 13126.

Example 22B

Construction of Double MAE1 Deletion Strain 13221 pKWB24 was digested with PmeI, and the 4451 bp fragment corresponding to the MAE::MEL5 deletion cassette was gel purified. This purified fragment was then transformed into *I. orientalis* strain 13126. Transformants were selected on YNB+melibiose+x-gal and screened by PCR using flanking primers oGPB1 (SEQ ID NO:201) and oGPB4 (SEQ ID NO:202) and nested primers oGPB54 (SEQ ID NO:150) and oGPB55 (SEQ ID NO:151) to verify correct insertion at the MAE1 locus. A homozygous strain with both copies of the MAE1 gene deleted was designated strain 13221.

The various MAE1 deletion strains generated in Example 22 are summarized in Table 26.

TABLE 26

*I. orientalis* MAE deletion strains:

| Strain name | Description | Parent strain |
|---|---|---|
| 13126 | CYB2A deletion (2)<br>MAE1 deletion (1)<br>*I. orientalis* PYC1 insertion at PDC1 (2)<br>*I. orientalis* FUM1 insertion at CYB2B (2)<br>*S. cerevisiae* FRD insertion at ADHa (2)<br>*Z. rouxii* MDH insertion at ATO2 (2)<br>*S. pombe* MAE insertion at RIOR43690 (2) | 13053 |
| 13221 | CYB2A deletion (2)<br>MAE1 deletion (2)<br>*I. orientalis* PYC1 insertion at PDC1 (2)<br>*I. orientalis* FUM1 insertion at CYB2B (2)<br>*S. cerevisiae* FRD insertion at ADHa (2)<br>*Z. rouxii* MDH insertion at ATO2 (2)<br>*S. pombe* MAE insertion at RIOR43690 (2) | 13216 |

Example 22C

Shake Flask Characterization of Malate Production in *I. orientalis* Strains 13053 and 13221

Shake flasks were used to test the parental control (13053) and MAE deletion (13221) strains. Shake flasks were inoculated with biomass harvested from yeast peptone glucose plates (YPD). 250 mL baffled flasks (50 mL working volume) were inoculated to an $OD_{600}$ of 0.3. Incubation conditions were 150 rpm and 30° C. DM defined medium (adapted from Verduyn et al. Yeast 8:501-517 (1992); see Tables 18-20) was used in flasks, with pH control and $CO_2$ provided by calcium carbonate addition at a concentration of 0.355M (1.33 g CaCO₃ per 50 ml culture). Samples were taken at 24 to 66 hours and analyzed for biomass growth via $OD_{600}$. Malate and glucose are detected by high performance liquid chromatography with refractive index detector.

Figure 58:
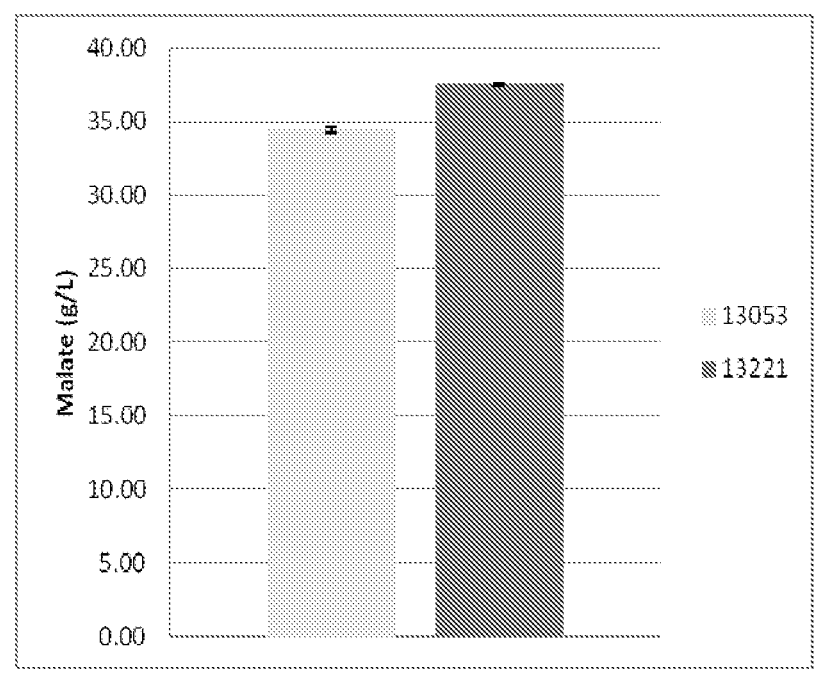
FIG. 58: Malate production (g/L) in strain 13053 (control) and 13221 (malic enzyme deletion).

As malate is the compound directly impacted by this enzyme, increased malate production was used as an indicator of an improved strain. Malate production results are shown in FIG. 58. A greater than 3 g/L increase in malate production was observed with the deletion of MAE1 from strain 13221 compared to the parental strain 13053 after 66 hours.

Example 23

Insertion of *T. brucei*, *T. cruzi*, *L. braziliensis*, or *L. mexicana* FRD1 at the ADHb Locus in *I. orientalis* Strain 13053

An FRD1 expression cassette is inserted at one or both ADHb alleles of *I. orientalis* strain 13053 (Example 21D).

Example 23A

Figure 59:
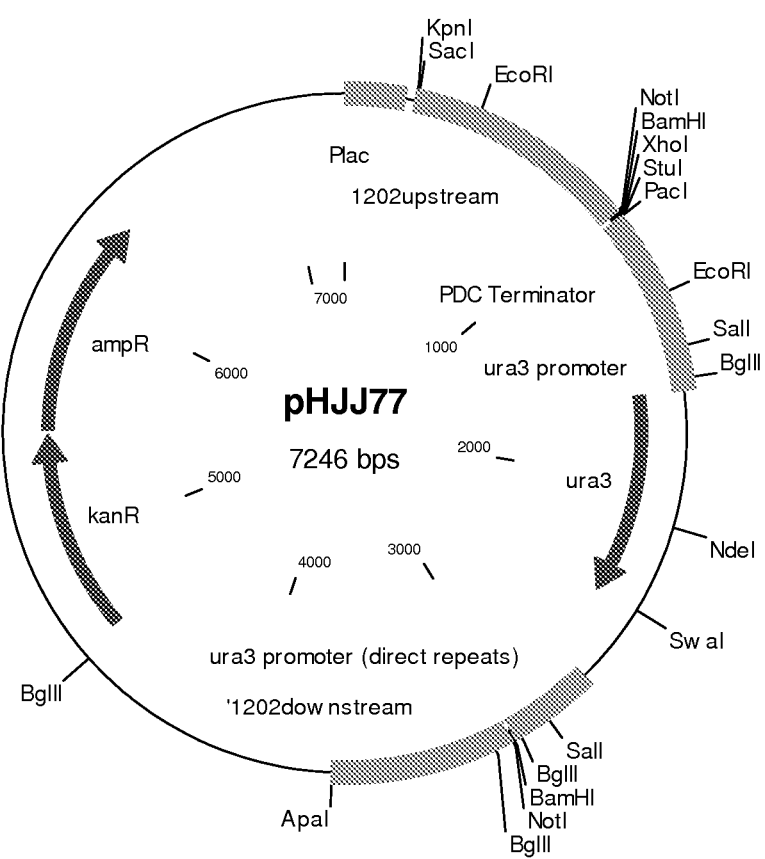
FIG. 59: pHJJ77.
Figure 60:
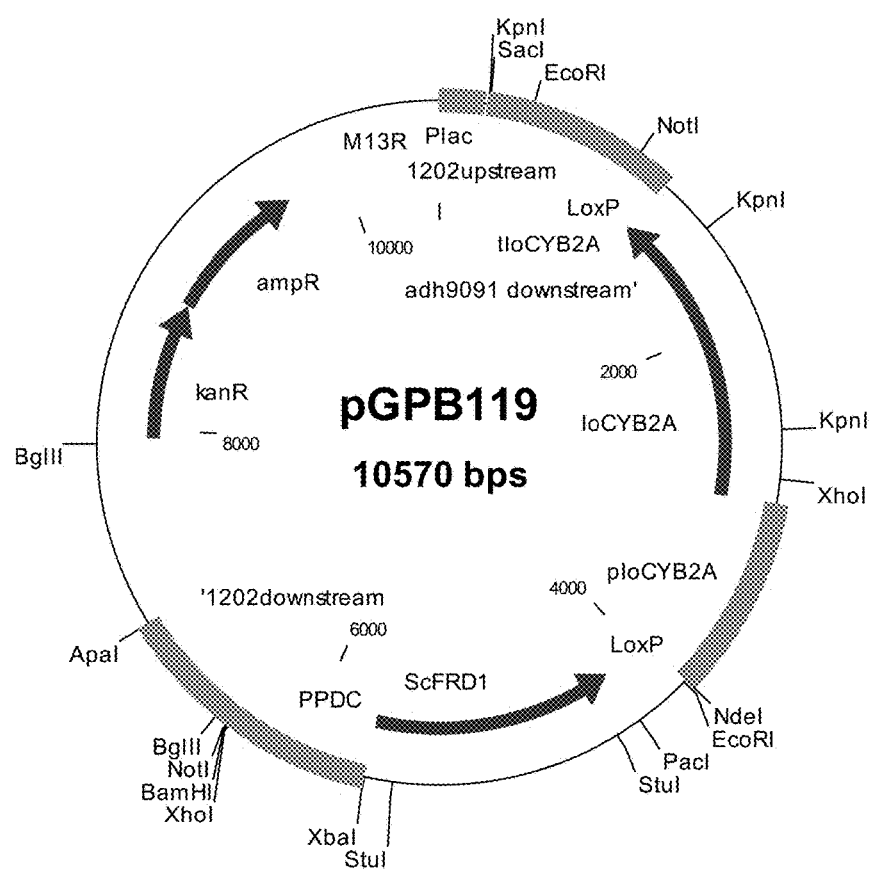
FIG. 60: pGPB119.

Construction of ADHb Deletion Construct pGPB119 pGPB26 was digested with NotI and the resultant fragment ligated to NotI digested pHJJ77 (FIG. 59). The resulting ADHb deletion construct, designated pGPB119 (FIG. 60), contains the *I. orientalis* PDC1 promoter (amplified using primers oJLJ3 (SEQ ID NO:156) and oJLJ19 (SEQ ID NO:157)) and terminator (amplified using primers oJLJ1 (SEQ ID NO:154) and oJLJ2 (SEQ ID NO:155)) and a CYB2A marker element between a 770 bp fragment corresponding to the region immediately 5' of the *I. orientalis* AHD2b open reading frame (amplified using primers oHJJ124 (SEQ ID NO:211) and oHJJ125 (SEQ ID NO:212)) and a 615 bp fragment corresponding to the region immediately 3' of the *I. orientalis* ADHb open reading frame (amplified using primer oHJJ126 (SEQ ID NO:213) and oHJJ127 (SEQ ID NO:214)).

Example 23B

Construction of FRD Expression Constructs pGPB126, pGPB127, pGPB159, pGPB160, pGPB161, and ADHb Null Constructs pGPB148 and pGPB168

Expression cassettes for FRD1 genes were inserted into the ADHb deletion construct pGPB119: the FRD1 genes from *T. brucei* (SEQ ID NO:173), *T. cruzi* (SEQ ID NO:175), *L. braziliensis* (SEQ ID NO:177), and *L. mexicana* (SEQ ID NO:179), were codon optimized to *I. orientalis*, and lacked the C-terminal glyoxysomal targeting sequence from the native gene.

Figure 61:
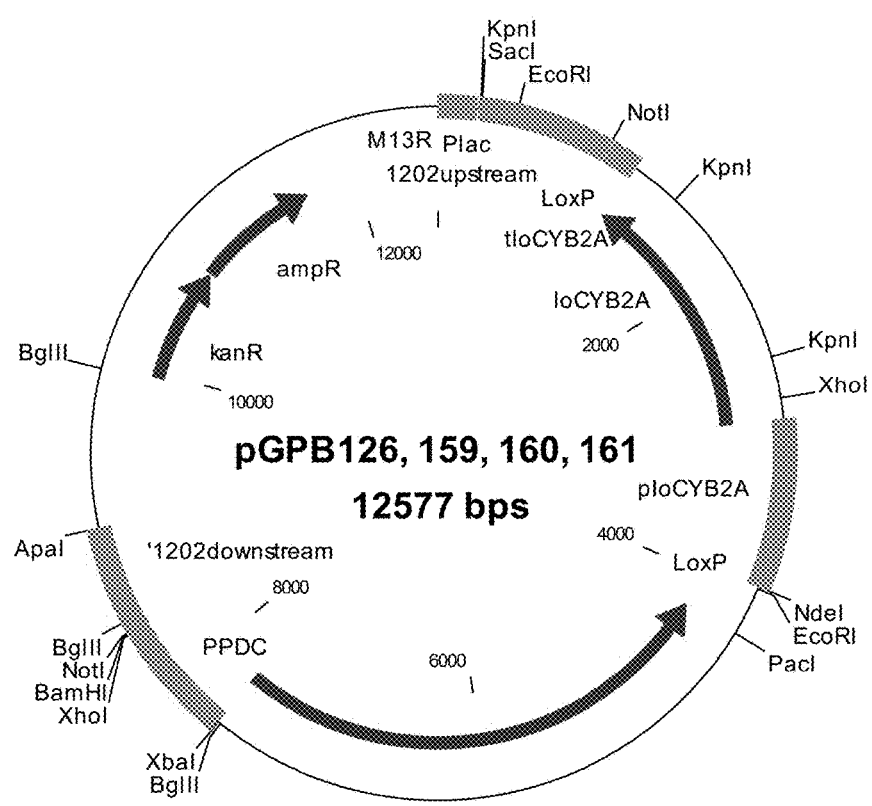
FIG. 61: pGPB126, 159, 160, and 161.
Figure 62:
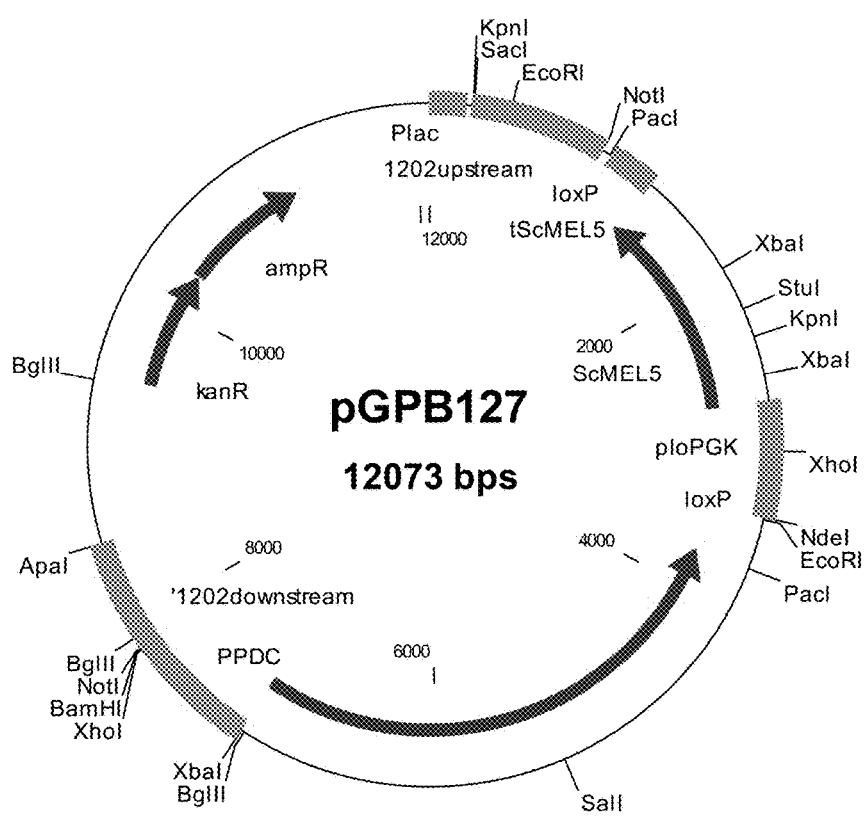
FIG. 62: pGPB127.
Figure 63:
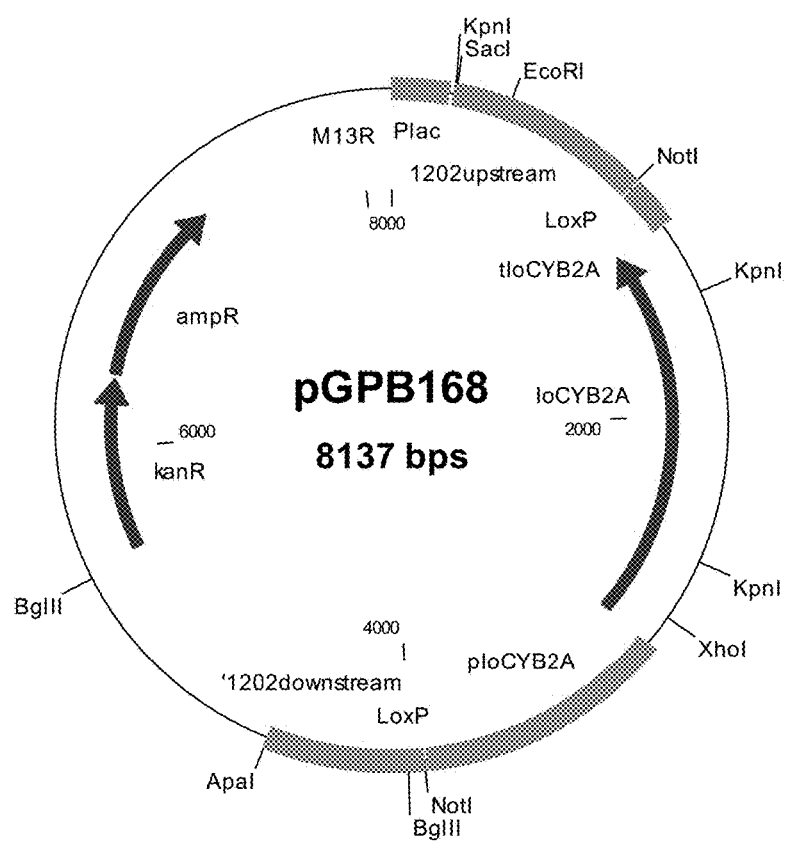
FIG. 63: pGPB168.
Figure 64:
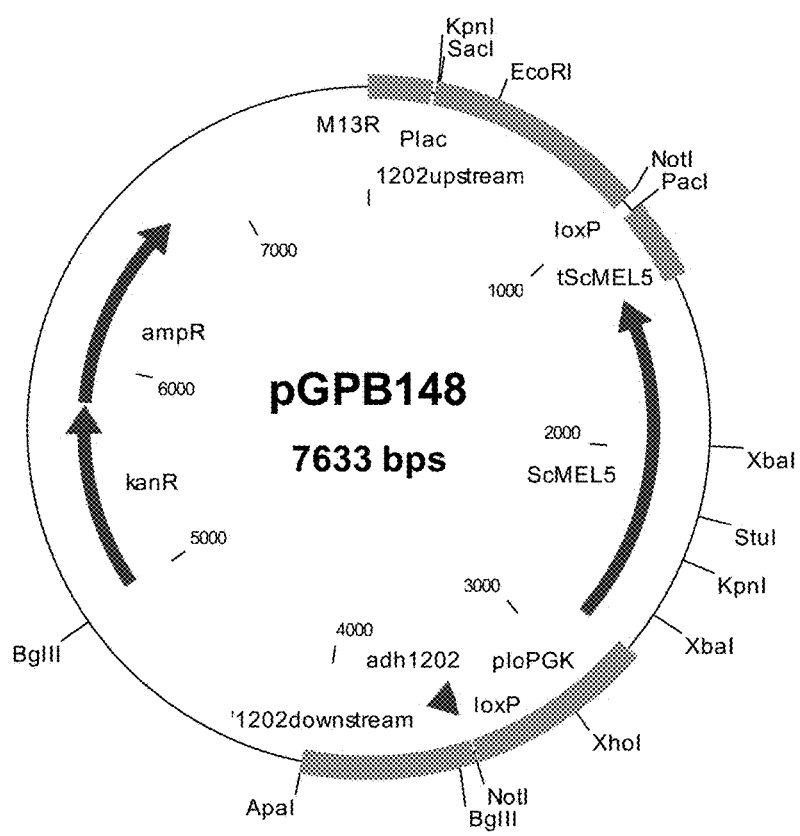
FIG. 64: pGPB148.

Plasmids containing the codon optimized FRD1 genes were digested with XbaI and PacI, and the FRD1 fragments were ligated to similarly digested pGPB119. The resulting plasmids, containing the FRD1 coding sequence flanked by the *I. orientalis* PDC1 promoter and terminator and the *I. orientalis* CYB2A selectable marker, were designated pGPB126 (*T. brucei*), pGPB159 (*T. cruzi*), pGPB160 (*L. braziliensis*), and pGPB161 (*L. mexicana*) (FIG. 61).

pGPB126 was digested with NdeI and a partial NotI digest to remove the CYB2A selectable marker, and the resulting vector was ligated to the NdeI and NotI fragment from pGPB14, which contained the MEL5 selectable marker. The resulting plasmid, which contained the FRD1 coding sequence flanked by the *I. orientalis* PDC1 promoter and terminator and the *S. cerevisiae* MEL5 selectable marker was designated pGPB127 (FIG. 62).

pGPB126 (CYB2A) and pGPB127 (MEL5) were each digested with NdeI and BamHI to remove those portions of the plasmids corresponding to the PDC promoter, *T. brucei* FRD, and PDC terminator, and each plasmid backbone was blunted with Klenow fragment and ligated to recircularize the plasmid. The plasmids were then transformed into *E. coli*. Plasmids isolated from positive colonies were designated pGPB168 (FIG. 63, derived from pGPB126) and pGPB148 (FIG. 64, derived from pGPB127).

Example 23C

Insertion of FRD1 at First and Second ADHb loci of *I. orientalis* Strain 13053 pGPB126, pGPB159, pGPB160, pGPB161 and pGPB148 were digested with SacI and ApaI and transformed into *I. orientalis* strain 13053 by lithium acetate transformation. Transformants were selected on YNB+2% lactic plates or YNB+2% melibiose plates (pGPB148). After around six days, transformants were picked and plated for single colonies on YP+20 g/L glucose plates. Colonies were picked, and genomic DNA was isolated and screened by PCR to confirm integration of the FRD1 expression cassette at the ADHb locus using primers oGPB106 (SEQ ID NO:215), oGPB56 (SEQ ID NO:187), oGPB52 (SEQ ID NO:148), oGPB54 (SEQ ID NO:150), oGPB55 (SEQ ID NO:151), and oGPB107 (SEQ ID NO:196). Strains with the correct integration of the FRD1 gene were designated ySBCG261, 13171, ySBCG263 (*T. brucei* FRD); ySBCG283, 13256, ySBCG285 (*T. cruzi* FRD); ySBCG286, 13257, ySBCG288 (*L. braziliensis* FRD); and ySBCG289, 13258, ySBCG291 (*L. mexicana* FRD). Strains with a single ADHb allele deleted are designated ySBCG280, 13255, and ySBCG282.

pGPB127 and pGPB168 were digested with SacI and ApaI and transformed into *I. orientalis* strains ySBCG261, 13171, ySBCG263, ySBCG280, 13255, and ySBCG282 by lithium acetate transformation. Transformants were selected on either YNB+2% lactic plates overlaid with α-x-gal or YNB+2% melibiose plates overlaid with α-x-gal. After around seven days, transformants were picked and plated for single colonies on YP+20 g/L glucose plates. Colonies are picked, and genomic DNA is isolated and screened by PCR to confirm integration of the FRD1 expression cassette at the ADHb locus using primers oGPB106 (SEQ ID NO:215), oGPB54 (SEQ ID NO:150), oGPB52 (SEQ ID NO:148), oGPB53 (SEQ ID NO:149), oGPB55 (SEQ ID NO:151), and oGPB107 (SEQ ID NO:196). Strains with the correct integration of the FRD1 gene were designated 13143, 13144, and ySBCG270. Strains with a homozygous knockout of the ADHb allele were designated ySBCGH460, ySBCGH461, and ySBCGH462.

The various FRD1 insertion/ADHb deletion strains generated in Example 23 are summarized in Table 27.

TABLE 27

*I. orientalis* FRD1 insertion strains:

| Strain name | Description | Parent strain |
|---|---|---|
| ySBCG261/ | CYB2A deletion (2) | 13053 |
| 13171/ | *I. orientalis* PYC1 insertion at | |

TABLE 27-continued

I. orientalis FRD1 insertion strains:

| Strain name | Description | Parent strain |
|---|---|---|
| ySBCG263 | PDC1 (2)<br>S. cerevisiae FRD1 insertion at ADHa (2)<br>Z. rouxii MDH insertion at ATO2 (2)<br>I. orientalis FUM1 insertion at CYB2B (2)<br>T. brucei FRD1 insertion at ADHb (1) | |
| ySBCG283/<br>13256/<br>ySBCG285 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>T. cruzi FRD1 insertion at ADHb (1) | 13053 |
| ySBCG286/<br>13257/<br>ySBCG288 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>L. braziliensis FRD1 insertion at ADHb (1) | 13053 |
| ySBCG289/<br>13258/<br>ySBCG291 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>L. mexicana FRD1 insertion at ADHb (1) | 13053 |
| ySBCG280/<br>13255/<br>ySBCG282 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>Null insertion at ADHb (1) | 13053 |
| 13143/13144/<br>ySBCG270 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>T. brucei FRD1 insertion at ADHb (2) | ySBCG261/<br>13171/<br>ySBCG263 |
| ySBCGH460/<br>ySBCGH461/<br>ySBCGH462 | CYB2A deletion (2)<br>I. orientalis PYC1 insertion at PDC1 (2)<br>S. cerevisiae FRD1 insertion at ADHa (2)<br>Z. rouxii MDH insertion at ATO2 (2)<br>I. orientalis FUM1 insertion at CYB2B (2)<br>Null insertion at ADHb (2) | ySBCG280/<br>13255/<br>ySBCG282 |

Example 23D

Shake Flask Characterization of Malate Production in I. orientalis Strains 13053, ySBCG261/13171/ySBCG263, ySBCG283/13256/ySBCG285, ySBCG286/13257/ySBCG288, ySBCG289/13258/ySBCG291, and ySBCG280/13255/ySBCG282

Shake flasks are used to test the parental control (13053), FRD expression strains (ySBCG261/13171/ySBCG263, ySBCG283/13256/ySBCG285, ySBCG286/13257/ySBCG288, and ySBCG289/13258/ySBCG291), and site controls (ySBCG280/13255/ySBCG282). Shake flasks are inoculated with biomass harvested from yeast peptone glucose plates (YPD). 250 mL baffled flasks (50 mL working volume) were inoculated to an $OD_{600}$ of 0.3. Incubation conditions were 150 rpm and 30° C. DM defined medium (adapted from Verduyn et al. Yeast 8:501-517 (1992); see Tables 18-20) was used in flasks, with pH control and $CO_2$ provided by calcium carbonate addition at a concentration of 0.355M (1.33 g $CaCO_3$ per 50 ml culture). Samples were taken at 68 hours and analyzed for biomass growth via $OD_{600}$. Succinate and glucose were detected by high performance liquid chromatography with refractive index detector.

Figure 65:
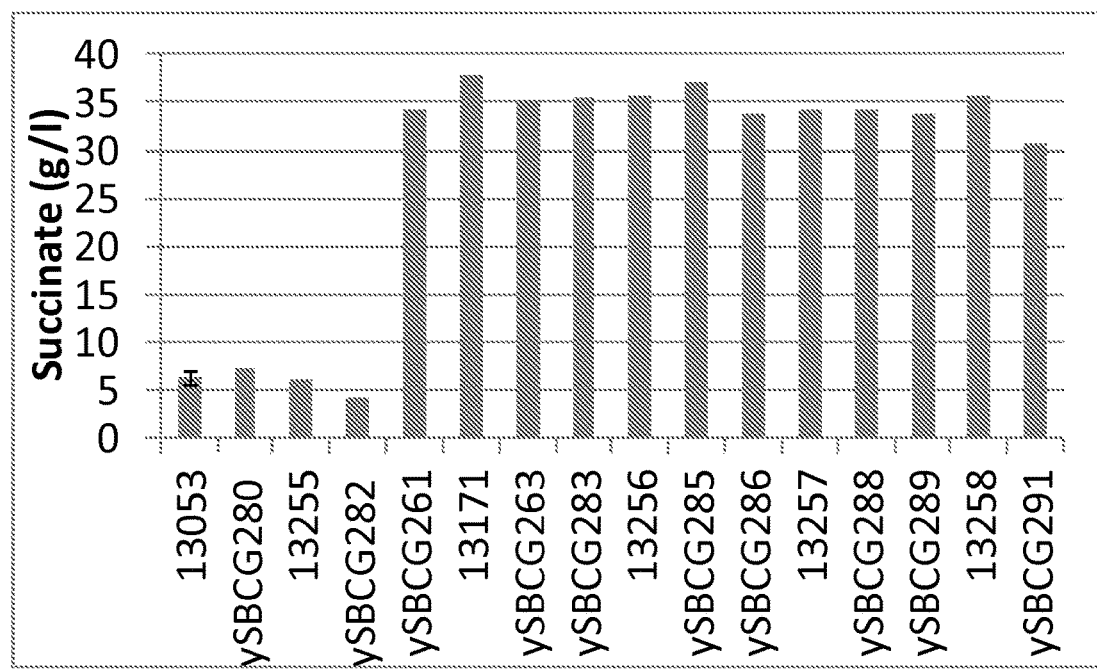
FIG. 65: Succinate production (g/L) in yeast strains expressing various fumarate reductases.

Results are shown in FIG. 65. Increased succinate production was observed with gene insertion.

Example 24

Succinate Production by I. orientalis Strain 13171

I. orientalis strain 13171 (Example 23C) was run in fermentors to test succinic acid production. Fermentors are inoculated with biomass grown in defined medium (adapted from Verduyn et al. Yeast 8:501-517 (1992); see Tables 18-20). Seeds are run in 1 L baffled flasks (250 mL working volume) at 250 rpm and 30° C. The contents of the flasks are harvested at approximately 24 hours incubation time with 10% v/v inoculum used to start fermentors. Fermentor initial working volume is 1.2 L for fed-batch glucose and 1.5 L for straight batch glucose. Fermentor media is outlined in Tables 18-20. Glucose was provided by either controlling feed addition to the fermentor, with feed maintained at <10 g/l residual glucose, or by the addition of 115 g/l at the start of the batch (straight batch). Straight batch is used in this organism as a preferred mode of operation, due to the lack of a Crabtree positive phenotype. This mode offers simplicity in industrial operation.

pH is controlled at 3.0 with 5 N KOH. The fermentor systems are sparged at 0.24 slpm with a blend of pure $CO_2$ and air to yield 10% $CO_2$ in the inlet gas stream. Different oxygen uptake rates are applied to the vessels by changing vessel agitation rate. These fermentations are operated such that oxygen limitation was maintained (e.g. dissolved oxygen <5%).

Samples are taken at 90 hour batch time and analyzed for biomass growth via $OD_{600}$, succinate via gas chromatography with flame ionization detector and glucose by high performance liquid chromatography with refractive index detector.

Figure 66:
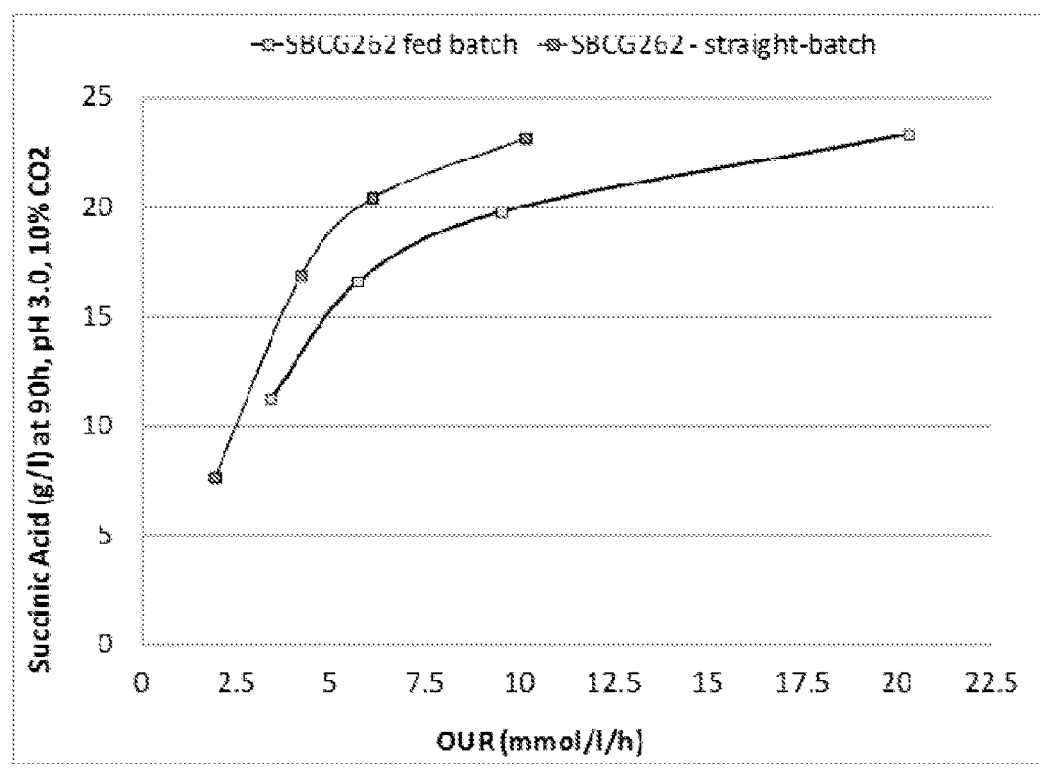
FIG. 66: Succinate production (g/L) at 90 hour fermentation time at pH 3.0, 10% $CO_2$, OUR (mmol/h) variable.

FIG. 66 illustrates succinic acid production under the conditions outline above in both fed-batch and straight batch glucose. A previous experiment (WO2010/0032728, p. 9, lines 15-18) reported that "an Oxygen Uptake Rate (OUR) above 5 mmol/l/h resulted in lower succinic acid production". Surprisingly, we found improving production above 5 mmol/l/h with succinic acid titer increases with increasing OUR such that the no decrease in succinic production was observed even at the highest OUR tested, 20 mmol/l/h.

What is claimed is:

1. A genetically modified yeast cell having an active succinate fermentation pathway from phosphoenolpyruvate or pyruvate to succinate, wherein the active succinate fermentation pathway comprises an exogenous malate dehydrogenase gene encoding a polypeptide comprising an amino acid sequence with at least 90% sequence identity to the amino acid sequence set forth in SEQ ID NO:172.

2. The genetically modified yeast cell of claim 1, wherein the active succinate fermentation pathway includes the reactions:
   (a) pyruvate to oxaloacetate;
   (b) oxaloacetate to malate;
   (c) malate to fumarate; and
   (d) fumarate to succinate.

3. The genetically modified yeast cell of claim 2, wherein the active succinate fermentation pathway further includes:
   (e) export of succinate from inside the cell to the extracellular environment.

4. The genetically modified yeast cell of claim 3, wherein the cell comprises one or more exogenous genes that encode an enzyme that catalyzes any of reactions (a) through (e).

5. The genetically modified yeast cell of claim 4, wherein the cell comprises one or more copies of one or more exogenous genes selected from the group consisting of pyruvate carboxylase, fumarate reductase, and succinate exporter genes.

6. The genetically modified yeast cell of claim 5, wherein said exogenous pyruvate carboxylase gene is derived from a fungal pyruvate carboxylase source gene and encodes a polypeptide with at least 95% sequence identity to a polypeptide encoded by the fungal pyruvate carboxylase source gene, wherein the fungal pyruvate carboxylase source gene is not derived from *R. oryzae*.

7. The genetically modified yeast cell of claim 5, wherein said exogenous fumarase gene is derived from a yeast fumarase source gene and encodes a polypeptide with at least 95% sequence identity to a polypeptide encoded by the yeast fumarase source gene.

8. The genetically modified yeast cell of claim 7, wherein said exogenous fumarase gene encodes a polypeptide comprising an amino acid sequence with at least 95% sequence identity to the amino acid sequence set forth in SEQ ID NO:2.

9. The genetically modified yeast cell of claim 5, wherein said exogenous fumarate reductase gene is derived from a protozoan fumarate reductase source gene and encodes a polypeptide with at least 95% sequence identity to a polypeptide encoded by the protozoan fumarate reductase source gene.

10. The genetically modified yeast cell of claim 9, wherein said exogenous fumarate reductase gene encodes a polypeptide comprising an amino acid sequence with at least 95% sequence identity to the amino acid sequence set forth in SEQ ID NO:174, SEQ ID NO:176, SEQ ID NO:178, or SEQ ID NO:180.

11. The genetically modified yeast cell of claim 2, wherein the active succinate fermentation pathway comprises the reaction phosphoenolpyruvate to oxaloacetate in addition to reaction (a).

12. The genetically modified yeast cell of claim 11, wherein the cell comprises one or more copies of one or more exogenous phosphoenolpyruvate carboxylase genes.

13. The genetically modified yeast cell of claim 2, wherein the cell comprises a deletion or disruption of an endogenous malic enzyme gene.

14. The genetically modified yeast cell of claim 2, wherein the cell comprises a deletion or disruption of an endogenous pyruvate decarboxylase gene.

15. The genetically modified yeast cell of claim 1, wherein the yeast cell is from the *Pichia fermentans/Issatchenkia orientalis* clade.

16. A method of producing succinate comprising culturing the genetically modified yeast cell of claim 1 in the presence of at least one carbon source and isolating succinate from the culture.

17. The A-genetically modified yeast cell of claim 1, wherein the yeast cell comprises the species *Issatchenkia orientalis*.

18. The genetically modified yeast cell of 15, wherein the yeast cell is succinate resistant.

19. The genetically modified yeast cell of claim 15, wherein the genetically modified yeast cell comprises one or more copies of an exogenous pyruvate carboxylase gene derived from a yeast pyruvate carboxylase source gene and encodes a polypeptide with at least 95% sequence identity to a polypeptide encoded by the yeast pyruvate carboxylase source gene.

20. The genetically modified yeast cell of claim 19, wherein said exogenous pyruvate carboxylase gene encodes a polypeptide comprising an amino acid sequence with at least 95% sequence identity to the amino acid sequence set forth in SEQ ID NO:8, SEQ ID NO:10, or SEQ ID NO:12.

* * * * *

SEQUENCE LISTING

<160> NUMBER OF SEQ ID NOS: 219

<210> SEQ ID NO 1
<211> LENGTH: 1458
<212> TYPE: DNA
<213> ORGANISM: Issatchenkia orientalis
<220> FEATURE:
<221> NAME/KEY: CDS
<222> LOCATION: (1)..(1458)

<400> SEQUENCE: 1

| atg | tta | gct | gct | aga | tca | tta | aag | gca | aga | atg | tca | aca | aga | gct | ttc | 48 |
|---|---|---|---|---|---|---|---|---|---|---|---|---|---|---|---|---|
| Met | Leu | Ala | Ala | Arg | Ser | Leu | Lys | Ala | Arg | Met | Ser | Thr | Arg | Ala | Phe | |
| 1 | | | | 5 | | | | | 10 | | | | | 15 | | |

| tca | act | acc | tca | att | gca | aaa | aga | atc | gaa | aaa | gat | gca | ttt | ggt | gac | 96 |
|---|---|---|---|---|---|---|---|---|---|---|---|---|---|---|---|---|
| Ser | Thr | Thr | Ser | Ile | Ala | Lys | Arg | Ile | Glu | Lys | Asp | Ala | Phe | Gly | Asp | |
| | | | 20 | | | | | 25 | | | | | 30 | | | |

| att | gaa | gtc | cca | aat | gag | aaa | tat | tgg | ggt | gct | caa | act | caa | aga | tct | 144 |
|---|---|---|---|---|---|---|---|---|---|---|---|---|---|---|---|---|
| Ile | Glu | Val | Pro | Asn | Glu | Lys | Tyr | Trp | Gly | Ala | Gln | Thr | Gln | Arg | Ser | |
| | | | | 35 | | | | | 40 | | | | | 45 | | |

| tta | caa | aat | ttc | aaa | att | ggt | ggt | aag | aga | gaa | gtt | atg | cca | gaa | cca | 192 |
|---|---|---|---|---|---|---|---|---|---|---|---|---|---|---|---|---|
| Leu | Gln | Asn | Phe | Lys | Ile | Gly | Gly | Lys | Arg | Glu | Val | Met | Pro | Glu | Pro | |
| | 50 | | | | | 55 | | | | | 60 | | | | | |

| atc | atc | aaa | tct | ttt | ggt | att | tta | aag | aag | gct | act | gct | aag | atc | aat | 240 |
|---|---|---|---|---|---|---|---|---|---|---|---|---|---|---|---|---|
| Ile | Ile | Lys | Ser | Phe | Gly | Ile | Leu | Lys | Lys | Ala | Thr | Ala | Lys | Ile | Asn | |
| 65 | | | | | 70 | | | | | 75 | | | | | 80 | |

| gct | gag | tct | ggt | gct | tta | gac | cca | aag | tta | tct | gaa | gcc | atc | caa | caa | 288 |
|---|---|---|---|---|---|---|---|---|---|---|---|---|---|---|---|---|
| Ala | Glu | Ser | Gly | Ala | Leu | Asp | Pro | Lys | Leu | Ser | Glu | Ala | Ile | Gln | Gln | |
| | | | | 85 | | | | | 90 | | | | | 95 | | |

| gct | gca | acc | gaa | gtt | tat | gaa | ggt | aaa | cta | atg | gac | cat | ttc | cca | tta | 336 |
|---|---|---|---|---|---|---|---|---|---|---|---|---|---|---|---|---|
| Ala | Ala | Thr | Glu | Val | Tyr | Glu | Gly | Lys | Leu | Met | Asp | His | Phe | Pro | Leu | |
| | | | 100 | | | | | 105 | | | | | 110 | | | |

| gtt | gtc | ttt | caa | acc | ggt | tct | ggt | act | caa | tct | aac | atg | aat | gcc | aat | 384 |
|---|---|---|---|---|---|---|---|---|---|---|---|---|---|---|---|---|
| Val | Val | Phe | Gln | Thr | Gly | Ser | Gly | Thr | Gln | Ser | Asn | Met | Asn | Ala | Asn | |
| | | 115 | | | | | 120 | | | | | 125 | | | | |

| gaa | gtc | atc | tct | aat | aga | gca | att | gaa | atc | ttg | ggt | ggt | gaa | tta | ggc | 432 |
|---|---|---|---|---|---|---|---|---|---|---|---|---|---|---|---|---|
| Glu | Val | Ile | Ser | Asn | Arg | Ala | Ile | Glu | Ile | Leu | Gly | Gly | Glu | Leu | Gly | |
| 130 | | | | | 135 | | | | | 140 | | | | | | |

| tct | aaa | act | cca | gtc | cat | cct | aat | gat | cat | gtt | aat | atg | tcc | caa | tct | 480 |
|---|---|---|---|---|---|---|---|---|---|---|---|---|---|---|---|---|
| Ser | Lys | Thr | Pro | Val | His | Pro | Asn | Asp | His | Val | Asn | Met | Ser | Gln | Ser | |
| 145 | | | | | 150 | | | | | 155 | | | | | 160 | |

| tct | aat | gat | act | ttc | cct | act | gtc | atg | cat | att | gca | gca | gtt | aca | gaa | 528 |
|---|---|---|---|---|---|---|---|---|---|---|---|---|---|---|---|---|
| Ser | Asn | Asp | Thr | Phe | Pro | Thr | Val | Met | His | Ile | Ala | Ala | Val | Thr | Glu | |
| | | | | 165 | | | | | 170 | | | | | 175 | | |

| gtt | tca | tcc | cat | tta | tta | cca | gaa | tta | act | gca | cta | aga | gat | gca | ttg | 576 |
|---|---|---|---|---|---|---|---|---|---|---|---|---|---|---|---|---|
| Val | Ser | Ser | His | Leu | Leu | Pro | Glu | Leu | Thr | Ala | Leu | Arg | Asp | Ala | Leu | |
| | | | 180 | | | | | 185 | | | | | 190 | | | |

| caa | aag | aaa | tcc | gat | gaa | ttt | aag | aat | att | atc | aaa | atc | ggt | aga | acc | 624 |
|---|---|---|---|---|---|---|---|---|---|---|---|---|---|---|---|---|
| Gln | Lys | Lys | Ser | Asp | Glu | Phe | Lys | Asn | Ile | Ile | Lys | Ile | Gly | Arg | Thr | |
| | | 195 | | | | | 200 | | | | | 205 | | | | |

| cat | tta | caa | gat | gca | act | cct | tta | act | tta | ggt | caa | gaa | ttt | tct | ggt | 672 |
|---|---|---|---|---|---|---|---|---|---|---|---|---|---|---|---|---|
| His | Leu | Gln | Asp | Ala | Thr | Pro | Leu | Thr | Leu | Gly | Gln | Glu | Phe | Ser | Gly | |
| | 210 | | | | | 215 | | | | | 220 | | | | | |

| tat | gtt | caa | caa | tgt | act | aat | ggt | atc | aaa | aga | atc | gaa | att | gct | ctt | 720 |
|---|---|---|---|---|---|---|---|---|---|---|---|---|---|---|---|---|
| Tyr | Val | Gln | Gln | Cys | Thr | Asn | Gly | Ile | Lys | Arg | Ile | Glu | Ile | Ala | Leu | |
| 225 | | | | | 230 | | | | | 235 | | | | | 240 | |

| gaa | cat | ttg | aga | tac | tta | gct | caa | ggt | ggt | act | gcc | gtt | ggt | act | ggt | 768 |
|---|---|---|---|---|---|---|---|---|---|---|---|---|---|---|---|---|
| Glu | His | Leu | Arg | Tyr | Leu | Ala | Gln | Gly | Gly | Thr | Ala | Val | Gly | Thr | Gly | |
| | | | | 245 | | | | | 250 | | | | | 255 | | |

| ctt | aac | acc | aag | aaa | ggt | ttt | gct | gaa | aag | gtt | gca | aat | gaa | gtc | act | 816 |
|---|---|---|---|---|---|---|---|---|---|---|---|---|---|---|---|---|
| Leu | Asn | Thr | Lys | Lys | Gly | Phe | Ala | Glu | Lys | Val | Ala | Asn | Glu | Val | Thr | |

```
                        260                 265                 270
aaa ttg act ggt tta caa ttc tat acc gct cca aat aaa ttc gaa gcc      864
Lys Leu Thr Gly Leu Gln Phe Tyr Thr Ala Pro Asn Lys Phe Glu Ala
            275                 280                 285 ctt gca gct cac gat gct gtt gtt gaa atg tct ggt gct ttg aat acc      912
Leu Ala Ala His Asp Ala Val Val Glu Met Ser Gly Ala Leu Asn Thr
        290                 295                 300 gtt gca gtc tca tta ttc aaa atc gct caa gat atc aga tat ttg ggt      960
Val Ala Val Ser Leu Phe Lys Ile Ala Gln Asp Ile Arg Tyr Leu Gly
305                 310                 315                 320 tcc ggc cca aga tgt ggt tat ggt gaa ttg gct tta cca gaa aat gaa     1008
Ser Gly Pro Arg Cys Gly Tyr Gly Glu Leu Ala Leu Pro Glu Asn Glu
                325                 330                 335 cca ggt tct tcc atc atg ccg ggt aaa gtt aac cca act caa aac gaa     1056
Pro Gly Ser Ser Ile Met Pro Gly Lys Val Asn Pro Thr Gln Asn Glu
            340                 345                 350 gct ttg act atg ctt tgt acc caa gtc ttt ggt aac cac tct tgt att     1104
Ala Leu Thr Met Leu Cys Thr Gln Val Phe Gly Asn His Ser Cys Ile
        355                 360                 365 acc ttt gca ggt gct tca ggt caa ttc gaa ttg aat gtc ttt aag cca     1152
Thr Phe Ala Gly Ala Ser Gly Gln Phe Glu Leu Asn Val Phe Lys Pro
370                 375                 380 gtt atg atc tcc aac ttg tta tct tct att agg tta tta ggt gat ggt     1200
Val Met Ile Ser Asn Leu Leu Ser Ser Ile Arg Leu Leu Gly Asp Gly
385                 390                 395                 400 tgt aat tct ttt aga atc cac tgt gtt gaa ggt atc att gca aat acc     1248
Cys Asn Ser Phe Arg Ile His Cys Val Glu Gly Ile Ile Ala Asn Thr
                405                 410                 415 gac aag att gat aaa tta cta cat gaa tct ctc atg tta gtt act gct     1296
Asp Lys Ile Asp Lys Leu Leu His Glu Ser Leu Met Leu Val Thr Ala
            420                 425                 430 ttg aac cca cac att ggt tac gat aag gct tcc aag att gca aag aat     1344
Leu Asn Pro His Ile Gly Tyr Asp Lys Ala Ser Lys Ile Ala Lys Asn
        435                 440                 445 gca cac aag aag ggc ttg aca ttg aaa caa tct gca ttg gaa tta ggt     1392
Ala His Lys Lys Gly Leu Thr Leu Lys Gln Ser Ala Leu Glu Leu Gly
450                 455                 460 tac ttg acc gaa gaa caa ttc aat gaa tgg gtt aga cca gaa aac atg     1440
Tyr Leu Thr Glu Glu Gln Phe Asn Glu Trp Val Arg Pro Glu Asn Met
465                 470                 475                 480 att ggt cca aag gat taa                                             1458
Ile Gly Pro Lys Asp
                485

<210> SEQ ID NO 2
<211> LENGTH: 485
<212> TYPE: PRT
<213> ORGANISM: Issatchenkia orientalis

<400> SEQUENCE: 2

Met Leu Ala Ala Arg Ser Leu Lys Ala Arg Met Ser Thr Arg Ala Phe
1               5                   10                  15

Ser Thr Thr Ser Ile Ala Lys Arg Ile Glu Lys Asp Ala Phe Gly Asp
            20                  25                  30

Ile Glu Val Pro Asn Glu Lys Tyr Trp Gly Ala Gln Thr Gln Arg Ser
        35                  40                  45

Leu Gln Asn Phe Lys Ile Gly Gly Lys Arg Glu Val Met Pro Glu Pro
    50                  55                  60

Ile Ile Lys Ser Phe Gly Ile Leu Lys Lys Ala Thr Ala Lys Ile Asn
```

```
               65                  70                  75                  80
Ala Glu Ser Gly Ala Leu Asp Pro Lys Leu Ser Glu Ala Ile Gln Gln
                    85                  90                  95
Ala Ala Thr Glu Val Tyr Glu Gly Lys Leu Met Asp His Phe Pro Leu
                    100                 105                 110
Val Val Phe Gln Thr Gly Ser Gly Thr Gln Ser Asn Met Asn Ala Asn
                    115                 120                 125
Glu Val Ile Ser Asn Arg Ala Ile Glu Ile Leu Gly Gly Glu Leu Gly
                    130                 135                 140
Ser Lys Thr Pro Val His Pro Asn Asp His Val Asn Met Ser Gln Ser
145                 150                 155                 160
Ser Asn Asp Thr Phe Pro Thr Val Met His Ile Ala Ala Val Thr Glu
                    165                 170                 175
Val Ser Ser His Leu Leu Pro Glu Leu Thr Ala Leu Arg Asp Ala Leu
                    180                 185                 190
Gln Lys Lys Ser Asp Glu Phe Lys Asn Ile Ile Lys Ile Gly Arg Thr
                    195                 200                 205
His Leu Gln Asp Ala Thr Pro Leu Thr Leu Gly Gln Glu Phe Ser Gly
                    210                 215                 220
Tyr Val Gln Gln Cys Thr Asn Gly Ile Lys Arg Ile Glu Ile Ala Leu
225                 230                 235                 240
Glu His Leu Arg Tyr Leu Ala Gln Gly Gly Thr Ala Val Gly Thr Gly
                    245                 250                 255
Leu Asn Thr Lys Lys Gly Phe Ala Glu Lys Val Ala Asn Glu Val Thr
                    260                 265                 270
Lys Leu Thr Gly Leu Gln Phe Tyr Thr Ala Pro Asn Lys Phe Glu Ala
                    275                 280                 285
Leu Ala Ala His Asp Ala Val Val Glu Met Ser Gly Ala Leu Asn Thr
                    290                 295                 300
Val Ala Val Ser Leu Phe Lys Ile Ala Gln Asp Ile Arg Tyr Leu Gly
305                 310                 315                 320
Ser Gly Pro Arg Cys Gly Tyr Gly Glu Leu Ala Leu Pro Glu Asn Glu
                    325                 330                 335
Pro Gly Ser Ser Ile Met Pro Gly Lys Val Asn Pro Thr Gln Asn Glu
                    340                 345                 350
Ala Leu Thr Met Leu Cys Thr Gln Val Phe Gly Asn His Ser Cys Ile
                    355                 360                 365
Thr Phe Ala Gly Ala Ser Gly Gln Phe Glu Leu Asn Val Phe Lys Pro
                    370                 375                 380
Val Met Ile Ser Asn Leu Leu Ser Ser Ile Arg Leu Leu Gly Asp Gly
385                 390                 395                 400
Cys Asn Ser Phe Arg Ile His Cys Val Glu Gly Ile Ile Ala Asn Thr
                    405                 410                 415
Asp Lys Ile Asp Lys Leu Leu His Glu Ser Leu Met Leu Val Thr Ala
                    420                 425                 430
Leu Asn Pro His Ile Gly Tyr Asp Lys Ala Ser Lys Ile Ala Lys Asn
                    435                 440                 445
Ala His Lys Lys Gly Leu Thr Leu Lys Gln Ser Ala Leu Glu Leu Gly
                    450                 455                 460
Tyr Leu Thr Glu Glu Gln Phe Asn Glu Trp Val Arg Pro Glu Asn Met
465                 470                 475                 480
Ile Gly Pro Lys Asp
                    485
```

<210> SEQ ID NO 3
<211> LENGTH: 2652
<212> TYPE: DNA
<213> ORGANISM: Escherichia coli
<220> FEATURE:
<221> NAME/KEY: CDS
<222> LOCATION: (1)..(2652)

<400> SEQUENCE: 3

```
atg aac gaa caa tat tcc gca ttg cgt agt aat gtc agt atg ctc ggc      48
Met Asn Glu Gln Tyr Ser Ala Leu Arg Ser Asn Val Ser Met Leu Gly
1               5                  10                  15 aaa gtg ctg gga gaa acc atc aag gat gcg ttg gga gaa cac att ctt      96
Lys Val Leu Gly Glu Thr Ile Lys Asp Ala Leu Gly Glu His Ile Leu
            20                  25                  30 gaa cgc gta gaa act atc cgt aag ttg tcg aaa tct tca cgc gct ggc     144
Glu Arg Val Glu Thr Ile Arg Lys Leu Ser Lys Ser Ser Arg Ala Gly
        35                  40                  45 aat gat gct aac cgc cag gag ttg ctc acc acc tta caa aat ttg tcg     192
Asn Asp Ala Asn Arg Gln Glu Leu Leu Thr Thr Leu Gln Asn Leu Ser
    50                  55                  60 aac gac gag ctg ctg ccc gtt gcg cgt gcg ttt agt cag ttc ctg aac     240
Asn Asp Glu Leu Leu Pro Val Ala Arg Ala Phe Ser Gln Phe Leu Asn
65                  70                  75                  80 ctg gcc aac acc gcc gag caa tac cac agc att tcg ccg aaa ggc gaa     288
Leu Ala Asn Thr Ala Glu Gln Tyr His Ser Ile Ser Pro Lys Gly Glu
                85                  90                  95 gct gcc agc aac ccg gaa gtg atc gcc cgc acc ctg cgt aaa ctg aaa     336
Ala Ala Ser Asn Pro Glu Val Ile Ala Arg Thr Leu Arg Lys Leu Lys
            100                 105                 110 aac cag ccg gaa ctg agc gaa gac acc atc aaa aaa gca gtg gaa tcg     384
Asn Gln Pro Glu Leu Ser Glu Asp Thr Ile Lys Lys Ala Val Glu Ser
        115                 120                 125 ctg tcg ctg gaa ctg gtc ctc acg gct cac cca acc gaa att acc cgt     432
Leu Ser Leu Glu Leu Val Leu Thr Ala His Pro Thr Glu Ile Thr Arg
    130                 135                 140 cgt aca ctg atc cac aaa atg gtg gaa gtg aac gcc tgt tta aaa cag     480
Arg Thr Leu Ile His Lys Met Val Glu Val Asn Ala Cys Leu Lys Gln
145                 150                 155                 160 ctc gat aac aaa gat atc gct gac tac gaa cac aac cag ctg atg cgt     528
Leu Asp Asn Lys Asp Ile Ala Asp Tyr Glu His Asn Gln Leu Met Arg
                165                 170                 175 cgc ctg cgc cag ttg atc gcc cag tca tgg cat acc gat gaa atc cgt     576
Arg Leu Arg Gln Leu Ile Ala Gln Ser Trp His Thr Asp Glu Ile Arg
            180                 185                 190 aag ctg cgt cca agc ccg gta gat gaa gcc aaa tgg ggc ttt gcc gta     624
Lys Leu Arg Pro Ser Pro Val Asp Glu Ala Lys Trp Gly Phe Ala Val
        195                 200                 205 gtg gaa aac agc ctg tgg caa ggc gta cca aat tac ctg cgc gaa ctg     672
Val Glu Asn Ser Leu Trp Gln Gly Val Pro Asn Tyr Leu Arg Glu Leu
    210                 215                 220 aac gaa caa ctg gaa gag aac ctc ggc tac aaa ctg ccc gtc gaa ttt     720
Asn Glu Gln Leu Glu Glu Asn Leu Gly Tyr Lys Leu Pro Val Glu Phe
225                 230                 235                 240 gtt ccg gtc cgt ttt act tcg tgg atg ggc ggc gac cgc gac ggc aac     768
Val Pro Val Arg Phe Thr Ser Trp Met Gly Gly Asp Arg Asp Gly Asn
                245                 250                 255 ccg aac gtc act gcc gat atc acc cgc cac gtc ctg cta ctc agc cgc     816
Pro Asn Val Thr Ala Asp Ile Thr Arg His Val Leu Leu Leu Ser Arg
            260                 265                 270
```

```
tgg aaa gcc acc gat ttg ttc ctg aaa gat att cag gtg ctg gtt tct        864
Trp Lys Ala Thr Asp Leu Phe Leu Lys Asp Ile Gln Val Leu Val Ser
            275                 280                 285 gaa ctg tcg atg gtt gaa gcg acc cct gaa ctg ctg gcg ctg gtt ggc        912
Glu Leu Ser Met Val Glu Ala Thr Pro Glu Leu Leu Ala Leu Val Gly
        290                 295                 300 gaa gaa ggt gcc gca gaa ccg tat cgc tat ctg atg aaa aac ctg cgt        960
Glu Glu Gly Ala Ala Glu Pro Tyr Arg Tyr Leu Met Lys Asn Leu Arg
305                 310                 315                 320 tct cgc ctg atg gcg aca cag gca tgg ctg gaa gcg cgc ctg aaa ggc       1008
Ser Arg Leu Met Ala Thr Gln Ala Trp Leu Glu Ala Arg Leu Lys Gly
                325                 330                 335 gaa gaa ctg cca aaa cca gaa ggc ctg ctg aca caa aac gaa gaa ctg       1056
Glu Glu Leu Pro Lys Pro Glu Gly Leu Leu Thr Gln Asn Glu Glu Leu
            340                 345                 350 tgg gaa ccg ctc tac gct tgc tac cag tca ctt cag gcg tgt ggc atg       1104
Trp Glu Pro Leu Tyr Ala Cys Tyr Gln Ser Leu Gln Ala Cys Gly Met
        355                 360                 365 ggt att atc gcc aac ggc gat ctg ctc gac acc ctg cgc cgc gtg aaa       1152
Gly Ile Ile Ala Asn Gly Asp Leu Leu Asp Thr Leu Arg Arg Val Lys
370                 375                 380 tgt ttc ggc gta ccg ctg gtc cgt att gat atc cgt cag gag agc acg       1200
Cys Phe Gly Val Pro Leu Val Arg Ile Asp Ile Arg Gln Glu Ser Thr
385                 390                 395                 400 cgt cat acc gaa gcg ctg ggc gag ctg acc cgc tac ctc ggt atc ggc       1248
Arg His Thr Glu Ala Leu Gly Glu Leu Thr Arg Tyr Leu Gly Ile Gly
                405                 410                 415 gac tac gaa agc tgg tca gag gcc gac aaa cag gcg ttc ctg atc cgc       1296
Asp Tyr Glu Ser Trp Ser Glu Ala Asp Lys Gln Ala Phe Leu Ile Arg
            420                 425                 430 gaa ctg aac tcc aaa cgt ccg ctt ctg ccg cgc aac tgg caa cca agc       1344
Glu Leu Asn Ser Lys Arg Pro Leu Leu Pro Arg Asn Trp Gln Pro Ser
        435                 440                 445 gcc gaa acg cgc gaa gtg ctc gat acc tgc cag gtg att gcc gaa gca       1392
Ala Glu Thr Arg Glu Val Leu Asp Thr Cys Gln Val Ile Ala Glu Ala
450                 455                 460 ccg caa ggc tcc att gcc gcc tac gtg atc tcg atg gcg aaa acg ccg       1440
Pro Gln Gly Ser Ile Ala Ala Tyr Val Ile Ser Met Ala Lys Thr Pro
465                 470                 475                 480 tcc gac gta ctg gct gtc cac ctg ctg ctg aaa gaa gcg ggt atc ggg       1488
Ser Asp Val Leu Ala Val His Leu Leu Leu Lys Glu Ala Gly Ile Gly
                485                 490                 495 ttt gcg atg ccg gtt gct ccg ctg ttt gaa acc ctc gat gat ctg aac       1536
Phe Ala Met Pro Val Ala Pro Leu Phe Glu Thr Leu Asp Asp Leu Asn
            500                 505                 510 aac gcc aac gat gtc atg acc cag ctg ctc aat att gac tgg tat cgt       1584
Asn Ala Asn Asp Val Met Thr Gln Leu Leu Asn Ile Asp Trp Tyr Arg
        515                 520                 525 ggc ctg att cag ggc aaa cag atg gtg atg att ggc tat tcc gac tca       1632
Gly Leu Ile Gln Gly Lys Gln Met Val Met Ile Gly Tyr Ser Asp Ser
    530                 535                 540 gca aaa gat gcg gga gtg atg gca gct tcc tgg gcg caa tat cag gca       1680
Ala Lys Asp Ala Gly Val Met Ala Ala Ser Trp Ala Gln Tyr Gln Ala
545                 550                 555                 560 cag gat gca tta atc aaa acc tgc gaa aaa gcg ggt att gag ctg acg       1728
Gln Asp Ala Leu Ile Lys Thr Cys Glu Lys Ala Gly Ile Glu Leu Thr
                565                 570                 575 ttg ttc cac ggt cgc ggc ggt tcc att ggt cgc ggc ggc gca cct gct       1776
Leu Phe His Gly Arg Gly Gly Ser Ile Gly Arg Gly Gly Ala Pro Ala
```

```
                580             585              590
cat gcg gcg ctg ctg tca caa ccg cca gga agc ctg aaa ggc ggc ctg      1824
His Ala Ala Leu Leu Ser Gln Pro Pro Gly Ser Leu Lys Gly Gly Leu
        595                 600                 605 cgc gta acc gaa cag ggc gag atg atc cgc ttt aaa tat ggt ctg cca      1872
Arg Val Thr Glu Gln Gly Glu Met Ile Arg Phe Lys Tyr Gly Leu Pro
    610                 615                 620 gaa atc acc gtc agc agc ctg tcg ctt tat acc ggg gcg att ctg gaa      1920
Glu Ile Thr Val Ser Ser Leu Ser Leu Tyr Thr Gly Ala Ile Leu Glu
625                 630                 635                 640 gcc aac ctg ctg cca ccg ccg gag ccg aaa gag agc tgg cgt cgc att      1968
Ala Asn Leu Leu Pro Pro Pro Glu Pro Lys Glu Ser Trp Arg Arg Ile
                645                 650                 655 atg gat gaa ctg tca gtc atc tcc tgc gat gtc tac cgc ggc tac gta      2016
Met Asp Glu Leu Ser Val Ile Ser Cys Asp Val Tyr Arg Gly Tyr Val
            660                 665                 670 cgt gaa aac aaa gat ttt gtg cct tac ttc cgc tcc gct acg ccg gaa      2064
Arg Glu Asn Lys Asp Phe Val Pro Tyr Phe Arg Ser Ala Thr Pro Glu
        675                 680                 685 caa gaa ctg ggc aaa ctg ccg ttg ggt tca cgt ccg gcg aaa cgt cgc      2112
Gln Glu Leu Gly Lys Leu Pro Leu Gly Ser Arg Pro Ala Lys Arg Arg
    690                 695                 700 cca acc ggc ggc gtc gag tca cta cgc gcc att ccg tgg atc ttc gcc      2160
Pro Thr Gly Gly Val Glu Ser Leu Arg Ala Ile Pro Trp Ile Phe Ala
705                 710                 715                 720 tgg acg caa aac cgt ctg atg ctc ccc gcc tgg ctg ggt gca ggt acg      2208
Trp Thr Gln Asn Arg Leu Met Leu Pro Ala Trp Leu Gly Ala Gly Thr
                725                 730                 735 gcg ctg caa aaa gtg gtc gaa gac ggc aaa cag agc gag ctg gag gct      2256
Ala Leu Gln Lys Val Val Glu Asp Gly Lys Gln Ser Glu Leu Glu Ala
            740                 745                 750 atg tgc cgc gat tgg cca ttc ttc tcg acg cgt ctc ggc atg ctg gag      2304
Met Cys Arg Asp Trp Pro Phe Phe Ser Thr Arg Leu Gly Met Leu Glu
        755                 760                 765 atg gtc ttc gcc aaa gca gac ctg tgg ctg gcg gaa tac tat gac caa      2352
Met Val Phe Ala Lys Ala Asp Leu Trp Leu Ala Glu Tyr Tyr Asp Gln
    770                 775                 780 cgc ctg gta gac aaa gca ctg tgg ccg tta ggt aaa gag tta cgc aac      2400
Arg Leu Val Asp Lys Ala Leu Trp Pro Leu Gly Lys Glu Leu Arg Asn
785                 790                 795                 800 ctg caa gaa gaa gac atc aaa gtg gtg ctg gcg att gcc aac gat tcc      2448
Leu Gln Glu Glu Asp Ile Lys Val Val Leu Ala Ile Ala Asn Asp Ser
                805                 810                 815 cat ctg atg gcc gat ctg ccg tgg att gca gag tct att cag cta cgg      2496
His Leu Met Ala Asp Leu Pro Trp Ile Ala Glu Ser Ile Gln Leu Arg
            820                 825                 830 aat att tac acc gac ccg ctg aac gta ttg cag gcc gag ttg ctg cac      2544
Asn Ile Tyr Thr Asp Pro Leu Asn Val Leu Gln Ala Glu Leu Leu His
        835                 840                 845 cgc tcc cgc cag gca gaa aaa gaa ggc cag gaa ccg gat cct cgc gtc      2592
Arg Ser Arg Gln Ala Glu Lys Glu Gly Gln Glu Pro Asp Pro Arg Val
    850                 855                 860 gaa caa gcg tta atg gtc act att gcc ggg att gcg gca ggt atg cgt      2640
Glu Gln Ala Leu Met Val Thr Ile Ala Gly Ile Ala Ala Gly Met Arg
865                 870                 875                 880 aat acc ggc taa                                                       2652
Asn Thr Gly

<210> SEQ ID NO 4
```

```
<211> LENGTH: 883
<212> TYPE: PRT
<213> ORGANISM: Escherichia coli

<400> SEQUENCE: 4

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
```

-continued

```
            385                 390                 395                 400

Arg His Thr Glu Ala Leu Gly Glu Leu Thr Arg Tyr Leu Gly Ile Gly
                        405                 410                 415

Asp Tyr Glu Ser Trp Ser Glu Ala Asp Lys Gln Ala Phe Leu Ile Arg
                        420                 425                 430

Glu Leu Asn Ser Lys Arg Pro Leu Leu Pro Arg Asn Trp Gln Pro Ser
                        435                 440                 445

Ala Glu Thr Arg Glu Val Leu Asp Thr Cys Gln Val Ile Ala Glu Ala
                        450                 455                 460

Pro Gln Gly Ser Ile Ala Ala Tyr Val Ile Ser Met Ala Lys Thr Pro
        465                 470                 475                 480

Ser Asp Val Leu Ala Val His Leu Leu Leu Lys Glu Ala Gly Ile Gly
                        485                 490                 495

Phe Ala Met Pro Val Ala Pro Leu Phe Glu Thr Leu Asp Asp Leu Asn
                        500                 505                 510

Asn Ala Asn Asp Val Met Thr Gln Leu Leu Asn Ile Asp Trp Tyr Arg
                        515                 520                 525

Gly Leu Ile Gln Gly Lys Gln Met Val Met Ile Gly Tyr Ser Asp Ser
                        530                 535                 540

Ala Lys Asp Ala Gly Val Met Ala Ala Ser Trp Ala Gln Tyr Gln Ala
        545                 550                 555                 560

Gln Asp Ala Leu Ile Lys Thr Cys Glu Lys Ala Gly Ile Glu Leu Thr
                        565                 570                 575

Leu Phe His Gly Arg Gly Gly Ser Ile Gly Arg Gly Gly Ala Pro Ala
                        580                 585                 590

His Ala Ala Leu Leu Ser Gln Pro Pro Gly Ser Leu Lys Gly Gly Leu
                        595                 600                 605

Arg Val Thr Glu Gln Gly Glu Met Ile Arg Phe Lys Tyr Gly Leu Pro
                        610                 615                 620

Glu Ile Thr Val Ser Ser Leu Ser Leu Tyr Thr Gly Ala Ile Leu Glu
        625                 630                 635                 640

Ala Asn Leu Leu Pro Pro Pro Glu Pro Lys Glu Ser Trp Arg Arg Ile
                        645                 650                 655

Met Asp Glu Leu Ser Val Ile Ser Cys Asp Val Tyr Arg Gly Tyr Val
                        660                 665                 670

Arg Glu Asn Lys Asp Phe Val Pro Tyr Phe Arg Ser Ala Thr Pro Glu
                        675                 680                 685

Gln Glu Leu Gly Lys Leu Pro Leu Gly Ser Arg Pro Ala Lys Arg Arg
                        690                 695                 700

Pro Thr Gly Gly Val Glu Ser Leu Arg Ala Ile Pro Trp Ile Phe Ala
        705                 710                 715                 720

Trp Thr Gln Asn Arg Leu Met Leu Pro Ala Trp Leu Gly Ala Gly Thr
                        725                 730                 735

Ala Leu Gln Lys Val Val Glu Asp Gly Lys Gln Ser Glu Leu Glu Ala
                        740                 745                 750

Met Cys Arg Asp Trp Pro Phe Phe Ser Thr Arg Leu Gly Met Leu Glu
                        755                 760                 765

Met Val Phe Ala Lys Ala Asp Leu Trp Leu Ala Glu Tyr Tyr Asp Gln
                        770                 775                 780

Arg Leu Val Asp Lys Ala Leu Trp Pro Leu Gly Lys Glu Leu Arg Asn
        785                 790                 795                 800

Leu Gln Glu Glu Asp Ile Lys Val Val Leu Ala Ile Ala Asn Asp Ser
                        805                 810                 815
```

```
His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
            835                 840                 845

Arg Ser Arg Gln Ala Glu Lys Glu Gly Gln Pro Asp Pro Arg Val
850                 855                 860

Glu Gln Ala Leu Met Val Thr Ile Ala Gly Ile Ala Ala Gly Met Arg
865                 870                 875                 880

Asn Thr Gly

<210> SEQ ID NO 5
<211> LENGTH: 2643
<212> TYPE: DNA
<213> ORGANISM: Mannheimia succiniproducens
<220> FEATURE:
<221> NAME/KEY: CDS
<222> LOCATION: (1)..(2643)

<400> SEQUENCE: 5 atg aca gaa gaa tat tta atg atg cgt aat aac atc aat atg ctg ggg      48
Met Thr Glu Glu Tyr Leu Met Met Arg Asn Asn Ile Asn Met Leu Gly
1               5                  10                  15 cgc ttt ttg ggc gaa act att cag gag gcg caa ggt gac gat att ctc      96
Arg Phe Leu Gly Glu Thr Ile Gln Glu Ala Gln Gly Asp Asp Ile Leu
            20                  25                  30 gaa ctg att gaa aat atc cgc gta ctg tcc cgc aat tcc cgt agc ggc     144
Glu Leu Ile Glu Asn Ile Arg Val Leu Ser Arg Asn Ser Arg Ser Gly
        35                  40                  45 gat gac aaa gcc cgg gcg gca tta tta gac acc ctt tcc act att tcg     192
Asp Asp Lys Ala Arg Ala Ala Leu Leu Asp Thr Leu Ser Thr Ile Ser
    50                  55                  60 gcg gat aat att att ccg gtt gcc cgc gct ttc agc cag ttt ctg aac     240
Ala Asp Asn Ile Ile Pro Val Ala Arg Ala Phe Ser Gln Phe Leu Asn
65                  70                  75                  80 ctg aca aat gtg gcg gaa caa tat caa acc atg tct cgc tcc cat gaa     288
Leu Thr Asn Val Ala Glu Gln Tyr Gln Thr Met Ser Arg Ser His Glu
                85                  90                  95 gat aag gtt tct gcg gaa cgt tcc act gct gcg ctg ttc gcc cgc ctg     336
Asp Lys Val Ser Ala Glu Arg Ser Thr Ala Ala Leu Phe Ala Arg Leu
            100                 105                 110 aaa gaa caa cat gtt tct cag gaa gaa atc att aaa acc gta cag aaa     384
Lys Glu Gln His Val Ser Gln Glu Glu Ile Ile Lys Thr Val Gln Lys
        115                 120                 125 ctg ttg att gaa atc gtc ctt acc gct cac ccg acg gaa gtt acc cgc     432
Leu Leu Ile Glu Ile Val Leu Thr Ala His Pro Thr Glu Val Thr Arg
    130                 135                 140 cgt tca tta atg cac aaa cag gtt gaa atc aac aaa tgt ctg gct cag     480
Arg Ser Leu Met His Lys Gln Val Glu Ile Asn Lys Cys Leu Ala Gln
145                 150                 155                 160 ctg gat cat acg gat tta acc gcc gaa gaa caa aaa aat att gag tat     528
Leu Asp His Thr Asp Leu Thr Ala Glu Glu Gln Lys Asn Ile Glu Tyr
                165                 170                 175 aaa tta ctt cgt ctt atc gcc gaa gcc tgg cat acc aat gaa atc cgt     576
Lys Leu Leu Arg Leu Ile Ala Glu Ala Trp His Thr Asn Glu Ile Arg
            180                 185                 190 acc aat cgg ccg aca cct ctg gaa gaa gcc aaa tgg ggt ttt gcc gtt     624
Thr Asn Arg Pro Thr Pro Leu Glu Glu Ala Lys Trp Gly Phe Ala Val
        195                 200                 205 atc gaa aac agt tta tgg gaa ggt ttg ccc gcc ttt atc cgc aaa ctt     672
```

```
Ile Glu Asn Ser Leu Trp Glu Gly Leu Pro Ala Phe Ile Arg Lys Leu
    210                 215                 220 aac gat gcc gcc gtc gaa cat tta aat tat gct ttg ccg gta gac ctc      720
Asn Asp Ala Ala Val Glu His Leu Asn Tyr Ala Leu Pro Val Asp Leu
225                 230                 235                 240 aca ccg gta cgc ttc tct tcc tgg atg ggc ggt gac cgt gac ggc aac      768
Thr Pro Val Arg Phe Ser Ser Trp Met Gly Gly Asp Arg Asp Gly Asn
                245                 250                 255 ccc ttc gtt acc gca aaa att acc cgg gaa gcg ctg caa ctt gcg cgc      816
Pro Phe Val Thr Ala Lys Ile Thr Arg Glu Ala Leu Gln Leu Ala Arg
            260                 265                 270 tgg aaa gcg gcg gat tta ttt tta acc gat att cag gaa ctc tgc gac      864
Trp Lys Ala Ala Asp Leu Phe Leu Thr Asp Ile Gln Glu Leu Cys Asp
        275                 280                 285 gag ttg tca atg aca caa tgc act gcg gaa ttc cga gaa aaa tac ggt      912
Glu Leu Ser Met Thr Gln Cys Thr Ala Glu Phe Arg Glu Lys Tyr Gly
    290                 295                 300 gat cat tta gaa ccc tat cgt gta gtt gtg aag gat tta cgc agc aaa      960
Asp His Leu Glu Pro Tyr Arg Val Val Val Lys Asp Leu Arg Ser Lys
305                 310                 315                 320 tta aaa aat acg ctg gat tat tac aac gat ata ctt gcg ggt cgc att     1008
Leu Lys Asn Thr Leu Asp Tyr Tyr Asn Asp Ile Leu Ala Gly Arg Ile
                325                 330                 335 ccg ccg ttt aaa caa gat gaa atc atc agt gaa gac caa caa ctc tgg     1056
Pro Pro Phe Lys Gln Asp Glu Ile Ile Ser Glu Asp Gln Gln Leu Trp
            340                 345                 350 caa ccg ctt tat gac tgt tat caa tcc cta acc gcc tgc ggt atg cgt     1104
Gln Pro Leu Tyr Asp Cys Tyr Gln Ser Leu Thr Ala Cys Gly Met Arg
        355                 360                 365 att att gcc aat gga tta ttg ctg gat acc tta cgc cgc gtt cgt tgt     1152
Ile Ile Ala Asn Gly Leu Leu Leu Asp Thr Leu Arg Arg Val Arg Cys
    370                 375                 380 ttc ggc gtc aca tta ctg cgt tta gat atc cgt cag gaa agc acc cgc     1200
Phe Gly Val Thr Leu Leu Arg Leu Asp Ile Arg Gln Glu Ser Thr Arg
385                 390                 395                 400 cat agc gac gcc atc ggc gaa att acc cgc tac atc ggt tta ggc gat     1248
His Ser Asp Ala Ile Gly Glu Ile Thr Arg Tyr Ile Gly Leu Gly Asp
                405                 410                 415 tac agc caa tgg aca gaa gat gac aaa caa gcc ttc ctg atc cgg gaa     1296
Tyr Ser Gln Trp Thr Glu Asp Asp Lys Gln Ala Phe Leu Ile Arg Glu
            420                 425                 430 tta agt tcc cgt cgt ccg cta att ccc cat aac tgg acg cct tcg gaa     1344
Leu Ser Ser Arg Arg Pro Leu Ile Pro His Asn Trp Thr Pro Ser Glu
        435                 440                 445 cac act cgg gaa att tta gac acc tgt aaa gtc att gca aaa cag ccg     1392
His Thr Arg Glu Ile Leu Asp Thr Cys Lys Val Ile Ala Lys Gln Pro
    450                 455                 460 gaa ggc gtt att tcc tgc tat atc att tcc atg gcg cgc acc gct tcc     1440
Glu Gly Val Ile Ser Cys Tyr Ile Ile Ser Met Ala Arg Thr Ala Ser
465                 470                 475                 480 gat gtt ttg gcg gtg cat tta tta ttg aaa gaa gcg ggc att tca tac     1488
Asp Val Leu Ala Val His Leu Leu Leu Lys Glu Ala Gly Ile Ser Tyr
                485                 490                 495 cat ctg ccg gta gtt cct cta ttt gaa aca ttg gac gac ctg gac gct     1536
His Leu Pro Val Val Pro Leu Phe Glu Thr Leu Asp Asp Leu Asp Ala
            500                 505                 510 tct aaa gaa gtg atg acg caa ctg ttt aac gta ggc tgg tat cgc ggc     1584
Ser Lys Glu Val Met Thr Gln Leu Phe Asn Val Gly Trp Tyr Arg Gly
        515                 520                 525
```

```
gta atc aaa aac cgc caa atg atc atg atc ggc tat tcc gat agc gcc    1632
Val Ile Lys Asn Arg Gln Met Ile Met Ile Gly Tyr Ser Asp Ser Ala
    530                 535                 540 aaa gat gcg ggc atg atg gcg gcc tca tgg gcg caa tac cgg gcg cag    1680
Lys Asp Ala Gly Met Met Ala Ala Ser Trp Ala Gln Tyr Arg Ala Gln
545                 550                 555                 560 gac gct tta gtc aaa ctt tgc gaa caa acc ggc atc gaa ctt acc ctc    1728
Asp Ala Leu Val Lys Leu Cys Glu Gln Thr Gly Ile Glu Leu Thr Leu
                565                 570                 575 ttc cac ggc cgc ggc ggc acc gta gga cgt ggc ggt gca ccg gct cac    1776
Phe His Gly Arg Gly Gly Thr Val Gly Arg Gly Gly Ala Pro Ala His
            580                 585                 590 gcc gca tta tta tcc caa ccg cca cgt tct ctg aaa aac ggc tta cgg    1824
Ala Ala Leu Leu Ser Gln Pro Pro Arg Ser Leu Lys Asn Gly Leu Arg
        595                 600                 605 gta acc gaa caa ggg gaa atg atc cgc ttc aaa ctg gga tta ccg gct    1872
Val Thr Glu Gln Gly Glu Met Ile Arg Phe Lys Leu Gly Leu Pro Ala
    610                 615                 620 atc gcc gca gaa agt ctg gat ctc tac gcc agc gcc att ctt gag gcc    1920
Ile Ala Ala Glu Ser Leu Asp Leu Tyr Ala Ser Ala Ile Leu Glu Ala
625                 630                 635                 640 aac ctc ctg ccg ccg ccg gaa ccg aaa gcc agc tgg tgc cgg gta atg    1968
Asn Leu Leu Pro Pro Pro Glu Pro Lys Ala Ser Trp Cys Arg Val Met
                645                 650                 655 gac gaa ctt gcc gtc gct tct tgc gaa atc tat cgc aat gtg gtg cgc    2016
Asp Glu Leu Ala Val Ala Ser Cys Glu Ile Tyr Arg Asn Val Val Arg
            660                 665                 670 ggc gat aaa gat ttt gtg cct tac ttc cgc agc gcc aca ccg gaa cag    2064
Gly Asp Lys Asp Phe Val Pro Tyr Phe Arg Ser Ala Thr Pro Glu Gln
        675                 680                 685 gaa ctg gca aaa ctg cct tta ggt tcc cga ccg gca aaa cgc aat ccg    2112
Glu Leu Ala Lys Leu Pro Leu Gly Ser Arg Pro Ala Lys Arg Asn Pro
    690                 695                 700 aac ggc ggc gtt gaa agc ctg cgt gcc att ccc tgg atc ttc gcc tgg    2160
Asn Gly Gly Val Glu Ser Leu Arg Ala Ile Pro Trp Ile Phe Ala Trp
705                 710                 715                 720 atg caa aac cgc ctg atg ctg ccc gcc tgg ctc ggt gcc ggc gcc tca    2208
Met Gln Asn Arg Leu Met Leu Pro Ala Trp Leu Gly Ala Gly Ala Ser
                725                 730                 735 atc cgt cag gcg atg gaa agc ggc aaa gcg gcg gtg att gaa gaa atg    2256
Ile Arg Gln Ala Met Glu Ser Gly Lys Ala Ala Val Ile Glu Glu Met
            740                 745                 750 tgc aac cat tgg ccg ttt ttc aat acc cga atc ggc atg ctt gaa atg    2304
Cys Asn His Trp Pro Phe Phe Asn Thr Arg Ile Gly Met Leu Glu Met
        755                 760                 765 gta ttc agt aaa acc gat agc tgg ctg tcc gaa tat tac gac cag cgt    2352
Val Phe Ser Lys Thr Asp Ser Trp Leu Ser Glu Tyr Tyr Asp Gln Arg
    770                 775                 780 tta gtg aaa aaa gag ctt tgg tat tta ggc gaa tcg ctg cgc aaa cag    2400
Leu Val Lys Lys Glu Leu Trp Tyr Leu Gly Glu Ser Leu Arg Lys Gln
785                 790                 795                 800 tta agc gaa gat atc gct acc gtg tta cgg ctt tcc ggc aaa ggc gat    2448
Leu Ser Glu Asp Ile Ala Thr Val Leu Arg Leu Ser Gly Lys Gly Asp
                805                 810                 815 caa tta atg tcg gat ttg cct tgg gtg gcg gaa tct att gca ctg cgt    2496
Gln Leu Met Ser Asp Leu Pro Trp Val Ala Glu Ser Ile Ala Leu Arg
            820                 825                 830 aac gtt tac acc gac ccg tta aac tta ttg caa gtg gaa tta ttg cgt    2544
Asn Val Tyr Thr Asp Pro Leu Asn Leu Leu Gln Val Glu Leu Leu Arg
        835                 840                 845
```

-continued

```
cgt ttg cga gcg gat ccc gaa cat ccg aat ccg gat atc gag caa gcg    2592
Arg Leu Arg Ala Asp Pro Glu His Pro Asn Pro Asp Ile Glu Gln Ala
850                 855                 860 ctg atg atc acc att acc ggt atc gcc gcg ggt atg cgt aat acg ggt    2640
Leu Met Ile Thr Ile Thr Gly Ile Ala Ala Gly Met Arg Asn Thr Gly
865                 870                 875                 880 tag                                                                2643
```

<210> SEQ ID NO 6
<211> LENGTH: 880
<212> TYPE: PRT
<213> ORGANISM: Mannheimia succiniproducens

<400> SEQUENCE: 6

```
Met Thr Glu Glu Tyr Leu Met Met Arg Asn Asn Ile Asn Met Leu Gly
1               5                   10                  15

Arg Phe Leu Gly Glu Thr Ile Gln Glu Ala Gln Gly Asp Asp Ile Leu
            20                  25                  30

Glu Leu Ile Glu Asn Ile Arg Val Leu Ser Arg Asn Ser Arg Ser Gly
        35                  40                  45

Asp Asp Lys Ala Arg Ala Ala Leu Leu Asp Thr Leu Ser Thr Ile Ser
    50                  55                  60

Ala Asp Asn Ile Ile Pro Val Ala Arg Ala Phe Ser Gln Phe Leu Asn
65                  70                  75                  80

Leu Thr Asn Val Ala Glu Gln Tyr Gln Thr Met Ser Arg Ser His Glu
                85                  90                  95

Asp Lys Val Ser Ala Glu Arg Ser Thr Ala Ala Leu Phe Ala Arg Leu
            100                 105                 110

Lys Glu Gln His Val Ser Gln Glu Ile Ile Lys Thr Val Gln Lys
        115                 120                 125

Leu Leu Ile Glu Ile Val Leu Thr Ala His Pro Thr Glu Val Thr Arg
    130                 135                 140

Arg Ser Leu Met His Lys Gln Val Glu Ile Asn Lys Cys Leu Ala Gln
145                 150                 155                 160

Leu Asp His Thr Asp Leu Thr Ala Glu Glu Gln Lys Asn Ile Glu Tyr
                165                 170                 175

Lys Leu Leu Arg Leu Ile Ala Glu Ala Trp His Thr Asn Glu Ile Arg
            180                 185                 190

Thr Asn Arg Pro Thr Pro Leu Glu Glu Ala Lys Trp Gly Phe Ala Val
        195                 200                 205

Ile Glu Asn Ser Leu Trp Glu Gly Leu Pro Ala Phe Ile Arg Lys Leu
    210                 215                 220

Asn Asp Ala Ala Val Glu His Leu Asn Tyr Ala Leu Pro Val Asp Leu
225                 230                 235                 240

Thr Pro Val Arg Phe Ser Ser Trp Met Gly Gly Asp Arg Asp Gly Asn
                245                 250                 255

Pro Phe Val Thr Ala Lys Ile Thr Arg Glu Ala Leu Gln Leu Ala Arg
            260                 265                 270

Trp Lys Ala Ala Asp Leu Phe Leu Thr Asp Ile Gln Glu Leu Cys Asp
        275                 280                 285

Glu Leu Ser Met Thr Gln Cys Thr Ala Glu Phe Arg Glu Lys Tyr Gly
    290                 295                 300

Asp His Leu Glu Pro Tyr Arg Val Val Lys Asp Leu Arg Ser Lys
305                 310                 315                 320
```

```
Leu Lys Asn Thr Leu Asp Tyr Tyr Asn Asp Ile Leu Ala Gly Arg Ile
                325                 330                 335

Pro Pro Phe Lys Gln Asp Glu Ile Ile Ser Glu Asp Gln Gln Leu Trp
            340                 345                 350

Gln Pro Leu Tyr Asp Cys Tyr Gln Ser Leu Thr Ala Cys Gly Met Arg
        355                 360                 365

Ile Ile Ala Asn Gly Leu Leu Leu Asp Thr Leu Arg Arg Val Arg Cys
370                 375                 380

Phe Gly Val Thr Leu Leu Arg Leu Asp Ile Arg Gln Glu Ser Thr Arg
385                 390                 395                 400

His Ser Asp Ala Ile Gly Glu Ile Thr Arg Tyr Ile Gly Leu Gly Asp
                405                 410                 415

Tyr Ser Gln Trp Thr Glu Asp Lys Gln Ala Phe Leu Ile Arg Glu
            420                 425                 430

Leu Ser Ser Arg Arg Pro Leu Ile Pro His Asn Trp Thr Pro Ser Glu
        435                 440                 445

His Thr Arg Glu Ile Leu Asp Thr Cys Lys Val Ile Ala Lys Gln Pro
    450                 455                 460

Glu Gly Val Ile Ser Cys Tyr Ile Ile Ser Met Ala Arg Thr Ala Ser
465                 470                 475                 480

Asp Val Leu Ala Val His Leu Leu Lys Glu Ala Gly Ile Ser Tyr
                485                 490                 495

His Leu Pro Val Val Pro Leu Phe Glu Thr Leu Asp Asp Leu Asp Ala
            500                 505                 510

Ser Lys Glu Val Met Thr Gln Leu Phe Asn Val Gly Trp Tyr Arg Gly
        515                 520                 525

Val Ile Lys Asn Arg Gln Met Ile Met Ile Gly Tyr Ser Asp Ser Ala
    530                 535                 540

Lys Asp Ala Gly Met Met Ala Ala Ser Trp Ala Gln Tyr Arg Ala Gln
545                 550                 555                 560

Asp Ala Leu Val Lys Leu Cys Glu Gln Thr Gly Ile Glu Leu Thr Leu
                565                 570                 575

Phe His Gly Arg Gly Gly Thr Val Gly Arg Gly Gly Ala Pro Ala His
            580                 585                 590

Ala Ala Leu Leu Ser Gln Pro Pro Arg Ser Leu Lys Asn Gly Leu Arg
        595                 600                 605

Val Thr Glu Gln Gly Glu Met Ile Arg Phe Lys Leu Gly Leu Pro Ala
    610                 615                 620

Ile Ala Ala Glu Ser Leu Asp Leu Tyr Ala Ser Ala Ile Leu Glu Ala
625                 630                 635                 640

Asn Leu Leu Pro Pro Pro Glu Pro Lys Ala Ser Trp Cys Arg Val Met
                645                 650                 655

Asp Glu Leu Ala Val Ala Ser Cys Glu Ile Tyr Arg Asn Val Val Arg
            660                 665                 670

Gly Asp Lys Asp Phe Val Pro Tyr Phe Arg Ser Ala Thr Pro Glu Gln
        675                 680                 685

Glu Leu Ala Lys Leu Pro Leu Gly Ser Arg Pro Ala Lys Arg Asn Pro
    690                 695                 700

Asn Gly Gly Val Glu Ser Leu Arg Ala Ile Pro Trp Ile Phe Ala Trp
705                 710                 715                 720

Met Gln Asn Arg Leu Met Leu Pro Ala Trp Leu Gly Ala Gly Ala Ser
                725                 730                 735

Ile Arg Gln Ala Met Glu Ser Gly Lys Ala Ala Val Ile Glu Glu Met
```

|     |     |     |     | 740 |     |     |     |     | 745 |     |     |     |     | 750 |     |     |
| --- | --- | --- | --- | --- | --- | --- | --- | --- | --- | --- | --- | --- | --- | --- | --- | --- |
| Cys | Asn | His | Trp | Pro | Phe | Phe | Asn | Thr | Arg | Ile | Gly | Met | Leu | Glu | Met |     |
|     |     | 755 |     |     |     |     | 760 |     |     |     |     | 765 |     |     |     |     |

| Val | Phe | Ser | Lys | Thr | Asp | Ser | Trp | Leu | Ser | Glu | Tyr | Tyr | Asp | Gln | Arg |
| --- | --- | --- | --- | --- | --- | --- | --- | --- | --- | --- | --- | --- | --- | --- | --- |
| 770 |     |     |     |     | 775 |     |     |     |     | 780 |     |     |     |     |     |

| Leu | Val | Lys | Lys | Glu | Leu | Trp | Tyr | Leu | Gly | Glu | Ser | Leu | Arg | Lys | Gln |
| --- | --- | --- | --- | --- | --- | --- | --- | --- | --- | --- | --- | --- | --- | --- | --- |
| 785 |     |     |     |     | 790 |     |     |     |     | 795 |     |     |     |     | 800 |

| Leu | Ser | Glu | Asp | Ile | Ala | Thr | Val | Leu | Arg | Leu | Ser | Gly | Lys | Gly | Asp |
| --- | --- | --- | --- | --- | --- | --- | --- | --- | --- | --- | --- | --- | --- | --- | --- |
|     |     |     |     | 805 |     |     |     |     | 810 |     |     |     |     | 815 |     |

| Gln | Leu | Met | Ser | Asp | Leu | Pro | Trp | Val | Ala | Glu | Ser | Ile | Ala | Leu | Arg |
| --- | --- | --- | --- | --- | --- | --- | --- | --- | --- | --- | --- | --- | --- | --- | --- |
|     |     | 820 |     |     |     |     | 825 |     |     |     |     | 830 |     |     |     |

| Asn | Val | Tyr | Thr | Asp | Pro | Leu | Asn | Leu | Leu | Gln | Val | Glu | Leu | Leu | Arg |
| --- | --- | --- | --- | --- | --- | --- | --- | --- | --- | --- | --- | --- | --- | --- | --- |
|     |     | 835 |     |     |     |     | 840 |     |     |     |     | 845 |     |     |     |

| Arg | Leu | Arg | Ala | Asp | Pro | Glu | His | Pro | Asn | Pro | Asp | Ile | Glu | Gln | Ala |
| --- | --- | --- | --- | --- | --- | --- | --- | --- | --- | --- | --- | --- | --- | --- | --- |
|     | 850 |     |     |     |     | 855 |     |     |     |     | 860 |     |     |     |     |

| Leu | Met | Ile | Thr | Ile | Thr | Gly | Ile | Ala | Ala | Gly | Met | Arg | Asn | Thr | Gly |
| --- | --- | --- | --- | --- | --- | --- | --- | --- | --- | --- | --- | --- | --- | --- | --- |
| 865 |     |     |     |     | 870 |     |     |     |     | 875 |     |     |     |     | 880 |

<210> SEQ ID NO 7
<211> LENGTH: 3543
<212> TYPE: DNA
<213> ORGANISM: Issatchenkia orientalis
<220> FEATURE:
<221> NAME/KEY: CDS
<222> LOCATION: (1)..(3543)

<400> SEQUENCE: 7

| atg | tca | act | gtg | gaa | gat | cac | tcc | tcc | cta | cat | aaa | ttg | aga | aag | gaa | 48 |
| --- | --- | --- | --- | --- | --- | --- | --- | --- | --- | --- | --- | --- | --- | --- | --- | --- |
| Met | Ser | Thr | Val | Glu | Asp | His | Ser | Ser | Leu | His | Lys | Leu | Arg | Lys | Glu |     |
| 1   |     |     |     | 5   |     |     |     |     | 10  |     |     |     |     | 15  |     |     |

| tct | gag | att | ctt | tcc | aat | gca | aac | aaa | atc | tta | gtg | gct | aat | aga | ggt | 96 |
| --- | --- | --- | --- | --- | --- | --- | --- | --- | --- | --- | --- | --- | --- | --- | --- | --- |
| Ser | Glu | Ile | Leu | Ser | Asn | Ala | Asn | Lys | Ile | Leu | Val | Ala | Asn | Arg | Gly |     |
|     |     |     | 20  |     |     |     |     | 25  |     |     |     |     | 30  |     |     |     |

| gaa | att | cca | att | aga | att | ttc | agg | tca | gcc | cat | gaa | ttg | tca | atg | cat | 144 |
| --- | --- | --- | --- | --- | --- | --- | --- | --- | --- | --- | --- | --- | --- | --- | --- | --- |
| Glu | Ile | Pro | Ile | Arg | Ile | Phe | Arg | Ser | Ala | His | Glu | Leu | Ser | Met | His |     |
|     |     | 35  |     |     |     |     | 40  |     |     |     |     | 45  |     |     |     |     |

| act | gtg | gcg | atc | tat | tcc | cat | gaa | gat | cgg | ttg | tcc | atg | cat | agg | ttg | 192 |
| --- | --- | --- | --- | --- | --- | --- | --- | --- | --- | --- | --- | --- | --- | --- | --- | --- |
| Thr | Val | Ala | Ile | Tyr | Ser | His | Glu | Asp | Arg | Leu | Ser | Met | His | Arg | Leu |     |
| 50  |     |     |     |     | 55  |     |     |     |     | 60  |     |     |     |     |     |     |

| aag | gcc | gac | gag | gct | tat | gca | atc | ggt | aag | act | ggt | caa | tat | tcg | cca | 240 |
| --- | --- | --- | --- | --- | --- | --- | --- | --- | --- | --- | --- | --- | --- | --- | --- | --- |
| Lys | Ala | Asp | Glu | Ala | Tyr | Ala | Ile | Gly | Lys | Thr | Gly | Gln | Tyr | Ser | Pro |     |
| 65  |     |     |     |     | 70  |     |     |     |     | 75  |     |     |     |     | 80  |     |

| gtt | caa | gct | tat | cta | caa | att | gac | gaa | att | atc | aaa | ata | gca | aag | gaa | 288 |
| --- | --- | --- | --- | --- | --- | --- | --- | --- | --- | --- | --- | --- | --- | --- | --- | --- |
| Val | Gln | Ala | Tyr | Leu | Gln | Ile | Asp | Glu | Ile | Ile | Lys | Ile | Ala | Lys | Glu |     |
|     |     |     |     | 85  |     |     |     |     | 90  |     |     |     |     | 95  |     |     |

| cat | gat | gtt | tcc | atg | atc | cat | cca | ggt | tat | ggt | ttc | tta | tct | gaa | aac | 336 |
| --- | --- | --- | --- | --- | --- | --- | --- | --- | --- | --- | --- | --- | --- | --- | --- | --- |
| His | Asp | Val | Ser | Met | Ile | His | Pro | Gly | Tyr | Gly | Phe | Leu | Ser | Glu | Asn |     |
|     |     |     | 100 |     |     |     |     | 105 |     |     |     |     | 110 |     |     |     |

| tcc | gaa | ttc | gca | aag | aag | gtt | gaa | gaa | tcc | ggt | atg | att | tgg | gtt | ggg | 384 |
| --- | --- | --- | --- | --- | --- | --- | --- | --- | --- | --- | --- | --- | --- | --- | --- | --- |
| Ser | Glu | Phe | Ala | Lys | Lys | Val | Glu | Glu | Ser | Gly | Met | Ile | Trp | Val | Gly |     |
|     |     | 115 |     |     |     |     | 120 |     |     |     |     | 125 |     |     |     |     |

| cct | cct | gct | gaa | gtt | att | gat | tct | gtt | ggt | gac | aag | gtt | tct | gca | aga | 432 |
| --- | --- | --- | --- | --- | --- | --- | --- | --- | --- | --- | --- | --- | --- | --- | --- | --- |
| Pro | Pro | Ala | Glu | Val | Ile | Asp | Ser | Val | Gly | Asp | Lys | Val | Ser | Ala | Arg |     |
| 130 |     |     |     |     | 135 |     |     |     |     | 140 |     |     |     |     |     |     |

| aat | ttg | gca | att | aaa | tgt | gac | gtt | cct | gtt | gtt | cct | ggt | acc | gat | ggt | 480 |
| --- | --- | --- | --- | --- | --- | --- | --- | --- | --- | --- | --- | --- | --- | --- | --- | --- |
| Asn | Leu | Ala | Ile | Lys | Cys | Asp | Val | Pro | Val | Val | Pro | Gly | Thr | Asp | Gly |     |
| 145 |     |     |     |     | 150 |     |     |     |     | 155 |     |     |     |     | 160 |     |

| cca | att | gaa | gac | att | gaa | cag | gct | aaa | cag | ttt | gtg | gaa | caa | tat | ggt | 528 |
| --- | --- | --- | --- | --- | --- | --- | --- | --- | --- | --- | --- | --- | --- | --- | --- | --- |
| Pro | Ile | Glu | Asp | Ile | Glu | Gln | Ala | Lys | Gln | Phe | Val | Glu | Gln | Tyr | Gly |     |

| | | | | | | | | | | | | | | | | |
|---|---|---|---|---|---|---|---|---|---|---|---|---|---|---|---|---|
| | | 165 | | | | | 170 | | | | | 175 | | | | |
| tat | cct | gtc | att | ata | aag | gct | gca | ttt | ggt | ggt | ggt | ggt | aga | ggt | atg | 576 |
| Tyr | Pro | Val | Ile | Ile | Lys | Ala | Ala | Phe | Gly | Gly | Gly | Gly | Arg | Gly | Met | |
| | | | 180 | | | | | 185 | | | | | 190 | | | |
| aga | gtt | gtt | aga | gaa | ggt | gat | gat | ata | gtt | gat | gct | ttc | caa | aga | gcg | 624 |
| Arg | Val | Val | Arg | Glu | Gly | Asp | Asp | Ile | Val | Asp | Ala | Phe | Gln | Arg | Ala | |
| | | 195 | | | | | 200 | | | | | 205 | | | | |
| tca | tct | gaa | gca | aag | tct | gcc | ttt | ggt | aat | ggt | act | tgt | ttt | att | gaa | 672 |
| Ser | Ser | Glu | Ala | Lys | Ser | Ala | Phe | Gly | Asn | Gly | Thr | Cys | Phe | Ile | Glu | |
| 210 | | | | | 215 | | | | | 220 | | | | | | |
| aga | ttt | ttg | gat | aag | cca | aaa | cat | att | gag | gtt | caa | tta | ttg | gct | gat | 720 |
| Arg | Phe | Leu | Asp | Lys | Pro | Lys | His | Ile | Glu | Val | Gln | Leu | Leu | Ala | Asp | |
| 225 | | | | | 230 | | | | | 235 | | | | | 240 | |
| aat | tat | ggt | aac | aca | atc | cat | ctc | ttt | gaa | aga | gat | tgt | tct | gtt | caa | 768 |
| Asn | Tyr | Gly | Asn | Thr | Ile | His | Leu | Phe | Glu | Arg | Asp | Cys | Ser | Val | Gln | |
| | | | | 245 | | | | | 250 | | | | | 255 | | |
| aga | aga | cat | caa | aag | gtt | gtt | gaa | att | gca | cct | gcc | aaa | act | tta | cct | 816 |
| Arg | Arg | His | Gln | Lys | Val | Val | Glu | Ile | Ala | Pro | Ala | Lys | Thr | Leu | Pro | |
| | | | 260 | | | | | 265 | | | | | 270 | | | |
| gtt | gaa | gtt | aga | aat | gct | ata | tta | aag | gat | gct | gta | acg | tta | gct | aaa | 864 |
| Val | Glu | Val | Arg | Asn | Ala | Ile | Leu | Lys | Asp | Ala | Val | Thr | Leu | Ala | Lys | |
| | | 275 | | | | | 280 | | | | | 285 | | | | |
| acc | gct | aac | tat | aga | aat | gct | ggt | act | gca | gaa | ttt | tta | gtt | gat | tcc | 912 |
| Thr | Ala | Asn | Tyr | Arg | Asn | Ala | Gly | Thr | Ala | Glu | Phe | Leu | Val | Asp | Ser | |
| | 290 | | | | | 295 | | | | | 300 | | | | | |
| caa | aac | aga | cat | tat | ttt | att | gaa | att | aat | cca | aga | att | caa | gtt | gaa | 960 |
| Gln | Asn | Arg | His | Tyr | Phe | Ile | Glu | Ile | Asn | Pro | Arg | Ile | Gln | Val | Glu | |
| 305 | | | | | 310 | | | | | 315 | | | | | 320 | |
| cat | aca | att | act | gaa | gaa | atc | acg | ggt | gtt | gat | att | gtt | gcc | gct | caa | 1008 |
| His | Thr | Ile | Thr | Glu | Glu | Ile | Thr | Gly | Val | Asp | Ile | Val | Ala | Ala | Gln | |
| | | | | 325 | | | | | 330 | | | | | 335 | | |
| att | caa | att | gct | gca | ggt | gca | tca | ttg | gaa | caa | ttg | ggt | cta | tta | caa | 1056 |
| Ile | Gln | Ile | Ala | Ala | Gly | Ala | Ser | Leu | Glu | Gln | Leu | Gly | Leu | Leu | Gln | |
| | | | 340 | | | | | 345 | | | | | 350 | | | |
| aac | aaa | att | aca | act | aga | ggt | ttt | gca | att | caa | tgt | aga | att | aca | acc | 1104 |
| Asn | Lys | Ile | Thr | Thr | Arg | Gly | Phe | Ala | Ile | Gln | Cys | Arg | Ile | Thr | Thr | |
| | | 355 | | | | | 360 | | | | | 365 | | | | |
| gag | gat | cct | gct | aag | aat | ttt | gcc | cca | gat | aca | ggt | aaa | att | gag | gtt | 1152 |
| Glu | Asp | Pro | Ala | Lys | Asn | Phe | Ala | Pro | Asp | Thr | Gly | Lys | Ile | Glu | Val | |
| | 370 | | | | | 375 | | | | | 380 | | | | | |
| tat | aga | tct | gca | ggt | ggt | aac | ggt | gtc | aga | tta | gat | ggt | ggt | aat | ggg | 1200 |
| Tyr | Arg | Ser | Ala | Gly | Gly | Asn | Gly | Val | Arg | Leu | Asp | Gly | Gly | Asn | Gly | |
| 385 | | | | | 390 | | | | | 395 | | | | | 400 | |
| ttt | gcc | ggt | gct | gtt | ata | tct | cct | cat | tat | gac | tcg | atg | ttg | gtt | aaa | 1248 |
| Phe | Ala | Gly | Ala | Val | Ile | Ser | Pro | His | Tyr | Asp | Ser | Met | Leu | Val | Lys | |
| | | | | 405 | | | | | 410 | | | | | 415 | | |
| tgt | tca | aca | tct | ggt | tct | aac | tat | gaa | att | gcc | aga | aga | aag | atg | att | 1296 |
| Cys | Ser | Thr | Ser | Gly | Ser | Asn | Tyr | Glu | Ile | Ala | Arg | Arg | Lys | Met | Ile | |
| | | | 420 | | | | | 425 | | | | | 430 | | | |
| aga | gct | tta | gtt | gaa | ttt | aga | atc | aga | ggt | gtc | aag | acc | aat | att | cct | 1344 |
| Arg | Ala | Leu | Val | Glu | Phe | Arg | Ile | Arg | Gly | Val | Lys | Thr | Asn | Ile | Pro | |
| | | 435 | | | | | 440 | | | | | 445 | | | | |
| ttc | tta | ttg | gca | ttg | cta | act | cat | cca | gtt | ttc | att | tcg | ggt | gat | tgt | 1392 |
| Phe | Leu | Leu | Ala | Leu | Leu | Thr | His | Pro | Val | Phe | Ile | Ser | Gly | Asp | Cys | |
| | 450 | | | | | 455 | | | | | 460 | | | | | |
| tgg | aca | act | ttt | att | gat | gat | acc | cct | tcg | tta | ttc | gaa | atg | gtt | tct | 1440 |
| Trp | Thr | Thr | Phe | Ile | Asp | Asp | Thr | Pro | Ser | Leu | Phe | Glu | Met | Val | Ser | |
| 465 | | | | | 470 | | | | | 475 | | | | | 480 | |
| tca | aag | aat | aga | gcc | caa | aaa | tta | ttg | gca | tat | att | ggt | gac | ttg | tgt | 1488 |

```
                Ser Lys Asn Arg Ala Gln Lys Leu Leu Ala Tyr Ile Gly Asp Leu Cys
                            485                 490                 495 gtc aat ggt tct tca att aaa ggt caa att ggt ttc cct aaa ttg aac            1536
Val Asn Gly Ser Ser Ile Lys Gly Gln Ile Gly Phe Pro Lys Leu Asn
        500                 505                 510 aag gaa gca gaa atc cca gat ttg ttg gat cca aat gat gag gtt att            1584
Lys Glu Ala Glu Ile Pro Asp Leu Leu Asp Pro Asn Asp Glu Val Ile
            515                 520                 525 gat gtt tct aaa cct tct acc aat ggt cta aga ccg tat cta tta aag            1632
Asp Val Ser Lys Pro Ser Thr Asn Gly Leu Arg Pro Tyr Leu Leu Lys
        530                 535                 540 tat gga cca gat gcg ttt tcc aaa aaa gtt cgt gaa ttc gat ggt tgt            1680
Tyr Gly Pro Asp Ala Phe Ser Lys Lys Val Arg Glu Phe Asp Gly Cys
545                 550                 555                 560 atg att atg gat acc acc tgg aga gat gca cat caa tca tta ttg gct            1728
Met Ile Met Asp Thr Thr Trp Arg Asp Ala His Gln Ser Leu Leu Ala
                565                 570                 575 aca aga gtt aga act att gat tta ctg aga att gct cca acg act agt            1776
Thr Arg Val Arg Thr Ile Asp Leu Leu Arg Ile Ala Pro Thr Thr Ser
            580                 585                 590 cat gcc tta caa aat gca ttt gca tta gaa tgt tgg ggt ggc gca aca            1824
His Ala Leu Gln Asn Ala Phe Ala Leu Glu Cys Trp Gly Gly Ala Thr
        595                 600                 605 ttt gat gtt gcg atg agg ttc ctc tat gaa gat cct tgg gag aga tta            1872
Phe Asp Val Ala Met Arg Phe Leu Tyr Glu Asp Pro Trp Glu Arg Leu
610                 615                 620 aga caa ctt aga aag gca gtt cca aat att cct ttc caa atg tta ttg            1920
Arg Gln Leu Arg Lys Ala Val Pro Asn Ile Pro Phe Gln Met Leu Leu
625                 630                 635                 640 aga ggt gct aat ggt gtt gct tat tcg tca tta cct gat aat gca att            1968
Arg Gly Ala Asn Gly Val Ala Tyr Ser Ser Leu Pro Asp Asn Ala Ile
                645                 650                 655 gat cat ttt gtt aag caa gca aag gat aat ggt gtt gat att ttc aga            2016
Asp His Phe Val Lys Gln Ala Lys Asp Asn Gly Val Asp Ile Phe Arg
            660                 665                 670 gtc ttt gat gct ttg aac gat ttg gaa caa ttg aag gtt ggt gtt gat            2064
Val Phe Asp Ala Leu Asn Asp Leu Glu Gln Leu Lys Val Gly Val Asp
        675                 680                 685 gct gtc aag aaa gcc gga ggt gtt gtt gaa gct aca gtt tgt tac tca            2112
Ala Val Lys Lys Ala Gly Gly Val Val Glu Ala Thr Val Cys Tyr Ser
    690                 695                 700 ggt gat atg tta att cca ggt aaa aag tat aac ttg gat tat tat tta            2160
Gly Asp Met Leu Ile Pro Gly Lys Lys Tyr Asn Leu Asp Tyr Tyr Leu
705                 710                 715                 720 gag act gtt gga aag att gtg gaa atg ggt acc cat att tta ggt att            2208
Glu Thr Val Gly Lys Ile Val Glu Met Gly Thr His Ile Leu Gly Ile
                725                 730                 735 aag gat atg gct ggc acg tta aag cca aag gct gct aag ttg ttg att            2256
Lys Asp Met Ala Gly Thr Leu Lys Pro Lys Ala Ala Lys Leu Leu Ile
            740                 745                 750 ggc tcg atc aga tca aaa tac cct gac ttg gtt atc cat gtc cat acc            2304
Gly Ser Ile Arg Ser Lys Tyr Pro Asp Leu Val Ile His Val His Thr
        755                 760                 765 cat gac tct gct ggt acc ggt att tca act tat gtt gca tgc gca ttg            2352
His Asp Ser Ala Gly Thr Gly Ile Ser Thr Tyr Val Ala Cys Ala Leu
    770                 775                 780 gca ggt gcc gac att gtc gat tgt gca atc aat tcg atg tct ggt tta            2400
Ala Gly Ala Asp Ile Val Asp Cys Ala Ile Asn Ser Met Ser Gly Leu
785                 790                 795                 800
```

```
acc tct caa cct tca atg agt gct ttt att gct gct tta gat ggt gat    2448
Thr Ser Gln Pro Ser Met Ser Ala Phe Ile Ala Ala Leu Asp Gly Asp
                805                 810                 815 atc gaa act ggt gtt cca gaa cat ttt gca aga caa tta gat gca tac    2496
Ile Glu Thr Gly Val Pro Glu His Phe Ala Arg Gln Leu Asp Ala Tyr
    820                 825                 830 tgg gca gaa atg aga ttg tta tac tca tgt ttc gaa gcc gac ttg aag    2544
Trp Ala Glu Met Arg Leu Leu Tyr Ser Cys Phe Glu Ala Asp Leu Lys
835                 840                 845 gga cca gac cca gaa gtt tat aaa cat gaa att cca ggt gga cag ttg    2592
Gly Pro Asp Pro Glu Val Tyr Lys His Glu Ile Pro Gly Gly Gln Leu
    850                 855                 860 act aac cta atc ttc caa gcc caa caa gtt ggt ttg ggt gaa caa tgg    2640
Thr Asn Leu Ile Phe Gln Ala Gln Gln Val Gly Leu Gly Glu Gln Trp
865                 870                 875                 880 gaa gaa act aag aag aag tat gaa gat gct aac atg ttg ttg ggt gat    2688
Glu Glu Thr Lys Lys Lys Tyr Glu Asp Ala Asn Met Leu Leu Gly Asp
                885                 890                 895 att gtc aag gtt acc cca acc tcc aag gtt gtt ggt gat tta gcc caa    2736
Ile Val Lys Val Thr Pro Thr Ser Lys Val Val Gly Asp Leu Ala Gln
        900                 905                 910 ttt atg gtt tct aat aaa tta gaa aaa gaa gat gtt gaa aaa ctt gct    2784
Phe Met Val Ser Asn Lys Leu Glu Lys Glu Asp Val Glu Lys Leu Ala
    915                 920                 925 aat gaa tta gat ttc cca gat tca gtt ctt gat ttc ttt gaa gga tta    2832
Asn Glu Leu Asp Phe Pro Asp Ser Val Leu Asp Phe Phe Glu Gly Leu
930                 935                 940 atg ggt aca cca tat ggt gga ttc cca gag cct ttg aga aca aat gtc    2880
Met Gly Thr Pro Tyr Gly Gly Phe Pro Glu Pro Leu Arg Thr Asn Val
945                 950                 955                 960 att tcc ggc aag aga aga aaa tta aag ggt aga cca ggt tta gaa tta    2928
Ile Ser Gly Lys Arg Arg Lys Leu Lys Gly Arg Pro Gly Leu Glu Leu
                965                 970                 975 gaa cct ttc aac ctc gag gaa atc aga gaa aat ttg gtt tcc aga ttt    2976
Glu Pro Phe Asn Leu Glu Glu Ile Arg Glu Asn Leu Val Ser Arg Phe
        980                 985                 990 ggt cca ggt att act gaa tgt gat gtt gca tct tat aac atg tat cca    3024
Gly Pro Gly Ile Thr Glu Cys Asp Val Ala Ser Tyr Asn Met Tyr Pro
    995                 1000                1005 aag gtt tac gag caa tat cgt aag gtg gtt gaa aaa tat ggt gat       3069
Lys Val Tyr Glu Gln Tyr Arg Lys Val Val Glu Lys Tyr Gly Asp
    1010                1015                1020 tta tct gtt tta cca aca aaa gca ttt ttg gct cct cca act att       3114
Leu Ser Val Leu Pro Thr Lys Ala Phe Leu Ala Pro Pro Thr Ile
    1025                1030                1035 ggt gaa gaa gtt cat gtg gaa att gag caa ggt aag act ttg att       3159
Gly Glu Glu Val His Val Glu Ile Glu Gln Gly Lys Thr Leu Ile
    1040                1045                1050 att aag tta tta gcc att tct gac ttg tct aaa tct cat ggt aca       3204
Ile Lys Leu Leu Ala Ile Ser Asp Leu Ser Lys Ser His Gly Thr
    1055                1060                1065 aga gaa gta tac ttt gaa ttg aat ggt gaa atg aga aag gtt aca       3249
Arg Glu Val Tyr Phe Glu Leu Asn Gly Glu Met Arg Lys Val Thr
    1070                1075                1080 att gaa gat aaa aca gct gca att gag act gtt aca aga gca aag       3294
Ile Glu Asp Lys Thr Ala Ala Ile Glu Thr Val Thr Arg Ala Lys
    1085                1090                1095 gct gac gga cac aat cca aat gaa gtt ggt gcg cca atg gct ggt       3339
Ala Asp Gly His Asn Pro Asn Glu Val Gly Ala Pro Met Ala Gly
    1100                1105                1110
```

```
gtc gtt gtt gaa gtt aga gtg aag cat gga aca gaa gtt aag aag    3384
Val Val Val Glu Val Arg Val Lys His Gly Thr Glu Val Lys Lys
        1115                1120                1125 ggt gat cca tta gcc gtt ttg agt gca atg aaa atg gaa atg gtt    3429
Gly Asp Pro Leu Ala Val Leu Ser Ala Met Lys Met Glu Met Val
1130                1135                1140 att tct gct cct gtt agt ggt agg gtc ggt gaa gtt ttt gtc aac    3474
Ile Ser Ala Pro Val Ser Gly Arg Val Gly Glu Val Phe Val Asn
    1145                1150                1155 gaa ggc gat tcc gtt gat atg ggt gat ttg ctt gtg aaa att gcc    3519
Glu Gly Asp Ser Val Asp Met Gly Asp Leu Leu Val Lys Ile Ala
1160                1165                1170 aaa gat gaa gcg cca gca gct taa                                 3543
Lys Asp Glu Ala Pro Ala Ala
    1175                1180

<210> SEQ ID NO 8
<211> LENGTH: 1180
<212> TYPE: PRT
<213> ORGANISM: Issatchenkia orientalis

<400> SEQUENCE: 8

Met Ser Thr Val Glu Asp His Ser Ser Leu His Lys Leu Arg Lys Glu
1               5                   10                  15

Ser Glu Ile Leu Ser Asn Ala Asn Lys Ile Leu Val Ala Asn Arg Gly
            20                  25                  30

Glu Ile Pro Ile Arg Ile Phe Arg Ser Ala His Glu Leu Ser Met His
        35                  40                  45

Thr Val Ala Ile Tyr Ser His Glu Asp Arg Leu Ser Met His Arg Leu
    50                  55                  60

Lys Ala Asp Glu Ala Tyr Ala Ile Gly Lys Thr Gly Gln Tyr Ser Pro
65                  70                  75                  80

Val Gln Ala Tyr Leu Gln Ile Asp Glu Ile Ile Lys Ile Ala Lys Glu
                85                  90                  95

His Asp Val Ser Met Ile His Pro Gly Tyr Gly Phe Leu Ser Glu Asn
            100                 105                 110

Ser Glu Phe Ala Lys Lys Val Glu Glu Ser Gly Met Ile Trp Val Gly
        115                 120                 125

Pro Pro Ala Glu Val Ile Asp Ser Val Gly Asp Lys Val Ser Ala Arg
    130                 135                 140

Asn Leu Ala Ile Lys Cys Asp Val Pro Val Pro Gly Thr Asp Gly
145                 150                 155                 160

Pro Ile Glu Asp Ile Glu Gln Ala Lys Gln Phe Val Glu Gln Tyr Gly
                165                 170                 175

Tyr Pro Val Ile Ile Lys Ala Ala Phe Gly Gly Gly Gly Arg Gly Met
            180                 185                 190

Arg Val Val Arg Glu Gly Asp Asp Ile Val Asp Ala Phe Gln Arg Ala
        195                 200                 205

Ser Ser Glu Ala Lys Ser Ala Phe Gly Asn Gly Thr Cys Phe Ile Glu
    210                 215                 220

Arg Phe Leu Asp Lys Pro Lys His Ile Glu Val Gln Leu Leu Ala Asp
225                 230                 235                 240

Asn Tyr Gly Asn Thr Ile His Leu Phe Glu Arg Asp Cys Ser Val Gln
                245                 250                 255

Arg Arg His Gln Lys Val Val Glu Ile Ala Pro Ala Lys Thr Leu Pro
            260                 265                 270
```

```
Val Glu Val Arg Asn Ala Ile Leu Lys Asp Ala Val Thr Leu Ala Lys
            275                 280                 285

Thr Ala Asn Tyr Arg Asn Ala Gly Thr Ala Glu Phe Leu Val Asp Ser
        290                 295                 300

Gln Asn Arg His Tyr Phe Ile Glu Ile Asn Pro Arg Ile Gln Val Glu
305                 310                 315                 320

His Thr Ile Thr Glu Glu Ile Thr Gly Val Asp Ile Val Ala Ala Gln
                325                 330                 335

Ile Gln Ile Ala Ala Gly Ala Ser Leu Glu Gln Leu Gly Leu Leu Gln
                340                 345                 350

Asn Lys Ile Thr Thr Arg Gly Phe Ala Ile Gln Cys Arg Ile Thr Thr
            355                 360                 365

Glu Asp Pro Ala Lys Asn Phe Ala Pro Asp Thr Gly Lys Ile Glu Val
        370                 375                 380

Tyr Arg Ser Ala Gly Gly Asn Gly Val Arg Leu Asp Gly Gly Asn Gly
385                 390                 395                 400

Phe Ala Gly Ala Val Ile Ser Pro His Tyr Asp Ser Met Leu Val Lys
                405                 410                 415

Cys Ser Thr Ser Gly Ser Asn Tyr Glu Ile Ala Arg Arg Lys Met Ile
                420                 425                 430

Arg Ala Leu Val Glu Phe Arg Ile Arg Gly Val Lys Thr Asn Ile Pro
            435                 440                 445

Phe Leu Leu Ala Leu Leu Thr His Pro Val Phe Ile Ser Gly Asp Cys
        450                 455                 460

Trp Thr Thr Phe Ile Asp Thr Pro Ser Leu Phe Glu Met Val Ser
465                 470                 475                 480

Ser Lys Asn Arg Ala Gln Lys Leu Leu Ala Tyr Ile Gly Asp Leu Cys
                485                 490                 495

Val Asn Gly Ser Ser Ile Lys Gly Gln Ile Gly Phe Pro Lys Leu Asn
            500                 505                 510

Lys Glu Ala Glu Ile Pro Asp Leu Leu Asp Pro Asn Asp Glu Val Ile
        515                 520                 525

Asp Val Ser Lys Pro Ser Thr Asn Gly Leu Arg Pro Tyr Leu Leu Lys
530                 535                 540

Tyr Gly Pro Asp Ala Phe Ser Lys Lys Val Arg Glu Phe Asp Gly Cys
545                 550                 555                 560

Met Ile Met Asp Thr Thr Trp Arg Asp Ala His Gln Ser Leu Leu Ala
                565                 570                 575

Thr Arg Val Arg Thr Ile Asp Leu Leu Arg Ile Ala Pro Thr Thr Ser
            580                 585                 590

His Ala Leu Gln Asn Ala Phe Ala Leu Glu Cys Trp Gly Gly Ala Thr
        595                 600                 605

Phe Asp Val Ala Met Arg Phe Leu Tyr Glu Asp Pro Trp Glu Arg Leu
        610                 615                 620

Arg Gln Leu Arg Lys Ala Val Pro Asn Ile Pro Phe Gln Met Leu Leu
625                 630                 635                 640

Arg Gly Ala Asn Gly Val Ala Tyr Ser Ser Leu Pro Asp Asn Ala Ile
                645                 650                 655

Asp His Phe Val Lys Gln Ala Lys Asp Asn Gly Val Asp Ile Phe Arg
            660                 665                 670

Val Phe Asp Ala Leu Asn Asp Leu Glu Gln Leu Lys Val Gly Val Asp
        675                 680                 685
```

-continued

Ala Val Lys Lys Ala Gly Gly Val Val Glu Ala Thr Val Cys Tyr Ser
690             695             700

Gly Asp Met Leu Ile Pro Gly Lys Lys Tyr Asn Leu Asp Tyr Tyr Leu
705             710             715             720

Glu Thr Val Gly Lys Ile Val Glu Met Gly Thr His Ile Leu Gly Ile
            725             730             735

Lys Asp Met Ala Gly Thr Leu Lys Pro Lys Ala Ala Lys Leu Leu Ile
            740             745             750

Gly Ser Ile Arg Ser Lys Tyr Pro Asp Leu Val Ile His Val His Thr
            755             760             765

His Asp Ser Ala Gly Thr Gly Ile Ser Thr Tyr Val Ala Cys Ala Leu
770             775             780

Ala Gly Ala Asp Ile Val Asp Cys Ala Ile Asn Ser Met Ser Gly Leu
785             790             795             800

Thr Ser Gln Pro Ser Met Ser Ala Phe Ile Ala Ala Leu Asp Gly Asp
            805             810             815

Ile Glu Thr Gly Val Pro Glu His Phe Ala Arg Gln Leu Asp Ala Tyr
            820             825             830

Trp Ala Glu Met Arg Leu Leu Tyr Ser Cys Phe Glu Ala Asp Leu Lys
835             840             845

Gly Pro Asp Pro Glu Val Tyr Lys His Glu Ile Pro Gly Gly Gln Leu
850             855             860

Thr Asn Leu Ile Phe Gln Ala Gln Gln Val Gly Leu Gly Glu Gln Trp
865             870             875             880

Glu Glu Thr Lys Lys Lys Tyr Glu Asp Ala Asn Met Leu Leu Gly Asp
            885             890             895

Ile Val Lys Val Thr Pro Thr Ser Lys Val Val Gly Asp Leu Ala Gln
            900             905             910

Phe Met Val Ser Asn Lys Leu Glu Lys Glu Asp Val Glu Lys Leu Ala
            915             920             925

Asn Glu Leu Asp Phe Pro Asp Ser Val Leu Asp Phe Phe Glu Gly Leu
930             935             940

Met Gly Thr Pro Tyr Gly Gly Phe Pro Glu Pro Leu Arg Thr Asn Val
945             950             955             960

Ile Ser Gly Lys Arg Arg Lys Leu Lys Gly Arg Pro Gly Leu Glu Leu
            965             970             975

Glu Pro Phe Asn Leu Glu Glu Ile Arg Glu Asn Leu Val Ser Arg Phe
            980             985             990

Gly Pro Gly Ile Thr Glu Cys Asp Val Ala Ser Tyr Asn Met Tyr Pro
            995             1000             1005

Lys Val Tyr Glu Gln Tyr Arg Lys Val Val Glu Lys Tyr Gly Asp
    1010             1015             1020

Leu Ser Val Leu Pro Thr Lys Ala Phe Leu Ala Pro Pro Thr Ile
    1025             1030             1035

Gly Glu Glu Val His Val Glu Ile Glu Gln Gly Lys Thr Leu Ile
    1040             1045             1050

Ile Lys Leu Leu Ala Ile Ser Asp Leu Ser Lys Ser His Gly Thr
    1055             1060             1065

Arg Glu Val Tyr Phe Glu Leu Asn Gly Glu Met Arg Lys Val Thr
    1070             1075             1080

Ile Glu Asp Lys Thr Ala Ala Ile Glu Thr Val Thr Arg Ala Lys
    1085             1090             1095

Ala Asp Gly His Asn Pro Asn Glu Val Gly Ala Pro Met Ala Gly

-continued

```
              1100               1105               1110
Val Val Val Glu Val Arg Val Lys His Gly Thr Glu Val Lys Lys
          1115               1120               1125

Gly Asp Pro Leu Ala Val Leu Ser Ala Met Lys Met Glu Met Val
          1130               1135               1140

Ile Ser Ala Pro Val Ser Gly Arg Val Gly Glu Val Phe Val Asn
          1145               1150               1155

Glu Gly Asp Ser Val Asp Met Gly Asp Leu Leu Val Lys Ile Ala
          1160               1165               1170

Lys Asp Glu Ala Pro Ala Ala
          1175               1180

<210> SEQ ID NO 9
<211> LENGTH: 3537
<212> TYPE: DNA
<213> ORGANISM: Saccharomyces cerevisiae
<220> FEATURE:
<221> NAME/KEY: CDS
<222> LOCATION: (1)..(3537)

<400> SEQUENCE: 9 atg tcg caa aga aaa ttc gcc ggc ttg aga gat aac ttc aat ctc ttg     48
Met Ser Gln Arg Lys Phe Ala Gly Leu Arg Asp Asn Phe Asn Leu Leu
1               5                   10                  15 ggt gaa aag aac aaa ata ttg gtg gct aat aga gga gaa att cca atc     96
Gly Glu Lys Asn Lys Ile Leu Val Ala Asn Arg Gly Glu Ile Pro Ile
                20                  25                  30 aga att ttt cgt acc gct cat gaa ctg tct atg cag acg gta gct ata    144
Arg Ile Phe Arg Thr Ala His Glu Leu Ser Met Gln Thr Val Ala Ile
            35                  40                  45 tat tct cat gaa gat cgt ctt tca acg cac aaa caa aag gct gac gaa    192
Tyr Ser His Glu Asp Arg Leu Ser Thr His Lys Gln Lys Ala Asp Glu
        50                  55                  60 gca tac gtc ata ggt gaa gta ggc caa tat acc ccc gtc ggc gct tat    240
Ala Tyr Val Ile Gly Glu Val Gly Gln Tyr Thr Pro Val Gly Ala Tyr
    65                  70                  75                  80 ttg gcc att gac gaa atc att tcc att gcc caa aaa cac cag gta gat    288
Leu Ala Ile Asp Glu Ile Ile Ser Ile Ala Gln Lys His Gln Val Asp
                85                  90                  95 ttc atc cat cca ggt tat ggg ttc ttg tct gaa aat tcg gaa ttt gcc    336
Phe Ile His Pro Gly Tyr Gly Phe Leu Ser Glu Asn Ser Glu Phe Ala
                100                 105                 110 gac aaa gta gtg aag gcc ggt atc act tgg att ggc cct cca gct gaa    384
Asp Lys Val Val Lys Ala Gly Ile Thr Trp Ile Gly Pro Pro Ala Glu
            115                 120                 125 gtt att gac tcc gtg ggt gat aag gtc tca gct aga aac ctg gca gca    432
Val Ile Asp Ser Val Gly Asp Lys Val Ser Ala Arg Asn Leu Ala Ala
        130                 135                 140 aaa gct aat gtg ccc acc gtt cct ggt aca cca ggt cct ata gaa act    480
Lys Ala Asn Val Pro Thr Val Pro Gly Thr Pro Gly Pro Ile Glu Thr
    145                 150                 155                 160 gta gag gaa gca ctt gac ttc gtc aat gaa tac ggc tac ccg gtg atc    528
Val Glu Glu Ala Leu Asp Phe Val Asn Glu Tyr Gly Tyr Pro Val Ile
                165                 170                 175 att aag gcc gcc ttt ggt ggt ggt gga aga ggt atg aga gtc gtt aga    576
Ile Lys Ala Ala Phe Gly Gly Gly Gly Arg Gly Met Arg Val Val Arg
                180                 185                 190 gaa ggt gac gac gtg gca gat gcc ttt caa cgt gct acc tcc gaa gcc    624
Glu Gly Asp Asp Val Ala Asp Ala Phe Gln Arg Ala Thr Ser Glu Ala
            195                 200                 205
```

| | | | | | | | | | | | | | | | | |
|---|---|---|---|---|---|---|---|---|---|---|---|---|---|---|---|---|
| cgt | act | gcc | ttc | ggt | aat | ggt | acc | tgc | ttt | gtg | gaa | aga | ttc | ttg | gac | 672 |
| Arg | Thr | Ala | Phe | Gly | Asn | Gly | Thr | Cys | Phe | Val | Glu | Arg | Phe | Leu | Asp | |
| 210 | | | | 215 | | | | 220 | | | | | | | | |
| aag | cca | aag | cat | att | gaa | gtt | caa | ttg | ttg | gcc | gat | aac | cac | gga | aac | 720 |
| Lys | Pro | Lys | His | Ile | Glu | Val | Gln | Leu | Leu | Ala | Asp | Asn | His | Gly | Asn | |
| 225 | | | | 230 | | | | 235 | | | | 240 | | | | |
| gtg | gtt | cat | ctt | ttc | gaa | aga | gac | tgt | tcc | gtg | cag | aga | aga | cac | caa | 768 |
| Val | Val | His | Leu | Phe | Glu | Arg | Asp | Cys | Ser | Val | Gln | Arg | Arg | His | Gln | |
| | | | | 245 | | | | 250 | | | | 255 | | | | |
| aag | gtt | gtc | gaa | gtg | gcc | cca | gca | aag | act | tta | ccc | cgt | gaa | gtc | cgt | 816 |
| Lys | Val | Val | Glu | Val | Ala | Pro | Ala | Lys | Thr | Leu | Pro | Arg | Glu | Val | Arg | |
| | | | 260 | | | | | 265 | | | | 270 | | | | |
| gac | gcc | att | ttg | aca | gat | gca | gtt | aaa | ttg | gcc | aaa | gag | tgt | ggc | tac | 864 |
| Asp | Ala | Ile | Leu | Thr | Asp | Ala | Val | Lys | Leu | Ala | Lys | Glu | Cys | Gly | Tyr | |
| | | | 275 | | | | 280 | | | | 285 | | | | | |
| aga | aat | gcg | ggt | act | gct | gaa | ttc | ttg | gtt | gat | aac | caa | aat | aga | cac | 912 |
| Arg | Asn | Ala | Gly | Thr | Ala | Glu | Phe | Leu | Val | Asp | Asn | Gln | Asn | Arg | His | |
| | 290 | | | | 295 | | | | 300 | | | | | | | |
| tat | ttc | att | gaa | att | aat | cca | aga | atc | caa | gtg | gaa | cat | acc | atc | aca | 960 |
| Tyr | Phe | Ile | Glu | Ile | Asn | Pro | Arg | Ile | Gln | Val | Glu | His | Thr | Ile | Thr | |
| 305 | | | | 310 | | | | 315 | | | | 320 | | | | |
| gaa | gaa | att | acc | ggt | ata | gat | att | gtg | gcg | gct | cag | atc | caa | att | gcg | 1008 |
| Glu | Glu | Ile | Thr | Gly | Ile | Asp | Ile | Val | Ala | Ala | Gln | Ile | Gln | Ile | Ala | |
| | | | | 325 | | | | 330 | | | | | 335 | | | |
| gca | ggt | gcc | tct | cta | ccc | cag | ctg | ggc | cta | ttc | cag | gac | aaa | att | acg | 1056 |
| Ala | Gly | Ala | Ser | Leu | Pro | Gln | Leu | Gly | Leu | Phe | Gln | Asp | Lys | Ile | Thr | |
| | | | 340 | | | | 345 | | | | | 350 | | | | |
| act | cgt | ggc | ttt | gcc | att | cag | tgc | cgt | att | acc | acg | gaa | gac | cct | gct | 1104 |
| Thr | Arg | Gly | Phe | Ala | Ile | Gln | Cys | Arg | Ile | Thr | Thr | Glu | Asp | Pro | Ala | |
| | | 355 | | | | 360 | | | | | 365 | | | | | |
| aag | aac | ttc | caa | cca | gat | acc | ggt | aga | ata | gaa | gtg | tac | cgt | tct | gca | 1152 |
| Lys | Asn | Phe | Gln | Pro | Asp | Thr | Gly | Arg | Ile | Glu | Val | Tyr | Arg | Ser | Ala | |
| | 370 | | | | 375 | | | | | 380 | | | | | | |
| ggt | ggt | aat | ggt | gtt | aga | ctg | gat | ggt | ggt | aac | gcc | tat | gca | gga | aca | 1200 |
| Gly | Gly | Asn | Gly | Val | Arg | Leu | Asp | Gly | Gly | Asn | Ala | Tyr | Ala | Gly | Thr | |
| 385 | | | | 390 | | | | | 395 | | | | | 400 | | |
| ata | atc | tca | cct | cat | tac | gac | tca | atg | ctg | gtc | aaa | tgc | tca | tgc | tcc | 1248 |
| Ile | Ile | Ser | Pro | His | Tyr | Asp | Ser | Met | Leu | Val | Lys | Cys | Ser | Cys | Ser | |
| | | | | 405 | | | | | 410 | | | | | 415 | | |
| ggt | tcc | acc | tac | gaa | atc | gtt | cgt | aga | aaa | atg | att | cgt | gca | tta | atc | 1296 |
| Gly | Ser | Thr | Tyr | Glu | Ile | Val | Arg | Arg | Lys | Met | Ile | Arg | Ala | Leu | Ile | |
| | | | 420 | | | | 425 | | | | | 430 | | | | |
| gag | ttc | aga | att | aga | ggt | gtc | aag | acc | aac | att | ccc | ttc | cta | ttg | act | 1344 |
| Glu | Phe | Arg | Ile | Arg | Gly | Val | Lys | Thr | Asn | Ile | Pro | Phe | Leu | Leu | Thr | |
| | | 435 | | | | 440 | | | | | 445 | | | | | |
| ctt | ttg | acc | aat | cca | gta | ttt | att | gag | ggt | aca | tac | tgg | acg | act | ttt | 1392 |
| Leu | Leu | Thr | Asn | Pro | Val | Phe | Ile | Glu | Gly | Thr | Tyr | Trp | Thr | Thr | Phe | |
| | 450 | | | | 455 | | | | | 460 | | | | | | |
| att | gac | gac | acc | cca | caa | ctg | ttc | caa | atg | gtt | tca | tca | caa | aac | aga | 1440 |
| Ile | Asp | Asp | Thr | Pro | Gln | Leu | Phe | Gln | Met | Val | Ser | Ser | Gln | Asn | Arg | |
| 465 | | | | 470 | | | | | 475 | | | | | 480 | | |
| gcc | caa | aaa | ctt | tta | cat | tac | ctc | gcc | gac | gtg | gca | gtc | aat | ggt | tca | 1488 |
| Ala | Gln | Lys | Leu | Leu | His | Tyr | Leu | Ala | Asp | Val | Ala | Val | Asn | Gly | Ser | |
| | | | | 485 | | | | | 490 | | | | | 495 | | |
| tct | atc | aag | ggt | caa | att | ggc | ttg | cca | aaa | tta | aaa | tca | aat | cca | agt | 1536 |
| Ser | Ile | Lys | Gly | Gln | Ile | Gly | Leu | Pro | Lys | Leu | Lys | Ser | Asn | Pro | Ser | |
| | | | 500 | | | | 505 | | | | | 510 | | | | |
| gtc | ccc | cat | ttg | cac | gat | gct | cag | ggc | aat | gtc | atc | aac | gtt | aca | aag | 1584 |
| Val | Pro | His | Leu | His | Asp | Ala | Gln | Gly | Asn | Val | Ile | Asn | Val | Thr | Lys | |

-continued

```
                515                 520                 525
tct gca cca cca tcc gga tgg agg caa gtg cta cta gaa aag ggg cca       1632
Ser Ala Pro Pro Ser Gly Trp Arg Gln Val Leu Leu Glu Lys Gly Pro
    530                 535                 540 gct gaa ttt gcc aga caa gtt aga cag ttc aat ggt act tta ttg atg       1680
Ala Glu Phe Ala Arg Gln Val Arg Gln Phe Asn Gly Thr Leu Leu Met
545                 550                 555                 560 gac acc acc tgg aga gac gct cat caa tct cta ctt gca aca aga gtc       1728
Asp Thr Thr Trp Arg Asp Ala His Gln Ser Leu Leu Ala Thr Arg Val
                565                 570                 575 aga acc cac gat ttg gct aca atc gct cca aca acc gca cat gcc ctt       1776
Arg Thr His Asp Leu Ala Thr Ile Ala Pro Thr Thr Ala His Ala Leu
            580                 585                 590 gca ggt cgt ttc gcc tta gaa tgt tgg ggt ggt gcc aca ttc gat gtt       1824
Ala Gly Arg Phe Ala Leu Glu Cys Trp Gly Gly Ala Thr Phe Asp Val
        595                 600                 605 gca atg aga ttt ttg cat gag gat cca tgg gaa cgt ttg aga aaa tta       1872
Ala Met Arg Phe Leu His Glu Asp Pro Trp Glu Arg Leu Arg Lys Leu
    610                 615                 620 aga tct ctg gtg cct aat att cca ttc caa atg tta ttg cgt ggt gcc       1920
Arg Ser Leu Val Pro Asn Ile Pro Phe Gln Met Leu Leu Arg Gly Ala
625                 630                 635                 640 aat ggt gtg gct tat tct tca ttg cct gac aat gct att gac cat ttc       1968
Asn Gly Val Ala Tyr Ser Ser Leu Pro Asp Asn Ala Ile Asp His Phe
                645                 650                 655 gtc aag caa gcc aag gat aat ggt gtt gat ata ttt aga gtc ttt gat       2016
Val Lys Gln Ala Lys Asp Asn Gly Val Asp Ile Phe Arg Val Phe Asp
            660                 665                 670 gcc tta aat gac ttg gaa caa ttg aag gtc ggt gta gat gct gtg aag       2064
Ala Leu Asn Asp Leu Glu Gln Leu Lys Val Gly Val Asp Ala Val Lys
        675                 680                 685 aag gca ggt ggt gtt gta gaa gcc act gtt tgt ttc tct ggg gat atg       2112
Lys Ala Gly Gly Val Val Glu Ala Thr Val Cys Phe Ser Gly Asp Met
    690                 695                 700 ctt cag cca ggc aag aaa tac aat ttg gat tac tac ttg gaa att gct       2160
Leu Gln Pro Gly Lys Lys Tyr Asn Leu Asp Tyr Tyr Leu Glu Ile Ala
705                 710                 715                 720 gaa aaa att gtc caa atg ggc act cat atc ctg ggt atc aaa gat atg       2208
Glu Lys Ile Val Gln Met Gly Thr His Ile Leu Gly Ile Lys Asp Met
                725                 730                 735 gca ggt acc atg aag cca gca gct gcc aaa cta ctg att gga tct ttg       2256
Ala Gly Thr Met Lys Pro Ala Ala Ala Lys Leu Leu Ile Gly Ser Leu
            740                 745                 750 agg gct aag tac cct gat ctc cca ata cat gtt cac act cac gat tct       2304
Arg Ala Lys Tyr Pro Asp Leu Pro Ile His Val His Thr His Asp Ser
        755                 760                 765 gca ggt act gct gtt gca tca atg act gcg tgt gct ctg gcg ggc gcc       2352
Ala Gly Thr Ala Val Ala Ser Met Thr Ala Cys Ala Leu Ala Gly Ala
    770                 775                 780 gat gtc gtt gat gtt gcc atc aac tca atg tct ggt tta act tca caa       2400
Asp Val Val Asp Val Ala Ile Asn Ser Met Ser Gly Leu Thr Ser Gln
785                 790                 795                 800 cca tca atc aat gct ctg ttg gct tca tta gaa ggt aat att gac act       2448
Pro Ser Ile Asn Ala Leu Leu Ala Ser Leu Glu Gly Asn Ile Asp Thr
                805                 810                 815 ggt att aac gtt gag cat gtc cgt gaa cta gat gca tat tgg gca gag       2496
Gly Ile Asn Val Glu His Val Arg Glu Leu Asp Ala Tyr Trp Ala Glu
            820                 825                 830 atg aga ttg tta tac tct tgt ttc gag gct gac ttg aag ggc cca gat       2544
```

-continued

| | | |
|---|---|---|
| Met Arg Leu Leu Tyr Ser Cys Phe Glu Ala Asp Leu Lys Gly Pro Asp<br>835                840                845 | | |
| cca gaa gtt tat caa cat gaa atc cca ggt ggt caa ttg aca aac ttg<br>Pro Glu Val Tyr Gln His Glu Ile Pro Gly Gly Gln Leu Thr Asn Leu<br>850                855                860 | 2592 | |
| ttg ttt caa gcc caa caa ttg ggt ctt gga gaa caa tgg gcc gaa aca<br>Leu Phe Gln Ala Gln Gln Leu Gly Leu Gly Glu Gln Trp Ala Glu Thr<br>865                870                875                880 | 2640 | |
| aaa aga gct tac aga gaa gcc aat tat tta ttg ggt gat att gtc aaa<br>Lys Arg Ala Tyr Arg Glu Ala Asn Tyr Leu Leu Gly Asp Ile Val Lys<br>                885                890                895 | 2688 | |
| gtt acc cca act tcg aag gtc gtt ggt gat ctg gca caa ttt atg gtc<br>Val Thr Pro Thr Ser Lys Val Val Gly Asp Leu Ala Gln Phe Met Val<br>900                905                910 | 2736 | |
| tcc aat aaa tta act tcc gat gat gtg aga cgc ctg gct aat tct ttg<br>Ser Asn Lys Leu Thr Ser Asp Asp Val Arg Arg Leu Ala Asn Ser Leu<br>                915                920                925 | 2784 | |
| gat ttc cct gac tct gtt atg gat ttc ttc gaa ggc tta atc ggc caa<br>Asp Phe Pro Asp Ser Val Met Asp Phe Phe Glu Gly Leu Ile Gly Gln<br>930                935                940 | 2832 | |
| cca tac ggt ggg ttc cca gaa cca ttt aga tca gac gtt tta agg aac<br>Pro Tyr Gly Gly Phe Pro Glu Pro Phe Arg Ser Asp Val Leu Arg Asn<br>945                950                955                960 | 2880 | |
| aag aga aga aag ttg act tgt cgt cca ggc ctg gaa cta gag cca ttt<br>Lys Arg Arg Lys Leu Thr Cys Arg Pro Gly Leu Glu Leu Glu Pro Phe<br>                965                970                975 | 2928 | |
| gat ctc gaa aaa att aga gaa gac ttg cag aat aga ttt ggt gat gtt<br>Asp Leu Glu Lys Ile Arg Glu Asp Leu Gln Asn Arg Phe Gly Asp Val<br>980                985                990 | 2976 | |
| gat gag tgc gac gtt gct tct tat aac atg tac cca aga gtt tat gaa<br>Asp Glu Cys Asp Val Ala Ser Tyr Asn Met Tyr Pro Arg Val Tyr Glu<br>995                1000                1005 | 3024 | |
| gac ttc caa aag atg aga gaa acg tat ggt gat tta tct gta ttg<br>Asp Phe Gln Lys Met Arg Glu Thr Tyr Gly Asp Leu Ser Val Leu<br>1010                1015                1020 | 3069 | |
| cca aca aga agc ttt ttg tct cca cta gag act gac gaa gaa att<br>Pro Thr Arg Ser Phe Leu Ser Pro Leu Glu Thr Asp Glu Glu Ile<br>1025                1030                1035 | 3114 | |
| gaa gtt gta atc gaa caa ggt aaa acg cta att atc aag cta cag<br>Glu Val Val Ile Glu Gln Gly Lys Thr Leu Ile Ile Lys Leu Gln<br>1040                1045                1050 | 3159 | |
| gct gtg ggt gat ttg aac aaa aag acc ggt gaa aga gaa gtt tac<br>Ala Val Gly Asp Leu Asn Lys Lys Thr Gly Glu Arg Glu Val Tyr<br>1055                1060                1065 | 3204 | |
| ttt gat ttg aat ggt gaa atg aga aaa att cgt gtt gct gac aga<br>Phe Asp Leu Asn Gly Glu Met Arg Lys Ile Arg Val Ala Asp Arg<br>1070                1075                1080 | 3249 | |
| tca caa aaa gtg gaa act gtt act aaa tcc aaa gca gac atg cat<br>Ser Gln Lys Val Glu Thr Val Thr Lys Ser Lys Ala Asp Met His<br>1085                1090                1095 | 3294 | |
| gat cca tta cac att ggt gca cca atg gca ggt gtc att gtt gaa<br>Asp Pro Leu His Ile Gly Ala Pro Met Ala Gly Val Ile Val Glu<br>1100                1105                1110 | 3339 | |
| gtt aaa gtt cat aaa gga tca cta ata aag aag ggc caa cct gta<br>Val Lys Val His Lys Gly Ser Leu Ile Lys Lys Gly Gln Pro Val<br>1115                1120                1125 | 3384 | |
| gcc gta tta agc gcc atg aaa atg gaa atg att ata tct tct cca<br>Ala Val Leu Ser Ala Met Lys Met Glu Met Ile Ile Ser Ser Pro<br>1130                1135                1140 | 3429 | |

| tcc | gat | gga | caa | gtt | aaa | gaa | gtg | ttt | gtc | tct | gat | ggt | gaa | aat | 3474 |
|---|---|---|---|---|---|---|---|---|---|---|---|---|---|---|---|
| Ser | Asp | Gly | Gln | Val | Lys | Glu | Val | Phe | Val | Ser | Asp | Gly | Glu | Asn | |
| 1145 | | | | 1150 | | | | | 1155 | | | | | | |

| gtg | gac | tct | tct | gat | tta | tta | gtt | cta | tta | gaa | gac | caa | gtt | cct | 3519 |
|---|---|---|---|---|---|---|---|---|---|---|---|---|---|---|---|
| Val | Asp | Ser | Ser | Asp | Leu | Leu | Val | Leu | Leu | Glu | Asp | Gln | Val | Pro | |
| 1160 | | | | | 1165 | | | | | 1170 | | | | | |

| gtt | gaa | act | aag | gca | taa | | | | | | | | | | 3537 |
|---|---|---|---|---|---|---|---|---|---|---|---|---|---|---|---|
| Val | Glu | Thr | Lys | Ala | | | | | | | | | | | |
| 1175 | | | | | | | | | | | | | | | |

<210> SEQ ID NO 10
<211> LENGTH: 1178
<212> TYPE: PRT
<213> ORGANISM: Saccharomyces cerevisiae

<400> SEQUENCE: 10

```
Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
        35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Phe Gly Asn Gly Thr Cys Phe Val Glu Arg Phe Leu Asp
    210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
    290                 295                 300

Tyr Phe Ile Glu Ile Asn Pro Arg Ile Gln Val Glu His Thr Ile Thr
305                 310                 315                 320
```

-continued

```
Glu Glu Ile Thr Gly Ile Asp Ile Val Ala Ala Gln Ile Gln Ile Ala
                325                 330                 335
Ala Gly Ala Ser Leu Pro Gln Leu Gly Leu Phe Gln Asp Lys Ile Thr
                340                 345                 350
Thr Arg Gly Phe Ala Ile Gln Cys Arg Ile Thr Thr Glu Asp Pro Ala
                355                 360                 365
Lys Asn Phe Gln Pro Asp Thr Gly Arg Ile Glu Val Tyr Arg Ser Ala
                370                 375                 380
Gly Gly Asn Gly Val Arg Leu Asp Gly Gly Asn Ala Tyr Ala Gly Thr
385                 390                 395                 400
Ile Ile Ser Pro His Tyr Asp Ser Met Leu Val Lys Cys Ser Cys Ser
                405                 410                 415
Gly Ser Thr Tyr Glu Ile Val Arg Arg Lys Met Ile Arg Ala Leu Ile
                420                 425                 430
Glu Phe Arg Ile Arg Gly Val Lys Thr Asn Ile Pro Phe Leu Leu Thr
                435                 440                 445
Leu Leu Thr Asn Pro Val Phe Ile Glu Gly Thr Tyr Trp Thr Thr Phe
                450                 455                 460
Ile Asp Asp Thr Pro Gln Leu Phe Gln Met Val Ser Ser Gln Asn Arg
465                 470                 475                 480
Ala Gln Lys Leu Leu His Tyr Leu Ala Asp Val Ala Val Asn Gly Ser
                485                 490                 495
Ser Ile Lys Gly Gln Ile Gly Leu Pro Lys Leu Lys Ser Asn Pro Ser
                500                 505                 510
Val Pro His Leu His Asp Ala Gln Gly Asn Val Ile Asn Val Thr Lys
                515                 520                 525
Ser Ala Pro Pro Ser Gly Trp Arg Gln Val Leu Leu Glu Lys Gly Pro
                530                 535                 540
Ala Glu Phe Ala Arg Gln Val Arg Gln Phe Asn Gly Thr Leu Leu Met
545                 550                 555                 560
Asp Thr Thr Trp Arg Asp Ala His Gln Ser Leu Leu Ala Thr Arg Val
                565                 570                 575
Arg Thr His Asp Leu Ala Thr Ile Ala Pro Thr Thr Ala His Ala Leu
                580                 585                 590
Ala Gly Arg Phe Ala Leu Glu Cys Trp Gly Gly Ala Thr Phe Asp Val
                595                 600                 605
Ala Met Arg Phe Leu His Glu Asp Pro Trp Glu Arg Leu Arg Lys Leu
                610                 615                 620
Arg Ser Leu Val Pro Asn Ile Pro Phe Gln Met Leu Leu Arg Gly Ala
625                 630                 635                 640
Asn Gly Val Ala Tyr Ser Ser Leu Pro Asp Asn Ala Ile Asp His Phe
                645                 650                 655
Val Lys Gln Ala Lys Asp Asn Gly Val Asp Ile Phe Arg Val Phe Asp
                660                 665                 670
Ala Leu Asn Asp Leu Glu Gln Leu Lys Val Gly Val Asp Ala Val Lys
                675                 680                 685
Lys Ala Gly Gly Val Val Glu Ala Thr Val Cys Phe Ser Gly Asp Met
                690                 695                 700
Leu Gln Pro Gly Lys Lys Tyr Asn Leu Asp Tyr Tyr Leu Glu Ile Ala
705                 710                 715                 720
Glu Lys Ile Val Gln Met Gly Thr His Ile Leu Gly Ile Lys Asp Met
                725                 730                 735
```

```
Ala Gly Thr Met Lys Pro Ala Ala Lys Leu Leu Ile Gly Ser Leu
                740                 745                 750
Arg Ala Lys Tyr Pro Asp Leu Pro Ile His Val His Thr His Asp Ser
            755                 760                 765
Ala Gly Thr Ala Val Ala Ser Met Thr Ala Cys Ala Leu Ala Gly Ala
        770                 775                 780
Asp Val Val Asp Val Ala Ile Asn Ser Met Ser Gly Leu Thr Ser Gln
785                 790                 795                 800
Pro Ser Ile Asn Ala Leu Leu Ala Ser Leu Glu Gly Asn Ile Asp Thr
                805                 810                 815
Gly Ile Asn Val Glu His Val Arg Glu Leu Asp Ala Tyr Trp Ala Glu
                820                 825                 830
Met Arg Leu Leu Tyr Ser Cys Phe Glu Ala Asp Leu Lys Gly Pro Asp
            835                 840                 845
Pro Glu Val Tyr Gln His Glu Ile Pro Gly Gly Gln Leu Thr Asn Leu
        850                 855                 860
Leu Phe Gln Ala Gln Gln Leu Gly Leu Gly Glu Gln Trp Ala Glu Thr
865                 870                 875                 880
Lys Arg Ala Tyr Arg Glu Ala Asn Tyr Leu Leu Gly Asp Ile Val Lys
                885                 890                 895
Val Thr Pro Thr Ser Lys Val Val Gly Asp Leu Ala Gln Phe Met Val
                900                 905                 910
Ser Asn Lys Leu Thr Ser Asp Asp Val Arg Arg Leu Ala Asn Ser Leu
            915                 920                 925
Asp Phe Pro Asp Ser Val Met Asp Phe Phe Glu Gly Leu Ile Gly Gln
        930                 935                 940
Pro Tyr Gly Gly Phe Pro Glu Pro Phe Arg Ser Asp Val Leu Arg Asn
945                 950                 955                 960
Lys Arg Arg Lys Leu Thr Cys Arg Pro Gly Leu Glu Leu Glu Pro Phe
                965                 970                 975
Asp Leu Glu Lys Ile Arg Glu Asp Leu Gln Asn Arg Phe Gly Asp Val
            980                 985                 990
Asp Glu Cys Asp Val Ala Ser Tyr Asn Met Tyr Pro Arg Val Tyr Glu
        995                 1000                1005
Asp Phe Gln Lys Met Arg Glu Thr Tyr Gly Asp Leu Ser Val Leu
        1010                1015                1020
Pro Thr Arg Ser Phe Leu Ser Pro Leu Glu Thr Asp Glu Glu Ile
        1025                1030                1035
Glu Val Val Ile Glu Gln Gly Lys Thr Leu Ile Ile Lys Leu Gln
        1040                1045                1050
Ala Val Gly Asp Leu Asn Lys Lys Thr Gly Glu Arg Glu Val Tyr
        1055                1060                1065
Phe Asp Leu Asn Gly Glu Met Arg Lys Ile Arg Val Ala Asp Arg
        1070                1075                1080
Ser Gln Lys Val Glu Thr Val Thr Lys Ser Lys Ala Asp Met His
        1085                1090                1095
Asp Pro Leu His Ile Gly Ala Pro Met Ala Gly Val Ile Val Glu
        1100                1105                1110
Val Lys Val His Lys Gly Ser Leu Ile Lys Lys Gly Gln Pro Val
        1115                1120                1125
Ala Val Leu Ser Ala Met Lys Met Glu Met Ile Ile Ser Ser Pro
        1130                1135                1140
Ser Asp Gly Gln Val Lys Glu Val Phe Val Ser Asp Gly Glu Asn
```

```
                1145                1150                1155
         Val Asp Ser Ser Asp Leu Leu Val Leu Leu Glu Asp Gln Val Pro
             1160                1165                1170

Val Glu Thr Lys Ala
             1175

<210> SEQ ID NO 11
<211> LENGTH: 3528
<212> TYPE: DNA
<213> ORGANISM: Kluyveromyces marxianus
<220> FEATURE:
<221> NAME/KEY: CDS
<222> LOCATION: (1)..(3528)

<400> SEQUENCE: 11 atg tct acc caa aac gat ctg gcc ggg ttg cgt gat aac tcg aac cta      48
Met Ser Thr Gln Asn Asp Leu Ala Gly Leu Arg Asp Asn Ser Asn Leu
1               5                  10                  15 tta ggt gaa aag aac aag att ctt gtt gcc aac cgt ggt gaa att cca      96
Leu Gly Glu Lys Asn Lys Ile Leu Val Ala Asn Arg Gly Glu Ile Pro
            20                  25                  30 att aga atc ttt aga acg gct cat gaa ctt tcg atg aag act gtt gcg     144
Ile Arg Ile Phe Arg Thr Ala His Glu Leu Ser Met Lys Thr Val Ala
        35                  40                  45 atc tat tcg cac gag gat aga cta tct atg cac aga ttg aag gca gac     192
Ile Tyr Ser His Glu Asp Arg Leu Ser Met His Arg Leu Lys Ala Asp
    50                  55                  60 gaa gct tac gtt att ggt gag cca gga aaa tac act cca gtt ggt gcg     240
Glu Ala Tyr Val Ile Gly Glu Pro Gly Lys Tyr Thr Pro Val Gly Ala
65                  70                  75                  80 tat ttg gcg atc gat gag att atc aag att gct caa ttg cac gga gtg     288
Tyr Leu Ala Ile Asp Glu Ile Ile Lys Ile Ala Gln Leu His Gly Val
                85                  90                  95 agc ttc atc cac cct ggt tat ggg ttc tta tcg gaa aac tct gag ttt     336
Ser Phe Ile His Pro Gly Tyr Gly Phe Leu Ser Glu Asn Ser Glu Phe
            100                 105                 110 gcc aag aag gtg gcc gac tct ggt atc acg tgg gtt ggt cct cca gcc     384
Ala Lys Lys Val Ala Asp Ser Gly Ile Thr Trp Val Gly Pro Pro Ala
        115                 120                 125 gat gtg atc gat gct gtt ggt gac aag gtt tct gcc aga aac ttg gcc     432
Asp Val Ile Asp Ala Val Gly Asp Lys Val Ser Ala Arg Asn Leu Ala
    130                 135                 140 gag aga gcg gat gtt cca gtg gtt cca ggt acg cct ggt cca ata gag     480
Glu Arg Ala Asp Val Pro Val Val Pro Gly Thr Pro Gly Pro Ile Glu
145                 150                 155                 160 aca gtt gaa gaa gca gtt gaa ttt gtg gag aag tac gga tac cca gtc     528
Thr Val Glu Glu Ala Val Glu Phe Val Glu Lys Tyr Gly Tyr Pro Val
                165                 170                 175 atc atc aag gct gcc ttc ggt ggt ggt ggt cgt ggt atg aga gtt gtt     576
Ile Ile Lys Ala Ala Phe Gly Gly Gly Gly Arg Gly Met Arg Val Val
            180                 185                 190 cgt gaa ggt gat gat atc gcc gat gct ttc caa aga gcc aag tcc gaa     624
Arg Glu Gly Asp Asp Ile Ala Asp Ala Phe Gln Arg Ala Lys Ser Glu
        195                 200                 205 gct gtt act gct ttc ggt aac ggt act tgt ttc gtt gaa aga ttc ttg     672
Ala Val Thr Ala Phe Gly Asn Gly Thr Cys Phe Val Glu Arg Phe Leu
    210                 215                 220 gac aag cca aag cac atc gaa gtt cag ttg ttg gct gat cac tac ggt     720
Asp Lys Pro Lys His Ile Glu Val Gln Leu Leu Ala Asp His Tyr Gly
225                 230                 235                 240
```

| | | |
|---|---|---|
| aat gtc atc cat cta ttc gaa aga gac tgt tct gtg caa aga aga cat<br>Asn Val Ile His Leu Phe Glu Arg Asp Cys Ser Val Gln Arg Arg His<br>                                      245                            250                            255 | 768 |
| caa aag gtc gtt gaa gta gcg cca gcc aag act ttg cca gag agc gtg<br>Gln Lys Val Val Glu Val Ala Pro Ala Lys Thr Leu Pro Glu Ser Val<br>                260                            265                            270 | 816 |
| cgt aat gca atc ttg act gac gct gtc aag ttg gct aag gag gca gga<br>Arg Asn Ala Ile Leu Thr Asp Ala Val Lys Leu Ala Lys Glu Ala Gly<br>         275                            280                            285 | 864 |
| tac aga aat gct ggt acc gct gaa ttt ttg gtc gac aac caa aac aga<br>Tyr Arg Asn Ala Gly Thr Ala Glu Phe Leu Val Asp Asn Gln Asn Arg<br>290                            295                            300 | 912 |
| cac tac ttt att gaa atc aac cca aga att caa gtc gaa cat acc atc<br>His Tyr Phe Ile Glu Ile Asn Pro Arg Ile Gln Val Glu His Thr Ile<br>305                        310                            315                    320 | 960 |
| acc gaa gaa att acc ggt atc gac att gtc gcc gca caa att caa atc<br>Thr Glu Glu Ile Thr Gly Ile Asp Ile Val Ala Ala Gln Ile Gln Ile<br>                            325                            330                            335 | 1008 |
| gca gca ggt gct tcc ttg gaa caa ttg gga cta ttg caa gat aga atc<br>Ala Ala Gly Ala Ser Leu Glu Gln Leu Gly Leu Leu Gln Asp Arg Ile<br>         340                            345                            350 | 1056 |
| acc acc cgt ggt ttc gct att caa tgt cgt atc act act gaa gat cct<br>Thr Thr Arg Gly Phe Ala Ile Gln Cys Arg Ile Thr Thr Glu Asp Pro<br>                355                            360                            365 | 1104 |
| tcc aag aac ttc cag cca gat act ggt cgt atc gat gtt tac cgt tcc<br>Ser Lys Asn Phe Gln Pro Asp Thr Gly Arg Ile Asp Val Tyr Arg Ser<br>         370                            375                            380 | 1152 |
| gct ggt ggt aac ggt gtc aga ttg gat ggt ggt aac gca ttc gct ggt<br>Ala Gly Gly Asn Gly Val Arg Leu Asp Gly Gly Asn Ala Phe Ala Gly<br>385                        390                            395                    400 | 1200 |
| tcg gtc att tca cct cat tat gat tcc atg ttg gtc aaa tgt tct tgt<br>Ser Val Ile Ser Pro His Tyr Asp Ser Met Leu Val Lys Cys Ser Cys<br>                            405                            410                            415 | 1248 |
| tcc ggt tcc act tac gaa atc gtt cgt cgt aag atg ttg cgt gcc ttg<br>Ser Gly Ser Thr Tyr Glu Ile Val Arg Arg Lys Met Leu Arg Ala Leu<br>         420                            425                            430 | 1296 |
| atc gaa ttc aga atc aga ggt gtg aag aca aac att cca ttc ttg cta<br>Ile Glu Phe Arg Ile Arg Gly Val Lys Thr Asn Ile Pro Phe Leu Leu<br>                435                            440                            445 | 1344 |
| acg ttg ttg act cat cct gtg ttc aag tcc ggt gac tac tgg act acc<br>Thr Leu Leu Thr His Pro Val Phe Lys Ser Gly Asp Tyr Trp Thr Thr<br>         450                            455                            460 | 1392 |
| ttc atc gat gac act cca caa ttg ttc gaa atg gtt tct tct caa aac<br>Phe Ile Asp Asp Thr Pro Gln Leu Phe Glu Met Val Ser Ser Gln Asn<br>465                        470                            475                    480 | 1440 |
| aga gca caa aaa cta ttg cac tac ttg gcc gat ctt gcc gtt aac ggt<br>Arg Ala Gln Lys Leu Leu His Tyr Leu Ala Asp Leu Ala Val Asn Gly<br>                485                            490                            495 | 1488 |
| tca tcg atc aag ggt caa att ggt cta cca aag tta aag act cat cct<br>Ser Ser Ile Lys Gly Gln Ile Gly Leu Pro Lys Leu Lys Thr His Pro<br>                    500                            505                            510 | 1536 |
| act atc cca cat ttg cat aag gcc gat ggc tcc att cta gat gtg tct<br>Thr Ile Pro His Leu His Lys Ala Asp Gly Ser Ile Leu Asp Val Ser<br>                515                            520                            525 | 1584 |
| gcc aag cct cct gcc ggg tgg aga gat gtt cta ttg caa cac ggc cca<br>Ala Lys Pro Pro Ala Gly Trp Arg Asp Val Leu Leu Gln His Gly Pro<br>         530                            535                            540 | 1632 |
| gaa gaa ttt gca aag caa gtt aga aag ttc aag ggt act ttg cta atg<br>Glu Glu Phe Ala Lys Gln Val Arg Lys Phe Lys Gly Thr Leu Leu Met<br>545                        550                            555                    560 | 1680 |

```
gac acc acc tgg aga gat gct cat caa tct cta ttg gcc act aga gtc    1728
Asp Thr Thr Trp Arg Asp Ala His Gln Ser Leu Leu Ala Thr Arg Val
            565                 570                 575 aga act tac gat ttg gct gcc atc gct cca act act gct cat gct ttg    1776
Arg Thr Tyr Asp Leu Ala Ala Ile Ala Pro Thr Thr Ala His Ala Leu
        580                 585                 590 agc ggt gct ttc gct ttg gaa tgt tgg ggt ggt gcc act ttc gat gtc    1824
Ser Gly Ala Phe Ala Leu Glu Cys Trp Gly Gly Ala Thr Phe Asp Val
            595                 600                 605 tcc atg aga ttc ttg cac gaa gat cca tgg gaa cgt ttg aga act ttg    1872
Ser Met Arg Phe Leu His Glu Asp Pro Trp Glu Arg Leu Arg Thr Leu
        610                 615                 620 aga aag ttg gtt cct aac att cca ttc caa atg ttg cta cgt ggt gcc    1920
Arg Lys Leu Val Pro Asn Ile Pro Phe Gln Met Leu Leu Arg Gly Ala
625                 630                 635                 640 aac ggt gtt gca tac tct tct cta cca gat aac gct atc gac cac ttt    1968
Asn Gly Val Ala Tyr Ser Ser Leu Pro Asp Asn Ala Ile Asp His Phe
            645                 650                 655 gtc aag caa gca aag gat aac ggt gtt gac att ttc aga gtc ttc gat    2016
Val Lys Gln Ala Lys Asp Asn Gly Val Asp Ile Phe Arg Val Phe Asp
        660                 665                 670 gct cta aac gat ttg gag caa ttg act gtc ggt gtt gac gct gtc aag    2064
Ala Leu Asn Asp Leu Glu Gln Leu Thr Val Gly Val Asp Ala Val Lys
            675                 680                 685 aag gct ggt ggt gtt gtc gaa gct acc att tgt tac tcc ggt gac atg    2112
Lys Ala Gly Gly Val Val Glu Ala Thr Ile Cys Tyr Ser Gly Asp Met
        690                 695                 700 cta gca cca ggt aag aag tac aac ctt gac tac tac ttg gac att gtt    2160
Leu Ala Pro Gly Lys Lys Tyr Asn Leu Asp Tyr Tyr Leu Asp Ile Val
705                 710                 715                 720 gaa caa gtg gtt aag aga ggt acc cat att ctt ggt atc aag gat atg    2208
Glu Gln Val Val Lys Arg Gly Thr His Ile Leu Gly Ile Lys Asp Met
            725                 730                 735 gca ggt act ttg aag cca tct gct gct aag ctc ttg atc ggt tct atc    2256
Ala Gly Thr Leu Lys Pro Ser Ala Ala Lys Leu Leu Ile Gly Ser Ile
        740                 745                 750 aga aca aag tac cct gac ttg cca att cac gtc cat acc cat gac tcc    2304
Arg Thr Lys Tyr Pro Asp Leu Pro Ile His Val His Thr His Asp Ser
            755                 760                 765 gcc ggt acc ggt gtt gct tcc atg gct gca tgt gct ttc gct ggt gct    2352
Ala Gly Thr Gly Val Ala Ser Met Ala Ala Cys Ala Phe Ala Gly Ala
        770                 775                 780 gat gtt gtt gat gtt gca acc aac tct atg tct ggt atg act tct caa    2400
Asp Val Val Asp Val Ala Thr Asn Ser Met Ser Gly Met Thr Ser Gln
785                 790                 795                 800 cca tct gtc aat gca cta ttg gct gct ctt gat ggt gaa atc gac tgt    2448
Pro Ser Val Asn Ala Leu Leu Ala Ala Leu Asp Gly Glu Ile Asp Cys
            805                 810                 815 aat gtc aac gtc agc tac atc agt cag cta gat gct tac tgg gct gaa    2496
Asn Val Asn Val Ser Tyr Ile Ser Gln Leu Asp Ala Tyr Trp Ala Glu
        820                 825                 830 atg aga cta ttg tac tca tgt ttc gaa gcc gac ttg aag ggt cct gat    2544
Met Arg Leu Leu Tyr Ser Cys Phe Glu Ala Asp Leu Lys Gly Pro Asp
            835                 840                 845 cca gaa gtt tac gtc cat gaa att cca ggt ggt caa ttg acc aac ttg    2592
Pro Glu Val Tyr Val His Glu Ile Pro Gly Gly Gln Leu Thr Asn Leu
850                 855                 860 ctc ttc caa gcc caa caa ttg ggt ctt ggt gag caa tgg gct gaa acc    2640
Leu Phe Gln Ala Gln Gln Leu Gly Leu Gly Glu Gln Trp Ala Glu Thr
```

```
                865                 870                 875                 880
aag aga gct tac cgt gaa gca aac ctg ttg ttg ggt gat gtt gtt aag              2688
Lys Arg Ala Tyr Arg Glu Ala Asn Leu Leu Leu Gly Asp Val Val Lys
                        885                 890                 895 gtc act cca aca tcc aag gtt gtc ggt gat ttg gct caa ttc atg gtc              2736
Val Thr Pro Thr Ser Lys Val Val Gly Asp Leu Ala Gln Phe Met Val
                900                 905                 910 act aac aag ttg acc tcg gat gat gtt aag aga tta gct tca tct ttg              2784
Thr Asn Lys Leu Thr Ser Asp Asp Val Lys Arg Leu Ala Ser Ser Leu
                915                 920                 925 gat ttc cca gac tcc gtc atg gac ttc ttt gaa ggt tta atc ggt caa              2832
Asp Phe Pro Asp Ser Val Met Asp Phe Phe Glu Gly Leu Ile Gly Gln
            930                 935                 940 cca tac ggt ggt ttc cca gaa cct cta aga tct gat gtt ttg aag aac              2880
Pro Tyr Gly Gly Phe Pro Glu Pro Leu Arg Ser Asp Val Leu Lys Asn
945                 950                 955                 960 aag aga aga aag ttg acc aag aga cca ggt ttg gaa ttg gct cca ttc              2928
Lys Arg Arg Lys Leu Thr Lys Arg Pro Gly Leu Glu Leu Ala Pro Phe
                965                 970                 975 gat ttg gaa ggc att aag gaa gat ttg act aac aga ttt ggt gac att              2976
Asp Leu Glu Gly Ile Lys Glu Asp Leu Thr Asn Arg Phe Gly Asp Ile
                980                 985                 990 gac gac tgt gat gtt gct tct tac  aac atg tat cca aag  gtc tac gaa           3024
Asp Asp Cys Asp Val Ala Ser Tyr Asn Met Tyr Pro Lys Val Tyr Glu
                995                 1000                1005 gat ttc cgt aag atc aga gaa aag tac ggt gat cta tct gtt ttg                  3069
Asp Phe Arg Lys Ile Arg Glu Lys Tyr Gly Asp Leu Ser Val Leu
    1010                1015                1020 cca acc aag aac ttc ttg tct cca cct tca atc ggt gaa gaa atc                  3114
Pro Thr Lys Asn Phe Leu Ser Pro Pro Ser Ile Gly Glu Glu Ile
    1025                1030                1035 gtc gtt aca att gaa caa ggt aag act ttg atc att aag cca caa                  3159
Val Val Thr Ile Glu Gln Gly Lys Thr Leu Ile Ile Lys Pro Gln
    1040                1045                1050 gct att ggt gat ttg aac aag gag act ggt atc aga gaa gtt tac                  3204
Ala Ile Gly Asp Leu Asn Lys Glu Thr Gly Ile Arg Glu Val Tyr
    1055                1060                1065 ttc gaa ttg aac ggt gaa ttg aga aag gtc tct gtt gct gac aga                  3249
Phe Glu Leu Asn Gly Glu Leu Arg Lys Val Ser Val Ala Asp Arg
    1070                1075                1080 tct caa aag gtt gaa acg atc tcc aag cca aag gct gac gcc cac                  3294
Ser Gln Lys Val Glu Thr Ile Ser Lys Pro Lys Ala Asp Ala His
    1085                1090                1095 gat cca ttc caa gtt ggt tct cca atg gca ggt gtt gtt gtc gaa                  3339
Asp Pro Phe Gln Val Gly Ser Pro Met Ala Gly Val Val Val Glu
    1100                1105                1110 gtc aag gta cac aag ggt tct ttg atc tcc aag ggc caa cca gtc                  3384
Val Lys Val His Lys Gly Ser Leu Ile Ser Lys Gly Gln Pro Val
    1115                1120                1125 gct gtc cta agt gcc atg aag atg gaa atg gtt atc tcc tcc cca                  3429
Ala Val Leu Ser Ala Met Lys Met Glu Met Val Ile Ser Ser Pro
    1130                1135                1140 tct gat ggt caa gtc aag gaa gtg ctt gtc aag gat ggt gaa aac                  3474
Ser Asp Gly Gln Val Lys Glu Val Leu Val Lys Asp Gly Glu Asn
    1145                1150                1155 gtt gac gct tct gac ttg ctc gtt gtt ttg gaa gaa gct cca gct                  3519
Val Asp Ala Ser Asp Leu Leu Val Val Leu Glu Glu Ala Pro Ala
    1160                1165                1170 aaa gaa taa                                                                  3528
```

```
Lys Glu
    1175

<210> SEQ ID NO 12
<211> LENGTH: 1175
<212> TYPE: PRT
<213> ORGANISM: Kluyveromyces marxianus

<400> SEQUENCE: 12

Met Ser Thr Gln Asn Asp Leu Ala Gly Leu Arg Asp Asn Ser Asn Leu
1               5                   10                  15

Leu Gly Glu Lys Asn Lys Ile Leu Val Ala Asn Arg Gly Glu Ile Pro
            20                  25                  30

Ile Arg Ile Phe Arg Thr Ala His Glu Leu Ser Met Lys Thr Val Ala
        35                  40                  45

Ile Tyr Ser His Glu Asp Arg Leu Ser Met His Arg Leu Lys Ala Asp
    50                  55                  60

Glu Ala Tyr Val Ile Gly Glu Pro Gly Lys Tyr Thr Pro Val Gly Ala
65                  70                  75                  80

Tyr Leu Ala Ile Asp Glu Ile Ile Lys Ile Ala Gln Leu His Gly Val
                85                  90                  95

Ser Phe Ile His Pro Gly Tyr Gly Phe Leu Ser Glu Asn Ser Glu Phe
            100                 105                 110

Ala Lys Lys Val Ala Asp Ser Gly Ile Thr Trp Val Gly Pro Pro Ala
        115                 120                 125

Asp Val Ile Asp Ala Val Gly Asp Lys Val Ser Ala Arg Asn Leu Ala
    130                 135                 140

Glu Arg Ala Asp Val Pro Val Val Pro Gly Thr Pro Gly Pro Ile Glu
145                 150                 155                 160

Thr Val Glu Glu Ala Val Glu Phe Val Glu Lys Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Ile Ala Asp Ala Phe Gln Arg Ala Lys Ser Glu
        195                 200                 205

Ala Val Thr Ala Phe Gly Asn Gly Thr Cys Phe Val Glu Arg Phe Leu
    210                 215                 220

Asp Lys Pro Lys His Ile Glu Val Gln Leu Leu Ala Asp His Tyr Gly
225                 230                 235                 240

Asn Val Ile His Leu Phe Glu Arg Asp Cys Ser Val Gln Arg Arg His
                245                 250                 255

Gln Lys Val Val Glu Val Ala Pro Ala Lys Thr Leu Pro Glu Ser Val
            260                 265                 270

Arg Asn Ala Ile Leu Thr Asp Ala Val Lys Leu Ala Lys Glu Ala Gly
        275                 280                 285

Tyr Arg Asn Ala Gly Thr Ala Glu Phe Leu Val Asp Asn Gln Asn Arg
    290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ala Ala Gln Ile Gln Ile
                325                 330                 335

Ala Ala Gly Ala Ser Leu Glu Gln Leu Gly Leu Leu Gln Asp Arg Ile
            340                 345                 350

Thr Thr Arg Gly Phe Ala Ile Gln Cys Arg Ile Thr Thr Glu Asp Pro
        355                 360                 365
```

```
Ser Lys Asn Phe Gln Pro Asp Thr Gly Arg Ile Asp Val Tyr Arg Ser
    370                 375                 380

Ala Gly Gly Asn Gly Val Arg Leu Asp Gly Asn Ala Phe Ala Gly
385                 390                 395                 400

Ser Val Ile Ser Pro His Tyr Asp Ser Met Leu Val Lys Cys Ser Cys
            405                 410                 415

Ser Gly Ser Thr Tyr Glu Ile Val Arg Arg Lys Met Leu Arg Ala Leu
            420                 425                 430

Ile Glu Phe Arg Ile Arg Gly Val Lys Thr Asn Ile Pro Phe Leu Leu
        435                 440                 445

Thr Leu Leu Thr His Pro Val Phe Lys Ser Gly Asp Tyr Trp Thr Thr
    450                 455                 460

Phe Ile Asp Asp Thr Pro Gln Leu Phe Glu Met Val Ser Ser Gln Asn
465                 470                 475                 480

Arg Ala Gln Lys Leu Leu His Tyr Leu Ala Asp Leu Ala Val Asn Gly
            485                 490                 495

Ser Ser Ile Lys Gly Gln Ile Gly Leu Pro Lys Leu Lys Thr His Pro
            500                 505                 510

Thr Ile Pro His Leu His Lys Ala Asp Gly Ser Ile Leu Asp Val Ser
        515                 520                 525

Ala Lys Pro Pro Ala Gly Trp Arg Asp Val Leu Leu Gln His Gly Pro
530                 535                 540

Glu Glu Phe Ala Lys Gln Val Arg Lys Phe Lys Gly Thr Leu Leu Met
545                 550                 555                 560

Asp Thr Thr Trp Arg Asp Ala His Gln Ser Leu Leu Ala Thr Arg Val
            565                 570                 575

Arg Thr Tyr Asp Leu Ala Ala Ile Ala Pro Thr Thr His Ala Leu
            580                 585                 590

Ser Gly Ala Phe Ala Leu Glu Cys Trp Gly Gly Ala Thr Phe Asp Val
        595                 600                 605

Ser Met Arg Phe Leu His Glu Asp Pro Trp Glu Arg Leu Arg Thr Leu
    610                 615                 620

Arg Lys Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
            645                 650                 655

Val Lys Gln Ala Lys Asp Asn Gly Val Asp Ile Phe Arg Val Phe Asp
            660                 665                 670

Ala Leu Asn Asp Leu Glu Gln Leu Thr Val Gly Val Asp Ala Val Lys
        675                 680                 685

Lys Ala Gly Gly Val Val Glu Ala Thr Ile Cys Tyr Ser Gly Asp Met
690                 695                 700

Leu Ala Pro Gly Lys Lys Tyr Asn Leu Asp Tyr Tyr Leu Asp Ile Val
705                 710                 715                 720

Glu Gln Val Val Lys Arg Gly Thr His Ile Leu Gly Ile Lys Asp Met
            725                 730                 735

Ala Gly Thr Leu Lys Pro Ser Ala Ala Lys Leu Leu Ile Gly Ser Ile
            740                 745                 750

Arg Thr Lys Tyr Pro Asp Leu Pro Ile His Val His Thr His Asp Ser
        755                 760                 765

Ala Gly Thr Gly Val Ala Ser Met Ala Ala Cys Ala Phe Ala Gly Ala
    770                 775                 780
```

```
Asp Val Val Asp Val Ala Thr Asn Ser Met Ser Gly Met Thr Ser Gln
785                 790                 795                 800

Pro Ser Val Asn Ala Leu Leu Ala Ala Leu Asp Gly Glu Ile Asp Cys
            805                 810                 815

Asn Val Asn Val Ser Tyr Ile Ser Gln Leu Asp Ala Tyr Trp Ala Glu
            820                 825                 830

Met Arg Leu Leu Tyr Ser Cys Phe Glu Ala Asp Leu Lys Gly Pro Asp
            835                 840                 845

Pro Glu Val Tyr Val His Glu Ile Pro Gly Gly Leu Thr Asn Leu
850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Leu Leu Leu Gly Asp Val Val Lys
            885                 890                 895

Val Thr Pro Thr Ser Lys Val Val Gly Asp Leu Ala Gln Phe Met Val
            900                 905                 910

Thr Asn Lys Leu Thr Ser Asp Asp Val Lys Arg Leu Ala Ser Ser Leu
            915                 920                 925

Asp Phe Pro Asp Ser Val Met Asp Phe Phe Glu Gly Leu Ile Gly Gln
930                 935                 940

Pro Tyr Gly Gly Phe Pro Glu Pro Leu Arg Ser Asp Val Leu Lys Asn
945                 950                 955                 960

Lys Arg Arg Lys Leu Thr Lys Arg Pro Gly Leu Glu Leu Ala Pro Phe
                965                 970                 975

Asp Leu Glu Gly Ile Lys Glu Asp Leu Thr Asn Arg Phe Gly Asp Ile
            980                 985                 990

Asp Asp Cys Asp Val Ala Ser Tyr Asn Met Tyr Pro Lys Val Tyr Glu
            995                 1000                1005

Asp Phe Arg Lys Ile Arg Glu Lys Tyr Gly Asp Leu Ser Val Leu
    1010                1015                1020

Pro Thr Lys Asn Phe Leu Ser Pro Pro Ser Ile Gly Glu Glu Ile
    1025                1030                1035

Val Val Thr Ile Glu Gln Gly Lys Thr Leu Ile Ile Lys Pro Gln
    1040                1045                1050

Ala Ile Gly Asp Leu Asn Lys Glu Thr Gly Ile Arg Glu Val Tyr
    1055                1060                1065

Phe Glu Leu Asn Gly Glu Leu Arg Lys Val Ser Val Ala Asp Arg
    1070                1075                1080

Ser Gln Lys Val Glu Thr Ile Ser Lys Pro Lys Ala Asp Ala His
    1085                1090                1095

Asp Pro Phe Gln Val Gly Ser Pro Met Ala Gly Val Val Val Glu
    1100                1105                1110

Val Lys Val His Lys Gly Ser Leu Ile Ser Lys Gly Gln Pro Val
    1115                1120                1125

Ala Val Leu Ser Ala Met Lys Met Glu Met Val Ile Ser Ser Pro
    1130                1135                1140

Ser Asp Gly Gln Val Lys Glu Val Leu Val Lys Asp Gly Glu Asn
    1145                1150                1155

Val Asp Ala Ser Asp Leu Leu Val Val Leu Glu Glu Ala Pro Ala
    1160                1165                1170

Lys Glu
    1175
```

-continued

```
<210> SEQ ID NO 13
<211> LENGTH: 1029
<212> TYPE: DNA
<213> ORGANISM: Issatchenkia orientalis
<220> FEATURE:
<221> NAME/KEY: CDS
<222> LOCATION: (1)..(1029)

<400> SEQUENCE: 13
```

| | | | | | | | | | | | | | | | | |
|---|---|---|---|---|---|---|---|---|---|---|---|---|---|---|---|---|
| atg | tcc | aat | gtt | aaa | gta | gct | cta | cta | ggt | gcc | gct | ggt | ggt | atc | ggc | 48 |
| Met | Ser | Asn | Val | Lys | Val | Ala | Leu | Leu | Gly | Ala | Ala | Gly | Gly | Ile | Gly | |
| 1 | | | | 5 | | | | | 10 | | | | | 15 | | |
| caa | cca | ctt | gct | cta | tta | ctt | aag | ctt | aat | cca | aac | ata | acc | cat | ttg | 96 |
| Gln | Pro | Leu | Ala | Leu | Leu | Leu | Lys | Leu | Asn | Pro | Asn | Ile | Thr | His | Leu | |
| | | | 20 | | | | | 25 | | | | | 30 | | | |
| gca | ctc | tat | gac | gtt | gtg | cat | gtt | cct | gga | gtg | gct | gcc | gac | cta | cac | 144 |
| Ala | Leu | Tyr | Asp | Val | Val | His | Val | Pro | Gly | Val | Ala | Ala | Asp | Leu | His | |
| | | 35 | | | | | 40 | | | | | 45 | | | | |
| cat | ata | gac | aca | gat | gta | gtg | att | acc | cac | cat | ttg | aaa | gat | gaa | gac | 192 |
| His | Ile | Asp | Thr | Asp | Val | Val | Ile | Thr | His | His | Leu | Lys | Asp | Glu | Asp | |
| | 50 | | | | | 55 | | | | | 60 | | | | | |
| ggt | acg | gcc | ttg | gca | aac | gcc | ctc | aag | gac | gct | acg | ttt | gtt | att | gtc | 240 |
| Gly | Thr | Ala | Leu | Ala | Asn | Ala | Leu | Lys | Asp | Ala | Thr | Phe | Val | Ile | Val | |
| 65 | | | | | 70 | | | | | 75 | | | | | 80 | |
| ccc | gcc | ggt | gtt | ccg | aga | aag | ccc | ggc | atg | act | aga | ggt | gat | ttg | ttc | 288 |
| Pro | Ala | Gly | Val | Pro | Arg | Lys | Pro | Gly | Met | Thr | Arg | Gly | Asp | Leu | Phe | |
| | | | | 85 | | | | | 90 | | | | | 95 | | |
| aca | att | aat | gcc | ggt | ata | tgt | gcc | gaa | ttg | gct | aat | gct | att | agt | ttg | 336 |
| Thr | Ile | Asn | Ala | Gly | Ile | Cys | Ala | Glu | Leu | Ala | Asn | Ala | Ile | Ser | Leu | |
| | | | 100 | | | | | 105 | | | | | 110 | | | |
| aac | gct | cct | aat | gca | ttc | acc | ctt | gtc | att | acc | aat | ccg | gtc | aac | tcg | 384 |
| Asn | Ala | Pro | Asn | Ala | Phe | Thr | Leu | Val | Ile | Thr | Asn | Pro | Val | Asn | Ser | |
| | | 115 | | | | | 120 | | | | | 125 | | | | |
| acc | gtt | cct | ata | ttt | aag | gaa | ata | ttt | gct | aaa | aat | gaa | gcc | ttc | aat | 432 |
| Thr | Val | Pro | Ile | Phe | Lys | Glu | Ile | Phe | Ala | Lys | Asn | Glu | Ala | Phe | Asn | |
| | 130 | | | | | 135 | | | | | 140 | | | | | |
| cca | agg | aga | ctg | ttt | ggt | gta | act | gct | cta | gat | cat | gtt | aga | tca | aat | 480 |
| Pro | Arg | Arg | Leu | Phe | Gly | Val | Thr | Ala | Leu | Asp | His | Val | Arg | Ser | Asn | |
| 145 | | | | | 150 | | | | | 155 | | | | | 160 | |
| act | ttt | ctc | tcg | gaa | tta | att | gac | ggt | aaa | aat | ccc | caa | cat | ttt | gat | 528 |
| Thr | Phe | Leu | Ser | Glu | Leu | Ile | Asp | Gly | Lys | Asn | Pro | Gln | His | Phe | Asp | |
| | | | | 165 | | | | | 170 | | | | | 175 | | |
| gtc | act | gtt | gtt | ggc | gga | cac | tct | ggt | aac | tca | att | gtc | ccc | cta | ttc | 576 |
| Val | Thr | Val | Val | Gly | Gly | His | Ser | Gly | Asn | Ser | Ile | Val | Pro | Leu | Phe | |
| | | | 180 | | | | | 185 | | | | | 190 | | | |
| tcc | ctt | gtt | aag | gct | gcc | gaa | aat | tta | gac | gat | gaa | att | ata | gat | gcc | 624 |
| Ser | Leu | Val | Lys | Ala | Ala | Glu | Asn | Leu | Asp | Asp | Glu | Ile | Ile | Asp | Ala | |
| | | 195 | | | | | 200 | | | | | 205 | | | | |
| ttg | att | cat | aga | gtt | caa | tac | ggt | gga | gat | gaa | gtt | gtg | gaa | gca | aag | 672 |
| Leu | Ile | His | Arg | Val | Gln | Tyr | Gly | Gly | Asp | Glu | Val | Val | Glu | Ala | Lys | |
| | 210 | | | | | 215 | | | | | 220 | | | | | |
| agc | ggt | gcg | ggc | tcg | gca | act | ctt | tca | atg | gct | tat | gcc | gct | aac | aag | 720 |
| Ser | Gly | Ala | Gly | Ser | Ala | Thr | Leu | Ser | Met | Ala | Tyr | Ala | Ala | Asn | Lys | |
| 225 | | | | | 230 | | | | | 235 | | | | | 240 | |
| ttc | ttc | aat | ata | ttg | ctt | aat | gga | tac | ttg | ggt | ttg | aag | aag | aca | atg | 768 |
| Phe | Phe | Asn | Ile | Leu | Leu | Asn | Gly | Tyr | Leu | Gly | Leu | Lys | Lys | Thr | Met | |
| | | | | 245 | | | | | 250 | | | | | 255 | | |
| att | tca | agt | tat | gtc | ttt | tta | gac | gat | tca | atc | aac | ggc | gtc | cct | caa | 816 |
| Ile | Ser | Ser | Tyr | Val | Phe | Leu | Asp | Asp | Ser | Ile | Asn | Gly | Val | Pro | Gln | |
| | | | 260 | | | | | 265 | | | | | 270 | | | |
| tta | aag | gaa | aat | ttg | tct | aaa | ctt | ttg | aaa | ggt | tcc | gag | gtt | gag | tta | 864 |

```
Leu Lys Glu Asn Leu Ser Lys Leu Lys Gly Ser Glu Val Glu Leu
            275                 280                 285 cca agt tat ttg gct gtt cca atg acc tat ggt aaa gaa ggt att gaa        912
Pro Ser Tyr Leu Ala Val Pro Met Thr Tyr Gly Lys Glu Gly Ile Glu
            290                 295                 300 caa gtc ttt tac gat tgg gtg ttt gaa atg tca cca aag gaa aag gaa        960
Gln Val Phe Tyr Asp Trp Val Phe Glu Met Ser Pro Lys Glu Lys Glu
305                 310                 315                 320 aac ttc att aca gcg att gaa tac att gat caa aat att gaa aaa ggt       1008
Asn Phe Ile Thr Ala Ile Glu Tyr Ile Asp Gln Asn Ile Glu Lys Gly
                325                 330                 335 ctg aat ttt atg gta cgt taa                                           1029
Leu Asn Phe Met Val Arg
            340

<210> SEQ ID NO 14
<211> LENGTH: 342
<212> TYPE: PRT
<213> ORGANISM: Issatchenkia orientalis

<400> SEQUENCE: 14

Met Ser Asn Val Lys Val Ala Leu Leu Gly Ala Ala Gly Gly Ile Gly
1               5                   10                  15

Gln Pro Leu Ala Leu Leu Lys Leu Asn Pro Asn Ile Thr His Leu
            20                  25                  30

Ala Leu Tyr Asp Val Val His Val Pro Gly Val Ala Ala Asp Leu His
            35                  40                  45

His Ile Asp Thr Asp Val Val Ile Thr His His Leu Lys Asp Glu Asp
50                  55                  60

Gly Thr Ala Leu Ala Asn Ala Leu Lys Asp Ala Thr Phe Val Ile Val
65                  70                  75                  80

Pro Ala Gly Val Pro Arg Lys Pro Gly Met Thr Arg Gly Asp Leu Phe
                85                  90                  95

Thr Ile Asn Ala Gly Ile Cys Ala Glu Leu Ala Asn Ala Ile Ser Leu
            100                 105                 110

Asn Ala Pro Asn Ala Phe Thr Leu Val Ile Thr Asn Pro Val Asn Ser
            115                 120                 125

Thr Val Pro Ile Phe Lys Glu Ile Phe Ala Lys Asn Glu Ala Phe Asn
130                 135                 140

Pro Arg Arg Leu Phe Gly Val Thr Ala Leu Asp His Val Arg Ser Asn
145                 150                 155                 160

Thr Phe Leu Ser Glu Leu Ile Asp Gly Lys Asn Pro Gln His Phe Asp
                165                 170                 175

Val Thr Val Val Gly Gly His Ser Gly Asn Ser Ile Val Pro Leu Phe
            180                 185                 190

Ser Leu Val Lys Ala Ala Glu Asn Leu Asp Asp Glu Ile Ile Asp Ala
            195                 200                 205

Leu Ile His Arg Val Gln Tyr Gly Gly Asp Glu Val Val Glu Ala Lys
210                 215                 220

Ser Gly Ala Gly Ser Ala Thr Leu Ser Met Ala Tyr Ala Ala Asn Lys
225                 230                 235                 240

Phe Phe Asn Ile Leu Leu Asn Gly Tyr Leu Gly Leu Lys Lys Thr Met
                245                 250                 255

Ile Ser Ser Tyr Val Phe Leu Asp Asp Ser Ile Asn Gly Val Pro Gln
            260                 265                 270

Leu Lys Glu Asn Leu Ser Lys Leu Leu Lys Gly Ser Glu Val Glu Leu
```

```
                275                 280                 285
Pro Ser Tyr Leu Ala Val Pro Met Thr Tyr Gly Lys Glu Gly Ile Glu
    290                 295                 300

Gln Val Phe Tyr Asp Trp Val Phe Glu Met Ser Pro Lys Glu Lys Glu
305                 310                 315                 320

Asn Phe Ile Thr Ala Ile Glu Tyr Ile Asp Gln Asn Ile Glu Lys Gly
                325                 330                 335

Leu Asn Phe Met Val Arg
            340

<210> SEQ ID NO 15
<211> LENGTH: 1011
<212> TYPE: DNA
<213> ORGANISM: Issatchenkia orientalis
<220> FEATURE:
<221> NAME/KEY: CDS
<222> LOCATION: (1)..(1011)

<400> SEQUENCE: 15 atg gtc aag gtg act att tta ggc gct gcc ggt gga att gga caa cca      48
Met Val Lys Val Thr Ile Leu Gly Ala Ala Gly Gly Ile Gly Gln Pro
1               5                   10                  15 ctc tca ttg tta ttg aga ctt aat cca tgg att gac gaa ttg gcc ttg      96
Leu Ser Leu Leu Leu Arg Leu Asn Pro Trp Ile Asp Glu Leu Ala Leu
            20                  25                  30 ttt gat att gtc aat acc ccc ggc gtg agt tgt gat ttg tcg cat att     144
Phe Asp Ile Val Asn Thr Pro Gly Val Ser Cys Asp Leu Ser His Ile
        35                  40                  45 cct gca tca cag gtt gtt aat ggc tat gct ccg aaa tcg aaa tca gat     192
Pro Ala Ser Gln Val Val Asn Gly Tyr Ala Pro Lys Ser Lys Ser Asp
    50                  55                  60 aca gag aca atc aag act gcc ttg aaa ggt gct gat att gtt gtt att     240
Thr Glu Thr Ile Lys Thr Ala Leu Lys Gly Ala Asp Ile Val Val Ile
65                  70                  75                  80 cct gca gga att cca cgt aaa cct ggt atg aca aga aac gat ctc ttt     288
Pro Ala Gly Ile Pro Arg Lys Pro Gly Met Thr Arg Asn Asp Leu Phe
                85                  90                  95 aaa atc aat gcc gga atc gtt aag agt ttg att cat agt gca gga acc     336
Lys Ile Asn Ala Gly Ile Val Lys Ser Leu Ile His Ser Ala Gly Thr
            100                 105                 110 act tgc cct gat gca ttt att tgt gtc att tcg aac cct gtc aac tcg     384
Thr Cys Pro Asp Ala Phe Ile Cys Val Ile Ser Asn Pro Val Asn Ser
        115                 120                 125 aca gtt cca att gcc gtt gaa gaa cta aag cgt ttg aat gtt ttt aat     432
Thr Val Pro Ile Ala Val Glu Glu Leu Lys Arg Leu Asn Val Phe Asn
    130                 135                 140 cca cat aaa gtt ttc ggt att acc aca ttg gac aat ttc aga tta gaa     480
Pro His Lys Val Phe Gly Ile Thr Thr Leu Asp Asn Phe Arg Leu Glu
145                 150                 155                 160 gaa ttt ctg agt gga gaa ctt ggt gga att gtc aaa cca aat gat tta     528
Glu Phe Leu Ser Gly Glu Leu Gly Gly Ile Val Lys Pro Asn Asp Leu
                165                 170                 175 tat ggt gat gta gtt gct ata ggt ggc cat tcg ggc gac tct ata gta     576
Tyr Gly Asp Val Val Ala Ile Gly Gly His Ser Gly Asp Ser Ile Val
            180                 185                 190 ccg atc ttg aat tcg tgg aat ttg aat ttc atc aat gat gga gat tct     624
Pro Ile Leu Asn Ser Trp Asn Leu Asn Phe Ile Asn Asp Gly Asp Ser
        195                 200                 205 tat aac aat ttg gtc aag agg gtc cag ttt gga ggc gat gag gtt gtc     672
Tyr Asn Asn Leu Val Lys Arg Val Gln Phe Gly Gly Asp Glu Val Val
```

```
aag gca aag gac ggg aaa ggt tcg gct aca ttg tca atg gct aca gct      720
Lys Ala Lys Asp Gly Lys Gly Ser Ala Thr Leu Ser Met Ala Thr Ala
225             230                 235                 240 gca tac agg ttt gtc aac aac ctc ttg gac gcc att gtc aat aac aag      768
Ala Tyr Arg Phe Val Asn Asn Leu Leu Asp Ala Ile Val Asn Asn Lys
                245                 250                 255 aaa gtc aag gaa gtg gcc ttt gtg aaa atc gac caa ttg cca act aca      816
Lys Val Lys Glu Val Ala Phe Val Lys Ile Asp Gln Leu Pro Thr Thr
            260                 265                 270 agg gtt cct tat ttt gtt gtt gat gaa act cag tat ttt agt cta ccc      864
Arg Val Pro Tyr Phe Val Val Asp Glu Thr Gln Tyr Phe Ser Leu Pro
        275                 280                 285 att att ctc ggt aga cag ggg att gag agg gtc acg ttc cca gaa tct      912
Ile Ile Leu Gly Arg Gln Gly Ile Glu Arg Val Thr Phe Pro Glu Ser
    290                 295                 300 ctg aca gag caa gag gtg aga atg aca aag cac gct gtt gct aaa gtt      960
Leu Thr Glu Gln Glu Val Arg Met Thr Lys His Ala Val Ala Lys Val
305                 310                 315                 320 aaa gtt gac gtt aat aaa ggc ttc aat ttt gtc cat ggc cca aaa ctg     1008
Lys Val Asp Val Asn Lys Gly Phe Asn Phe Val His Gly Pro Lys Leu
                325                 330                 335 taa                                                                 1011

<210> SEQ ID NO 16
<211> LENGTH: 336
<212> TYPE: PRT
<213> ORGANISM: Issatchenkia orientalis

<400> SEQUENCE: 16

Met Val Lys Val Thr Ile Leu Gly Ala Ala Gly Gly Ile Gly Gln Pro
1               5                   10                  15

Leu Ser Leu Leu Leu Arg Leu Asn Pro Trp Ile Asp Glu Leu Ala Leu
            20                  25                  30

Phe Asp Ile Val Asn Thr Pro Gly Val Ser Cys Asp Leu Ser His Ile
        35                  40                  45

Pro Ala Ser Gln Val Val Asn Gly Tyr Ala Pro Lys Ser Lys Ser Asp
    50                  55                  60

Thr Glu Thr Ile Lys Thr Ala Leu Lys Gly Ala Asp Ile Val Val Ile
65                  70                  75                  80

Pro Ala Gly Ile Pro Arg Lys Pro Gly Met Thr Arg Asn Asp Leu Phe
                85                  90                  95

Lys Ile Asn Ala Gly Ile Val Lys Ser Leu Ile His Ser Ala Gly Thr
            100                 105                 110

Thr Cys Pro Asp Ala Phe Ile Cys Val Ile Ser Asn Pro Val Asn Ser
        115                 120                 125

Thr Val Pro Ile Ala Val Glu Glu Leu Lys Arg Leu Asn Val Phe Asn
    130                 135                 140

Pro His Lys Val Phe Gly Ile Thr Thr Leu Asp Asn Phe Arg Leu Glu
145                 150                 155                 160

Glu Phe Leu Ser Gly Glu Leu Gly Gly Ile Val Lys Pro Asn Asp Leu
                165                 170                 175

Tyr Gly Asp Val Val Ala Ile Gly Gly His Ser Gly Asp Ser Ile Val
            180                 185                 190

Pro Ile Leu Asn Ser Trp Asn Leu Asn Phe Ile Asn Asp Gly Asp Ser
        195                 200                 205
```

```
Tyr Asn Asn Leu Val Lys Arg Val Gln Phe Gly Gly Asp Glu Val Val
    210                 215                 220

Lys Ala Lys Asp Gly Lys Gly Ser Ala Thr Leu Ser Met Ala Thr Ala
225                 230                 235                 240

Ala Tyr Arg Phe Val Asn Asn Leu Leu Asp Ala Ile Val Asn Asn Lys
                245                 250                 255

Lys Val Lys Glu Val Ala Phe Val Lys Ile Asp Gln Leu Pro Thr Thr
            260                 265                 270

Arg Val Pro Tyr Phe Val Val Asp Glu Thr Gln Tyr Phe Ser Leu Pro
        275                 280                 285

Ile Ile Leu Gly Arg Gln Gly Ile Glu Arg Val Thr Phe Pro Glu Ser
    290                 295                 300

Leu Thr Glu Gln Glu Val Arg Met Thr Lys His Ala Val Ala Lys Val
305                 310                 315                 320

Lys Val Asp Val Asn Lys Gly Phe Asn Phe Val His Gly Pro Lys Leu
                325                 330                 335

<210> SEQ ID NO 17
<211> LENGTH: 1005
<212> TYPE: DNA
<213> ORGANISM: Issatchenkia orientalis
<220> FEATURE:
<221> NAME/KEY: CDS
<222> LOCATION: (1)..(1005)

<400> SEQUENCE: 17
```

| | | | | | | | | | | | | | | | | |
|---|---|---|---|---|---|---|---|---|---|---|---|---|---|---|---|---|
| atg ttc tcc aga atc tct gct aga caa ttc tcc tcc tct gct gct tcc | | | | | | | | | | | | | | | | 48 |
| Met Phe Ser Arg Ile Ser Ala Arg Gln Phe Ser Ser Ser Ala Ala Ser | | | | | | | | | | | | | | | | |
| 1               5                   10                  15 | | | | | | | | | | | | | | | | |

```
gct tac aag gtc acc gtt tta ggt gct gca ggt ggt att ggc caa cca        96
Ala Tyr Lys Val Thr Val Leu Gly Ala Ala Gly Gly Ile Gly Gln Pro
                20                  25                  30 cta tct ctt ttg atg aag ttg aac cac aag gtc acc aac tta tcc ttg       144
Leu Ser Leu Leu Met Lys Leu Asn His Lys Val Thr Asn Leu Ser Leu
            35                  40                  45 tac gac ttg aga ttg ggt gct ggt gtt gcc act gac ttg tcc cac att       192
Tyr Asp Leu Arg Leu Gly Ala Gly Val Ala Thr Asp Leu Ser His Ile
        50                  55                  60 cca acc aac tcc gtt gtc aag ggc tat ggt cca gaa aac aat ggt ttg       240
Pro Thr Asn Ser Val Val Lys Gly Tyr Gly Pro Glu Asn Asn Gly Leu
65                  70                  75                  80 aag gac gcc ttg acc ggc tcc gat gtt gtt ctt att cca gct ggt gtt       288
Lys Asp Ala Leu Thr Gly Ser Asp Val Val Leu Ile Pro Ala Gly Val
                85                  90                  95 cca aga aaa cca ggt atg act aga gac gat ctc ttc aac acc aat gca       336
Pro Arg Lys Pro Gly Met Thr Arg Asp Asp Leu Phe Asn Thr Asn Ala
                100                 105                 110 tcg att gtc aga gac ttg gca aag gct gct gca gac cac tgt cca aac       384
Ser Ile Val Arg Asp Leu Ala Lys Ala Ala Ala Asp His Cys Pro Asn
            115                 120                 125 gcc gtc ttg ttg atc att tca aac cct gtc aac tca act gtc cca att       432
Ala Val Leu Leu Ile Ile Ser Asn Pro Val Asn Ser Thr Val Pro Ile
        130                 135                 140 gtt gct gag gtt ttg aaa tca aag ggc gtc tac aac cca aag aag ttg       480
Val Ala Glu Val Leu Lys Ser Lys Gly Val Tyr Asn Pro Lys Lys Leu
145                 150                 155                 160 ttt ggt gtc acc act ttg gac gtt ttg aga tcc tcg aga ttc ttg agt       528
Phe Gly Val Thr Thr Leu Asp Val Leu Arg Ser Ser Arg Phe Leu Ser
                165                 170                 175
```

```
gaa gtc gtc aac acc gac cca acc acc gaa acc gtc act gtt gtt ggt       576
Glu Val Val Asn Thr Asp Pro Thr Thr Glu Thr Val Thr Val Val Gly
            180                 185                 190 ggc cac tct ggt gtc acc att gtt cct tta atc tcc caa acc aaa cac       624
Gly His Ser Gly Val Thr Ile Val Pro Leu Ile Ser Gln Thr Lys His
        195                 200                 205 aag gac ttg cca aag gaa acc tac gaa gca ttg gtc cac aga atc caa       672
Lys Asp Leu Pro Lys Glu Thr Tyr Glu Ala Leu Val His Arg Ile Gln
    210                 215                 220 ttc ggt ggt gat gag gtt gtc aag gcc aag gac ggt gca ggt tcc gct       720
Phe Gly Gly Asp Glu Val Val Lys Ala Lys Asp Gly Ala Gly Ser Ala
225                 230                 235                 240 acc ttg tcc atg gcc caa gcc ggt gca aga atg gcc tcc tcc gtc ttg       768
Thr Leu Ser Met Ala Gln Ala Gly Ala Arg Met Ala Ser Ser Val Leu
            245                 250                 255 aag ggt ttg gct ggt gaa gtt gac att gtc gaa cca acc ttt att gac       816
Lys Gly Leu Ala Gly Glu Val Asp Ile Val Glu Pro Thr Phe Ile Asp
        260                 265                 270 tct cca ttg ttc aag tcc gaa ggt gtc gaa ttc ttc tcc tcc aga gtc       864
Ser Pro Leu Phe Lys Ser Glu Gly Val Glu Phe Phe Ser Ser Arg Val
    275                 280                 285 acc ctt ggt cca gaa ggt gtc caa gaa gtc cac cca ttg ggc gtc tta       912
Thr Leu Gly Pro Glu Gly Val Gln Glu Val His Pro Leu Gly Val Leu
290                 295                 300 tct act gct gaa gaa gaa atg gtt gct act gct aag gaa acc ttg aag       960
Ser Thr Ala Glu Glu Glu Met Val Ala Thr Ala Lys Glu Thr Leu Lys
            305                 310                 315             320 aag aac atc caa aag ggt gtc gac ttt gtc aag gct aac cca taa          1005
Lys Asn Ile Gln Lys Gly Val Asp Phe Val Lys Ala Asn Pro
                    325                 330

<210> SEQ ID NO 18
<211> LENGTH: 334
<212> TYPE: PRT
<213> ORGANISM: Issatchenkia orientalis

<400> SEQUENCE: 18

Met Phe Ser Arg Ile Ser Ala Arg Gln Phe Ser Ser Ala Ala Ser
1               5                   10                  15

Ala Tyr Lys Val Thr Val Leu Gly Ala Ala Gly Gly Ile Gly Gln Pro
                20                  25                  30

Leu Ser Leu Leu Met Lys Leu Asn His Lys Val Thr Asn Leu Ser Leu
            35                  40                  45

Tyr Asp Leu Arg Leu Gly Ala Gly Val Ala Thr Asp Leu Ser His Ile
    50                  55                  60

Pro Thr Asn Ser Val Val Lys Gly Tyr Gly Pro Glu Asn Asn Gly Leu
65                  70                  75                  80

Lys Asp Ala Leu Thr Gly Ser Asp Val Val Leu Ile Pro Ala Gly Val
                85                  90                  95

Pro Arg Lys Pro Gly Met Thr Arg Asp Asp Leu Phe Asn Thr Asn Ala
                100                 105                 110

Ser Ile Val Arg Asp Leu Ala Lys Ala Ala Asp His Cys Pro Asn
            115                 120                 125

Ala Val Leu Leu Ile Ile Ser Asn Pro Val Asn Ser Thr Val Pro Ile
    130                 135                 140

Val Ala Glu Val Leu Lys Ser Lys Gly Val Tyr Asn Pro Lys Lys Leu
145                 150                 155                 160

Phe Gly Val Thr Thr Leu Asp Val Leu Arg Ser Ser Arg Phe Leu Ser
```

165                 170                 175
Glu Val Asn Thr Asp Pro Thr Thr Glu Thr Val Thr Val Val Gly
            180                 185                 190

Gly His Ser Gly Val Thr Ile Val Pro Leu Ile Ser Gln Thr Lys His
            195                 200                 205

Lys Asp Leu Pro Lys Glu Thr Tyr Glu Ala Leu Val His Arg Ile Gln
            210                 215                 220

Phe Gly Asp Glu Val Val Lys Ala Lys Asp Gly Ala Gly Ser Ala
225                 230                 235                 240

Thr Leu Ser Met Ala Gln Ala Gly Ala Arg Met Ala Ser Ser Val Leu
            245                 250                 255

Lys Gly Leu Ala Gly Glu Val Asp Ile Val Glu Pro Thr Phe Ile Asp
            260                 265                 270

Ser Pro Leu Phe Lys Ser Glu Gly Val Glu Phe Phe Ser Ser Arg Val
            275                 280                 285

Thr Leu Gly Pro Glu Gly Val Gln Glu Val His Pro Leu Gly Val Leu
            290                 295                 300

Ser Thr Ala Glu Glu Met Val Ala Thr Ala Lys Glu Thr Leu Lys
305                 310                 315                 320

Lys Asn Ile Gln Lys Gly Val Asp Phe Val Lys Ala Asn Pro
                325                 330

<210> SEQ ID NO 19
<211> LENGTH: 1017
<212> TYPE: DNA
<213> ORGANISM: Kluyveromyces marxianus
<220> FEATURE:
<221> NAME/KEY: CDS
<222> LOCATION: (1)..(1017)

<400> SEQUENCE: 19 atg ctt aga gcc cta act cgc cgt caa ttt tcc tcc act gcc ttc aac      48
Met Leu Arg Ala Leu Thr Arg Arg Gln Phe Ser Ser Thr Ala Phe Asn
1               5                   10                  15 cca tac aag gtc acc gtt cta ggt gct ggt ggt ggt att ggt caa cca      96
Pro Tyr Lys Val Thr Val Leu Gly Ala Gly Gly Gly Ile Gly Gln Pro
                20                  25                  30 ttg tcc ttg ttg ttg aag cta aac cac aag gtc act gac ttg aga cta     144
Leu Ser Leu Leu Leu Lys Leu Asn His Lys Val Thr Asp Leu Arg Leu
            35                  40                  45 tac gac ttg aag ggt gcc aag ggt gtc gct gct gac ttg tct cac atc     192
Tyr Asp Leu Lys Gly Ala Lys Gly Val Ala Ala Asp Leu Ser His Ile
        50                  55                  60 cca acc aac tct acc gtt act ggt tac act cca gaa tcc aag gac tct     240
Pro Thr Asn Ser Thr Val Thr Gly Tyr Thr Pro Glu Ser Lys Asp Ser
65                  70                  75                  80 caa gaa gaa ttg gct gct gct ttg aag gac act gag gtt gtt ttg atc     288
Gln Glu Glu Leu Ala Ala Ala Leu Lys Asp Thr Glu Val Val Leu Ile
                85                  90                  95 cca gct ggt gtg cca aga aag cca ggt atg acc cgt gac gat ttg ttc     336
Pro Ala Gly Val Pro Arg Lys Pro Gly Met Thr Arg Asp Asp Leu Phe
                100                 105                 110 gcc atc aat gcc ggt att gtc aga gat ttg gcc act tcc atc gcc aag     384
Ala Ile Asn Ala Gly Ile Val Arg Asp Leu Ala Thr Ser Ile Ala Lys
            115                 120                 125 aac gct cca aac gcc gcc atc ttg gtc atc tcc aac cca gtc aac tct     432
Asn Ala Pro Asn Ala Ala Ile Leu Val Ile Ser Asn Pro Val Asn Ser
        130                 135                 140

| | | |
|---|---|---|
| act gtc cca atc gtc gcc gag gtc ttg aag caa aac ggc gtc tac aac<br>Thr Val Pro Ile Val Ala Glu Val Leu Lys Gln Asn Gly Val Tyr Asn<br>145                        150                      155                    160 | 480 | |
| cca aag aag ttg ttc ggt gtc acc act ttg gac gtt atc cgt gcc tcc<br>Pro Lys Lys Leu Phe Gly Val Thr Thr Leu Asp Val Ile Arg Ala Ser<br>                        165                      170                    175 | 528 | |
| aga ttc atc tcc gag gtt aga ggt acc gac cca acc act gag cac gtg<br>Arg Phe Ile Ser Glu Val Arg Gly Thr Asp Pro Thr Thr Glu His Val<br>                  180                      185                    190 | 576 | |
| acc gtc gtc ggt ggt cac tcc ggt atc acc atc ttg ccg cta gtg tcc<br>Thr Val Val Gly Gly His Ser Gly Ile Thr Ile Leu Pro Leu Val Ser<br>              195                      200                    205 | 624 | |
| cag acc aag cac aag tcc gtc atc aag ggc gag gaa ttg gac aac ttg<br>Gln Thr Lys His Lys Ser Val Ile Lys Gly Glu Glu Leu Asp Asn Leu<br>210                        215                      220 | 672 | |
| atc cac aga atc caa ttc ggt ggt gac gaa gtc gtc cag gca aag aac<br>Ile His Arg Ile Gln Phe Gly Gly Asp Glu Val Val Gln Ala Lys Asn<br>225                        230                      235                    240 | 720 | |
| ggt gct ggt tct gcc act ttg tcc atg gcc caa gcc ggt gcc cgt ttc<br>Gly Ala Gly Ser Ala Thr Leu Ser Met Ala Gln Ala Gly Ala Arg Phe<br>                  245                      250                    255 | 768 | |
| gct aac agc gtt cta agc ggt ttc gaa ggt gaa aga gac gtc att gag<br>Ala Asn Ser Val Leu Ser Gly Phe Glu Gly Glu Arg Asp Val Ile Glu<br>            260                      265                    270 | 816 | |
| cca act ttc gtc gac tcc cca ttg ttc aag gac gaa ggt atc gaa ttc<br>Pro Thr Phe Val Asp Ser Pro Leu Phe Lys Asp Glu Gly Ile Glu Phe<br>        275                      280                    285 | 864 | |
| ttc gct tcc cca gtc act ttg ggc cca gaa ggt gtc gaa aag atc cac<br>Phe Ala Ser Pro Val Thr Leu Gly Pro Glu Gly Val Glu Lys Ile His<br>        290                      295                    300 | 912 | |
| ggt ttg ggt gtc ttg tcc gac aag gaa gaa caa atg ttg gcc act tgt<br>Gly Leu Gly Val Leu Ser Asp Lys Glu Glu Gln Met Leu Ala Thr Cys<br>305                        310                      315                    320 | 960 | |
| aag gaa acc ttg aag aag aac atc gaa aag ggt caa aac ttt gtc aag<br>Lys Glu Thr Leu Lys Lys Asn Ile Glu Lys Gly Gln Asn Phe Val Lys<br>                        325                      330                    335 | 1008 | |
| caa aac taa<br>Gln Asn | 1017 | |

<210> SEQ ID NO 20
<211> LENGTH: 338
<212> TYPE: PRT
<213> ORGANISM: Kluyveromyces marxianus

<400> SEQUENCE: 20

Met Leu Arg Ala Leu Thr Arg Arg Gln Phe Ser Ser Thr Ala Phe Asn
1               5                    10                    15

Pro Tyr Lys Val Thr Val Leu Gly Ala Gly Gly Ile Gly Gln Pro
                    20                    25                    30

Leu Ser Leu Leu Leu Lys Leu Asn His Lys Val Thr Asp Leu Arg Leu
              35                    40                    45

Tyr Asp Leu Lys Gly Ala Lys Gly Val Ala Ala Asp Leu Ser His Ile
       50                    55                    60

Pro Thr Asn Ser Thr Val Thr Gly Tyr Thr Pro Glu Ser Lys Asp Ser
65                    70                    75                    80

Gln Glu Glu Leu Ala Ala Ala Leu Lys Asp Thr Glu Val Val Leu Ile
                    85                    90                    95

Pro Ala Gly Val Pro Arg Lys Pro Gly Met Thr Arg Asp Asp Leu Phe
                    100                    105                    110

```
Ala Ile Asn Ala Gly Ile Val Arg Asp Leu Ala Thr Ser Ile Ala Lys
            115                 120                 125

Asn Ala Pro Asn Ala Ala Ile Leu Val Ile Ser Asn Pro Val Asn Ser
        130                 135                 140

Thr Val Pro Ile Val Ala Glu Val Leu Lys Gln Asn Gly Val Tyr Asn
145                 150                 155                 160

Pro Lys Lys Leu Phe Gly Val Thr Thr Leu Asp Val Ile Arg Ala Ser
                165                 170                 175

Arg Phe Ile Ser Glu Val Arg Gly Thr Asp Pro Thr Glu His Val
            180                 185                 190

Thr Val Val Gly Gly His Ser Gly Ile Thr Ile Leu Pro Leu Val Ser
            195                 200                 205

Gln Thr Lys His Lys Ser Val Ile Lys Gly Glu Glu Leu Asp Asn Leu
    210                 215                 220

Ile His Arg Ile Gln Phe Gly Gly Asp Glu Val Val Gln Ala Lys Asn
225                 230                 235                 240

Gly Ala Gly Ser Ala Thr Leu Ser Met Ala Gln Ala Gly Ala Arg Phe
                245                 250                 255

Ala Asn Ser Val Leu Ser Gly Phe Glu Gly Glu Arg Asp Val Ile Glu
            260                 265                 270

Pro Thr Phe Val Asp Ser Pro Leu Phe Lys Asp Glu Gly Ile Glu Phe
        275                 280                 285

Phe Ala Ser Pro Val Thr Leu Gly Pro Glu Gly Val Glu Lys Ile His
290                 295                 300

Gly Leu Gly Val Leu Ser Asp Lys Glu Glu Gln Met Leu Ala Thr Cys
305                 310                 315                 320

Lys Glu Thr Leu Lys Lys Asn Ile Glu Lys Gly Gln Asn Phe Val Lys
                325                 330                 335

Gln Asn

<210> SEQ ID NO 21
<211> LENGTH: 1017
<212> TYPE: DNA
<213> ORGANISM: Kluyveromyces marxianus
<220> FEATURE:
<221> NAME/KEY: CDS
<222> LOCATION: (1)..(1017)

<400> SEQUENCE: 21 atg gtt agc gtt gca gta tta gga tca tcc gga ggc att ggc caa cca      48
Met Val Ser Val Ala Val Leu Gly Ser Ser Gly Gly Ile Gly Gln Pro
1               5                   10                  15 ctc tca ctc ttg ttg aag ctg gac cct cgc gtg tcc agc ttg aga ttg      96
Leu Ser Leu Leu Leu Lys Leu Asp Pro Arg Val Ser Ser Leu Arg Leu
                20                  25                  30 tac gac ttg aag atg tcc cac ggg atc gcc acc gat ttg tcg cac atg     144
Tyr Asp Leu Lys Met Ser His Gly Ile Ala Thr Asp Leu Ser His Met
            35                  40                  45 gac tcc aac tcc atc tgc gag ggc ttc aac acc gac gag atc gcg ctc     192
Asp Ser Asn Ser Ile Cys Glu Gly Phe Asn Thr Asp Glu Ile Ala Leu
        50                  55                  60 gcg ctc aag ggc gcc cag atc gtc gtc atc ccc gcg ggt gtc cca aga     240
Ala Leu Lys Gly Ala Gln Ile Val Val Ile Pro Ala Gly Val Pro Arg
65                  70                  75                  80 aag ccc ggg atg tca cgt gac gac ctt ttc aag atc aac gcc aag atc     288
Lys Pro Gly Met Ser Arg Asp Asp Leu Phe Lys Ile Asn Ala Lys Ile
                85                  90                  95
```

| | | |
|---|---|---|
| atc aag tcg ttg gcg ttg caa ata gcc gag cac gcg ccc gag gcg cgc<br>Ile Lys Ser Leu Ala Leu Gln Ile Ala Glu His Ala Pro Glu Ala Arg<br>               100                      105                         110 | | 336 |
| gtc ctc gtg atc tcg aac ccg gtc aac tcc ttg gtg ccc att gtg tac<br>Val Leu Val Ile Ser Asn Pro Val Asn Ser Leu Val Pro Ile Val Tyr<br>             115                      120                     125 | | 384 |
| gag act ttg aag agc gtc ggc aag ttc gag ccg ggt aaa gtg atg gga<br>Glu Thr Leu Lys Ser Val Gly Lys Phe Glu Pro Gly Lys Val Met Gly<br>130                       135                      140 | | 432 |
| att acc aca ttg gac att atc cgc tca cac acg ttc ctg gtg gac gtc<br>Ile Thr Thr Leu Asp Ile Ile Arg Ser His Thr Phe Leu Val Asp Val<br>145                   150                   155                 160 | | 480 |
| ttg ggc cgc aag gcg tac agc gtc gag aag ttg cgc agc gcg gtt act<br>Leu Gly Arg Lys Ala Tyr Ser Val Glu Lys Leu Arg Ser Ala Val Thr<br>                     165                     170                    175 | | 528 |
| gtg gtg ggc ggc cac tcg ggc gag acc att gtt ccg att ttc acc gac<br>Val Val Gly Gly His Ser Gly Glu Thr Ile Val Pro Ile Phe Thr Asp<br>             180                      185                     190 | | 576 |
| cag aag ttc tac agg cgt ctc aga gac aga gag ctc tat gac gcg tac<br>Gln Lys Phe Tyr Arg Arg Leu Arg Asp Arg Glu Leu Tyr Asp Ala Tyr<br>         195                     200                     205 | | 624 |
| gtg cat agg gtc caa ttc ggc gga gac gag gtc gtg aag gcc aag gac<br>Val His Arg Val Gln Phe Gly Gly Asp Glu Val Val Lys Ala Lys Asp<br>210                       215                      220 | | 672 |
| ggc agc ggt agt gct act ttg tct atg gcc tgg gcg ggt tac agt ttt<br>Gly Ser Gly Ser Ala Thr Leu Ser Met Ala Trp Ala Gly Tyr Ser Phe<br>225                   230                   235                 240 | | 720 |
| gtg aag cag ttg ctc aac agc ttg cac cta gaa aca ggc gaa gac gtg<br>Val Lys Gln Leu Leu Asn Ser Leu His Leu Glu Thr Gly Glu Asp Val<br>                 245                     250                    255 | | 768 |
| cat ccg atc cca acg ttt gtg tac ttg ccg ggt tta ccg ggc ggg aag<br>His Pro Ile Pro Thr Phe Val Tyr Leu Pro Gly Leu Pro Gly Gly Lys<br>             260                      265                     270 | | 816 |
| gag ctc cag cag aag ttg ggc acc tct gtt gag ttt ttt gcc gcg ccc<br>Glu Leu Gln Gln Lys Leu Gly Thr Ser Val Glu Phe Phe Ala Ala Pro<br>         275                     280                     285 | | 864 |
| gtg aag ctt tcc aag ggt att gtg gtt gaa gtt gag cac gac tgg gtc<br>Val Lys Leu Ser Lys Gly Ile Val Val Glu Val Glu His Asp Trp Val<br>290                       295                      300 | | 912 |
| gac aag ttg aac gat gcc gag aag aag ttg att gca aag tgt ctt cca<br>Asp Lys Leu Asn Asp Ala Glu Lys Lys Leu Ile Ala Lys Cys Leu Pro<br>305                   310                   315                 320 | | 960 |
| atc ctt gac aag aac atc aag aag ggt ctc gcc ttt tcg cag cag aca<br>Ile Leu Asp Lys Asn Ile Lys Lys Gly Leu Ala Phe Ser Gln Gln Thr<br>                 325                     330                    335 | | 1008 |
| aag ttg tga<br>Lys Leu | | 1017 |

<210> SEQ ID NO 22
<211> LENGTH: 338
<212> TYPE: PRT
<213> ORGANISM: Kluyveromyces marxianus

<400> SEQUENCE: 22

Met Val Ser Val Ala Val Leu Gly Ser Ser Gly Gly Ile Gly Gln Pro
1                 5                      10                      15

Leu Ser Leu Leu Leu Lys Leu Asp Pro Arg Val Ser Ser Leu Arg Leu
                 20                      25                      30

Tyr Asp Leu Lys Met Ser His Gly Ile Ala Thr Asp Leu Ser His Met

```
                 35                  40                  45
Asp Ser Asn Ser Ile Cys Glu Gly Phe Asn Thr Asp Glu Ile Ala Leu
 50                  55                  60

Ala Leu Lys Gly Ala Gln Ile Val Val Ile Pro Ala Gly Val Pro Arg
 65                  70                  75                  80

Lys Pro Gly Met Ser Arg Asp Asp Leu Phe Lys Ile Asn Ala Lys Ile
                 85                  90                  95

Ile Lys Ser Leu Ala Leu Gln Ile Ala Glu His Ala Pro Glu Ala Arg
                100                 105                 110

Val Leu Val Ile Ser Asn Pro Val Asn Ser Leu Val Pro Ile Val Tyr
            115                 120                 125

Glu Thr Leu Lys Ser Val Gly Lys Phe Glu Pro Gly Lys Val Met Gly
130                 135                 140

Ile Thr Thr Leu Asp Ile Ile Arg Ser His Thr Phe Leu Val Asp Val
145                 150                 155                 160

Leu Gly Arg Lys Ala Tyr Ser Val Glu Lys Leu Arg Ser Ala Val Thr
                165                 170                 175

Val Val Gly Gly His Ser Gly Glu Thr Ile Val Pro Ile Phe Thr Asp
            180                 185                 190

Gln Lys Phe Tyr Arg Arg Leu Arg Asp Arg Glu Leu Tyr Asp Ala Tyr
        195                 200                 205

Val His Arg Val Gln Phe Gly Gly Asp Glu Val Val Lys Ala Lys Asp
210                 215                 220

Gly Ser Gly Ser Ala Thr Leu Ser Met Ala Trp Ala Gly Tyr Ser Phe
225                 230                 235                 240

Val Lys Gln Leu Leu Asn Ser Leu His Leu Glu Thr Gly Glu Asp Val
                245                 250                 255

His Pro Ile Pro Thr Phe Val Tyr Leu Pro Gly Leu Pro Gly Gly Lys
            260                 265                 270

Glu Leu Gln Gln Lys Leu Gly Thr Ser Val Glu Phe Phe Ala Ala Pro
        275                 280                 285

Val Lys Leu Ser Lys Gly Ile Val Val Glu Val Glu His Asp Trp Val
290                 295                 300

Asp Lys Leu Asn Asp Ala Glu Lys Lys Leu Ile Ala Lys Cys Leu Pro
305                 310                 315                 320

Ile Leu Asp Lys Asn Ile Lys Lys Gly Leu Ala Phe Ser Gln Gln Thr
                325                 330                 335

Lys Leu

<210> SEQ ID NO 23
<211> LENGTH: 1125
<212> TYPE: DNA
<213> ORGANISM: Kluyveromyces marxianus
<220> FEATURE:
<221> NAME/KEY: CDS
<222> LOCATION: (1)..(1125)

<400> SEQUENCE: 23 atg cca gca gta tca tat gat gtc cag caa cgg gat atc ctc aag atc     48
Met Pro Ala Val Ser Tyr Asp Val Gln Gln Arg Asp Ile Leu Lys Ile
 1               5                  10                  15 gca gtt cta ggg gcg gca ggc ggt att ggc caa tcc ttg tcg ctc ttg     96
Ala Val Leu Gly Ala Ala Gly Gly Ile Gly Gln Ser Leu Ser Leu Leu
             20                  25                  30 ttg aag tcg aac gct tct ttt ttg tta cca cgt gac tcg tca aga cac    144
Leu Lys Ser Asn Ala Ser Phe Leu Leu Pro Arg Asp Ser Ser Arg His
```

```
                35                  40                  45
ata agc cta gcg cta tac gac gtg aac aaa gat gcc atc gtg ggc aca    192
Ile Ser Leu Ala Leu Tyr Asp Val Asn Lys Asp Ala Ile Val Gly Thr
 50                  55                  60 gca gca gac ttg tca cac ata gac acc cct atc acc acc act cca cac    240
Ala Ala Asp Leu Ser His Ile Asp Thr Pro Ile Thr Thr Thr Pro His
 65                  70                  75                  80 tac cca aat gat ggg aat ggc ggt atc gca cgg tgc ttg caa gat gca    288
Tyr Pro Asn Asp Gly Asn Gly Gly Ile Ala Arg Cys Leu Gln Asp Ala
                     85                  90                  95 gac atg gtc atc atc cca gca ggt gtg ccc aga aaa ccc ggt atg tca    336
Asp Met Val Ile Ile Pro Ala Gly Val Pro Arg Lys Pro Gly Met Ser
            100                 105                 110 cgt gat gac cta atc ggt gtc aac gcc aag atc atc aag tcg cta gga    384
Arg Asp Asp Leu Ile Gly Val Asn Ala Lys Ile Ile Lys Ser Leu Gly
        115                 120                 125 aac gac atc gca gag tac tgt gac ttg tct aaa gtg cat gta ttg gtt    432
Asn Asp Ile Ala Glu Tyr Cys Asp Leu Ser Lys Val His Val Leu Val
    130                 135                 140 att tcg aac cca gtg aac tcg ttg gtc cca ctg atg gtg tcg act ttg    480
Ile Ser Asn Pro Val Asn Ser Leu Val Pro Leu Met Val Ser Thr Leu
145                 150                 155                 160 gca aac agc cca cac agt gcg aac aca aac atc gag gct aga gtg tac    528
Ala Asn Ser Pro His Ser Ala Asn Thr Asn Ile Glu Ala Arg Val Tyr
                165                 170                 175 ggg atc acc cat ttg gac cta gtg aga gct tcc acc ttt gtg caa cag    576
Gly Ile Thr His Leu Asp Leu Val Arg Ala Ser Thr Phe Val Gln Gln
            180                 185                 190 cta aac tct ttc aaa tca aat aac gca cct gac att ccg gtc att ggt    624
Leu Asn Ser Phe Lys Ser Asn Asn Ala Pro Asp Ile Pro Val Ile Gly
        195                 200                 205 ggt cat tcc gga gat acc atc atc ccc gtt ttt tcc gtc ttg aat cac    672
Gly His Ser Gly Asp Thr Ile Ile Pro Val Phe Ser Val Leu Asn His
    210                 215                 220 cgc gct tct aac tcc gga tac gct aat ttg cta gat aat ggc gtt agg    720
Arg Ala Ser Asn Ser Gly Tyr Ala Asn Leu Leu Asp Asn Gly Val Arg
225                 230                 235                 240 caa aag ttg gtc cac aga gtt caa tat ggt ggg gac gaa atc gtc caa    768
Gln Lys Leu Val His Arg Val Gln Tyr Gly Gly Asp Glu Ile Val Gln
                245                 250                 255 gca aag aac ggt aac ggg agc gcg aca tta tcc atg gca tac gcg ggc    816
Ala Lys Asn Gly Asn Gly Ser Ala Thr Leu Ser Met Ala Tyr Ala Gly
            260                 265                 270 ttc aaa atc gca gca caa ttc atc gac ctt ttg gtc gga aat atc cgc    864
Phe Lys Ile Ala Ala Gln Phe Ile Asp Leu Leu Val Gly Asn Ile Arg
        275                 280                 285 act atc gaa aat att tgc atg tat gtt ccg ctc act aac agg tat aat    912
Thr Ile Glu Asn Ile Cys Met Tyr Val Pro Leu Thr Asn Arg Tyr Asn
    290                 295                 300 acc gag atc gcc cca ggc tct gac gaa tta aga tca aag tac atc aac    960
Thr Glu Ile Ala Pro Gly Ser Asp Glu Leu Arg Ser Lys Tyr Ile Asn
305                 310                 315                 320 gga acc ctt tat ttc tcg att cca ctt tcc atc gga ata aac ggt atc   1008
Gly Thr Leu Tyr Phe Ser Ile Pro Leu Ser Ile Gly Ile Asn Gly Ile
                325                 330                 335 gaa aga gtc cac tac gag atc atg gaa cat cta gac agc tac gag cgt   1056
Glu Arg Val His Tyr Glu Ile Met Glu His Leu Asp Ser Tyr Glu Arg
            340                 345                 350 gag acg cta cta ccg atc tgc ttg gaa act cta aag ggt aat att gac   1104
Glu Thr Leu Leu Pro Ile Cys Leu Glu Thr Leu Lys Gly Asn Ile Asp
```

Glu Thr Leu Leu Pro Ile Cys Leu Glu Thr Leu Lys Gly Asn Ile Asp
            355                 360                 365 aag ggt cta agc ttg gta taa                                                    1125
Lys Gly Leu Ser Leu Val
    370

<210> SEQ ID NO 24
<211> LENGTH: 374
<212> TYPE: PRT
<213> ORGANISM: Kluyveromyces marxianus

<400> SEQUENCE: 24

Met Pro Ala Val Ser Tyr Asp Val Gln Gln Arg Asp Ile Leu Lys Ile
1               5                   10                  15

Ala Val Leu Gly Ala Ala Gly Gly Ile Gly Gln Ser Leu Ser Leu Leu
            20                  25                  30

Leu Lys Ser Asn Ala Ser Phe Leu Leu Pro Arg Asp Ser Ser Arg His
        35                  40                  45

Ile Ser Leu Ala Leu Tyr Asp Val Asn Lys Asp Ala Ile Val Gly Thr
    50                  55                  60

Ala Ala Asp Leu Ser His Ile Asp Thr Pro Ile Thr Thr Thr Pro His
65                  70                  75                  80

Tyr Pro Asn Asp Gly Asn Gly Gly Ile Ala Arg Cys Leu Gln Asp Ala
                85                  90                  95

Asp Met Val Ile Ile Pro Ala Gly Val Pro Arg Lys Pro Gly Met Ser
            100                 105                 110

Arg Asp Asp Leu Ile Gly Val Asn Ala Lys Ile Ile Lys Ser Leu Gly
        115                 120                 125

Asn Asp Ile Ala Glu Tyr Cys Asp Leu Ser Lys Val His Val Leu Val
    130                 135                 140

Ile Ser Asn Pro Val Asn Ser Leu Val Pro Leu Met Val Ser Thr Leu
145                 150                 155                 160

Ala Asn Ser Pro His Ser Ala Asn Thr Asn Ile Glu Ala Arg Val Tyr
                165                 170                 175

Gly Ile Thr His Leu Asp Leu Val Arg Ala Ser Thr Phe Val Gln Gln
            180                 185                 190

Leu Asn Ser Phe Lys Ser Asn Asn Ala Pro Asp Ile Pro Val Ile Gly
        195                 200                 205

Gly His Ser Gly Asp Thr Ile Ile Pro Val Phe Ser Val Leu Asn His
    210                 215                 220

Arg Ala Ser Asn Ser Gly Tyr Ala Asn Leu Leu Asp Asn Gly Val Arg
225                 230                 235                 240

Gln Lys Leu Val His Arg Val Gln Tyr Gly Gly Asp Glu Ile Val Gln
                245                 250                 255

Ala Lys Asn Gly Asn Gly Ser Ala Thr Leu Ser Met Ala Tyr Ala Gly
            260                 265                 270

Phe Lys Ile Ala Ala Gln Phe Ile Asp Leu Leu Val Gly Asn Ile Arg
        275                 280                 285

Thr Ile Glu Asn Ile Cys Met Tyr Val Pro Leu Thr Asn Arg Tyr Asn
    290                 295                 300

Thr Glu Ile Ala Pro Gly Ser Asp Glu Leu Arg Ser Lys Tyr Ile Asn
305                 310                 315                 320

Gly Thr Leu Tyr Phe Ser Ile Pro Leu Ser Ile Gly Ile Asn Gly Ile
                325                 330                 335

Glu Arg Val His Tyr Glu Ile Met Glu His Leu Asp Ser Tyr Glu Arg

```
                     340                 345                 350
Glu Thr Leu Leu Pro Ile Cys Leu Glu Thr Leu Lys Gly Asn Ile Asp
            355                 360                 365

Lys Gly Leu Ser Leu Val
        370

<210> SEQ ID NO 25
<211> LENGTH: 1413
<212> TYPE: DNA
<213> ORGANISM: Saccharomyces cerevisiae
<220> FEATURE:
<221> NAME/KEY: CDS
<222> LOCATION: (1)..(1413)

<400> SEQUENCE: 25 atg tct ctc tct ccc gtt gtt gtt att gga acc ggt ttg gcc ggg ctg    48
Met Ser Leu Ser Pro Val Val Val Ile Gly Thr Gly Leu Ala Gly Leu
1               5                   10                  15 gct gct gcc aac gaa ttg gtt aac aag tat aac atc cct gta acc atc    96
Ala Ala Ala Asn Glu Leu Val Asn Lys Tyr Asn Ile Pro Val Thr Ile
            20                  25                  30 ctc gaa aag gct tcc tcg atc ggt ggg aac tct atc aag gcc tcc agt   144
Leu Glu Lys Ala Ser Ser Ile Gly Gly Asn Ser Ile Lys Ala Ser Ser
        35                  40                  45 ggt att aac ggt gct tgc acc gag act caa cgt cac ttc cac atc gag   192
Gly Ile Asn Gly Ala Cys Thr Glu Thr Gln Arg His Phe His Ile Glu
    50                  55                  60 gac tcc cca cgc tta ttt gaa gat gac acc atc aag tct gct aaa ggt   240
Asp Ser Pro Arg Leu Phe Glu Asp Asp Thr Ile Lys Ser Ala Lys Gly
65                  70                  75                  80 aaa ggt gtc caa gag tta atg gct aag ttg gcc aat gat tct ccc ctg   288
Lys Gly Val Gln Glu Leu Met Ala Lys Leu Ala Asn Asp Ser Pro Leu
                85                  90                  95 gct att gaa tgg ttg aaa aac gaa ttt gat ttg aaa ttg gac cta ttg   336
Ala Ile Glu Trp Leu Lys Asn Glu Phe Asp Leu Lys Leu Asp Leu Leu
            100                 105                 110 gct caa ttg ggt ggc cac tct gtg gca aga act cac aga tcg tct ggg   384
Ala Gln Leu Gly Gly His Ser Val Ala Arg Thr His Arg Ser Ser Gly
        115                 120                 125 aag ttg cct cca ggt ttc gaa att gtt tct gcc tta tct aac aat ttg   432
Lys Leu Pro Pro Gly Phe Glu Ile Val Ser Ala Leu Ser Asn Asn Leu
    130                 135                 140 aag aaa tta gct gag act aaa cca gag tta gtt aag att aac tta gac   480
Lys Lys Leu Ala Glu Thr Lys Pro Glu Leu Val Lys Ile Asn Leu Asp
145                 150                 155                 160 agt aaa gtc gta gac atc cat gaa aag gat ggc tcc att tct gct gta   528
Ser Lys Val Val Asp Ile His Glu Lys Asp Gly Ser Ile Ser Ala Val
                165                 170                 175 gtg tac gag gat aag aat ggc gaa aag cac atg gtg agt gct aac gat   576
Val Tyr Glu Asp Lys Asn Gly Glu Lys His Met Val Ser Ala Asn Asp
            180                 185                 190 gtc gtt ttt tgt tct gga ggg ttt ggc ttt tct aag gaa atg ctt aaa   624
Val Val Phe Cys Ser Gly Gly Phe Gly Phe Ser Lys Glu Met Leu Lys
        195                 200                 205 gaa tat gca ccc gaa ctg gtg aac ttg cca acg aca aac ggg caa caa   672
Glu Tyr Ala Pro Glu Leu Val Asn Leu Pro Thr Thr Asn Gly Gln Gln
    210                 215                 220 aca act ggt gat ggt caa agg ctt ctg cag aag tta ggc gct gat ctg   720
Thr Thr Gly Asp Gly Gln Arg Leu Leu Gln Lys Leu Gly Ala Asp Leu
225                 230                 235                 240
```

```
att gac atg gac caa att caa gtt cat cca act ggg ttc att gat cca    768
Ile Asp Met Asp Gln Ile Gln Val His Pro Thr Gly Phe Ile Asp Pro
            245                 250                 255 aat gac cgt agc tca agc tgg aaa ttc ttg gct gcc gaa tcc tta aga    816
Asn Asp Arg Ser Ser Ser Trp Lys Phe Leu Ala Ala Glu Ser Leu Arg
        260                 265                 270 ggt ctt ggt ggt atc cta tta aac cct att acc ggt aga aga ttt gtc    864
Gly Leu Gly Gly Ile Leu Leu Asn Pro Ile Thr Gly Arg Arg Phe Val
    275                 280                 285 aac gaa ttg acc aca aga gat gta gtc act gca gct att caa aag gtt    912
Asn Glu Leu Thr Thr Arg Asp Val Val Thr Ala Ala Ile Gln Lys Val
290                 295                 300 tgt cct caa gag gat aac aga gca cta ttg gtt atg ggc gaa aaa atg    960
Cys Pro Gln Glu Asp Asn Arg Ala Leu Leu Val Met Gly Glu Lys Met
305                 310                 315                 320 tac aca gat ttg aag aat aat tta gat ttt tac atg ttc aag aaa ctt   1008
Tyr Thr Asp Leu Lys Asn Asn Leu Asp Phe Tyr Met Phe Lys Lys Leu
                325                 330                 335 gta cag aaa ttg aca tta tct caa gtt gtg tct gaa tat aat tta cca   1056
Val Gln Lys Leu Thr Leu Ser Gln Val Val Ser Glu Tyr Asn Leu Pro
            340                 345                 350 atc act gtc acc caa tta tgc gag gaa ttg caa aca tac tct tcg ttc   1104
Ile Thr Val Thr Gln Leu Cys Glu Glu Leu Gln Thr Tyr Ser Ser Phe
        355                 360                 365 act acc aag gct gat ccg ttg gga cgt acc gtt att ctc aac gaa ttt   1152
Thr Thr Lys Ala Asp Pro Leu Gly Arg Thr Val Ile Leu Asn Glu Phe
    370                 375                 380 ggc tct gac gtt act cca gaa acc gtg gtt ttt att ggt gaa gta aca   1200
Gly Ser Asp Val Thr Pro Glu Thr Val Val Phe Ile Gly Glu Val Thr
385                 390                 395                 400 ccg gtt gtc cat ttc acc atg ggt ggt gct aga atc aat gtc aag gct   1248
Pro Val Val His Phe Thr Met Gly Gly Ala Arg Ile Asn Val Lys Ala
                405                 410                 415 caa gtc att ggc aag aac gac gaa agg cta cta aaa ggc ctg tac gcg   1296
Gln Val Ile Gly Lys Asn Asp Glu Arg Leu Leu Lys Gly Leu Tyr Ala
            420                 425                 430 gcc ggt gaa gtt tct ggc ggt gtt cat ggc gcc aat agg ttg ggt ggt   1344
Ala Gly Glu Val Ser Gly Gly Val His Gly Ala Asn Arg Leu Gly Gly
        435                 440                 445 tca agt ttg tta gaa tgc gtt gtc ttt ggg aga act gca gct gaa tct   1392
Ser Ser Leu Leu Glu Cys Val Val Phe Gly Arg Thr Ala Ala Glu Ser
    450                 455                 460 att gcc aat gac cgc aag taa                                        1413
Ile Ala Asn Asp Arg Lys
465                 470
```

<210> SEQ ID NO 26
<211> LENGTH: 470
<212> TYPE: PRT
<213> ORGANISM: Saccharomyces cerevisiae

<400> SEQUENCE: 26

```
Met Ser Leu Ser Pro Val Val Ile Gly Thr Gly Leu Ala Gly Leu
1               5                   10                  15

Ala Ala Ala Asn Glu Leu Val Asn Lys Tyr Asn Ile Pro Val Thr Ile
            20                  25                  30

Leu Glu Lys Ala Ser Ser Ile Gly Gly Asn Ser Ile Lys Ala Ser Ser
        35                  40                  45

Gly Ile Asn Gly Ala Cys Thr Glu Thr Gln Arg His Phe His Ile Glu
    50                  55                  60
```

```
Asp Ser Pro Arg Leu Phe Glu Asp Thr Ile Lys Ser Ala Lys Gly
 65                  70                  75                  80

Lys Gly Val Gln Glu Leu Met Ala Lys Leu Ala Asn Asp Ser Pro Leu
                 85                  90                  95

Ala Ile Glu Trp Leu Lys Asn Glu Phe Asp Leu Lys Leu Asp Leu Leu
            100                 105                 110

Ala Gln Leu Gly Gly His Ser Val Ala Arg Thr His Arg Ser Ser Gly
        115                 120                 125

Lys Leu Pro Pro Gly Phe Glu Ile Val Ser Ala Leu Ser Asn Asn Leu
130                 135                 140

Lys Lys Leu Ala Glu Thr Lys Pro Glu Leu Val Lys Ile Asn Leu Asp
145                 150                 155                 160

Ser Lys Val Val Asp Ile His Glu Lys Asp Gly Ser Ile Ser Ala Val
                165                 170                 175

Val Tyr Glu Asp Lys Asn Gly Glu Lys His Met Val Ser Ala Asn Asp
            180                 185                 190

Val Val Phe Cys Ser Gly Gly Phe Gly Phe Ser Lys Glu Met Leu Lys
        195                 200                 205

Glu Tyr Ala Pro Glu Leu Val Asn Leu Pro Thr Thr Asn Gly Gln Gln
210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Ser Ser Trp Lys Phe Leu Ala Ala Glu Ser Leu Arg
            260                 265                 270

Gly Leu Gly Gly Ile Leu Leu Asn Pro Ile Thr Gly Arg Arg Phe Val
        275                 280                 285

Asn Glu Leu Thr Thr Arg Asp Val Val Thr Ala Ala Ile Gln Lys Val
290                 295                 300

Cys Pro Gln Glu Asp Asn Arg Ala Leu Leu Val Met Gly Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Thr Leu Ser Gln Val Val Ser Glu Tyr Asn Leu Pro
            340                 345                 350

Ile Thr Val Thr Gln Leu Cys Glu Glu Leu Gln Thr Tyr Ser Ser Phe
        355                 360                 365

Thr Thr Lys Ala Asp Pro Leu Gly Arg Thr Val Ile Leu Asn Glu Phe
370                 375                 380

Gly Ser Asp Val Thr Pro Glu Thr Val Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Arg Leu Leu Lys Gly Leu Tyr Ala
            420                 425                 430

Ala Gly Glu Val Ser Gly Gly Val His Gly Ala Asn Arg Leu Gly Gly
        435                 440                 445

Ser Ser Leu Leu Glu Cys Val Val Phe Gly Arg Thr Ala Ala Glu Ser
450                 455                 460

Ile Ala Asn Asp Arg Lys
465                 470
```

<210> SEQ ID NO 27
<211> LENGTH: 1413
<212> TYPE: DNA
<213> ORGANISM: Saccharomyces mikatae
<220> FEATURE:
<221> NAME/KEY: CDS
<222> LOCATION: (1)..(1413)

<400> SEQUENCE: 27

| | | | | | | | | | | | | | | | | |
|---|---|---|---|---|---|---|---|---|---|---|---|---|---|---|---|---|
| atg | tca | tct | tct | cca | gtt | gtc | gtt | att | ggt | aca | ggc | ttg | gca | ggt | ttg | 48 |
| Met | Ser | Ser | Ser | Pro | Val | Val | Val | Ile | Gly | Thr | Gly | Leu | Ala | Gly | Leu | |
| 1 | | | | 5 | | | | | 10 | | | | | 15 | | |
| gca | act | gct | aat | gag | tta | gtc | aat | aag | tac | aac | att | cct | gtt | acc | att | 96 |
| Ala | Thr | Ala | Asn | Glu | Leu | Val | Asn | Lys | Tyr | Asn | Ile | Pro | Val | Thr | Ile | |
| | | | 20 | | | | | 25 | | | | | 30 | | | |
| ttg | gaa | aag | gca | tcc | tct | atc | ggt | ggc | aat | tcc | att | aag | gca | tct | tct | 144 |
| Leu | Glu | Lys | Ala | Ser | Ser | Ile | Gly | Gly | Asn | Ser | Ile | Lys | Ala | Ser | Ser | |
| | | 35 | | | | | 40 | | | | | 45 | | | | |
| ggt | atc | aat | ggt | gca | tgt | aca | gaa | acc | caa | cgt | cat | ttt | cac | att | gaa | 192 |
| Gly | Ile | Asn | Gly | Ala | Cys | Thr | Glu | Thr | Gln | Arg | His | Phe | His | Ile | Glu | |
| | 50 | | | | | 55 | | | | | 60 | | | | | |
| gat | act | cct | aga | ctt | ttt | gaa | gat | gat | act | gtt | caa | tcc | gcc | aag | ggc | 240 |
| Asp | Thr | Pro | Arg | Leu | Phe | Glu | Asp | Asp | Thr | Val | Gln | Ser | Ala | Lys | Gly | |
| 65 | | | | | 70 | | | | | 75 | | | | | 80 | |
| aaa | ggt | gtt | caa | gag | tta | atg | ggt | aaa | ctt | gct | aat | gat | tct | cca | ctt | 288 |
| Lys | Gly | Val | Gln | Glu | Leu | Met | Gly | Lys | Leu | Ala | Asn | Asp | Ser | Pro | Leu | |
| | | | | 85 | | | | | 90 | | | | | 95 | | |
| gct | att | gaa | tgg | tta | aag | act | gaa | ttc | gac | tta | aag | tta | gac | ctt | ttg | 336 |
| Ala | Ile | Glu | Trp | Leu | Lys | Thr | Glu | Phe | Asp | Leu | Lys | Leu | Asp | Leu | Leu | |
| | | | 100 | | | | | 105 | | | | | 110 | | | |
| gct | cag | tta | ggt | ggt | cac | tct | gtt | gct | aga | act | cat | aga | tct | tcc | ggt | 384 |
| Ala | Gln | Leu | Gly | Gly | His | Ser | Val | Ala | Arg | Thr | His | Arg | Ser | Ser | Gly | |
| | | 115 | | | | | 120 | | | | | 125 | | | | |
| aaa | ctt | cca | cca | ggt | ttc | gaa | atc | gtt | tcc | gcc | tta | tcc | aat | aac | ttg | 432 |
| Lys | Leu | Pro | Pro | Gly | Phe | Glu | Ile | Val | Ser | Ala | Leu | Ser | Asn | Asn | Leu | |
| | 130 | | | | | 135 | | | | | 140 | | | | | |
| aaa | aag | ttg | gca | gaa | acc | aag | cca | gag | tta | gtt | aag | att | aac | tta | gac | 480 |
| Lys | Lys | Leu | Ala | Glu | Thr | Lys | Pro | Glu | Leu | Val | Lys | Ile | Asn | Leu | Asp | |
| 145 | | | | | 150 | | | | | 155 | | | | | 160 | |
| tca | aag | gtc | gtt | gac | atc | cac | aaa | aag | gac | ggc | tct | att | tcc | gca | att | 528 |
| Ser | Lys | Val | Val | Asp | Ile | His | Lys | Lys | Asp | Gly | Ser | Ile | Ser | Ala | Ile | |
| | | | | 165 | | | | | 170 | | | | | 175 | | |
| gtc | tat | gat | gac | aaa | aac | ggt | gaa | aga | cat | acc | tta | tcc | act | tca | aat | 576 |
| Val | Tyr | Asp | Asp | Lys | Asn | Gly | Glu | Arg | His | Thr | Leu | Ser | Thr | Ser | Asn | |
| | | | 180 | | | | | 185 | | | | | 190 | | | |
| gtt | gtt | ttc | tgc | tct | ggt | ggt | ttc | ggt | ttt | tct | aag | gaa | atg | tta | aac | 624 |
| Val | Val | Phe | Cys | Ser | Gly | Gly | Phe | Gly | Phe | Ser | Lys | Glu | Met | Leu | Asn | |
| | | 195 | | | | | 200 | | | | | 205 | | | | |
| gag | tat | gct | cca | caa | ttg | gtc | aac | ttg | cca | acc | act | aac | ggt | cag | caa | 672 |
| Glu | Tyr | Ala | Pro | Gln | Leu | Val | Asn | Leu | Pro | Thr | Thr | Asn | Gly | Gln | Gln | |
| | 210 | | | | | 215 | | | | | 220 | | | | | |
| aca | aca | ggt | gac | ggc | caa | aga | ttg | tta | caa | aag | ctt | ggt | gca | gat | ttg | 720 |
| Thr | Thr | Gly | Asp | Gly | Gln | Arg | Leu | Leu | Gln | Lys | Leu | Gly | Ala | Asp | Leu | |
| 225 | | | | | 230 | | | | | 235 | | | | | 240 | |
| att | gat | atg | gat | caa | att | caa | gtc | cat | cct | act | ggt | ttc | atc | gac | cca | 768 |
| Ile | Asp | Met | Asp | Gln | Ile | Gln | Val | His | Pro | Thr | Gly | Phe | Ile | Asp | Pro | |
| | | | | 245 | | | | | 250 | | | | | 255 | | |
| aac | gat | aga | aac | tcc | tct | tgg | aag | ttt | ttg | gct | gct | gaa | tct | tta | aga | 816 |
| Asn | Asp | Arg | Asn | Ser | Ser | Trp | Lys | Phe | Leu | Ala | Ala | Glu | Ser | Leu | Arg | |
| | | | 260 | | | | | 265 | | | | | 270 | | | |

| | | |
|---|---|---|
| ggt ttg ggt ggt atc tta ttg aat cca att act ggt cgt aga ttt gtc<br>Gly Leu Gly Gly Ile Leu Leu Asn Pro Ile Thr Gly Arg Arg Phe Val<br>275                280                285 | | 864 |
| aac gaa ttg acc act aga gat gtc gtt act gaa gca atc cag aag cac<br>Asn Glu Leu Thr Thr Arg Asp Val Val Thr Glu Ala Ile Gln Lys His<br>290                295                300 | | 912 |
| tgt cca caa gat gat aac aga gct ttg tta gtt atg tcc gaa aag atg<br>Cys Pro Gln Asp Asp Asn Arg Ala Leu Leu Val Met Ser Glu Lys Met<br>305                310                315                320 | | 960 |
| tat aca gat ttg aaa aac aat ttg gac ttc tac atg ttc aaa aag tta<br>Tyr Thr Asp Leu Lys Asn Asn Leu Asp Phe Tyr Met Phe Lys Lys Leu<br>                325                330                335 | | 1008 |
| gtt caa aag tta tct ttg tcc caa gtt gtt tcc gag tat aag tta cca<br>Val Gln Lys Leu Ser Leu Ser Gln Val Val Ser Glu Tyr Lys Leu Pro<br>                340                345                350 | | 1056 |
| att act gtt tcc caa ttg tgt cag gaa tta caa acc tac tca tct ttt<br>Ile Thr Val Ser Gln Leu Cys Gln Glu Leu Gln Thr Tyr Ser Ser Phe<br>                355                360                365 | | 1104 |
| act tca aaa gcc gat cct ctt ggt aga acc gtt gtc tta aac gaa ttc<br>Thr Ser Lys Ala Asp Pro Leu Gly Arg Thr Val Val Leu Asn Glu Phe<br>370                375                380 | | 1152 |
| ggt gct gac atc acc cca gaa aca atg gtt ttc atc ggc gaa gtt acc<br>Gly Ala Asp Ile Thr Pro Glu Thr Met Val Phe Ile Gly Glu Val Thr<br>385                390                395                400 | | 1200 |
| cca gtc gtt cac ttt acc atg ggt ggt gct aga atc aat gtt aag gct<br>Pro Val Val His Phe Thr Met Gly Gly Ala Arg Ile Asn Val Lys Ala<br>                405                410                415 | | 1248 |
| caa gtt atc ggc aaa aac gat gag cct ttg tta aac ggt ttg tac gca<br>Gln Val Ile Gly Lys Asn Asp Glu Pro Leu Leu Asn Gly Leu Tyr Ala<br>                420                425                430 | | 1296 |
| gca ggt gaa gtt tct ggt ggt gtc cat ggt gcc aat aga tta ggt ggt<br>Ala Gly Glu Val Ser Gly Gly Val His Gly Ala Asn Arg Leu Gly Gly<br>435                440                445 | | 1344 |
| tca tct ttg ctt gaa tgt gtc gtt ttt ggt aga act gca gca gaa tca<br>Ser Ser Leu Leu Glu Cys Val Val Phe Gly Arg Thr Ala Ala Glu Ser<br>450                455                460 | | 1392 |
| att gcc aat aac cac aag taa<br>Ile Ala Asn Asn His Lys<br>465                470 | | 1413 |

<210> SEQ ID NO 28
<211> LENGTH: 470
<212> TYPE: PRT
<213> ORGANISM: Saccharomyces mikatae

<400> SEQUENCE: 28

Met Ser Ser Ser Pro Val Val Ile Gly Thr Gly Leu Ala Gly Leu
1               5                   10                  15

Ala Thr Ala Asn Glu Leu Val Asn Lys Tyr Asn Ile Pro Val Thr Ile
                20                  25                  30

Leu Glu Lys Ala Ser Ser Ile Gly Gly Asn Ser Ile Lys Ala Ser Ser
            35                  40                  45

Gly Ile Asn Gly Ala Cys Thr Glu Thr Gln Arg His Phe His Ile Glu
        50                  55                  60

Asp Thr Pro Arg Leu Phe Glu Asp Thr Val Gln Ser Ala Lys Gly
65                  70                  75                  80

Lys Gly Val Gln Glu Leu Met Gly Lys Leu Ala Asn Asp Ser Pro Leu
                85                  90                  95

Ala Ile Glu Trp Leu Lys Thr Glu Phe Asp Leu Lys Leu Asp Leu Leu

```
                100             105             110
Ala Gln Leu Gly Gly His Ser Val Ala Arg Thr His Arg Ser Ser Gly
            115                 120                 125

Lys Leu Pro Pro Gly Phe Glu Ile Val Ser Ala Leu Ser Asn Asn Leu
    130                 135                 140

Lys Lys Leu Ala Glu Thr Lys Pro Glu Leu Val Lys Ile Asn Leu Asp
145                 150                 155                 160

Ser Lys Val Val Asp Ile His Lys Lys Asp Gly Ser Ile Ser Ala Ile
                165                 170                 175

Val Tyr Asp Asp Lys Asn Gly Glu Arg His Thr Leu Ser Thr Ser Asn
            180                 185                 190

Val Val Phe Cys Ser Gly Gly Phe Gly Phe Ser Lys Glu Met Leu Asn
        195                 200                 205

Glu Tyr Ala Pro Gln Leu Val Asn Leu Pro Thr Thr Asn Gly Gln Gln
    210                 215                 220

Thr Thr Gly Asp Gly Gln Arg Leu Leu Gln Lys Leu Gly Ala Asp Leu
225                 230                 235                 240

Ile Asp Met Asp Gln Ile Gln Val His Pro Thr Gly Phe Ile Asp Pro
                245                 250                 255

Asn Asp Arg Asn Ser Ser Trp Lys Phe Leu Ala Ala Glu Ser Leu Arg
            260                 265                 270

Gly Leu Gly Gly Ile Leu Leu Asn Pro Ile Thr Gly Arg Arg Phe Val
        275                 280                 285

Asn Glu Leu Thr Thr Arg Asp Val Val Thr Glu Ala Ile Gln Lys His
    290                 295                 300

Cys Pro Gln Asp Asp Asn Arg Ala Leu Leu Val Met Ser Glu Lys Met
305                 310                 315                 320

Tyr Thr Asp Leu Lys Asn Asn Leu Asp Phe Tyr Met Phe Lys Lys Leu
                325                 330                 335

Val Gln Lys Leu Ser Leu Ser Gln Val Val Ser Glu Tyr Lys Leu Pro
            340                 345                 350

Ile Thr Val Ser Gln Leu Cys Gln Glu Leu Gln Thr Tyr Ser Ser Phe
        355                 360                 365

Thr Ser Lys Ala Asp Pro Leu Gly Arg Thr Val Val Leu Asn Glu Phe
    370                 375                 380

Gly Ala Asp Ile Thr Pro Glu Thr Met Val Phe Ile Gly Glu Val Thr
385                 390                 395                 400

Pro Val Val His Phe Thr Met Gly Gly Ala Arg Ile Asn Val Lys Ala
                405                 410                 415

Gln Val Ile Gly Lys Asn Asp Glu Pro Leu Leu Asn Gly Leu Tyr Ala
            420                 425                 430

Ala Gly Glu Val Ser Gly Gly Val His Gly Ala Asn Arg Leu Gly Gly
        435                 440                 445

Ser Ser Leu Leu Glu Cys Val Val Phe Gly Arg Thr Ala Ala Glu Ser
    450                 455                 460

Ile Ala Asn Asn His Lys
465                 470

<210> SEQ ID NO 29
<211> LENGTH: 1413
<212> TYPE: DNA
<213> ORGANISM: Kluyveromyces polysporus
<220> FEATURE:
<221> NAME/KEY: CDS
<222> LOCATION: (1)..(1413)
```

```
<400> SEQUENCE: 29 atg tca acc aaa aag cca gtc gtc atc att ggt act ggt tta gcc ggt      48
Met Ser Thr Lys Lys Pro Val Val Ile Ile Gly Thr Gly Leu Ala Gly
1               5                   10                  15 ttg tct gct ggt aat caa ttg gtc aat atg cat aaa gtt cct atc att      96
Leu Ser Ala Gly Asn Gln Leu Val Asn Met His Lys Val Pro Ile Ile
                20                  25                  30 atg ttg gac aag gca tcc tcc att ggt ggt aat tct aca aag gct tcc     144
Met Leu Asp Lys Ala Ser Ser Ile Gly Gly Asn Ser Thr Lys Ala Ser
            35                  40                  45 tct ggt atc aac ggt gct tct act att act caa cag caa ctt aat gtt     192
Ser Gly Ile Asn Gly Ala Ser Thr Ile Thr Gln Gln Gln Leu Asn Val
50                  55                  60 aaa gac tct cct gac tta ttc ctt caa gat act gtt aag tct gct aag     240
Lys Asp Ser Pro Asp Leu Phe Leu Gln Asp Thr Val Lys Ser Ala Lys
65                  70                  75                  80 ggt aga ggt att gag tcc ctt atg aaa aag tta tca caa gac tcc aac     288
Gly Arg Gly Ile Glu Ser Leu Met Lys Lys Leu Ser Gln Asp Ser Asn
                85                  90                  95 tct gct atc cat tgg ttg caa cag gat ttt gat ttg aag ttg gat ttg     336
Ser Ala Ile His Trp Leu Gln Gln Asp Phe Asp Leu Lys Leu Asp Leu
            100                 105                 110 tta gct caa ttg ggt ggt cat tcc gtt cct aga aca cac cgt tcc tca     384
Leu Ala Gln Leu Gly Gly His Ser Val Pro Arg Thr His Arg Ser Ser
        115                 120                 125 ggc aag tta cct cca ggc ttc gaa att gtc caa gct tta tct aac aag     432
Gly Lys Leu Pro Pro Gly Phe Glu Ile Val Gln Ala Leu Ser Asn Lys
    130                 135                 140 tta aag gct att tct gag tcc gat cca gaa ttc gtt aga atc tta ctt     480
Leu Lys Ala Ile Ser Glu Ser Asp Pro Glu Phe Val Arg Ile Leu Leu
145                 150                 155                 160 aac tcc aag gtt gtt gat gtt tcc gtt aac aat gag ggc aag gtc gaa     528
Asn Ser Lys Val Val Asp Val Ser Val Asn Asn Glu Gly Lys Val Glu
                165                 170                 175 tct att gac tat gtt gat gca gaa ggt aaa cat cac aaa atc gct act     576
Ser Ile Asp Tyr Val Asp Ala Glu Gly Lys His His Lys Ile Ala Thr
            180                 185                 190 gat aac gtt gtc ttt tgt tcc ggt ggt ttc ggt cac tca gca gaa atg     624
Asp Asn Val Val Phe Cys Ser Gly Gly Phe Gly His Ser Ala Glu Met
        195                 200                 205 ttg aac aag tat gca cca gaa tta gct aac ttg cca act act aac ggt     672
Leu Asn Lys Tyr Ala Pro Glu Leu Ala Asn Leu Pro Thr Thr Asn Gly
    210                 215                 220 caa caa acc act ggc gat ggt cag aga atc ttg gag aaa ttg ggt gca     720
Gln Gln Thr Thr Gly Asp Gly Gln Arg Ile Leu Glu Lys Leu Gly Ala
225                 230                 235                 240 gac ttg att gat atg tcc caa att caa gtt cac cca aca ggt ttc atc     768
Asp Leu Ile Asp Met Ser Gln Ile Gln Val His Pro Thr Gly Phe Ile
                245                 250                 255 gat cca gca aac aga gat tct aag tgg aag ttt ttg gct gcc gaa gca     816
Asp Pro Ala Asn Arg Asp Ser Lys Trp Lys Phe Leu Ala Ala Glu Ala
            260                 265                 270 tta aga ggt tta ggt ggt atc tta ctt aat cca tct acc ggc aag aga     864
Leu Arg Gly Leu Gly Gly Ile Leu Leu Asn Pro Ser Thr Gly Lys Arg
        275                 280                 285 ttc gtt aat gag tta acc acc aga gat ttg gtc aca gaa gct atc caa     912
Phe Val Asn Glu Leu Thr Thr Arg Asp Leu Val Thr Glu Ala Ile Gln
    290                 295                 300
```

```
tca caa tgt cca aga gat gac aat aag gca ttc ctt gtt atg tct gaa    960
Ser Gln Cys Pro Arg Asp Asp Asn Lys Ala Phe Leu Val Met Ser Glu
305                 310                 315                 320 aag gtc tat gag aat tac aaa aac aac atg gac ttt tac tta ttc aaa    1008
Lys Val Tyr Glu Asn Tyr Lys Asn Asn Met Asp Phe Tyr Leu Phe Lys
            325                 330                 335 aag tta gtt tcc aag atg acc att aag gaa ttt gtc gaa act tac aag    1056
Lys Leu Val Ser Lys Met Thr Ile Lys Glu Phe Val Glu Thr Tyr Lys
        340                 345                 350 ttg cca att tct gcc gac gcc gtt acc caa gac tta atc gac tat tca    1104
Leu Pro Ile Ser Ala Asp Ala Val Thr Gln Asp Leu Ile Asp Tyr Ser
    355                 360                 365 gtt gat aag acc gat aag ttt ggt aga cca ttg gtt atc aac gtt ttt    1152
Val Asp Lys Thr Asp Lys Phe Gly Arg Pro Leu Val Ile Asn Val Phe
370                 375                 380 gat gaa aag ttg acc gaa gat tcc gaa atc tat gtt ggt gaa gtt aca    1200
Asp Glu Lys Leu Thr Glu Asp Ser Glu Ile Tyr Val Gly Glu Val Thr
385                 390                 395                 400 cca gtt gtc cat ttc act atg ggt ggt gca aag atc aat act gaa tct    1248
Pro Val Val His Phe Thr Met Gly Gly Ala Lys Ile Asn Thr Glu Ser
            405                 410                 415 caa gtt atc aac aaa aac ggt caa gtt ttg gca aag ggt atc tac gca    1296
Gln Val Ile Asn Lys Asn Gly Gln Val Leu Ala Lys Gly Ile Tyr Ala
        420                 425                 430 gca ggt gaa gtc tcc ggt ggt gtt cac ggt tct aat aga tta ggt ggt    1344
Ala Gly Glu Val Ser Gly Gly Val His Gly Ser Asn Arg Leu Gly Gly
    435                 440                 445 tca tct ttg tta gaa tgc gtc gtt tac ggt aga tct gct gca gat aac    1392
Ser Ser Leu Leu Glu Cys Val Val Tyr Gly Arg Ser Ala Ala Asp Asn
450                 455                 460 att gcc aaa aac att gaa taa                                        1413
Ile Ala Lys Asn Ile Glu
465                 470

<210> SEQ ID NO 30
<211> LENGTH: 470
<212> TYPE: PRT
<213> ORGANISM: Kluyveromyces polysporus

<400> SEQUENCE: 30

Met Ser Thr Lys Lys Pro Val Val Ile Ile Gly Thr Gly Leu Ala Gly
1               5                   10                  15

Leu Ser Ala Gly Asn Gln Leu Val Asn Met His Lys Val Pro Ile Ile
            20                  25                  30

Met Leu Asp Lys Ala Ser Ser Ile Gly Gly Asn Ser Thr Lys Ala Ser
        35                  40                  45

Ser Gly Ile Asn Gly Ala Ser Thr Ile Thr Gln Gln Leu Asn Val
    50                  55                  60

Lys Asp Ser Pro Asp Leu Phe Leu Gln Asp Thr Val Lys Ser Ala Lys
65                  70                  75                  80

Gly Arg Gly Ile Glu Ser Leu Met Lys Lys Leu Ser Gln Asp Ser Asn
                85                  90                  95

Ser Ala Ile His Trp Leu Gln Gln Asp Phe Asp Leu Lys Leu Asp Leu
            100                 105                 110

Leu Ala Gln Leu Gly Gly His Ser Val Pro Arg Thr His Arg Ser Ser
        115                 120                 125

Gly Lys Leu Pro Pro Gly Phe Glu Ile Val Gln Ala Leu Ser Asn Lys
    130                 135                 140
```

```
Leu Lys Ala Ile Ser Glu Ser Asp Pro Glu Phe Val Arg Ile Leu Leu
145                 150                 155                 160

Asn Ser Lys Val Val Asp Val Ser Val Asn Asn Glu Gly Lys Val Glu
            165                 170                 175

Ser Ile Asp Tyr Val Asp Ala Glu Gly Lys His His Lys Ile Ala Thr
        180                 185                 190

Asp Asn Val Val Phe Cys Ser Gly Phe Gly His Ser Ala Glu Met
    195                 200                 205

Leu Asn Lys Tyr Ala Pro Glu Leu Ala Asn Leu Pro Thr Thr Asn Gly
    210                 215                 220

Gln Gln Thr Thr Gly Asp Gly Gln Arg Ile Leu Glu Lys Leu Gly Ala
225                 230                 235                 240

Asp Leu Ile Asp Met Ser Gln Ile Gln Val His Pro Thr Gly Phe Ile
                245                 250                 255

Asp Pro Ala Asn Arg Asp Ser Lys Trp Lys Phe Leu Ala Ala Glu Ala
                260                 265                 270

Leu Arg Gly Leu Gly Gly Ile Leu Leu Asn Pro Ser Thr Gly Lys Arg
            275                 280                 285

Phe Val Asn Glu Leu Thr Thr Arg Asp Leu Val Thr Glu Ala Ile Gln
    290                 295                 300

Ser Gln Cys Pro Arg Asp Asp Asn Lys Ala Phe Leu Val Met Ser Glu
305                 310                 315                 320

Lys Val Tyr Glu Asn Tyr Lys Asn Asn Met Asp Phe Tyr Leu Phe Lys
                325                 330                 335

Lys Leu Val Ser Lys Met Thr Ile Lys Glu Phe Val Thr Tyr Lys
            340                 345                 350

Leu Pro Ile Ser Ala Asp Ala Val Thr Gln Asp Leu Ile Asp Tyr Ser
        355                 360                 365

Val Asp Lys Thr Asp Lys Phe Gly Arg Pro Leu Val Ile Asn Val Phe
    370                 375                 380

Asp Glu Lys Leu Thr Glu Asp Ser Glu Ile Tyr Val Gly Glu Val Thr
385                 390                 395                 400

Pro Val Val His Phe Thr Met Gly Gly Ala Lys Ile Asn Thr Glu Ser
                405                 410                 415

Gln Val Ile Asn Lys Asn Gly Gln Val Leu Ala Lys Gly Ile Tyr Ala
            420                 425                 430

Ala Gly Glu Val Ser Gly Gly Val His Gly Ser Asn Arg Leu Gly Gly
        435                 440                 445

Ser Ser Leu Leu Glu Cys Val Val Tyr Gly Arg Ser Ala Ala Asp Asn
    450                 455                 460

Ile Ala Lys Asn Ile Glu
465                 470

<210> SEQ ID NO 31
<211> LENGTH: 1464
<212> TYPE: DNA
<213> ORGANISM: Kluyveromyces marxianus
<220> FEATURE:
<221> NAME/KEY: CDS
<222> LOCATION: (1)..(1464)

<400> SEQUENCE: 31 atg ttg cac aga tac atc cgt ttg ttc tcc ttc tgc gtc atc ttg tac        48
Met Leu His Arg Tyr Ile Arg Leu Phe Ser Phe Cys Val Ile Leu Tyr
1               5                   10                  15 tta gtc tat ttg tta ctt act aag gag tca aac gtc atg tct aag cct        96
```

```
                Leu Val Tyr Leu Leu Thr Lys Glu Ser Asn Val Met Ser Lys Pro
                             20                  25                  30 gtt gtt gtt att ggt tct ggt tta gca ggc tta aca aca tct tca caa          144
Val Val Val Ile Gly Ser Gly Leu Ala Gly Leu Thr Thr Ser Ser Gln
             35                  40                  45 tta gca aag ttt aac att cca atc gtc ctt tta gaa aag aca tct tcc          192
Leu Ala Lys Phe Asn Ile Pro Ile Val Leu Leu Glu Lys Thr Ser Ser
 50                  55                  60 att ggt ggt aat tcc att aag gca tct tct ggt atc aat ggc gca ggc          240
Ile Gly Gly Asn Ser Ile Lys Ala Ser Ser Gly Ile Asn Gly Ala Gly
 65                  70                  75                  80 acc gaa act caa tct cgt tta cac gtt gaa gat cac cca gaa ttg ttt          288
Thr Glu Thr Gln Ser Arg Leu His Val Glu Asp His Pro Glu Leu Phe
                 85                  90                  95 gct gat gat acc att aag tct gca aaa ggt aaa ggt gtt gtc gct ttg          336
Ala Asp Asp Thr Ile Lys Ser Ala Lys Gly Lys Gly Val Val Ala Leu
                100                 105                 110 atg gaa aag tta tct aaa gac tcc tct gat gct att tcc tgg tta caa          384
Met Glu Lys Leu Ser Lys Asp Ser Ser Asp Ala Ile Ser Trp Leu Gln
            115                 120                 125 aac gac ttc aag att cct ttg gat aag tta gct caa tta ggc ggt cat          432
Asn Asp Phe Lys Ile Pro Leu Asp Lys Leu Ala Gln Leu Gly Gly His
130                 135                 140 tcc gtt cct aga acc cat aga tca tcc ggc aag ctt cca cca ggt ttc          480
Ser Val Pro Arg Thr His Arg Ser Ser Gly Lys Leu Pro Pro Gly Phe
145                 150                 155                 160 caa att gtc gat acc ttg aaa aag gcc ttg gag tct tat gac tct aaa          528
Gln Ile Val Asp Thr Leu Lys Lys Ala Leu Glu Ser Tyr Asp Ser Lys
                165                 170                 175 gca gtt aag atc caa ttg aat tct aag gtc gtt gat gtt aag ctt gat          576
Ala Val Lys Ile Gln Leu Asn Ser Lys Val Val Asp Val Lys Leu Asp
            180                 185                 190 tcc aat aac aga gtt tca tct gtt gtt ttc gaa gat caa gat ggt act          624
Ser Asn Asn Arg Val Ser Ser Val Val Phe Glu Asp Gln Asp Gly Thr
        195                 200                 205 cac acc att gaa acc aac aac gtc gtt ttc tgt act ggt ggt ttc ggt          672
His Thr Ile Glu Thr Asn Asn Val Val Phe Cys Thr Gly Gly Phe Gly
    210                 215                 220 ttc aac aaa aag tta ttg gag aag tat gca cca cac ttg gtc gac ttg          720
Phe Asn Lys Lys Leu Leu Glu Lys Tyr Ala Pro His Leu Val Asp Leu
225                 230                 235                 240 cca act acc aac ggt gag caa acc tta ggt gaa ggt cag gtc tta ttg          768
Pro Thr Thr Asn Gly Glu Gln Thr Leu Gly Glu Gly Gln Val Leu Leu
                245                 250                 255 gaa aaa ctt ggt gct aag ttg att gat atg gac caa att caa gtt cat          816
Glu Lys Leu Gly Ala Lys Leu Ile Asp Met Asp Gln Ile Gln Val His
            260                 265                 270 cca act ggc ttt atc gat cca gcc aat cca gat tct aat tgg aag ttt          864
Pro Thr Gly Phe Ile Asp Pro Ala Asn Pro Asp Ser Asn Trp Lys Phe
        275                 280                 285 ttg gct gcc gag gcc tta aga ggt tta ggt ggt gtc ttg atc aat cca          912
Leu Ala Ala Glu Ala Leu Arg Gly Leu Gly Gly Val Leu Ile Asn Pro
    290                 295                 300 cac act ggt cag aga ttt gtt aac gaa ttg aca act aga gac atg gtc          960
His Thr Gly Gln Arg Phe Val Asn Glu Leu Thr Thr Arg Asp Met Val
305                 310                 315                 320 acc gaa gct atc cag tct aag tcc gaa tcc aag act gct tac ttg gtt         1008
Thr Glu Ala Ile Gln Ser Lys Ser Glu Ser Lys Thr Ala Tyr Leu Val
                325                 330                 335
```

```
atg tcc gag tcc tta tac gag aac tac aag cca aac atg gac ttc tat    1056
Met Ser Glu Ser Leu Tyr Glu Asn Tyr Lys Pro Asn Met Asp Phe Tyr
        340                 345                 350 atg ttc aaa aag ctt gtt tcc aaa aag acc gtt gct gaa ttt gct gaa    1104
Met Phe Lys Lys Leu Val Ser Lys Lys Thr Val Ala Glu Phe Ala Glu
    355                 360                 365 gat ttg cca gtt tct gtt gac caa ctt att gca gaa ctt tca act tat    1152
Asp Leu Pro Val Ser Val Asp Gln Leu Ile Ala Glu Leu Ser Thr Tyr
370                 375                 380 tcc gac ttg tct aag gat gat cat ttg ggt aga aag ttt aga gaa aac    1200
Ser Asp Leu Ser Lys Asp Asp His Leu Gly Arg Lys Phe Arg Glu Asn
385                 390                 395                 400 act ttt ggt tcc tca tta tca tca gac tca acc att ttc gtt ggc aag    1248
Thr Phe Gly Ser Ser Leu Ser Ser Asp Ser Thr Ile Phe Val Gly Lys
                405                 410                 415 att act cct gtt gtt cac ttc aca atg ggt ggt gca aag att gat gaa    1296
Ile Thr Pro Val Val His Phe Thr Met Gly Gly Ala Lys Ile Asp Glu
            420                 425                 430 caa gct aga gtc ttg aat gca gaa ggt aaa cca tta gct act ggt atc    1344
Gln Ala Arg Val Leu Asn Ala Glu Gly Lys Pro Leu Ala Thr Gly Ile
        435                 440                 445 tac gcc gct ggt gaa gtt tct ggt ggt gtc cat ggt gct aat aga tta    1392
Tyr Ala Ala Gly Glu Val Ser Gly Gly Val His Gly Ala Asn Arg Leu
450                 455                 460 ggt ggt tcc tct ttg tta gaa tgt gtt gtc ttt ggt aga caa gca gca    1440
Gly Gly Ser Ser Leu Leu Glu Cys Val Val Phe Gly Arg Gln Ala Ala
465                 470                 475                 480 aaa tcc att aga gca aac ttg taa                                    1464
Lys Ser Ile Arg Ala Asn Leu
                485

<210> SEQ ID NO 32
<211> LENGTH: 487
<212> TYPE: PRT
<213> ORGANISM: Kluyveromyces marxianus

<400> SEQUENCE: 32

Met Leu His Arg Tyr Ile Arg Leu Phe Ser Phe Cys Val Ile Leu Tyr
1               5                   10                  15

Leu Val Tyr Leu Leu Thr Lys Glu Ser Asn Val Met Ser Lys Pro
            20                  25                  30

Val Val Val Ile Gly Ser Gly Leu Ala Gly Leu Thr Thr Ser Ser Gln
        35                  40                  45

Leu Ala Lys Phe Asn Ile Pro Ile Val Leu Leu Glu Lys Thr Ser Ser
    50                  55                  60

Ile Gly Gly Asn Ser Ile Lys Ala Ser Ser Gly Ile Asn Gly Ala Gly
65                  70                  75                  80

Thr Glu Thr Gln Ser Arg Leu His Val Glu Asp His Pro Glu Leu Phe
                85                  90                  95

Ala Asp Asp Thr Ile Lys Ser Ala Lys Gly Lys Gly Val Val Ala Leu
            100                 105                 110

Met Glu Lys Leu Ser Lys Asp Ser Ser Asp Ala Ile Ser Trp Leu Gln
        115                 120                 125

Asn Asp Phe Lys Ile Pro Leu Asp Lys Leu Ala Gln Leu Gly Gly His
    130                 135                 140

Ser Val Pro Arg Thr His Arg Ser Ser Gly Lys Leu Pro Pro Gly Phe
145                 150                 155                 160

Gln Ile Val Asp Thr Leu Lys Lys Ala Leu Glu Ser Tyr Asp Ser Lys
```

```
                    165                 170                 175
Ala Val Lys Ile Gln Leu Asn Ser Lys Val Asp Val Lys Leu Asp
                180                 185                 190

Ser Asn Asn Arg Val Ser Ser Val Phe Glu Asp Gln Asp Gly Thr
            195                 200                 205

His Thr Ile Glu Thr Asn Asn Val Val Phe Cys Thr Gly Gly Phe Gly
    210                 215                 220

Phe Asn Lys Lys Leu Leu Glu Lys Tyr Ala Pro His Leu Val Asp Leu
225                 230                 235                 240

Pro Thr Thr Asn Gly Glu Gln Thr Leu Gly Glu Gly Gln Val Leu Leu
                245                 250                 255

Glu Lys Leu Gly Ala Lys Leu Ile Asp Met Asp Gln Ile Gln Val His
            260                 265                 270

Pro Thr Gly Phe Ile Asp Pro Ala Asn Pro Asp Ser Asn Trp Lys Phe
        275                 280                 285

Leu Ala Ala Glu Ala Leu Arg Gly Leu Gly Gly Val Leu Ile Asn Pro
    290                 295                 300

His Thr Gly Gln Arg Phe Val Asn Glu Leu Thr Thr Arg Asp Met Val
305                 310                 315                 320

Thr Glu Ala Ile Gln Ser Lys Ser Glu Ser Lys Thr Ala Tyr Leu Val
                325                 330                 335

Met Ser Glu Ser Leu Tyr Glu Asn Tyr Lys Pro Asn Met Asp Phe Tyr
            340                 345                 350

Met Phe Lys Lys Leu Val Ser Lys Lys Thr Val Ala Glu Phe Ala Glu
        355                 360                 365

Asp Leu Pro Val Ser Val Asp Gln Leu Ile Ala Glu Leu Ser Thr Tyr
    370                 375                 380

Ser Asp Leu Ser Lys Asp Asp His Leu Gly Arg Lys Phe Arg Glu Asn
385                 390                 395                 400

Thr Phe Gly Ser Ser Leu Ser Ser Asp Ser Thr Ile Phe Val Gly Lys
                405                 410                 415

Ile Thr Pro Val Val His Phe Thr Met Gly Gly Ala Lys Ile Asp Glu
            420                 425                 430

Gln Ala Arg Val Leu Asn Ala Glu Gly Lys Pro Leu Ala Thr Gly Ile
        435                 440                 445

Tyr Ala Ala Gly Glu Val Ser Gly Gly Val His Gly Ala Asn Arg Leu
    450                 455                 460

Gly Gly Ser Ser Leu Leu Glu Cys Val Val Phe Gly Arg Gln Ala Ala
465                 470                 475                 480

Lys Ser Ile Arg Ala Asn Leu
                485

<210> SEQ ID NO 33
<211> LENGTH: 1518
<212> TYPE: DNA
<213> ORGANISM: Issatchenkia orientalis
<220> FEATURE:
<221> NAME/KEY: CDS
<222> LOCATION: (1)..(1518)

<400> SEQUENCE: 33 atg ggt gtc cag ttt atc gaa aat acc att atc gtt gtc ttt ggt gcg    48
Met Gly Val Gln Phe Ile Glu Asn Thr Ile Ile Val Val Phe Gly Ala
1               5                   10                  15 tct gga gat tta gcc aag aag aag act ttc ccc gcc ctg ttt gga cta    96
Ser Gly Asp Leu Ala Lys Lys Lys Thr Phe Pro Ala Leu Phe Gly Leu
```

```
                        20                  25                  30
ttc agg gag ggc cag ctc tca gaa aca acc aaa atc att ggg ttt gct       144
Phe Arg Glu Gly Gln Leu Ser Glu Thr Thr Lys Ile Ile Gly Phe Ala
            35                  40                  45 cga tca aaa cta tca aat gat gac ttg agg aac aga ata aag ccg tac       192
Arg Ser Lys Leu Ser Asn Asp Asp Leu Arg Asn Arg Ile Lys Pro Tyr
 50                  55                  60 ttg aaa ttg aac aag aga aca gat gct gaa agg cag tct ctg gag aag       240
Leu Lys Leu Asn Lys Arg Thr Asp Ala Glu Arg Gln Ser Leu Glu Lys
 65                  70                  75                  80 ttt ctg cag att ctc gag tat cac cag tca aac tac gac gac agt gaa       288
Phe Leu Gln Ile Leu Glu Tyr His Gln Ser Asn Tyr Asp Asp Ser Glu
                85                  90                  95 ggt ttt gaa aaa ttg gag aag cta atc aat aag tac gac gat gag gca       336
Gly Phe Glu Lys Leu Glu Lys Leu Ile Asn Lys Tyr Asp Asp Glu Ala
            100                 105                 110 aac gtg aaa gag tct cac agg ttg tac tat ttg gct tta cca ccg tct       384
Asn Val Lys Glu Ser His Arg Leu Tyr Tyr Leu Ala Leu Pro Pro Ser
        115                 120                 125 gtc ttt aca acc gtt gca aca atg ttg aaa aaa cat tgt cat cca ggt       432
Val Phe Thr Thr Val Ala Thr Met Leu Lys Lys His Cys His Pro Gly
130                 135                 140 gat tct ggt att gct agg cta att gtc gag aaa ccc ttt ggc cat gac       480
Asp Ser Gly Ile Ala Arg Leu Ile Val Glu Lys Pro Phe Gly His Asp
145                 150                 155                 160 ttg agc tcg tcc cgt gag cta caa aag tct tta gct cca ctt tgg aat       528
Leu Ser Ser Ser Arg Glu Leu Gln Lys Ser Leu Ala Pro Leu Trp Asn
                165                 170                 175 gaa gat gaa ttg ttt aga att gat cat tat ttg ggc aaa gaa atg gtt       576
Glu Asp Glu Leu Phe Arg Ile Asp His Tyr Leu Gly Lys Glu Met Val
            180                 185                 190 aag aat tta att cct ttg agg ttt tca aat acg ttt ttg agc agt tct       624
Lys Asn Leu Ile Pro Leu Arg Phe Ser Asn Thr Phe Leu Ser Ser Ser
        195                 200                 205 tgg aac aat caa ttt att gac acc atc caa atc act ttt aag gag aac       672
Trp Asn Asn Gln Phe Ile Asp Thr Ile Gln Ile Thr Phe Lys Glu Asn
210                 215                 220 ttt gga act gaa gga cgt ggt ggt tac ttt gat tcc att ggt ata ata       720
Phe Gly Thr Glu Gly Arg Gly Gly Tyr Phe Asp Ser Ile Gly Ile Ile
225                 230                 235                 240 aga gat gtt atc caa aat cat ttg tta caa gtc ttg act att gtt ttg       768
Arg Asp Val Ile Gln Asn His Leu Leu Gln Val Leu Thr Ile Val Leu
                245                 250                 255 atg gaa aaa cca gcg gat ttt aat gga gaa tct atc aga gat gaa aag       816
Met Glu Lys Pro Ala Asp Phe Asn Gly Glu Ser Ile Arg Asp Glu Lys
            260                 265                 270 gtt aaa gtg tta aag gca att gaa caa att gat ttc aat aat gtg ttg       864
Val Lys Val Leu Lys Ala Ile Glu Gln Ile Asp Phe Asn Asn Val Leu
        275                 280                 285 gta ggt caa tat gat aaa tct gaa gat ggt agt aaa cct ggt tac ttg       912
Val Gly Gln Tyr Asp Lys Ser Glu Asp Gly Ser Lys Pro Gly Tyr Leu
290                 295                 300 gat gat gat acc gtc aat cca gat tct aaa gct gtc act tat gct gcc       960
Asp Asp Asp Thr Val Asn Pro Asp Ser Lys Ala Val Thr Tyr Ala Ala
305                 310                 315                 320 tta gtt tta aat gtg gca aac gaa aga tgg aat aat gtt ccg atc att      1008
Leu Val Leu Asn Val Ala Asn Glu Arg Trp Asn Asn Val Pro Ile Ile
                325                 330                 335 cta aag gca ggc aag gcc ttg aat caa tcc aag gtg gaa att aga atc      1056
```

-continued

```
Leu Lys Ala Gly Lys Ala Leu Asn Gln Ser Lys Val Glu Ile Arg Ile
                340                 345                 350 cag ttc aaa cca gta gaa aat gga atc ttc aaa aac tct gct agg aat      1104
Gln Phe Lys Pro Val Glu Asn Gly Ile Phe Lys Asn Ser Ala Arg Asn
            355                 360                 365 gag ttg gtt att agg atc caa cca aac gag gca atg tat ttg aaa atg      1152
Glu Leu Val Ile Arg Ile Gln Pro Asn Glu Ala Met Tyr Leu Lys Met
370                 375                 380 aac atc aaa gta cct ggt gtt tcc aat caa gtg tcg att tca gaa atg      1200
Asn Ile Lys Val Pro Gly Val Ser Asn Gln Val Ser Ile Ser Glu Met
385                 390                 395                 400 gat ttg act tac aag aat agg tat tcc tcc gaa ttt tac att cca gaa      1248
Asp Leu Thr Tyr Lys Asn Arg Tyr Ser Ser Glu Phe Tyr Ile Pro Glu
            405                 410                 415 gct tat gaa tct ttg att aaa gat gcc tta atg gat gat cat tca aat      1296
Ala Tyr Glu Ser Leu Ile Lys Asp Ala Leu Met Asp Asp His Ser Asn
            420                 425                 430 ttt gtt aga gac gat gaa ttg gac att tca tgg gct ttg ttc act cca      1344
Phe Val Arg Asp Asp Glu Leu Asp Ile Ser Trp Ala Leu Phe Thr Pro
            435                 440                 445 tta cta gaa cat atc gaa ggc ccc gat ggt cca act cca acc aag tat      1392
Leu Leu Glu His Ile Glu Gly Pro Asp Gly Pro Thr Pro Thr Lys Tyr
450                 455                 460 cct tac ggt tcc aga ggt cca aag gag att gac gaa ttt ttg aga aac      1440
Pro Tyr Gly Ser Arg Gly Pro Lys Glu Ile Asp Glu Phe Leu Arg Asn
465                 470                 475                 480 cat ggt tat gta aag gaa cca aga gaa aat tac caa tgg cca tta act      1488
His Gly Tyr Val Lys Glu Pro Arg Glu Asn Tyr Gln Trp Pro Leu Thr
            485                 490                 495 act cct aaa gaa ttg aac agt tca aag ttt                              1518
Thr Pro Lys Glu Leu Asn Ser Ser Lys Phe
            500                 505

<210> SEQ ID NO 34
<211> LENGTH: 506
<212> TYPE: PRT
<213> ORGANISM: Issatchenkia orientalis

<400> SEQUENCE: 34

Met Gly Val Gln Phe Ile Glu Asn Thr Ile Val Val Phe Gly Ala
1               5                   10                  15

Ser Gly Asp Leu Ala Lys Lys Thr Phe Pro Ala Leu Phe Gly Leu
                20                  25                  30

Phe Arg Glu Gly Gln Leu Ser Glu Thr Thr Lys Ile Ile Gly Phe Ala
            35                  40                  45

Arg Ser Lys Leu Ser Asn Asp Asp Leu Arg Asn Arg Ile Lys Pro Tyr
50                  55                  60

Leu Lys Leu Asn Lys Arg Thr Asp Ala Glu Arg Gln Ser Leu Glu Lys
65                  70                  75                  80

Phe Leu Gln Ile Leu Glu Tyr His Gln Ser Asn Tyr Asp Asp Ser Glu
                85                  90                  95

Gly Phe Glu Lys Leu Glu Lys Leu Ile Asn Lys Tyr Asp Asp Glu Ala
            100                 105                 110

Asn Val Lys Glu Ser His Arg Leu Tyr Tyr Leu Ala Leu Pro Pro Ser
            115                 120                 125

Val Phe Thr Thr Val Ala Thr Met Leu Lys Lys His Cys His Pro Gly
130                 135                 140

Asp Ser Gly Ile Ala Arg Leu Ile Val Glu Lys Pro Phe Gly His Asp
```

```
        145                 150                 155                 160
Leu Ser Ser Arg Glu Leu Gln Lys Ser Leu Ala Pro Leu Trp Asn
                165                 170                 175

Glu Asp Glu Leu Phe Arg Ile Asp His Tyr Leu Gly Lys Glu Met Val
            180                 185                 190

Lys Asn Leu Ile Pro Leu Arg Phe Ser Asn Thr Phe Leu Ser Ser Ser
                195                 200                 205

Trp Asn Asn Gln Phe Ile Asp Thr Ile Gln Ile Thr Phe Lys Glu Asn
210                 215                 220

Phe Gly Thr Glu Gly Arg Gly Gly Tyr Phe Asp Ser Ile Gly Ile Ile
225                 230                 235                 240

Arg Asp Val Ile Gln Asn His Leu Leu Gln Val Leu Thr Ile Val Leu
                245                 250                 255

Met Glu Lys Pro Ala Asp Phe Asn Gly Glu Ser Ile Arg Asp Glu Lys
                260                 265                 270

Val Lys Val Leu Lys Ala Ile Glu Gln Ile Asp Phe Asn Asn Val Leu
            275                 280                 285

Val Gly Gln Tyr Asp Lys Ser Glu Asp Gly Ser Lys Pro Gly Tyr Leu
        290                 295                 300

Asp Asp Asp Thr Val Asn Pro Asp Ser Lys Ala Val Thr Tyr Ala Ala
305                 310                 315                 320

Leu Val Leu Asn Val Ala Asn Glu Arg Trp Asn Asn Val Pro Ile Ile
                325                 330                 335

Leu Lys Ala Gly Lys Ala Leu Asn Gln Ser Lys Val Glu Ile Arg Ile
                340                 345                 350

Gln Phe Lys Pro Val Glu Asn Gly Ile Phe Lys Asn Ser Ala Arg Asn
            355                 360                 365

Glu Leu Val Ile Arg Ile Gln Pro Asn Glu Ala Met Tyr Leu Lys Met
        370                 375                 380

Asn Ile Lys Val Pro Gly Val Ser Asn Gln Val Ser Ile Ser Glu Met
385                 390                 395                 400

Asp Leu Thr Tyr Lys Asn Arg Tyr Ser Ser Glu Phe Tyr Ile Pro Glu
                405                 410                 415

Ala Tyr Glu Ser Leu Ile Lys Asp Ala Leu Met Asp Asp His Ser Asn
                420                 425                 430

Phe Val Arg Asp Asp Glu Leu Asp Ile Ser Trp Ala Leu Phe Thr Pro
            435                 440                 445

Leu Leu Glu His Ile Glu Gly Pro Asp Gly Pro Thr Pro Thr Lys Tyr
        450                 455                 460

Pro Tyr Gly Ser Arg Gly Pro Lys Glu Ile Asp Glu Phe Leu Arg Asn
465                 470                 475                 480

His Gly Tyr Val Lys Glu Pro Arg Glu Asn Tyr Gln Trp Pro Leu Thr
                485                 490                 495

Thr Pro Lys Glu Leu Asn Ser Ser Lys Phe
                500                 505

<210> SEQ ID NO 35
<211> LENGTH: 759
<212> TYPE: DNA
<213> ORGANISM: Issatchenkia orientalis
<220> FEATURE:
<221> NAME/KEY: CDS
<222> LOCATION: (1)..(759)

<400> SEQUENCE: 35
```

```
atg gtc aag gtt tat tca tat tcc aac aat gat gag ata gct caa tca      48
Met Val Lys Val Tyr Ser Tyr Ser Asn Asn Asp Glu Ile Ala Gln Ser
1               5                   10                  15 ttg gca aag ttt ata gtt tca caa cag gat tcg gtt ctt gca acc aag      96
Leu Ala Lys Phe Ile Val Ser Gln Gln Asp Ser Val Leu Ala Thr Lys
            20                  25                  30 gag aaa ttc aac att gct att agc ggt ggt tca cta ata ggt att tta     144
Glu Lys Phe Asn Ile Ala Ile Ser Gly Gly Ser Leu Ile Gly Ile Leu
        35                  40                  45 ggg aaa ggc tta ctg aac aac aaa gat atc aaa tgg gat aag tgg gta     192
Gly Lys Gly Leu Leu Asn Asn Lys Asp Ile Lys Trp Asp Lys Trp Val
    50                  55                  60 atc tat ttc agt gat gag aga att gta cca ttg agt gac aac gat tcc     240
Ile Tyr Phe Ser Asp Glu Arg Ile Val Pro Leu Ser Asp Asn Asp Ser
65              70                  75                  80 aat ttt ggt gct ttt gaa aag gag gtt ttg gag aaa ctc gcc cat gca     288
Asn Phe Gly Ala Phe Glu Lys Glu Val Leu Glu Lys Leu Ala His Ala
                85                  90                  95 ggg aaa gtt ggg cca acg gtt gtt aca atc aac gaa aat tta att cat     336
Gly Lys Val Gly Pro Thr Val Val Thr Ile Asn Glu Asn Leu Ile His
            100                 105                 110 ccg gat gat cac act acg gat ggt gag att gcc cag aca tat gca tct     384
Pro Asp Asp His Thr Thr Asp Gly Glu Ile Ala Gln Thr Tyr Ala Ser
        115                 120                 125 gag ttg cct gaa tcc gga ctg gat ttg gtc ttg cta ggg tgt gga cca     432
Glu Leu Pro Glu Ser Gly Leu Asp Leu Val Leu Leu Gly Cys Gly Pro
    130                 135                 140 gac ggc cac aca tgt tct ttg ttc cca ggc cac aag ttg ttg gag gag     480
Asp Gly His Thr Cys Ser Leu Phe Pro Gly His Lys Leu Leu Glu Glu
145                 150                 155                 160 aac gag ctt gat gtt gct gcg ctt cat gat tct cca aag cca cca cca     528
Asn Glu Leu Asp Val Ala Ala Leu His Asp Ser Pro Lys Pro Pro Pro
                165                 170                 175 agg aga atc aca ttg aca ttc aag tat ctt gct aaa tgt act aca cta     576
Arg Arg Ile Thr Leu Thr Phe Lys Tyr Leu Ala Lys Cys Thr Thr Leu
            180                 185                 190 gct ttt gtt gcc act ggt gca agc aag cag gaa gct cta aaa gag att     624
Ala Phe Val Ala Thr Gly Ala Ser Lys Gln Glu Ala Leu Lys Glu Ile
        195                 200                 205 ttt gga aac gaa aac agc caa cta ccc tgt gct att act aac agg ttg     672
Phe Gly Asn Glu Asn Ser Gln Leu Pro Cys Ala Ile Thr Asn Arg Leu
    210                 215                 220 gtt tca aaa gtt aag ggg ggt atc tgt tgg ttt gta gat gat gat gcc     720
Val Ser Lys Val Lys Gly Gly Ile Cys Trp Phe Val Asp Asp Asp Ala
225                 230                 235                 240 att gaa ggc gtc gac gtc caa acc ctc aag tac tga ttc                 759
Ile Glu Gly Val Asp Val Gln Thr Leu Lys Tyr     Phe
                245                 250
```

<210> SEQ ID NO 36
<211> LENGTH: 251
<212> TYPE: PRT
<213> ORGANISM: Issatchenkia orientalis

<400> SEQUENCE: 36

```
Met Val Lys Val Tyr Ser Tyr Ser Asn Asn Asp Glu Ile Ala Gln Ser
1               5                   10                  15

Leu Ala Lys Phe Ile Val Ser Gln Gln Asp Ser Val Leu Ala Thr Lys
            20                  25                  30

Glu Lys Phe Asn Ile Ala Ile Ser Gly Gly Ser Leu Ile Gly Ile Leu
```

```
                 35                  40                  45
Gly Lys Gly Leu Leu Asn Asn Lys Asp Ile Lys Trp Asp Lys Trp Val
 50                  55                  60

Ile Tyr Phe Ser Asp Glu Arg Ile Val Pro Leu Ser Asp Asn Asp Ser
 65                  70                  75                  80

Asn Phe Gly Ala Phe Glu Lys Glu Val Leu Glu Lys Leu Ala His Ala
                 85                  90                  95

Gly Lys Val Gly Pro Thr Val Val Thr Ile Asn Glu Asn Leu Ile His
                100                 105                 110

Pro Asp Asp His Thr Thr Asp Gly Glu Ile Ala Gln Thr Tyr Ala Ser
                115                 120                 125

Glu Leu Pro Glu Ser Gly Leu Asp Leu Val Leu Leu Gly Cys Gly Pro
                130                 135                 140

Asp Gly His Thr Cys Ser Leu Phe Pro Gly His Lys Leu Leu Glu Glu
145                 150                 155                 160

Asn Glu Leu Asp Val Ala Ala Leu His Asp Ser Pro Lys Pro Pro Pro
                165                 170                 175

Arg Arg Ile Thr Leu Thr Phe Lys Tyr Leu Ala Lys Cys Thr Thr Leu
                180                 185                 190

Ala Phe Val Ala Thr Gly Ala Ser Lys Gln Glu Ala Leu Lys Glu Ile
                195                 200                 205

Phe Gly Asn Glu Asn Ser Gln Leu Pro Cys Ala Ile Thr Asn Arg Leu
                210                 215                 220

Val Ser Lys Val Lys Gly Gly Ile Cys Trp Phe Val Asp Asp Asp Ala
225                 230                 235                 240

Ile Glu Gly Val Asp Val Gln Thr Leu Lys Tyr
                245                 250

<210> SEQ ID NO 37
<211> LENGTH: 1431
<212> TYPE: DNA
<213> ORGANISM: Issatchenkia orientalis
<220> FEATURE:
<221> NAME/KEY: CDS
<222> LOCATION: (1)..(1431)

<400> SEQUENCE: 37 atg ggt caa aac ttg att ctt aat gca gca gat cat ggt ttt act gtt         48
Met Gly Gln Asn Leu Ile Leu Asn Ala Ala Asp His Gly Phe Thr Val
 1               5                  10                  15 gtt gca tac aac aga act gtc tct aaa gtt gac cat ttc ctt caa aat         96
Val Ala Tyr Asn Arg Thr Val Ser Lys Val Asp His Phe Leu Gln Asn
                20                  25                  30 gaa gca aag ggt aaa tcc att att ggt gca cac tcc att gaa gaa tta        144
Glu Ala Lys Gly Lys Ser Ile Ile Gly Ala His Ser Ile Glu Glu Leu
            35                  40                  45 tgt gct aag ttg aag aaa cca aga aga att atg ttg tta gtc aag gca        192
Cys Ala Lys Leu Lys Lys Pro Arg Arg Ile Met Leu Leu Val Lys Ala
 50                  55                  60 ggt aat cca gtt gat caa ttc att gaa caa ttg tta cct cat tta gat        240
Gly Asn Pro Val Asp Gln Phe Ile Glu Gln Leu Leu Pro His Leu Asp
 65                  70                  75                  80 gaa ggc gat atc att att gac ggt ggt aac tct cac ttc cct gac tcc        288
Glu Gly Asp Ile Ile Ile Asp Gly Gly Asn Ser His Phe Pro Asp Ser
                85                  90                  95 aac aga aga tac gag gaa tta aag aag aag ggt att ctc ttt gtc ggt        336
Asn Arg Arg Tyr Glu Glu Leu Lys Lys Lys Gly Ile Leu Phe Val Gly
            100                 105                 110
```

```
tct ggt gtt tct ggt ggt gaa gaa ggt gca aga tat ggt cct tct ttg      384
Ser Gly Val Ser Gly Gly Glu Glu Gly Ala Arg Tyr Gly Pro Ser Leu
        115                 120                 125 atg cct ggt ggt gca aag gaa gca tgg cct cat att aag gac atc ttc      432
Met Pro Gly Gly Ala Lys Glu Ala Trp Pro His Ile Lys Asp Ile Phe
130                 135                 140 caa tct atc tct gca aag gcc gat ggt gag cca tgt tgt gat tgg gtt      480
Gln Ser Ile Ser Ala Lys Ala Asp Gly Glu Pro Cys Cys Asp Trp Val
145                 150                 155                 160 ggt gat gca ggt gca ggt cat tac gtt aag atg gtc cac aat ggt atc      528
Gly Asp Ala Gly Ala Gly His Tyr Val Lys Met Val His Asn Gly Ile
            165                 170                 175 gag tat ggt gat atg cag ttg atc tgt gaa gct tac gat ttg atg aag      576
Glu Tyr Gly Asp Met Gln Leu Ile Cys Glu Ala Tyr Asp Leu Met Lys
        180                 185                 190 aga gtt ggt ggt tta act gac aag gaa ata tct gat gtt ttc ggt gaa      624
Arg Val Gly Gly Leu Thr Asp Lys Glu Ile Ser Asp Val Phe Gly Glu
        195                 200                 205 tgg aac gag ggt gtt ctc gat tct ttc tta gtt gaa att acc aga gat      672
Trp Asn Glu Gly Val Leu Asp Ser Phe Leu Val Glu Ile Thr Arg Asp
210                 215                 220 atc tta gct ttc aac gat aag gat ggt acc cca tta gtt gaa aag atc      720
Ile Leu Ala Phe Asn Asp Lys Asp Gly Thr Pro Leu Val Glu Lys Ile
225                 230                 235                 240 tta gat act gcc gga cag aag ggt act ggt aaa tgg act gca ata aat      768
Leu Asp Thr Ala Gly Gln Lys Gly Thr Gly Lys Trp Thr Ala Ile Asn
            245                 250                 255 gct tta gac ttg ggt atg cca gtc act tta att ggt gaa gct gtt ttt      816
Ala Leu Asp Leu Gly Met Pro Val Thr Leu Ile Gly Glu Ala Val Phe
        260                 265                 270 gcg aga tgt tta tcc gct ttg aag cca gaa aga gag aga gct tct gaa      864
Ala Arg Cys Leu Ser Ala Leu Lys Pro Glu Arg Glu Arg Ala Ser Glu
        275                 280                 285 atc tta aac ggt ccg gaa gtt gaa caa gtt tct gct gaa ggt aga gca      912
Ile Leu Asn Gly Pro Glu Val Glu Gln Val Ser Ala Glu Gly Arg Ala
        290                 295                 300 caa ttt att gca gat ttg atg caa gct tta tat gca tca aag att att      960
Gln Phe Ile Ala Asp Leu Met Gln Ala Leu Tyr Ala Ser Lys Ile Ile
305                 310                 315                 320 tct tac gca caa ggt ttc atg tta atc aga gaa gca gca aag gaa tac     1008
Ser Tyr Ala Gln Gly Phe Met Leu Ile Arg Glu Ala Ala Lys Glu Tyr
            325                 330                 335 aac tgg aaa tta aac ttc cct tct att gca ctt atg tgg aga ggt ggt     1056
Asn Trp Lys Leu Asn Phe Pro Ser Ile Ala Leu Met Trp Arg Gly Gly
        340                 345                 350 tgt att atc agg tct gtt ttc ttg gct gaa att act gca gct tat agg     1104
Cys Ile Ile Arg Ser Val Phe Leu Ala Glu Ile Thr Ala Ala Tyr Arg
        355                 360                 365 gaa aac cct gac tta gag aac tta cta ttc aac aag ttc ttc caa gat     1152
Glu Asn Pro Asp Leu Glu Asn Leu Leu Phe Asn Lys Phe Phe Gln Asp
        370                 375                 380 gct att cat aag gca cag tct ggt tgg aga aag act gtt gca tta gct     1200
Ala Ile His Lys Ala Gln Ser Gly Trp Arg Lys Thr Val Ala Leu Ala
385                 390                 395                 400 gtt acc caa ggt att cca act cca gca ttc tct act gca ttg tct ttc     1248
Val Thr Gln Gly Ile Pro Thr Pro Ala Phe Ser Thr Ala Leu Ser Phe
            405                 410                 415 tac gat ggt tac aga tcc aag aag tta cca gct aac ttg ttg caa gca     1296
Tyr Asp Gly Tyr Arg Ser Lys Lys Leu Pro Ala Asn Leu Leu Gln Ala
```

```
                    420                 425                 430
caa aga gat tac ttc ggt gct cac act ttc caa att tta cct gaa tgt    1344
Gln Arg Asp Tyr Phe Gly Ala His Thr Phe Gln Ile Leu Pro Glu Cys
        435                 440                 445 gca gat gac gaa aag aag gtt ggt gat tac atc cat gtc aac tgg act    1392
Ala Asp Asp Glu Lys Lys Val Gly Asp Tyr Ile His Val Asn Trp Thr
450                 455                 460 ggt aag ggt ggt aat gtt tct gct agt act tac gat gct                1431
Gly Lys Gly Gly Asn Val Ser Ala Ser Thr Tyr Asp Ala
465                 470                 475

<210> SEQ ID NO 38
<211> LENGTH: 477
<212> TYPE: PRT
<213> ORGANISM: Issatchenkia orientalis

<400> SEQUENCE: 38
```

Met Gly Gln Asn Leu Ile Leu Asn Ala Ala Asp His Gly Phe Thr Val
1               5                   10                  15

Val Ala Tyr Asn Arg Thr Val Ser Lys Val Asp His Phe Leu Gln Asn
                20                  25                  30

Glu Ala Lys Gly Lys Ser Ile Ile Gly Ala His Ser Ile Glu Glu Leu
            35                  40                  45

Cys Ala Lys Leu Lys Lys Pro Arg Arg Ile Met Leu Leu Val Lys Ala
        50                  55                  60

Gly Asn Pro Val Asp Gln Phe Ile Glu Gln Leu Leu Pro His Leu Asp
65                  70                  75                  80

Glu Gly Asp Ile Ile Ile Asp Gly Gly Asn Ser His Phe Pro Asp Ser
                85                  90                  95

Asn Arg Arg Tyr Glu Glu Leu Lys Lys Lys Gly Ile Leu Phe Val Gly
            100                 105                 110

Ser Gly Val Ser Gly Gly Glu Glu Gly Ala Arg Tyr Gly Pro Ser Leu
        115                 120                 125

Met Pro Gly Gly Ala Lys Glu Ala Trp Pro His Ile Lys Asp Ile Phe
130                 135                 140

Gln Ser Ile Ser Ala Lys Ala Asp Gly Glu Pro Cys Cys Asp Trp Val
145                 150                 155                 160

Gly Asp Ala Gly Ala Gly His Tyr Val Lys Met Val His Asn Gly Ile
                165                 170                 175

Glu Tyr Gly Asp Met Gln Leu Ile Cys Glu Ala Tyr Asp Leu Met Lys
            180                 185                 190

Arg Val Gly Gly Leu Thr Asp Lys Glu Ile Ser Asp Val Phe Gly Glu
        195                 200                 205

Trp Asn Glu Gly Val Leu Asp Ser Phe Leu Val Glu Ile Thr Arg Asp
210                 215                 220

Ile Leu Ala Phe Asn Asp Lys Asp Gly Thr Pro Leu Val Glu Lys Ile
225                 230                 235                 240

Leu Asp Thr Ala Gly Gln Lys Gly Thr Gly Lys Trp Thr Ala Ile Asn
                245                 250                 255

Ala Leu Asp Leu Gly Met Pro Val Thr Leu Ile Gly Glu Ala Val Phe
            260                 265                 270

Ala Arg Cys Leu Ser Ala Leu Lys Pro Glu Arg Glu Arg Ala Ser Glu
        275                 280                 285

Ile Leu Asn Gly Pro Glu Val Glu Gln Val Ser Ala Glu Gly Arg Ala
        290                 295                 300

```
Gln Phe Ile Ala Asp Leu Met Gln Ala Leu Tyr Ala Ser Lys Ile Ile
305                 310                 315                 320

Ser Tyr Ala Gln Gly Phe Met Leu Ile Arg Glu Ala Ala Lys Glu Tyr
                325                 330                 335

Asn Trp Lys Leu Asn Phe Pro Ser Ile Ala Leu Met Trp Arg Gly Gly
            340                 345                 350

Cys Ile Ile Arg Ser Val Phe Leu Ala Glu Ile Thr Ala Ala Tyr Arg
        355                 360                 365

Glu Asn Pro Asp Leu Glu Asn Leu Leu Phe Asn Lys Phe Phe Gln Asp
370                 375                 380

Ala Ile His Lys Ala Gln Ser Gly Trp Arg Lys Thr Val Ala Leu Ala
385                 390                 395                 400

Val Thr Gln Gly Ile Pro Thr Pro Ala Phe Ser Thr Ala Leu Ser Phe
                405                 410                 415

Tyr Asp Gly Tyr Arg Ser Lys Lys Leu Pro Ala Asn Leu Leu Gln Ala
            420                 425                 430

Gln Arg Asp Tyr Phe Gly Ala His Thr Phe Gln Ile Leu Pro Glu Cys
        435                 440                 445

Ala Asp Asp Glu Lys Lys Val Gly Asp Tyr Ile His Val Asn Trp Thr
450                 455                 460

Gly Lys Gly Gly Asn Val Ser Ala Ser Thr Tyr Asp Ala
465                 470                 475

<210> SEQ ID NO 39
<211> LENGTH: 3761
<212> TYPE: DNA
<213> ORGANISM: Issatchenkia orientalis
<220> FEATURE:
<221> NAME/KEY: CDS
<222> LOCATION: (1037)..(2764)

<400> SEQUENCE: 39
aaagatacag gtggctcagc tgttgcaggt gtacttctag tatatggaat tgacggctca      60
tcaacattgc ttaatcggcg gcgctttaaa gggttgttag tagtgtctat agtgtctata     120
gtgtctatag tatctgtatt gttgttgttg ttttttgggat tattggtgtt aagactctca    180
gtaagtttcg gacgcagatc tgtgttgaag agacgtacaa gatccgcctt tctgtccctt     240
ggcgacgccc tgatcccatg gcttgccaac agcgggcgaa gatccttcac ccgcagcgtc     300
catggattga actcgggcga taggtactgt gacgagtcca tcggttcctg tcagatggga     360
tactcttgac gtggaaaatt caaacagaaa aaaaccccca ataatgaaaa ataacactac     420
gttatatccg tggtatcctc tatcgtatcg tatcgtagcg tatcgtagcg taccgtatca     480
cagtatagtc taatattccg tatcttattg tatcctatcc tattcgatcc tattgtattt     540
ctgtgcacca ttttaatttc tattgctata atgtccttat tagttgccac tgtgaggtga     600
ccaatggacg agggcgagcc gttcagaagc cgcgaagggt gttcttccca tgaatttctt     660
aaggagggcg gctcagctcc gagagtgagg cgagacgtct cggtcagcgt atccccttc      720
ctcggctttt acaaatgatg cgctcttaat agtgtgtcgt tatcctttg gcattgacgg      780
gggagggaaa ttgattgagc gcatccatat ttttgcggac tgctgaggac aatggtggtt     840
tttccgggtg gcgtgggcta caaatgatac gatggttttt ttcttttcgg agaaggcgta     900
taaaaaggac acggagaacc catttattct aataacagtt gagcttcttt aattatttgt     960
taatataata ttctattatt atatattttc ttcccaataa aacaaataa aacaaaacac     1020
agcaaaacac aaaaat atg act gac aaa atc tcc cta ggt act tat ctg ttt    1072
```

```
                Met Thr Asp Lys Ile Ser Leu Gly Thr Tyr Leu Phe
                 1               5                  10 gaa aag tta aag gaa gca ggc tct tat tcc atc ttt ggt gtt cct ggt    1120
Glu Lys Leu Lys Glu Ala Gly Ser Tyr Ser Ile Phe Gly Val Pro Gly
             15                  20                  25 gat ttc aat ttg gca ttg ttg gac cac gtc aag gaa gtt gaa ggc att    1168
Asp Phe Asn Leu Ala Leu Leu Asp His Val Lys Glu Val Glu Gly Ile
         30                  35                  40 aga tgg gtc ggt aac gct aac gag ttg aat gcc ggc tac gaa gct gat    1216
Arg Trp Val Gly Asn Ala Asn Glu Leu Asn Ala Gly Tyr Glu Ala Asp
 45                  50                  55                  60 ggt tat gca aga atc aat gga ttt gca tcc cta atc acc acc ttt ggt    1264
Gly Tyr Ala Arg Ile Asn Gly Phe Ala Ser Leu Ile Thr Thr Phe Gly
                 65                  70                  75 gtc ggt gaa ttg tct gcc gtc aat gcc att gca ggt tct tat gct gaa    1312
Val Gly Glu Leu Ser Ala Val Asn Ala Ile Ala Gly Ser Tyr Ala Glu
             80                  85                  90 cac gtc cca ttg atc cat att gtt ggt atg cct tcc ttg tct gct atg    1360
His Val Pro Leu Ile His Ile Val Gly Met Pro Ser Leu Ser Ala Met
         95                 100                 105 aag aac aac ttg ttg tta cac cat acc ttg ggt gac aca aga ttc gac    1408
Lys Asn Asn Leu Leu Leu His His Thr Leu Gly Asp Thr Arg Phe Asp
    110                 115                 120 aac ttc acc gaa atg tca aag aaa atc agt gca aag gtt gaa att gtt    1456
Asn Phe Thr Glu Met Ser Lys Lys Ile Ser Ala Lys Val Glu Ile Val
125                 130                 135                 140 tac gat ttg gaa tca gct cca aaa tta att aat aac ttg att gaa acc    1504
Tyr Asp Leu Glu Ser Ala Pro Lys Leu Ile Asn Asn Leu Ile Glu Thr
                145                 150                 155 gct tat cac aca aag aga cca gtc tac ttg gga ctt cct tcc aac ttt    1552
Ala Tyr His Thr Lys Arg Pro Val Tyr Leu Gly Leu Pro Ser Asn Phe
            160                 165                 170 gct gat gaa ttg gtt cca gcg gca tta gtt aag gaa aac aag tta cat    1600
Ala Asp Glu Leu Val Pro Ala Ala Leu Val Lys Glu Asn Lys Leu His
        175                 180                 185 tta gaa gaa cct cta aac aac ccc gtt gct gaa gaa gaa ttc att cat    1648
Leu Glu Glu Pro Leu Asn Asn Pro Val Ala Glu Glu Glu Phe Ile His
    190                 195                 200 aac gtt gtt gaa atg gtc aag aag gca gaa aaa cca atc att ctc gtt    1696
Asn Val Val Glu Met Val Lys Lys Ala Glu Lys Pro Ile Ile Leu Val
205                 210                 215                 220 gac gct tgt gct gca aga cat aac att tct aag gaa gtg aga gag ttg    1744
Asp Ala Cys Ala Ala Arg His Asn Ile Ser Lys Glu Val Arg Glu Leu
                225                 230                 235 gct aaa ttg act aaa ttc cct gtc ttc acc acc cca atg ggt aaa tct    1792
Ala Lys Leu Thr Lys Phe Pro Val Phe Thr Thr Pro Met Gly Lys Ser
            240                 245                 250 act gtt gat gaa gat gat gaa gaa ttc ttt ggc tta tac ttg ggt tct    1840
Thr Val Asp Glu Asp Asp Glu Glu Phe Phe Gly Leu Tyr Leu Gly Ser
        255                 260                 265 cta tct gct cca gat gtt aag gac att gtt ggc cca acc gat tgt atc    1888
Leu Ser Ala Pro Asp Val Lys Asp Ile Val Gly Pro Thr Asp Cys Ile
    270                 275                 280 tta tcc tta ggt ggt tta cct tct gat ttc aac acc ggt tcc ttc tca    1936
Leu Ser Leu Gly Gly Leu Pro Ser Asp Phe Asn Thr Gly Ser Phe Ser
285                 290                 295                 300 tat ggt tac acc act aag aat gtc gtt gaa ttc cat tcc aac tac tgt    1984
Tyr Gly Tyr Thr Thr Lys Asn Val Val Glu Phe His Ser Asn Tyr Cys
                305                 310                 315
```

-continued

| | | |
|---|---|---|
| aaa ttc aaa tct gca act tat gaa aac ttg atg atg aag ggc gca gtc<br>Lys Phe Lys Ser Ala Thr Tyr Glu Asn Leu Met Met Lys Gly Ala Val<br>320                                325                              330 | | 2032 |
| caa aga ttg atc agc gaa ttg aag aat att aag tat tcc aat gtc tca<br>Gln Arg Leu Ile Ser Glu Leu Lys Asn Ile Lys Tyr Ser Asn Val Ser<br>335                                340                              345 | | 2080 |
| act tta tct cca cca aaa tct aaa ttt gct tac gaa tct gca aag gtt<br>Thr Leu Ser Pro Pro Lys Ser Lys Phe Ala Tyr Glu Ser Ala Lys Val<br>350                                355                              360 | | 2128 |
| gct cca gaa ggt atc atc act caa gat tac ctg tgg aag aga tta tct<br>Ala Pro Glu Gly Ile Ile Thr Gln Asp Tyr Leu Trp Lys Arg Leu Ser<br>365                                370                              375                              380 | | 2176 |
| tac ttc tta aag cca aga gat atc att gtc act gaa act ggt act tcc<br>Tyr Phe Leu Lys Pro Arg Asp Ile Ile Val Thr Glu Thr Gly Thr Ser<br>385                                390                              395 | | 2224 |
| tcc ttt ggt gtc ttg gct acc cac tta cca aga gat tca aag tct atc<br>Ser Phe Gly Val Leu Ala Thr His Leu Pro Arg Asp Ser Lys Ser Ile<br>400                                405                              410 | | 2272 |
| tcc caa gtc tta tgg ggt tcc att ggt ttc tcc tta cca gct gca gtt<br>Ser Gln Val Leu Trp Gly Ser Ile Gly Phe Ser Leu Pro Ala Ala Val<br>415                                420                              425 | | 2320 |
| ggt gct gca ttt gct gct gaa gat gca cac aaa caa act ggc gaa caa<br>Gly Ala Ala Phe Ala Ala Glu Asp Ala His Lys Gln Thr Gly Glu Gln<br>430                                435                              440 | | 2368 |
| gaa aga aga act gtt ttg ttt att ggt gat ggt tct tta caa ttg act<br>Glu Arg Arg Thr Val Leu Phe Ile Gly Asp Gly Ser Leu Gln Leu Thr<br>445                                450                              455                              460 | | 2416 |
| gtc caa tca atc tca gat gct gca aga tgg aac atc aag cca tac atc<br>Val Gln Ser Ile Ser Asp Ala Ala Arg Trp Asn Ile Lys Pro Tyr Ile<br>465                                470                              475 | | 2464 |
| ttc atc tta aac aac aga ggt tac act atc gaa aag ttg atc cac ggt<br>Phe Ile Leu Asn Asn Arg Gly Tyr Thr Ile Glu Lys Leu Ile His Gly<br>480                                485                              490 | | 2512 |
| cgt cat gag gac tac aac caa att caa cca tgg gat cac caa ttg tta<br>Arg His Glu Asp Tyr Asn Gln Ile Gln Pro Trp Asp His Gln Leu Leu<br>495                                500                              505 | | 2560 |
| ttg aag ctc ttt gct gac aag acc caa tat gaa aac cat gtt gtt aaa<br>Leu Lys Leu Phe Ala Asp Lys Thr Gln Tyr Glu Asn His Val Val Lys<br>510                                515                              520 | | 2608 |
| tcc gct aag gac ttg gac gct ttg atg aag gat gaa gca ttc aac aag<br>Ser Ala Lys Asp Leu Asp Ala Leu Met Lys Asp Glu Ala Phe Asn Lys<br>525                                530                              535                              540 | | 2656 |
| gaa gat aag att aga gtc att gaa tta ttc ttg gat gaa ttc gat gct<br>Glu Asp Lys Ile Arg Val Ile Glu Leu Phe Leu Asp Glu Phe Asp Ala<br>545                                550                              555 | | 2704 |
| cca gaa atc ttg gtt gct caa gct aaa tta tct gat gaa atc aac tct<br>Pro Glu Ile Leu Val Ala Gln Ala Lys Leu Ser Asp Glu Ile Asn Ser<br>560                                565                              570 | | 2752 |
| aaa gcc gct taa tgacatctga atgtaaaatg aacattaaaa tgaattacta<br>Lys Ala Ala<br>575 | | 2804 |
| aactttacgt ctactttaca atctataaac tttgtttaat catataacga aatacactaa | | 2864 |
| tacacaatcc tgtacgtatg taatactttt atccatcaag gattgagaaa aaaagtaat | | 2924 |
| gattccctgg gccattaaaa cttagacccc cgagcttgga taggtcactc tctatttttcg | | 2984 |
| tttctccctt ccctgataga agggtgatat gtaattaaga ataatatata attttataat | | 3044 |
| aaaaactaaa acaatccatc aatctcacca tcttcgttga cttcaacatt cataaatccg | | 3104 |
| gcataagttg atagacctgg aattgtcatg atctttgcag ctagtgcata taaatatcct | | 3164 |

```
gctcctgcac ttattctaac ttctctgatt gggaagatga aatcctttgg aacacctttc    3224
aatgttggat catgggagag agaatattgc gtctttgcaa tacaaacagg cagcttgcca    3284
aaaccttgac tctcatactc ttcaatctgt ttcttggcca actcagatag ttcaatatct    3344
tttgctccat acatcttggt ggcaattgtt cttagtctat cttctaacga accatctaat    3404
gaataaagat agttaggagg ttgactttct tccaacggtc tttcctcggt agcacgtaca    3464
attgcctcag ctaacttgat tgcaccctta ccaccttgtg accaatggtc tgactcaaca    3524
gcatcaaatg caccagcctt gatggcttct tctctaatgg tctcaatttc cttctcggtg    3584
tcggtagcaa atttgttaat tgcaacaaca actggggccc cataactctt ggcattttca    3644
atttgttttc ttaagttgga tgatgcacca ttcctaacaa attcaatgtt ttcagtgacg    3704
tattctgttg gcaatacttg accaggtttg acgtcgcttg caccaccatg caacttc       3761
```

<210> SEQ ID NO 40
<211> LENGTH: 575
<212> TYPE: PRT
<213> ORGANISM: Issatchenkia orientalis

<400> SEQUENCE: 40

```
Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
            20                  25                  30

Ala Leu Leu Asp His Val Lys Glu Val Glu Gly Ile Arg Trp Val Gly
        35                  40                  45

Asn Ala Asn Glu Leu Asn Ala Gly Tyr Glu Ala Asp Gly Tyr Ala Arg
    50                  55                  60

Ile Asn Gly Phe Ala Ser Leu Ile Thr Thr Phe Gly Val Gly Glu Leu
65                  70                  75                  80

Ser Ala Val Asn Ala Ile Ala Gly Ser Tyr Ala Glu His Val Pro Leu
                85                  90                  95

Ile His Ile Val Gly Met Pro Ser Leu Ser Ala Met Lys Asn Asn Leu
            100                 105                 110

Leu Leu His His Thr Leu Gly Asp Thr Arg Phe Asp Asn Phe Thr Glu
        115                 120                 125

Met Ser Lys Lys Ile Ser Ala Lys Val Glu Ile Val Tyr Asp Leu Glu
    130                 135                 140

Ser Ala Pro Lys Leu Ile Asn Asn Leu Ile Glu Thr Ala Tyr His Thr
145                 150                 155                 160

Lys Arg Pro Val Tyr Leu Gly Leu Pro Ser Asn Phe Ala Asp Glu Leu
                165                 170                 175

Val Pro Ala Ala Leu Val Lys Glu Asn Lys Leu His Leu Glu Glu Pro
            180                 185                 190

Leu Asn Asn Pro Val Ala Glu Glu Phe Ile His Asn Val Val Glu
        195                 200                 205

Met Val Lys Lys Ala Glu Lys Pro Ile Ile Leu Val Asp Ala Cys Ala
    210                 215                 220

Ala Arg His Asn Ile Ser Lys Glu Val Arg Glu Leu Ala Lys Leu Thr
225                 230                 235                 240

Lys Phe Pro Val Phe Thr Thr Pro Met Gly Lys Ser Thr Val Asp Glu
                245                 250                 255

Asp Asp Glu Glu Phe Phe Gly Leu Tyr Leu Gly Ser Leu Ser Ala Pro
            260                 265                 270
```

```
Asp Val Lys Asp Ile Val Gly Pro Thr Asp Cys Ile Leu Ser Leu Gly
            275                 280                 285

Gly Leu Pro Ser Asp Phe Asn Thr Gly Ser Phe Ser Tyr Gly Tyr Thr
    290                 295                 300

Thr Lys Asn Val Val Glu Phe His Ser Asn Tyr Cys Lys Phe Lys Ser
305                 310                 315                 320

Ala Thr Tyr Glu Asn Leu Met Met Lys Gly Ala Val Gln Arg Leu Ile
                325                 330                 335

Ser Glu Leu Lys Asn Ile Lys Tyr Ser Asn Val Ser Thr Leu Ser Pro
            340                 345                 350

Pro Lys Ser Lys Phe Ala Tyr Glu Ser Ala Lys Val Ala Pro Glu Gly
        355                 360                 365

Ile Ile Thr Gln Asp Tyr Leu Trp Lys Arg Leu Ser Tyr Phe Leu Lys
    370                 375                 380

Pro Arg Asp Ile Ile Val Thr Glu Thr Gly Thr Ser Ser Phe Gly Val
385                 390                 395                 400

Leu Ala Thr His Leu Pro Arg Asp Ser Lys Ser Ile Ser Gln Val Leu
                405                 410                 415

Trp Gly Ser Ile Gly Phe Ser Leu Pro Ala Ala Val Gly Ala Ala Phe
            420                 425                 430

Ala Ala Glu Asp Ala His Lys Gln Thr Gly Glu Gln Glu Arg Arg Thr
        435                 440                 445

Val Leu Phe Ile Gly Asp Gly Ser Leu Gln Leu Thr Val Gln Ser Ile
    450                 455                 460

Ser Asp Ala Ala Arg Trp Asn Ile Lys Pro Tyr Ile Phe Ile Leu Asn
465                 470                 475                 480

Asn Arg Gly Tyr Thr Ile Glu Lys Leu Ile His Gly Arg His Glu Asp
                485                 490                 495

Tyr Asn Gln Ile Gln Pro Trp Asp His Gln Leu Leu Leu Lys Leu Phe
            500                 505                 510

Ala Asp Lys Thr Gln Tyr Glu Asn His Val Val Lys Ser Ala Lys Asp
        515                 520                 525

Leu Asp Ala Leu Met Lys Asp Glu Ala Phe Asn Lys Glu Asp Lys Ile
    530                 535                 540

Arg Val Ile Glu Leu Phe Leu Asp Glu Phe Asp Ala Pro Glu Ile Leu
545                 550                 555                 560

Val Ala Gln Ala Lys Leu Ser Asp Glu Ile Asn Ser Lys Ala Ala
                565                 570                 575

<210> SEQ ID NO 41
<211> LENGTH: 3179
<212> TYPE: DNA
<213> ORGANISM: Issatchenkia orientalis
<220> FEATURE:
<221> NAME/KEY: CDS
<222> LOCATION: (1052)..(2182)

<400> SEQUENCE: 41
gatttggacc tacaaggtgc tgtaaagagt atgaacactt ctggggagga ggaatggaac      60
agtgatgacg atgatgatga agaaagtgac gaaagtaacg aaagtgatta ctattcttac     120
gatgaaggcg aagaaacaga tgatagtgag ggagcccaag agggagagga agacgaaaat     180
gaacgaatca ttgaagctct aagtagtggt gttggtgaac tcaagatgga ctctttaggt     240
aattatattc ttgaatagtt gtgtaaagcg aatatgcaaa tagatttgtt ttataattat     300
```

```
gcatctcttt gaaagaggtt tagaggcaaa gttcttgcat acaatattgt gattgtttta      360
atgtcattct tgattttcat aaagagatta aaaaaaaaaa aaaaaaactt ataaaattga      420
gtagaaccat ttatatataa gacaaagatt gtctgtatta gtcctcaaca cactaaacct      480
tacatactta gggtaaattt gctaatagag tgatatgttc atgagaactc caacgacaac      540
acaaccacct atttgcacaa caaacaccat tgtcgcacgc tgcgcgccct agaagtagaa      600
agaaagggaa atgacattaa gagaatcata ccccgtgccc gtaacgccga aaaaatcaca      660
ccccgtcccc cacaccttaa aacctcaacc gcttaacacc gccacaccct ttctctttat      720
aaacgccgtt tgcattactc attcttctta taaaccgcac cccccaaaac gcggaatagc      780
ttcaaccccc caatcagata tgagtttccc gggaaacccg cttttcccga cagccccaca      840 agggggttggt ctataaaaga ggacgttttc cccgtcatcg agattgaaga ttcttacagg      900
cccatttatt caaattggag ttgattcttc ttgtctttac tttctttctc tctttttctt      960
ccttttttaa tattatcttt tgtcaagcct ggttccctaa gttgaactct cttttcttgt     1020
gatcctccta tatagatacg ccttgccaaa t atg ttt gca tca acc ttc aga        1072
                                   Met Phe Ala Ser Thr Phe Arg
                                    1               5 agt caa gct gta aga gct gca aga ttt act aga ttc caa tcc act ttt      1120
Ser Gln Ala Val Arg Ala Ala Arg Phe Thr Arg Phe Gln Ser Thr Phe
        10                  15                  20 gcc att cct gag aag caa atg ggt gtt atc ttt gaa act cat ggt ggt      1168
Ala Ile Pro Glu Lys Gln Met Gly Val Ile Phe Glu Thr His Gly Gly
    25                  30                  35 cct tta caa tac aag gaa att cca gtt cca aaa cca aaa cca act gaa      1216
Pro Leu Gln Tyr Lys Glu Ile Pro Val Pro Lys Pro Lys Pro Thr Glu
40                  45                  50                  55 att tta atc aat gtt aaa tac tct ggt gtc tgc cat acc gat tta cac      1264
Ile Leu Ile Asn Val Lys Tyr Ser Gly Val Cys His Thr Asp Leu His
                60                  65                  70 gca tgg aaa ggt gac tgg cca tta cca gca aag tta ccc cta gtt ggt      1312
Ala Trp Lys Gly Asp Trp Pro Leu Pro Ala Lys Leu Pro Leu Val Gly
            75                  80                  85 ggt cac gaa ggt gcg ggc att gtt gtt gcg aaa ggt tct gca gtt acc      1360
Gly His Glu Gly Ala Gly Ile Val Val Ala Lys Gly Ser Ala Val Thr
        90                  95                 100 aac ttt gag att ggc gat tat gct ggt att aag tgg tta aac ggt tca      1408
Asn Phe Glu Ile Gly Asp Tyr Ala Gly Ile Lys Trp Leu Asn Gly Ser
    105                 110                 115 tgt atg tca tgt gaa ttc tgt gaa caa ggt gat gaa tct aac tgt gaa      1456
Cys Met Ser Cys Glu Phe Cys Glu Gln Gly Asp Glu Ser Asn Cys Glu
120                 125                 130                 135 cat gcc gat ttg agt ggt tat act cat gat ggt tct ttc caa caa tat      1504
His Ala Asp Leu Ser Gly Tyr Thr His Asp Gly Ser Phe Gln Gln Tyr
                140                 145                 150 gcc act gct gac gct att caa gct gca aag atc cca aag ggt acc gac      1552
Ala Thr Ala Asp Ala Ile Gln Ala Ala Lys Ile Pro Lys Gly Thr Asp
            155                 160                 165 tta tct gaa gtt gcg cca att tta tgt gct ggt gtt act gtc tat aaa      1600
Leu Ser Glu Val Ala Pro Ile Leu Cys Ala Gly Val Thr Val Tyr Lys
        170                 175                 180 gct ttg aaa act gct gat tta aga gca ggt caa tgg gtt gcg att tct      1648
Ala Leu Lys Thr Ala Asp Leu Arg Ala Gly Gln Trp Val Ala Ile Ser
    185                 190                 195 ggt gcc gct ggt ggt cta ggt tct ctt gct gtc caa tat gca aag gca      1696
Gly Ala Ala Gly Gly Leu Gly Ser Leu Ala Val Gln Tyr Ala Lys Ala
200                 205                 210                 215
```

```
atg ggt cta aga gtt tta ggt atc gat ggt ggt gaa ggt aaa aag gaa      1744
Met Gly Leu Arg Val Leu Gly Ile Asp Gly Gly Glu Gly Lys Lys Glu
        220                 225                 230 ctt ttt gaa caa tgt ggt ggt gat gtg ttt atc gat ttc acc aga tac      1792
Leu Phe Glu Gln Cys Gly Gly Asp Val Phe Ile Asp Phe Thr Arg Tyr
            235                 240                 245 cca aga gat gca cct gaa aag atg gtt gct gat att aag gct gca act      1840
Pro Arg Asp Ala Pro Glu Lys Met Val Ala Asp Ile Lys Ala Ala Thr
        250                 255                 260 aac ggt ttg ggt cca cac ggt gtt atc aat gtc tct gtc tcc cca gct      1888
Asn Gly Leu Gly Pro His Gly Val Ile Asn Val Ser Val Ser Pro Ala
    265                 270                 275 gct atc tct caa tca tgt gac tat gtt aga gca act ggt aag gtt gtc      1936
Ala Ile Ser Gln Ser Cys Asp Tyr Val Arg Ala Thr Gly Lys Val Val
280                 285                 290                 295 ctt gtc ggt atg cca tct ggt gct gtc tgt aag tct gat gtc ttc act      1984
Leu Val Gly Met Pro Ser Gly Ala Val Cys Lys Ser Asp Val Phe Thr
                300                 305                 310 cat gtt gtt aaa tcc tta caa att aaa ggt tct tat gtt ggt aac aga      2032
His Val Val Lys Ser Leu Gln Ile Lys Gly Ser Tyr Val Gly Asn Arg
            315                 320                 325 gca gat acc aga gaa gct ttg gaa ttc ttt aat gaa ggt aag gtc aga      2080
Ala Asp Thr Arg Glu Ala Leu Glu Phe Phe Asn Glu Gly Lys Val Arg
        330                 335                 340 tct cca atc aag gtt gtc cca tta tct act tta cct gaa att tac gaa      2128
Ser Pro Ile Lys Val Val Pro Leu Ser Thr Leu Pro Glu Ile Tyr Glu
    345                 350                 355 ttg atg gag caa ggt aag att tta ggt aga tac gtt gtt gat act tct      2176
Leu Met Glu Gln Gly Lys Ile Leu Gly Arg Tyr Val Val Asp Thr Ser
360                 365                 370                 375 aaa taa tgaagatgaa gaaacagca aactttttat gactacccccc aaccatctaa      2232
Lys cgatttatga tctatatata gctttctaga acatccattt atttattcac ttactcatgt   2292
atttatatta tataatacaa ataactaat tacaatgtgt acatttttt ttttcattac    2352
cataatgtat gcgttgagcc tcttgcacct tctttattag gaaatcagtt gaaaaatttc   2412
cggattgtct ttattattgg cccattttt tttggtcaca cctttatttt tgtacacttc    2472
tcgggcaaag caaaaactat agtaccggat aggcctttat aaaactccag tgtgtatgat   2532
tttagttggt gtgccatcta cacgttctct tagtttcttt atcatgtcac agaaagcaag   2592
catgcaaacc cttacaaaaa ataacaacat acaaatgcct aaacaactgg actataatga   2652
tggtgagtca gttacgaaaa gagcaagtgg gttaatacga tttcgtaagg gacagtctga   2712
ggaagactac aattttcaaa aggagcagtt ctggtccacg ggtcctttag tacagaatca   2772
cacatttgtg actgaatttg ttgaaaagtt tattgaaaac acaattagtg aagattattc   2832
aatcacagat agatcgaaaa tagaacgtga acaatcata cacggattgg agaagctgta    2892
ttttcaaagg gaatatgagc gatgtctaaa agatgttcaa ctattgaagg acaatatcga   2952
taagttcaat cctaatttgg atcttaatga aaagaattta taatgagctg aattatattt   3012
cttggatgtg catcaaaaag atccatgaga gtaacgaaaa gaaactgggg gaaatctaat   3072
aatttacaat ttcaatatac acttctatat cctttaatgt aatggcttta taaataaaca   3132
cgaacttcta cagcaccgac gtttcttttt cttaccagct cctcttc                 3179

<210> SEQ ID NO 42
<211> LENGTH: 376
```

<212> TYPE: PRT
<213> ORGANISM: Issatchenkia orientalis

<400> SEQUENCE: 42

```
Met Phe Ala Ser Thr Phe Arg Ser Gln Ala Val Arg Ala Ala Arg Phe
1               5                   10                  15

Thr Arg Phe Gln Ser Thr Phe Ala Ile Pro Glu Lys Gln Met Gly Val
            20                  25                  30

Ile Phe Glu Thr His Gly Gly Pro Leu Gln Tyr Lys Glu Ile Pro Val
        35                  40                  45

Pro Lys Pro Lys Pro Thr Glu Ile Leu Ile Asn Val Lys Tyr Ser Gly
    50                  55                  60

Val Cys His Thr Asp Leu His Ala Trp Lys Gly Asp Trp Pro Leu Pro
65                  70                  75                  80

Ala Lys Leu Pro Leu Val Gly Gly His Glu Gly Ala Gly Ile Val Val
                85                  90                  95

Ala Lys Gly Ser Ala Val Thr Asn Phe Glu Ile Gly Asp Tyr Ala Gly
            100                 105                 110

Ile Lys Trp Leu Asn Gly Ser Cys Met Ser Cys Glu Phe Cys Glu Gln
        115                 120                 125

Gly Asp Glu Ser Asn Cys Glu His Ala Asp Leu Ser Gly Tyr Thr His
    130                 135                 140

Asp Gly Ser Phe Gln Gln Tyr Ala Thr Ala Asp Ala Ile Gln Ala Ala
145                 150                 155                 160

Lys Ile Pro Lys Gly Thr Asp Leu Ser Glu Val Ala Pro Ile Leu Cys
                165                 170                 175

Ala Gly Val Thr Val Tyr Lys Ala Leu Lys Thr Ala Asp Leu Arg Ala
            180                 185                 190

Gly Gln Trp Val Ala Ile Ser Gly Ala Ala Gly Gly Leu Gly Ser Leu
        195                 200                 205

Ala Val Gln Tyr Ala Lys Ala Met Gly Leu Arg Val Leu Gly Ile Asp
    210                 215                 220

Gly Gly Glu Gly Lys Lys Glu Leu Phe Glu Gln Cys Gly Gly Asp Val
225                 230                 235                 240

Phe Ile Asp Phe Thr Arg Tyr Pro Arg Asp Ala Pro Glu Lys Met Val
                245                 250                 255

Ala Asp Ile Lys Ala Ala Thr Asn Gly Leu Gly Pro His Gly Val Ile
            260                 265                 270

Asn Val Ser Val Ser Pro Ala Ala Ile Ser Gln Ser Cys Asp Tyr Val
        275                 280                 285

Arg Ala Thr Gly Lys Val Val Leu Val Gly Met Pro Ser Gly Ala Val
    290                 295                 300

Cys Lys Ser Asp Val Phe Thr His Val Val Lys Ser Leu Gln Ile Lys
305                 310                 315                 320

Gly Ser Tyr Val Gly Asn Arg Ala Asp Thr Arg Glu Ala Leu Glu Phe
                325                 330                 335

Phe Asn Glu Gly Lys Val Arg Ser Pro Ile Lys Val Val Pro Leu Ser
            340                 345                 350

Thr Leu Pro Glu Ile Tyr Glu Leu Met Glu Gln Gly Lys Ile Leu Gly
        355                 360                 365

Arg Tyr Val Val Asp Thr Ser Lys
    370                 375
```

<210> SEQ ID NO 43

```
<211> LENGTH: 3181
<212> TYPE: DNA
<213> ORGANISM: Issatchenkia orientalis
<220> FEATURE:
<221> NAME/KEY: CDS
<222> LOCATION: (1015)..(2181)

<400> SEQUENCE: 43
```

| | | | | | |
|---|---|---|---|---|---|
| tttttctttt | ttttttcttt | tttttcctc | tttttcttt | gttttgtttc | gtttcttttc | 60 |
| cgccagttcc | cgttttccat | ttccggaaca | acaatgggac | tccactgttt | tcttcccccc | 120 |
| ttccctttc | ggctcgcagt | ctgtacatgc | acgtttatcc | gacacctgtc | ttgtttggcg | 180 |
| cgtaattaat | acagtttctc | cggagtccag | gtctcggacg | ggtaatttac | acgtcatcat | 240 |
| tcatttctgt | gtcaagagag | gtagcgcaaa | aagtagaaat | ggtgaaccac | gggaatgact | 300 |
| tgctggaaat | cgacgccaga | gtccatttga | aaacctacct | ctacaagaga | ggaaacacac | 360 |
| tacagggtgt | ccctggtccg | taaaatggcg | taatatgatg | acttccctct | atagacgttg | 420 |
| tatttccagc | tccaacatgg | ttaaactatt | gctatggtga | tggtattaca | gatagtaaaa | 480 |
| gaaggaaggg | ggggtggcaa | tctcacccta | acagttacta | agaacgtcta | cttcatctac | 540 |
| tgtcaatata | cattggccac | atgccgagaa | attacgtcga | cgccaaagaa | gggcccagcc | 600 |
| gaaaaagaa | atggaaaact | tggccgaaaa | gggaaacaaa | caaaaaggtg | atgtaaaatt | 660 |
| agcggaaagg | ggaattggca | aattgaggga | gaaaaaaaaa | aaggcagaaa | aggaggcgga | 720 |
| aagtcagtac | gttttgaagg | cgtcattggt | tttcccttt | gcagagtgtt | tcatttcttt | 780 |
| tgttttatga | cgtagtggcg | tttcttttcc | tgcacttag | aaatctatct | tttccttatc | 840 |
| aagtaacaag | cggttggcaa | aggtgtatat | aaatcaagga | attcccactt | tgaaccctt | 900 |
| gaattttgat | atcgtttatt | ttaaatttat | tttatgtttc | taatctcaaa | gagtttacac | 960 |
| tttacaagga | gtttctcaaa | tactatcaag | acattgaata | gatcaaacat | taaa atg | 1017 |
| | | | | | Met |
| | | | | | 1 |

| gtg | tcc | cct | gct | gaa | aga | tta | tct | act | att | gcg | tcc | aca | atc | aag | cca | 1065 |
|---|---|---|---|---|---|---|---|---|---|---|---|---|---|---|---|---|
| Val | Ser | Pro | Ala | Glu | Arg | Leu | Ser | Thr | Ile | Ala | Ser | Thr | Ile | Lys | Pro | |
| | | | 5 | | | | 10 | | | | | 15 | | | | |

| aac | aga | aaa | gat | tct | aca | tca | tta | caa | cca | gaa | gac | tat | ccg | gaa | cat | 1113 |
|---|---|---|---|---|---|---|---|---|---|---|---|---|---|---|---|---|
| Asn | Arg | Lys | Asp | Ser | Thr | Ser | Leu | Gln | Pro | Glu | Asp | Tyr | Pro | Glu | His | |
| | 20 | | | | | 25 | | | | | 30 | | | | | |

| ccg | ttc | aag | gtg | acg | gtt | gtt | ggt | tcc | ggt | aac | tgg | ggg | tgt | aca | att | 1161 |
|---|---|---|---|---|---|---|---|---|---|---|---|---|---|---|---|---|
| Pro | Phe | Lys | Val | Thr | Val | Val | Gly | Ser | Gly | Asn | Trp | Gly | Cys | Thr | Ile | |
| 35 | | | | | 40 | | | | | 45 | | | | | | |

| gcc | aag | gtt | ata | gcg | gaa | aac | acc | gtt | gag | aga | cct | cgt | caa | ttt | caa | 1209 |
|---|---|---|---|---|---|---|---|---|---|---|---|---|---|---|---|---|
| Ala | Lys | Val | Ile | Ala | Glu | Asn | Thr | Val | Glu | Arg | Pro | Arg | Gln | Phe | Gln | |
| 50 | | | | | 55 | | | | | 60 | | | | | 65 | |

| aga | gat | gtt | aat | atg | tgg | gtc | tat | gaa | gaa | ttg | att | gaa | ggc | gaa | aag | 1257 |
|---|---|---|---|---|---|---|---|---|---|---|---|---|---|---|---|---|
| Arg | Asp | Val | Asn | Met | Trp | Val | Tyr | Glu | Glu | Leu | Ile | Glu | Gly | Glu | Lys | |
| | | | 70 | | | | | 75 | | | | | 80 | | | |

| ttg | act | gaa | atc | ata | aat | acc | aaa | cac | gaa | aac | gtc | aag | tac | ttg | cca | 1305 |
|---|---|---|---|---|---|---|---|---|---|---|---|---|---|---|---|---|
| Leu | Thr | Glu | Ile | Ile | Asn | Thr | Lys | His | Glu | Asn | Val | Lys | Tyr | Leu | Pro | |
| | | | 85 | | | | | 90 | | | | | 95 | | | |

| ggt | atc | aag | ttg | cca | gtt | aac | gtt | gtt | gca | gtt | cca | gac | att | gtt | gag | 1353 |
|---|---|---|---|---|---|---|---|---|---|---|---|---|---|---|---|---|
| Gly | Ile | Lys | Leu | Pro | Val | Asn | Val | Val | Ala | Val | Pro | Asp | Ile | Val | Glu | |
| | | 100 | | | | | 105 | | | | | 110 | | | | |

| gct | tgt | gca | ggc | tca | gac | ttg | att | gtc | ttt | aat | att | cct | cac | caa | ttt | 1401 |
|---|---|---|---|---|---|---|---|---|---|---|---|---|---|---|---|---|
| Ala | Cys | Ala | Gly | Ser | Asp | Leu | Ile | Val | Phe | Asn | Ile | Pro | His | Gln | Phe | |
| | 115 | | | | | 120 | | | | | 125 | | | | | |

| tta | cca | aga | att | tta | tcc | caa | tta | aag | ggt | aag | gtg | aat | cca | aag | gct | 1449 |
|---|---|---|---|---|---|---|---|---|---|---|---|---|---|---|---|---|
| Leu | Pro | Arg | Ile | Leu | Ser | Gln | Leu | Lys | Gly | Lys | Val | Asn | Pro | Lys | Ala | |

```
                  130                 135                 140                 145
aga gca att tct tgt ttg aaa ggt ttg gat gtc aat cct aat gga tgt          1497
Arg Ala Ile Ser Cys Leu Lys Gly Leu Asp Val Asn Pro Asn Gly Cys
                150                 155                 160 aag ttg ctc tcc act gtt att act gaa gag ttg ggt att tat tgt ggt          1545
Lys Leu Leu Ser Thr Val Ile Thr Glu Glu Leu Gly Ile Tyr Cys Gly
                165                 170                 175 gcc tta tca ggt gct aat tta gct cct gaa gtt gca caa tgt aaa tgg          1593
Ala Leu Ser Gly Ala Asn Leu Ala Pro Glu Val Ala Gln Cys Lys Trp
                180                 185                 190 tcg gaa aca act gtt gca tat aca att ccg gac gat ttc aga ggt aaa          1641
Ser Glu Thr Thr Val Ala Tyr Thr Ile Pro Asp Asp Phe Arg Gly Lys
        195                 200                 205 ggc aag gat att gac cat caa att cta aag agt ttg ttc cat aga cct          1689
Gly Lys Asp Ile Asp His Gln Ile Leu Lys Ser Leu Phe His Arg Pro
210                 215                 220                 225 tat ttc cat gtt cgt gtt att agt gat gtt gca ggt att tcc att gcc          1737
Tyr Phe His Val Arg Val Ile Ser Asp Val Ala Gly Ile Ser Ile Ala
                    230                 235                 240 ggt gca ctc aag aat gtc gtt gct atg gct gct gga ttt gtc gaa ggt          1785
Gly Ala Leu Lys Asn Val Val Ala Met Ala Ala Gly Phe Val Glu Gly
                245                 250                 255 tta ggt tgg ggt gat aat gca aag gct gca gtc atg aga ata ggt ttg          1833
Leu Gly Trp Gly Asp Asn Ala Lys Ala Ala Val Met Arg Ile Gly Leu
            260                 265                 270 gtg gaa acc att caa ttt gcc aag act ttt ttc gat ggc tgt cat gct          1881
Val Glu Thr Ile Gln Phe Ala Lys Thr Phe Phe Asp Gly Cys His Ala
        275                 280                 285 gca acc ttt act cat gaa tct gca ggt gtt gcc gac cta atc act acc          1929
Ala Thr Phe Thr His Glu Ser Ala Gly Val Ala Asp Leu Ile Thr Thr
290                 295                 300                 305 tgt gcc ggc ggc cgt aac gtt aga gtt ggt aga tat atg gca caa cat          1977
Cys Ala Gly Gly Arg Asn Val Arg Val Gly Arg Tyr Met Ala Gln His
                    310                 315                 320 tct gtc tct gca acg gag gct gaa gaa aag ttg ttg aat ggc caa tcc          2025
Ser Val Ser Ala Thr Glu Ala Glu Glu Lys Leu Leu Asn Gly Gln Ser
                325                 330                 335 tgt caa ggt atc cac aca act agg gaa gtt tac gag ttc ctc tcc aac          2073
Cys Gln Gly Ile His Thr Thr Arg Glu Val Tyr Glu Phe Leu Ser Asn
            340                 345                 350 atg ggc agg aca gat gag ttc cca cta ttt acc acc acc tac cgt atc          2121
Met Gly Arg Thr Asp Glu Phe Pro Leu Phe Thr Thr Thr Tyr Arg Ile
        355                 360                 365 atc tac gaa aac ttc cca att gag aag ctg cca gaa tgc ctt gaa cct          2169
Ile Tyr Glu Asn Phe Pro Ile Glu Lys Leu Pro Glu Cys Leu Glu Pro
370                 375                 380                 385 gtg gaa gat taa ataacctcag ggagaacttt ggcattgtac tctccattga              2221
Val Glu Asp cgagtccgct aacccattct tgttaaacct aaccttgcat tatcacattc cctttgaccc        2281
cctttagctg catttccact tgtctacatt aagattcatt acacattctt tttcgtattt        2341
ctcttacctc cctccccccct ccatggatct tatatataaa tctttctat aacaataata        2401 tctactagag ttaaacaaca attccacttg gcatggctgt tcagcaaat ctgcttctac         2461 ctactgcacg ggtttgcatg tcattgtttc tagcagggaa tcgtccatgt acgttgtcct        2521
ccatgatggt cttcccgctg ccactttctt tagtatctta aatagagcag atcttacgtc        2581
cactgtgcat ccgtgcaccc cgaaaatcgt atggttttcc ttgccacctc tcacaatttt       2641
```

-continued

```
gaatatgctc aacgcgaaag agagggaag aggaatcgca ttcgtagagt ggctacattc  2701
aaccctgaca aaggaatagc gtttgtgcag gagagagtgg tttgcataga tttcctttcc  2761
tttgcaagca tattatatag agtagccaat acagtaacag ctacagcaca aaaagagaa   2821 cgagaacgag aacgagaaca agaacaagaa ctagcactac tgtcactgcc agcatcaaca  2881
tcactaccat tattccaaca tgtttgcaac tagaaatata accattggtg tcagaacact  2941
cagaccaacc agtttcttga aaacaaggtc ttttctgcaa cagaggctac aatcaacgct  3001
aaagaagagc tatgaaccaa ccaaatccga gctcgacatt gcaagcaaga tgtcctggga  3061
acagtttcta accatgagaa agcaacagag aagattggga ggcattgggt ccattgcagc  3121
agcaattttg gcaatgggcg cctccttctc gtatttctca cagattgaaa tcgatcctac  3181
```

<210> SEQ ID NO 44
<211> LENGTH: 388
<212> TYPE: PRT
<213> ORGANISM: Issatchenkia orientalis

<400> SEQUENCE: 44

```
Met Val Ser Pro Ala Glu Arg Leu Ser Thr Ile Ala Ser Thr Ile Lys
1               5                   10                  15

Pro Asn Arg Lys Asp Ser Thr Ser Leu Gln Pro Glu Asp Tyr Pro Glu
            20                  25                  30

His Pro Phe Lys Val Thr Val Val Gly Ser Gly Asn Trp Gly Cys Thr
        35                  40                  45

Ile Ala Lys Val Ile Ala Glu Asn Thr Val Glu Arg Pro Arg Gln Phe
    50                  55                  60

Gln Arg Asp Val Asn Met Trp Val Tyr Glu Glu Leu Ile Glu Gly Glu
65                  70                  75                  80

Lys Leu Thr Glu Ile Ile Asn Thr Lys His Glu Asn Val Lys Tyr Leu
                85                  90                  95

Pro Gly Ile Lys Leu Pro Val Asn Val Ala Val Pro Asp Ile Val
            100                 105                 110

Glu Ala Cys Ala Gly Ser Asp Leu Ile Val Phe Asn Ile Pro His Gln
        115                 120                 125

Phe Leu Pro Arg Ile Leu Ser Gln Leu Lys Gly Lys Val Asn Pro Lys
    130                 135                 140

Ala Arg Ala Ile Ser Cys Leu Lys Gly Leu Asp Val Asn Pro Asn Gly
145                 150                 155                 160

Cys Lys Leu Leu Ser Thr Val Ile Thr Glu Glu Leu Gly Ile Tyr Cys
                165                 170                 175

Gly Ala Leu Ser Gly Ala Asn Leu Ala Pro Glu Val Ala Gln Cys Lys
            180                 185                 190

Trp Ser Glu Thr Thr Val Ala Tyr Thr Ile Pro Asp Asp Phe Arg Gly
        195                 200                 205

Lys Gly Lys Asp Ile Asp His Gln Ile Leu Lys Ser Leu Phe His Arg
    210                 215                 220

Pro Tyr Phe His Val Arg Val Ile Ser Asp Val Ala Gly Ile Ser Ile
225                 230                 235                 240

Ala Gly Ala Leu Lys Asn Val Val Ala Met Ala Gly Phe Val Glu
                245                 250                 255

Gly Leu Gly Trp Gly Asp Asn Ala Lys Ala Ala Val Met Arg Ile Gly
            260                 265                 270

Leu Val Glu Thr Ile Gln Phe Ala Lys Thr Phe Phe Asp Gly Cys His
        275                 280                 285
```

```
Ala Ala Thr Phe Thr His Glu Ser Ala Gly Val Ala Asp Leu Ile Thr
    290                 295                 300
Thr Cys Ala Gly Gly Arg Asn Val Arg Val Gly Arg Tyr Met Ala Gln
305                 310                 315                 320
His Ser Val Ser Ala Thr Glu Ala Glu Glu Lys Leu Leu Asn Gly Gln
                325                 330                 335
Ser Cys Gln Gly Ile His Thr Thr Arg Glu Val Tyr Glu Phe Leu Ser
            340                 345                 350
Asn Met Gly Arg Thr Asp Glu Phe Pro Leu Phe Thr Thr Thr Tyr Arg
        355                 360                 365
Ile Ile Tyr Glu Asn Phe Pro Ile Glu Lys Leu Pro Glu Cys Leu Glu
    370                 375                 380
Pro Val Glu Asp
385

<210> SEQ ID NO 45
<211> LENGTH: 2587
<212> TYPE: DNA
<213> ORGANISM: Issatchenkia orientalis
<220> FEATURE:
<221> NAME/KEY: CDS
<222> LOCATION: (433)..(2115)

<400> SEQUENCE: 45
ccagttcgga aactaagaca taacaaaaaa gcatgggatg aatggggaaa aaatttagaa      60
atgtaaaaaa aaataggaaa ggggcttttc ctattgtcaa taaacaact ctgttaggag      120 aaaatagttt tataatattt tcatggactc tttcccccac atttattacc gaattgggaa     180
attcccgggc aatatccctc gctccttaga aattccgtac tcccggggag gctaactct      240 ccgagttatt cctaacactc tggggggaac aacattactc atagaatact ataaataccg     300
agcgtaccgc atatatgtag tatgtgacag aaattggtat ccgataatcc cttaccttgg     360
caaggttttg tttcaataaa acattcaaat aacttaaatt caaataatat tcatttaaat     420
tgctttaaaa aa atg gct cca act gct gtt gat atc cat aac gag tac aaa    471
              Met Ala Pro Thr Ala Val Asp Ile His Asn Glu Tyr Lys
                1               5                  10 cag aat gtt tcc aac gaa cag gaa att cct ttc aac aaa act gaa aga    519
Gln Asn Val Ser Asn Glu Gln Glu Ile Pro Phe Asn Lys Thr Glu Arg
 15                  20                  25 aag tca tcg att gca tct aaa tta gga ctg aat cca gac gct aag att    567
Lys Ser Ser Ile Ala Ser Lys Leu Gly Leu Asn Pro Asp Ala Lys Ile
 30                  35                  40                  45 cac tac aat tct gct gtt cct ata tta tac gaa gat ggt tta aag gaa    615
His Tyr Asn Ser Ala Val Pro Ile Leu Tyr Glu Asp Gly Leu Lys Glu
                 50                  55                  60 aaa ggt aca acc att tcc tct tct ggt gca ttg att gca ttc tct ggt    663
Lys Gly Thr Thr Ile Ser Ser Ser Gly Ala Leu Ile Ala Phe Ser Gly
             65                  70                  75 tcc aaa aca ggt aga tct cca aag gac aaa aga att gtc gat gaa gag    711
Ser Lys Thr Gly Arg Ser Pro Lys Asp Lys Arg Ile Val Asp Glu Glu
         80                  85                  90 act tca aca gac aac atc tgg tgg ggt cca gtc aat aag aag gtt gat    759
Thr Ser Thr Asp Asn Ile Trp Trp Gly Pro Val Asn Lys Lys Val Asp
     95                 100                 105 gaa aac act tgg aat atc tcg aaa tct aga gcg att gat tat ttg aga    807
Glu Asn Thr Trp Asn Ile Ser Lys Ser Arg Ala Ile Asp Tyr Leu Arg
110                 115                 120                 125
```

```
aca aga gag aag gtt tac att atc gat gct ttt gct ggt tgg gat cca      855
Thr Arg Glu Lys Val Tyr Ile Ile Asp Ala Phe Ala Gly Trp Asp Pro
            130                 135                 140 aga tac aga att aag gtt aga att gtc tgt gct aga gct tac cat gct      903
Arg Tyr Arg Ile Lys Val Arg Ile Val Cys Ala Arg Ala Tyr His Ala
145                 150                 155 ttg ttc atg aag aat atg tta att aga cca aca acg gaa gaa tta aag      951
Leu Phe Met Lys Asn Met Leu Ile Arg Pro Thr Thr Glu Glu Leu Lys
        160                 165                 170 aac ttt ggt gag cct gat ttc acc att tgg aat gca ggt caa ttc cct      999
Asn Phe Gly Glu Pro Asp Phe Thr Ile Trp Asn Ala Gly Gln Phe Pro
    175                 180                 185 gct aat gtt tac act aag ggt atg act tct tca act tct gtt gaa ata     1047
Ala Asn Val Tyr Thr Lys Gly Met Thr Ser Ser Thr Ser Val Glu Ile
190                 195                 200                 205 aat ttc aag tct atg gaa atg gtt atc cta ggt act gaa tac gca ggt     1095
Asn Phe Lys Ser Met Glu Met Val Ile Leu Gly Thr Glu Tyr Ala Gly
        210                 215                 220 gaa atg aag aaa ggt atc ttt acc gtt atg ttc tac ttg atg cca atc     1143
Glu Met Lys Lys Gly Ile Phe Thr Val Met Phe Tyr Leu Met Pro Ile
    225                 230                 235 aga cac aag gtt tta act tta cac tct tct gca aat caa ggt aaa aag     1191
Arg His Lys Val Leu Thr Leu His Ser Ser Ala Asn Gln Gly Lys Lys
240                 245                 250 gat ggt gat gtc aca tta ttc ttt ggt tta tct ggt aca ggt aaa aca     1239
Asp Gly Asp Val Thr Leu Phe Phe Gly Leu Ser Gly Thr Gly Lys Thr
        255                 260                 265 acc ttg tct gca gat cct cat aga gaa ttg att ggt gat gat gaa cat     1287
Thr Leu Ser Ala Asp Pro His Arg Glu Leu Ile Gly Asp Asp Glu His
270                 275                 280                 285 tgc tgg tct gat cat ggt gtt ttc aac att gaa ggt gga tgt tat gct     1335
Cys Trp Ser Asp His Gly Val Phe Asn Ile Glu Gly Gly Cys Tyr Ala
                290                 295                 300 aag tgt ttg gac tta tct gct gaa aga gaa cct gag att ttc aat gca     1383
Lys Cys Leu Asp Leu Ser Ala Glu Arg Glu Pro Glu Ile Phe Asn Ala
            305                 310                 315 att agg ttt gga tct gtc ttg gag aat gtt gtc tat gat cca gtt gat     1431
Ile Arg Phe Gly Ser Val Leu Glu Asn Val Val Tyr Asp Pro Val Asp
        320                 325                 330 aga act gtt gac tat tcc gct gct aat gtc act gaa aat act aga tgt     1479
Arg Thr Val Asp Tyr Ser Ala Ala Asn Val Thr Glu Asn Thr Arg Cys
335                 340                 345 gct tat cct atc gac ttt att cct tct gct aag atc cca tgt ctg gca     1527
Ala Tyr Pro Ile Asp Phe Ile Pro Ser Ala Lys Ile Pro Cys Leu Ala
350                 355                 360                 365 gat tct cat cca aag aat att gtt ctt tta act tgt gat gca aga ggt     1575
Asp Ser His Pro Lys Asn Ile Val Leu Leu Thr Cys Asp Ala Arg Gly
        370                 375                 380 gtt ttg cca cct gtc tcc aag cta act aat gca caa gtc atg tat cac     1623
Val Leu Pro Pro Val Ser Lys Leu Thr Asn Ala Gln Val Met Tyr His
                385                 390                 395 ttt atc tct ggt tac acc tcc aag atg gca ggt acc gaa gtt ggt gtc     1671
Phe Ile Ser Gly Tyr Thr Ser Lys Met Ala Gly Thr Glu Val Gly Val
            400                 405                 410 act gaa cca gaa gca acc ttc tct gca tgt ttt ggt caa cct ttc tta     1719
Thr Glu Pro Glu Ala Thr Phe Ser Ala Cys Phe Gly Gln Pro Phe Leu
        415                 420                 425 gtt tta cat cca atg aaa tac gca caa caa ctc tct gat aaa atg gct     1767
Val Leu His Pro Met Lys Tyr Ala Gln Gln Leu Ser Asp Lys Met Ala
430                 435                 440                 445
```

```
gaa cat tct tcc acc gct tgg tta ttg aat acc ggt tgg act ggt caa      1815
Glu His Ser Ser Thr Ala Trp Leu Leu Asn Thr Gly Trp Thr Gly Gln
            450                 455                 460 tct tat gtt aaa ggt ggt aag aga tgt cca ttg aag tat act aga gca      1863
Ser Tyr Val Lys Gly Gly Lys Arg Cys Pro Leu Lys Tyr Thr Arg Ala
                465                 470                 475 att tta gat gct att cac tct ggt gag ctt gca aaa cag gaa ttc gaa      1911
Ile Leu Asp Ala Ile His Ser Gly Glu Leu Ala Lys Gln Glu Phe Glu
                    480                 485                 490 aca tac cct act ttc ggt tta caa gtt cca aaa act tgt cca ggt gtc      1959
Thr Tyr Pro Thr Phe Gly Leu Gln Val Pro Lys Thr Cys Pro Gly Val
        495                 500                 505 cca gaa agt gtt ctg aac cca tct aaa cac tgg gct act ggt gaa gct      2007
Pro Glu Ser Val Leu Asn Pro Ser Lys His Trp Ala Thr Gly Glu Ala
510                 515                 520                 525 gat ttc aag gct gaa gtc act aac ttg gct aaa tta ttt gct gag aac      2055
Asp Phe Lys Ala Glu Val Thr Asn Leu Ala Lys Leu Phe Ala Glu Asn
                530                 535                 540 ttt gaa aag tat tct gca gaa tgt act gca gaa gtt gtt gct gct ggt      2103
Phe Glu Lys Tyr Ser Ala Glu Cys Thr Ala Glu Val Val Ala Ala Gly
                    545                 550                 555 cct gct tta taa atggtttgat atcaatatta tgactcggtt atgtttgtgt          2155
Pro Ala Leu
        560 atttaattcc ctcttttttgt ttattctttt tttcttccac ccttgtttat cattagtgtc   2215 gccctttct tttcaaagga caattattag catttatata aaattcaatt cagtactata    2275 ttcgatcctt ttaatcactt cagtgtgtcg tgtaggatta ataccagagc tagaaacaat   2335 atggattgga catgtctacc aattatatta tatgtatata tgaatctaat tatctctata   2395 taaaatcaat taactaaatg tttattgatc ggtaatttcc catcaattaa tactggttta  2455 ggaatatatt tgtcatcaac ttgaatctcg aaacctggtt tacaggatag tttttcatga  2515 aattggataa tcagtttcga tagtggttcc gcgtaccatc tctcattgtt ccatttgaaa  2575 aagccaacat gg                                                       2587

<210> SEQ ID NO 46
<211> LENGTH: 560
<212> TYPE: PRT
<213> ORGANISM: Issatchenkia orientalis

<400> SEQUENCE: 46

Met Ala Pro Thr Ala Val Asp Ile His Asn Glu Tyr Lys Gln Asn Val
1               5                   10                  15

Ser Asn Glu Gln Glu Ile Pro Phe Asn Lys Thr Glu Arg Lys Ser Ser
            20                  25                  30

Ile Ala Ser Lys Leu Gly Leu Asn Pro Asp Ala Lys Ile His Tyr Asn
        35                  40                  45

Ser Ala Val Pro Ile Leu Tyr Glu Asp Gly Leu Lys Glu Lys Gly Thr
    50                  55                  60

Thr Ile Ser Ser Gly Ala Leu Ile Ala Phe Ser Gly Ser Lys Thr
65                  70                  75                  80

Gly Arg Ser Pro Lys Asp Lys Arg Ile Val Asp Glu Thr Ser Thr
                85                  90                  95

Asp Asn Ile Trp Trp Gly Pro Val Asn Lys Lys Val Asp Glu Asn Thr
            100                 105                 110

Trp Asn Ile Ser Lys Ser Arg Ala Ile Asp Tyr Leu Arg Thr Arg Glu
```

-continued

```
            115                 120                 125
Lys Val Tyr Ile Ile Asp Ala Phe Ala Gly Trp Asp Pro Arg Tyr Arg
130                 135                 140

Ile Lys Val Arg Ile Val Cys Ala Arg Ala Tyr His Ala Leu Phe Met
145                 150                 155                 160

Lys Asn Met Leu Ile Arg Pro Thr Thr Glu Leu Lys Asn Phe Gly
                165                 170                 175

Glu Pro Asp Phe Thr Ile Trp Asn Ala Gly Gln Phe Pro Ala Asn Val
                180                 185                 190

Tyr Thr Lys Gly Met Thr Ser Ser Thr Ser Val Glu Ile Asn Phe Lys
                195                 200                 205

Ser Met Glu Met Val Ile Leu Gly Thr Glu Tyr Ala Gly Glu Met Lys
210                 215                 220

Lys Gly Ile Phe Thr Val Met Phe Tyr Leu Met Pro Ile Arg His Lys
225                 230                 235                 240

Val Leu Thr Leu His Ser Ser Ala Asn Gln Gly Lys Lys Asp Gly Asp
                245                 250                 255

Val Thr Leu Phe Phe Gly Leu Ser Gly Thr Gly Lys Thr Thr Leu Ser
                260                 265                 270

Ala Asp Pro His Arg Glu Leu Ile Gly Asp Asp Glu His Cys Trp Ser
                275                 280                 285

Asp His Gly Val Phe Asn Ile Glu Gly Gly Cys Tyr Ala Lys Cys Leu
                290                 295                 300

Asp Leu Ser Ala Glu Arg Glu Pro Glu Ile Phe Asn Ala Ile Arg Phe
305                 310                 315                 320

Gly Ser Val Leu Glu Asn Val Val Tyr Asp Pro Val Asp Arg Thr Val
                325                 330                 335

Asp Tyr Ser Ala Ala Asn Val Thr Glu Asn Thr Arg Cys Ala Tyr Pro
                340                 345                 350

Ile Asp Phe Ile Pro Ser Ala Lys Ile Pro Cys Leu Ala Asp Ser His
                355                 360                 365

Pro Lys Asn Ile Val Leu Leu Thr Cys Asp Ala Arg Gly Val Leu Pro
370                 375                 380

Pro Val Ser Lys Leu Thr Asn Ala Gln Val Met Tyr His Phe Ile Ser
385                 390                 395                 400

Gly Tyr Thr Ser Lys Met Ala Gly Thr Glu Val Gly Val Thr Glu Pro
                405                 410                 415

Glu Ala Thr Phe Ser Ala Cys Phe Gly Gln Pro Phe Leu Val Leu His
                420                 425                 430

Pro Met Lys Tyr Ala Gln Gln Leu Ser Asp Lys Met Ala Glu His Ser
                435                 440                 445

Ser Thr Ala Trp Leu Leu Asn Thr Gly Trp Thr Gly Gln Ser Tyr Val
                450                 455                 460

Lys Gly Gly Lys Arg Cys Pro Leu Lys Tyr Thr Arg Ala Ile Leu Asp
465                 470                 475                 480

Ala Ile His Ser Gly Glu Leu Ala Lys Gln Glu Phe Glu Thr Tyr Pro
                485                 490                 495

Thr Phe Gly Leu Gln Val Pro Lys Thr Cys Pro Gly Val Pro Glu Ser
                500                 505                 510

Val Leu Asn Pro Ser Lys His Trp Ala Thr Gly Glu Ala Asp Phe Lys
                515                 520                 525

Ala Glu Val Thr Asn Leu Ala Lys Leu Phe Ala Glu Asn Phe Glu Lys
                530                 535                 540
```

```
Tyr Ser Ala Glu Cys Thr Ala Glu Val Val Ala Ala Gly Pro Ala Leu
545                 550                 555                 560

<210> SEQ ID NO 47
<211> LENGTH: 2562
<212> TYPE: DNA
<213> ORGANISM: Issatchenkia orientalis
<220> FEATURE:
<221> NAME/KEY: CDS
<222> LOCATION: (363)..(2174)

<400> SEQUENCE: 47
ctactatgta cactgtataa gtaaaaagac gatacccccc tcccactctg ggtgctacgg      60
tgtagatctc tccgtaaaca caaaaaggcg gctcagatga taattggggt ccgggcgcaa     120
ccggaagggg ggagagaggg gagcgatggc ttctcctccg gggggctacg ggagtttcct     180
ctttgggaag gataaagagg ggatggattg atacaagatt ctgagaacct attacgatga     240
tgttcagtgg tattttgtct tttgttattt aaagggaggg gactttcctc aataccttag     300
ttgtaaaatt acgctattat ctttaacccct ttcttttgag caataattaa aaagaacacg     360
```

| | | | | | | | | | | | | | | | | |
|---|---|---|---|---|---|---|---|---|---|---|---|---|---|---|---|---|
| cc atg aca aaa gat tgc tgt gag gtt aca aag att cca gtg gga gag | | | | | | | | | | | | | | | | 407 |
| Met Thr Lys Asp Cys Cys Glu Val Thr Lys Ile Pro Val Gly Glu | | | | | | | | | | | | | | | | |
| 1 | | 5 | | | | | 10 | | | | | 15 | | | | |

```
gag gcc aaa gtg acc gtt cct cgt tcc aca aga tta tca gca act ggt      455
Glu Ala Lys Val Thr Val Pro Arg Ser Thr Arg Leu Ser Ala Thr Gly
             20                  25                  30 cca gtt gaa tgt gat tta tct ggt ttc caa gtt ttg aac tct cca ctt      503
Pro Val Glu Cys Asp Leu Ser Gly Phe Gln Val Leu Asn Ser Pro Leu
     35                  40                  45 ttc aac aag ggc act gca ttc act att gca gaa aga gaa gca ttt ggt      551
Phe Asn Lys Gly Thr Ala Phe Thr Ile Ala Glu Arg Glu Ala Phe Gly
 50                  55                  60 tta aac ggg tta ctt cct ccg gtt gta aac act cta gaa gaa caa gtt      599
Leu Asn Gly Leu Leu Pro Pro Val Val Asn Thr Leu Glu Glu Gln Val
 65                  70                  75 gag aga agc tat aag caa cta cat ttt ctc aag act cca ttg gca aag      647
Glu Arg Ser Tyr Lys Gln Leu His Phe Leu Lys Thr Pro Leu Ala Lys
80                  85                  90                  95 aat gac ttt tgc acg tca ttg aga ttg caa aac aag gtt ctg ttt tat      695
Asn Asp Phe Cys Thr Ser Leu Arg Leu Gln Asn Lys Val Leu Phe Tyr
                 100                 105                 110 agg tta gtc aag gaa cac att aag gag ttg att cca att gtg tat aca      743
Arg Leu Val Lys Glu His Ile Lys Glu Leu Ile Pro Ile Val Tyr Thr
             115                 120                 125 cca aca gag ggt gat gca att atc gct tat tct gac aga ttc aga aaa      791
Pro Thr Glu Gly Asp Ala Ile Ile Ala Tyr Ser Asp Arg Phe Arg Lys
         130                 135                 140 cca gag ggg tta ttc ctt gat att aca aga cca aat gaa att gat caa      839
Pro Glu Gly Leu Phe Leu Asp Ile Thr Arg Pro Asn Glu Ile Asp Gln
     145                 150                 155 aga ctg gaa cag ttt gga gaa gat aaa gat gtg gat tac att gtt ata      887
Arg Leu Glu Gln Phe Gly Glu Asp Lys Asp Val Asp Tyr Ile Val Ile
160                 165                 170                 175 aca gat tct gaa ggt att cta ggt att ggt gac caa ggt gtt ggc ggt      935
Thr Asp Ser Glu Gly Ile Leu Gly Ile Gly Asp Gln Gly Val Gly Gly
                 180                 185                 190 gtc aga atc aca att gca aag gct gct cta atg act gta tgt gct ggt      983
Val Arg Ile Thr Ile Ala Lys Ala Ala Leu Met Thr Val Cys Ala Gly
             195                 200                 205
```

| | |
|---|---|
| ttg cat cca ggt aga gtt gtc tct tgt gtc ttg gac gtt ggc act aac<br>Leu His Pro Gly Arg Val Val Ser Cys Val Leu Asp Val Gly Thr Asn<br>210                    215                    220 | 1031 |
| aat gtg aaa ttg cta gaa gat gat cta tat ctt ggt aac aga ttc cca<br>Asn Val Lys Leu Leu Glu Asp Asp Leu Tyr Leu Gly Asn Arg Phe Pro<br>225                    230                    235 | 1079 |
| aga gtt aga ggt aag gag tat gac gat ttt gtg aat aaa act att cgt<br>Arg Val Arg Gly Lys Glu Tyr Asp Asp Phe Val Asn Lys Thr Ile Arg<br>240                    245                  250                  255 | 1127 |
| gca atg aag aag aga ttt cca agt gct gtt att cat ttt gaa gat ttt<br>Ala Met Lys Lys Arg Phe Pro Ser Ala Val Ile His Phe Glu Asp Phe<br>                260                    265                    270 | 1175 |
| ggt gtt aca act gct aga cct gtg ttg gaa aga ttc aga gat gaa att<br>Gly Val Thr Thr Ala Arg Pro Val Leu Glu Arg Phe Arg Asp Glu Ile<br>275                    280                    285 | 1223 |
| cct tgc ttt aat gat gac atc caa ggt acc ggc gct gtt gtc atg gct<br>Pro Cys Phe Asn Asp Asp Ile Gln Gly Thr Gly Ala Val Val Met Ala<br>                290                    295                    300 | 1271 |
| tcg atg gcg gct gct ctt aaa tta acc cat aga aat cta cta gac tcc<br>Ser Met Ala Ala Ala Leu Lys Leu Thr His Arg Asn Leu Leu Asp Ser<br>305                    310                    315 | 1319 |
| aaa gtt ttg att tat ggg gct ggt tca gcc ggt ttg ggt att gcc gat<br>Lys Val Leu Ile Tyr Gly Ala Gly Ser Ala Gly Leu Gly Ile Ala Asp<br>320                    325                  330                  335 | 1367 |
| caa att gtt aat cat atg gtt agc cat ggt gcg act aaa gaa gaa gct<br>Gln Ile Val Asn His Met Val Ser His Gly Ala Thr Lys Glu Glu Ala<br>                340                    345                    350 | 1415 |
| aga agg aag att tac tgt atg gac agg tat ggt ttg att tta aaa ggt<br>Arg Arg Lys Ile Tyr Cys Met Asp Arg Tyr Gly Leu Ile Leu Lys Gly<br>                    355                    360                    365 | 1463 |
| atg act tcg aat tct cct gct caa gaa gat tat gct cat gat cca aaa<br>Met Thr Ser Asn Ser Pro Ala Gln Glu Asp Tyr Ala His Asp Pro Lys<br>                370                    375                    380 | 1511 |
| gat tgg gaa aat att tca acc act tcg tta gtg gat gtt atc gaa aaa<br>Asp Trp Glu Asn Ile Ser Thr Thr Ser Leu Val Asp Val Ile Glu Lys<br>385                    390                    395 | 1559 |
| gtc aag cct act act tta gtt ggg tgc tcc acg caa gcg ggc gct ttc<br>Val Lys Pro Thr Thr Leu Val Gly Cys Ser Thr Gln Ala Gly Ala Phe<br>400                    405                  410                  415 | 1607 |
| aat gaa gaa gtc atc aaa aca atg tat aaa cat aat cca aga cca atg<br>Asn Glu Glu Val Ile Lys Thr Met Tyr Lys His Asn Pro Arg Pro Met<br>                420                    425                    430 | 1655 |
| att ttc cca ttg tcc aac cca act aga tta cat gag tgt ttc cct gaa<br>Ile Phe Pro Leu Ser Asn Pro Thr Arg Leu His Glu Cys Phe Pro Glu<br>                    435                    440                    445 | 1703 |
| gac gca ctt aaa tgg acc gat ttc aac gct tta gtt gcc act ggt tct<br>Asp Ala Leu Lys Trp Thr Asp Phe Asn Ala Leu Val Ala Thr Gly Ser<br>                450                    455                    460 | 1751 |
| cct ttc cca cct gtt gaa ggt cat gtt att tct gaa aat aac aat tgt<br>Pro Phe Pro Pro Val Glu Gly His Val Ile Ser Glu Asn Asn Asn Cys<br>465                    470                    475 | 1799 |
| ttt gcc ttc ccg ggt att ggt cta ggt gca gtg ctc gct aga act act<br>Phe Ala Phe Pro Gly Ile Gly Leu Gly Ala Val Leu Ala Arg Thr Thr<br>480                    485                  490                  495 | 1847 |
| agg ata tca gac aac atg att tcg gct gcc gtt gac gag cta gct tct<br>Arg Ile Ser Asp Asn Met Ile Ser Ala Ala Val Asp Glu Leu Ala Ser<br>                500                    505                    510 | 1895 |
| ctt tct cca gct caa aaa gat cct aaa ttg ggc ctt tta cct cca att<br>Leu Ser Pro Ala Gln Lys Asp Pro Lys Leu Gly Leu Leu Pro Pro Ile<br>                    515                    520                    525 | 1943 |

```
gag gaa atc gac gag acc tct gca aga atc gca act gca gtt atc ttg      1991
Glu Glu Ile Asp Glu Thr Ser Ala Arg Ile Ala Thr Ala Val Ile Leu
        530                 535                 540 aag gct gtc gag gaa gga ttt gca aga gta gaa gaa gaa gat tct cca      2039
Lys Ala Val Glu Glu Gly Phe Ala Arg Val Glu Glu Glu Asp Ser Pro
545                 550                 555 tta ggt ggt aaa gtt aaa att cca aga gag ttt gat cca tgt cta aga      2087
Leu Gly Gly Lys Val Lys Ile Pro Arg Glu Phe Asp Pro Cys Leu Arg
560                 565                 570                 575 tgg gtt aaa gaa cag atg tgg cat cca att tac aga cca atg atc aaa      2135
Trp Val Lys Glu Gln Met Trp His Pro Ile Tyr Arg Pro Met Ile Lys
                580                 585                 590 gtc gca cac tca gac aat att cat act cac caa tac taa tggacacata       2184
Val Ala His Ser Asp Asn Ile His Thr His Gln Tyr
                595                 600 cacattatca aatgcattta ttcctaatat cacactaaaa cgtattatat aattttaatc    2244
tttatagact tcatagcacc aattggattt gctttctttc agaataccgc acttaatctc    2304
aatgtacgta acgtaggcaa atctgtcga taaggatctg tatgccgtaa acggaaactc     2364
caagcgccca gaaacttac attatattct tgccagtttc atctcaccag ccagtcacag     2424
tttaaaaggt ttgattgcgt ttcttgtttc gtcggattca gtgctaattg gtaacgcact    2484
gtaccgccac accaaagcaa aaatgcagaa acaaacaaca atgagtgtat gtttaccaac    2544
tttggttttg aaagaaaaa                                                 2562

<210> SEQ ID NO 48
<211> LENGTH: 603
<212> TYPE: PRT
<213> ORGANISM: Issatchenkia orientalis

<400> SEQUENCE: 48

Met Thr Lys Asp Cys Cys Glu Val Thr Lys Ile Pro Val Gly Glu Glu
1               5                   10                  15

Ala Lys Val Thr Val Pro Arg Ser Thr Arg Leu Ser Ala Thr Gly Pro
            20                  25                  30

Val Glu Cys Asp Leu Ser Gly Phe Gln Val Leu Asn Ser Pro Leu Phe
        35                  40                  45

Asn Lys Gly Thr Ala Phe Thr Ile Ala Glu Arg Glu Ala Phe Gly Leu
    50                  55                  60

Asn Gly Leu Leu Pro Pro Val Val Asn Thr Leu Glu Glu Gln Val Glu
65                  70                  75                  80

Arg Ser Tyr Lys Gln Leu His Phe Leu Lys Thr Pro Leu Ala Lys Asn
                85                  90                  95

Asp Phe Cys Thr Ser Leu Arg Leu Gln Asn Lys Val Leu Phe Tyr Arg
            100                 105                 110

Leu Val Lys Glu His Ile Lys Glu Leu Ile Pro Ile Val Tyr Thr Pro
        115                 120                 125

Thr Glu Gly Asp Ala Ile Ile Ala Tyr Ser Asp Arg Phe Arg Lys Pro
    130                 135                 140

Glu Gly Leu Phe Leu Asp Ile Thr Arg Pro Asn Glu Ile Asp Gln Arg
145                 150                 155                 160

Leu Glu Gln Phe Gly Glu Asp Lys Asp Val Asp Tyr Ile Val Ile Thr
                165                 170                 175

Asp Ser Glu Gly Ile Leu Gly Ile Gly Asp Gln Gly Val Gly Gly Val
            180                 185                 190
```

```
Arg Ile Thr Ile Ala Lys Ala Ala Leu Met Thr Val Cys Ala Gly Leu
            195                 200                 205

His Pro Gly Arg Val Val Ser Cys Val Leu Asp Val Gly Thr Asn Asn
210                 215                 220

Val Lys Leu Leu Glu Asp Asp Leu Tyr Leu Gly Asn Arg Phe Pro Arg
225                 230                 235                 240

Val Arg Gly Lys Glu Tyr Asp Asp Phe Val Asn Lys Thr Ile Arg Ala
                245                 250                 255

Met Lys Lys Arg Phe Pro Ser Ala Val Ile His Phe Glu Asp Phe Gly
            260                 265                 270

Val Thr Thr Ala Arg Pro Val Leu Glu Arg Phe Arg Asp Glu Ile Pro
        275                 280                 285

Cys Phe Asn Asp Asp Ile Gln Gly Thr Gly Ala Val Val Met Ala Ser
    290                 295                 300

Met Ala Ala Ala Leu Lys Leu Thr His Arg Asn Leu Leu Asp Ser Lys
305                 310                 315                 320

Val Leu Ile Tyr Gly Ala Gly Ser Ala Gly Leu Gly Ile Ala Asp Gln
                325                 330                 335

Ile Val Asn His Met Val Ser His Gly Ala Thr Lys Glu Glu Ala Arg
            340                 345                 350

Arg Lys Ile Tyr Cys Met Asp Arg Tyr Gly Leu Ile Leu Lys Gly Met
        355                 360                 365

Thr Ser Asn Ser Pro Ala Gln Glu Asp Tyr Ala His Asp Pro Lys Asp
    370                 375                 380

Trp Glu Asn Ile Ser Thr Thr Ser Leu Val Asp Val Ile Glu Lys Val
385                 390                 395                 400

Lys Pro Thr Thr Leu Val Gly Cys Ser Thr Gln Ala Gly Ala Phe Asn
                405                 410                 415

Glu Glu Val Ile Lys Thr Met Tyr Lys His Asn Pro Arg Pro Met Ile
            420                 425                 430

Phe Pro Leu Ser Asn Pro Thr Arg Leu His Glu Cys Phe Pro Glu Asp
        435                 440                 445

Ala Leu Lys Trp Thr Asp Phe Asn Ala Leu Val Ala Thr Gly Ser Pro
    450                 455                 460

Phe Pro Pro Val Glu Gly His Val Ile Ser Glu Asn Asn Asn Cys Phe
465                 470                 475                 480

Ala Phe Pro Gly Ile Gly Leu Gly Ala Val Leu Ala Arg Thr Thr Arg
                485                 490                 495

Ile Ser Asp Asn Met Ile Ser Ala Ala Val Asp Glu Leu Ala Ser Leu
            500                 505                 510

Ser Pro Ala Gln Lys Asp Pro Lys Leu Gly Leu Leu Pro Pro Ile Glu
        515                 520                 525

Glu Ile Asp Glu Thr Ser Ala Arg Ile Ala Thr Ala Val Ile Leu Lys
    530                 535                 540

Ala Val Glu Glu Gly Phe Ala Arg Val Glu Glu Asp Ser Pro Leu
545                 550                 555                 560

Gly Gly Lys Val Lys Ile Pro Arg Glu Phe Asp Pro Cys Leu Arg Trp
                565                 570                 575

Val Lys Glu Gln Met Trp His Pro Ile Tyr Arg Pro Met Ile Lys Val
            580                 585                 590

Ala His Ser Asp Asn Ile His Thr His Gln Tyr
        595                 600
```

<210> SEQ ID NO 49
<211> LENGTH: 3743
<212> TYPE: DNA
<213> ORGANISM: Issatchenkia orientalis
<220> FEATURE:
<221> NAME/KEY: CDS
<222> LOCATION: (1010)..(2746)

<400> SEQUENCE: 49

| | |
|---|---|
| atttgtgtgt gtgtgtcagt gtaagtgtta gtatacttgt tttcctcttt ccctagagt | 60 |
| tggtggtgtg ttttgttgga acgtacatta gatgcataat gcgtgacacc gccatgatgg | 120 |
| ttgtattcta ccaatgagac atggccgctg atcctgttgt gtgggtcatg ggacatcacc | 180 |
| tcttgggggg gattctccta taattggcac cgtgtatgcc tcaaccacta acttccaccc | 240 |
| tataactgaa tatattacat aagcaaatct acttttgtt tgtgttgatc gccatcgttg | 300 |
| aaattcgcgc aacttctggt ggctcaacgc tgctgttcta tcggtatcct aagagatgtc | 360 |
| tttgccctga gtctagggta aactatccac cttcgttgct gtttgactag acagctacta | 420 |
| actttacggt agtaaatgaa taacggctcg ctctcatgat cacttctcta catcacccta | 480 |
| acaagtgtat tattttttt tcaggtgggt gttgctgttg gtgctagcct tagtgccctc | 540 |
| gttaatagtt gaacaaacac tggcatttgg agtataatga aaagggatca ctaccccccg | 600 |
| cttcctgttc cgcttctccc ttccggaaaa accacccacc ctttcttttc ccccactaat | 660 |
| gtatgaattt ttccgttccc aggggaatgg cccacttggt tctctgttaa cccacacaat | 720 |
| tttgacgcat cccacacacc ttttttttt ctaccccaca cttcccttg aaaaatctcc | 780 |
| aatttgaact ggcaattttc acccccacc acttgcattc attagtgagt caatccatcc | 840 |
| cgcggtcgga gattcggaat ccacctactg gtaatctgta atctatattc ccgctgaccc | 900 |
| tttataaatg aactattgtc gtcaattgcg gtagtgctcc aacaaattgt aaggaccttc | 960 |
| tttaaccttt tcgattcaat ccatctccac ataaacctag ttgcacaca atg tta ctc | 1018 |
|                                                                                                           Met Leu Leu<br>                                                                                                           1 | |
| aga tca cta aac tct tct gct cgt tgt gtc aaa caa aca acc aga aca<br>Arg Ser Leu Asn Ser Ser Ala Arg Cys Val Lys Gln Thr Thr Arg Thr<br> 5                       10                   15 | 1066 |
| aag gtt agg tat ctc agc cac gtc agt ggt gca agc atg gcg aaa cct<br>Lys Val Arg Tyr Leu Ser His Val Ser Gly Ala Ser Met Ala Lys Pro<br>20                     25                   30                   35 | 1114 |
| aca ttg aag aac aac tcg aga gaa tcc aac aaa tcc aga aac tat cta<br>Thr Leu Lys Asn Asn Ser Arg Glu Ser Asn Lys Ser Arg Asn Tyr Leu<br>               40                   45                   50 | 1162 |
| att gct gct gtg aca gca ttg gct gta tca acc tca att gga gtt gcc<br>Ile Ala Ala Val Thr Ala Leu Ala Val Ser Thr Ser Ile Gly Val Ala<br>             55                   60                   65 | 1210 |
| gta cat gtg aag gac ccc ttg tat aac gat gct acc ggc agt gat tct<br>Val His Val Lys Asp Pro Leu Tyr Asn Asp Ala Thr Gly Ser Asp Ser<br>70                     75                   80 | 1258 |
| ccg aga agt ata tct gtt gac gag ttt gtc aag cat aat tca caa aac<br>Pro Arg Ser Ile Ser Val Asp Glu Phe Val Lys His Asn Ser Gln Asn<br>85                     90                   95 | 1306 |
| gac tgt tgg att gca atc aat ggc aag gtt tat gat ttc act gat ttt<br>Asp Cys Trp Ile Ala Ile Asn Gly Lys Val Tyr Asp Phe Thr Asp Phe<br>100                 105                110              115 | 1354 |
| att cca aac cat cca ggt ggg gta cct cca tta gtt aat cat gct ggt<br>Ile Pro Asn His Pro Gly Gly Val Pro Pro Leu Val Asn His Ala Gly<br>               120                 125              130 | 1402 |
| tat gat ggt act aaa ctt tat gag aaa ttg cat cca aaa ggt aca att | 1450 |

```
                Tyr Asp Gly Thr Lys Leu Tyr Glu Lys Leu His Pro Lys Gly Thr Ile
                            135                 140                 145 gag aaa ttc ttg cca aag gat aag ttt ctg ggt gtg tta gat ggt gaa         1498
Glu Lys Phe Leu Pro Lys Asp Lys Phe Leu Gly Val Leu Asp Gly Glu
            150                 155                 160 gcg cca aaa ttg gaa gca gac tat ttg gtg gac gat gat gaa caa gag         1546
Ala Pro Lys Leu Glu Ala Asp Tyr Leu Val Asp Asp Asp Glu Gln Glu
165                 170                 175 aga ctg gat tat ttg aac aac tta cct cct ttg tca tct att cag aat         1594
Arg Leu Asp Tyr Leu Asn Asn Leu Pro Pro Leu Ser Ser Ile Gln Asn
180                 185                 190                 195 gtt tat gat ttc gaa tac ttg gcc aag aag att tta cct aaa gat gcc         1642
Val Tyr Asp Phe Glu Tyr Leu Ala Lys Lys Ile Leu Pro Lys Asp Ala
                200                 205                 210 tgg gca tat tat tct tgt ggt gcc gat gat gaa atc aca atg aga gaa         1690
Trp Ala Tyr Tyr Ser Cys Gly Ala Asp Asp Glu Ile Thr Met Arg Glu
                215                 220                 225 aac cat tat gct tat caa aga gtt tat ttc aga cca aga att tgt gtt         1738
Asn His Tyr Ala Tyr Gln Arg Val Tyr Phe Arg Pro Arg Ile Cys Val
            230                 235                 240 gat gtc aag gaa gtt gat act tct tat gaa atg tta ggc act aaa acc         1786
Asp Val Lys Glu Val Asp Thr Ser Tyr Glu Met Leu Gly Thr Lys Thr
245                 250                 255 tct gtt cct ttt tat gta tct gcc acc gct ttg gct aaa tta ggc cat         1834
Ser Val Pro Phe Tyr Val Ser Ala Thr Ala Leu Ala Lys Leu Gly His
260                 265                 270                 275 cct gat ggt gaa tgc tca att gct aga ggc gct ggt aag gaa ggt gtc         1882
Pro Asp Gly Glu Cys Ser Ile Ala Arg Gly Ala Gly Lys Glu Gly Val
                280                 285                 290 gtt caa atg att tcg acc ctt tcc tca atg tca tta gat gaa att gcc         1930
Val Gln Met Ile Ser Thr Leu Ser Ser Met Ser Leu Asp Glu Ile Ala
                295                 300                 305 gct gct aga att cca ggt gca acc caa tgg ttc caa tta tac att aat         1978
Ala Ala Arg Ile Pro Gly Ala Thr Gln Trp Phe Gln Leu Tyr Ile Asn
            310                 315                 320 gag gat aga aat gtc gct aaa ggt ctg gtc aaa cat gca gaa gac ttg         2026
Glu Asp Arg Asn Val Ala Lys Gly Leu Val Lys His Ala Glu Asp Leu
325                 330                 335 ggt atg aag gct atc ttt ata act gtt gat gct cct tct cta ggt aac         2074
Gly Met Lys Ala Ile Phe Ile Thr Val Asp Ala Pro Ser Leu Gly Asn
340                 345                 350                 355 aga gaa aag gat aaa aga tta aag ttt gtt aat gac acc gat gtc gat         2122
Arg Glu Lys Asp Lys Arg Leu Lys Phe Val Asn Asp Thr Asp Val Asp
                360                 365                 370 ttg ggt gat tcc gca gat cga aac agt ggt gct tca aag gca cta tct         2170
Leu Gly Asp Ser Ala Asp Arg Asn Ser Gly Ala Ser Lys Ala Leu Ser
                375                 380                 385 tcg ttc att gat gct tct gtc tct tgg aat gac gtc aaa gcg gtc aag         2218
Ser Phe Ile Asp Ala Ser Val Ser Trp Asn Asp Val Lys Ala Val Lys
            390                 395                 400 tcg tgg act aaa ttg cct gtc tta gtt aaa ggt gtt caa aca gtt gaa         2266
Ser Trp Thr Lys Leu Pro Val Leu Val Lys Gly Val Gln Thr Val Glu
405                 410                 415 gac gtt att gaa gct tac gat gct ggt tgt caa ggt gtt gtt ttg tca         2314
Asp Val Ile Glu Ala Tyr Asp Ala Gly Cys Gln Gly Val Val Leu Ser
420                 425                 430                 435 aac cac ggt ggt agg caa cta gat act gct cct cct cca atc gaa tta         2362
Asn His Gly Gly Arg Gln Leu Asp Thr Ala Pro Pro Pro Ile Glu Leu
                440                 445                 450
```

| | | |
|---|---|---|
| tta gct gaa act gtt cca act ttg aag aga ttg ggt aaa tta aga cca<br>Leu Ala Glu Thr Val Pro Thr Leu Lys Arg Leu Gly Lys Leu Arg Pro<br>455 460 465 | | 2410 |
| gat ttt gaa att tta att gac ggt ggt gtc aaa aga ggt acc gat att<br>Asp Phe Glu Ile Leu Ile Asp Gly Gly Val Lys Arg Gly Thr Asp Ile<br>470 475 480 | | 2458 |
| ttg aaa gca gtc gca atc ggt ggc caa gat gtc aga gtt tca gtt ggt<br>Leu Lys Ala Val Ala Ile Gly Gly Gln Asp Val Arg Val Ser Val Gly<br>485 490 495 | | 2506 |
| atg ggt aga cct ttc tta tat gcc aac tct tgc tat ggt gaa gca ggt<br>Met Gly Arg Pro Phe Leu Tyr Ala Asn Ser Cys Tyr Gly Glu Ala Gly<br>500 505 510 515 | | 2554 |
| gtt aga aaa tta att caa aat cta aag gat gaa tta gaa atg gat atg<br>Val Arg Lys Leu Ile Gln Asn Leu Lys Asp Glu Leu Glu Met Asp Met<br>520 525 530 | | 2602 |
| aga ttg ttg ggt gtc act aaa atg gac cag cta tct tcg aaa cat gtc<br>Arg Leu Leu Gly Val Thr Lys Met Asp Gln Leu Ser Ser Lys His Val<br>535 540 545 | | 2650 |
| gat act aaa cgt ttg att ggt aga gat gcg atc aac tat ttg tat gat<br>Asp Thr Lys Arg Leu Ile Gly Arg Asp Ala Ile Asn Tyr Leu Tyr Asp<br>550 555 560 | | 2698 |
| aat gta tac agc cca atc gaa acc gtt aaa ttc aac aat gaa gat tga<br>Asn Val Tyr Ser Pro Ile Glu Thr Val Lys Phe Asn Asn Glu Asp<br>565 570 575 | | 2746 |
| ttgttggaaa tatattattc ataaaggcga aacattccc ttggtatttt attccaaatt | | 2806 |
| tatgatacat agacgtattt tttatatata aagttatatt attaatgatt caagaaaaag | | 2866 |
| ttcaaataaa ctaatggatc aacctatttc gaccctttct tcattgctac ttcttcctta | | 2926 |
| agcaacagat gattaagtag atactgtttt tttagccaat agtatctcgc cgaggagtta | | 2986 |
| tacttgacta gctcttgctc aagaatcttc ctaagacgta ctagcctagc atagtaatct | | 3046 |
| gtttgtttct gtattgtttg ttctaactgt tctacagtca ttgaatcaat atctccaatg | | 3106 |
| tcttcgacgt tgacaacttt ccccccttg gcagcattct ctttttttgtt ggaatacgac | | 3166 |
| attaaagatt ccttgatttt ctgggtacct tcaatgacca ttgagggatt aaatttgatt | | 3226 |
| tctttgattt tataatggtc ggctattagc tcttccactt cgtcatcatg atcatcagat | | 3286 |
| atgtcacgtt gccttttcaa tttattaaaa ttgtttatca gtttattgtg atcttgtatc | | 3346 |
| aattcattgc gtactctttt ctcaatatca aaagctattt tcttcccgct agactcaaaa | | 3406 |
| tcaactctga agtcattttc tcgctggaat tcatgtattt catggattaa ttctctattg | | 3466 |
| atattctcat atgcatcctg taaactgttg ccgttgatat tatgaaccgc ctttaaatgt | | 3526 |
| ttcaataagg catctgctct agtaaatgcc ttcagacatt caggtaataa acagtaaaat | | 3586 |
| ggcttctcgg ctgtatgcgt cctaaatatga gacaatagcg caaatctact gtgttgtgga | | 3646 |
| gtaccatatc ttggacaatt tccccactta catgaatggt ctgtgttggg ttgtttaaaa | | 3706 |
| tgattagtat ttatgtgatt aaccatctca tccattt | | 3743 |

<210> SEQ ID NO 50
<211> LENGTH: 578
<212> TYPE: PRT
<213> ORGANISM: Issatchenkia orientalis
<400> SEQUENCE: 50

Met Leu Leu Arg Ser Leu Asn Ser Ser Ala Arg Cys Val Lys Gln Thr
1               5                   10                  15

Thr Arg Thr Lys Val Arg Tyr Leu Ser His Val Ser Gly Ala Ser Met
            20                  25                  30

```
Ala Lys Pro Thr Leu Lys Asn Asn Ser Arg Glu Ser Asn Lys Ser Arg
         35                  40                  45

Asn Tyr Leu Ile Ala Ala Val Thr Ala Leu Ala Val Ser Thr Ser Ile
 50                  55                  60

Gly Val Ala Val His Val Lys Asp Pro Leu Tyr Asn Asp Ala Thr Gly
 65                  70                  75                  80

Ser Asp Ser Pro Arg Ser Ile Ser Val Asp Glu Phe Val Lys His Asn
                 85                  90                  95

Ser Gln Asn Asp Cys Trp Ile Ala Ile Asn Gly Lys Val Tyr Asp Phe
                100                 105                 110

Thr Asp Phe Ile Pro Asn His Pro Gly Gly Val Pro Pro Leu Val Asn
                115                 120                 125

His Ala Gly Tyr Asp Gly Thr Lys Leu Tyr Glu Lys Leu His Pro Lys
130                 135                 140

Gly Thr Ile Glu Lys Phe Leu Pro Lys Asp Lys Phe Leu Gly Val Leu
145                 150                 155                 160

Asp Gly Glu Ala Pro Lys Leu Glu Ala Asp Tyr Leu Val Asp Asp Asp
                165                 170                 175

Glu Gln Glu Arg Leu Asp Tyr Leu Asn Asn Leu Pro Pro Leu Ser Ser
                180                 185                 190

Ile Gln Asn Val Tyr Asp Phe Glu Tyr Leu Ala Lys Lys Ile Leu Pro
                195                 200                 205

Lys Asp Ala Trp Ala Tyr Tyr Ser Cys Gly Ala Asp Asp Glu Ile Thr
                210                 215                 220

Met Arg Glu Asn His Tyr Ala Tyr Gln Arg Val Tyr Phe Arg Pro Arg
225                 230                 235                 240

Ile Cys Val Asp Val Lys Glu Val Asp Thr Ser Tyr Glu Met Leu Gly
                245                 250                 255

Thr Lys Thr Ser Val Pro Phe Tyr Val Ser Ala Thr Ala Leu Ala Lys
                260                 265                 270

Leu Gly His Pro Asp Gly Glu Cys Ser Ile Ala Arg Gly Ala Gly Lys
                275                 280                 285

Glu Gly Val Val Gln Met Ile Ser Thr Leu Ser Ser Met Ser Leu Asp
                290                 295                 300

Glu Ile Ala Ala Ala Arg Ile Pro Gly Ala Thr Gln Trp Phe Gln Leu
305                 310                 315                 320

Tyr Ile Asn Glu Asp Arg Asn Val Ala Lys Gly Leu Val Lys His Ala
                325                 330                 335

Glu Asp Leu Gly Met Lys Ala Ile Phe Ile Thr Val Asp Ala Pro Ser
                340                 345                 350

Leu Gly Asn Arg Glu Lys Asp Lys Arg Leu Lys Phe Val Asn Asp Thr
                355                 360                 365

Asp Val Asp Leu Gly Asp Ser Ala Asp Arg Asn Ser Gly Ala Ser Lys
                370                 375                 380

Ala Leu Ser Ser Phe Ile Asp Ala Ser Val Ser Trp Asn Asp Val Lys
385                 390                 395                 400

Ala Val Lys Ser Trp Thr Lys Leu Pro Val Leu Val Lys Gly Val Gln
                405                 410                 415

Thr Val Glu Asp Val Ile Glu Ala Tyr Asp Ala Gly Cys Gln Gly Val
                420                 425                 430

Val Leu Ser Asn His Gly Gly Arg Gln Leu Asp Thr Ala Pro Pro Pro
                435                 440                 445
```

```
Ile Glu Leu Leu Ala Glu Thr Val Pro Thr Leu Lys Arg Leu Gly Lys
450                 455                 460

Leu Arg Pro Asp Phe Glu Ile Leu Ile Asp Gly Gly Val Lys Arg Gly
465                 470                 475                 480

Thr Asp Ile Leu Lys Ala Val Ala Ile Gly Gly Gln Asp Val Arg Val
                485                 490                 495

Ser Val Gly Met Gly Arg Pro Phe Leu Tyr Ala Asn Ser Cys Tyr Gly
            500                 505                 510

Glu Ala Gly Val Arg Lys Leu Ile Gln Asn Leu Lys Asp Glu Leu Glu
        515                 520                 525

Met Asp Met Arg Leu Leu Gly Val Thr Lys Met Asp Gln Leu Ser Ser
530                 535                 540

Lys His Val Asp Thr Lys Arg Leu Ile Gly Arg Asp Ala Ile Asn Tyr
545                 550                 555                 560

Leu Tyr Asp Asn Val Tyr Ser Pro Ile Glu Thr Val Lys Phe Asn Asn
                565                 570                 575

Glu Asp

<210> SEQ ID NO 51
<211> LENGTH: 3695
<212> TYPE: DNA
<213> ORGANISM: Issatchenkia orientalis
<220> FEATURE:
<221> NAME/KEY: CDS
<222> LOCATION: (1001)..(2698)

<400> SEQUENCE: 51
ctcgtttcct gtgatatgtt tgccgtgcgc ctggtcgatt ttcaccttct ttgaaatccg      60
agttcgggaa tgcaattggg aaaaagccaa ggagaaagaa acaaaaaga gagttgcgta     120 gaaactcgga atgctcgaag aaaccagaca gttgatggct ggtttccgtt ttgaggacgc    180
ttggtgtgtg taacttggat ttgcacacta gagccgtctc tgcattgtat taaggtgtaa    240
ggacggtgaa tcatcgcgat ggagcggggt ttttctttt ggcaggtttt tccgcggaag    300
gcgagagggc gagaggggg gggggtgtat gtagttcata tttcggcatt actacaagga    360
tgtttccgta cattgcatgg tactgggggtt ctccttttct tgcacatctc cataaactaa    420
atatcaatag atgtatccgt ttggaatctc atgactttg gtgtgtggtc tgtgtcttcc    480
cagttatcta cttgagtgat tatgatccag ttttcaccat tggttacata ccaaacagag    540
aacttatacg caccagaacg ccttttgtgt cttttgtttt ctcaagtatt tctatcagtt    600
tccttcatgt atcccgggac tccattgtcc tcggtagtgc ctaccaattt aatgtttgac    660
tccttgcgtt ttctcctgtc gcggacaaac ggtgcggctc ccccgatgat tcacgtaata    720
agccggagtc aaccacagag gtccctatg actcaacaag gctcgtaga aactcggctt     780 ctcggagaaa gagtcttttc tttttcactg gaaaatattt tttttttcctt tatattcttt    840 tgaaccaaaa tgtggctact ataaaagtgc ctttattccc cagcttttct agcatgattg    900
agtcaccttc cacaatgagt cttctttatt gttagtattg tgaatattat ccgtgcagtt    960
ttcaagaacg taaatcaaca gcagtgataa taccttcaaa atg tta aga tcc cag    1015
                                              Met Leu Arg Ser Gln
                                                1               5 ttc aaa aac att ttg aaa aat gtt aac aag aac cat tct cta agg aga    1063
Phe Lys Asn Ile Leu Lys Asn Val Asn Lys Asn His Ser Leu Arg Arg
             10                  15                  20 act ttt act tcc agc acc tca aag gct gga aaa aat gct tca tac aat    1111
Thr Phe Thr Ser Ser Thr Ser Lys Ala Gly Lys Asn Ala Ser Tyr Asn
```

-continued

```
                    25                  30                  35 gcc aag att ata tct gca acc gtg gcc tcg att gtt gca gca gct ggc    1159
Ala Lys Ile Ile Ser Ala Thr Val Ala Ser Ile Val Ala Ala Ala Gly
         40                  45                  50 tct tat atg ttg gtc cag cct tca cta gct aat gat gag gca cag tct    1207
Ser Tyr Met Leu Val Gln Pro Ser Leu Ala Asn Asp Glu Ala Gln Ser
 55                  60                  65 gct aat cca act agg aag atc tct gtt gac gaa ttt gtt aaa cac aac    1255
Ala Asn Pro Thr Arg Lys Ile Ser Val Asp Glu Phe Val Lys His Asn
 70                  75                  80                  85 cat gcc gat gat tgt tgg atc act gtt aac ggt aac gtc tat gac ttg    1303
His Ala Asp Asp Cys Trp Ile Thr Val Asn Gly Asn Val Tyr Asp Leu
                 90                  95                 100 act gat ttc att tca atg cat cca ggt ggt act acc cca ttg att caa    1351
Thr Asp Phe Ile Ser Met His Pro Gly Gly Thr Thr Pro Leu Ile Gln
            105                 110                 115 aat gca ggt cac gac gca act gaa att tac aac aag att cat cca aag    1399
Asn Ala Gly His Asp Ala Thr Glu Ile Tyr Asn Lys Ile His Pro Lys
        120                 125                 130 ggt aca atc gag aac ttc tta cca aag gaa aag caa ttg ggt gtt ttg    1447
Gly Thr Ile Glu Asn Phe Leu Pro Lys Glu Lys Gln Leu Gly Val Leu
135                 140                 145 gat ggt gaa gct cct aaa atc gaa gtt gtg ctt gac gaa aag gag aaa    1495
Asp Gly Glu Ala Pro Lys Ile Glu Val Val Leu Asp Glu Lys Glu Lys
150                 155                 160                 165 cac aga ttg gag ttg ttg aat cat ctc cct gct ctt tcc aga att caa    1543
His Arg Leu Glu Leu Leu Asn His Leu Pro Ala Leu Ser Arg Ile Gln
                170                 175                 180 aac att tat gat ttc gaa cat att gct tct aga gtt ttg agc gac caa    1591
Asn Ile Tyr Asp Phe Glu His Ile Ala Ser Arg Val Leu Ser Asp Gln
            185                 190                 195 gca tgg aac tac tat tca tgt ggt gcc gaa gat gaa atc acc ttg agg    1639
Ala Trp Asn Tyr Tyr Ser Cys Gly Ala Glu Asp Glu Ile Thr Leu Arg
        200                 205                 210 gaa aat cat tat gct tac caa aga atc tac ttt aag cca aaa tgt tgt    1687
Glu Asn His Tyr Ala Tyr Gln Arg Ile Tyr Phe Lys Pro Lys Cys Cys
    215                 220                 225 gtc aat gtt gca gaa gtt gat acc tct cat gaa att tta ggt aca aaa    1735
Val Asn Val Ala Glu Val Asp Thr Ser His Glu Ile Leu Gly Thr Lys
230                 235                 240                 245 gct tct gtt cct ttc tac gtt tcc gca gcc gct tca gca aag ttg ggg    1783
Ala Ser Val Pro Phe Tyr Val Ser Ala Ala Ala Ser Ala Lys Leu Gly
                250                 255                 260 cac gag gat ggt gaa tgt tcc att gct aga ggt gca ggt aag gaa ggc    1831
His Glu Asp Gly Glu Cys Ser Ile Ala Arg Gly Ala Gly Lys Glu Gly
            265                 270                 275 gtt att caa atg att tct tcc ttc tct tcc aac tct ttg gag gaa att    1879
Val Ile Gln Met Ile Ser Ser Phe Ser Ser Asn Ser Leu Glu Glu Ile
        280                 285                 290 gca gaa tcc aga att cct ggt gca aca caa tgg ttt caa tta tac gtt    1927
Ala Glu Ser Arg Ile Pro Gly Ala Thr Gln Trp Phe Gln Leu Tyr Val
    295                 300                 305 aat gaa gac aag gat gtt gtg aag aag act tta aaa agg gcc gaa aac    1975
Asn Glu Asp Lys Asp Val Val Lys Lys Thr Leu Lys Arg Ala Glu Asn
310                 315                 320                 325 ttg ggt atg aag gcc atc ttt gtc act gtg gac gct gct agt aga ggt    2023
Leu Gly Met Lys Ala Ile Phe Val Thr Val Asp Ala Ala Ser Arg Gly
                330                 335                 340 aat aga gaa aaa gac att aga atg aga att acc gaa gat aca gat gag    2071
```

```
                Asn Arg Glu Lys Asp Ile Arg Met Arg Ile Thr Glu Asp Thr Asp Glu
                                345                 350                 355 tta atc gac gat tct tct gtt aga gct ggt tct acc tct ggt gca ttg           2119
Leu Ile Asp Asp Ser Ser Val Arg Ala Gly Ser Thr Ser Gly Ala Leu
                360                 365                 370 cca gct ttc att gac aag agg ctg act tgg gat gaa gtt aag gat atc           2167
Pro Ala Phe Ile Asp Lys Arg Leu Thr Trp Asp Glu Val Lys Asp Ile
375                 380                 385 att tca tgg acc aag tta cca gtt ttg ctg aag ggt gtt caa aga act           2215
Ile Ser Trp Thr Lys Leu Pro Val Leu Leu Lys Gly Val Gln Arg Thr
390                 395                 400                 405 gat gat att gag aag gca att gat att ggt tgt aag ggt gtt gtc ttg           2263
Asp Asp Ile Glu Lys Ala Ile Asp Ile Gly Cys Lys Gly Val Val Leu
                410                 415                 420 tcc aat cat ggt ggt aga caa tta gat act tct cct cct cca ata gaa           2311
Ser Asn His Gly Gly Arg Gln Leu Asp Thr Ser Pro Pro Pro Ile Glu
                425                 430                 435 gtt atg gct gaa tct gtt cca atc cta aag caa aag ggt aaa ctg gat           2359
Val Met Ala Glu Ser Val Pro Ile Leu Lys Gln Lys Gly Lys Leu Asp
                440                 445                 450 cca aat ttc agt att ttc gtt gat ggt ggt gtt aga aga ggt aca gat           2407
Pro Asn Phe Ser Ile Phe Val Asp Gly Gly Val Arg Arg Gly Thr Asp
455                 460                 465 att ttg aaa gct ttg gct att ggt ggc aga gac tgt aaa gtt gct gtt           2455
Ile Leu Lys Ala Leu Ala Ile Gly Gly Arg Asp Cys Lys Val Ala Val
470                 475                 480                 485 ggt ctg ggt aga cct ttc ctt tat gca aat act ggt tat ggt gaa aag           2503
Gly Leu Gly Arg Pro Phe Leu Tyr Ala Asn Thr Gly Tyr Gly Glu Lys
                490                 495                 500 ggt gtc aga aag gcc gtg caa att cta aga gaa gaa tta aag gct gat           2551
Gly Val Arg Lys Ala Val Gln Ile Leu Arg Glu Glu Leu Lys Ala Asp
                505                 510                 515 atg aga atg ttg ggc gtt acc tct ttg aac gag cta gac gac tct tac           2599
Met Arg Met Leu Gly Val Thr Ser Leu Asn Glu Leu Asp Asp Ser Tyr
                520                 525                 530 att gac acc aga aga tta cta ggt aga gat gct gtt aac cac ata tac           2647
Ile Asp Thr Arg Arg Leu Leu Gly Arg Asp Ala Val Asn His Ile Tyr
535                 540                 545 aac aac aac tac tac cca atg tct aag att caa ttc aaa aac gaa aaa           2695
Asn Asn Asn Tyr Tyr Pro Met Ser Lys Ile Gln Phe Lys Asn Glu Lys
550                 555                 560                 565 taa gtctgatatt tgctaaattg aaatgaacct taccatgcca catctataga               2748
catcaaaaca ttttcaattt gtcgatatct tttgcatatc aaagtaatac caagcatgtt         2808 caaaagaaa agaaagcata actttaatac tctattcgaa acattccgat ccacaacaca         2868
ttagtctttt taggcccgtt gttcatcttt ctattacttt attcctaact gtattttat         2928 aattccgggt ttataaaaga ttaaactaat atagcgcatt cttttgggt acaaacatac         2988 ataacggagc tcattcatac atcgcttttc agttcgactg gtgtttcgga tgcctctttt       3048
tctaaggagc tagattctgg ccccacacta gtctttgaac tcgttgctcc cttaccaccc       3108
ttaccaccag ccttacttgt aggttttca gtagcatact ctgcgtgttt gactaaattc       3168 ccttcctaa ctttgtgcca gcttggccat atcattaaat acccactgaa acttctaaca       3228
actcttcgac cttcctgatg ggcctttgaa attgtatcta ccaaacctgc cttcaaggga       3288
tgttctttat atccctgac gtctttcata ctttgaactt cctctgggac gtcttccttt         3348
ccatattttt cccattggcc cggcttgttt ttagatttgt ctatctcacg gaaaattgag       3408
```

-continued

```
gggttcatac ttaatccact cacaccaacc ctgatgttag aagacagttt tgctaaatta    3468
tttacattct gacttgtgtt tgtcgatata actgaatcag atggtttcat cgatgattct    3528
cgggagattg gttctgatgg cgtcaccggc gtctcagatg ctgctggatt tagctttagt    3588
ttgagccgtt taataggttc ttcatttaat gtttgttttc ttttttttgtc gtagaaatgt    3648 gctgtgagat caggaaattg ttcaagctgt tcacgactca gttttag    3695
```

<210> SEQ ID NO 52
<211> LENGTH: 565
<212> TYPE: PRT
<213> ORGANISM: Issatchenkia orientalis

<400> SEQUENCE: 52

```
Met Leu Arg Ser Gln Phe Lys Asn Ile Leu Lys Asn Val Asn Lys Asn
1               5                   10                  15

His Ser Leu Arg Arg Thr Phe Thr Ser Ser Thr Ser Lys Ala Gly Lys
                20                  25                  30

Asn Ala Ser Tyr Asn Ala Lys Ile Ile Ser Ala Thr Val Ala Ser Ile
        35                  40                  45

Val Ala Ala Ala Gly Ser Tyr Met Leu Val Gln Pro Ser Leu Ala Asn
    50                  55                  60

Asp Glu Ala Gln Ser Ala Asn Pro Thr Arg Lys Ile Ser Val Asp Glu
65                  70                  75                  80

Phe Val Lys His Asn His Ala Asp Asp Cys Trp Ile Thr Val Asn Gly
                85                  90                  95

Asn Val Tyr Asp Leu Thr Asp Phe Ile Ser Met His Pro Gly Gly Thr
            100                 105                 110

Thr Pro Leu Ile Gln Asn Ala Gly His Asp Ala Thr Glu Ile Tyr Asn
        115                 120                 125

Lys Ile His Pro Lys Gly Thr Ile Glu Asn Phe Leu Pro Lys Glu Lys
    130                 135                 140

Gln Leu Gly Val Leu Asp Gly Glu Ala Pro Lys Ile Glu Val Val Leu
145                 150                 155                 160

Asp Glu Lys Glu Lys His Arg Leu Glu Leu Leu Asn His Leu Pro Ala
                165                 170                 175

Leu Ser Arg Ile Gln Asn Ile Tyr Asp Phe Glu His Ile Ala Ser Arg
            180                 185                 190

Val Leu Ser Asp Gln Ala Trp Asn Tyr Tyr Ser Cys Gly Ala Glu Asp
        195                 200                 205

Glu Ile Thr Leu Arg Glu Asn His Tyr Ala Tyr Gln Arg Ile Tyr Phe
    210                 215                 220

Lys Pro Lys Cys Cys Val Asn Val Ala Glu Val Asp Thr Ser His Glu
225                 230                 235                 240

Ile Leu Gly Thr Lys Ala Ser Val Pro Phe Tyr Val Ser Ala Ala Ala
                245                 250                 255

Ser Ala Lys Leu Gly His Glu Asp Gly Glu Cys Ser Ile Ala Arg Gly
            260                 265                 270

Ala Gly Lys Glu Gly Val Ile Gln Met Ile Ser Ser Phe Ser Ser Asn
        275                 280                 285

Ser Leu Glu Glu Ile Ala Glu Ser Arg Ile Pro Gly Ala Thr Gln Trp
    290                 295                 300

Phe Gln Leu Tyr Val Asn Glu Asp Lys Asp Val Val Lys Lys Thr Leu
305                 310                 315                 320

Lys Arg Ala Glu Asn Leu Gly Met Lys Ala Ile Phe Val Thr Val Asp
```

```
                    325                 330                 335
Ala Ala Ser Arg Gly Asn Arg Glu Lys Asp Ile Arg Met Arg Ile Thr
                340                 345                 350

Glu Asp Thr Asp Glu Leu Ile Asp Asp Ser Ser Val Arg Ala Gly Ser
            355                 360                 365

Thr Ser Gly Ala Leu Pro Ala Phe Ile Asp Lys Arg Leu Thr Trp Asp
370                 375                 380

Glu Val Lys Asp Ile Ile Ser Trp Thr Lys Leu Pro Val Leu Leu Lys
385                 390                 395                 400

Gly Val Gln Arg Thr Asp Asp Ile Glu Lys Ala Ile Asp Ile Gly Cys
                405                 410                 415

Lys Gly Val Val Leu Ser Asn His Gly Gly Arg Gln Leu Asp Thr Ser
                420                 425                 430

Pro Pro Pro Ile Glu Val Met Ala Glu Ser Val Pro Ile Leu Lys Gln
            435                 440                 445

Lys Gly Lys Leu Asp Pro Asn Phe Ser Ile Phe Val Asp Gly Gly Val
450                 455                 460

Arg Arg Gly Thr Asp Ile Leu Lys Ala Leu Ala Ile Gly Gly Arg Asp
465                 470                 475                 480

Cys Lys Val Ala Val Gly Leu Gly Arg Pro Phe Leu Tyr Ala Asn Thr
                485                 490                 495

Gly Tyr Gly Glu Lys Gly Val Arg Lys Ala Val Gln Ile Leu Arg Glu
            500                 505                 510

Glu Leu Lys Ala Asp Met Arg Met Leu Gly Val Thr Ser Leu Asn Glu
            515                 520                 525

Leu Asp Asp Ser Tyr Ile Asp Thr Arg Arg Leu Leu Gly Arg Asp Ala
530                 535                 540

Val Asn His Ile Tyr Asn Asn Tyr Tyr Pro Met Ser Lys Ile Gln
545                 550                 555                 560

Phe Lys Asn Glu Lys
            565

<210> SEQ ID NO 53
<211> LENGTH: 1960
<212> TYPE: DNA
<213> ORGANISM: Issatchenkia orientalis
<220> FEATURE:
<221> NAME/KEY: CDS
<222> LOCATION: (411)..(1343)

<400> SEQUENCE: 53
gtacgactca tgggctttta caaacacctt acatgttgta tacagtagag cggggggcaa    60
caacctatgg gggtgaatat gaagctctta tgacgagtca ccccgatttc cccgttatcc   120
gacacgagcg atttgaaagc ccgttttctt acctgttagg gaaattgtcc gtgggcatgt   180
ttctccgttc caagggttcc gtttgccgtc aggtatctaa ggatagggca caatagtcag   240
cggggaaacg gagttcccga gggtgtcgga gatactccag ctaattgacc cctagataaa   300
tattcatgat taattcgact attataaggt cattcttccc atgttctttc cattcatcta   360
tataaggtgt ccctggttcc tttattaaga agaaaacaac tgcaacactt atg act      416
                                                        Met Thr
                                                        1 ttg aag tcc aaa tca aaa tcc aaa aag aag cac gca tcc tca aaa cca    464
Leu Lys Ser Lys Ser Lys Ser Lys Lys Lys His Ala Ser Ser Lys Pro
        5                   10                  15 ctg gaa tca tct aat aaa atg tcc aaa agt agt gtt gaa cac cat gaa    512
```

-continued

| | | | | | | | | | | | | | | |
|---|---|---|---|---|---|---|---|---|---|---|---|---|---|---|
| Leu | Glu | Ser | Ser | Asn | Lys | Met | Ser | Lys | Ser | Ser | Val | Glu | His | His | Glu |
| | 20 | | | | 25 | | | | | 30 | | | | |

```
cat acc tca aat aag gaa aat gac cat att tcc ttg cat tcc cgc ttg       560
His Thr Ser Asn Lys Glu Asn Asp His Ile Ser Leu His Ser Arg Leu
 35              40                  45                  50 acg aat att gaa cat cag atc atg ggc aaa gta cat aca agt gat gac       608
Thr Asn Ile Glu His Gln Ile Met Gly Lys Val His Thr Ser Asp Asp
                     55                  60                  65 ggc gcc tat gtt atc tta gac aac aaa aag tat cct aag tca gaa tta       656
Gly Ala Tyr Val Ile Leu Asp Asn Lys Lys Tyr Pro Lys Ser Glu Leu
             70                  75                  80 ttg aag gcc ttt ggt ggt ttt atg aac cct ggt tgg gca gtg cct tcc       704
Leu Lys Ala Phe Gly Gly Phe Met Asn Pro Gly Trp Ala Val Pro Ser
             85                  90                  95 gaa cac aag ttt ggt aat cca gct cct ttg ggt cta tct gca ttt gcg       752
Glu His Lys Phe Gly Asn Pro Ala Pro Leu Gly Leu Ser Ala Phe Ala
        100                 105                 110 tat tgt act ttt gtt gca tct ttg gtc aac atg caa act aga cat gtt       800
Tyr Cys Thr Phe Val Ala Ser Leu Val Asn Met Gln Thr Arg His Val
115                 120                 125                 130 gaa aat gat gct gtt aat gtc ggt gct gca atg ttt tat ggt ggt ttt       848
Glu Asn Asp Ala Val Asn Val Gly Ala Ala Met Phe Tyr Gly Gly Phe
                    135                 140                 145 atc cag ttc att gcc gga ctt tgg gaa ata tcg ctt gaa aac gct ttt       896
Ile Gln Phe Ile Ala Gly Leu Trp Glu Ile Ser Leu Glu Asn Ala Phe
            150                 155                 160 ggt ggt ttg gca ttt tgc tct ttt gga ggt tac tgg atg gca tcg gcc       944
Gly Gly Leu Ala Phe Cys Ser Phe Gly Gly Tyr Trp Met Ala Ser Ala
            165                 170                 175 tca aac cat atc ccc tgg ttc cat att gct agc tct tat act aca gaa       992
Ser Asn His Ile Pro Trp Phe His Ile Ala Ser Ser Tyr Thr Thr Glu
        180                 185                 190 gca gaa ttc aaa tca ggt atg gga ttt ttc tac ctt ggt tgg cta ctc      1040
Ala Glu Phe Lys Ser Gly Met Gly Phe Phe Tyr Leu Gly Trp Leu Leu
195                 200                 205                 210 ttt aca ata atc ttg cta gct tgt tca atc aaa tct acc att tta ttt      1088
Phe Thr Ile Ile Leu Leu Ala Cys Ser Ile Lys Ser Thr Ile Leu Phe
                    215                 220                 225 ttc ctg ttg ttt gtg ctg gtc ttt atg aga ttg ctg tta tta aca tgt      1136
Phe Leu Leu Phe Val Leu Val Phe Met Arg Leu Leu Leu Leu Thr Cys
            230                 235                 240 tgg aag ttt gcg gac agt cat gcc tgt gag ttt gct gct ggt gtt ttc      1184
Trp Lys Phe Ala Asp Ser His Ala Cys Glu Phe Ala Ala Gly Val Phe
            245                 250                 255 ggt gtt ttg gca tct ctg tta gca tgg tat cat gca tat gca ggt att      1232
Gly Val Leu Ala Ser Leu Leu Ala Trp Tyr His Ala Tyr Ala Gly Ile
        260                 265                 270 gca aca cct cag aat tct tac tat gtt gtt aat cca aca cct atg cct      1280
Ala Thr Pro Gln Asn Ser Tyr Tyr Val Val Asn Pro Thr Pro Met Pro
275                 280                 285                 290 gtt att gga tca aag agc aaa gat atg ttt gat tct gac gac ttt gac      1328
Val Ile Gly Ser Lys Ser Lys Asp Met Phe Asp Ser Asp Asp Phe Asp
                    295                 300                 305 caa tct tca tct tga tctagagtcc ctctaattct tcctgttgtt ttttctcgg      1383
Gln Ser Ser Ser
                310 ttcacttctt ccaccacttt gggtttgaaa cctcctttta taaactgtgt ttttatccat   1443 ttttttttgt tcttactgct tacaacttaa tataatacac tatataacaa aaaattccgt   1503
```

```
ttatttctac atcactatgt gacgaattgt atattcatct gttcatcaag gtcccacact   1563
tcttacctga atgttccacc aatattaga  aaacctgcac ttatcactct aacttatgta   1623
tagtacttag aggaagttac aattatcagt gtctgtaccg gccacaatgg ttgatatcct   1683
ccaatacgat acagccccac atacttaagt tttcacatat tgcgcataat aaataggtgc   1743
aatctgaccc ttgccaaata attcggtcat tccacgtcta gaccggacaa caagtggaaa   1803
aaatagatct atgaggatct gagcaacgtc aatcaaatcc atattattct cctgcccgat   1863
tttgaccgtt gtgagtccta cagaacacag atggacacac actgagtcat ctccacaact   1923 acaccccat ctcgtataaa tgagtgctcg atcactg                              1960
```

<210> SEQ ID NO 54
<211> LENGTH: 310
<212> TYPE: PRT
<213> ORGANISM: Issatchenkia orientalis

<400> SEQUENCE: 54

```
Met Thr Leu Lys Ser Lys Ser Lys Ser Lys Lys His Ala Ser Ser
1               5                   10                  15

Lys Pro Leu Glu Ser Ser Asn Lys Met Ser Lys Ser Ser Val Glu His
                20                  25                  30

His Glu His Thr Ser Asn Lys Glu Asn Asp His Ile Ser Leu His Ser
            35                  40                  45

Arg Leu Thr Asn Ile Glu His Gln Ile Met Gly Lys Val His Thr Ser
        50                  55                  60

Asp Asp Gly Ala Tyr Val Ile Leu Asp Asn Lys Lys Tyr Pro Lys Ser
65                  70                  75                  80

Glu Leu Leu Lys Ala Phe Gly Gly Phe Met Asn Pro Gly Trp Ala Val
                85                  90                  95

Pro Ser Glu His Lys Phe Gly Asn Pro Ala Pro Leu Gly Leu Ser Ala
                100                 105                 110

Phe Ala Tyr Cys Thr Phe Val Ala Ser Leu Val Asn Met Gln Thr Arg
            115                 120                 125

His Val Glu Asn Asp Ala Val Asn Val Gly Ala Ala Met Phe Tyr Gly
        130                 135                 140

Gly Phe Ile Gln Phe Ile Ala Gly Leu Trp Glu Ile Ser Leu Glu Asn
145                 150                 155                 160

Ala Phe Gly Gly Leu Ala Phe Cys Ser Phe Gly Gly Tyr Trp Met Ala
                165                 170                 175

Ser Ala Ser Asn His Ile Pro Trp Phe His Ile Ala Ser Ser Tyr Thr
                180                 185                 190

Thr Glu Ala Glu Phe Lys Ser Gly Met Gly Phe Phe Tyr Leu Gly Trp
            195                 200                 205

Leu Leu Phe Thr Ile Ile Leu Leu Ala Cys Ser Ile Lys Ser Thr Ile
        210                 215                 220

Leu Phe Phe Leu Leu Phe Val Leu Val Phe Met Arg Leu Leu Leu Leu
225                 230                 235                 240

Thr Cys Trp Lys Phe Ala Asp Ser His Ala Cys Glu Phe Ala Ala Gly
                245                 250                 255

Val Phe Gly Val Leu Ala Ser Leu Leu Ala Trp Tyr His Ala Tyr Ala
                260                 265                 270

Gly Ile Ala Thr Pro Gln Asn Ser Tyr Tyr Val Val Asn Pro Thr Pro
            275                 280                 285

Met Pro Val Ile Gly Ser Lys Ser Lys Asp Met Phe Asp Ser Asp Asp
```

```
                    290                 295                 300
Phe Asp Gln Ser Ser Ser
305                 310

<210> SEQ ID NO 55
<211> LENGTH: 1032
<212> TYPE: DNA
<213> ORGANISM: Bacteriophage P1
<220> FEATURE:
<221> NAME/KEY: CDS
<222> LOCATION: (1)..(1032)

<400> SEQUENCE: 55 atg tct aat tta ctt act gtt cac caa aac ttg cct gca tta cca gtt          48
Met Ser Asn Leu Leu Thr Val His Gln Asn Leu Pro Ala Leu Pro Val
1               5                   10                  15 gac gca acc tcc gat gaa gtc aga aag aac ctt atg gat atg ttt aga          96
Asp Ala Thr Ser Asp Glu Val Arg Lys Asn Leu Met Asp Met Phe Arg
                20                  25                  30 gat aga caa gct ttc tcc gaa cat act tgg aaa atg tta tta tcc gtt         144
Asp Arg Gln Ala Phe Ser Glu His Thr Trp Lys Met Leu Leu Ser Val
            35                  40                  45 tgt aga tcc tgg gcc gct tgg tgt aaa ctt aac aat aga aaa tgg ttt         192
Cys Arg Ser Trp Ala Ala Trp Cys Lys Leu Asn Asn Arg Lys Trp Phe
        50                  55                  60 cct gct gaa cca gaa gac gtc aga gat tac tta ctt tac tta caa gct         240
Pro Ala Glu Pro Glu Asp Val Arg Asp Tyr Leu Leu Tyr Leu Gln Ala
65                  70                  75                  80 aga ggt ttg gct gtt aaa act atc caa caa cac tta ggt caa ttg aat         288
Arg Gly Leu Ala Val Lys Thr Ile Gln Gln His Leu Gly Gln Leu Asn
                85                  90                  95 atg tta cac aga aga tcc ggt tta cca aga cca tcc gat tcc aac gca         336
Met Leu His Arg Arg Ser Gly Leu Pro Arg Pro Ser Asp Ser Asn Ala
                100                 105                 110 gtt tcc ctt gtt atg aga aga att aga aaa gaa aat gtt gac gct ggt         384
Val Ser Leu Val Met Arg Arg Ile Arg Lys Glu Asn Val Asp Ala Gly
            115                 120                 125 gaa aga gct aaa caa gca tta gca ttt gaa aga acc gat ttc gat caa         432
Glu Arg Ala Lys Gln Ala Leu Ala Phe Glu Arg Thr Asp Phe Asp Gln
        130                 135                 140 gtt aga tcc tta atg gaa aat tcc gat aga tgt caa gat att aga aac         480
Val Arg Ser Leu Met Glu Asn Ser Asp Arg Cys Gln Asp Ile Arg Asn
145                 150                 155                 160 tta gct ttc tta ggt att gct tac aac aca tta tta aga atc gct gaa         528
Leu Ala Phe Leu Gly Ile Ala Tyr Asn Thr Leu Leu Arg Ile Ala Glu
                165                 170                 175 att gct aga att aga gtt aaa gat att tca aga acc gat ggc ggt aga         576
Ile Ala Arg Ile Arg Val Lys Asp Ile Ser Arg Thr Asp Gly Gly Arg
            180                 185                 190 atg tta atc cac att ggc aga aca aaa acc tta gtc tcc aca gca ggc         624
Met Leu Ile His Ile Gly Arg Thr Lys Thr Leu Val Ser Thr Ala Gly
        195                 200                 205 gtc gaa aaa gca tta tca tta ggt gtt act aaa tta gtt gaa cgt tgg         672
Val Glu Lys Ala Leu Ser Leu Gly Val Thr Lys Leu Val Glu Arg Trp
210                 215                 220 att tcc gtt tcc ggt gtt gca gat gac cca aac aac tac tta ttc tgt         720
Ile Ser Val Ser Gly Val Ala Asp Asp Pro Asn Asn Tyr Leu Phe Cys
225                 230                 235                 240 cgt gtt aga aaa aat ggt gtt gcc gct cct tcc gct acc tca caa tta         768
Arg Val Arg Lys Asn Gly Val Ala Ala Pro Ser Ala Thr Ser Gln Leu
                245                 250                 255
```

| | | |
|---|---|---|
| tcc aca aga gca tta gaa ggc att ttt gaa gct acc cac aga ctt att<br>Ser Thr Arg Ala Leu Glu Gly Ile Phe Glu Ala Thr His Arg Leu Ile<br>           260                          265                        270 | | 816 |
| tat ggt gca aaa gac gat tcc ggt caa aga tat tta gct tgg tct ggt<br>Tyr Gly Ala Lys Asp Asp Ser Gly Gln Arg Tyr Leu Ala Trp Ser Gly<br>      275                          280                        285 | | 864 |
| cat tcc gct aga gtt ggt gcc gca aga gac atg gca aga gct ggt gtt<br>His Ser Ala Arg Val Gly Ala Ala Arg Asp Met Ala Arg Ala Gly Val<br>290                          295                        300 | | 912 |
| tct att cct gaa att atg caa gcc ggt ggt tgg act aat gtt aac att<br>Ser Ile Pro Glu Ile Met Gln Ala Gly Gly Trp Thr Asn Val Asn Ile<br>305                      310                          315                        320 | | 960 |
| gtt atg aac tat atc aga aac tta gat tcc gaa aca ggt gct atg gtt<br>Val Met Asn Tyr Ile Arg Asn Leu Asp Ser Glu Thr Gly Ala Met Val<br>                       325                          330                        335 | | 1008 |
| aga tta ctt gaa gac ggt gat taa<br>Arg Leu Leu Glu Asp Gly Asp<br>                       340 | | 1032 |

<210> SEQ ID NO 56
<211> LENGTH: 343
<212> TYPE: PRT
<213> ORGANISM: Bacteriophage P1

<400> SEQUENCE: 56

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu

```
                    245                 250                 255
Ser Thr Arg Ala Leu Glu Gly Ile Phe Glu Ala Thr His Arg Leu Ile
        260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 57
<211> LENGTH: 20
<212> TYPE: DNA
<213> ORGANISM: Artificial Sequence
<220> FEATURE:
<223> OTHER INFORMATION: PCR primer

<400> SEQUENCE: 57
caacggcaac agtttacagg                                           20

<210> SEQ ID NO 58
<211> LENGTH: 20
<212> TYPE: DNA
<213> ORGANISM: Artificial Sequence
<220> FEATURE:
<223> OTHER INFORMATION: PCR primer

<400> SEQUENCE: 58
tctctggtct tcaaacatgg                                           20

<210> SEQ ID NO 59
<211> LENGTH: 20
<212> TYPE: DNA
<213> ORGANISM: Artificial Sequence
<220> FEATURE:
<223> OTHER INFORMATION: PCR primer

<400> SEQUENCE: 59
ttggcgcttc accatctaac                                           20

<210> SEQ ID NO 60
<211> LENGTH: 20
<212> TYPE: DNA
<213> ORGANISM: Artificial Sequence
<220> FEATURE:
<223> OTHER INFORMATION: PCR primer

<400> SEQUENCE: 60
actcttctgc tcgttgtgtc                                           20

<210> SEQ ID NO 61
<211> LENGTH: 20
<212> TYPE: DNA
<213> ORGANISM: Artificial Sequence
<220> FEATURE:
<223> OTHER INFORMATION: PCR primer

<400> SEQUENCE: 61
gtttgaccag acctttagcg                                           20
```

```
<210> SEQ ID NO 62
<211> LENGTH: 24
<212> TYPE: DNA
<213> ORGANISM: Artificial Sequence
<220> FEATURE:
<223> OTHER INFORMATION: PCR primer

<400> SEQUENCE: 62
cttcaaagtg gtgcatgcgg tgag                                          24

<210> SEQ ID NO 63
<211> LENGTH: 34
<212> TYPE: DNA
<213> ORGANISM: Artificial Sequence
<220> FEATURE:
<223> OTHER INFORMATION: PCR primer

<400> SEQUENCE: 63
gaaaatgcat gcaacggcaa catcaatgtc cacg                               34

<210> SEQ ID NO 64
<211> LENGTH: 35
<212> TYPE: DNA
<213> ORGANISM: Artificial Sequence
<220> FEATURE:
<223> OTHER INFORMATION: PCR primer

<400> SEQUENCE: 64
gaaagtcgac ggtaaggccc gggaattcag cttgc                              35

<210> SEQ ID NO 65
<211> LENGTH: 32
<212> TYPE: DNA
<213> ORGANISM: Artificial Sequence
<220> FEATURE:
<223> OTHER INFORMATION: PCR primer

<400> SEQUENCE: 65
ataattcccg ggaacctcag ggagaacttt gg                                 32

<210> SEQ ID NO 66
<211> LENGTH: 35
<212> TYPE: DNA
<213> ORGANISM: Artificial Sequence
<220> FEATURE:
<223> OTHER INFORMATION: PCR primer

<400> SEQUENCE: 66
tataatgaat tcggctactc tatataatat gcttg                              35

<210> SEQ ID NO 67
<211> LENGTH: 30
<212> TYPE: DNA
<213> ORGANISM: Artificial Sequence
<220> FEATURE:
<223> OTHER INFORMATION: PCR primer

<400> SEQUENCE: 67
aaaaaagagc tcacattcgc cacattcgac                                    30

<210> SEQ ID NO 68
<211> LENGTH: 31
<212> TYPE: DNA
<213> ORGANISM: Artificial Sequence
<220> FEATURE:
```

```
<223> OTHER INFORMATION: PCR primer

<400> SEQUENCE: 68
aaaaaacctg caggtggaag gtgactcaat c                                      31

<210> SEQ ID NO 69
<211> LENGTH: 32
<212> TYPE: DNA
<213> ORGANISM: Artificial Sequence
<220> FEATURE:
<223> OTHER INFORMATION: PCR primer

<400> SEQUENCE: 69
aaaaaagcta gccctctttg aacgagctag ac                                     32

<210> SEQ ID NO 70
<211> LENGTH: 30
<212> TYPE: DNA
<213> ORGANISM: Artificial Sequence
<220> FEATURE:
<223> OTHER INFORMATION: PCR primer

<400> SEQUENCE: 70
aaaaaagggc ccgtcgtgaa cagcttgaac                                        30

<210> SEQ ID NO 71
<211> LENGTH: 20
<212> TYPE: DNA
<213> ORGANISM: Artificial Sequence
<220> FEATURE:
<223> OTHER INFORMATION: PCR primer

<400> SEQUENCE: 71
ggtgcttcaa aggcactatc                                                   20

<210> SEQ ID NO 72
<211> LENGTH: 34
<212> TYPE: DNA
<213> ORGANISM: Artificial Sequence
<220> FEATURE:
<223> OTHER INFORMATION: PCR primer

<400> SEQUENCE: 72
gaaaggatcc atgtctaatt tacttactgt tcac                                   34

<210> SEQ ID NO 73
<211> LENGTH: 41
<212> TYPE: DNA
<213> ORGANISM: Artificial Sequence
<220> FEATURE:
<223> OTHER INFORMATION: PCR primer

<400> SEQUENCE: 73
gaaattaatt aacttaatca ccgtcttcaa gtaatctaac c                           41

<210> SEQ ID NO 74
<211> LENGTH: 48
<212> TYPE: DNA
<213> ORGANISM: Artificial Sequence
<220> FEATURE:
<223> OTHER INFORMATION: PCR primer

<400> SEQUENCE: 74
cacgcgtggc gcgccgcggc cgcatgtcca atgttaaagt agctctac                    48
```

```
<210> SEQ ID NO 75
<211> LENGTH: 45
<212> TYPE: DNA
<213> ORGANISM: Artificial Sequence
<220> FEATURE:
<223> OTHER INFORMATION: PCR primer

<400> SEQUENCE: 75
ctggcaaacc tgcagggcgg ccgcttaacg taccataaaa ttcag            45

<210> SEQ ID NO 76
<211> LENGTH: 46
<212> TYPE: DNA
<213> ORGANISM: Artificial Sequence
<220> FEATURE:
<223> OTHER INFORMATION: PCR primer

<400> SEQUENCE: 76
cacgcgtggc gcgccgcggc cgcatggtca aggtgactat tttagg           46

<210> SEQ ID NO 77
<211> LENGTH: 45
<212> TYPE: DNA
<213> ORGANISM: Artificial Sequence
<220> FEATURE:
<223> OTHER INFORMATION: PCR primer

<400> SEQUENCE: 77
ctggcaaacc tgcagggcgg ccgcttacag ttttgggcca tggac            45

<210> SEQ ID NO 78
<211> LENGTH: 44
<212> TYPE: DNA
<213> ORGANISM: Artificial Sequence
<220> FEATURE:
<223> OTHER INFORMATION: PCR primer

<400> SEQUENCE: 78
cacgcgtggc gcgccgcggc cgcatgttgt tcttattcca gctg             44

<210> SEQ ID NO 79
<211> LENGTH: 46
<212> TYPE: DNA
<213> ORGANISM: Artificial Sequence
<220> FEATURE:
<223> OTHER INFORMATION: PCR primer

<400> SEQUENCE: 79
ctggcaaacc tgcagggcgg ccgcttatgg gttagccttg acaaag           46

<210> SEQ ID NO 80
<211> LENGTH: 41
<212> TYPE: DNA
<213> ORGANISM: Artificial Sequence
<220> FEATURE:
<223> OTHER INFORMATION: PCR primer

<400> SEQUENCE: 80
cacgcgtggc gcgccgcggc cgcatgtcgc aaagaaaatt c                41

<210> SEQ ID NO 81
<211> LENGTH: 48
<212> TYPE: DNA
<213> ORGANISM: Artificial Sequence
<220> FEATURE:
<223> OTHER INFORMATION: PCR primer
```

<400> SEQUENCE: 81
ctggcaaacc tgcagggcgg ccgcttatgc cttagtttca acaggaac   48

<210> SEQ ID NO 82
<211> LENGTH: 36
<212> TYPE: DNA
<213> ORGANISM: Artificial Sequence
<220> FEATURE:
<223> OTHER INFORMATION: PCR primer

<400> SEQUENCE: 82
gtttaaacct actatgtaca ctgtataagt aaaaag   36

<210> SEQ ID NO 83
<211> LENGTH: 47
<212> TYPE: DNA
<213> ORGANISM: Artificial Sequence
<220> FEATURE:
<223> OTHER INFORMATION: PCR primer

<400> SEQUENCE: 83
gagctcagcg gccgctcata tgggcgtgtt cttttttaatt attgctc   47

<210> SEQ ID NO 84
<211> LENGTH: 46
<212> TYPE: DNA
<213> ORGANISM: Artificial Sequence
<220> FEATURE:
<223> OTHER INFORMATION: PCR primer

<400> SEQUENCE: 84
catatgagcg gccgctgagc tctggacaca tacacattat caaatg   46

<210> SEQ ID NO 85
<211> LENGTH: 36
<212> TYPE: DNA
<213> ORGANISM: Artificial Sequence
<220> FEATURE:
<223> OTHER INFORMATION: PCR primer

<400> SEQUENCE: 85
gtttaaacct ttcaaaacca aagttggtaa acatac   36

<210> SEQ ID NO 86
<211> LENGTH: 42
<212> TYPE: DNA
<213> ORGANISM: Artificial Sequence
<220> FEATURE:
<223> OTHER INFORMATION: PCR primer

<400> SEQUENCE: 86
gaaattgccg ctgctagaat cccaggtgca acccaatggt tc   42

<210> SEQ ID NO 87
<211> LENGTH: 42
<212> TYPE: DNA
<213> ORGANISM: Artificial Sequence
<220> FEATURE:
<223> OTHER INFORMATION: PCR primer

<400> SEQUENCE: 87
gaaccattgg gttgcacctg ggattctagc agcggcaatt tc   42

<210> SEQ ID NO 88
<211> LENGTH: 33

-continued

<210> SEQ ID NO 88
<211> LENGTH: 33
<212> TYPE: DNA
<213> ORGANISM: Artificial Sequence
<220> FEATURE:
<223> OTHER INFORMATION: PCR primer

<400> SEQUENCE: 88
gtttaaacgt acgactcatg gggctttaca aac                            33

<210> SEQ ID NO 89
<211> LENGTH: 53
<212> TYPE: DNA
<213> ORGANISM: Artificial Sequence
<220> FEATURE:
<223> OTHER INFORMATION: PCR primer

<400> SEQUENCE: 89
gagctcagcg ccgctcata tgaagtgttg cagttgtttt cttcttaata aag       53

<210> SEQ ID NO 90
<211> LENGTH: 50
<212> TYPE: DNA
<213> ORGANISM: Artificial Sequence
<220> FEATURE:
<223> OTHER INFORMATION: PCR primer

<400> SEQUENCE: 90
catatgagcg gccgctgagc tctctagagt ccctctaatt cttcctgttg          50

<210> SEQ ID NO 91
<211> LENGTH: 38
<212> TYPE: DNA
<213> ORGANISM: Artificial Sequence
<220> FEATURE:
<223> OTHER INFORMATION: PCR primer

<400> SEQUENCE: 91
gtttaaacca gtgatcgagc actcatttat acgagatg                      38

<210> SEQ ID NO 92
<211> LENGTH: 35
<212> TYPE: DNA
<213> ORGANISM: Artificial Sequence
<220> FEATURE:
<223> OTHER INFORMATION: PCR primer

<400> SEQUENCE: 92
gtttaaacca ttttaatttc tattgctata atgtc                         35

<210> SEQ ID NO 93
<211> LENGTH: 46
<212> TYPE: DNA
<213> ORGANISM: Artificial Sequence
<220> FEATURE:
<223> OTHER INFORMATION: PCR primer

<400> SEQUENCE: 93
gagctcagcg gccgctcata tgattttgt gttttgctgt gttttg              46

<210> SEQ ID NO 94
<211> LENGTH: 45
<212> TYPE: DNA
<213> ORGANISM: Artificial Sequence
<220> FEATURE:
<223> OTHER INFORMATION: PCR primer

<400> SEQUENCE: 94
catatgagcg gccgctgagc tctgacatct gaatgtaaaa tgaac            45

<210> SEQ ID NO 95
<211> LENGTH: 36
<212> TYPE: DNA
<213> ORGANISM: Artificial Sequence
<220> FEATURE:
<223> OTHER INFORMATION: PCR primer

<400> SEQUENCE: 95
gtttaaacgt caaggttttg gcaagctgcc tgtttg                      36

<210> SEQ ID NO 96
<211> LENGTH: 36
<212> TYPE: DNA
<213> ORGANISM: Artificial Sequence
<220> FEATURE:
<223> OTHER INFORMATION: PCR primer

<400> SEQUENCE: 96
ttaattaaca agggcgattt ctgcagatat cggccg                      36

<210> SEQ ID NO 97
<211> LENGTH: 36
<212> TYPE: DNA
<213> ORGANISM: Artificial Sequence
<220> FEATURE:
<223> OTHER INFORMATION: PCR primer

<400> SEQUENCE: 97
cggccgatat ctgcagaaat cgcccttgtt aattaa                      36

<210> SEQ ID NO 98
<211> LENGTH: 40
<212> TYPE: DNA
<213> ORGANISM: Artificial Sequence
<220> FEATURE:
<223> OTHER INFORMATION: PCR primer

<400> SEQUENCE: 98
gtttaaacga aactaagaca taacaaaaaa gcatgggatg                  40

<210> SEQ ID NO 99
<211> LENGTH: 54
<212> TYPE: DNA
<213> ORGANISM: Artificial Sequence
<220> FEATURE:
<223> OTHER INFORMATION: PCR primer

<400> SEQUENCE: 99
gagctcagcg gccgctcata tgttttttaa agcaatttaa atgaatatta tttg            54

<210> SEQ ID NO 100
<211> LENGTH: 56
<212> TYPE: DNA
<213> ORGANISM: Artificial Sequence
<220> FEATURE:
<223> OTHER INFORMATION: PCR primer

<400> SEQUENCE: 100
catatgagcg gccgctgagc tcctttataa atggtttcat atcaatatta tgactc          56

<210> SEQ ID NO 101
<211> LENGTH: 40
<212> TYPE: DNA
<213> ORGANISM: Artificial Sequence

```
<220> FEATURE:
<223> OTHER INFORMATION: PCR primer

<400> SEQUENCE: 101
gtttaaacca aatggaacaa tgagagatgg tacgcggaac                                40

<210> SEQ ID NO 102
<211> LENGTH: 35
<212> TYPE: DNA
<213> ORGANISM: Artificial Sequence
<220> FEATURE:
<223> OTHER INFORMATION: PCR primer

<400> SEQUENCE: 102
ttaatcggcc aaccatacgg tgggttccca gaacc                                     35

<210> SEQ ID NO 103
<211> LENGTH: 35
<212> TYPE: DNA
<213> ORGANISM: Artificial Sequence
<220> FEATURE:
<223> OTHER INFORMATION: PCR primer

<400> SEQUENCE: 103
ggttctggga acccaccgta tggttggccg attaa                                     35

<210> SEQ ID NO 104
<211> LENGTH: 32
<212> TYPE: DNA
<213> ORGANISM: Artificial Sequence
<220> FEATURE:
<223> OTHER INFORMATION: PCR primer

<400> SEQUENCE: 104
cttctcaaaa cagagcacaa aaactattgc ac                                        32

<210> SEQ ID NO 105
<211> LENGTH: 32
<212> TYPE: DNA
<213> ORGANISM: Artificial Sequence
<220> FEATURE:
<223> OTHER INFORMATION: PCR primer

<400> SEQUENCE: 105
gtgcaatagt ttttgtgctc tgttttgaga ag                                        32

<210> SEQ ID NO 106
<211> LENGTH: 42
<212> TYPE: DNA
<213> ORGANISM: Artificial Sequence
<220> FEATURE:
<223> OTHER INFORMATION: PCR primer

<400> SEQUENCE: 106
cacgcgtggc gcgccgcggc catgtctacc caaaacgatc tg                             42

<210> SEQ ID NO 107
<211> LENGTH: 46
<212> TYPE: DNA
<213> ORGANISM: Artificial Sequence
<220> FEATURE:
<223> OTHER INFORMATION: PCR primer

<400> SEQUENCE: 107
ctggcaaacc tgcagggcgg ccttattctt tagctggagc ttcttc                         46
```

```
<210> SEQ ID NO 108
<211> LENGTH: 23
<212> TYPE: DNA
<213> ORGANISM: Artificial Sequence
<220> FEATURE:
<223> OTHER INFORMATION: PCR primer

<400> SEQUENCE: 108
cagagagagg aagaagttgg aac                                              23

<210> SEQ ID NO 109
<211> LENGTH: 24
<212> TYPE: DNA
<213> ORGANISM: Artificial Sequence
<220> FEATURE:
<223> OTHER INFORMATION: PCR primer

<400> SEQUENCE: 109
gtacagagaa cttgtaaaca attc                                             24

<210> SEQ ID NO 110
<211> LENGTH: 32
<212> TYPE: DNA
<213> ORGANISM: Artificial Sequence
<220> FEATURE:
<223> OTHER INFORMATION: PCR primer

<400> SEQUENCE: 110
taatgggtac accatacggt ggattcccag ag                                    32

<210> SEQ ID NO 111
<211> LENGTH: 32
<212> TYPE: DNA
<213> ORGANISM: Artificial Sequence
<220> FEATURE:
<223> OTHER INFORMATION: PCR primer

<400> SEQUENCE: 111
ctctgggaat ccaccgtatg gtgtacccat ta                                    32

<210> SEQ ID NO 112
<211> LENGTH: 40
<212> TYPE: DNA
<213> ORGANISM: Artificial Sequence
<220> FEATURE:
<223> OTHER INFORMATION: PCR primer

<400> SEQUENCE: 112
cacgcgtggc gcgccgcggc catgcttaga gccctaactc                            40

<210> SEQ ID NO 113
<211> LENGTH: 41
<212> TYPE: DNA
<213> ORGANISM: Artificial Sequence
<220> FEATURE:
<223> OTHER INFORMATION: PCR primer

<400> SEQUENCE: 113
ctggcaaacc tgcagggcgg ccttagtttt gcttgacaaa g                          41

<210> SEQ ID NO 114
<211> LENGTH: 37
<212> TYPE: DNA
<213> ORGANISM: Artificial Sequence
<220> FEATURE:
<223> OTHER INFORMATION: PCR primer
```

<400> SEQUENCE: 114
cacgcgtggc gcgccgcggc catggttagc gttgcag                37

<210> SEQ ID NO 115
<211> LENGTH: 40
<212> TYPE: DNA
<213> ORGANISM: Artificial Sequence
<220> FEATURE:
<223> OTHER INFORMATION: PCR primer

<400> SEQUENCE: 115
ctggcaaacc tgcagggcgg ccttacaact ttgtctgctg                40

<210> SEQ ID NO 116
<211> LENGTH: 43
<212> TYPE: DNA
<213> ORGANISM: Artificial Sequence
<220> FEATURE:
<223> OTHER INFORMATION: PCR primer

<400> SEQUENCE: 116
cacgcgtggc gcgccgcggc catgccagca gtatcatatg atg                43

<210> SEQ ID NO 117
<211> LENGTH: 44
<212> TYPE: DNA
<213> ORGANISM: Artificial Sequence
<220> FEATURE:
<223> OTHER INFORMATION: PCR primer

<400> SEQUENCE: 117
ctggcaaacc tgcagggcgg ccttatacca agcttagacc cttg                44

<210> SEQ ID NO 118
<211> LENGTH: 46
<212> TYPE: DNA
<213> ORGANISM: Artificial Sequence
<220> FEATURE:
<223> OTHER INFORMATION: PCR primer

<400> SEQUENCE: 118
cacgcgtggc gcgccgcggc cgcatgttct ccagaatctc tgctag                46

<210> SEQ ID NO 119
<211> LENGTH: 33
<212> TYPE: DNA
<213> ORGANISM: Artificial Sequence
<220> FEATURE:
<223> OTHER INFORMATION: PCR primer

<400> SEQUENCE: 119
gtttaaacct cggtagtgcc taccaattta atg                33

<210> SEQ ID NO 120
<211> LENGTH: 29
<212> TYPE: DNA
<213> ORGANISM: Artificial Sequence
<220> FEATURE:
<223> OTHER INFORMATION: PCR primer

<400> SEQUENCE: 120
gtttaaacct ccgttatgta tgtttgtac                29

<210> SEQ ID NO 121

<211> LENGTH: 23
<212> TYPE: DNA
<213> ORGANISM: Artificial Sequence
<220> FEATURE:
<223> OTHER INFORMATION: PCR primer

<400> SEQUENCE: 121
cacttgactt cgtcaatgaa tac                                           23

<210> SEQ ID NO 122
<211> LENGTH: 20
<212> TYPE: DNA
<213> ORGANISM: Artificial Sequence
<220> FEATURE:
<223> OTHER INFORMATION: PCR primer

<400> SEQUENCE: 122
gtctgatcta aatggttctg                                               20

<210> SEQ ID NO 123
<211> LENGTH: 33
<212> TYPE: DNA
<213> ORGANISM: Artificial Sequence
<220> FEATURE:
<223> OTHER INFORMATION: PCR primer

<400> SEQUENCE: 123
gtctcagaga cagagaactc tatgacgcgt acg                                33

<210> SEQ ID NO 124
<211> LENGTH: 33
<212> TYPE: DNA
<213> ORGANISM: Artificial Sequence
<220> FEATURE:
<223> OTHER INFORMATION: PCR primer

<400> SEQUENCE: 124
cgtacgcgtc atagagttct ctgtctctga gac                                33

<210> SEQ ID NO 125
<211> LENGTH: 33
<212> TYPE: DNA
<213> ORGANISM: Artificial Sequence
<220> FEATURE:
<223> OTHER INFORMATION: PCR primer

<400> SEQUENCE: 125
taccgggcgg gaaggaactc cagcagaagt tgg                                33

<210> SEQ ID NO 126
<211> LENGTH: 33
<212> TYPE: DNA
<213> ORGANISM: Artificial Sequence
<220> FEATURE:
<223> OTHER INFORMATION: PCR primer

<400> SEQUENCE: 126
ccaacttctg ctggagttcc ttcccgcccg gta                                33

<210> SEQ ID NO 127
<211> LENGTH: 34
<212> TYPE: DNA
<213> ORGANISM: Artificial Sequence
<220> FEATURE:
<223> OTHER INFORMATION: PCR primer

<400> SEQUENCE: 127

```
cttgaggcgg ccgcgctggt acttgaaaga tgac                          34
```

<210> SEQ ID NO 128
<211> LENGTH: 20
<212> TYPE: DNA
<213> ORGANISM: Artificial Sequence
<220> FEATURE:
<223> OTHER INFORMATION: PCR primer

<400> SEQUENCE: 128

```
gggtttcaga agggtttcac                                          20
```

<210> SEQ ID NO 129
<211> LENGTH: 20
<212> TYPE: DNA
<213> ORGANISM: Artificial Sequence
<220> FEATURE:
<223> OTHER INFORMATION: PCR primer

<400> SEQUENCE: 129

```
ggagtgacac aacctgaaag                                          20
```

<210> SEQ ID NO 130
<211> LENGTH: 43
<212> TYPE: DNA
<213> ORGANISM: Artificial Sequence
<220> FEATURE:
<223> OTHER INFORMATION: PCR primer

<400> SEQUENCE: 130

```
aaaaaacctg caggttaaaa ctttgaactg ttcaattctt tag                 43
```

<210> SEQ ID NO 131
<211> LENGTH: 31
<212> TYPE: DNA
<213> ORGANISM: Artificial Sequence
<220> FEATURE:
<223> OTHER INFORMATION: PCR primer

<400> SEQUENCE: 131

```
aaaaaaacgc gtatgggtgt ccagtttatc g                             31
```

<210> SEQ ID NO 132
<211> LENGTH: 94
<212> TYPE: DNA
<213> ORGANISM: Artificial Sequence
<220> FEATURE:
<223> OTHER INFORMATION: PCR primer

<400> SEQUENCE: 132

```
aatattctat tattatatat tttcttccca ataaaacaaa ataaaacaaa acacagcaaa    60
acacaaaaat cctggaattc gcccttacat atgg                               94
```

<210> SEQ ID NO 133
<211> LENGTH: 90
<212> TYPE: DNA
<213> ORGANISM: Artificial Sequence
<220> FEATURE:
<223> OTHER INFORMATION: PCR primer

<400> SEQUENCE: 133

```
tatagattgt aaagtagacg taaagtttag taattcattt taatgttcat tttacattca    60
gatgtcatta cggctcgtgc tatattcttg                                    90
```

<210> SEQ ID NO 134
<211> LENGTH: 33
<212> TYPE: DNA
<213> ORGANISM: Artificial Sequence
<220> FEATURE:
<223> OTHER INFORMATION: PCR primer

<400> SEQUENCE: 134
aaaaaaacgc gtatgtcaac tgtggaagat cac                          33

<210> SEQ ID NO 135
<211> LENGTH: 40
<212> TYPE: DNA
<213> ORGANISM: Artificial Sequence
<220> FEATURE:
<223> OTHER INFORMATION: PCR primer

<400> SEQUENCE: 135
aaaaaacctg caggttaagc tgctggcgct tcatctttgg                   40

<210> SEQ ID NO 136
<211> LENGTH: 20
<212> TYPE: DNA
<213> ORGANISM: Artificial Sequence
<220> FEATURE:
<223> OTHER INFORMATION: PCR primer

<400> SEQUENCE: 136
aaaggctgac ggacacaatc                                         20

<210> SEQ ID NO 137
<211> LENGTH: 90
<212> TYPE: DNA
<213> ORGANISM: Artificial Sequence
<220> FEATURE:
<223> OTHER INFORMATION: PCR primer

<400> SEQUENCE: 137
attctattat tatatatttt cttcccaata aaacaaaata aaacaaaaca cagcaaaaca   60
caaaaatcct ggaattcgcc cttacatatg                              90

<210> SEQ ID NO 138
<211> LENGTH: 20
<212> TYPE: DNA
<213> ORGANISM: Artificial Sequence
<220> FEATURE:
<223> OTHER INFORMATION: PCR primer

<400> SEQUENCE: 138
gcgcatccat attttggcgg                                         20

<210> SEQ ID NO 139
<211> LENGTH: 32
<212> TYPE: DNA
<213> ORGANISM: Artificial Sequence
<220> FEATURE:
<223> OTHER INFORMATION: PCR primer

<400> SEQUENCE: 139
atattagtcg acccttctat cagggaaggg ag                           32

<210> SEQ ID NO 140
<211> LENGTH: 23
<212> TYPE: DNA
<213> ORGANISM: Artificial Sequence

```
<220> FEATURE:
<223> OTHER INFORMATION: PCR primer

<400> SEQUENCE: 140
gtgggctaca aatgatacga tgg                                              23

<210> SEQ ID NO 141
<211> LENGTH: 20
<212> TYPE: DNA
<213> ORGANISM: Artificial Sequence
<220> FEATURE:
<223> OTHER INFORMATION: PCR primer

<400> SEQUENCE: 141
tcggccactt gtttattggg                                                  20

<210> SEQ ID NO 142
<211> LENGTH: 20
<212> TYPE: DNA
<213> ORGANISM: Artificial Sequence
<220> FEATURE:
<223> OTHER INFORMATION: PCR primer

<400> SEQUENCE: 142
ctgcaggttt gccagcttac                                                  20

<210> SEQ ID NO 143
<211> LENGTH: 22
<212> TYPE: DNA
<213> ORGANISM: Artificial Sequence
<220> FEATURE:
<223> OTHER INFORMATION: PCR primer

<400> SEQUENCE: 143
gattgtgtat tagtgtattt cg                                               22

<210> SEQ ID NO 144
<211> LENGTH: 39
<212> TYPE: DNA
<213> ORGANISM: Artificial Sequence
<220> FEATURE:
<223> OTHER INFORMATION: PCR primer

<400> SEQUENCE: 144
catgcatgca tgtctagata aaatgttagc tgctagatc                             39

<210> SEQ ID NO 145
<211> LENGTH: 43
<212> TYPE: DNA
<213> ORGANISM: Artificial Sequence
<220> FEATURE:
<223> OTHER INFORMATION: PCR primer

<400> SEQUENCE: 145
catgcatgca tgttaattaa cttaatcctt tggaccaatc atg                        43

<210> SEQ ID NO 146
<211> LENGTH: 27
<212> TYPE: DNA
<213> ORGANISM: Artificial Sequence
<220> FEATURE:
<223> OTHER INFORMATION: PCR primer

<400> SEQUENCE: 146
catcactgtt aaaggaatgg gtaaatc                                          27
```

<210> SEQ ID NO 147
<211> LENGTH: 22
<212> TYPE: DNA
<213> ORGANISM: Artificial Sequence
<220> FEATURE:
<223> OTHER INFORMATION: PCR primer

<400> SEQUENCE: 147
ggaggaatgg aacagtgatg ac                                            22

<210> SEQ ID NO 148
<211> LENGTH: 23
<212> TYPE: DNA
<213> ORGANISM: Artificial Sequence
<220> FEATURE:
<223> OTHER INFORMATION: PCR primer

<400> SEQUENCE: 148
cgaaaccgtt aaattcaaca atg                                           23

<210> SEQ ID NO 149
<211> LENGTH: 21
<212> TYPE: DNA
<213> ORGANISM: Artificial Sequence
<220> FEATURE:
<223> OTHER INFORMATION: PCR primer

<400> SEQUENCE: 149
gcatctaatg tacgttccaa c                                             21

<210> SEQ ID NO 150
<211> LENGTH: 19
<212> TYPE: DNA
<213> ORGANISM: Artificial Sequence
<220> FEATURE:
<223> OTHER INFORMATION: PCR primer

<400> SEQUENCE: 150
cttctatagg ttgagaccc                                                19

<210> SEQ ID NO 151
<211> LENGTH: 19
<212> TYPE: DNA
<213> ORGANISM: Artificial Sequence
<220> FEATURE:
<223> OTHER INFORMATION: PCR primer

<400> SEQUENCE: 151
gagtgacaca acctgaaag                                                19

<210> SEQ ID NO 152
<211> LENGTH: 16
<212> TYPE: DNA
<213> ORGANISM: Artificial Sequence
<220> FEATURE:
<223> OTHER INFORMATION: PCR primer

<400> SEQUENCE: 152
gtaaaacgac ggccag                                                   16

<210> SEQ ID NO 153
<211> LENGTH: 17
<212> TYPE: DNA
<213> ORGANISM: Artificial Sequence
<220> FEATURE:
<223> OTHER INFORMATION: PCR primer

```
<400> SEQUENCE: 153
caggaaacag ctatgac                                                      17

<210> SEQ ID NO 154
<211> LENGTH: 72
<212> TYPE: DNA
<213> ORGANISM: Artificial Sequence
<220> FEATURE:
<223> OTHER INFORMATION: PCR primer

<400> SEQUENCE: 154
ggtaccgcgg ccgcggatcc ctcgaggcct taattaacat ctgaatgtaa aatgaacatt       60
aaaatgaatt ac                                                           72

<210> SEQ ID NO 155
<211> LENGTH: 70
<212> TYPE: DNA
<213> ORGANISM: Artificial Sequence
<220> FEATURE:
<223> OTHER INFORMATION: PCR primer

<400> SEQUENCE: 155
gagctcgcgg ccgcggattc gccgaatcct tttattataa aattatatat tattcttaat       60
tacatatcac                                                              70

<210> SEQ ID NO 156
<211> LENGTH: 32
<212> TYPE: DNA
<213> ORGANISM: Artificial Sequence
<220> FEATURE:
<223> OTHER INFORMATION: PCR primer

<400> SEQUENCE: 156
gtccaggagt ccatcggttc ctgtcagatg gg                                     32

<210> SEQ ID NO 157
<211> LENGTH: 43
<212> TYPE: DNA
<213> ORGANISM: Artificial Sequence
<220> FEATURE:
<223> OTHER INFORMATION: PCR primer

<400> SEQUENCE: 157
gcgtctagaa tttttgtgtt ttgctgtgtt ttgttttatt ttg                         43

<210> SEQ ID NO 158
<211> LENGTH: 31
<212> TYPE: DNA
<213> ORGANISM: Artificial Sequence
<220> FEATURE:
<223> OTHER INFORMATION: PCR primer

<400> SEQUENCE: 158
caagagtatc ccatctgaca ggaaccgatg g                                      31

<210> SEQ ID NO 159
<211> LENGTH: 45
<212> TYPE: DNA
<213> ORGANISM: Artificial Sequence
<220> FEATURE:
<223> OTHER INFORMATION: PCR primer

<400> SEQUENCE: 159
```
gatgaacgaa ggtaccgagc tctaagtagt ggtgttggtg aactc                    45

<210> SEQ ID NO 160
<211> LENGTH: 45
<212> TYPE: DNA
<213> ORGANISM: Artificial Sequence
<220> FEATURE:
<223> OTHER INFORMATION: PCR primer

<400> SEQUENCE: 160
attatggtag cggccgcatt tggcaaggcg tatctatata ggagg                    45

<210> SEQ ID NO 161
<211> LENGTH: 45
<212> TYPE: DNA
<213> ORGANISM: Artificial Sequence
<220> FEATURE:
<223> OTHER INFORMATION: PCR primer

<400> SEQUENCE: 161
ttgccaaatg cggccgctac cataatgtat gcgttgagcc tcttg                    45

<210> SEQ ID NO 162
<211> LENGTH: 46
<212> TYPE: DNA
<213> ORGANISM: Artificial Sequence
<220> FEATURE:
<223> OTHER INFORMATION: PCR primer

<400> SEQUENCE: 162
ggttcaatgg gccctaaaag tgttggtgta ttagatgagt ttgtcc                   46

<210> SEQ ID NO 163
<211> LENGTH: 88
<212> TYPE: DNA
<213> ORGANISM: Artificial Sequence
<220> FEATURE:
<223> OTHER INFORMATION: PCR primer

<400> SEQUENCE: 163
cttgtttgaa aggtttggat gtcaatccta atggatgtaa gttgctctcc actgttatta   60
ctgaccctgg aattcgccct tacatatg                                       88

<210> SEQ ID NO 164
<211> LENGTH: 84
<212> TYPE: DNA
<213> ORGANISM: Artificial Sequence
<220> FEATURE:
<223> OTHER INFORMATION: PCR primer

<400> SEQUENCE: 164
gtttccgacc atttacattg tgcaacttcw ggagctaaat tagcacctga taaggcaccc   60
cgggcggctc gtgctatatt cttg                                           84

<210> SEQ ID NO 165
<211> LENGTH: 21
<212> TYPE: DNA
<213> ORGANISM: Artificial Sequence
<220> FEATURE:
<223> OTHER INFORMATION: PCR primer

<400> SEQUENCE: 165
ggatgtcaat cctaatggat g                                              21

<210> SEQ ID NO 166
<211> LENGTH: 18
<212> TYPE: DNA
<213> ORGANISM: Artificial Sequence
<220> FEATURE:
<223> OTHER INFORMATION: PCR primer

<400> SEQUENCE: 166
gagctaaatt agcacctg                                                    18

<210> SEQ ID NO 167
<211> LENGTH: 1071
<212> TYPE: DNA
<213> ORGANISM: Zygosaccharomyces rouxii
<220> FEATURE:
<221> NAME/KEY: CDS
<222> LOCATION: (1)..(1071)

<400> SEQUENCE: 167

```
atg cct cat tct atc aac ggt gat gtt aaa atc gca gta ttg gga gct        48
Met Pro His Ser Ile Asn Gly Asp Val Lys Ile Ala Val Leu Gly Ala
1               5                   10                  15 gca ggt ggt att gga caa tca ctt tcg cta ctt ttg aag acc cag tta        96
Ala Gly Gly Ile Gly Gln Ser Leu Ser Leu Leu Leu Lys Thr Gln Leu
            20                  25                  30 act aga gaa ttg cca aat cat cgt cat gct cag tta gcc cta tac gac       144
Thr Arg Glu Leu Pro Asn His Arg His Ala Gln Leu Ala Leu Tyr Asp
        35                  40                  45 gtc aat gct gac gca gtt cgg ggt gtc gca gcc gac tta tct cat att       192
Val Asn Ala Asp Ala Val Arg Gly Val Ala Ala Asp Leu Ser His Ile
    50                  55                  60 gat aca ggt gtt act gta aca gga tat gaa ggt gat agg atc ggc gaa       240
Asp Thr Gly Val Thr Val Thr Gly Tyr Glu Gly Asp Arg Ile Gly Glu
65                  70                  75                  80 gcg tta gaa ggt acg gat atc gtc ctg atc cct gca ggt gtt cct aga       288
Ala Leu Glu Gly Thr Asp Ile Val Leu Ile Pro Ala Gly Val Pro Arg
                85                  90                  95 aaa cct ggt atg aca aga gaa gat cta ttg gtt gtt aat gca aag att       336
Lys Pro Gly Met Thr Arg Glu Asp Leu Leu Val Val Asn Ala Lys Ile
            100                 105                 110 gtc aag agt ata ggg tca tcg att gcg cag cat tgc gat tta aac aaa       384
Val Lys Ser Ile Gly Ser Ser Ile Ala Gln His Cys Asp Leu Asn Lys
        115                 120                 125 gtg ttc att cta cta atc tca aac cca ata aat tcc ctt gtt cca gta       432
Val Phe Ile Leu Leu Ile Ser Asn Pro Ile Asn Ser Leu Val Pro Val
    130                 135                 140 ctc gtt aag gaa ctg gaa tct aaa tct caa ggc act caa gtt gag aga       480
Leu Val Lys Glu Leu Glu Ser Lys Ser Gln Gly Thr Gln Val Glu Arg
145                 150                 155                 160 cgt gtg ctt ggt ctc act aag ttg gat tcc gtt aga gca agt gca ttt       528
Arg Val Leu Gly Leu Thr Lys Leu Asp Ser Val Arg Ala Ser Ala Phe
                165                 170                 175 ttg cac gag gtt acg att aaa cat ggt cta aaa cct aaa tct aat act       576
Leu His Glu Val Thr Ile Lys His Gly Leu Lys Pro Lys Ser Asn Thr
            180                 185                 190 ctt gat gat gtt cca gta gtt ggt ggt cat tct ggt gaa act att gta       624
Leu Asp Asp Val Pro Val Val Gly Gly His Ser Gly Glu Thr Ile Val
        195                 200                 205 cct tta ttc tcc caa gcc cct aat ggt aac cgt tta tca cag gac gcc       672
Pro Leu Phe Ser Gln Ala Pro Asn Gly Asn Arg Leu Ser Gln Asp Ala
    210                 215                 220 ttg gaa gct ctt gtt cag cgt gta caa ttc gga ggc gat gaa gtc gtt       720
Leu Glu Ala Leu Val Gln Arg Val Gln Phe Gly Gly Asp Glu Val Val
```

```
Leu Glu Ala Leu Val Gln Arg Val Gln Phe Gly Gly Asp Glu Val Val
225                 230                 235                 240 aga gct aaa aat ggt gct ggt agt gcc act ctg tgt atg gcc cat gcc    768
Arg Ala Lys Asn Gly Ala Gly Ser Ala Thr Leu Cys Met Ala His Ala
            245                 250                 255 gct tat act gtt gct gca tct ttt att cca ctt atc act ggt caa aag    816
Ala Tyr Thr Val Ala Ala Ser Phe Ile Pro Leu Ile Thr Gly Gln Lys
        260                 265                 270 cgt tcc atc tct ggt aca ttc tat gtt gcc tta aag gat gct caa ggt    864
Arg Ser Ile Ser Gly Thr Phe Tyr Val Ala Leu Lys Asp Ala Gln Gly
                275                 280                 285 cag cct atc aac agt agc gct aag cgt ctt ttg ggc tca atc aac gat    912
Gln Pro Ile Asn Ser Ser Ala Lys Arg Leu Leu Gly Ser Ile Asn Asp
    290                 295                 300 tta cca tat ttt gca gtg cca ttg gag att act tct cag ggt gtg gat    960
Leu Pro Tyr Phe Ala Val Pro Leu Glu Ile Thr Ser Gln Gly Val Asp
305                 310                 315                 320 gaa tta gat acc agc gtt ttg gaa aga atg acc aag tat gag aga gaa   1008
Glu Leu Asp Thr Ser Val Leu Glu Arg Met Thr Lys Tyr Glu Arg Glu
                325                 330                 335 aga ctc tta gct cct tgt ctg ggt aaa ttg gaa ggt ggt atc aga aac   1056
Arg Leu Leu Ala Pro Cys Leu Gly Lys Leu Glu Gly Gly Ile Arg Asn
            340                 345                 350 ggt ttg agt ttg tga                                                1071
Gly Leu Ser Leu
            355

<210> SEQ ID NO 168
<211> LENGTH: 356
<212> TYPE: PRT
<213> ORGANISM: Zygosaccharomyces rouxii

<400> SEQUENCE: 168

Met Pro His Ser Ile Asn Gly Asp Val Lys Ile Ala Val Leu Gly Ala
1               5                   10                  15

Ala Gly Gly Ile Gly Gln Ser Leu Ser Leu Leu Leu Lys Thr Gln Leu
            20                  25                  30

Thr Arg Glu Leu Pro Asn His Arg His Ala Gln Leu Ala Leu Tyr Asp
        35                  40                  45

Val Asn Ala Asp Ala Val Arg Gly Val Ala Ala Asp Leu Ser His Ile
    50                  55                  60

Asp Thr Gly Val Thr Val Thr Gly Tyr Glu Gly Asp Arg Ile Gly Glu
65                  70                  75                  80

Ala Leu Glu Gly Thr Asp Ile Val Leu Ile Pro Ala Gly Val Pro Arg
            85                  90                  95

Lys Pro Gly Met Thr Arg Glu Asp Leu Leu Val Val Asn Ala Lys Ile
            100                 105                 110

Val Lys Ser Ile Gly Ser Ser Ile Ala Gln His Cys Asp Leu Asn Lys
        115                 120                 125

Val Phe Ile Leu Leu Ile Ser Asn Pro Ile Asn Ser Leu Val Pro Val
    130                 135                 140

Leu Val Lys Glu Leu Glu Ser Lys Ser Gln Gly Thr Gln Val Glu Arg
145                 150                 155                 160

Arg Val Leu Gly Leu Thr Lys Leu Asp Ser Val Arg Ala Ser Ala Phe
            165                 170                 175

Leu His Glu Val Thr Ile Lys His Gly Leu Lys Pro Leu Ser Asn Thr
        180                 185                 190
```

```
Leu Asp Asp Val Pro Val Val Gly Gly His Ser Gly Glu Thr Ile Val
            195                 200                 205
Pro Leu Phe Ser Gln Ala Pro Asn Gly Asn Arg Leu Ser Gln Asp Ala
    210                 215                 220
Leu Glu Ala Leu Val Gln Arg Val Gln Phe Gly Gly Asp Glu Val Val
225                 230                 235                 240
Arg Ala Lys Asn Gly Ala Gly Ser Ala Thr Leu Cys Met Ala His Ala
                245                 250                 255
Ala Tyr Thr Val Ala Ala Ser Phe Ile Pro Leu Ile Thr Gly Gln Lys
            260                 265                 270
Arg Ser Ile Ser Gly Thr Phe Tyr Val Ala Leu Lys Asp Ala Gln Gly
        275                 280                 285
Gln Pro Ile Asn Ser Ser Ala Lys Arg Leu Leu Gly Ser Ile Asn Asp
    290                 295                 300
Leu Pro Tyr Phe Ala Val Pro Leu Glu Ile Thr Ser Gln Gly Val Asp
305                 310                 315                 320
Glu Leu Asp Thr Ser Val Leu Glu Arg Met Thr Lys Tyr Glu Arg Glu
                325                 330                 335
Arg Leu Leu Ala Pro Cys Leu Gly Lys Leu Glu Gly Gly Ile Arg Asn
            340                 345                 350
Gly Leu Ser Leu
        355

<210> SEQ ID NO 169
<211> LENGTH: 939
<212> TYPE: DNA
<213> ORGANISM: Escherichia coli
<220> FEATURE:
<221> NAME/KEY: CDS
<222> LOCATION: (1)..(939)

<400> SEQUENCE: 169 atg aaa gtc gca gtc ctc ggc gct gct ggc ggt att ggc cag gcg ctt      48
Met Lys Val Ala Val Leu Gly Ala Ala Gly Gly Ile Gly Gln Ala Leu
1               5                   10                  15 gca cta ctg tta aaa acc caa ctg cct tca ggt tca gaa ctc tct ctg      96
Ala Leu Leu Leu Lys Thr Gln Leu Pro Ser Gly Ser Glu Leu Ser Leu
            20                  25                  30 tat gat atc gct cca gtg act ccc ggt gtg gct gtc gat ctg agc cat     144
Tyr Asp Ile Ala Pro Val Thr Pro Gly Val Ala Val Asp Leu Ser His
        35                  40                  45 atc cct act gct gtg aaa atc aaa ggt ttt tct ggt gaa gat gcg act     192
Ile Pro Thr Ala Val Lys Ile Lys Gly Phe Ser Gly Glu Asp Ala Thr
    50                  55                  60 ccg gcg ctg gaa ggc gca gat gtc gtt ctt atc tct gca ggc gta gcg     240
Pro Ala Leu Glu Gly Ala Asp Val Val Leu Ile Ser Ala Gly Val Ala
65                  70                  75                  80 cgt aaa ccg ggt atg gat cgt tcc gac ctg ttt aac gtt aac gcc ggc     288
Arg Lys Pro Gly Met Asp Arg Ser Asp Leu Phe Asn Val Asn Ala Gly
                85                  90                  95 atc gtg aaa aac ctg gta cag caa gtt gcg aaa acc tgc ccg aaa gcg     336
Ile Val Lys Asn Leu Val Gln Gln Val Ala Lys Thr Cys Pro Lys Ala
            100                 105                 110 tgc att ggt att atc act aac ccg gtt aac acc aca gtt gca att gct     384
Cys Ile Gly Ile Ile Thr Asn Pro Val Asn Thr Thr Val Ala Ile Ala
        115                 120                 125 gct gaa gtg ctg aaa aaa gcc ggt gtt tat gac aaa aac aaa ctg ttc     432
Ala Glu Val Leu Lys Lys Ala Gly Val Tyr Asp Lys Asn Lys Leu Phe
    130                 135                 140
```

```
ggc gtt acc acg ctg gat atc att cgt tcc aac acc ttt gtt gcg gaa      480
Gly Val Thr Thr Leu Asp Ile Ile Arg Ser Asn Thr Phe Val Ala Glu
145                 150                 155                 160 ctg aaa ggc aaa cag cca ggc gaa gtt gaa gtg ccg gtt att ggc ggt      528
Leu Lys Gly Lys Gln Pro Gly Glu Val Glu Val Pro Val Ile Gly Gly
                165                 170                 175 cac tct ggt gtt acc att ctg ccg ctg ctg tca cag gtt cct ggc gtt      576
His Ser Gly Val Thr Ile Leu Pro Leu Leu Ser Gln Val Pro Gly Val
            180                 185                 190 agt ttt acc gag cag gaa gtg gct gat ctg acc aaa cgc atc cag aac      624
Ser Phe Thr Glu Gln Glu Val Ala Asp Leu Thr Lys Arg Ile Gln Asn
        195                 200                 205 gcg ggt act gaa gtg gtt gaa gcg aag gcc ggt ggg tct gca acc          672
Ala Gly Thr Glu Val Val Glu Ala Lys Ala Gly Gly Ser Ala Thr
    210                 215                 220 ctg tct atg ggc cag gca gct gca cgt ttt ggt ctg tct ctg gtt cgt      720
Leu Ser Met Gly Gln Ala Ala Ala Arg Phe Gly Leu Ser Leu Val Arg
225                 230                 235                 240 gca ctg cag ggc gaa caa ggc gtt gtc gaa tgt gcc tac gtt gaa ggc      768
Ala Leu Gln Gly Glu Gln Gly Val Val Glu Cys Ala Tyr Val Glu Gly
                245                 250                 255 gac ggt cag tac gcc cgt ttc ttc tct caa ccg ctg ctg ctg ggt aaa      816
Asp Gly Gln Tyr Ala Arg Phe Phe Ser Gln Pro Leu Leu Leu Gly Lys
            260                 265                 270 aac ggc gtg gaa gag cgt aaa tct atc ggt acc ctg agc gca ttt gaa      864
Asn Gly Val Glu Glu Arg Lys Ser Ile Gly Thr Leu Ser Ala Phe Glu
        275                 280                 285 cag aac gcg ctg gaa ggt atg ctg gat acg ctg aag aaa gat atc gcc      912
Gln Asn Ala Leu Glu Gly Met Leu Asp Thr Leu Lys Lys Asp Ile Ala
    290                 295                 300 ctg ggc gaa gag ttc gtt aat aag taa                                  939
Leu Gly Glu Glu Phe Val Asn Lys
305                 310
```

<210> SEQ ID NO 170
<211> LENGTH: 312
<212> TYPE: PRT
<213> ORGANISM: Escherichia coli

<400> SEQUENCE: 170

```
Met Lys Val Ala Val Leu Gly Ala Ala Gly Gly Ile Gly Gln Ala Leu
1               5                   10                  15

Ala Leu Leu Leu Lys Thr Gln Leu Pro Ser Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Lys Ile Lys Gly Phe Ser Gly Glu Asp Ala Thr
    50                  55                  60

Pro Ala Leu Glu Gly Ala Asp Val Val Leu Ile Ser Ala Gly Val Ala
65                  70                  75                  80

Arg Lys Pro Gly Met Asp Arg Ser Asp Leu Phe Asn Val Asn Ala Gly
                85                  90                  95

Ile Val Lys Asn Leu Val Gln Gln Val Ala Lys Thr Cys Pro Lys Ala
            100                 105                 110

Cys Ile Gly Ile Ile Thr Asn Pro Val Asn Thr Thr Val Ala Ile Ala
        115                 120                 125

Ala Glu Val Leu Lys Lys Ala Gly Val Tyr Asp Lys Asn Lys Leu Phe
    130                 135                 140
```

```
Gly Val Thr Thr Leu Asp Ile Ile Arg Ser Asn Thr Phe Val Ala Glu
145                 150                 155                 160

Leu Lys Gly Lys Gln Pro Gly Glu Val Glu Val Pro Val Ile Gly Gly
            165                 170                 175

His Ser Gly Val Thr Ile Leu Pro Leu Leu Ser Gln Val Pro Gly Val
            180                 185                 190

Ser Phe Thr Glu Gln Glu Val Ala Asp Leu Thr Lys Arg Ile Gln Asn
            195                 200                 205

Ala Gly Thr Glu Val Val Glu Ala Lys Ala Gly Gly Ser Ala Thr
            210                 215                 220

Leu Ser Met Gly Gln Ala Ala Arg Phe Gly Leu Ser Leu Val Arg
225                 230                 235                 240

Ala Leu Gln Gly Glu Gln Gly Val Val Glu Cys Ala Tyr Val Glu Gly
            245                 250                 255

Asp Gly Gln Tyr Ala Arg Phe Phe Ser Gln Pro Leu Leu Gly Lys
            260                 265                 270

Asn Gly Val Glu Glu Arg Lys Ser Ile Gly Thr Leu Ser Ala Phe Glu
            275                 280                 285

Gln Asn Ala Leu Glu Gly Met Leu Asp Thr Leu Lys Lys Asp Ile Ala
            290                 295                 300

Leu Gly Glu Glu Phe Val Asn Lys
305                 310

<210> SEQ ID NO 171
<211> LENGTH: 987
<212> TYPE: DNA
<213> ORGANISM: Rhizopus oryzae
<220> FEATURE:
<221> NAME/KEY: CDS
<222> LOCATION: (1)..(987)

<400> SEQUENCE: 171 atg gtt aaa gtt aca gtt tgt ggt gct gct ggt ggt att ggt caa ccc      48
Met Val Lys Val Thr Val Cys Gly Ala Ala Gly Gly Ile Gly Gln Pro
1               5                   10                  15 ctt tct tta ctc ttg aag caa tcc tct cac att act cac tta tct ctt     96
Leu Ser Leu Leu Leu Lys Gln Ser Ser His Ile Thr His Leu Ser Leu
            20                  25                  30 tat gat atc gtt aat act cct ggt gtt gct gct gat ctt agt cat atc    144
Tyr Asp Ile Val Asn Thr Pro Gly Val Ala Ala Asp Leu Ser His Ile
        35                  40                  45 gat acc aaa tcc aag gtc act ggt cat gta ggt gct gct caa ctt gaa    192
Asp Thr Lys Ser Lys Val Thr Gly His Val Gly Ala Ala Gln Leu Glu
    50                  55                  60 gaa gct atc aag gat tct gat gtt gtc gtt att ccc gct ggt gtc cca    240
Glu Ala Ile Lys Asp Ser Asp Val Val Val Ile Pro Ala Gly Val Pro
65                  70                  75                  80 aga aag cca ggt atg acg cgt gat gat ctt ttc aag att aat gct ggt    288
Arg Lys Pro Gly Met Thr Arg Asp Asp Leu Phe Lys Ile Asn Ala Gly
                85                  90                  95 att gta cgt gat ttg gct aca gct gct gca aag tac gct cca aag gcc    336
Ile Val Arg Asp Leu Ala Thr Ala Ala Ala Lys Tyr Ala Pro Lys Ala
            100                 105                 110 ttc atg tgt atc att tct aac cca gtc aac tcg act gtc cca atc gtt    384
Phe Met Cys Ile Ile Ser Asn Pro Val Asn Ser Thr Val Pro Ile Val
        115                 120                 125 act gaa gta ttc aaa cag cac aat gtt tat gac ccc aaa aga atc ttt    432
Thr Glu Val Phe Lys Gln His Asn Val Tyr Asp Pro Lys Arg Ile Phe
```

```
                    130                 135                 140
ggt gtt aca aca ctt gat att gtt cgt gca tcc acc ttt gta tcc gaa    480
Gly Val Thr Thr Leu Asp Ile Val Arg Ala Ser Thr Phe Val Ser Glu
145                 150                 155                 160 ttg att gga ggt gaa cct aat tca ctt cgt gtt ccc gtc att ggt ggt    528
Leu Ile Gly Gly Glu Pro Asn Ser Leu Arg Val Pro Val Ile Gly Gly
            165                 170                 175 cac agc ggc gta acc atc tta cct tta ctc tca cag gtc ccc ggc att    576
His Ser Gly Val Thr Ile Leu Pro Leu Leu Ser Gln Val Pro Gly Ile
        180                 185                 190 gaa aag tta aac caa gaa caa att gag aag gta act cat cgt att caa    624
Glu Lys Leu Asn Gln Glu Gln Ile Glu Lys Val Thr His Arg Ile Gln
    195                 200                 205 ttt ggt ggc gat gaa gtt gtc aag gcc aag gat ggt gct ggt tct gcc    672
Phe Gly Gly Asp Glu Val Val Lys Ala Lys Asp Gly Ala Gly Ser Ala
210                 215                 220 act ctt tcc atg gct tat gct ggt gct cgt ttt gct aca aac atc att    720
Thr Leu Ser Met Ala Tyr Ala Gly Ala Arg Phe Ala Thr Asn Ile Ile
225                 230                 235                 240 gag gct gct ttt gct gga aag aag ggc att gtt gaa tgt acc tat gtt    768
Glu Ala Ala Phe Ala Gly Lys Lys Gly Ile Val Glu Cys Thr Tyr Val
            245                 250                 255 caa ttg gat gct gat aaa tct ggt gcc caa tct gtc aag gat ttg gtt    816
Gln Leu Asp Ala Asp Lys Ser Gly Ala Gln Ser Val Lys Asp Leu Val
        260                 265                 270 ggt agt gaa ctt gaa tat ttc tct gtt ccc gtt gaa ttg ggt cct agt    864
Gly Ser Glu Leu Glu Tyr Phe Ser Val Pro Val Glu Leu Gly Pro Ser
    275                 280                 285 ggt gtt gaa aag att tta ccc att gga aac gtt aat gaa tat gaa aag    912
Gly Val Glu Lys Ile Leu Pro Ile Gly Asn Val Asn Glu Tyr Glu Lys
290                 295                 300 aag ttg ttg aac gag gct tct cct gaa tta aaa acc aac att gat aaa    960
Lys Leu Leu Asn Glu Ala Ser Pro Glu Leu Lys Thr Asn Ile Asp Lys
305                 310                 315                 320 ggt tgt act ttt gtt act gaa ggc taa                                987
Gly Cys Thr Phe Val Thr Glu Gly
            325

<210> SEQ ID NO 172
<211> LENGTH: 328
<212> TYPE: PRT
<213> ORGANISM: Rhizopus oryzae

<400> SEQUENCE: 172

Met Val Lys Val Thr Val Cys Gly Ala Ala Gly Gly Ile Gly Gln Pro
1               5                   10                  15

Leu Ser Leu Leu Leu Lys Gln Ser Ser His Ile Thr His Leu Ser Leu
            20                  25                  30

Tyr Asp Ile Val Asn Thr Pro Gly Val Ala Ala Asp Leu Ser His Ile
        35                  40                  45

Asp Thr Lys Ser Lys Val Thr Gly His Val Gly Ala Ala Gln Leu Glu
    50                  55                  60

Glu Ala Ile Lys Asp Ser Asp Val Val Ile Pro Ala Gly Val Pro
65                  70                  75                  80

Arg Lys Pro Gly Met Thr Arg Asp Asp Leu Phe Lys Ile Asn Ala Gly
            85                  90                  95

Ile Val Arg Asp Leu Ala Thr Ala Ala Lys Tyr Ala Pro Lys Ala
        100                 105                 110
```

```
Phe Met Cys Ile Ile Ser Asn Pro Val Asn Ser Thr Val Pro Ile Val
            115                 120                 125

Thr Glu Val Phe Lys Gln His Asn Val Tyr Asp Pro Lys Arg Ile Phe
    130                 135                 140

Gly Val Thr Thr Leu Asp Ile Val Arg Ala Ser Thr Phe Val Ser Glu
145                 150                 155                 160

Leu Ile Gly Gly Glu Pro Asn Ser Leu Arg Val Pro Val Ile Gly Gly
                165                 170                 175

His Ser Gly Val Thr Ile Leu Pro Leu Leu Ser Gln Val Pro Gly Ile
            180                 185                 190

Glu Lys Leu Asn Gln Glu Gln Ile Glu Lys Val Thr His Arg Ile Gln
        195                 200                 205

Phe Gly Gly Asp Glu Val Val Lys Ala Lys Asp Gly Ala Gly Ser Ala
    210                 215                 220

Thr Leu Ser Met Ala Tyr Ala Gly Ala Arg Phe Ala Thr Asn Ile Ile
225                 230                 235                 240

Glu Ala Ala Phe Ala Gly Lys Lys Gly Ile Val Glu Cys Thr Tyr Val
                245                 250                 255

Gln Leu Asp Ala Asp Lys Ser Gly Ala Gln Ser Val Lys Asp Leu Val
            260                 265                 270

Gly Ser Glu Leu Glu Tyr Phe Ser Val Pro Val Glu Leu Gly Pro Ser
        275                 280                 285

Gly Val Glu Lys Ile Leu Pro Ile Gly Asn Val Asn Glu Tyr Glu Lys
    290                 295                 300

Lys Leu Leu Asn Glu Ala Ser Pro Glu Leu Lys Thr Asn Ile Asp Lys
305                 310                 315                 320

Gly Cys Thr Phe Val Thr Glu Gly
                325

<210> SEQ ID NO 173
<211> LENGTH: 3420
<212> TYPE: DNA
<213> ORGANISM: Trypanosoma brucei
<220> FEATURE:
<221> NAME/KEY: CDS
<222> LOCATION: (1)..(3420)

<400> SEQUENCE: 173 atg gtt gat ggt aga tct tca gct tct att gtt gca gtt gat cca gaa      48
Met Val Asp Gly Arg Ser Ser Ala Ser Ile Val Ala Val Asp Pro Glu
1               5                   10                  15 aga gca gca aga gaa aga gat gct gca gct aga gct ttg tta caa gat      96
Arg Ala Ala Arg Glu Arg Asp Ala Ala Ala Arg Ala Leu Leu Gln Asp
            20                  25                  30 tct cca ttg cac act acc atg caa tat gct acc tcc ggt tta gaa ttg     144
Ser Pro Leu His Thr Thr Met Gln Tyr Ala Thr Ser Gly Leu Glu Leu
        35                  40                  45 acc gtc cct tat gca ttg aaa gtt gtt gca tct gcc gac acc ttc gat     192
Thr Val Pro Tyr Ala Leu Lys Val Val Ala Ser Ala Asp Thr Phe Asp
    50                  55                  60 aga gct aag gaa gtt gca gat gaa gtc ctt aga tgt gcc tgg caa ttg     240
Arg Ala Lys Glu Val Ala Asp Glu Val Leu Arg Cys Ala Trp Gln Leu
65                  70                  75                  80 gct gat aca gtc ctt aac tcc ttt aac cca aac tct gaa gtc tct ctt     288
Ala Asp Thr Val Leu Asn Ser Phe Asn Pro Asn Ser Glu Val Ser Leu
                85                  90                  95 gtt ggt aga ctt cca gtc ggt cag aag cat caa atg tcc gcc cca ctt     336
Val Gly Arg Leu Pro Val Gly Gln Lys His Gln Met Ser Ala Pro Leu
```

```
              100                 105                 110
aag aga gtt atg gct tgt tgt caa aga gtt tac aat tcc tct gct ggt     384
Lys Arg Val Met Ala Cys Cys Gln Arg Val Tyr Asn Ser Ser Ala Gly
            115                 120                 125 tgt ttc gac cca tcc acc gcc cca gtt gca aag gct ttg cgt gaa atc     432
Cys Phe Asp Pro Ser Thr Ala Pro Val Ala Lys Ala Leu Arg Glu Ile
130                 135                 140 gct tta ggc aag gag aga aac aat gcc tgt ttg gag gct tta aca caa     480
Ala Leu Gly Lys Glu Arg Asn Asn Ala Cys Leu Glu Ala Leu Thr Gln
145                 150                 155                 160 gca tgc act ttg cca aac tct ttc gtc att gac ttt gaa gca ggt act     528
Ala Cys Thr Leu Pro Asn Ser Phe Val Ile Asp Phe Glu Ala Gly Thr
                165                 170                 175 atc tca cgt aaa cat gaa cat gct tca ctt gac tta ggt ggt gtt tca     576
Ile Ser Arg Lys His Glu His Ala Ser Leu Asp Leu Gly Gly Val Ser
                180                 185                 190 aag ggt tac atc gtt gac tat gtt att gat aac att aac gca gct ggt     624
Lys Gly Tyr Ile Val Asp Tyr Val Ile Asp Asn Ile Asn Ala Ala Gly
                195                 200                 205 ttc caa aat gtc ttt ttc gat tgg ggt ggt gat tgt aga gcc tcc ggt     672
Phe Gln Asn Val Phe Phe Asp Trp Gly Gly Asp Cys Arg Ala Ser Gly
210                 215                 220 atg aat gct aga aat acc cct tgg gtt gtt ggt att act aga cca cca     720
Met Asn Ala Arg Asn Thr Pro Trp Val Val Gly Ile Thr Arg Pro Pro
225                 230                 235                 240 tca tta gat atg tta cca aac cca cca aag gaa gca tcc tat atc tct     768
Ser Leu Asp Met Leu Pro Asn Pro Pro Lys Glu Ala Ser Tyr Ile Ser
                245                 250                 255 gtt atc tca ttg gac aac gaa gct ttg gca acc tcc ggt gat tac gag     816
Val Ile Ser Leu Asp Asn Glu Ala Leu Ala Thr Ser Gly Asp Tyr Glu
                260                 265                 270 aat ttg atc tac aca gct gat gac aag cct tta act tgt act tac gat     864
Asn Leu Ile Tyr Thr Ala Asp Asp Lys Pro Leu Thr Cys Thr Tyr Asp
                275                 280                 285 tgg aag ggc aag gaa ctt atg aag cca tct caa tca aac att gcc caa     912
Trp Lys Gly Lys Glu Leu Met Lys Pro Ser Gln Ser Asn Ile Ala Gln
290                 295                 300 gtt tca gtt aag tgc tat tca gca atg tac gct gac gct tta gcc acc     960
Val Ser Val Lys Cys Tyr Ser Ala Met Tyr Ala Asp Ala Leu Ala Thr
305                 310                 315                 320 gct tgt ttc atc aaa aga gat cca gcc aag gtt aga caa ttg tta gat    1008
Ala Cys Phe Ile Lys Arg Asp Pro Ala Lys Val Arg Gln Leu Leu Asp
                325                 330                 335 ggt tgg aga tac gtt aga gat act gtc aga gat tac aga gtt tat gtt    1056
Gly Trp Arg Tyr Val Arg Asp Thr Val Arg Asp Tyr Arg Val Tyr Val
                340                 345                 350 aga gaa aat gag aga gtc gct aag atg ttt gaa att gca acc gaa gat    1104
Arg Glu Asn Glu Arg Val Ala Lys Met Phe Glu Ile Ala Thr Glu Asp
                355                 360                 365 gct gaa atg aga aaa aga cgt atc tct aat act ttg cct gca aga gtc    1152
Ala Glu Met Arg Lys Arg Arg Ile Ser Asn Thr Leu Pro Ala Arg Val
370                 375                 380 atc gtt gtc ggt ggc ggt tta gca ggt tta tct gca gca att gaa gct    1200
Ile Val Val Gly Gly Gly Leu Ala Gly Leu Ser Ala Ala Ile Glu Ala
385                 390                 395                 400 gca ggc tgc ggt gca caa gtc gtt ttg atg gaa aag gaa gct aag tta    1248
Ala Gly Cys Gly Ala Gln Val Val Leu Met Glu Lys Glu Ala Lys Leu
                405                 410                 415 ggt ggt aac tct gca aag gca acc tct ggt atc aat ggt tgg ggt act    1296
```

-continued

```
                Gly Gly Asn Ser Ala Lys Ala Thr Ser Gly Ile Asn Gly Trp Gly Thr
                                420                 425                 430 aga gcc caa gca aag gct tcc att gtt gac ggt ggc aag tat ttc gaa         1344
Arg Ala Gln Ala Lys Ala Ser Ile Val Asp Gly Gly Lys Tyr Phe Glu
            435                 440                 445 aga gat act tac aaa tct ggt att ggt ggt aat acc gac cca gct tta         1392
Arg Asp Thr Tyr Lys Ser Gly Ile Gly Gly Asn Thr Asp Pro Ala Leu
        450                 455                 460 gtt aag act ctt tcc atg aag tct gct gac gct att ggt tgg tta aca         1440
Val Lys Thr Leu Ser Met Lys Ser Ala Asp Ala Ile Gly Trp Leu Thr
465                 470                 475                 480 tca tta ggt gtt cct tta aca gtc tta tca caa ttg ggt ggt cat tcc         1488
Ser Leu Gly Val Pro Leu Thr Val Leu Ser Gln Leu Gly Gly His Ser
                485                 490                 495 aga aag aga act cac aga gca cca gac aaa aag gat ggc acc cca tta         1536
Arg Lys Arg Thr His Arg Ala Pro Asp Lys Lys Asp Gly Thr Pro Leu
            500                 505                 510 cct att ggt ttt acc att atg aaa acc tta gaa gat cac gtc aga ggt         1584
Pro Ile Gly Phe Thr Ile Met Lys Thr Leu Glu Asp His Val Arg Gly
        515                 520                 525 aat ctt tct ggt aga att act atc atg gaa aac tgt tcc gtt acc tct         1632
Asn Leu Ser Gly Arg Ile Thr Ile Met Glu Asn Cys Ser Val Thr Ser
    530                 535                 540 tta ctt tct gaa act aag gaa aga cca gat ggt act aaa caa atc aga         1680
Leu Leu Ser Glu Thr Lys Glu Arg Pro Asp Gly Thr Lys Gln Ile Arg
545                 550                 555                 560 gtt acc ggt gtt gag ttc act caa gca ggc tct ggc aaa act acc att         1728
Val Thr Gly Val Glu Phe Thr Gln Ala Gly Ser Gly Lys Thr Thr Ile
                565                 570                 575 ttg gcc gac gca gtc atc ttg gcc act ggt ggt ttc tct aac gac aag         1776
Leu Ala Asp Ala Val Ile Leu Ala Thr Gly Gly Phe Ser Asn Asp Lys
            580                 585                 590 acc gca gac tct ttg ttg aga gaa cat gcc cct cac tta gtt aac ttt         1824
Thr Ala Asp Ser Leu Leu Arg Glu His Ala Pro His Leu Val Asn Phe
        595                 600                 605 cct aca act aac ggt cct tgg gca act ggt gac ggt gtt aag ctt gct         1872
Pro Thr Thr Asn Gly Pro Trp Ala Thr Gly Asp Gly Val Lys Leu Ala
    610                 615                 620 caa aga tta ggt gca caa ttg gtc gac atg gat aag gtt caa ttg cat         1920
Gln Arg Leu Gly Ala Gln Leu Val Asp Met Asp Lys Val Gln Leu His
625                 630                 635                 640 cca act ggt ttg att aac cca aaa gat cca gct aat cca aca aag ttt         1968
Pro Thr Gly Leu Ile Asn Pro Lys Asp Pro Ala Asn Pro Thr Lys Phe
                645                 650                 655 ttg ggt cca gaa gct tta aga ggt tcc ggt ggt gtc ttg tta aac aaa         2016
Leu Gly Pro Glu Ala Leu Arg Gly Ser Gly Gly Val Leu Leu Asn Lys
            660                 665                 670 cag ggt aaa aga ttt gtt aac gaa tta gat ttg cgt tct gtt gtt tcc         2064
Gln Gly Lys Arg Phe Val Asn Glu Leu Asp Leu Arg Ser Val Val Ser
        675                 680                 685 aag gcc att atg gaa caa ggt gct gaa tac cca ggc tct ggt ggt tct         2112
Lys Ala Ile Met Glu Gln Gly Ala Glu Tyr Pro Gly Ser Gly Gly Ser
    690                 695                 700 atg ttc gca tat tgt gtc ctt aat gca gct gca caa aag ttg ttt ggt         2160
Met Phe Ala Tyr Cys Val Leu Asn Ala Ala Ala Gln Lys Leu Phe Gly
705                 710                 715                 720 gtc tct tcc cac gag ttc tac tgg aaa aag atg ggt ttg ttc gtt aag         2208
Val Ser Ser His Glu Phe Tyr Trp Lys Lys Met Gly Leu Phe Val Lys
                725                 730                 735
```

```
gct gat act atg aga gat ttg gca gca ttg att ggt tgt cca gtc gag    2256
Ala Asp Thr Met Arg Asp Leu Ala Ala Leu Ile Gly Cys Pro Val Glu
            740                 745                 750 tct gtt caa caa act tta gag gaa tat gaa aga tta tct att tct cag    2304
Ser Val Gln Gln Thr Leu Glu Glu Tyr Glu Arg Leu Ser Ile Ser Gln
            755                 760                 765 aga tcc tgt cca atc act aga aaa tct gtt tac cca tgt gtt ttg ggc    2352
Arg Ser Cys Pro Ile Thr Arg Lys Ser Val Tyr Pro Cys Val Leu Gly
            770                 775                 780 act aag ggt cca tac tac gtt gct ttc gtc acc cca tct att cac tat    2400
Thr Lys Gly Pro Tyr Tyr Val Ala Phe Val Thr Pro Ser Ile His Tyr
785             790                 795                 800 aca atg ggt ggt tgt ttg att tcc cca tca gca gaa att cag atg aaa    2448
Thr Met Gly Gly Cys Leu Ile Ser Pro Ser Ala Glu Ile Gln Met Lys
            805                 810                 815 aac acc tcc tcc cgt gct cca ttg tcc cat tcc aac cct atc ttg ggt    2496
Asn Thr Ser Ser Arg Ala Pro Leu Ser His Ser Asn Pro Ile Leu Gly
            820                 825                 830 ttg ttc ggt gct ggt gaa gtt act ggt ggt gtc cac ggt ggc aat aga    2544
Leu Phe Gly Ala Gly Glu Val Thr Gly Gly Val His Gly Gly Asn Arg
            835                 840                 845 tta ggt ggt aac tca ttg tta gaa tgt gtt gtc ttt ggt aga att gct    2592
Leu Gly Gly Asn Ser Leu Leu Glu Cys Val Val Phe Gly Arg Ile Ala
850             855                 860 ggt gat aga gct tct acc att ttg cag aga aag tcc tcc gca tta tct    2640
Gly Asp Arg Ala Ser Thr Ile Leu Gln Arg Lys Ser Ser Ala Leu Ser
865             870                 875                 880 ttc aag gtc tgg act acc gtt gtt ttg aga gaa gtt aga gaa ggt ggc    2688
Phe Lys Val Trp Thr Thr Val Val Leu Arg Glu Val Arg Glu Gly Gly
                885                 890                 895 gtc tat ggt gcc ggt tca aga gtt ttg aga ttc aac ttg cct ggt gct    2736
Val Tyr Gly Ala Gly Ser Arg Val Leu Arg Phe Asn Leu Pro Gly Ala
            900                 905                 910 tta caa aga tcc ggt ttg tcc ttg ggt caa ttc atc gca atc aga ggt    2784
Leu Gln Arg Ser Gly Leu Ser Leu Gly Gln Phe Ile Ala Ile Arg Gly
            915                 920                 925 gac tgg gat ggt caa caa ttg att ggt tac tat tcc cca att aca ttg    2832
Asp Trp Asp Gly Gln Gln Leu Ile Gly Tyr Tyr Ser Pro Ile Thr Leu
            930                 935                 940 cca gat gac ttg ggt atg att gac att ttg gct aga tcc gat aaa ggt    2880
Pro Asp Asp Leu Gly Met Ile Asp Ile Leu Ala Arg Ser Asp Lys Gly
945             950                 955                 960 act tta aga gaa tgg att tct gct tta gaa cca ggc gac gct gtt gag    2928
Thr Leu Arg Glu Trp Ile Ser Ala Leu Glu Pro Gly Asp Ala Val Glu
                965                 970                 975 atg aaa gca tgc ggt ggt tta gtc atc gag aga aga ttg tca gat aag    2976
Met Lys Ala Cys Gly Gly Leu Val Ile Glu Arg Arg Leu Ser Asp Lys
            980                 985                 990 cac ttt gtc ttt atg ggt cac atc att aac aag tta tgt ttg atc gct    3024
His Phe Val Phe Met Gly His Ile Ile Asn Lys Leu Cys Leu Ile Ala
            995                 1000                1005 ggt ggt aca ggc gtt gca cct atg tta caa atc att aag gca gca       3069
Gly Gly Thr Gly Val Ala Pro Met Leu Gln Ile Ile Lys Ala Ala
            1010                1015                1020 ttc atg aaa cct ttt atc gat acc tta gaa tct gtc cat ctt atc       3114
Phe Met Lys Pro Phe Ile Asp Thr Leu Glu Ser Val His Leu Ile
            1025                1030                1035 tat gct gca gaa gat gtt acc gag tta act tat aga gaa gtt tta       3159
Tyr Ala Ala Glu Asp Val Thr Glu Leu Thr Tyr Arg Glu Val Leu
            1040                1045                1050
```

```
gag gag cgt aga aga gag tct cgt ggc aag ttc aaa aag acc ttt    3204
Glu Glu Arg Arg Arg Glu Ser Arg Gly Lys Phe Lys Lys Thr Phe
1055                1060                1065 gtt ttg aac aga cct cca cca ctt tgg act gat ggt gtt ggt ttc    3249
Val Leu Asn Arg Pro Pro Pro Leu Trp Thr Asp Gly Val Gly Phe
    1070                1075                1080 atc gat aga ggt atc tta act aat cat gtc caa cca cca tcc gat    3294
Ile Asp Arg Gly Ile Leu Thr Asn His Val Gln Pro Pro Ser Asp
1085                1090                1095 aac ctt ttg gtt gca atc tgt ggt cca cct gtc atg cag cgt att    3339
Asn Leu Leu Val Ala Ile Cys Gly Pro Pro Val Met Gln Arg Ile
    1100                1105                1110 gtt aag gcc acc tta aag act ttg ggt tac aat atg aat ctt gtt    3384
Val Lys Ala Thr Leu Lys Thr Leu Gly Tyr Asn Met Asn Leu Val
1115                1120                1125 aga aca gtt gac gaa aca gaa cca tcc ggt tcc taa                3420
Arg Thr Val Asp Glu Thr Glu Pro Ser Gly Ser
    1130                1135
```

<210> SEQ ID NO 174
<211> LENGTH: 1139
<212> TYPE: PRT
<213> ORGANISM: Trypanosoma brucei

<400> SEQUENCE: 174

```
Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
    50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
    130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
    210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
```

```
            245                 250                 255
Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
            275                 280                 285

Trp Lys Gly Lys Glu Leu Met Lys Pro Ser Gln Ser Asn Ile Ala Gln
            290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
                340                 345                 350

Arg Glu Asn Glu Arg Val Ala Lys Met Phe Glu Ile Ala Thr Glu Asp
                355                 360                 365

Ala Glu Met Arg Lys Arg Ile Ser Asn Thr Leu Pro Ala Arg Val
370                 375                 380

Ile Val Val Gly Gly Gly Leu Ala Gly Leu Ser Ala Ala Ile Glu Ala
385                 390                 395                 400

Ala Gly Cys Gly Ala Gln Val Val Leu Met Glu Lys Glu Ala Lys Leu
                405                 410                 415

Gly Gly Asn Ser Ala Lys Ala Thr Ser Gly Ile Asn Gly Trp Gly Thr
                420                 425                 430

Arg Ala Gln Ala Lys Ala Ser Ile Val Asp Gly Gly Lys Tyr Phe Glu
                435                 440                 445

Arg Asp Thr Tyr Lys Ser Gly Ile Gly Gly Asn Thr Asp Pro Ala Leu
                450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
                500                 505                 510

Pro Ile Gly Phe Thr Ile Met Lys Thr Leu Glu Asp His Val Arg Gly
                515                 520                 525

Asn Leu Ser Gly Arg Ile Thr Ile Met Glu Asn Cys Ser Val Thr Ser
                530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
                580                 585                 590

Thr Ala Asp Ser Leu Leu Arg Glu His Ala Pro His Leu Val Asn Phe
                595                 600                 605

Pro Thr Thr Asn Gly Pro Trp Ala Thr Gly Asp Gly Val Lys Leu Ala
                610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Gly Val Leu Leu Asn Lys
                660                 665                 670
```

```
Gln Gly Lys Arg Phe Val Asn Glu Leu Asp Leu Arg Ser Val Val Ser
        675                 680                 685
Lys Ala Ile Met Glu Gln Gly Ala Glu Tyr Pro Gly Ser Gly Gly Ser
    690                 695                 700
Met Phe Ala Tyr Cys Val Leu Asn Ala Ala Gln Lys Leu Phe Gly
705                 710                 715                 720
Val Ser Ser His Glu Phe Tyr Trp Lys Lys Met Gly Leu Phe Val Lys
            725                 730                 735
Ala Asp Thr Met Arg Asp Leu Ala Ala Leu Ile Gly Cys Pro Val Glu
        740                 745                 750
Ser Val Gln Gln Thr Leu Glu Tyr Glu Arg Leu Ser Ile Ser Gln
        755                 760                 765
Arg Ser Cys Pro Ile Thr Arg Lys Ser Val Tyr Pro Cys Val Leu Gly
        770                 775                 780
Thr Lys Gly Pro Tyr Tyr Val Ala Phe Val Thr Pro Ser Ile His Tyr
785                 790                 795                 800
Thr Met Gly Gly Cys Leu Ile Ser Pro Ser Ala Glu Ile Gln Met Lys
                805                 810                 815
Asn Thr Ser Ser Arg Ala Pro Leu Ser His Ser Asn Pro Ile Leu Gly
        820                 825                 830
Leu Phe Gly Ala Gly Glu Val Thr Gly Gly Val His Gly Gly Asn Arg
        835                 840                 845
Leu Gly Gly Asn Ser Leu Leu Glu Cys Val Val Phe Gly Arg Ile Ala
    850                 855                 860
Gly Asp Arg Ala Ser Thr Ile Leu Gln Arg Lys Ser Ser Ala Leu Ser
865                 870                 875                 880
Phe Lys Val Trp Thr Thr Val Val Leu Arg Glu Val Arg Glu Gly Gly
                885                 890                 895
Val Tyr Gly Ala Gly Ser Arg Val Leu Arg Phe Asn Leu Pro Gly Ala
        900                 905                 910
Leu Gln Arg Ser Gly Leu Ser Leu Gly Gln Phe Ile Ala Ile Arg Gly
        915                 920                 925
Asp Trp Asp Gly Gln Gln Leu Ile Gly Tyr Tyr Ser Pro Ile Thr Leu
    930                 935                 940
Pro Asp Asp Leu Gly Met Ile Asp Ile Leu Ala Arg Ser Asp Lys Gly
945                 950                 955                 960
Thr Leu Arg Glu Trp Ile Ser Ala Leu Glu Pro Gly Asp Ala Val Glu
                965                 970                 975
Met Lys Ala Cys Gly Gly Leu Val Ile Glu Arg Arg Leu Ser Asp Lys
        980                 985                 990
His Phe Val Phe Met Gly His Ile Ile Asn Lys Leu Cys Leu Ile Ala
        995                 1000                1005
Gly Gly Thr Gly Val Ala Pro Met Leu Gln Ile Ile Lys Ala Ala
    1010                1015                1020
Phe Met Lys Pro Phe Ile Asp Thr Leu Glu Ser Val His Leu Ile
    1025                1030                1035
Tyr Ala Ala Glu Asp Val Thr Glu Leu Thr Tyr Arg Glu Val Leu
    1040                1045                1050
Glu Glu Arg Arg Arg Glu Ser Arg Gly Lys Phe Lys Lys Thr Phe
    1055                1060                1065
Val Leu Asn Arg Pro Pro Leu Trp Thr Asp Gly Val Gly Phe
    1070                1075                1080
```

| | | | | | | | | | | | | | | | |
|---|---|---|---|---|---|---|---|---|---|---|---|---|---|---|---|
|Ile|Asp|Arg|Gly|Ile|Leu|Thr|Asn|His|Val|Gln|Pro|Pro|Ser|Asp| |
| |1085| | | |1090| | | |1095| | | | | | |

| | | | | | | | | | | | | | | | |
|---|---|---|---|---|---|---|---|---|---|---|---|---|---|---|---|
|Asn|Leu|Leu|Val|Ala|Ile|Cys|Gly|Pro|Pro|Val|Met|Gln|Arg|Ile| |
| |1100| | | |1105| | | |1110| | | | | | |

| | | | | | | | | | | | | | | | |
|---|---|---|---|---|---|---|---|---|---|---|---|---|---|---|---|
|Val|Lys|Ala|Thr|Leu|Lys|Thr|Leu|Gly|Tyr|Asn|Met|Asn|Leu|Val| |
| |1115| | | |1120| | | |1125| | | | | | |

| | | | | | | | | |
|---|---|---|---|---|---|---|---|---|
|Arg|Thr|Val|Asp|Glu|Thr|Glu|Pro|Ser|Gly|Ser|
| |1130| | | |1135| | | | | |

<210> SEQ ID NO 175
<211> LENGTH: 3420
<212> TYPE: DNA
<213> ORGANISM: Trypanosoma cruzi
<220> FEATURE:
<221> NAME/KEY: CDS
<222> LOCATION: (1)..(3420)

<400> SEQUENCE: 175

```
atg gct gac ggt aga tcc tct gca tct gtt gtt gca gtt gat cca gaa      48
Met Ala Asp Gly Arg Ser Ser Ala Ser Val Val Ala Val Asp Pro Glu
1               5                   10                  15 aag gct gca aga gaa aga gat gaa gca gct cgt gct ttg tta aga gac      96
Lys Ala Ala Arg Glu Arg Asp Glu Ala Ala Arg Ala Leu Leu Arg Asp
                20                  25                  30 tct cca tta caa act cat ctt cag tac atg act aat ggt tta gag ttg     144
Ser Pro Leu Gln Thr His Leu Gln Tyr Met Thr Asn Gly Leu Glu Leu
            35                  40                  45 act gtc cca ttc acc tta aag gtt gtc gct gaa gca gtt gca ttt tcc     192
Thr Val Pro Phe Thr Leu Lys Val Val Ala Glu Ala Val Ala Phe Ser
        50                  55                  60 aga gca aag gaa gtt gct gac gaa gtt ttg agg tca gcc tgg cat ctt     240
Arg Ala Lys Glu Val Ala Asp Glu Val Leu Arg Ser Ala Trp His Leu
65                  70                  75                  80 gca gac acc gtc ttg aac aac ttt aac cct aac tcc gag att tct atg     288
Ala Asp Thr Val Leu Asn Asn Phe Asn Pro Asn Ser Glu Ile Ser Met
                85                  90                  95 att ggt aga tta cca gtt ggt caa aaa cat aca atg tcc gct aca ttg     336
Ile Gly Arg Leu Pro Val Gly Gln Lys His Thr Met Ser Ala Thr Leu
                100                 105                 110 aag tct gtt atc aca tgc tgt cag cat gtt ttc aat tca tcc aga ggt     384
Lys Ser Val Ile Thr Cys Cys Gln His Val Phe Asn Ser Ser Arg Gly
            115                 120                 125 gtt ttt gat cca gct act ggt cct atc att gaa gct tta aga gct aag     432
Val Phe Asp Pro Ala Thr Gly Pro Ile Ile Glu Ala Leu Arg Ala Lys
        130                 135                 140 gtt gct gag aaa gcc tct gtt tct gat gaa cag atg gag aag ttg ttt     480
Val Ala Glu Lys Ala Ser Val Ser Asp Glu Gln Met Glu Lys Leu Phe
145                 150                 155                 160 cgt gtt tgt aac ttc tct tcc tca ttc atc gtt gat ttg gaa atg ggt     528
Arg Val Cys Asn Phe Ser Ser Ser Phe Ile Val Asp Leu Glu Met Gly
                165                 170                 175 act att gcc aga aaa cac gaa gat gca aga ttt gac tta ggt ggt gtt     576
Thr Ile Ala Arg Lys His Glu Asp Ala Arg Phe Asp Leu Gly Gly Val
                180                 185                 190 tcc aag ggt tac atc gtt gac tac gtt gtt gaa aga ttg aac gct gct     624
Ser Lys Gly Tyr Ile Val Asp Tyr Val Val Glu Arg Leu Asn Ala Ala
            195                 200                 205 ggt att gtc gat gtc tac ttc gaa tgg ggt ggt gac tgt aga gct tcc     672
Gly Ile Val Asp Val Tyr Phe Glu Trp Gly Gly Asp Cys Arg Ala Ser
        210                 215                 220
```

```
ggt act aac gca aga cgt acc cca tgg atg gtt ggt atc att aga cct        720
Gly Thr Asn Ala Arg Arg Thr Pro Trp Met Val Gly Ile Ile Arg Pro
225                 230                 235                 240 cca tct tta gaa caa ttg aga aac cca cca aaa gat cca tcc tac att        768
Pro Ser Leu Glu Gln Leu Arg Asn Pro Pro Lys Asp Pro Ser Tyr Ile
                245                 250                 255 agg gtt tta cca ctt aac gat gaa gca ctt tgt acc tct ggt gac tat        816
Arg Val Leu Pro Leu Asn Asp Glu Ala Leu Cys Thr Ser Gly Asp Tyr
            260                 265                 270 gag aat ttg acc gaa ggc tct aac aaa aag ttg tat aca tcc att ttc        864
Glu Asn Leu Thr Glu Gly Ser Asn Lys Lys Leu Tyr Thr Ser Ile Phe
        275                 280                 285 gat tgg aaa aag aga tcc ttg ttg gaa cca gtt gaa tca gaa ttg gcc        912
Asp Trp Lys Lys Arg Ser Leu Leu Glu Pro Val Glu Ser Glu Leu Ala
    290                 295                 300 caa gtt tcc att aga tgt tat tct gcc atg tat gca gac gca tta gca        960
Gln Val Ser Ile Arg Cys Tyr Ser Ala Met Tyr Ala Asp Ala Leu Ala
305                 310                 315                 320 aca gct tct ctt atc aag aga gat atc aaa aag gtt aga caa atg ttg       1008
Thr Ala Ser Leu Ile Lys Arg Asp Ile Lys Lys Val Arg Gln Met Leu
                325                 330                 335 gaa gat tgg aga cac gtc cgt aat agg gtt act aac tat gtt acc tat       1056
Glu Asp Trp Arg His Val Arg Asn Arg Val Thr Asn Tyr Val Thr Tyr
            340                 345                 350 acc aga caa ggt gaa aga gtc gca cgt atg ttt gaa att gct act gat       1104
Thr Arg Gln Gly Glu Arg Val Ala Arg Met Phe Glu Ile Ala Thr Asp
        355                 360                 365 aac gct gag att agg aaa aag aga att gca ggc tct tta cct gct agg       1152
Asn Ala Glu Ile Arg Lys Lys Arg Ile Ala Gly Ser Leu Pro Ala Arg
    370                 375                 380 gtt att gtt gtc ggt ggt ggt tta gct ggt ttg tct gca gca att gaa       1200
Val Ile Val Val Gly Gly Gly Leu Ala Gly Leu Ser Ala Ala Ile Glu
385                 390                 395                 400 gca act gca tgt ggt gcc caa gtt atc ctt tta gaa aag gaa cct aaa       1248
Ala Thr Ala Cys Gly Ala Gln Val Ile Leu Leu Glu Lys Glu Pro Lys
                405                 410                 415 gtt ggt ggt aat tcc gca aag gct aca tct ggt atc aac ggt tgg ggt       1296
Val Gly Gly Asn Ser Ala Lys Ala Thr Ser Gly Ile Asn Gly Trp Gly
            420                 425                 430 act aga gca caa gct gaa caa gat gtc tac gac tct ggc aag tac ttc       1344
Thr Arg Ala Gln Ala Glu Gln Asp Val Tyr Asp Ser Gly Lys Tyr Phe
        435                 440                 445 gaa aga gat aca cac aaa tct ggt tta ggt ggt tct acc gat cca ggc       1392
Glu Arg Asp Thr His Lys Ser Gly Leu Gly Gly Ser Thr Asp Pro Gly
    450                 455                 460 tta gtt cgt act tta tca gtc aag tct ggt gac gct att tca tgg tta       1440
Leu Val Arg Thr Leu Ser Val Lys Ser Gly Asp Ala Ile Ser Trp Leu
465                 470                 475                 480 tct tct ctt ggt gtt cca tta act gtc ttg tca caa tta ggc ggt cat       1488
Ser Ser Leu Gly Val Pro Leu Thr Val Leu Ser Gln Leu Gly Gly His
                485                 490                 495 tcc aga aaa agg act cac aga gcc cct gat aag gca gat ggt act cca       1536
Ser Arg Lys Arg Thr His Arg Ala Pro Asp Lys Ala Asp Gly Thr Pro
            500                 505                 510 gtt cca att ggt ttc acc att atg caa acc tta gaa cag cat gtt aga       1584
Val Pro Ile Gly Phe Thr Ile Met Gln Thr Leu Glu Gln His Val Arg
        515                 520                 525 acc aag tta gca gac aga gtt act atc atg gag aat acc acc gtt acc       1632
Thr Lys Leu Ala Asp Arg Val Thr Ile Met Glu Asn Thr Thr Val Thr
    530                 535                 540
```

```
tcc ttg ctt tct aag tcc aga gtt aga cat gat ggt gca aag caa gtt       1680
Ser Leu Leu Ser Lys Ser Arg Val Arg His Asp Gly Ala Lys Gln Val
545                 550                 555                 560 aga gtc tac ggt gtt gaa gtc tta caa gac gaa ggt gtc gtt tct cgt       1728
Arg Val Tyr Gly Val Glu Val Leu Gln Asp Glu Gly Val Val Ser Arg
                565                 570                 575 atc ttg gcc gat gct gtc att ttg gca aca ggt ggt ttc tcc aat gac       1776
Ile Leu Ala Asp Ala Val Ile Leu Ala Thr Gly Gly Phe Ser Asn Asp
            580                 585                 590 aaa acc cca aac tcc tta ttg caa gag ttc gct cca caa ttg tca ggt       1824
Lys Thr Pro Asn Ser Leu Leu Gln Glu Phe Ala Pro Gln Leu Ser Gly
        595                 600                 605 ttt cca aca acc aac ggt cca tgg gct act ggc gat ggt gtt aag tta       1872
Phe Pro Thr Thr Asn Gly Pro Trp Ala Thr Gly Asp Gly Val Lys Leu
    610                 615                 620 gca aga gaa ctt ggt gtc aag ttg gtt gat atg gat aag gtc caa ctt       1920
Ala Arg Glu Leu Gly Val Lys Leu Val Asp Met Asp Lys Val Gln Leu
625                 630                 635                 640 cat cca act ggt ttg att gac cct aag gac cca gca aat cca acc aaa       1968
His Pro Thr Gly Leu Ile Asp Pro Lys Asp Pro Ala Asn Pro Thr Lys
                645                 650                 655 tac tta ggt cca gaa gca ttg aga ggt tct ggt ggt gtc ttg tta aac       2016
Tyr Leu Gly Pro Glu Ala Leu Arg Gly Ser Gly Gly Val Leu Leu Asn
            660                 665                 670 aaa aag ggt gaa aga ttt gtc aat gag ttg gac ttg cgt tcc gtc gtt       2064
Lys Lys Gly Glu Arg Phe Val Asn Glu Leu Asp Leu Arg Ser Val Val
        675                 680                 685 tca aat gct atc att gaa caa ggt gat gaa tat cca gat gcc ggt ggt       2112
Ser Asn Ala Ile Ile Glu Gln Gly Asp Glu Tyr Pro Asp Ala Gly Gly
    690                 695                 700 tcc aag ttc gcc ttc tgt gtt ttg aat gat gca gca gtt aag tta ttc       2160
Ser Lys Phe Ala Phe Cys Val Leu Asn Asp Ala Ala Val Lys Leu Phe
705                 710                 715                 720 ggt gtc aac tcc cac ggt ttc tac tgg aag aga ctt ggt ttg ttt gtt       2208
Gly Val Asn Ser His Gly Phe Tyr Trp Lys Arg Leu Gly Leu Phe Val
                725                 730                 735 aag gct gat acc gtt gaa aag tta gcc gca ttg atc ggt tgc cca gtc       2256
Lys Ala Asp Thr Val Glu Lys Leu Ala Ala Leu Ile Gly Cys Pro Val
            740                 745                 750 gaa aat gtt aga aac aca tta ggt gat tat gag caa ttg tcc aag gaa       2304
Glu Asn Val Arg Asn Thr Leu Gly Asp Tyr Glu Gln Leu Ser Lys Glu
        755                 760                 765 aac aga caa tgt cca aag act aga aaa gtt gtc tat cca tgt gtt gtt       2352
Asn Arg Gln Cys Pro Lys Thr Arg Lys Val Val Tyr Pro Cys Val Val
    770                 775                 780 ggt cca caa ggt cca ttc tat gtt gct ttt gtt acc cca tct att cac       2400
Gly Pro Gln Gly Pro Phe Tyr Val Ala Phe Val Thr Pro Ser Ile His
785                 790                 795                 800 tat acc atg ggt ggt tgt ttg atc tca cca tct gct gag atg caa ttg       2448
Tyr Thr Met Gly Gly Cys Leu Ile Ser Pro Ser Ala Glu Met Gln Leu
                805                 810                 815 gaa gag aac act acc tcc cca ttt ggt cac aga agg cct atc ttc ggt       2496
Glu Glu Asn Thr Thr Ser Pro Phe Gly His Arg Arg Pro Ile Phe Gly
            820                 825                 830 ctt ttc ggt gcc ggt gaa gtt act ggt ggt gtc cat ggt ggt aac aga       2544
Leu Phe Gly Ala Gly Glu Val Thr Gly Gly Val His Gly Gly Asn Arg
        835                 840                 845 tta ggt ggc aac tct ttg ttg gag tgt gtt gtt ttt ggt aga atc gct       2592
Leu Gly Gly Asn Ser Leu Leu Glu Cys Val Val Phe Gly Arg Ile Ala
```

```
                      850                 855                 860
ggt gat aga gct gca acc att ttg caa aag aaa cca gtt cca ctt tcc       2640
Gly Asp Arg Ala Ala Thr Ile Leu Gln Lys Lys Pro Val Pro Leu Ser
865                 870                 875                 880 ttt aag act tgg acc acc gtc att ttg aga gag gtc cgt gaa ggt ggc       2688
Phe Lys Thr Trp Thr Thr Val Ile Leu Arg Glu Val Arg Glu Gly Gly
                885                 890                 895 atg tac ggt act ggt tca aga gtc tta aga ttc aat ttg cca ggt gct       2736
Met Tyr Gly Thr Gly Ser Arg Val Leu Arg Phe Asn Leu Pro Gly Ala
                900                 905                 910 tta caa aga tct ggt ttg caa ttg ggt caa ttc atc gct att aga ggc       2784
Leu Gln Arg Ser Gly Leu Gln Leu Gly Gln Phe Ile Ala Ile Arg Gly
            915                 920                 925 gaa tgg gat ggt caa caa ttg att ggc tac tat tcc cca atc act ttg       2832
Glu Trp Asp Gly Gln Gln Leu Ile Gly Tyr Tyr Ser Pro Ile Thr Leu
930                 935                 940 cca gac gat ttg ggt gtc atc ggc att ttg gct aga tcc gat aag ggt       2880
Pro Asp Asp Leu Gly Val Ile Gly Ile Leu Ala Arg Ser Asp Lys Gly
945                 950                 955                 960 act ttg aag gaa tgg att tct gct ttg gaa cct ggt gat gca gtt gag       2928
Thr Leu Lys Glu Trp Ile Ser Ala Leu Glu Pro Gly Asp Ala Val Glu
                965                 970                 975 atg aag ggt tgt ggc ggt tta gtt att gaa agg aga ttc tct gaa aga       2976
Met Lys Gly Cys Gly Gly Leu Val Ile Glu Arg Arg Phe Ser Glu Arg
                980                 985                 990 tac ttg tac ttt tct ggt cac gct ttg aaa aag tta tgc ctt att gct       3024
Tyr Leu Tyr Phe Ser Gly His Ala Leu Lys Lys Leu Cys Leu Ile Ala
                995                 1000                1005 ggt ggt act ggt gtc gca cca atg tta caa atc att aga gca gca          3069
Gly Gly Thr Gly Val Ala Pro Met Leu Gln Ile Ile Arg Ala Ala
1010                1015                1020 ttg aaa aag cca ttc ctt gag aat atc gaa tca att aga ctt atc          3114
Leu Lys Lys Pro Phe Leu Glu Asn Ile Glu Ser Ile Arg Leu Ile
1025                1030                1035 tat gct gct gag gac gtt tct gag ttg aca tac agg gaa ttg tta          3159
Tyr Ala Ala Glu Asp Val Ser Glu Leu Thr Tyr Arg Glu Leu Leu
1040                1045                1050 gaa cat cac caa aga gat tct aag ggc aag ttt aga tcc atc ttc          3204
Glu His His Gln Arg Asp Ser Lys Gly Lys Phe Arg Ser Ile Phe
1055                1060                1065 gtt ttg aat aga cca cct cca att tgg act gat ggt gtt ggc ttt          3249
Val Leu Asn Arg Pro Pro Pro Ile Trp Thr Asp Gly Val Gly Phe
1070                1075                1080 atc gac aaa aag ttg tta tct tca tcc gtt cag cca cct gct aag          3294
Ile Asp Lys Lys Leu Leu Ser Ser Ser Val Gln Pro Pro Ala Lys
1085                1090                1095 gat ttg tta gtc gcc att tgt ggt cct cct atc atg caa cgt gtt          3339
Asp Leu Leu Val Ala Ile Cys Gly Pro Pro Ile Met Gln Arg Val
1100                1105                1110 gtc aag act tgt ctt aag tca tta ggt tat gat atg cag tta gtc          3384
Val Lys Thr Cys Leu Lys Ser Leu Gly Tyr Asp Met Gln Leu Val
1115                1120                1125 aga aca gtt gat gaa gtc gaa act caa aac tcc taa                      3420
Arg Thr Val Asp Glu Val Glu Thr Gln Asn Ser
1130                1135

<210> SEQ ID NO 176
<211> LENGTH: 1139
<212> TYPE: PRT
<213> ORGANISM: Trypanosoma cruzi
```

<400> SEQUENCE: 176

Met Ala Asp Gly Arg Ser Ser Ala Ser Val Val Ala Val Asp Pro Glu
1               5                   10                  15

Lys Ala Ala Arg Glu Arg Asp Glu Ala Ala Arg Ala Leu Leu Arg Asp
            20                  25                  30

Ser Pro Leu Gln Thr His Leu Gln Tyr Met Thr Asn Gly Leu Glu Leu
        35                  40                  45

Thr Val Pro Phe Thr Leu Lys Val Val Ala Glu Ala Val Ala Phe Ser
    50                  55                  60

Arg Ala Lys Glu Val Ala Asp Glu Val Leu Arg Ser Ala Trp His Leu
65              70                  75                  80

Ala Asp Thr Val Leu Asn Asn Phe Asn Pro Asn Ser Glu Ile Ser Met
                85                  90                  95

Ile Gly Arg Leu Pro Val Gly Gln Lys His Thr Met Ser Ala Thr Leu
            100                 105                 110

Lys Ser Val Ile Thr Cys Cys Gln His Val Phe Asn Ser Ser Arg Gly
        115                 120                 125

Val Phe Asp Pro Ala Thr Gly Pro Ile Ile Glu Ala Leu Arg Ala Lys
    130                 135                 140

Val Ala Glu Lys Ala Ser Val Ser Asp Glu Gln Met Glu Lys Leu Phe
145                 150                 155                 160

Arg Val Cys Asn Phe Ser Ser Ser Phe Ile Val Asp Leu Glu Met Gly
                165                 170                 175

Thr Ile Ala Arg Lys His Glu Asp Ala Arg Phe Asp Leu Gly Gly Val
            180                 185                 190

Ser Lys Gly Tyr Ile Val Asp Tyr Val Val Glu Arg Leu Asn Ala Ala
        195                 200                 205

Gly Ile Val Asp Val Tyr Phe Glu Trp Gly Gly Asp Cys Arg Ala Ser
    210                 215                 220

Gly Thr Asn Ala Arg Arg Thr Pro Trp Met Val Gly Ile Ile Arg Pro
225                 230                 235                 240

Pro Ser Leu Glu Gln Leu Arg Asn Pro Pro Lys Asp Pro Ser Tyr Ile
                245                 250                 255

Arg Val Leu Pro Leu Asn Asp Glu Ala Leu Cys Thr Ser Gly Asp Tyr
            260                 265                 270

Glu Asn Leu Thr Glu Gly Ser Asn Lys Lys Leu Tyr Thr Ser Ile Phe
        275                 280                 285

Asp Trp Lys Lys Arg Ser Leu Leu Glu Pro Val Glu Ser Glu Leu Ala
    290                 295                 300

Gln Val Ser Ile Arg Cys Tyr Ser Ala Met Tyr Ala Asp Ala Leu Ala
305                 310                 315                 320

Thr Ala Ser Leu Ile Lys Arg Asp Ile Lys Lys Val Arg Gln Met Leu
                325                 330                 335

Glu Asp Trp Arg His Val Arg Asn Arg Val Thr Asn Tyr Val Thr Tyr
            340                 345                 350

Thr Arg Gln Gly Glu Arg Val Ala Arg Met Phe Glu Ile Ala Thr Asp
        355                 360                 365

Asn Ala Glu Ile Arg Lys Lys Arg Ile Ala Gly Ser Leu Pro Ala Arg
    370                 375                 380

Val Ile Val Val Gly Gly Gly Leu Ala Gly Leu Ser Ala Ala Ile Glu
385                 390                 395                 400

Ala Thr Ala Cys Gly Ala Gln Val Ile Leu Leu Glu Lys Glu Pro Lys

-continued

```
            405                 410                 415
Val Gly Gly Asn Ser Ala Lys Ala Thr Ser Gly Ile Asn Gly Trp Gly
            420                 425                 430

Thr Arg Ala Gln Ala Glu Gln Asp Val Tyr Asp Ser Gly Lys Tyr Phe
            435                 440                 445

Glu Arg Asp Thr His Lys Ser Gly Leu Gly Gly Ser Thr Asp Pro Gly
450                 455                 460

Leu Val Arg Thr Leu Ser Val Lys Ser Gly Asp Ala Ile Ser Trp Leu
465                 470                 475                 480

Ser Ser Leu Gly Val Pro Leu Thr Val Leu Ser Gln Leu Gly Gly His
                485                 490                 495

Ser Arg Lys Arg Thr His Arg Ala Pro Asp Lys Ala Asp Gly Thr Pro
                500                 505                 510

Val Pro Ile Gly Phe Thr Ile Met Gln Thr Leu Glu Gln His Val Arg
                515                 520                 525

Thr Lys Leu Ala Asp Arg Val Thr Ile Met Glu Asn Thr Thr Val Thr
            530                 535                 540

Ser Leu Leu Ser Lys Ser Arg Val Arg His Asp Gly Ala Lys Gln Val
545                 550                 555                 560

Arg Val Tyr Gly Val Glu Val Leu Gln Asp Glu Gly Val Val Ser Arg
                565                 570                 575

Ile Leu Ala Asp Ala Val Ile Leu Ala Thr Gly Gly Phe Ser Asn Asp
                580                 585                 590

Lys Thr Pro Asn Ser Leu Leu Gln Glu Phe Ala Pro Gln Leu Ser Gly
                595                 600                 605

Phe Pro Thr Thr Asn Gly Pro Trp Ala Thr Gly Asp Gly Val Lys Leu
            610                 615                 620

Ala Arg Glu Leu Gly Val Lys Leu Val Asp Met Asp Lys Val Gln Leu
625                 630                 635                 640

His Pro Thr Gly Leu Ile Asp Pro Lys Asp Pro Ala Asn Pro Thr Lys
                645                 650                 655

Tyr Leu Gly Pro Glu Ala Leu Arg Gly Ser Gly Gly Val Leu Leu Asn
                660                 665                 670

Lys Lys Gly Glu Arg Phe Val Asn Glu Leu Asp Leu Arg Ser Val Val
            675                 680                 685

Ser Asn Ala Ile Ile Glu Gln Gly Asp Glu Tyr Pro Asp Ala Gly Gly
            690                 695                 700

Ser Lys Phe Ala Phe Cys Val Leu Asn Asp Ala Val Lys Leu Phe
705                 710                 715                 720

Gly Val Asn Ser His Gly Phe Tyr Trp Lys Arg Leu Gly Leu Phe Val
                725                 730                 735

Lys Ala Asp Thr Val Glu Lys Leu Ala Ala Leu Ile Gly Cys Pro Val
            740                 745                 750

Glu Asn Val Arg Asn Thr Leu Gly Asp Tyr Glu Gln Leu Ser Lys Glu
            755                 760                 765

Asn Arg Gln Cys Pro Lys Thr Arg Lys Val Val Tyr Pro Cys Val Val
            770                 775                 780

Gly Pro Gln Gly Pro Phe Tyr Val Ala Phe Val Thr Pro Ser Ile His
785                 790                 795                 800

Tyr Thr Met Gly Gly Cys Leu Ile Ser Pro Ser Ala Glu Met Gln Leu
                805                 810                 815

Glu Glu Asn Thr Thr Ser Pro Phe Gly His Arg Arg Pro Ile Phe Gly
            820                 825                 830
```

```
Leu Phe Gly Ala Gly Glu Val Thr Gly Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ala Thr Ile Leu Gln Lys Lys Pro Val Pro Leu Ser
865                 870                 875                 880

Phe Lys Thr Trp Thr Thr Val Ile Leu Arg Glu Val Arg Glu Gly Gly
                885                 890                 895

Met Tyr Gly Thr Gly Ser Arg Val Leu Arg Phe Asn Leu Pro Gly Ala
            900                 905                 910

Leu Gln Arg Ser Gly Leu Gln Leu Gly Gln Phe Ile Ala Ile Arg Gly
        915                 920                 925

Glu Trp Asp Gly Gln Gln Leu Ile Gly Tyr Tyr Ser Pro Ile Thr Leu
    930                 935                 940

Pro Asp Asp Leu Gly Val Ile Gly Ile Leu Ala Arg Ser Asp Lys Gly
945                 950                 955                 960

Thr Leu Lys Glu Trp Ile Ser Ala Leu Glu Pro Gly Asp Ala Val Glu
                965                 970                 975

Met Lys Gly Cys Gly Gly Leu Val Ile Glu Arg Arg Phe Ser Glu Arg
            980                 985                 990

Tyr Leu Tyr Phe Ser Gly His Ala Leu Lys Lys Leu Cys Leu Ile Ala
        995                 1000                1005

Gly Gly Thr Gly Val Ala Pro Met Leu Gln Ile Ile Arg Ala Ala
    1010                1015                1020

Leu Lys Lys Pro Phe Leu Glu Asn Ile Glu Ser Ile Arg Leu Ile
    1025                1030                1035

Tyr Ala Ala Glu Asp Val Ser Glu Leu Thr Tyr Arg Glu Leu Leu
    1040                1045                1050

Glu His His Gln Arg Asp Ser Lys Gly Lys Phe Arg Ser Ile Phe
    1055                1060                1065

Val Leu Asn Arg Pro Pro Pro Ile Trp Thr Asp Gly Val Gly Phe
    1070                1075                1080

Ile Asp Lys Lys Leu Leu Ser Ser Ser Val Gln Pro Pro Ala Lys
    1085                1090                1095

Asp Leu Leu Val Ala Ile Cys Gly Pro Pro Ile Met Gln Arg Val
    1100                1105                1110

Val Lys Thr Cys Leu Lys Ser Leu Gly Tyr Asp Met Gln Leu Val
    1115                1120                1125

Arg Thr Val Asp Glu Val Glu Thr Gln Asn Ser
    1130                1135

<210> SEQ ID NO 177
<211> LENGTH: 3435
<212> TYPE: DNA
<213> ORGANISM: Leishmania braziliensis
<220> FEATURE:
<221> NAME/KEY: CDS
<222> LOCATION: (1)..(3435)

<400> SEQUENCE: 177 atg gct gat ggt aaa acc tct gct tcc gtt gtt gct gtc gac cca gag    48
Met Ala Asp Gly Lys Thr Ser Ala Ser Val Val Ala Val Asp Pro Glu
1               5                   10                  15 cgt gca gca aag gag aga gat gca gca gca aga gca atg tta caa gac    96
Arg Ala Ala Lys Glu Arg Asp Ala Ala Ala Arg Ala Met Leu Gln Asp
            20                  25                  30
```

```
ggt ggt gtt tct cca gtt ggt aaa gct cag ttg ttg aaa aag ggt ttg           144
Gly Gly Val Ser Pro Val Gly Lys Ala Gln Leu Leu Lys Lys Gly Leu
            35              40              45 gca tat gct gtc cct tac acc ctt aag att gtt gtt gca gat cct aaa           192
Ala Tyr Ala Val Pro Tyr Thr Leu Lys Ile Val Val Ala Asp Pro Lys
    50              55              60 gct atg gaa aag acc acc gca gac gtt gag aag gtc ctt caa acc gca           240
Ala Met Glu Lys Thr Thr Ala Asp Val Glu Lys Val Leu Gln Thr Ala
65              70              75              80 ttc caa gtc gtt gac act ttg tta aac aat ttc aac gaa aac tcc gag           288
Phe Gln Val Val Asp Thr Leu Leu Asn Asn Phe Asn Glu Asn Ser Glu
                85              90              95 gtt tct cgt atc aac aga atg cca gtc ggt gag gaa cac caa atg tct           336
Val Ser Arg Ile Asn Arg Met Pro Val Gly Glu Glu His Gln Met Ser
            100             105             110 gct gca ttg aag aga gtt atg ggt tgc tgt cag cgt gtt tac aat tca           384
Ala Ala Leu Lys Arg Val Met Gly Cys Cys Gln Arg Val Tyr Asn Ser
        115             120             125 tct cgt ggt gct ttt gac cca gct gtt ggt cca ttg gtc aga gaa ttg           432
Ser Arg Gly Ala Phe Asp Pro Ala Val Gly Pro Leu Val Arg Glu Leu
130             135             140 agg gaa gct gca aga gaa ggc aga act tta cca gca gaa agg att aac           480
Arg Glu Ala Ala Arg Glu Gly Arg Thr Leu Pro Ala Glu Arg Ile Asn
145             150             155             160 gct ttg tta tcc aag tgt acc ttg aat atc tcc ttt tcc att gat ttg           528
Ala Leu Leu Ser Lys Cys Thr Leu Asn Ile Ser Phe Ser Ile Asp Leu
            165             170             175 aac aga ggt act att gcc aga aaa cac gca gat gca atg ttg gat ttg           576
Asn Arg Gly Thr Ile Ala Arg Lys His Ala Asp Ala Met Leu Asp Leu
        180             185             190 ggt ggt gtc aat aag ggt tat ggt gtt gat tat gtt gtc gaa cat ttg           624
Gly Gly Val Asn Lys Gly Tyr Gly Val Asp Tyr Val Val Glu His Leu
    195             200             205 aac aat ttg ggt tat gat gat gtc ttt ttc gaa tgg ggt ggt gat gtt           672
Asn Asn Leu Gly Tyr Asp Asp Val Phe Phe Glu Trp Gly Gly Asp Val
210             215             220 aga gca tct ggc aaa aac cca tca aac caa cat tgg gtt gtt ggt att           720
Arg Ala Ser Gly Lys Asn Pro Ser Asn Gln His Trp Val Val Gly Ile
225             230             235             240 gct aga cca cca gca ctt gct gat atc aga acc gtt gtt cca caa gac           768
Ala Arg Pro Pro Ala Leu Ala Asp Ile Arg Thr Val Val Pro Gln Asp
            245             250             255 aag caa tcc ttc atc aga gtt gtt tgt ctt aat gat gaa gca att gcc           816
Lys Gln Ser Phe Ile Arg Val Val Cys Leu Asn Asp Glu Ala Ile Ala
        260             265             270 acc tct ggt gat tac gaa aat ctt gtc gaa ggt cct ggt tct aag gtt           864
Thr Ser Gly Asp Tyr Glu Asn Leu Val Glu Gly Pro Gly Ser Lys Val
    275             280             285 tac tcc tct acc ttc aac gca acc tct aag tcc tta ttg gaa cca acc           912
Tyr Ser Ser Thr Phe Asn Ala Thr Ser Lys Ser Leu Leu Glu Pro Thr
290             295             300 gaa acc aat atc gca caa gtc tct gtt aag tgt tac tca tgc atg tat           960
Glu Thr Asn Ile Ala Gln Val Ser Val Lys Cys Tyr Ser Cys Met Tyr
305             310             315             320 gca gac gca ttg gct acc gct gcc tta ttg aaa aac aat cca act gct          1008
Ala Asp Ala Leu Ala Thr Ala Ala Leu Leu Lys Asn Asn Pro Thr Ala
            325             330             335 gtt cgt aga atg tta gat aac tgg aga tat gtt cgt gat act gtt acc          1056
Val Arg Arg Met Leu Asp Asn Trp Arg Tyr Val Arg Asp Thr Val Thr
```

```
              340               345               350
gac tat aca acc tat tcc aga gaa ggt gaa aga gtt gca aag atg ttt    1104
Asp Tyr Thr Thr Tyr Ser Arg Glu Gly Glu Arg Val Ala Lys Met Phe
        355               360               365 gag att gca acc gaa gat aag gaa atg aga gct aag aga att tcc ggt    1152
Glu Ile Ala Thr Glu Asp Lys Glu Met Arg Ala Lys Arg Ile Ser Gly
370               375               380 tcc ttg cca gca aga gtc att atc gtc ggt ggt gga tta gct ggt tgt    1200
Ser Leu Pro Ala Arg Val Ile Ile Val Gly Gly Gly Leu Ala Gly Cys
385               390               395               400 tct gca gct att gaa gca gtc aac tgt ggt gct caa gtc att ttg tta    1248
Ser Ala Ala Ile Glu Ala Val Asn Cys Gly Ala Gln Val Ile Leu Leu
                405               410               415 gaa aag gaa gcc aag att ggt ggc aac tcc gca aag gct acc tct ggt    1296
Glu Lys Glu Ala Lys Ile Gly Gly Asn Ser Ala Lys Ala Thr Ser Gly
            420               425               430 atc aac gcc tgg ggt act aga gcc cag gct aaa caa ggt gtt atg gat    1344
Ile Asn Ala Trp Gly Thr Arg Ala Gln Ala Lys Gln Gly Val Met Asp
        435               440               445 ggt ggc aag ttt ttc gag aga gac acc cat aga tcc ggt aaa ggt ggt    1392
Gly Gly Lys Phe Phe Glu Arg Asp Thr His Arg Ser Gly Lys Gly Gly
450               455               460 cac tgt gat cct tgt ttg gtt aag aca ctt tcc gtt aag tca tca gac    1440
His Cys Asp Pro Cys Leu Val Lys Thr Leu Ser Val Lys Ser Ser Asp
465               470               475               480 gca gtt aag tgg ttg tct gaa ttg ggt gtt cca tta acc gtc tta tcc    1488
Ala Val Lys Trp Leu Ser Glu Leu Gly Val Pro Leu Thr Val Leu Ser
                485               490               495 caa tta ggt ggt gca tcc aga aag agg tgt cat aga gcc cca gat aag    1536
Gln Leu Gly Gly Ala Ser Arg Lys Arg Cys His Arg Ala Pro Asp Lys
            500               505               510 tct gat ggt act cct gtt cca att ggt ttt aca atc atg aaa aca tta    1584
Ser Asp Gly Thr Pro Val Pro Ile Gly Phe Thr Ile Met Lys Thr Leu
        515               520               525 gaa aat cac atc att aac gat ctt tct cac caa gtt act gtt atg act    1632
Glu Asn His Ile Ile Asn Asp Leu Ser His Gln Val Thr Val Met Thr
530               535               540 ggt atc aag gtt act ggt ttg gag tcc act tct cac gct cgt cca gat    1680
Gly Ile Lys Val Thr Gly Leu Glu Ser Thr Ser His Ala Arg Pro Asp
545               550               555               560 ggt gtt tta gtt aag cac gtt act ggt gtt aga ttg att caa ggt gat    1728
Gly Val Leu Val Lys His Val Thr Gly Val Arg Leu Ile Gln Gly Asp
                565               570               575 ggc caa tcc aga gtt ttg aat gct gat gcc gtt atc tta gca act ggt    1776
Gly Gln Ser Arg Val Leu Asn Ala Asp Ala Val Ile Leu Ala Thr Gly
            580               585               590 ggt ttc tcc aat gac cat act gct aac tct tta ctt caa caa tac gct    1824
Gly Phe Ser Asn Asp His Thr Ala Asn Ser Leu Leu Gln Gln Tyr Ala
        595               600               605 cca caa ctt tca tcc ttt cca acc act aat ggt gtt tgg gcc act ggt    1872
Pro Gln Leu Ser Ser Phe Pro Thr Thr Asn Gly Val Trp Ala Thr Gly
610               615               620 gac ggt gtc aag gca gct aga gaa tta ggt gtt gag ttg gtt gac atg    1920
Asp Gly Val Lys Ala Ala Arg Glu Leu Gly Val Glu Leu Val Asp Met
625               630               635               640 gat aag gtc caa ttg cat cca aca ggt ttg tta gat cca aag gac cca    1968
Asp Lys Val Gln Leu His Pro Thr Gly Leu Leu Asp Pro Lys Asp Pro
                645               650               655 tcc aac agg act aag tac ttg ggt cca gaa gct tta agg ggt tca ggc    2016
```

```
                Ser Asn Arg Thr Lys Tyr Leu Gly Pro Glu Ala Leu Arg Gly Ser Gly
                                660                 665                 670 ggt gtc ttg tta aac aaa aac ggt gaa cgt ttc gtc aac gaa ctt gat         2064
Gly Val Leu Leu Asn Lys Asn Gly Glu Arg Phe Val Asn Glu Leu Asp
        675                 680                 685 ttg aga tct gtc gtt tct caa gcc att atc gaa caa aac aac gtt tac         2112
Leu Arg Ser Val Val Ser Gln Ala Ile Ile Glu Gln Asn Asn Val Tyr
690                 695                 700 cct ggt tct ggt ggt tcc aag ttt gct tac tgc gtt ttg aac gaa gca         2160
Pro Gly Ser Gly Gly Ser Lys Phe Ala Tyr Cys Val Leu Asn Glu Ala
705                 710                 715                 720 gca gct aag ttg ttc ggc aaa aac ttt ttg ggt ttc tat tgg cat aga         2208
Ala Ala Lys Leu Phe Gly Lys Asn Phe Leu Gly Phe Tyr Trp His Arg
            725                 730                 735 tta ggt ctt ttt gaa aag gtt gaa gat gtt gct ggt tta gcc aaa ttg         2256
Leu Gly Leu Phe Glu Lys Val Glu Asp Val Ala Gly Leu Ala Lys Leu
                740                 745                 750 atc ggt tgt cca gag gaa aat gtt acc gct aca ttg aag gaa tac aag         2304
Ile Gly Cys Pro Glu Glu Asn Val Thr Ala Thr Leu Lys Glu Tyr Lys
                    755                 760                 765 gaa ttg tcc tcc aaa aag ctt cat gcc tgt cct tta acc aac aaa aac         2352
Glu Leu Ser Ser Lys Lys Leu His Ala Cys Pro Leu Thr Asn Lys Asn
770                 775                 780 gtc ttt cct tgc act tta ggt act gaa ggc cct tac tat gtt gct ttc         2400
Val Phe Pro Cys Thr Leu Gly Thr Glu Gly Pro Tyr Tyr Val Ala Phe
785                 790                 795                 800 gtc aca cct tca att cac tac aca atg ggt ggt tgt ttg atc tcc cct         2448
Val Thr Pro Ser Ile His Tyr Thr Met Gly Gly Cys Leu Ile Ser Pro
            805                 810                 815 tca gca gaa atg cag acc att gat aac act ggt gtc aca cca gtt cgt         2496
Ser Ala Glu Met Gln Thr Ile Asp Asn Thr Gly Val Thr Pro Val Arg
                820                 825                 830 aga cca atc ttg ggc tta ttc ggt gct ggt gaa gtt act ggt ggt gtc         2544
Arg Pro Ile Leu Gly Leu Phe Gly Ala Gly Glu Val Thr Gly Gly Val
                    835                 840                 845 cat ggt ggt aac aga ttg ggt ggt aat tcc tta ttg gaa tgt gtt gtc         2592
His Gly Gly Asn Arg Leu Gly Gly Asn Ser Leu Leu Glu Cys Val Val
850                 855                 860 ttt ggt aga att gct ggt gat aga gcc gct acc att ttg caa aag aag         2640
Phe Gly Arg Ile Ala Gly Asp Arg Ala Ala Thr Ile Leu Gln Lys Lys
865                 870                 875                 880 aat gct ggt tta tca atg act gag tgg tct aca gtt gtc tta aga gaa         2688
Asn Ala Gly Leu Ser Met Thr Glu Trp Ser Thr Val Val Leu Arg Glu
                885                 890                 895 gtc aga gaa ggc ggt gtt tac ggt act ggt tct cgt gtc ctt aga ttc         2736
Val Arg Glu Gly Gly Val Tyr Gly Thr Gly Ser Arg Val Leu Arg Phe
                    900                 905                 910 aat atg cca ggt gcc tta caa aag act ggc tta gca ttg ggt caa ttc         2784
Asn Met Pro Gly Ala Leu Gln Lys Thr Gly Leu Ala Leu Gly Gln Phe
            915                 920                 925 atc gca atg aga ggt gat tgg gat ggt caa cag tta ttg ggt tac tat         2832
Ile Ala Met Arg Gly Asp Trp Asp Gly Gln Gln Leu Leu Gly Tyr Tyr
                930                 935                 940 tct cca att aca tta cca gac gac att ggt gtt att ggt atc tta gct         2880
Ser Pro Ile Thr Leu Pro Asp Asp Ile Gly Val Ile Gly Ile Leu Ala
945                 950                 955                 960 aga gct gac aaa ggt aga tta gct gaa tgg att tct gca tta caa cca         2928
Arg Ala Asp Lys Gly Arg Leu Ala Glu Trp Ile Ser Ala Leu Gln Pro
                965                 970                 975
```

| | | |
|---|---|---|
| ggt gat gct gtt gag atg aag gca tgt ggc ggt ttg att atc cat aga<br>Gly Asp Ala Val Glu Met Lys Ala Cys Gly Gly Leu Ile Ile His Arg<br>980                    985                    990 | 2976 |
| aga ttc gct gct aga cac ttg ttt ttc cgt tct cac aag att aga aag<br>Arg Phe Ala Ala Arg His Leu Phe Phe Arg Ser His Lys Ile Arg Lys<br>995                   1000                1005 | 3024 |
| ctt gct ctt att ggt ggt ggt act ggt gtt gca cca atg ttg caa<br>Leu Ala Leu Ile Gly Gly Gly Thr Gly Val Ala Pro Met Leu Gln<br>1010               1015                  1020 | 3069 |
| att gtc agg gct gca gtc aaa aag cca ttt gtt gac tct att gag<br>Ile Val Arg Ala Ala Val Lys Lys Pro Phe Val Asp Ser Ile Glu<br>1025             1030                  1035 | 3114 |
| tct att cag ttc atc tat gca gct gaa gat gtc tcc gaa ctt act<br>Ser Ile Gln Phe Ile Tyr Ala Ala Glu Asp Val Ser Glu Leu Thr<br>1040             1045                  1050 | 3159 |
| tat aga act ttg ttg gaa tca tat gaa aag gaa tac ggt tct ggc<br>Tyr Arg Thr Leu Leu Glu Ser Tyr Glu Lys Glu Tyr Gly Ser Gly<br>1055             1060                  1065 | 3204 |
| aaa ttc aag tgt cat ttc gtc ttg aat aac cca cca tca caa tgg<br>Lys Phe Lys Cys His Phe Val Leu Asn Asn Pro Pro Ser Gln Trp<br>1070             1075                  1080 | 3249 |
| acc gag ggc gtt ggt ttc gtt gat act gct ttg ttg cgt tct gcc<br>Thr Glu Gly Val Gly Phe Val Asp Thr Ala Leu Leu Arg Ser Ala<br>1085             1090                  1095 | 3294 |
| gtt caa gca cct tct aac gac ttg tta gtc gct att tgt ggc cca<br>Val Gln Ala Pro Ser Asn Asp Leu Leu Val Ala Ile Cys Gly Pro<br>1100             1105                  1110 | 3339 |
| cca atc atg caa aga gca gtc aaa tca gcc tta aag ggt tta ggt<br>Pro Ile Met Gln Arg Ala Val Lys Ser Ala Leu Lys Gly Leu Gly<br>1115             1120                  1125 | 3384 |
| tac aat atg aat ttg gtt aga aca gtt gat gaa cca gaa cca ttg<br>Tyr Asn Met Asn Leu Val Arg Thr Val Asp Glu Pro Glu Pro Leu<br>1130             1135                  1140 | 3429 |
| tct taa<br>Ser | 3435 |

<210> SEQ ID NO 178
<211> LENGTH: 1144
<212> TYPE: PRT
<213> ORGANISM: Leishmania braziliensis

<400> SEQUENCE: 178

Met Ala Asp Gly Lys Thr Ser Ala Ser Val Val Ala Val Asp Pro Glu
1                 5                   10                15

Arg Ala Ala Lys Glu Arg Asp Ala Ala Arg Ala Met Leu Gln Asp
               20                   25                30

Gly Gly Val Ser Pro Val Gly Lys Ala Gln Leu Leu Lys Gly Leu
        35                   40                45

Ala Tyr Ala Val Pro Tyr Thr Leu Lys Ile Val Val Ala Asp Pro Lys
50                55                   60

Ala Met Glu Lys Thr Thr Ala Asp Val Glu Lys Val Leu Gln Thr Ala
65                70                   75                80

Phe Gln Val Val Asp Thr Leu Leu Asn Asn Phe Asn Glu Asn Ser Glu
               85                   90                95

Val Ser Arg Ile Asn Arg Met Pro Val Gly Glu Glu His Gln Met Ser
              100                105              110

Ala Ala Leu Lys Arg Val Met Gly Cys Cys Gln Arg Val Tyr Asn Ser
             115                120              125

```
Ser Arg Gly Ala Phe Asp Pro Ala Val Gly Pro Leu Val Arg Glu Leu
    130                 135                 140

Arg Glu Ala Ala Arg Glu Gly Arg Thr Leu Pro Ala Glu Arg Ile Asn
145                 150                 155                 160

Ala Leu Leu Ser Lys Cys Thr Leu Asn Ile Ser Phe Ser Ile Asp Leu
                165                 170                 175

Asn Arg Gly Thr Ile Ala Arg Lys His Ala Asp Ala Met Leu Asp Leu
            180                 185                 190

Gly Gly Val Asn Lys Gly Tyr Gly Val Asp Tyr Val Glu His Leu
        195                 200                 205

Asn Asn Leu Gly Tyr Asp Asp Val Phe Phe Glu Trp Gly Gly Asp Val
210                 215                 220

Arg Ala Ser Gly Lys Asn Pro Ser Asn Gln His Trp Val Val Gly Ile
225                 230                 235                 240

Ala Arg Pro Pro Ala Leu Ala Asp Ile Arg Thr Val Val Pro Gln Asp
                245                 250                 255

Lys Gln Ser Phe Ile Arg Val Val Cys Leu Asn Asp Glu Ala Ile Ala
                260                 265                 270

Thr Ser Gly Asp Tyr Glu Asn Leu Val Glu Gly Pro Gly Ser Lys Val
        275                 280                 285

Tyr Ser Ser Thr Phe Asn Ala Thr Ser Lys Ser Leu Leu Glu Pro Thr
    290                 295                 300

Glu Thr Asn Ile Ala Gln Val Ser Val Lys Cys Tyr Ser Cys Met Tyr
305                 310                 315                 320

Ala Asp Ala Leu Ala Thr Ala Ala Leu Leu Lys Asn Asn Pro Thr Ala
                325                 330                 335

Val Arg Arg Met Leu Asp Asn Trp Arg Tyr Val Arg Asp Thr Val Thr
                340                 345                 350

Asp Tyr Thr Thr Tyr Ser Arg Glu Gly Glu Arg Val Ala Lys Met Phe
        355                 360                 365

Glu Ile Ala Thr Glu Asp Lys Glu Met Arg Ala Lys Arg Ile Ser Gly
    370                 375                 380

Ser Leu Pro Ala Arg Val Ile Ile Val Gly Gly Gly Leu Ala Gly Cys
385                 390                 395                 400

Ser Ala Ala Ile Glu Ala Val Asn Cys Gly Ala Gln Val Ile Leu Leu
                405                 410                 415

Glu Lys Glu Ala Lys Ile Gly Gly Asn Ser Ala Lys Ala Thr Ser Gly
                420                 425                 430

Ile Asn Ala Trp Gly Thr Arg Ala Gln Ala Lys Gln Gly Val Met Asp
            435                 440                 445

Gly Gly Lys Phe Phe Glu Arg Asp Thr His Arg Ser Gly Lys Gly Gly
    450                 455                 460

His Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
                485                 490                 495

Gln Leu Gly Gly Ala Ser Arg Lys Arg Cys His Arg Ala Pro Asp Lys
                500                 505                 510

Ser Asp Gly Thr Pro Val Pro Ile Gly Phe Thr Ile Met Lys Thr Leu
            515                 520                 525

Glu Asn His Ile Ile Asn Asp Leu Ser His Gln Val Thr Val Met Thr
530                 535                 540

Gly Ile Lys Val Thr Gly Leu Glu Ser Thr Ser His Ala Arg Pro Asp
```

-continued

```
               545                 550                 555                 560
           Gly Val Leu Val Lys His Val Thr Gly Val Arg Leu Ile Gln Gly Asp
                           565                 570                 575
           Gly Gln Ser Arg Val Leu Asn Ala Asp Ala Val Ile Leu Ala Thr Gly
                           580                 585                 590
           Gly Phe Ser Asn Asp His Thr Ala Asn Ser Leu Leu Gln Gln Tyr Ala
                           595                 600                 605
           Pro Gln Leu Ser Ser Phe Pro Thr Thr Asn Gly Val Trp Ala Thr Gly
                           610                 615                 620
           Asp Gly Val Lys Ala Ala Arg Glu Leu Gly Val Glu Leu Val Asp Met
           625                 630                 635                 640
           Asp Lys Val Gln Leu His Pro Thr Gly Leu Leu Asp Pro Lys Asp Pro
                           645                 650                 655
           Ser Asn Arg Thr Lys Tyr Leu Gly Pro Glu Ala Leu Arg Gly Ser Gly
                           660                 665                 670
           Gly Val Leu Leu Asn Lys Asn Gly Glu Arg Phe Val Asn Glu Leu Asp
                           675                 680                 685
           Leu Arg Ser Val Val Ser Gln Ala Ile Ile Glu Gln Asn Asn Val Tyr
                           690                 695                 700
           Pro Gly Ser Gly Gly Ser Lys Phe Ala Tyr Cys Val Leu Asn Glu Ala
           705                 710                 715                 720
           Ala Ala Lys Leu Phe Gly Lys Asn Phe Leu Gly Phe Tyr Trp His Arg
                           725                 730                 735
           Leu Gly Leu Phe Glu Lys Val Glu Asp Val Ala Gly Leu Ala Lys Leu
                           740                 745                 750
           Ile Gly Cys Pro Glu Glu Asn Val Thr Ala Thr Leu Lys Glu Tyr Lys
                           755                 760                 765
           Glu Leu Ser Ser Lys Lys Leu His Ala Cys Pro Leu Thr Asn Lys Asn
                           770                 775                 780
           Val Phe Pro Cys Thr Leu Gly Thr Glu Gly Pro Tyr Tyr Val Ala Phe
           785                 790                 795                 800
           Val Thr Pro Ser Ile His Tyr Thr Met Gly Gly Cys Leu Ile Ser Pro
                           805                 810                 815
           Ser Ala Glu Met Gln Thr Ile Asp Asn Thr Gly Val Thr Pro Val Arg
                           820                 825                 830
           Arg Pro Ile Leu Gly Leu Phe Gly Ala Gly Glu Val Thr Gly Gly Val
                           835                 840                 845
           His Gly Gly Asn Arg Leu Gly Gly Asn Ser Leu Leu Glu Cys Val Val
                           850                 855                 860
           Phe Gly Arg Ile Ala Gly Asp Arg Ala Ala Thr Ile Leu Gln Lys Lys
           865                 870                 875                 880
           Asn Ala Gly Leu Ser Met Thr Glu Trp Ser Thr Val Val Leu Arg Glu
                           885                 890                 895
           Val Arg Glu Gly Gly Val Tyr Gly Thr Gly Ser Arg Val Leu Arg Phe
                           900                 905                 910
           Asn Met Pro Gly Ala Leu Gln Lys Thr Gly Leu Ala Leu Gly Gln Phe
                           915                 920                 925
           Ile Ala Met Arg Gly Asp Trp Asp Gly Gln Gln Leu Leu Gly Tyr Tyr
                           930                 935                 940
           Ser Pro Ile Thr Leu Pro Asp Asp Ile Gly Val Ile Gly Ile Leu Ala
           945                 950                 955                 960
           Arg Ala Asp Lys Gly Arg Leu Ala Glu Trp Ile Ser Ala Leu Gln Pro
                           965                 970                 975
```

```
Gly Asp Ala Val Glu Met Lys Ala Cys Gly Gly Leu Ile Ile His Arg
            980                 985                 990

Arg Phe Ala Ala Arg His Leu Phe  Phe Arg Ser His Lys  Ile Arg Lys
        995                 1000                1005

Leu Ala Leu Ile Gly Gly Gly  Thr Gly Val Ala Pro  Met Leu Gln
        1010                1015                1020

Ile Val  Arg Ala Ala Val Lys  Lys Pro Phe Val Asp  Ser Ile Glu
        1025                1030                1035

Ser Ile  Gln Phe Ile Tyr Ala  Ala Glu Asp Val Ser  Glu Leu Thr
        1040                1045                1050

Tyr Arg  Thr Leu Leu Glu Ser  Tyr Glu Lys Glu Tyr  Gly Ser Gly
        1055                1060                1065

Lys Phe  Lys Cys His Phe Val  Leu Asn Asn Pro Pro  Ser Gln Trp
        1070                1075                1080

Thr Glu  Gly Val Gly Phe Val  Asp Thr Ala Leu Leu  Arg Ser Ala
        1085                1090                1095

Val Gln  Ala Pro Ser Asn Asp  Leu Leu Val Ala Ile  Cys Gly Pro
        1100                1105                1110

Pro Ile  Met Gln Arg Ala Val  Lys Ser Ala Leu Lys  Gly Leu Gly
        1115                1120                1125

Tyr Asn  Met Asn Leu Val Arg  Thr Val Asp Glu Pro  Glu Pro Leu
        1130                1135                1140

Ser

<210> SEQ ID NO 179
<211> LENGTH: 3435
<212> TYPE: DNA
<213> ORGANISM: Leishmania mexicana
<220> FEATURE:
<221> NAME/KEY: CDS
<222> LOCATION: (1)..(3435)

<400> SEQUENCE: 179 atg gct gat ggc aaa acc tct gca tca gtt gtt gct gtt gat gct gaa        48
Met Ala Asp Gly Lys Thr Ser Ala Ser Val Val Ala Val Asp Ala Glu
1               5                  10                  15 cgt gcc gct aag gaa aga gat gca gca gct aga gct atg ttg caa ggt        96
Arg Ala Ala Lys Glu Arg Asp Ala Ala Ala Arg Ala Met Leu Gln Gly
            20                  25                  30 ggt ggt gtc tct cct gct ggc aag gca caa ttg ttg aaa aag ggt ttg       144
Gly Gly Val Ser Pro Ala Gly Lys Ala Gln Leu Leu Lys Lys Gly Leu
        35                  40                  45 gtt cac act gtt cca tat acc tta aag gtt gtc gtc gca gat cca aag       192
Val His Thr Val Pro Tyr Thr Leu Lys Val Val Val Ala Asp Pro Lys
    50                  55                  60 gaa atg gag aag gca act gct gac gca gaa gag gtt tta caa gct gca       240
Glu Met Glu Lys Ala Thr Ala Asp Ala Glu Glu Val Leu Gln Ala Ala
65                  70                  75                  80 ttt caa gtc gtc gac acc ctt ttg aac aac ttt aac gaa aac tca gaa       288
Phe Gln Val Val Asp Thr Leu Leu Asn Asn Phe Asn Glu Asn Ser Glu
                85                  90                  95 gtt tca aga gtc aat agg ttg gca gtt ggt gag gaa cat caa atg tct       336
Val Ser Arg Val Asn Arg Leu Ala Val Gly Glu Glu His Gln Met Ser
            100                 105                 110 gaa aca ttg aaa cac gtc atg gcc tgt tgt caa aag gtt tat cat tcc       384
Glu Thr Leu Lys His Val Met Ala Cys Cys Gln Lys Val Tyr His Ser
        115                 120                 125
```

-continued

| | | |
|---|---|---|
| tcc aga ggt gtt ttt gac cca gca gtt ggt cca tta gtc cgt gaa ctt<br>Ser Arg Gly Val Phe Asp Pro Ala Val Gly Pro Leu Val Arg Glu Leu<br>130                    135                    140 | | 432 |
| aga gaa gct gct cac aag ggt aaa act gtt cca gcc gaa aga gtt aat<br>Arg Glu Ala Ala His Lys Gly Lys Thr Val Pro Ala Glu Arg Val Asn<br>145                    150                    155                    160 | | 480 |
| gat ttg tta tcc aaa tgt acc ctt aat gca tct ttt tca att gat atg<br>Asp Leu Leu Ser Lys Cys Thr Leu Asn Ala Ser Phe Ser Ile Asp Met<br>                    165                    170                    175 | | 528 |
| tcc aga ggt atg att gca agg aag cat cca gac gcc atg ttg gat ttg<br>Ser Arg Gly Met Ile Ala Arg Lys His Pro Asp Ala Met Leu Asp Leu<br>                        180                    185                    190 | | 576 |
| ggt ggt gtc aac aag ggt tat ggt atc gac tac att gtt gaa cac tta<br>Gly Gly Val Asn Lys Gly Tyr Gly Ile Asp Tyr Ile Val Glu His Leu<br>                195                    200                    205 | | 624 |
| aac tct ttg ggt tat gat gat gtc ttt ttc gaa tgg ggt ggt gat gtt<br>Asn Ser Leu Gly Tyr Asp Asp Val Phe Phe Glu Trp Gly Gly Asp Val<br>210                    215                    220 | | 672 |
| aga gca tcc ggc aaa aac cag tta tct caa cct tgg gct gtt ggt att<br>Arg Ala Ser Gly Lys Asn Gln Leu Ser Gln Pro Trp Ala Val Gly Ile<br>225                    230                    235                    240 | | 720 |
| gtt aga cca cct gcc ttg gcc gac att aga act gtt gtc cca gag gac<br>Val Arg Pro Pro Ala Leu Ala Asp Ile Arg Thr Val Val Pro Glu Asp<br>                        245                    250                    255 | | 768 |
| aaa aga tcc ttt atc cgt gtc gtc aga ttg aac aac gaa gct att gct<br>Lys Arg Ser Phe Ile Arg Val Val Arg Leu Asn Asn Glu Ala Ile Ala<br>                260                    265                    270 | | 816 |
| acc tct ggt gat tat gag aat ttg gtt gaa ggt cct ggt tct aag gtt<br>Thr Ser Gly Asp Tyr Glu Asn Leu Val Glu Gly Pro Gly Ser Lys Val<br>                    275                    280                    285 | | 864 |
| tac tct tcc acc ttc aat cca act tcc aaa aac ttg ttg gaa cct acc<br>Tyr Ser Ser Thr Phe Asn Pro Thr Ser Lys Asn Leu Leu Glu Pro Thr<br>290                    295                    300 | | 912 |
| gaa gca ggt atg gct caa gtt tct gtc aag tgt tgc tca tgt atc tac<br>Glu Ala Gly Met Ala Gln Val Ser Val Lys Cys Cys Ser Cys Ile Tyr<br>305                    310                    315                    320 | | 960 |
| gct gat gct tta gca aca gca gct ttg ttg aaa aac gat cct gct gcc<br>Ala Asp Ala Leu Ala Thr Ala Ala Leu Leu Lys Asn Asp Pro Ala Ala<br>                        325                    330                    335 | | 1008 |
| gtt aga agg atc tta gat aac tgg aga tat gtc aga gat act gtt act<br>Val Arg Arg Ile Leu Asp Asn Trp Arg Tyr Val Arg Asp Thr Val Thr<br>                    340                    345                    350 | | 1056 |
| gac tac acc act tac aca agg gaa ggt gaa aga gtt gct aag atg ttg<br>Asp Tyr Thr Thr Tyr Thr Arg Glu Gly Glu Arg Val Ala Lys Met Leu<br>                        355                    360                    365 | | 1104 |
| gaa att gct acc gaa gat gct gaa atg aga gca aag aga atc aag ggc<br>Glu Ile Ala Thr Glu Asp Ala Glu Met Arg Ala Lys Arg Ile Lys Gly<br>370                    375                    380 | | 1152 |
| tct tta cca gca aga gtt atc att gtt ggt ggt ggt ttg gcc ggt tgt<br>Ser Leu Pro Ala Arg Val Ile Ile Val Gly Gly Gly Leu Ala Gly Cys<br>385                    390                    395                    400 | | 1200 |
| tcc gca gct atc gaa gca gct aac tgt ggc gcc cac gtc atc ttg tta<br>Ser Ala Ala Ile Glu Ala Ala Asn Cys Gly Ala His Val Ile Leu Leu<br>                        405                    410                    415 | | 1248 |
| gaa aag gaa cca aag tta ggt ggt aac tct gca aag gct acc tcc ggt<br>Glu Lys Glu Pro Lys Leu Gly Gly Asn Ser Ala Lys Ala Thr Ser Gly<br>                        420                    425                    430 | | 1296 |
| atc aac gcc tgg ggt act aga gca caa gca aaa caa ggt gtc atg gac<br>Ile Asn Ala Trp Gly Thr Arg Ala Gln Ala Lys Gln Gly Val Met Asp<br>                435                    440                    445 | | 1344 |

```
ggc ggc aag ttt ttc gaa aga gat acc cat aga tcc ggc aag ggt ggt     1392
Gly Gly Lys Phe Phe Glu Arg Asp Thr His Arg Ser Gly Lys Gly Gly
        450                 455                 460 aat tgc gat cca tgc ctt gtt aag act ttg tcc gtt aag tcc tct gat     1440
Asn Cys Asp Pro Cys Leu Val Lys Thr Leu Ser Val Lys Ser Ser Asp
465                 470                 475                 480 gca gtt aag tgg tta tct gaa tta ggt gtt cca ttg act gtt ttg tct     1488
Ala Val Lys Trp Leu Ser Glu Leu Gly Val Pro Leu Thr Val Leu Ser
                    485                 490                 495 caa tta ggt ggt gct tca agg aaa cgt tgt cac cgt gca cca gat aag     1536
Gln Leu Gly Gly Ala Ser Arg Lys Arg Cys His Arg Ala Pro Asp Lys
                500                 505                 510 tct gat ggt aca cca gtc cca gtt ggt ttc acc att atg aaa acc ctt     1584
Ser Asp Gly Thr Pro Val Pro Val Gly Phe Thr Ile Met Lys Thr Leu
            515                 520                 525 gaa aac cac att gtc aac gat ttg tcc aga cat gtt aca gtt atg aca     1632
Glu Asn His Ile Val Asn Asp Leu Ser Arg His Val Thr Val Met Thr
530                 535                 540 ggt att acc gtc aca gct tta gaa tct aca tca aga gtc aga cct gat     1680
Gly Ile Thr Val Thr Ala Leu Glu Ser Thr Ser Arg Val Arg Pro Asp
545                 550                 555                 560 ggt gtt tta gtc aag cat gtt act ggt gtt cac ttg att cag gca tct     1728
Gly Val Leu Val Lys His Val Thr Gly Val His Leu Ile Gln Ala Ser
                    565                 570                 575 ggt caa tct atg gtt ttg aat gca gac gct gtt atc tta gct act ggt     1776
Gly Gln Ser Met Val Leu Asn Ala Asp Ala Val Ile Leu Ala Thr Gly
                580                 585                 590 ggt ttc tcc aat gat cat acc cca aac tcc ctt tta caa caa tac gcc     1824
Gly Phe Ser Asn Asp His Thr Pro Asn Ser Leu Leu Gln Gln Tyr Ala
            595                 600                 605 cca cag ttg tca tct ttt cca aca acc aat ggt gtc tgg gca act ggc     1872
Pro Gln Leu Ser Ser Phe Pro Thr Thr Asn Gly Val Trp Ala Thr Gly
610                 615                 620 gat ggt gtt aag atg gct tcc aag ttg ggt gtc gcc tta gtt gat atg     1920
Asp Gly Val Lys Met Ala Ser Lys Leu Gly Val Ala Leu Val Asp Met
625                 630                 635                 640 gat aag gtc caa tta cat cct acc ggc ttg tta gac cca aaa gat cca     1968
Asp Lys Val Gln Leu His Pro Thr Gly Leu Leu Asp Pro Lys Asp Pro
                    645                 650                 655 tct aat aga acc aag tat ctt ggt cca gag gcc tta aga ggt tcc ggc     2016
Ser Asn Arg Thr Lys Tyr Leu Gly Pro Glu Ala Leu Arg Gly Ser Gly
                660                 665                 670 ggt gtc ttg tta aac aaa aac ggt gaa aga ttt gtt aat gaa tta gac     2064
Gly Val Leu Leu Asn Lys Asn Gly Glu Arg Phe Val Asn Glu Leu Asp
            675                 680                 685 tta aga tct gtt gtc tct caa gct atc atc gca caa gat aat gag tac     2112
Leu Arg Ser Val Val Ser Gln Ala Ile Ile Ala Gln Asp Asn Glu Tyr
690                 695                 700 cca ggc tct ggt ggt tcc aag ttc gca tac tgt gtt ttg aac gaa act     2160
Pro Gly Ser Gly Gly Ser Lys Phe Ala Tyr Cys Val Leu Asn Glu Thr
705                 710                 715                 720 gca gca aag tta ttc ggc aaa aac ttc ctt ggt ttc tac tgg aat aga     2208
Ala Ala Lys Leu Phe Gly Lys Asn Phe Leu Gly Phe Tyr Trp Asn Arg
                    725                 730                 735 tta ggt ctt ttc caa aag gtt gat tcc gtt gct ggt tta gct aag ttg     2256
Leu Gly Leu Phe Gln Lys Val Asp Ser Val Ala Gly Leu Ala Lys Leu
                740                 745                 750 att ggt tgt cca gaa gct aat gtt gtt gct aca ttg aag caa tat gag     2304
Ile Gly Cys Pro Glu Ala Asn Val Val Ala Thr Leu Lys Gln Tyr Glu
```

```
                755                 760                 765
gag tta tct tcc aaa aag ctt aat cct tgt cca ttg act ggc aag tct      2352
Glu Leu Ser Ser Lys Lys Leu Asn Pro Cys Pro Leu Thr Gly Lys Ser
    770                 775                 780 gtc ttt cct tgt gtt tta ggc act caa ggt cca tac tat gtt gcc ttg      2400
Val Phe Pro Cys Val Leu Gly Thr Gln Gly Pro Tyr Tyr Val Ala Leu
785                 790                 795                 800 gtt acc cca tcc att cac tac act atg ggt ggt tgt ttg att tcc cca      2448
Val Thr Pro Ser Ile His Tyr Thr Met Gly Gly Cys Leu Ile Ser Pro
                805                 810                 815 tct gct gag atg caa acc att gac aac tct ggt gtt act cct gtc aga      2496
Ser Ala Glu Met Gln Thr Ile Asp Asn Ser Gly Val Thr Pro Val Arg
        820                 825                 830 cgt cca atc tta ggc tta ttc ggt gct ggt gaa gtt act ggc ggt gtc      2544
Arg Pro Ile Leu Gly Leu Phe Gly Ala Gly Glu Val Thr Gly Gly Val
            835                 840                 845 cat ggt ggt aac aga tta ggc ggt aac tct ttg tta gaa tgt gtt gtt      2592
His Gly Gly Asn Arg Leu Gly Gly Asn Ser Leu Leu Glu Cys Val Val
850                 855                 860 ttc ggc aag atc gct ggt gac aga gct gca acc atc ttg caa aag aaa      2640
Phe Gly Lys Ile Ala Gly Asp Arg Ala Ala Thr Ile Leu Gln Lys Lys
865                 870                 875                 880 aac acc ggc tta tca atg aca gaa tgg tct act gtc gtc tta aga gaa      2688
Asn Thr Gly Leu Ser Met Thr Glu Trp Ser Thr Val Val Leu Arg Glu
                885                 890                 895 gtt aga gaa ggt ggt gtc tat ggt gct ggt tcc aga gtt ttg agg ttt      2736
Val Arg Glu Gly Gly Val Tyr Gly Ala Gly Ser Arg Val Leu Arg Phe
        900                 905                 910 aac atg cct ggt gca tta cag aga act ggt tta gct tta ggt caa ttc      2784
Asn Met Pro Gly Ala Leu Gln Arg Thr Gly Leu Ala Leu Gly Gln Phe
            915                 920                 925 atc ggt atc aga ggt gat tgg gac ggt cac aga ttg atc ggt tac tat      2832
Ile Gly Ile Arg Gly Asp Trp Asp Gly His Arg Leu Ile Gly Tyr Tyr
930                 935                 940 tct cca atc act tta cct gat gat gtt ggt gtt att ggt atc tta gct      2880
Ser Pro Ile Thr Leu Pro Asp Asp Val Gly Val Ile Gly Ile Leu Ala
945                 950                 955                 960 aga gca gac aag ggt aga ttg gca gaa tgg att tct gca ttg cag cca      2928
Arg Ala Asp Lys Gly Arg Leu Ala Glu Trp Ile Ser Ala Leu Gln Pro
                965                 970                 975 ggt gac gct gtt gag atg aag gcc tgc ggt ggt ctt atc att gac aga      2976
Gly Asp Ala Val Glu Met Lys Ala Cys Gly Gly Leu Ile Ile Asp Arg
        980                 985                 990 aga ttc gct gaa aga cat ttc ttt ttc cgt ggt cat aag atc aga aag      3024
Arg Phe Ala Glu Arg His Phe Phe Phe Arg Gly His Lys Ile Arg Lys
            995                 1000                1005 ttg gcc ctt atc ggt ggt ggt act ggt gtt gca cca atg tta caa           3069
Leu Ala Leu Ile Gly Gly Gly Thr Gly Val Ala Pro Met Leu Gln
1010                1015                1020 atc gtc aga gct gct gtc aaa aag cca ttt gtc gat tca att gag           3114
Ile Val Arg Ala Ala Val Lys Lys Pro Phe Val Asp Ser Ile Glu
        1025                1030                1035 tcc att cag ttc atc tat gct gca gag gat gtt tcc gag ctt aca           3159
Ser Ile Gln Phe Ile Tyr Ala Ala Glu Asp Val Ser Glu Leu Thr
            1040                1045                1050 tac aga acc tta ctt gaa tct tac gaa gag gaa tat ggt tca gaa           3204
Tyr Arg Thr Leu Leu Glu Ser Tyr Glu Glu Glu Tyr Gly Ser Glu
                1055                1060                1065 aag ttt aag tgt cac ttc gtt ttg aat aac cca gct caa tgg              3249
```

-continued

```
               Lys Phe Lys Cys His Phe Val Leu Asn Asn Pro Pro Ala Gln Trp
                  1070                1075                1080 act gac ggt gtt ggt ttc gtt gat act gca ttg ttg aga tcc gca            3294
Thr Asp Gly Val Gly Phe Val Asp Thr Ala Leu Leu Arg Ser Ala
    1085                1090                1095 gtt caa gca cca tca aat gat ttg ctt gtt gca att tgt ggt cca            3339
Val Gln Ala Pro Ser Asn Asp Leu Leu Val Ala Ile Cys Gly Pro
    1100                1105                1110 cca atc atg caa aga gca gtt aag ggt gca ttg aaa ggt tta ggt            3384
Pro Ile Met Gln Arg Ala Val Lys Gly Ala Leu Lys Gly Leu Gly
    1115                1120                1125 tac aat atg aat ctt gtt aga acc gtt gac gaa act gaa cca cca            3429
Tyr Asn Met Asn Leu Val Arg Thr Val Asp Glu Thr Glu Pro Pro
    1130                1135                1140 tca taa                                                                3435
Ser
```

<210> SEQ ID NO 180
<211> LENGTH: 1144
<212> TYPE: PRT
<213> ORGANISM: Leishmania mexicana

<400> SEQUENCE: 180

```
Met Ala Asp Gly Lys Thr Ser Ala Ser Val Ala Val Asp Ala Glu
 1               5                  10                  15

Arg Ala Ala Lys Glu Arg Asp Ala Ala Arg Ala Met Leu Gln Gly
                20                  25                  30

Gly Gly Val Ser Pro Ala Gly Lys Ala Gln Leu Leu Lys Lys Gly Leu
                35                  40                  45

Val His Thr Val Pro Tyr Thr Leu Lys Val Val Ala Asp Pro Lys
        50                  55                  60

Glu Met Glu Lys Ala Thr Ala Asp Ala Glu Val Leu Gln Ala Ala
65                  70                  75                  80

Phe Gln Val Val Asp Thr Leu Asn Asn Phe Asn Glu Asn Ser Glu
                85                  90                  95

Val Ser Arg Val Asn Arg Leu Ala Val Gly Glu Glu His Gln Met Ser
                100                 105                 110

Glu Thr Leu Lys His Val Met Ala Cys Cys Gln Lys Val Tyr His Ser
                115                 120                 125

Ser Arg Gly Val Phe Asp Pro Ala Val Gly Pro Leu Val Arg Glu Leu
    130                 135                 140

Arg Glu Ala Ala His Lys Gly Lys Thr Val Pro Ala Glu Arg Val Asn
145                 150                 155                 160

Asp Leu Leu Ser Lys Cys Thr Leu Asn Ala Ser Phe Ser Ile Asp Met
                165                 170                 175

Ser Arg Gly Met Ile Ala Arg Lys His Pro Asp Ala Met Leu Asp Leu
                180                 185                 190

Gly Gly Val Asn Lys Gly Tyr Gly Ile Asp Tyr Ile Val Glu His Leu
                195                 200                 205

Asn Ser Leu Gly Tyr Asp Asp Val Phe Phe Glu Trp Gly Gly Asp Val
    210                 215                 220

Arg Ala Ser Gly Lys Asn Gln Leu Ser Gln Pro Trp Ala Val Gly Ile
225                 230                 235                 240

Val Arg Pro Pro Ala Leu Ala Asp Ile Arg Thr Val Val Pro Glu Asp
                245                 250                 255

Lys Arg Ser Phe Ile Arg Val Val Arg Leu Asn Asn Glu Ala Ile Ala
```

```
                    260                 265                 270
Thr Ser Gly Asp Tyr Glu Asn Leu Val Glu Gly Pro Gly Ser Lys Val
        275                 280                 285

Tyr Ser Ser Thr Phe Asn Pro Thr Ser Lys Asn Leu Leu Glu Pro Thr
        290                 295                 300

Glu Ala Gly Met Ala Gln Val Ser Val Lys Cys Cys Ser Cys Ile Tyr
305                 310                 315                 320

Ala Asp Ala Leu Ala Thr Ala Leu Leu Lys Asn Asp Pro Ala Ala
                325                 330                 335

Val Arg Arg Ile Leu Asp Asn Trp Arg Tyr Val Arg Asp Thr Val Thr
                340                 345                 350

Asp Tyr Thr Thr Tyr Thr Arg Glu Gly Arg Val Ala Lys Met Leu
            355                 360                 365

Glu Ile Ala Thr Glu Asp Ala Glu Met Arg Ala Lys Arg Ile Lys Gly
            370                 375                 380

Ser Leu Pro Ala Arg Val Ile Val Gly Gly Leu Ala Gly Cys
385                 390                 395                 400

Ser Ala Ala Ile Glu Ala Ala Asn Cys Gly Ala His Val Ile Leu Leu
                405                 410                 415

Glu Lys Glu Pro Lys Leu Gly Gly Asn Ser Ala Lys Ala Thr Ser Gly
                420                 425                 430

Ile Asn Ala Trp Gly Thr Arg Ala Gln Ala Lys Gln Gly Val Met Asp
            435                 440                 445

Gly Gly Lys Phe Phe Glu Arg Asp Thr His Arg Ser Gly Lys Gly Gly
            450                 455                 460

Asn Cys Asp Pro Cys Leu Val Lys Thr Leu Ser Val Lys Ser Ser Asp
465                 470                 475                 480

Ala Val Lys Trp Leu Ser Glu Leu Gly Val Pro Leu Thr Val Leu Ser
                485                 490                 495

Gln Leu Gly Gly Ala Ser Arg Lys Arg Cys His Arg Ala Pro Asp Lys
                500                 505                 510

Ser Asp Gly Thr Pro Val Pro Val Gly Phe Thr Ile Met Lys Thr Leu
            515                 520                 525

Glu Asn His Ile Val Asn Asp Leu Ser Arg His Val Thr Val Met Thr
            530                 535                 540

Gly Ile Thr Val Thr Ala Leu Glu Ser Thr Ser Arg Val Arg Pro Asp
545                 550                 555                 560

Gly Val Leu Val Lys His Val Thr Gly Val His Leu Ile Gln Ala Ser
                565                 570                 575

Gly Gln Ser Met Val Leu Asn Ala Asp Ala Val Ile Leu Ala Thr Gly
            580                 585                 590

Gly Phe Ser Asn Asp His Thr Pro Asn Ser Leu Leu Gln Gln Tyr Ala
            595                 600                 605

Pro Gln Leu Ser Ser Phe Pro Thr Thr Asn Gly Val Trp Ala Thr Gly
            610                 615                 620

Asp Gly Val Lys Met Ala Ser Lys Leu Gly Val Ala Leu Val Asp Met
625                 630                 635                 640

Asp Lys Val Gln Leu His Pro Thr Gly Leu Leu Asp Pro Lys Asp Pro
                645                 650                 655

Ser Asn Arg Thr Lys Tyr Leu Gly Pro Glu Ala Leu Arg Gly Ser Gly
            660                 665                 670

Gly Val Leu Leu Asn Lys Asn Gly Glu Arg Phe Val Asn Glu Leu Asp
            675                 680                 685
```

```
Leu Arg Ser Val Val Ser Gln Ala Ile Ile Ala Gln Asp Asn Glu Tyr
690                 695                 700

Pro Gly Ser Gly Gly Ser Lys Phe Ala Tyr Cys Val Leu Asn Glu Thr
705                 710                 715                 720

Ala Ala Lys Leu Phe Gly Lys Asn Phe Leu Gly Phe Tyr Trp Asn Arg
            725                 730                 735

Leu Gly Leu Phe Gln Lys Val Asp Ser Val Ala Gly Leu Ala Lys Leu
                740                 745                 750

Ile Gly Cys Pro Glu Ala Asn Val Val Ala Thr Leu Lys Gln Tyr Glu
            755                 760                 765

Glu Leu Ser Ser Lys Lys Leu Asn Pro Cys Pro Leu Thr Gly Lys Ser
    770                 775                 780

Val Phe Pro Cys Val Leu Gly Thr Gln Gly Pro Tyr Tyr Val Ala Leu
785                 790                 795                 800

Val Thr Pro Ser Ile His Tyr Thr Met Gly Gly Cys Leu Ile Ser Pro
                805                 810                 815

Ser Ala Glu Met Gln Thr Ile Asp Asn Ser Gly Val Thr Pro Val Arg
            820                 825                 830

Arg Pro Ile Leu Gly Leu Phe Gly Ala Gly Glu Val Thr Gly Gly Val
            835                 840                 845

His Gly Gly Asn Arg Leu Gly Gly Asn Ser Leu Leu Glu Cys Val Val
850                 855                 860

Phe Gly Lys Ile Ala Gly Asp Arg Ala Ala Thr Ile Leu Gln Lys Lys
865                 870                 875                 880

Asn Thr Gly Leu Ser Met Thr Glu Trp Ser Thr Val Val Leu Arg Glu
                885                 890                 895

Val Arg Glu Gly Gly Val Tyr Gly Ala Gly Ser Arg Val Leu Arg Phe
                900                 905                 910

Asn Met Pro Gly Ala Leu Gln Arg Thr Gly Leu Ala Leu Gly Gln Phe
            915                 920                 925

Ile Gly Ile Arg Gly Asp Trp Asp Gly His Arg Leu Ile Gly Tyr Tyr
            930                 935                 940

Ser Pro Ile Thr Leu Pro Asp Asp Val Gly Val Ile Gly Ile Leu Ala
945                 950                 955                 960

Arg Ala Asp Lys Gly Arg Leu Ala Glu Trp Ile Ser Ala Leu Gln Pro
                965                 970                 975

Gly Asp Ala Val Glu Met Lys Ala Cys Gly Gly Leu Ile Ile Asp Arg
            980                 985                 990

Arg Phe Ala Glu Arg His Phe Phe Phe Arg Gly His Lys Ile Arg Lys
            995                 1000                1005

Leu Ala Leu Ile Gly Gly Thr Gly Val Ala Pro Met Leu Gln
    1010                1015                1020

Ile Val Arg Ala Ala Val Lys Lys Pro Phe Val Asp Ser Ile Glu
    1025                1030                1035

Ser Ile Gln Phe Ile Tyr Ala Ala Glu Asp Val Ser Glu Leu Thr
    1040                1045                1050

Tyr Arg Thr Leu Leu Glu Ser Tyr Glu Glu Tyr Gly Ser Glu
    1055                1060                1065

Lys Phe Lys Cys His Phe Val Leu Asn Asn Pro Pro Ala Gln Trp
    1070                1075                1080

Thr Asp Gly Val Gly Phe Val Asp Thr Ala Leu Leu Arg Ser Ala
    1085                1090                1095
```

```
                                                                -continued

Val Gln Ala Pro Ser Asn Asp Leu Leu Val Ala Ile Cys Gly Pro
    1100                1105                1110

Pro Ile Met Gln Arg Ala Val Lys Gly Ala Leu Lys Gly Leu Gly
    1115                1120                1125

Tyr Asn Met Asn Leu Val Arg Thr Val Asp Glu Thr Glu Pro Pro
    1130                1135                1140

Ser

<210> SEQ ID NO 181
<211> LENGTH: 1317
<212> TYPE: DNA
<213> ORGANISM: Schizosaccharomyces pombe
<220> FEATURE:
<221> NAME/KEY: CDS
<222> LOCATION: (1)..(1317)

<400> SEQUENCE: 181 atg ggt gaa ttg aaa gag att ttg aaa caa aga tat cat gaa tta ctt        48
Met Gly Glu Leu Lys Glu Ile Leu Lys Gln Arg Tyr His Glu Leu Leu
1               5                   10                  15 gat tgg aat gtt aag gca cca cat gtc cct tta tcc cag aga ttg aag       96
Asp Trp Asn Val Lys Ala Pro His Val Pro Leu Ser Gln Arg Leu Lys
            20                  25                  30 cac ttt act tgg tca tgg ttt gct tgt act atg gca acc ggt ggt gtt     144
His Phe Thr Trp Ser Trp Phe Ala Cys Thr Met Ala Thr Gly Gly Val
        35                  40                  45 ggt ttg atc att ggt tcc ttc cca ttc aga ttc tac ggt ttg aac acc     192
Gly Leu Ile Ile Gly Ser Phe Pro Phe Arg Phe Tyr Gly Leu Asn Thr
    50                  55                  60 att ggc aag att gtt tac atc tta caa atc ttt ttg ttt tct ctt ttt     240
Ile Gly Lys Ile Val Tyr Ile Leu Gln Ile Phe Leu Phe Ser Leu Phe
65                  70                  75                  80 ggc tct tgt atg ttg ttt cgt ttc atc aag tat cca tct acc att aag     288
Gly Ser Cys Met Leu Phe Arg Phe Ile Lys Tyr Pro Ser Thr Ile Lys
                85                  90                  95 gac tct tgg aat cat cac ttg gaa aag ttg ttt atc gca act tgt ttg     336
Asp Ser Trp Asn His His Leu Glu Lys Leu Phe Ile Ala Thr Cys Leu
            100                 105                 110 tta tct att tcc aca ttc atc gac atg tta gct atc tat gct tat cca     384
Leu Ser Ile Ser Thr Phe Ile Asp Met Leu Ala Ile Tyr Ala Tyr Pro
        115                 120                 125 gat acc ggt gaa tgg atg gtc tgg gtc att aga atc tta tac tac atc     432
Asp Thr Gly Glu Trp Met Val Trp Val Ile Arg Ile Leu Tyr Tyr Ile
    130                 135                 140 tat gtc gct gtc tct ttc atc tac tgt gtt atg gcc ttt ttc acc att     480
Tyr Val Ala Val Ser Phe Ile Tyr Cys Val Met Ala Phe Phe Thr Ile
145                 150                 155                 160 ttc aac aat cat gtt tac act att gaa act gct tct cca gct tgg att     528
Phe Asn Asn His Val Tyr Thr Ile Glu Thr Ala Ser Pro Ala Trp Ile
                165                 170                 175 ttg cca atc ttc cct cca atg atc tgt ggt gtc att gct ggt gct gtt     576
Leu Pro Ile Phe Pro Pro Met Ile Cys Gly Val Ile Ala Gly Ala Val
            180                 185                 190 aac tcc acc caa cct gct cac caa ttg aaa aac atg gtc att ttc ggt     624
Asn Ser Thr Gln Pro Ala His Gln Leu Lys Asn Met Val Ile Phe Gly
        195                 200                 205 atc ttg ttt caa ggt tta ggt ttt tgg gtt tac ctt tta ctt ttc gcc     672
Ile Leu Phe Gln Gly Leu Gly Phe Trp Val Tyr Leu Leu Leu Phe Ala
    210                 215                 220 gtt aat gtt ttg aga ttc ttc aca gtc ggt tta gca aag cca caa gat     720
Val Asn Val Leu Arg Phe Phe Thr Val Gly Leu Ala Lys Pro Gln Asp
```

| | | | | | | | | | | | | | | | |
|---|---|---|---|---|---|---|---|---|---|---|---|---|---|---|---|
| Val | Asn | Val | Leu | Arg | Phe | Phe | Thr | Val | Gly | Leu | Ala | Lys | Pro | Gln | Asp |
| 225 | | | | 230 | | | | | 235 | | | | | 240 | |

| aga | cca | ggt | atg | ttt | atg | ttc | gtt | ggt | cca | cca | gct | ttc | tct | ggt | tta | 768 |
|---|---|---|---|---|---|---|---|---|---|---|---|---|---|---|---|---|
| Arg | Pro | Gly | Met | Phe | Met | Phe | Val | Gly | Pro | Pro | Ala | Phe | Ser | Gly | Leu | |
| | | | | 245 | | | | | 250 | | | | | 255 | | |

| gca | ttg | att | aac | att | gca | aga | ggt | gca | atg | ggc | tca | aga | cct | tac | att | 816 |
|---|---|---|---|---|---|---|---|---|---|---|---|---|---|---|---|---|
| Ala | Leu | Ile | Asn | Ile | Ala | Arg | Gly | Ala | Met | Gly | Ser | Arg | Pro | Tyr | Ile | |
| | | | 260 | | | | | 265 | | | | | 270 | | | |

| ttc | gtt | ggt | gca | aac | tct | tcc | gaa | tac | tta | ggt | ttt | gtc | tca | acc | ttc | 864 |
|---|---|---|---|---|---|---|---|---|---|---|---|---|---|---|---|---|
| Phe | Val | Gly | Ala | Asn | Ser | Ser | Glu | Tyr | Leu | Gly | Phe | Val | Ser | Thr | Phe | |
| | | | 275 | | | | | 280 | | | | | 285 | | | |

| atg | gcc | att | ttc | atc | tgg | ggt | tta | gcc | gca | tgg | tgt | tat | tgc | tta | gct | 912 |
|---|---|---|---|---|---|---|---|---|---|---|---|---|---|---|---|---|
| Met | Ala | Ile | Phe | Ile | Trp | Gly | Leu | Ala | Ala | Trp | Cys | Tyr | Cys | Leu | Ala | |
| | 290 | | | | | 295 | | | | | 300 | | | | | |

| atg | gtt | tcc | ttc | ctt | gcc | ggc | ttt | ttc | act | aga | gca | cca | ttg | aaa | ttc | 960 |
|---|---|---|---|---|---|---|---|---|---|---|---|---|---|---|---|---|
| Met | Val | Ser | Phe | Leu | Ala | Gly | Phe | Phe | Thr | Arg | Ala | Pro | Leu | Lys | Phe | |
| 305 | | | | | 310 | | | | | 315 | | | | | 320 | |

| gct | tgt | ggt | tgg | ttc | gct | ttc | atc | ttt | cca | aat | gtt | ggt | ttt | gtt | aac | 1008 |
|---|---|---|---|---|---|---|---|---|---|---|---|---|---|---|---|---|
| Ala | Cys | Gly | Trp | Phe | Ala | Phe | Ile | Phe | Pro | Asn | Val | Gly | Phe | Val | Asn | |
| | | | 325 | | | | | 330 | | | | | 335 | | | |

| tgt | act | atc | gaa | atc | ggc | aag | atg | att | gat | tct | aag | gct | ttt | caa | atg | 1056 |
|---|---|---|---|---|---|---|---|---|---|---|---|---|---|---|---|---|
| Cys | Thr | Ile | Glu | Ile | Gly | Lys | Met | Ile | Asp | Ser | Lys | Ala | Phe | Gln | Met | |
| | | | 340 | | | | | 345 | | | | | 350 | | | |

| ttt | ggt | cac | atc | att | ggt | gtt | atc | ttg | tgt | att | caa | tgg | att | ttg | tta | 1104 |
|---|---|---|---|---|---|---|---|---|---|---|---|---|---|---|---|---|
| Phe | Gly | His | Ile | Ile | Gly | Val | Ile | Leu | Cys | Ile | Gln | Trp | Ile | Leu | Leu | |
| | | | 355 | | | | | 360 | | | | | 365 | | | |

| atg | tac | tta | atg | gtt | aga | gca | ttc | ctt | gtt | aat | gac | ttg | tgc | tat | cct | 1152 |
|---|---|---|---|---|---|---|---|---|---|---|---|---|---|---|---|---|
| Met | Tyr | Leu | Met | Val | Arg | Ala | Phe | Leu | Val | Asn | Asp | Leu | Cys | Tyr | Pro | |
| 370 | | | | | 375 | | | | | 380 | | | | | | |

| ggt | aaa | gac | gaa | gat | gca | cac | cca | cca | cca | aag | cca | aac | act | ggt | gtc | 1200 |
|---|---|---|---|---|---|---|---|---|---|---|---|---|---|---|---|---|
| Gly | Lys | Asp | Glu | Asp | Ala | His | Pro | Pro | Pro | Lys | Pro | Asn | Thr | Gly | Val | |
| 385 | | | | | 390 | | | | | 395 | | | | | 400 | |

| tta | aac | cca | act | ttc | cca | cca | gag | aag | gct | cca | gca | tca | tta | gag | aag | 1248 |
|---|---|---|---|---|---|---|---|---|---|---|---|---|---|---|---|---|
| Leu | Asn | Pro | Thr | Phe | Pro | Pro | Glu | Lys | Ala | Pro | Ala | Ser | Leu | Glu | Lys | |
| | | | | 405 | | | | | 410 | | | | | 415 | | |

| gtt | gat | act | cat | gtt | aca | tca | aca | ggt | ggt | gaa | tcc | gat | cct | cca | tct | 1296 |
|---|---|---|---|---|---|---|---|---|---|---|---|---|---|---|---|---|
| Val | Asp | Thr | His | Val | Thr | Ser | Thr | Gly | Gly | Glu | Ser | Asp | Pro | Pro | Ser | |
| | | | 420 | | | | | 425 | | | | | 430 | | | |

| tcc | gaa | cat | gaa | tcc | gtt | taa | | | | | | | | | | 1317 |
|---|---|---|---|---|---|---|---|---|---|---|---|---|---|---|---|---|
| Ser | Glu | His | Glu | Ser | Val | | | | | | | | | | | |
| | | | 435 | | | | | | | | | | | | | |

<210> SEQ ID NO 182
<211> LENGTH: 438
<212> TYPE: PRT
<213> ORGANISM: Schizosaccharomyces pombe

<400> SEQUENCE: 182

| | | | | | | | | | | | | | | | |
|---|---|---|---|---|---|---|---|---|---|---|---|---|---|---|---|
| Met | Gly | Glu | Leu | Lys | Glu | Ile | Leu | Lys | Gln | Arg | Tyr | His | Glu | Leu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Asp | Trp | Asn | Val | Lys | Ala | Pro | His | Val | Pro | Leu | Ser | Gln | Arg | Leu | Lys |
| | | | 20 | | | | | 25 | | | | | 30 | | |

| | | | | | | | | | | | | | | | |
|---|---|---|---|---|---|---|---|---|---|---|---|---|---|---|---|
| His | Phe | Thr | Trp | Ser | Trp | Phe | Ala | Cys | Thr | Met | Ala | Thr | Gly | Gly | Val |
| | | 35 | | | | | 40 | | | | | 45 | | | |

| | | | | | | | | | | | | | | | |
|---|---|---|---|---|---|---|---|---|---|---|---|---|---|---|---|
| Gly | Leu | Ile | Ile | Gly | Ser | Phe | Pro | Phe | Arg | Phe | Tyr | Gly | Leu | Asn | Thr |
| | 50 | | | | | 55 | | | | | 60 | | | | |

| | | | | | | | | | | | | | | | |
|---|---|---|---|---|---|---|---|---|---|---|---|---|---|---|---|
| Ile | Gly | Lys | Ile | Val | Tyr | Ile | Leu | Gln | Ile | Phe | Leu | Phe | Ser | Leu | Phe |
| 65 | | | | | 70 | | | | | 75 | | | | | 80 |

| | | | | | | | | | | | | | | | |
|---|---|---|---|---|---|---|---|---|---|---|---|---|---|---|---|
| Gly | Ser | Cys | Met | Leu | Phe | Arg | Phe | Ile | Lys | Tyr | Pro | Ser | Thr | Ile | Lys |

```
                    85                  90                  95
Asp Ser Trp Asn His His Leu Glu Lys Leu Phe Ile Ala Thr Cys Leu
            100                 105                 110

Leu Ser Ile Ser Thr Phe Ile Asp Met Leu Ala Ile Tyr Ala Tyr Pro
            115                 120                 125

Asp Thr Gly Glu Trp Met Val Trp Val Ile Arg Ile Leu Tyr Tyr Ile
            130                 135                 140

Tyr Val Ala Val Ser Phe Ile Tyr Cys Val Met Ala Phe Phe Thr Ile
145                 150                 155                 160

Phe Asn Asn His Val Tyr Thr Ile Glu Thr Ala Ser Pro Ala Trp Ile
                165                 170                 175

Leu Pro Ile Phe Pro Pro Met Ile Cys Gly Val Ile Ala Gly Ala Val
            180                 185                 190

Asn Ser Thr Gln Pro Ala His Gln Leu Lys Asn Met Val Ile Phe Gly
            195                 200                 205

Ile Leu Phe Gln Gly Leu Gly Phe Trp Val Tyr Leu Leu Leu Phe Ala
            210                 215                 220

Val Asn Val Leu Arg Phe Phe Thr Val Gly Leu Ala Lys Pro Gln Asp
225                 230                 235                 240

Arg Pro Gly Met Phe Met Phe Val Gly Pro Pro Ala Phe Ser Gly Leu
                245                 250                 255

Ala Leu Ile Asn Ile Ala Arg Gly Ala Met Gly Ser Arg Pro Tyr Ile
            260                 265                 270

Phe Val Gly Ala Asn Ser Ser Glu Tyr Leu Gly Phe Val Ser Thr Phe
            275                 280                 285

Met Ala Ile Phe Ile Trp Gly Leu Ala Ala Trp Cys Tyr Cys Leu Ala
            290                 295                 300

Met Val Ser Phe Leu Ala Gly Phe Phe Thr Arg Ala Pro Leu Lys Phe
305                 310                 315                 320

Ala Cys Gly Trp Phe Ala Phe Ile Phe Pro Asn Val Gly Phe Val Asn
                325                 330                 335

Cys Thr Ile Glu Ile Gly Lys Met Ile Asp Ser Lys Ala Phe Gln Met
            340                 345                 350

Phe Gly His Ile Ile Gly Val Ile Leu Cys Ile Gln Trp Ile Leu Leu
            355                 360                 365

Met Tyr Leu Met Val Arg Ala Phe Leu Val Asn Asp Leu Cys Tyr Pro
            370                 375                 380

Gly Lys Asp Glu Asp Ala His Pro Pro Lys Pro Asn Thr Gly Val
385                 390                 395                 400

Leu Asn Pro Thr Phe Pro Pro Glu Lys Ala Pro Ala Ser Leu Glu Lys
            405                 410                 415

Val Asp Thr His Val Thr Ser Thr Gly Gly Glu Ser Asp Pro Pro Ser
            420                 425                 430

Ser Glu His Glu Ser Val
            435

<210> SEQ ID NO 183
<211> LENGTH: 1205
<212> TYPE: DNA
<213> ORGANISM: Aspergillus oryzae
<220> FEATURE:
<221> NAME/KEY: CDS
<222> LOCATION: (1)..(1197)

<400> SEQUENCE: 183
```

| | |
|---|---|
| atg ttt aac aat gag cac cat att cct cct ggt tcc tct cac tct gat<br>Met Phe Asn Asn Glu His His Ile Pro Pro Gly Ser Ser His Ser Asp<br>1               5                  10                 15 | 48 |
| atc gaa atg tta aca cca cca aag ttt gag gat gaa aaa cag tta ggt<br>Ile Glu Met Leu Thr Pro Pro Lys Phe Glu Asp Glu Lys Gln Leu Gly<br>        20                  25                  30 | 96 |
| cca gtc ggt att aga gaa aga ttg aga cat ttc act tgg gct tgg tat<br>Pro Val Gly Ile Arg Glu Arg Leu Arg His Phe Thr Trp Ala Trp Tyr<br>            35                  40                  45 | 144 |
| acc tta acc atg tcc ggt ggt ggt ttg gca gtt ttg att atc tct cag<br>Thr Leu Thr Met Ser Gly Gly Gly Leu Ala Val Leu Ile Ile Ser Gln<br>  50                  55                  60 | 192 |
| cca ttc ggt ttt aga ggt tta aga gaa att ggt att gca gtt tac att<br>Pro Phe Gly Phe Arg Gly Leu Arg Glu Ile Gly Ile Ala Val Tyr Ile<br>65                  70                  75                  80 | 240 |
| ttg aac tta atc tta ttc gct ttg gtt tgt tct acc atg gct att cgt<br>Leu Asn Leu Ile Leu Phe Ala Leu Val Cys Ser Thr Met Ala Ile Arg<br>            85                  90                  95 | 288 |
| ttc atc ttg cac ggt aac ctt ttg gaa tcc ctt aga cat gac aga gaa<br>Phe Ile Leu His Gly Asn Leu Leu Glu Ser Leu Arg His Asp Arg Glu<br>        100                 105                 110 | 336 |
| ggt ttg ttt ttc cct act ttc tgg ttg tct gtt gct acc atc att tgt<br>Gly Leu Phe Phe Pro Thr Phe Trp Leu Ser Val Ala Thr Ile Ile Cys<br>    115                 120                 125 | 384 |
| ggt ttg tca aga tac ttt ggt gag gaa tcc aac gaa tcc ttc caa ttg<br>Gly Leu Ser Arg Tyr Phe Gly Glu Glu Ser Asn Glu Ser Phe Gln Leu<br>130                 135                 140 | 432 |
| gca tta gaa gcc ttg ttc tgg atc tat tgc gtt tgt acc ttg ttg gtt<br>Ala Leu Glu Ala Leu Phe Trp Ile Tyr Cys Val Cys Thr Leu Leu Val<br>145                 150                 155                 160 | 480 |
| gca atc att caa tac tct ttt gtt ttc tca tcc cac aag tac ggt tta<br>Ala Ile Ile Gln Tyr Ser Phe Val Phe Ser Ser His Lys Tyr Gly Leu<br>            165                 170                 175 | 528 |
| caa aca atg atg cca tct tgg att ttg cca gcc ttt cct atc atg ttg<br>Gln Thr Met Met Pro Ser Trp Ile Leu Pro Ala Phe Pro Ile Met Leu<br>        180                 185                 190 | 576 |
| tca ggc aca att gca tct gtt atc ggt gaa caa caa cca gcc aga gct<br>Ser Gly Thr Ile Ala Ser Val Ile Gly Glu Gln Gln Pro Ala Arg Ala<br>    195                 200                 205 | 624 |
| gca tta cca atc att ggt gcc ggt gtc acc ttc caa ggt tta ggt ttt<br>Ala Leu Pro Ile Ile Gly Ala Gly Val Thr Phe Gln Gly Leu Gly Phe<br>210                 215                 220 | 672 |
| tct att tcc ttc atg atg tat gct cat tac att ggc aga ctt atg gaa<br>Ser Ile Ser Phe Met Met Tyr Ala His Tyr Ile Gly Arg Leu Met Glu<br>225                 230                 235                 240 | 720 |
| tcc ggt tta cct cac tcc gac cat aga cca ggc atg ttc atc tgt gtt<br>Ser Gly Leu Pro His Ser Asp His Arg Pro Gly Met Phe Ile Cys Val<br>            245                 250                 255 | 768 |
| ggc cca cca gcc ttt act gct ttg gct tta gtc ggt atg tcc aag ggt<br>Gly Pro Pro Ala Phe Thr Ala Leu Ala Leu Val Gly Met Ser Lys Gly<br>        260                 265                 270 | 816 |
| tta cca gaa gat ttc aag ctt tta cat gac gct cat gca tta gag gat<br>Leu Pro Glu Asp Phe Lys Leu Leu His Asp Ala His Ala Leu Glu Asp<br>    275                 280                 285 | 864 |
| ggt aga atc att gaa ttg tta gca att tca gca ggt gtt ttc ctt tgg<br>Gly Arg Ile Ile Glu Leu Leu Ala Ile Ser Ala Gly Val Phe Leu Trp<br>290                 295                 300 | 912 |
| gca tta tcc ctt tgg ttt ttc tgt att gct att gtc gct gtc att aga<br>Ala Leu Ser Leu Trp Phe Phe Cys Ile Ala Ile Val Ala Val Ile Arg<br>305                 310                 315                 320 | 960 |

```
tct cca cca gaa gct ttc cac ttg aac tgg tgg gct atg gtt ttc cca          1008
Ser Pro Pro Glu Ala Phe His Leu Asn Trp Trp Ala Met Val Phe Pro
            325                 330                 335 aat act ggt ttc acc tta gct act atc act ttg ggt aaa gct ttg aac          1056
Asn Thr Gly Phe Thr Leu Ala Thr Ile Thr Leu Gly Lys Ala Leu Asn
    340                 345                 350 tca aat ggt gtc aag ggt gtc ggt tct gca atg tcc att tgt att gtc          1104
Ser Asn Gly Val Lys Gly Val Gly Ser Ala Met Ser Ile Cys Ile Val
355                 360                 365 tgc atg tac atc ttt gtt ttc gtt aac aat gtt aga gct gtt att cgt          1152
Cys Met Tyr Ile Phe Val Phe Val Asn Asn Val Arg Ala Val Ile Arg
        370                 375                 380 aag gat atc atg tat cca ggc aaa gat gag gat gtt tct gat taa              1197
Lys Asp Ile Met Tyr Pro Gly Lys Asp Glu Asp Val Ser Asp
385                 390                 395 cctgcagg                                                                 1205

<210> SEQ ID NO 184
<211> LENGTH: 398
<212> TYPE: PRT
<213> ORGANISM: Aspergillus oryzae

<400> SEQUENCE: 184

Met Phe Asn Asn Glu His His Ile Pro Pro Gly Ser Ser His Ser Asp
1               5                   10                  15

Ile Glu Met Leu Thr Pro Pro Lys Phe Glu Asp Glu Lys Gln Leu Gly
            20                  25                  30

Pro Val Gly Ile Arg Glu Arg Leu Arg His Phe Thr Trp Ala Trp Tyr
        35                  40                  45

Thr Leu Thr Met Ser Gly Gly Leu Ala Val Leu Ile Ile Ser Gln
    50                  55                  60

Pro Phe Gly Phe Arg Gly Leu Arg Glu Ile Gly Ile Ala Val Tyr Ile
65                  70                  75                  80

Leu Asn Leu Ile Leu Phe Ala Leu Val Cys Ser Thr Met Ala Ile Arg
                85                  90                  95

Phe Ile Leu His Gly Asn Leu Leu Glu Ser Leu Arg His Asp Arg Glu
            100                 105                 110

Gly Leu Phe Phe Pro Thr Phe Trp Leu Ser Val Ala Thr Ile Ile Cys
        115                 120                 125

Gly Leu Ser Arg Tyr Phe Gly Glu Glu Ser Asn Glu Ser Phe Gln Leu
    130                 135                 140

Ala Leu Glu Ala Leu Phe Trp Ile Tyr Cys Val Cys Thr Leu Leu Val
145                 150                 155                 160

Ala Ile Ile Gln Tyr Ser Phe Val Phe Ser Ser His Lys Tyr Gly Leu
                165                 170                 175

Gln Thr Met Met Pro Ser Trp Ile Leu Pro Ala Phe Pro Ile Met Leu
            180                 185                 190

Ser Gly Thr Ile Ala Ser Val Ile Gly Glu Gln Gln Pro Ala Arg Ala
        195                 200                 205

Ala Leu Pro Ile Ile Gly Ala Gly Val Thr Phe Gln Gly Leu Gly Phe
    210                 215                 220

Ser Ile Ser Phe Met Met Tyr Ala His Tyr Ile Gly Arg Leu Met Glu
225                 230                 235                 240

Ser Gly Leu Pro His Ser Asp His Arg Pro Gly Met Phe Ile Cys Val
                245                 250                 255
```

```
Gly Pro Pro Ala Phe Thr Ala Leu Ala Leu Val Gly Met Ser Lys Gly
                260                 265                 270

Leu Pro Glu Asp Phe Lys Leu Leu His Asp Ala His Ala Leu Glu Asp
            275                 280                 285

Gly Arg Ile Ile Glu Leu Leu Ala Ile Ser Ala Gly Val Phe Leu Trp
        290                 295                 300

Ala Leu Ser Leu Trp Phe Phe Cys Ile Ala Ile Val Ala Val Ile Arg
305                 310                 315                 320

Ser Pro Pro Glu Ala Phe His Leu Asn Trp Trp Ala Met Val Phe Pro
                325                 330                 335

Asn Thr Gly Phe Thr Leu Ala Thr Ile Thr Leu Gly Lys Ala Leu Asn
            340                 345                 350

Ser Asn Gly Val Lys Gly Val Gly Ser Ala Met Ser Ile Cys Ile Val
        355                 360                 365

Cys Met Tyr Ile Phe Val Phe Val Asn Asn Val Arg Ala Val Ile Arg
    370                 375                 380

Lys Asp Ile Met Tyr Pro Gly Lys Asp Glu Asp Val Ser Asp
385                 390                 395

<210> SEQ ID NO 185
<211> LENGTH: 1620
<212> TYPE: DNA
<213> ORGANISM: Issatchenkia orientalis
<220> FEATURE:
<221> NAME/KEY: CDS
<222> LOCATION: (1)..(1620)

<400> SEQUENCE: 185 atg act tta cac aaa aat tcc aac gaa gga gtt caa gct tca ggg ttt      48
Met Thr Leu His Lys Asn Ser Asn Glu Gly Val Gln Ala Ser Gly Phe
1               5                   10                  15 gag ctc caa gat aat ctg gat gtt ccg cat tct aat gca tca ttc caa      96
Glu Leu Gln Asp Asn Leu Asp Val Pro His Ser Asn Ala Ser Phe Gln
                20                  25                  30 agc ttt aaa tcc gac gag gct gaa cag gct cac aat aat gaa cac ttg     144
Ser Phe Lys Ser Asp Glu Ala Glu Gln Ala His Asn Asn Glu His Leu
            35                  40                  45 atg gag aag cct cag ttt aat aag gca aca atc tcc aac tac tgt aaa     192
Met Glu Lys Pro Gln Phe Asn Lys Ala Thr Ile Ser Asn Tyr Cys Lys
        50                  55                  60 aca aga ttt act gag ttg ttc cca aca aag cag tcg atg gct gcc aac     240
Thr Arg Phe Thr Glu Leu Phe Pro Thr Lys Gln Ser Met Ala Ala Asn
65                  70                  75                  80 aag cac ctt ttg aat cct ctt cct ggt tta aga atg att ggt ttc aaa     288
Lys His Leu Leu Asn Pro Leu Pro Gly Leu Arg Met Ile Gly Phe Lys
                85                  90                  95 caa tgg ctc ttg att tta tct ggg ttc ctt gca tgg act tgg gat gcc     336
Gln Trp Leu Leu Ile Leu Ser Gly Phe Leu Ala Trp Thr Trp Asp Ala
                100                 105                 110 tat gat ttc ttt tcg att tct cta aat act gtc caa ttg gct aag gat     384
Tyr Asp Phe Phe Ser Ile Ser Leu Asn Thr Val Gln Leu Ala Lys Asp
            115                 120                 125 ttt gat aag aca gtc aag gat atc acc tgg ggt att act gtt gtt ttg     432
Phe Asp Lys Thr Val Lys Asp Ile Thr Trp Gly Ile Thr Val Val Leu
        130                 135                 140 atg ttg aga tct gtc ggt ggt ttc ttc ttt ggt tac ttg ggt gat aag     480
Met Leu Arg Ser Val Gly Gly Phe Phe Phe Gly Tyr Leu Gly Asp Lys
145                 150                 155                 160 tac ggt aga aaa tgg cct tta att gca aat cta atg tgt gtc tgt ttt     528
```

-continued

```
                Tyr Gly Arg Lys Trp Pro Leu Ile Ala Asn Leu Met Cys Val Cys Phe
                            165                 170                 175 ctt gaa atc ggt act gga ttt atc aaa aac tac tcc caa ttc ttg ggt         576
Leu Glu Ile Gly Thr Gly Phe Ile Lys Asn Tyr Ser Gln Phe Leu Gly
            180                 185                 190 gtt agg gct gtt ttc ggt att atg ttg ggt ggt gtc tat ggt aat gcg         624
Val Arg Ala Val Phe Gly Ile Met Leu Gly Gly Val Tyr Gly Asn Ala
        195                 200                 205 gct gca act gcg ttg gat gat tgt cct gca gag gca agg ggc ttt att         672
Ala Ala Thr Ala Leu Asp Asp Cys Pro Ala Glu Ala Arg Gly Phe Ile
    210                 215                 220 tct ggt ttc tta caa caa ggt tac gca ttt ggt tat ttg ttg gct gtt         720
Ser Gly Phe Leu Gln Gln Gly Tyr Ala Phe Gly Tyr Leu Leu Ala Val
225                 230                 235                 240 gtt ttc aaa aga gca att gct gat aat tcc cct cac aga tgg aga gca         768
Val Phe Lys Arg Ala Ile Ala Asp Asn Ser Pro His Arg Trp Arg Ala
            245                 250                 255 atg ttt tgg ttc ggt gct ggt gtc tgt ttc tta att tgt tgc ttc aga         816
Met Phe Trp Phe Gly Ala Gly Val Cys Phe Leu Ile Cys Cys Phe Arg
        260                 265                 270 gct gtc ttg ccg gaa act aag gct ttc caa aga aac aag gaa att gaa         864
Ala Val Leu Pro Glu Thr Lys Ala Phe Gln Arg Asn Lys Glu Ile Glu
    275                 280                 285 agg tat aat gaa gaa cat ggt att cac cag agg tct ttc aag gaa aag         912
Arg Tyr Asn Glu Glu His Gly Ile His Gln Arg Ser Phe Lys Glu Lys
290                 295                 300 gcc act gct tct ttg aag atc tac tgg ttg atg atc att tac atg gtt         960
Ala Thr Ala Ser Leu Lys Ile Tyr Trp Leu Met Ile Ile Tyr Met Val
305                 310                 315                 320 ctg tta atg gct ggt ttc aat ttc atg tcc cat ggt tct caa gat tta        1008
Leu Leu Met Ala Gly Phe Asn Phe Met Ser His Gly Ser Gln Asp Leu
            325                 330                 335 tat cca acc tta ttg act gtt aga tat aat ttt agt gat aat gct aca        1056
Tyr Pro Thr Leu Leu Thr Val Arg Tyr Asn Phe Ser Asp Asn Ala Thr
        340                 345                 350 act gtt aca aac tgt gtt gca aat att ggt gca atc aca ggt ggt atc        1104
Thr Val Thr Asn Cys Val Ala Asn Ile Gly Ala Ile Thr Gly Gly Ile
    355                 360                 365 att att gga cat ttc tcg aat ttc att ggt aga aga ttg tcg atc att        1152
Ile Ile Gly His Phe Ser Asn Phe Ile Gly Arg Arg Leu Ser Ile Ile
370                 375                 380 atc tgc tgt att att ggt ggt gct cta att tat cct tgg gcc ttt gtt        1200
Ile Cys Cys Ile Ile Gly Gly Ala Leu Ile Tyr Pro Trp Ala Phe Val
385                 390                 395                 400 gac aat gca aac att aat gca gga gct ttc ttt tta cag ttc ttt gtg        1248
Asp Asn Ala Asn Ile Asn Ala Gly Ala Phe Phe Leu Gln Phe Phe Val
            405                 410                 415 caa ggt gct tgg ggt gtt gtt cca gtt cat tta tcc gaa ttg gca cca        1296
Gln Gly Ala Trp Gly Val Val Pro Val His Leu Ser Glu Leu Ala Pro
        420                 425                 430 cct gac ttc aaa gcc ttt gtt gtt ggt att gca tac caa ttg ggt aat        1344
Pro Asp Phe Lys Ala Phe Val Val Gly Ile Ala Tyr Gln Leu Gly Asn
    435                 440                 445 ttg gca tcc tct gca agt tcc acc att gaa aca aca att ggt gtg cac        1392
Leu Ala Ser Ser Ala Ser Ser Thr Ile Glu Thr Thr Ile Gly Val His
450                 455                 460 ttc cca atg act tct cca ggt ggt gaa cca atc ttt gat tat gca aaa        1440
Phe Pro Met Thr Ser Pro Gly Gly Glu Pro Ile Phe Asp Tyr Ala Lys
465                 470                 475                 480
```

-continued

| | | | | | | | | | | | | | | | |
|---|---|---|---|---|---|---|---|---|---|---|---|---|---|---|---|
| gtt | atg | gca | att | ttc | gtt | ggc | tgt | gtc | ttt | gca | tat | gtg | tta | ctt | atc | 1488
| Val | Met | Ala | Ile | Phe | Val | Gly | Cys | Val | Phe | Ala | Tyr | Val | Leu | Leu | Ile |
| | | | 485 | | | | | 490 | | | | | 495 | | |
| aca | ttt | att | ggt | cca | gag | agg | aaa | tct | gtg | tcc | ttt | gag | gag | cca | gtt | 1536
| Thr | Phe | Ile | Gly | Pro | Glu | Arg | Lys | Ser | Val | Ser | Phe | Glu | Glu | Pro | Val |
| | | | 500 | | | | | 505 | | | | | 510 | | |
| gat | gag | gat | atc | gaa | atc | aat | gaa | aaa | atc | aaa | cac | aat | gaa | gaa | atc | 1584
| Asp | Glu | Asp | Ile | Glu | Ile | Asn | Glu | Lys | Ile | Lys | His | Asn | Glu | Glu | Ile |
| | | | 515 | | | | | 520 | | | | | 525 | | |
| gag | gct | ggc | tct | aac | ttg | gga | act | tca | aga | gca | taa | | | | | 1620
| Glu | Ala | Gly | Ser | Asn | Leu | Gly | Thr | Ser | Arg | Ala | | | | | |
| | | 530 | | | | | 535 | | | | | | | | |

<210> SEQ ID NO 186
<211> LENGTH: 539
<212> TYPE: PRT
<213> ORGANISM: Issatchenkia orientalis

<400> SEQUENCE: 186

Met Thr Leu His Lys Asn Ser Asn Glu Gly Val Gln Ala Ser Gly Phe
1               5                   10                  15

Glu Leu Gln Asp Asn Leu Asp Val Pro His Ser Asn Ala Ser Phe Gln
            20                  25                  30

Ser Phe Lys Ser Asp Glu Ala Glu Gln Ala His Asn Asn Glu His Leu
        35                  40                  45

Met Glu Lys Pro Gln Phe Asn Lys Ala Thr Ile Ser Asn Tyr Cys Lys
    50                  55                  60

Thr Arg Phe Thr Glu Leu Phe Pro Thr Lys Gln Ser Met Ala Ala Asn
65                  70                  75                  80

Lys His Leu Leu Asn Pro Leu Pro Gly Leu Arg Met Ile Gly Phe Lys
                85                  90                  95

Gln Trp Leu Leu Ile Leu Ser Gly Phe Leu Ala Trp Thr Trp Asp Ala
            100                 105                 110

Tyr Asp Phe Phe Ser Ile Ser Leu Asn Thr Val Gln Leu Ala Lys Asp
        115                 120                 125

Phe Asp Lys Thr Val Lys Asp Ile Thr Trp Gly Ile Thr Val Val Leu
    130                 135                 140

Met Leu Arg Ser Val Gly Gly Phe Phe Gly Tyr Leu Gly Asp Lys
145                 150                 155                 160

Tyr Gly Arg Lys Trp Pro Leu Ile Ala Asn Leu Met Cys Val Cys Phe
                165                 170                 175

Leu Glu Ile Gly Thr Gly Phe Ile Lys Asn Tyr Ser Gln Phe Leu Gly
            180                 185                 190

Val Arg Ala Val Phe Gly Ile Met Leu Gly Gly Val Tyr Gly Asn Ala
        195                 200                 205

Ala Ala Thr Ala Leu Asp Asp Cys Pro Ala Glu Ala Arg Gly Phe Ile
    210                 215                 220

Ser Gly Phe Leu Gln Gln Gly Tyr Ala Phe Gly Tyr Leu Leu Ala Val
225                 230                 235                 240

Val Phe Lys Arg Ala Ile Ala Asp Asn Ser Pro His Arg Trp Arg Ala
                245                 250                 255

Met Phe Trp Phe Gly Ala Gly Val Cys Phe Leu Ile Cys Cys Phe Arg
            260                 265                 270

Ala Val Leu Pro Glu Thr Lys Ala Phe Gln Arg Asn Lys Glu Ile Glu
        275                 280                 285

Arg Tyr Asn Glu Glu His Gly Ile His Gln Arg Ser Phe Lys Glu Lys

```
            290                 295                 300
Ala Thr Ala Ser Leu Lys Ile Tyr Trp Leu Met Ile Ile Tyr Met Val
305                 310                 315                 320

Leu Leu Met Ala Gly Phe Asn Phe Met Ser His Gly Ser Gln Asp Leu
                325                 330                 335

Tyr Pro Thr Leu Leu Thr Val Arg Tyr Asn Phe Ser Asp Asn Ala Thr
                340                 345                 350

Thr Val Thr Asn Cys Val Ala Asn Ile Gly Ala Ile Thr Gly Gly Ile
                355                 360                 365

Ile Ile Gly His Phe Ser Asn Phe Ile Gly Arg Arg Leu Ser Ile Ile
        370                 375                 380

Ile Cys Cys Ile Ile Gly Gly Ala Leu Ile Tyr Pro Trp Ala Phe Val
385                 390                 395                 400

Asp Asn Ala Asn Ile Asn Ala Gly Ala Phe Phe Leu Gln Phe Phe Val
                405                 410                 415

Gln Gly Ala Trp Gly Val Val Pro Val His Leu Ser Glu Leu Ala Pro
                420                 425                 430

Pro Asp Phe Lys Ala Phe Val Val Gly Ile Ala Tyr Gln Leu Gly Asn
                435                 440                 445

Leu Ala Ser Ser Ala Ser Ser Thr Ile Glu Thr Thr Ile Gly Val His
        450                 455                 460

Phe Pro Met Thr Ser Pro Gly Gly Glu Pro Ile Phe Asp Tyr Ala Lys
465                 470                 475                 480

Val Met Ala Ile Phe Val Gly Cys Val Phe Ala Tyr Val Leu Leu Ile
                485                 490                 495

Thr Phe Ile Gly Pro Glu Arg Lys Ser Val Ser Phe Glu Glu Pro Val
                500                 505                 510

Asp Glu Asp Ile Glu Ile Asn Glu Lys Ile Lys His Asn Glu Glu Ile
        515                 520                 525

Glu Ala Gly Ser Asn Leu Gly Thr Ser Arg Ala
        530                 535

<210> SEQ ID NO 187
<211> LENGTH: 31
<212> TYPE: DNA
<213> ORGANISM: Artificial Sequence
<220> FEATURE:
<223> OTHER INFORMATION: PCR primer

<400> SEQUENCE: 187
caagagtatc ccatctgaca ggaaccgatg g                              31

<210> SEQ ID NO 188
<211> LENGTH: 31
<212> TYPE: DNA
<213> ORGANISM: Artificial Sequence
<220> FEATURE:
<223> OTHER INFORMATION: PCR primer

<400> SEQUENCE: 188
aaaaaaacgc gtatgaaagt cgcagtcctc g                              31

<210> SEQ ID NO 189
<211> LENGTH: 37
<212> TYPE: DNA
<213> ORGANISM: Artificial Sequence
<220> FEATURE:
<223> OTHER INFORMATION: PCR primer
```

<400> SEQUENCE: 189
aaaaaacctg caggttactt attaacgaac tcttcgc        37

<210> SEQ ID NO 190
<211> LENGTH: 31
<212> TYPE: DNA
<213> ORGANISM: Artificial Sequence
<220> FEATURE:
<223> OTHER INFORMATION: PCR primer

<400> SEQUENCE: 190
aaaaaaacgc gtatgcctca ttctatcaac g        31

<210> SEQ ID NO 191
<211> LENGTH: 36
<212> TYPE: DNA
<213> ORGANISM: Artificial Sequence
<220> FEATURE:
<223> OTHER INFORMATION: PCR primer

<400> SEQUENCE: 191
aaaaaacctg caggttacaa actcaaaccg tttctg        36

<210> SEQ ID NO 192
<211> LENGTH: 35
<212> TYPE: DNA
<213> ORGANISM: Artificial Sequence
<220> FEATURE:
<223> OTHER INFORMATION: PCR primer

<400> SEQUENCE: 192
aaaaaaacgc gtatggttaa agttacagtt tgtgg        35

<210> SEQ ID NO 193
<211> LENGTH: 37
<212> TYPE: DNA
<213> ORGANISM: Artificial Sequence
<220> FEATURE:
<223> OTHER INFORMATION: PCR primer

<400> SEQUENCE: 193
aaaaaacctg caggttagcc ttcagtaaca aaagtac        37

<210> SEQ ID NO 194
<211> LENGTH: 26
<212> TYPE: DNA
<213> ORGANISM: Artificial Sequence
<220> FEATURE:
<223> OTHER INFORMATION: PCR primer

<400> SEQUENCE: 194
caaaacaact gtcccctatg tacatc        26

<210> SEQ ID NO 195
<211> LENGTH: 35
<212> TYPE: DNA
<213> ORGANISM: Artificial Sequence
<220> FEATURE:
<223> OTHER INFORMATION: PCR primer

<400> SEQUENCE: 195
ctgaagttga acaaatttat gccacgcagc ttttc        35

<210> SEQ ID NO 196
<211> LENGTH: 24

```
<212> TYPE: DNA
<213> ORGANISM: Artificial Sequence
<220> FEATURE:
<223> OTHER INFORMATION: PCR primer

<400> SEQUENCE: 196
gaacgtctac aacgaggtga acac                                              24

<210> SEQ ID NO 197
<211> LENGTH: 90
<212> TYPE: DNA
<213> ORGANISM: Artificial Sequence
<220> FEATURE:
<223> OTHER INFORMATION: PCR primer

<400> SEQUENCE: 197
ttctttccat tcatctatat aaggtgtccc tggttccttt attaagaaga aaacaactgc       60
aacacttcct ggaattcgcc cttacatatg                                        90

<210> SEQ ID NO 198
<211> LENGTH: 90
<212> TYPE: DNA
<213> ORGANISM: Artificial Sequence
<220> FEATURE:
<223> OTHER INFORMATION: PCR primer

<400> SEQUENCE: 198
caaacccaaa gtggtggaag aagtgaaccg agaaaaaaac aacaggaaga attagaggga       60
ctctagatca cggctcgtgc tatattcttg                                        90

<210> SEQ ID NO 199
<211> LENGTH: 29
<212> TYPE: DNA
<213> ORGANISM: Artificial Sequence
<220> FEATURE:
<223> OTHER INFORMATION: PCR primer

<400> SEQUENCE: 199
gaggaagttc aaagtatgaa agacgtcag                                         29

<210> SEQ ID NO 200
<211> LENGTH: 30
<212> TYPE: DNA
<213> ORGANISM: Artificial Sequence
<220> FEATURE:
<223> OTHER INFORMATION: PCR primer

<400> SEQUENCE: 200
gagaacttat acgcaccaga acgccttttg                                        30

<210> SEQ ID NO 201
<211> LENGTH: 33
<212> TYPE: DNA
<213> ORGANISM: Artificial Sequence
<220> FEATURE:
<223> OTHER INFORMATION: PCR primer

<400> SEQUENCE: 201
gatcgggccc gtcttggaag acgcactagt ctc                                    33

<210> SEQ ID NO 202
<211> LENGTH: 34
<212> TYPE: DNA
<213> ORGANISM: Artificial Sequence
<220> FEATURE:
```

```
<223> OTHER INFORMATION: PCR primer

<400> SEQUENCE: 202
gatcgagctc caccttattt atgggagtta tttc                                    34

<210> SEQ ID NO 203
<211> LENGTH: 20
<212> TYPE: DNA
<213> ORGANISM: Artificial Sequence
<220> FEATURE:
<223> OTHER INFORMATION: PCR primer

<400> SEQUENCE: 203
cggcatttac aagaggtgcg                                                    20

<210> SEQ ID NO 204
<211> LENGTH: 21
<212> TYPE: DNA
<213> ORGANISM: Artificial Sequence
<220> FEATURE:
<223> OTHER INFORMATION: PCR primer

<400> SEQUENCE: 204
gttgctctct cttaatccag g                                                  21

<210> SEQ ID NO 205
<211> LENGTH: 180
<212> TYPE: DNA
<213> ORGANISM: Issatchenkia orientalis

<400> SEQUENCE: 205
gtatctgttg ttgttttatt tcctttggaa gtgtataaaa caaacctagt ccccgctttt        60
gttttctctc acaacccctt tagagtaagg attagcttgg tatctatttt ttattttcgt       120
tgaaacaagt ttagtcaggt gcttgaaaca caaccaaaca agtaataagt ttgacataga       180

<210> SEQ ID NO 206
<211> LENGTH: 180
<212> TYPE: DNA
<213> ORGANISM: Issatchenkia orientalis

<400> SEQUENCE: 206
ttgtttccct tcgctttaac tcctatcaat aatacattca aaacttagta ttactgatgc        60
tgttacgact actaatacta ttgctactac caatactatt cacttctcta tctattttag       120
atatatatgc atatagtcat ttttctttt ttttttttga tatctatact ctacactata       180

<210> SEQ ID NO 207
<211> LENGTH: 1138
<212> TYPE: DNA
<213> ORGANISM: Schizosaccharomyces pombe

<400> SEQUENCE: 207
cggtttgaac accattggca agattgttta catcttacaa atcttttgt tttctctttt         60 tggctcttgt atgttgtttc gtttcatcaa gtatccatct accattaagg actcttggaa       120
tcatcacttg gaaaagttgt ttatcgcaac ttgtttgtta tctatttcca cattcatcga       180
catgttagct atctatgctt atccagatac cggtgaatgg atggtctggg tcattagaat       240
cttatactac atctatgtcg ctgtctcttt catctactgt gttatggcct ttttcaccat       300
tttcaacaat catgtttaca ctattgaaac tgcttctcca gcttggattt tgccaatctt       360
ccctccaatg atctgtggtg tcattgctgg tgctgttaac tccacccaac ctgctcacca       420
```

```
attgaaaaac atggtcattt tcggtatctt gtttcaaggt ttaggttttt gggtttacct      480
tttacttttc gccgttaatg ttttgagatt cttcacagtc ggtttagcaa agccacaaga      540
tagaccaggt atgtttatgt tcgttggtcc accagctttc tctggtttag cattgattaa      600
cattgcaaga ggtgcaatgg gctcaagacc ttacattttc gttggtgcaa actcttccga      660
atacttaggt tttgtctcaa ccttcatggc cattttcatc tggggtttag ccgcatggtg      720
ttattgctta gctatggttt ccttccttgc cggcttttc  actagagcac cattgaaatt      780
cgcttgtggt tggttcgctt tcatctttcc aaatgttggt tttgttaact gtactatcga      840
aatcggcaag atgattgatt ctaaggcttt tcaaatgttt ggtcacatca ttggtgttat      900
cttgtgtatt caatggattt tgttaatgta cttaatggtt agagcattcc ttgttaatga      960
cttgtgctat cctggtaaag acgaagatgc acacccacca ccaaagccaa acactggtgt     1020
cttaaaccca actttcccac cagagaaggc tccagcatca ttagagaagg ttgatactca     1080
tgttacatca acaggtggtg aatccgatcc tccatcttcc gaacatgaat ccgttttaa      1138
```

<210> SEQ ID NO 208
<211> LENGTH: 400
<212> TYPE: DNA
<213> ORGANISM: Schizosaccharomyces pombe

<400> SEQUENCE: 208

```
aaacgcgtat gggtgaattg aaagagattt tgaaacaaag atatcatgaa ttacttgatt       60
ggaatgttaa ggcaccacat gtccctttat cccagagatt gaagcacttt acttggtcat      120
ggtttgcttg tactatggca accggtggtg ttggtttgat cattggttcc ttcccattca      180
gattctacgg tttgaacacc attggcaaga ttgtttacat cttacaaatc tttttgtttt      240 ctcttttttgg ctcttgtatg ttgtttcgtt tcatcaagta tccatctacc attaaggact      300
cttggaatca tcacttggaa aagttgttta tcgcaacttg tttgttatct atttccacat      360
tcatcgacat gttagctatc tatgctcctg caggaatcct                            400
```

<210> SEQ ID NO 209
<211> LENGTH: 120
<212> TYPE: DNA
<213> ORGANISM: Artificial Sequence
<220> FEATURE:
<223> OTHER INFORMATION: PCR primer

<400> SEQUENCE: 209

```
ttcaaagccc tcgtcgcagg ccactgtatg ctacatcttg taatgtgcca tggattggct       60
cttcgatagg tctctagcca tgtgtatcac ctaacacaac aagcggaaga gcgcccaatg      120
```

<210> SEQ ID NO 210
<211> LENGTH: 139
<212> TYPE: DNA
<213> ORGANISM: Artificial Sequence
<220> FEATURE:
<223> OTHER INFORMATION: PCR primer

<400> SEQUENCE: 210

```
tatcgcatct ccgggttcac acgaggaaat acaatggctt tgacaagcag cagaacatcc       60
gtgcaccaaa gttcaccaag actggttcgt agaaacccgg agattgcgtg ggtgggaccc      120
ggctcgtgct atattcttg                                                   139
```

<210> SEQ ID NO 211

```
<211> LENGTH: 44
<212> TYPE: DNA
<213> ORGANISM: Artificial Sequence
<220> FEATURE:
<223> OTHER INFORMATION: PCR primer

<400> SEQUENCE: 211
catcaatagg taccgagctc ccgtttcgat gggattccca gaag                44

<210> SEQ ID NO 212
<211> LENGTH: 41
<212> TYPE: DNA
<213> ORGANISM: Artificial Sequence
<220> FEATURE:
<223> OTHER INFORMATION: PCR primer

<400> SEQUENCE: 212
cccctggtgc ggccgctccc ttctctaaat ggactgcttg g                   41

<210> SEQ ID NO 213
<211> LENGTH: 39
<212> TYPE: DNA
<213> ORGANISM: Artificial Sequence
<220> FEATURE:
<223> OTHER INFORMATION: PCR primer

<400> SEQUENCE: 213
agaagggagc ggccgcacca ggggtttagt gaagtcacc                      39

<210> SEQ ID NO 214
<211> LENGTH: 43
<212> TYPE: DNA
<213> ORGANISM: Artificial Sequence
<220> FEATURE:
<223> OTHER INFORMATION: PCR primer

<400> SEQUENCE: 214
acttacaagg gccccataac tgacatttat ggtaaggttg ctc                 43

<210> SEQ ID NO 215
<211> LENGTH: 26
<212> TYPE: DNA
<213> ORGANISM: Artificial Sequence
<220> FEATURE:
<223> OTHER INFORMATION: PCR primer

<400> SEQUENCE: 215
caggatcgaa gaatagaagt tgtgtg                                    26

<210> SEQ ID NO 216
<211> LENGTH: 1134
<212> TYPE: DNA
<213> ORGANISM: Issatchenkia orientalis
<220> FEATURE:
<221> NAME/KEY: CDS
<222> LOCATION: (1)..(1134)

<400> SEQUENCE: 216 atg tta tcc aag acc atc act gct gca ttg agg ggc aat aca act cgt      48
Met Leu Ser Lys Thr Ile Thr Ala Ala Leu Arg Gly Asn Thr Thr Arg
1               5                   10                  15 act gca ttc aga atc aat gcc att aga agt tta gcg atc cca gct att      96
Thr Ala Phe Arg Ile Asn Ala Ile Arg Ser Leu Ala Ile Pro Ala Ile
            20                  25                  30 cca gag aca caa aag ggt gtt atc ttt tat gag aac gga ggt gaa cta     144
Pro Glu Thr Gln Lys Gly Val Ile Phe Tyr Glu Asn Gly Gly Glu Leu
```

```
                  35                  40                  45
ttt tac aag gac att cca gtt cca aag cca aag cca aat gag att ttg        192
Phe Tyr Lys Asp Ile Pro Val Pro Lys Pro Lys Pro Asn Glu Ile Leu
 50                  55                  60 gtg aat gtc aag tat tct ggt gtt tgt cat acc gat tta cac gca tgg        240
Val Asn Val Lys Tyr Ser Gly Val Cys His Thr Asp Leu His Ala Trp
 65                  70                  75                  80 aaa ggt gac tgg cct ttg gcg acc aag ttg cca ttg gtt ggt gga cat        288
Lys Gly Asp Trp Pro Leu Ala Thr Lys Leu Pro Leu Val Gly Gly His
                 85                  90                  95 gaa ggt gcc gga gtt gtt gtt gct aag ggg gac aat gtc acc aac ttt        336
Glu Gly Ala Gly Val Val Val Ala Lys Gly Asp Asn Val Thr Asn Phe
                100                 105                 110 gaa att ggc gat tat gcc ggt atc aag tgg ttg aat ggt tca tgt atg        384
Glu Ile Gly Asp Tyr Ala Gly Ile Lys Trp Leu Asn Gly Ser Cys Met
            115                 120                 125 ggg tgt gaa ttt tgc caa caa ggt gca gag cca aac tgt cca cag gcc        432
Gly Cys Glu Phe Cys Gln Gln Gly Ala Glu Pro Asn Cys Pro Gln Ala
130                 135                 140 gac ttg agt ggt tac acc cat gac ggg tcc ttt caa caa tat gcc act        480
Asp Leu Ser Gly Tyr Thr His Asp Gly Ser Phe Gln Gln Tyr Ala Thr
145                 150                 155                 160 gcc gat gct gtt cag gca gcc aag att cct cag ggc act gat ttg gct        528
Ala Asp Ala Val Gln Ala Ala Lys Ile Pro Gln Gly Thr Asp Leu Ala
                165                 170                 175 caa gtt gcg cca att tta tgt gca ggt att act gtc tat aag gct tta        576
Gln Val Ala Pro Ile Leu Cys Ala Gly Ile Thr Val Tyr Lys Ala Leu
            180                 185                 190 aag act gca gaa tta aga cca ggt caa tgg gtt gcc att tct ggt gct        624
Lys Thr Ala Glu Leu Arg Pro Gly Gln Trp Val Ala Ile Ser Gly Ala
        195                 200                 205 gct gga ggt tta ggt tct ctt gct gtt caa tat gcc aag gcc atg ggt        672
Ala Gly Gly Leu Gly Ser Leu Ala Val Gln Tyr Ala Lys Ala Met Gly
    210                 215                 220 ttg aga gtt ttg ggt att gat ggt ggt gag gag aag ggc aag ttt gca        720
Leu Arg Val Leu Gly Ile Asp Gly Gly Glu Glu Lys Gly Lys Phe Ala
225                 230                 235                 240 aag tct ctt gga gct gaa gtt ttc att gat ttc acc aaa tcc aag gac        768
Lys Ser Leu Gly Ala Glu Val Phe Ile Asp Phe Thr Lys Ser Lys Asp
                245                 250                 255 att gtc aag gat atc caa gag gcc acc aat ggt ggt cca cat ggt gtc        816
Ile Val Lys Asp Ile Gln Glu Ala Thr Asn Gly Gly Pro His Gly Val
            260                 265                 270 att aat gtt tct gtt tct cca gct gct att tct caa agt acc cag tat        864
Ile Asn Val Ser Val Ser Pro Ala Ala Ile Ser Gln Ser Thr Gln Tyr
        275                 280                 285 gtc aga acc ttg ggt aag gtt gtc ctt gtt gga tta cca gcg cat gct        912
Val Arg Thr Leu Gly Lys Val Val Leu Val Gly Leu Pro Ala His Ala
    290                 295                 300 gta tgc gag tct tcg gtt ttc gac cat gtt gtc aag tcg att caa att        960
Val Cys Glu Ser Ser Val Phe Asp His Val Val Lys Ser Ile Gln Ile
305                 310                 315                 320 aga ggc tct tat gtt ggt aac agg gaa gat act agt gag gct att gat       1008
Arg Gly Ser Tyr Val Gly Asn Arg Glu Asp Thr Ser Glu Ala Ile Asp
                325                 330                 335 ttt ttc acc agg ggt tta gtg aag tca cca att aag att gtt ggt ttg       1056
Phe Phe Thr Arg Gly Leu Val Lys Ser Pro Ile Lys Ile Val Gly Leu
            340                 345                 350 agt gag ttg cca aag atc tat gaa ttg atg gag caa ggt aag att tta       1104
```

Ser Glu Leu Pro Lys Ile Tyr Glu Leu Met Glu Gln Gly Lys Ile Leu
            355                 360                 365 ggc aga tat gtt gtt gac act tcg aaa tga                                1134
Gly Arg Tyr Val Val Asp Thr Ser Lys
    370                 375

<210> SEQ ID NO 217
<211> LENGTH: 377
<212> TYPE: PRT
<213> ORGANISM: Issatchenkia orientalis

<400> SEQUENCE: 217

Met Leu Ser Lys Thr Ile Thr Ala Ala Leu Arg Gly Asn Thr Thr Arg
1               5                   10                  15

Thr Ala Phe Arg Ile Asn Ala Ile Arg Ser Leu Ala Ile Pro Ala Ile
            20                  25                  30

Pro Glu Thr Gln Lys Gly Val Ile Phe Tyr Glu Asn Gly Gly Glu Leu
        35                  40                  45

Phe Tyr Lys Asp Ile Pro Val Pro Lys Pro Asn Glu Ile Leu
 50                  55                  60

Val Asn Val Lys Tyr Ser Gly Val Cys His Thr Asp Leu His Ala Trp
65                  70                  75                  80

Lys Gly Asp Trp Pro Leu Ala Thr Lys Leu Pro Leu Val Gly His
                85                  90                  95

Glu Gly Ala Gly Val Val Ala Lys Gly Asp Asn Val Thr Asn Phe
            100                 105                 110

Glu Ile Gly Asp Tyr Ala Gly Ile Lys Trp Leu Asn Gly Ser Cys Met
        115                 120                 125

Gly Cys Glu Phe Cys Gln Gln Gly Ala Glu Pro Asn Cys Pro Gln Ala
130                 135                 140

Asp Leu Ser Gly Tyr Thr His Asp Gly Ser Phe Gln Gln Tyr Ala Thr
145                 150                 155                 160

Ala Asp Ala Val Gln Ala Lys Ile Pro Gln Gly Thr Asp Leu Ala
                165                 170                 175

Gln Val Ala Pro Ile Leu Cys Ala Gly Ile Thr Val Tyr Lys Ala Leu
            180                 185                 190

Lys Thr Ala Glu Leu Arg Pro Gly Gln Trp Val Ala Ile Ser Gly Ala
        195                 200                 205

Ala Gly Gly Leu Gly Ser Leu Ala Val Gln Tyr Ala Lys Ala Met Gly
    210                 215                 220

Leu Arg Val Leu Gly Ile Asp Gly Gly Glu Lys Gly Lys Phe Ala
225                 230                 235                 240

Lys Ser Leu Gly Ala Glu Val Phe Ile Asp Phe Thr Lys Ser Lys Asp
                245                 250                 255

Ile Val Lys Asp Ile Gln Glu Ala Thr Asn Gly Gly Pro His Gly Val
            260                 265                 270

Ile Asn Val Ser Val Ser Pro Ala Ala Ile Ser Gln Ser Thr Gln Tyr
        275                 280                 285

Val Arg Thr Leu Gly Lys Val Val Leu Val Gly Leu Pro Ala His Ala
    290                 295                 300

Val Cys Glu Ser Ser Val Phe Asp His Val Val Lys Ser Ile Gln Ile
305                 310                 315                 320

Arg Gly Ser Tyr Val Gly Asn Arg Glu Asp Thr Ser Glu Ala Ile Asp
                325                 330                 335

Phe Phe Thr Arg Gly Leu Val Lys Ser Pro Ile Lys Ile Val Gly Leu

```
                 340                 345                 350
Ser Glu Leu Pro Lys Ile Tyr Glu Leu Met Glu Gln Gly Lys Ile Leu
         355                 360                 365

Gly Arg Tyr Val Val Asp Thr Ser Lys
     370                 375

<210> SEQ ID NO 218
<211> LENGTH: 38
<212> TYPE: DNA
<213> ORGANISM: Artificial Sequence
<220> FEATURE:
<223> OTHER INFORMATION: PCR primer

<400> SEQUENCE: 218
gtttaaactt caaagccctc gtcgcaggcc actgtatg                              38

<210> SEQ ID NO 219
<211> LENGTH: 30
<212> TYPE: DNA
<213> ORGANISM: Artificial Sequence
<220> FEATURE:
<223> OTHER INFORMATION: PCR primer

<400> SEQUENCE: 219
gtttaaacta tcgcatctcc gggttcacac                                       30
```